US006897231B2

(12) United States Patent
Bhagwat et al.

(10) Patent No.: US 6,897,231 B2
(45) Date of Patent: May 24, 2005

(54) INDAZOLE DERIVATIVES AS JNK INHIBITORS AND COMPOSITIONS AND METHODS RELATED THERETO

(75) Inventors: Shripad S. Bhagwat, San Diego, CA (US); Yoshitaka Satoh, San Diego, CA (US); Steven T. Sakata, San Diego, CA (US); Chris A. Buhr, Redwood City, CA (US); Ronald Albers, La Jolla, CA (US); John Sapienza, Chula Vista, CA (US); Veronique Plantevin, San Diego, CA (US); Qi Chao, San Diego, CA (US); Kiran Sahasrabudhe, San Diego, CA (US); Rachel Ferri, San Diego, CA (US)

(73) Assignee: Signal Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/910,950

(22) Filed: Jul. 23, 2001

(65) Prior Publication Data

US 2002/0103229 A1 Aug. 1, 2002

Related U.S. Application Data

(60) Provisional application No. 60/221,799, filed on Jul. 31, 2000.

(51) Int. Cl.$^7$ ..................... A61K 31/416; C07D 231/56
(52) U.S. Cl. ................. 514/403; 548/362.5; 548/361.1; 548/305.1; 548/311.7; 548/266.4
(58) Field of Search ........................... 548/362.5, 361.1, 548/305.1, 311.7, 266.4; 514/403

(56) References Cited

U.S. PATENT DOCUMENTS

| | | | |
|---|---|---|---|
| 3,541,110 A | * 11/1970 | Bell et al. ................. | 548/361.1 |
| 3,994,890 A | 11/1976 | Fujimura | |
| 4,415,569 A | 11/1983 | Yasuo et al. | |
| 5,985,867 A | * 11/1999 | Rodgers et al. ............. | 514/218 |
| 6,162,613 A | 12/2000 | Su et al. | |
| 6,531,491 B1 | 3/2003 | Kania et al. | |
| 6,534,524 B1 | 3/2003 | Kania et al. | |
| 2002/0161022 A1 | * 10/2002 | Reich et al. ................. | 514/314 |

FOREIGN PATENT DOCUMENTS

| | | |
|---|---|---|
| DE | 12 66 763 B | 4/1968 |
| EP | 0 494 774 | 7/1992 |
| EP | 0 518 805 | 12/1992 |
| GB | 1293557 | 9/1970 |
| GB | 2 345 486 A | 7/2000 |
| GB | 2345486 | * 7/2000 |
| WO | WO 98/43969 | 10/1998 |
| WO | WO 99/53927 | 10/1999 |
| WO | WO 01/12621 A1 | 2/2001 |
| WO | WO 02/085396 | 10/2002 |

OTHER PUBLICATIONS

Boehm et al., Journal of Medicinal Chemistry (Jul. 13, 2000), 43(14), pp. 2664–2674.*
Kawakami et al., Organic Letters, (Feb. 10, 2000), 2(3), pp. 413–415.*
Patel et al., Bioorganic & Medicinal Chemistry Letters (Nov. 15, 1999), 9(22), pp. 3217–3220.*
Vasilevsky et al., CA 125 :114539, 1996.*
Andronati et al., CA 122:314528, 1995.*
Buck et al., CA 120:299030, 1994.*
Rickinger et al., CA 116:235509, 1992.*
Grayshan et al., CA 112:216936, 1990.*
Fujimura et al., CA 107:198159, 1987.*
Wrzeciono et al., CA 103:123405, 1985.*
Jones et al., CA 100:51503, 1984.*
Pfoertner et al., CA 97:72295, 1982.*
Arya et al., CA 88:37692, 1978.*
Fujimura et al., CA 84:31053, 1976.*
Walser et al., CA 83:164108, 1975.*
Horner et al., CA 70:77962, 1969.*
Aspenström et al., 1996, "Two GTPases, Cdc42 and Rac, bind directly to a protein implicated in the immunodeficiency disorder Wiskott–Aldrich syndrome", Curr. Biol. 6:70–75.
Chen et al., 1996, "Activation and inhibition of the AP–1 complex in human breast cancer cells", Mol. Carcinogenesis 15:215–226.
Dong et al., 1998, "Defective T cell differentiation in the absence of *Jnk1*", Science 282:2092–2095.
Faris et al.,. 1996, "Regulation of interleukin–2 transcription by inducible stabile expression of dominant negative and dominant active mitogen–activated protein kinase kinase kinase in Jurkat T cells", J. Biol. Chem. 271:27366–27373.
Gum et al., 1997, "Regulation of 92 kDa type IV collagenase expression by the *jun* aminoterminal kinase–and the extracellular signal–regulated kinase–dependent signaling cascades", Oncogene 14:1481–1493.

(Continued)

*Primary Examiner*—Laura L. Stockton
(74) *Attorney, Agent, or Firm*—Jones Day

(57) ABSTRACT

Compounds having activity as selective inhibitors of JNK are disclosed. The compounds of this invention are indazole derivatives having the following structure:

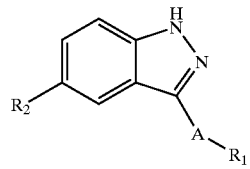

wherein $R_1$, $R_2$ and A are as defined herein. Such compounds have utility in the treatment of a wide range of conditions that are responsive to JNK inhibition. Thus, methods of treating such conditions are also disclosed, as are pharmaceutical compositions containing one or more compounds of the above compounds.

26 Claims, No Drawings

OTHER PUBLICATIONS

Han et al., 1999, "Jun N-terminal kinase in rheumatoid arthritis", J. Pharmacol. Exp. Therap. 291:124–130.

Hibi et al., 1993, "Identification of an oncoprotein-and UV-responsive protein kinase that binds and potentiates the c-Jun activation domain", Genes Dev. 7:2135–2148.

Ishizuka et al., 1997, "Mast cell tumor necrosis factor α production is regulated by MEK kinases", Proc. Natl. Acad. Sci. USA 94:6358–6363.

Karin et al., 1997, "AP-1 function and regulation", Curr. Opin. Cell. Biol. U9:240–246.

Lange–Carter et al., 1993, "A divergence in the MAP kinase regulatory network defined by MEK kinase and Raf", Science 260:315–319.

Li et al., 1996, "Blocked signal transduction to the ERK and JNK protein kinases in anergic $CD4^+$ T cells", Science 271:1272–1276.

Li et al., 1996, "The Ras–JNK pathway is involved in shear-induced gene expression", Mol. Cell. Biol. 16:5947–5954.

Lin et al., 1995, "Identification of a dual specificity kinase that activates the Jun kinases and p38–Mpk2", Science 268:286–290.

Manning and Mercurio, 1997, "Transcription inhibitors in inflammation", Exp. Opin. Invest. Drugs 6:555–567.

Milne et al., 1995, "p53 is phosphorylated in vitro and in vivo by an ultraviolet radiation–induced protein kinase characteristic of the c-Jun kinase, JNK1", J. Biol. Chem. 270:5511–5518.

Mohit et al., 1995, "$p49^{3F12}$ kinase: a novel MAP kinase expressed in a subset of neurons in the human nervous system", Neuron 14:67–78.

Nishina et al., 1997, "Impaired CD28–mediated interleukin 2 production and proliferation in stress kinase SAPK/ERK1 kinase (SEK1)/mitogen–activated protein kinase kinase 4 (MKK4)–deficient T lymphocytes", J. Exp. Med. 186:941–953.

Okamoto et al., 1997, "Selective activation of the JNK/AP-1 pathway in Fas–mediated apoptosis of rheumatoid arthritis synoviocytes", Arthritis & Rheumatism 40:919–926.

Pombo et al., 1994, "The stress–activated protein kinases are major c–Jun amino–terminal kinases activated by ischemia and reperfusion", J. Biol. Chem. 269:26546–26551.

Raitano et al., 1995, "The Bcr–Abl leukemia oncogene activates Jun kinase and requires Jun for transformation", Proc.Natl. Acad. Sci. USA 92:11746–11750.

Sabapathy et al., 1999, "JNK2 is required for efficient T–cell activation and apoptosis but not for normal lymphocyte development", Curr. Biol. 9:116–125.

Su et al., 1994, "JNK is involved in signal integration during costimulation of T lymphocytes", Cell 77:727–736.

Swantek et al., 1997, "Jun N–terminal kinase/stress–activated protein kinase (JNK/SAPK) is required for lipopolysaccharide stimulation of tumor necrosis factor alpha (TNF–α) translation: glucocorticoids inhibit TNF–α translation by blocking JNK/SAPK", Mol. Cell. Biol. 17:6274–6282.

Szabo et al., 1996, "Altered cJUN expression: an early event in human lung carcinogenesis", Cancer Res. 56:305–315.

Tournier et al., 1997, "Mitogen–activated protein kinase kinase 7 is an activator of the c–Jun $NH_2$–terminal kinase", Proc. Natl. Acad. Sci. USA 94:7337–7342.

Whitmarsh and Davis, 1996, "Transcription factor AP–1 regulation by mitogen–activated protein kinase signal transduction pathways", Mol. Med. 74:589–607.

Yan et al., 1994, "Activation of stress–activated protein kinase by MEKK1 phosphorylation of its activator SEK1", Nature 372:798–800.

Yang et al., 1998, "Differentiation of $CD4^+$ T cells to Th1 cell requires MAP kinase JNK2", Immunity 9:575–585.

Yin et al., 1997, "Tissue–specific pattern of stress kinase activation in ischemic/reperfused heart and kidney", J. Biol. Chem. 272:19943–19950.

Spiegelman et al., "Regulation of Adipocyte Gene Expression in Differentiation and Syndromes of Obesity/Diabetes", J. of Biol. Chem. 268:6823–6826 (1993).

Hirosumi et al., "A central role for JNK in obesity and insulin resistance", Letters to Nature 420:333–336 (2002).

* cited by examiner

INDAZOLE DERIVATIVES AS JNK INHIBITORS AND COMPOSITIONS AND METHODS RELATED THERETO

This application claims the benefit of U.S. Provisional Application No. 60/221,799, filed Jul. 31, 2000.

1. FIELD OF THE INVENTION

This invention is generally directed to indazole derivatives useful as Jun N-terminal kinase (JNK) inhibitors, compositions comprising the indazole derivatives and methods for their use.

2. BACKGROUND OF THE INVENTION

The Jun N-terminal kinase (JNK) pathway is activated by exposure of cells to environmental stress or by treatment of cells with pro-inflammatory cytokines. Targets of the JNK pathway include the transcription factors c-jun and ATF2 (Whitmarsh A. J., and Davis R. J. *J. Mol. Med.* 74:589–607, 1996). These transcription factors are members of the basic leucine zipper (bZIP) group that bind as homo- and heterodimeric complexes to AP-1 and AP-1-like sites in the promoters of many genes (Karin M., Liu Z. G. and Zandi E. *Curr. Opin. Cell Biol.* 9:240–246, 1997). JNK binds to the N-terminal region of c-jun and ATF-2 and phosphorylates two sites within the activation domain of each transcription factor (Hibi M., Lin A., Smeal T, Minden A., Karin M. *Genes Dev.* 7:2135–2148, 1993; Mohit A. A., Martin M. H., and Miller C. A. *Neuron* 14:67–75, 1995). Three JNK enzymes have been identified as products of distinct genes (Hibi et al, supra; Mohit et al., supra). Ten different isoforms of JNK have been identified. These represent alternatively spliced forms of three different genes: JNK1, JNK2 and JNK3. JNK1 and 2 are ubiquitously expressed in human tissues, whereas JNK3 is selectively expressed in the brain, heart and testis (Dong C., Yang D., Wysk M., Whitmarsh A., Davis R., Flavell R. *Science* 270:1–4, 1998). Gene transcripts are alternatively spliced to produce four-JNK1 isoforms, four-JNK2 isoforms and two-JNK3 isoforms. JNK1 and 2 are expressed widely in mammalian tissues, whereas JNK3 is expressed almost exclusively in the brain. Selectivity of JNK signaling is achieved via specific interactions of JNK pathway components and by use of scaffold proteins that selectively bind multiple components of the signaling cascade. JIP-1 (JNK-interacting protein-1) selectively binds the MAPK module, MLK→NKK2→JNK. It has no binding affinity for a variety of other MAPK cascade enzymes. Different scaffold proteins are likely to exist for other MAPK signaling cascades to preserve substrate specificity.

JNKs are activated by dual phosphorylation on Thr-183 and Tyr-185. JNKK1 (also known as MKK 4) and JNKK2 (MKK7), two MAPKK level enzymes, can mediate JNK activation in cells (Lin A., Minden A., Martinetto H., Claret F. -Z., Lange-Carter C., Mercurio F., Johnson G. L., and Karin M. *Science* 268:286–289, 1995; Toumier C., Whitmarsh A. J., Cavanagh J., Barrett T., and Davis R. J. *Proc. Nat. Acad. Sci. USA* 94:7337–7342, 1997). JNKK2 specifically phosphorylates JNK, whereas JNKK1 can also phosphorylate and activate p38. Both JNKK1 and JNKK2 are widely expressed in mammalian tissues. JNKK1 and JNKK2 are activated by the MAPKKK enzymes, MEKK1 and 2 (Lange-Carter C. A., Pleiman C. M., Gardner A. M., Blumer K. J., and Johnson G. L. *Science* 260:315–319, 1993; Yan M., Dai J. C., Deak J. C., Kyriakis J. M., Zon L. I., Woodgett J. R., and Templeton D. J. *Nature* 372:798–781, 1994). Both MEKK1 and MEKK2 are widely expressed in mammalian tissues.

Activation of the JNK pathway has been documented in a number of disease settings, providing the rationale for targeting this pathway for drug discovery. In addition, molecular genetic approaches have validated the pathogenic role of this pathway in several diseases. For example, autoimmune and inflammatory diseases arise from the overactivation of the immune system. Activated immune cells express many genes encoding inflammatory molecules, including cytokines, growth factors, cell surface receptors, cell adhesion molecules and degradative enzymes. Many of these genes are regulated by the JNK pathway, through activation of the transcription factors AP-1 and ATF-2, including TNFα, IL-2, E-selectin and matrix metalloproteinases such as collagenase-1 (Manning A.M. and Mercurio F. *Exp. Opin Invest. Drugs* 6: 555–567, 1997). Monocytes, tissue macrophages and tissue mast cells are key sources of TNFα production. The JNK pathway regulates TNFα production in bacterial lipopolysaccharide-stimulated macrophages, and in mast cells stimulated through the FceRII receptor (Swantek J. L., Cobb M. H., Geppert T. D. *Mol. Cell. Biol.* 17:6274–6282, 1997; Ishizuka T., Tereda N., Gerwins P., Hamelmann E., Oshiba A., Fanger G. R., Johnson G. L., and Gelfland E. W. *Proc. Nat. Acad. Sci. USA* 94:6358–6363, 1997). Inhibition of JNK activation effectively modulates TNFα secretion from these cells. The JNK pathway therefore regulates production of this key pro-inflammatory cytokine. Matrix metalloproteinases (MMPs) promote cartilage and bone erosion in rheumatoid arthritis, and generalized tissue destruction in other autoimmune diseases. Inducible expression of MMPs, including MMP-3 and MMP-9, type II and IV collagenases, are regulated via activation of the JNK pathway and AP-1 (Gum R., Wang H., Lengyel E., Juarez J., and Boyd D). *Oncogene* 14:1481–1493, 1997). In human rheumatoid synoviocytes activated with TNFα, IL-1, or Fas ligand the JNK pathway is activated (Han Z., Boyle D. L., Aupperle K. R., Bennett B., Manning A. M., Firestein G. S. *J. Pharm. Exp. Therap.* 291:1–7, 1999; Okamoto K., Fujisawa K., Hasunuma T., Kobata T., Sumida T., and Nishioka K. *Arth & Rheum* 40: 919–26, 1997). Inhibition of JNK activation results in decreased AP-1 activation and collagenase-1 expression (Han et al., supra). The JNK pathway therefore regulates MMP expression in cells involved in rheumatoid arthritis.

Inappropriate activation of T lymphocytes initiates and perpetuates many autoimmune diseases, including asthma, inflammatory bowel disease and multiple sclerosis. The JNK pathway is activated in T cells by antigen stimulation and CD28 receptor co-stimulation and regulates production of the growth factor IL-2 and cellular proliferation (Su B., Jacinto E., Hibi M., Kallunki T., Karin M., Ben-Neriah Y. *Cell* 77:727–736, 1994; Faris M., Kokot N., Lee L., and Nel A. E. *J. Biol. Chem.* 271:27366–27373, 1996). Peripheral T cells from mice genetically deficient in JNKK1 show decreased proliferation and IL-2 production after CD28 co-stimulation and PMA/Ca2+ ionophore activation, providing important validation for the role of the JNK pathway in these cells (Nishina H., Bachmann M., Oliveria-dos-Santos A. J., et al. *J. Exp. Med.* 186: 941–953, 1997). It is known that T cells activated by antigen receptor stimulation in the absence of accessory cell-derived co-stimulatory signals lose the capacity to synthesize IL-2, a state called clonal anergy. This is an important process by which auto-Reactive T cell populations are eliminated from the peripheral circulation. Of note, anergic T cells fail to activate the JNK pathway in response to CD3- and CD28-Receptor co-stimulation, even though expression of the JNK enzymes is unchanged (Li W., Whaley C. D., Mondino A., and Mueller D. L. *Science* 271: 1272–1276, 1996). Recently, the examination of JNK-deficient mice revealed that the JNK pathway plays a key role in T cell activation and differentiation to T helper 1 and 2 cell types. JNK1 or JNK2 knockout mice develop normally and are phenotypically unremarkable. Activated naïve CD4+ T cells from these mice fail to produce IL-2 and do not proliferate well (Sabapathy, K, Hu, Y, Kallunki, T, Schreiber, M, David, J-P, Jochum, W, Wagner, E, Karin, M. *Curr Biol* 9:116–125, 1999). It is possible to induce T cell differentiation in T cells from these mice, generating Th1 cells (producers of IFN-g and TNFβ) and Th2 effector cells (producers of IL-4, IL-5, IL-6, IL-10 and IL-13). Deletion of either JNK1 or JNK2 in mice resulted in a selective defect in the ability of Th1 effector cells to express IFNg. This suggests that JNK1 and JNK2 do not have redundant functions in T cells and that they play different roles in the control of cell growth, differentiation and death. The JNK pathway therefore, is an important point for regulation of T cell responses to antigen.

Cardiovascular disease ("CVD") accounts for nearly one quarter of total annual deaths worldwide. Vascular disorders such as atherosclerosis and restenosis result from dysregulated growth of the vessel wall, restricting blood flow to vital organs. The JNK pathway is activated by atherogenic stimuli and regulates local cytokine and growth factor production in vascular cells (Yang D D, Conze D, Whitmarsh A J, et al, *Immunity*, 9:575, 1998). In addition, alterations in blood flow, hemodynamic forces and blood volume lead to JNK activation in vascular endothelium, leading to AP-1 activation and pro-atherosclerotic gene expression (Aspenstrom P., Lindberg U., and Hall A. *Curr. Biol.* 6:70–77, 1996). Ischemia and ischemia coupled with reperfusion in the heart, kidney or brain result in cell death and scar formation, which can ultimately lead to congestive heart failure, renal failure or cerebral dysfunction. In organ transplantation, reperfusion of previously ischemic donor organs results in acute leukocyte-mediated tissue injury and delay of graft function. The JNK pathway is activated by ischemia and reperfusion (Li Y., Shyy J., Li S., Lee J., Su B., Karin M., Chien S *Mol. Cell. Biol.* 16:5947–5954, 1996), leading to the activation of JNK-Responsive genes and leukocyte-mediated tissue damage. In a number of different settings JNK activation can be either pro- or anti-apoptotic. JNK activation is correlated with enhanced apoptosis in cardiac tissues following ischemia and reperfusion (Pombo C M, Bonventre J V, Avruch J, Woodgett J R, Kyriakis J. M, Force T. *J. Biol. Chem.* 269:26546–26551, 1994).

Cancer is characterized by uncontrolled growth, proliferation and migration of cells. Cancer is the second leading cause of death with 500,000 deaths and an estimated 1.3 million new cases in the United States in 1996. The role of signal transduction pathways contributing to cell transformation and cancer is a generally accepted concept. The JNK pathway leading to AP-1 appears to play a critical role in cancer. Expression of c-jun is altered in early lung cancer and may mediate growth factor signaling in non-small cell lung cancer (Yin T., Sandhu G., Wolfgang C. D., Burrier A., Webb R. L., Rigel D. F. Hai T., and Whelan J. *J. Biol. Chem.* 272:19943–19950, 1997). Indeed, over-expression of c-jun in cells results in transformation, and blocking c-jun activity inhibits MCF-7 colony formation (Szabo E., Riffe M., Steinberg S. M., Birrer M. J., Linnoila R. I. *Cancer Res.* 56:305–315, 1996). DNA-damaging agents, ionizing radiation and tumor necrosis factor activate the JNK pathway. In addition to regulating c-jun production and activity, JNK activation can regulate phosphorylation of p53, and thus can modulate cell cycle progression (Chen T. K., Smith L. M., Gebhardt D. K., Birrer M. J., Brown P. H. *Mol. Carcinogenesis* 15:215–226, 1996). The oncogene BCR-Ab1, associated with t(9,22) Philadelphia chromosome translocation of chronic myelogenous leukemia, activates JNK and leads to transformation of hematopoietic cells (Milne D. M., Campbell L. E., Campbell D. G., Meek D. W. *J. Biol. Chem.* 270:5511–5518, 1995). Selective inhibition of JNK activation by a naturally occurring JNK inhibitory protein, called JIP-1, blocks cellular transformation caused by BCR-Ab1 expression (Raitano A. B., Halpern J. R., Hambuch T. M., Sawyers C. L. *Proc. Nat. Acad. Sci USA* 92:11746–11750, 1995). Thus, JNK inhibitors may block transformation and tumor cell growth.

In general, the class of compounds known as "indazoles" is well known. More specifically, an "indazole" is a compound containing a fused, bicyclic ring system having the following structure:

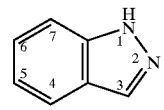

Compounds of the above structure are typically referred to as "1H-indazole" due to the presence of the hydrogen atom at the 1-position.

EP Patent Application 0 494 774 A1 discloses compounds of the following structure:

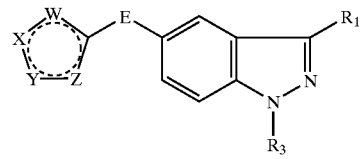

for use as agonists of the 5-hydroxytryptamine (5-HT) receptors. Such receptors exhibit selective vasoconstrictor activity, and the agonists of this published application are purported to have utility in the treatment of migraine, cluster headache, chronic paraxysmal hemicrania and headaches associated with vascular disorders. 1H-indazoles have also been made for synthetic and mechanistic studies, and as intermediates in the synthesis of other potential therapeutics. For example, the following references disclose 3-phenyl-5-methyl-1H-indazole: *Pharmazie* 54(2):99–101, 1999; *Dopov. Akad. Nauk Ukr.* 8:126–31, 1994; *Pokl. Akad. Nauk SSSR* 305(6):1378–81, 1989; *Yakugaku Zasshi* 106(J1):1002–7, 1986 (also reports 5-Ph-3-CHO derivative); *Yakugaku Zasshi* 106(11):995–1001, 1986; *Heterocycles* 24(10):2771–5, 1986; JP 60/004184; JP 60/004185; EP 23633; *J. Org. Chem.* 43(10):2037–41, 1978 (also reports 3-(4-Me-Ph)-5-Me derivative); JP 60/004824; JP 59/036627; U.S. Pat. No. 3,994,890; JP 58/030313; JP 60/003063. Additional 3-phenyl indazoles with the indicated 5-substituents are disclosed in the following references: EP 55450 (CHO); U.S. Pat. No. 5,760,028 and WO 97/23480 (CO$_2$Et; also disclose 3-C≡CPh-5-CO$_2$Et derivative); DE 1266763 and *Justus Liebigs Ann. Chem.* 697:17–41, 1966 (OMe). EP 470039 discloses the 3-(4-fluorophenyl)-5-trifluoromethyl indazole, and *Heterocycles* (36(11):2489–95, 1993) discloses the 3-(6,7-dimethoxyisoquinolin-1-yl)-5-hydroxy derivative.

Accordingly, there is a need in the art for selective inhibitors of JNK. In addition, there is a need for pharmaceutical compositions comprising one or more inhibitors, as well as for methods for treating conditions in animals which are responsive to such inhibitors. The present invention fulfills these needs, and provides further related advantages.

3. SUMMARY OF THE INVENTION

In brief, the present invention is directed to novel compounds having activity as selective inhibitors of JNK, and to compositions and methods related thereto. The novel compounds of the present invention may generally be classified as "indazole derivatives" having the following structure (I):

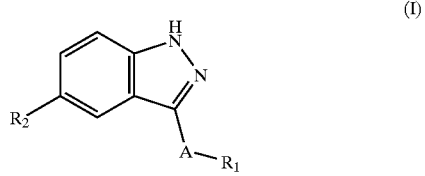

wherein A, $R_1$ and $R_2$ are as defined below, including isomers, prodrugs and pharmaceutically acceptable salts thereof.

The present invention is also directed to methods for treating a variety of conditions by administering an effective amount of a compound of structure (I) to an animal or subject in need thereof (referred to herein as a "patient"), typically a warm-blooded animal (including a human). Prior to administration, one or more compounds of this invention are typically formulated as a pharmaceutical composition which contains an effective dosage amount of one or more of such compounds in combination with one (or more) pharmaceutically acceptable carrier(s). Conditions that may be treated by the compounds of this invention, or a pharmaceutical composition containing the same, include any condition which may benefit from administration of JNK inhibitors, and are particularly useful for the prevention and/or treatment of various diseases including (but not limited to) rheumatoid arthritis; rheumatoid spondylitis; osteoarthritis; gout; asthma, bronchitis; allergic rhinitis; chronic obstructive pulmonary disease; cystic fibrosis; inflammatory bowel disease; irritable bowel syndrome; mucous colitis; ulcerative colitis; Crohn's disease; Huntington's disease; gastritis; esophagitis; hepatitis; pancreatitis; nepluitis; multiple sclerosis; lupus erythematosus; Type II diabetes; atherosclerosis; restenosis following angioplasty; left ventricular hypertrophy; myocardial infarction; stroke; ischemic damages of heart, lung, gut, kidney, liver, pancreas, spleen and brain; acute or chronic organ transplant rejection; preservation of the organ for transplantation; graft versus host disease; endotoxin shock; multiple organ failure; psoriasis; burn from exposure to fire, chemicals or radiation; eczema; dermatitis; skin graft; ischemia; ischemic conditions associated with surgery or traumatic injury; epilepsy; Alzheimer's disease; Parkinson's disease; immunological response to bacterial or viral infection; cachexia; angiogenic and proliferative dieseases; solid tumor; and cancers of a variety of tissues such as colon, rectum, prostate, liver, lung, bronchus, pancreas, brain, head, neck, stomach, skin, kidney, cervix, blood, larynx, esophagus, mouth, pharynx, urinary bladder, ovary or uterine.

The compounds described herein could also be useful as an adjunct to existing and/or experimental therapies.

These and other aspects of this invention will be evident upon reference to the following detailed description. To that end, certain patent and other documents are cited herein to more specifically set forth various aspects of this invention.

Each of these documents are hereby incorporated by reference in their entirety.

4. DETAILED DESCRIPTION OF THE INVENTION

As mentioned above, the present invention is directed to novel compounds which have activity as selective inhibitors of JNK. This invention is also directed to compositions and methods relating to the same.

The compounds of this invention have the following structure (I):

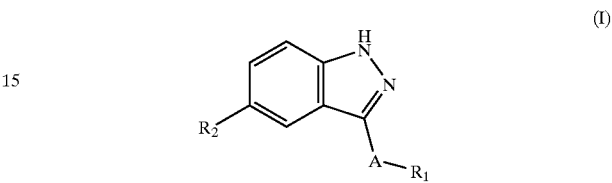

including isomers, prodrugs and pharmaceutically acceptable salts thereof,
wherein:
A is a direct bond, $—(CH_2)_a—$, $—(CH_2)_bCH=CH(CH_2)_c—$, or $—(CH_2)_bC≡C(CH_2)_c—$;
$R_1$ is aryl, heteroaryl or heterocycle fused to phenyl, each being optionally substituted with one to four substituents independently selected from $R_3$;
$R_2$ is $—R_3$, $—R_4$, $—(CH_2)_bC(=O)R_5$, $—(CH_2)_bC(=O)OR_5$, $—(CH_2)_bC(=O)NR_5R_6$, $—(CH_2)_bC(=O)NR_5(CH_2)_cC(=O)R_6$, $—(CH_2)_bNR_5C(=O)R_6$, $—(CH_2)_bNR_5C(=O)NR_6R_7$, $—(CH_2)_bNR_5R_6$, $—(CH_2)_bOR_5$, $—(CH_2)_bSO_dR_5$ or $—(CH_2)_bSO_2NR_5R_6$;
a is 1, 2, 3, 4, 5 or 6;
b and c are the same or different and at each occurrence independently selected from 0, 1, 2, 3 or 4;
d is at each occurrence 0, 1 or 2;
$R_3$ is at each occurrence independently halogen, hydroxy, carboxy, alkyl, alkoxy, haloalkyl, acyloxy, thioalkyl, sulfinylalkyl, sulfonylalkyl, hydroxyalkyl, aryl, substituted aryl, arylalkyl, substituted arylalkyl, heterocycle, substituted heterocycle, heterocycloalkyl, substituted heterocyclealkyl, $—C(=O)OR_8$, $—OC(=O)R_8$, $—C(=O)NR_8R_9$, $—C(=O)NR_8OR_9$, $—SO_2NR_8R_9$, $—NR_8SO_2R_9$, $—CN$, $—NO_2$, $—NR_8R_9$, $—NR_8C(=O)R_9$, $—NR_8C(=O)(CH_2)_bOR_9$, $—NR_8C(=O)(CH_2)_bR_9$, $—O(CH_2)_bNR_8R_9$, or heterocycle fused to phenyl;
$R_4$ is alkyl, aryl, arylalkyl, heterocycle or heterocycloalkyl, each being optionally substituted with one to four substituents independently selected from $R_3$, or $R_4$ is halogen or hydroxy;
$R_5$, $R_6$ and $R_7$ are the same or different and at each occurrence independently hydrogen, alkyl, aryl, arylalkyl, heterocycle or heterocycloalkyl, wherein each of $R_5$, $R_6$ and $R_7$ are optionally substituted with one to four substituents independently selected from $R_3$; and
$R_8$ and $R_9$ are the same or different and at each occurrence independently hydrogen, alkyl, aryl, arylalkyl, heterocycle, or heterocycloalkyl, or $R_8$ and $R_9$ taken together with the atom or atoms to which they are bonded form a heterocycle, wherein each of $R_8$, $R_9$, and $R_8$ and $R_9$ taken together to form a heterocycle are optionally substituted with one to four substituents independently selected from $R_3$;
with the proviso that:
when A is a direct bond and $R_1$ is phenyl, $R_2$ is not methyl, methoxy, C(=O)CH$_3$ or C(=O)H;

when A is a direct bond and $R_1$ is 4-Me-phenyl,
$R_2$ is not methyl;

when A is a direct bond and $R_1$ is 4-F-phenyl,
$R_2$ is not trifluoromethyl;

when A is a direct bond or —C≡C— and $R_1$ is phenyl,
$R_2$ is not —COOEt; and when A is a direct bond and $R_1$ is 6,7-dimethoxyisoquinolin-1-yl,
$R_2$ is not hydroxy.

In one embodiment, -A-$R_1$ is phenyl, optionally substituted with one to four substituents independently selected from halogen, alkoxy, —NR$_8$C(=O)R$_9$, —C(=O)NR$_8$R$_9$, and —O(CH$_2$)$_b$NR$_8$R, wherein b is 2 or 3 and wherein R$_8$ and R$_9$ are defined above.

In another embodiment, $R_2$ is —R$_4$, —(CH$_2$)$_b$C(=O)R$_5$, —(CH$_2$)$_b$C(=O)OR$_5$, —(CH$_2$)$_b$C(=O)NR$_5$R$_6$, —(CH$_2$)$_b$C(=O)NR$_5$(CH$_2$)$_c$C(=O)R$_6$, —(CH$_2$)$_b$NR$_5$C(=O)R$_6$, —(CH$_2$)$_b$NR$_5$C(=O)NR$_6$R$_7$, —(CH$_2$)$_b$NR$_5$R$_6$, —(CH$_2$)$_b$OR$_5$, —(CH$_2$)$_b$SO$_d$R$_5$ or —(CH$_2$)$_b$SO$_2$NR$_5$R$_6$, In another embodiment, $R_2$ is —(CH$_2$)$_b$C(=O)NR$_5$R$_6$, —(CH$_2$)$_b$NR$_5$C(=O)R$_6$, 3-triazolyl or 5-tetrazolyl, wherein b is 0 and wherein R$_8$ and R$_9$ are defined above.

In a preferred embodiment, $R_2$ is 3-triazolyl or 5-tetrazolyl.

In another preferred embodiment:
(a) -A-$R_1$ is phenyl, optionally substituted with one to four substituents independently selected from halogen, alkoxy, —NR$_8$C(=O)R$_9$, —C(=O)NR$_8$R$_9$, and —O(CH$_2$)$_b$NR$_8$R$_9$, wherein b is 2 or 3; and
(b) $R_2$ is —(CH$_2$)$_b$C(=O)NR$_5$R$_6$, —(CH$_2$)$_b$NR$_5$C(=O)R$_6$, 3-triazolyl or 5-tetrazolyl, wherein b is 0 and wherein R$_8$ and R$_9$ are defined above.

In a more preferred embodiment:
(a) -A-$R_1$ is phenyl, optionally substituted with one to four substituents independently selected from halogen, alkoxy, —NR$_8$C(=O)R$_9$, —C(=O)NR$_8$R$_9$, and —O(CH$_2$)$_b$NR$_8$R$_9$, wherein b is 2 or 3; and
(b) $R_2$ is 3-triazolyl or 5-tetrazolyl.

In another preferred embodiment, $R_2$ is $R_4$, and $R_4$ is 3-triazolyl, optionally substituted at its 5-position with:
(a) a $C_1$–$C_4$ straight or branched chain alkyl group optionally substituted with a hydroxyl, methylamino, dimethylamino or 1-pyrrolidinyl group; or
(b) a 2-pyrrolidinyl group.

In a more preferred embodiment, $R_2$ is $R_4$, and $R_4$ is methyl, n-propyl, isopropyl, 1-hydroxyethyl, 3-hydroxypropyl, methylaminomethyl, dimethylaminomethyl, 1-(dimethylamino)ethyl, 1-pyrrolidinylmethyl or 2-pyrrolidinyl.

As used herein, the terms used above having following meaning.

"Alkyl" means a straight chain or branched, saturated or unsaturated alkyl, cyclic or non-cyclic hydrocarbon having from 1 to 10 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Unsaturated alkyls contain at least one double or triple bond between adjacent carbon atoms (also referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-i-butenyl, 2-methyl-2-butenyl, 2,3-dimethyl 2-butenyl, and the like; while representative straight chain and branched alkynyls include acetylenyl, propynyl, 1-butynyl, 2-butynyl, 1-pentynyl, 2-pentynyl, 3-methyl-1 butynyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Cycloalkyls are also referred to herein as "carbocyclic" rings systems, and include bi- and tri-cyclic ring systems having from 8 to 14 carbon atoms such as a cycloalkyl (such as cyclopentane or cyclohexane) fused to one or more aromatic (such as phenyl) or non-aromatic (such as cyclohexane) carbocyclic rings.

"Halogen" means fluorine, chlorine, bromine or iodine.

"Keto" means a carbonyl group (i.e., C=O).

"Aryl" means an aromatic carbocyclic moiety such as phenyl or naphthyl.

"Acyloxy" means an —OC(O)alkyl group, wherein "alkyl" is defined above.

"Arylalkyl" means an alkyl having at least one alkyl hydrogen atom replaced with an aryl moiety, such as benzyl, —(CH$_2$)$_2$ phenyl, —(CH$_2$)$_3$ phenyl, —CH(phenyl)$_2$, and the like.

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, and quinazolinyl.

"Heteroarylalkyl" means an alkyl having at least one alkyl hydrogen atom replaced with a heteroaryl moiety, such as —CH$_2$ pyridinyl, —CH$_2$ pyrimidinyl, and the like.

"Heterocycle" means a heterocyclic ring containing from 5 to 10 ring atoms

"Heterocycle" means a 5- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined above. Thus, in addition to the heteroaryls listed above, heterocycles also include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Heterocycloalkyl" means an alkyl having at least one alkyl hydrogen atom replaced with a heterocycle, such as —CH$_2$ morpholinyl, and the like.

The term "substituted" as used herein means any of the above groups (i.e., aryl, arylalkyl, heterocycle and heterocycloalkyl) wherein at least one hydrogen atom is replaced with a substituent. In the case of a keto substituent, two hydrogen atoms are replaced. Substituents include halogen, hydroxyl, alkyl, substituted alkyl (such as haloalkyl, mono- or di-substituted aminoalkyl, alkyloxyalkyl, and the like), aryl, substituted aryl, arylalkyl, substituted arylalkyl, heterocycle, substituted heterocycle, heterocycloalkyl, substituted heterocycloalkyl, —NR$_a$R$_b$, —$NR_aC(=O)R_b$, —$NR_aC(=O)NR_aR_b$, —$NR_aC(=O)OR_b$ —$NR_aSO_2R_b$, —$OR_a$, —$C(=O)R_a$ $C(=O)OR_a$, —$C(=O)NR_aR_b$, —$OC(=O)R_a$, —$OC(=O)OR_a$, —$OC(=O)NR_aR_b$, —$NR_aSO_2R_b$, or a radical of the formula —Y-Z-$R_a$ where Y is alkanediyl, substituted alkanediyl, or a direct bond, Z is —O—, —S—, —$N(R_b)$—, —$C(=O)$—, —$C(=O)O$—, —$OC(=O)$—, —$N(R_b)C(=O)$—, —$C(=O)N(R_b)$— or a direct bond, wherein $R_a$ and $R_b$ are the same or different and independently hydrogen, amino, alkyl, substituted alkyl (including halogenated alkyl), aryl, substituted aryl, arylalkyl, substituted arylalkyl, heterocycle, substituted heterocycle, heterocylealkyl or substituted heterocycloalkyl, or wherein $R_a$ and $R_b$ taken together with the nitrogen atom to which they are attached form a heterocycle or substituted heterocycle.

"Haloalkyl" means alkyl having one or more hydrogen atoms replaced with halogen, such as —$CF_3$.

"Hydroxyalkyl" means alkyl having one or more hydrogen atoms replaced with hydroxy, such as —$CH_2OH$.

"Sulfonylalkyl" means —$SO_2$-(alkyl), wherein "alkyl" is defined above;

"Sulfinylalkyl" means —SO-(alkyl), wherein "alkyl" is defined above;

"Thioalky" means —S-(alkyl), wherein "alkyl" is defined above;

"Carboxyl" means —COOH.

"Alkoxy" means —O-(alkyl), wherein "alkyl" is defined above.

In one embodiment, compounds of this invention have structure (II) when A is a direct bond, and have structure (III) when A is —$(CH_2)_a$—:

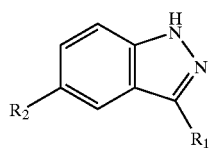

(II)

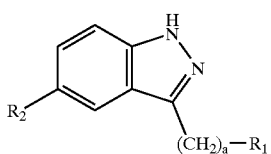

(III)

In other embodiments, compounds of this invention have structure (IV) when A is a —$(CH_2)_bCH=CH(CH_2)_c$—, and have structure (V) when A is —$(CH_2)_bC\equiv C(CH_2)_c$—;

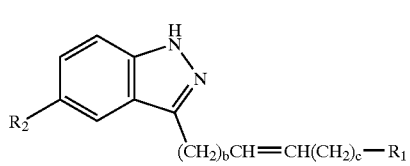

(IV)

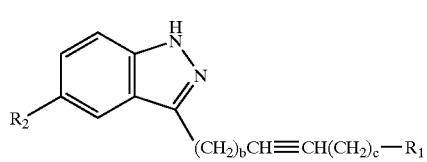

(V)

In further embodiments of this invention, $R_1$ is aryl or substituted aryl, such as phenyl or substituted phenyl as represented by the following structure (VI):

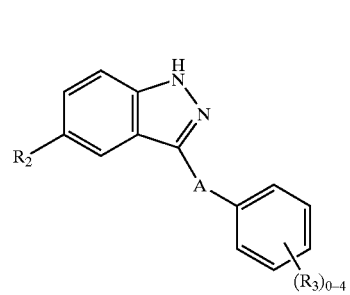

(VI)

In another embodiment, $R_2$ is —$(CH_2)_bNR_4(C=O)R_5$. In one aspect of this embodiment, b=0 and compounds of this invention have the following structure (VII):

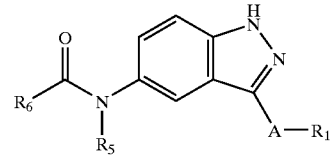

(VII)

Representative $R_2$ groups of this invention include alkyl (such as methyl and ethyl), halo (such as chloro and fluoro), haloalkyl (such as trifluoromethyl), hydroxy, alkoxy (such as methoxy and ethoxy), amino, arylalkyloxy (such as benzyloxy), mono- or di-alkylamine (such as —$NHCH_3$, —$N(CH_3)_2$ and —$NHCH_2CH_3$), —$NHC(=O)R_4$ wherein $R_6$ is a substitute or unsubstituted phenyl or heteroaryl (such as phenyl or heteroaryl substituted with hydroxy, carboxy, amino, alkylester, alkoxy, alkyl, aryl, haloalkyl, halo, —$CONH_2$ and —CONH alkyl), —NH(heteroarylalkyl) (such as —$NHCH_2$(3-pyridyl), —$NHCH_2$(4-pyridyl), heteroaryl (such as pyrazolo, triazolo and tetrazolo), —$C(=O)NHR_6$ wherein $R_6$ is hydrogen, alkyl, or as defined above (such as —$C(=O)NH_2$, —$C(=O)NHCH_3$, —$C(=O)NH$(H-carboxyphenyl), —$C(=O)N(CH_3)_2$), arylalkenyl (such as phenylvinyl, 3-nitrophenylvinyl, 4-carboxyphenylvinyl), heteroarylalkenyl (such as 2-pyridylvinyl, 4-pyridylvinyl).

Representative $R_3$ groups include halogen (such as chloro and fluoro), alkyl (such as methyl, ethyl and isopropyl), haloalkyl (such as trifluoromethyl), hydroxy, alkoxy (such as methoxy, ethoxy, n-propyloxy and isobutyloxy), amino, mono- or di-alkylamino (such as dimethylamine), aryl (such as phenyl), carboxy, nitro, cyano, sulfinylalkyl (such as methylsulfinyl), sulfonylalkyl (such as methylsulfonyl), sulfonamidoalkyl (such as —$NHSO_2CH_3$), —$NR_8C(=O)(CH_2)_bOR_9$ (such as —$NHC(=O)CH_2OCH_3$), $NHC(=O)R_9$ (such as —$NHC(=O)CH_3$, —$NHC(=O)CH_2C_6H_5$, —$NHC(=O)$(2-furanyl)), and —$O(CH_2)_bNR_8R_9$ (such as —$O(CH_2)_2N(CH_3)_2$).

The compounds of this invention may generally be made by organic synthesis techniques known to those skilled in the art, as well as by the following general techniques and by the procedures set forth in the Examples. To that end, the compounds of this invention may be made according to the following Reaction Schemes 1 through 7 (it should be noted that, in the following reaction schemes, hydrogen atoms are sometimes not depicted and one skilled in organic chemistry would appreciate such accepted shorthand notation):

Reaction Scheme 1

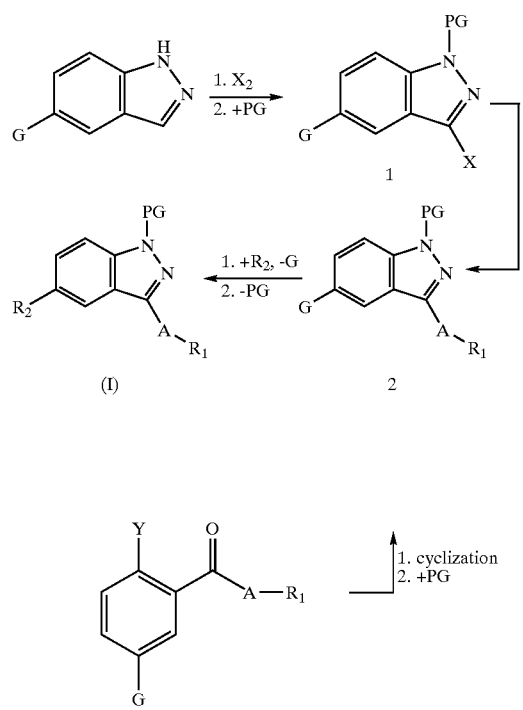

In Reaction Scheme 1, indazoles of this invention may be prepared by techniques well known to those skilled in the art of organic synthesis. Starting from an appropriately 5-substituted indazole, the 3-position may be activated for substitution by use of a suitable dihalogen ($X_2$). If necessary, a protecting group is then added to the nitrogen at the 1-position (N-1) to give 1. The halogen may be displaced by an appropriately activated A-$R_1$ moiety to give 2; see, e.g., Reaction Schemes 2 and 5. Alternatively, an appropriately substituted phenyl ketone may be cyclized to give indazole 2 see, e.g., Reaction Schemes 3 and 4. The G moiety may then be left unchanged, displaced or transformed into the desired $R_2$; see, e.g., Reaction Schemes 3 through 6. Deprotection of N-1 gives indazoles of structure (I).

Reaction Scheme 2

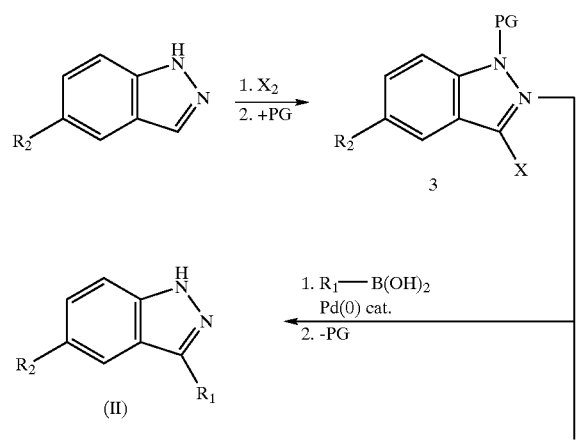

Reaction Scheme 2 illustrates synthetic sequences that yield compounds containing various A moieties. Suitable starting materials are commercially available indazoles with the desired $R_2$ or may be readily prepared, e.g., as in Reaction Schemes 5 and 6. The starting indazole is halogenated at the 3-position with a suitable reagent, e.g., $Br_2$. It is then protected at N-1 with any suitable nitrogen protecting group to give 3. Suitable protecting groups include but are not limited to acetyl, methoxyethoxymethyl and tetrahydropyranyl. Indazoles, wherein A is a direct bond, may be produced from 3 by displacement of the halogen with an appropriately activated $R_1$ moiety. For example, in the presence of a suitable Pd(0) or Pd(II) catalyst, $R_1$-boronic acids may be coupled via a Suzuki reaction to give, after deprotection, compound (II). Analogously, compounds (IV) and (V) may be prepared from suitable alkene and alkyne precursors in the presence of an appropriate Pd(0) catalyst. The cis isomer of indazole (IV) may also be prepared by partial reduction of (V) by, e.g., hydrogenation over $BaSO_4$ that has been treated with quinoline. Compound (III) may be prepared from (IV) via reduction, e.g., with hydrogen in the presence of Pd—C.

Reaction Scheme 3

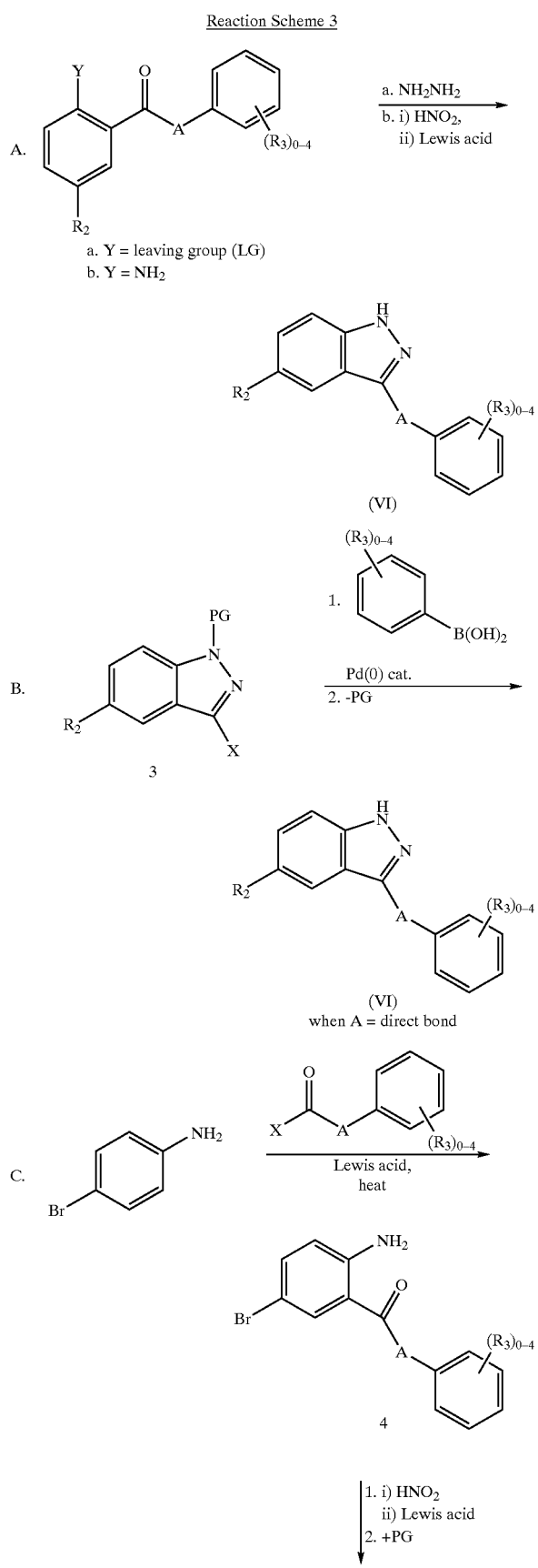

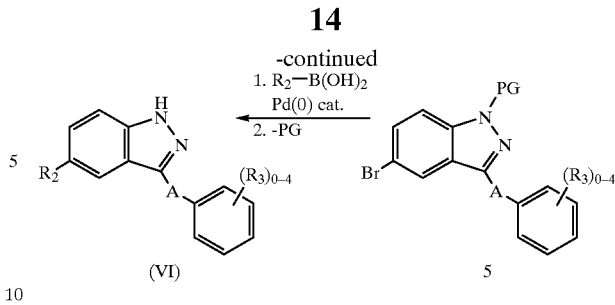

Reaction Scheme 3 illustrates several syntheses of compound (VI) wherein $R_1$ is depicted as a substituted phenyl group for purposes of illustration only. In Scheme 3A, a phenyl ketone, appropriately substituted at Y and $R_2$, serves as the starting material. When Y is an amino group, the starting material may be cyclized by exposure, first to $HNO_2$ and then to a reducing agent, such as $SnCl_2$, to give compound (VI). Alternatively, when Y is a leaving group such as halogen (e.g., F or Cl), heating the phenyl ketone in the presence of hydrazine effects cyclization to indazole (VI).

In Scheme 3B, halogenated indazole 3 may be coupled with a suitable substituted phenyl moiety and deprotected to give compound (VI), wherein A is a direct bond. By way of example, a phenyl boronic acid substituted with 0–4 $R_3$ groups will react with a protected 3-bromo-1H-indazole in the presence of a Pd(II) catalyst to yield compound (VI).

Scheme 3C illustrates an alternative synthesis of compound (VI) from the 5-halo-phenyl ketone; this route allows introduction of $R_2$ groups later in the sequence. 4-Bromo-aniline is acylated with a suitably activated A-$R_1$ moiety, heated in the presence of an appropriate Lewis acid such as $ZnCl_2$. For example, a suitably activated A-$R_1$ group is an acid halide such as carbonyl chloride. The resulting ketone 4 is cyclized as in Scheme 3A, and protected with appropriate groups at the N-1 position as in Scheme 2. The $R_2$ group may be introduced via a Pd-catalyzed coupling as in Scheme 2, and the protecting group removed to yield compound (VI).

Reaction Scheme 4

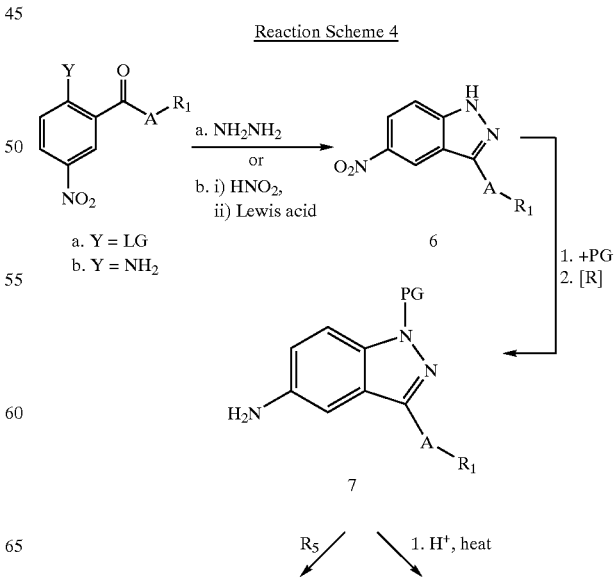

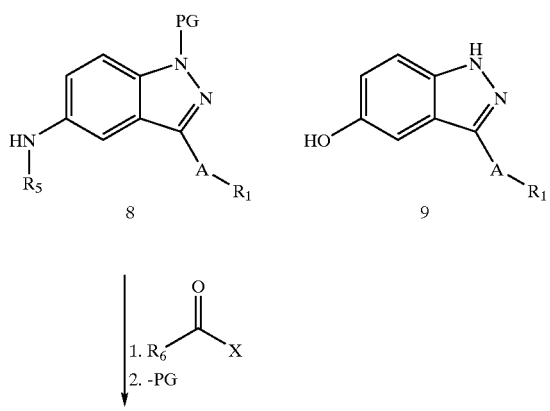

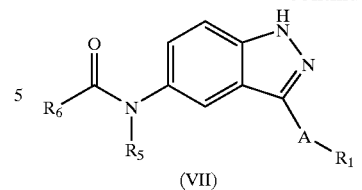

The synthesis of the embodiment wherein $R_2$ is an amino carbonyl-containing group is shown by Reaction Scheme 4. In analogy to Scheme 3A, a suitably substituted 4-nitrophenyl ketone may be cyclized, depending on Y, by exposure either to hydrazine or to $HNO_2$ and a reducing agent. After protection of N-1, the nitro-group may be reduced by, e.g., hydrogenation over Pd—C, to give 7. The resulting amine may optionally be substituted with $R_4$, by, e.g., reductive amination, using procedures well known to one skilled in the art of organic synthesis. Compound 8 is acylated with a suitable activated carbonyl moiety and deprotected to give compound (VII). Alternatively, 7 may be hydrolyzed to the 5-hydroxy compound, 9.

Reaction Scheme 5

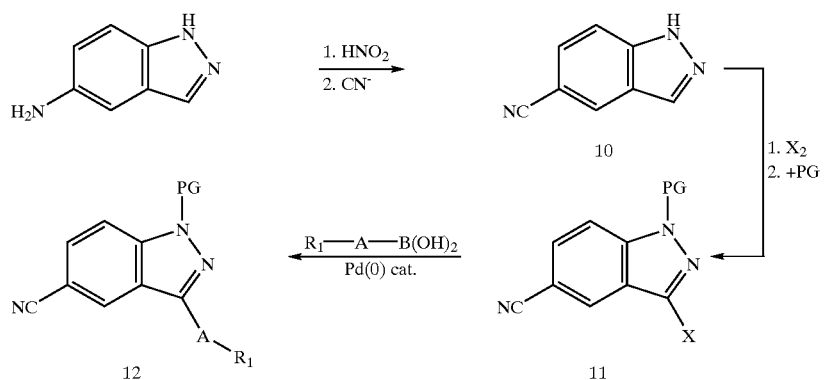

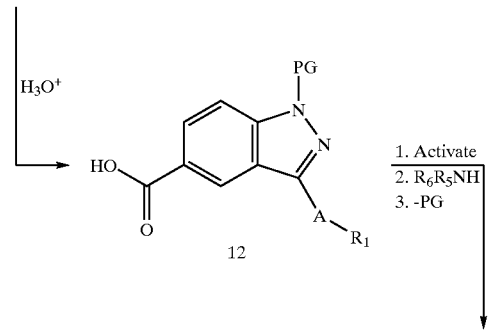

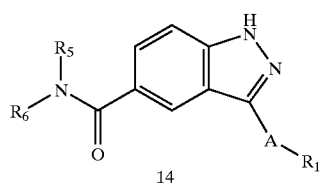

Reaction Scheme 5 illustrates a synthetic route for the further embodiment of (I) wherein $R_2$ is a carboxamide. Commercially available 5-amino-1H-indazole is substituted with cyanide at the 5-position to give 10 by treatment with $HNO_2$, followed, after neutralization to ca. pH 7, by treatment with a cyanide source, e.g., a mixture of CuCn and NaCN. Nitrile 10 may be activated at the 3-position, protected at N-1 and subsequently substituted with an appropriate $A-R_1$ moiety according to procedures of Scheme 2.

The resulting compound, 12, may be hydrolyzed in aqueous acid to give carboxylate 13. Activation of 13 by a suitable method, followed by treatment with $R_5R_4NH$ and deprotection gives the carboxamide, 14. Suitable activation methods include but are not limited to 1) conversion of the carboxylate to an acyl halide (e.g., chloride) and coupling in the presence of pyridine or a related base; and 2) use of a coupling agent suitable for amide bond formation (e.g., dicyclohexylcarbodiimide).

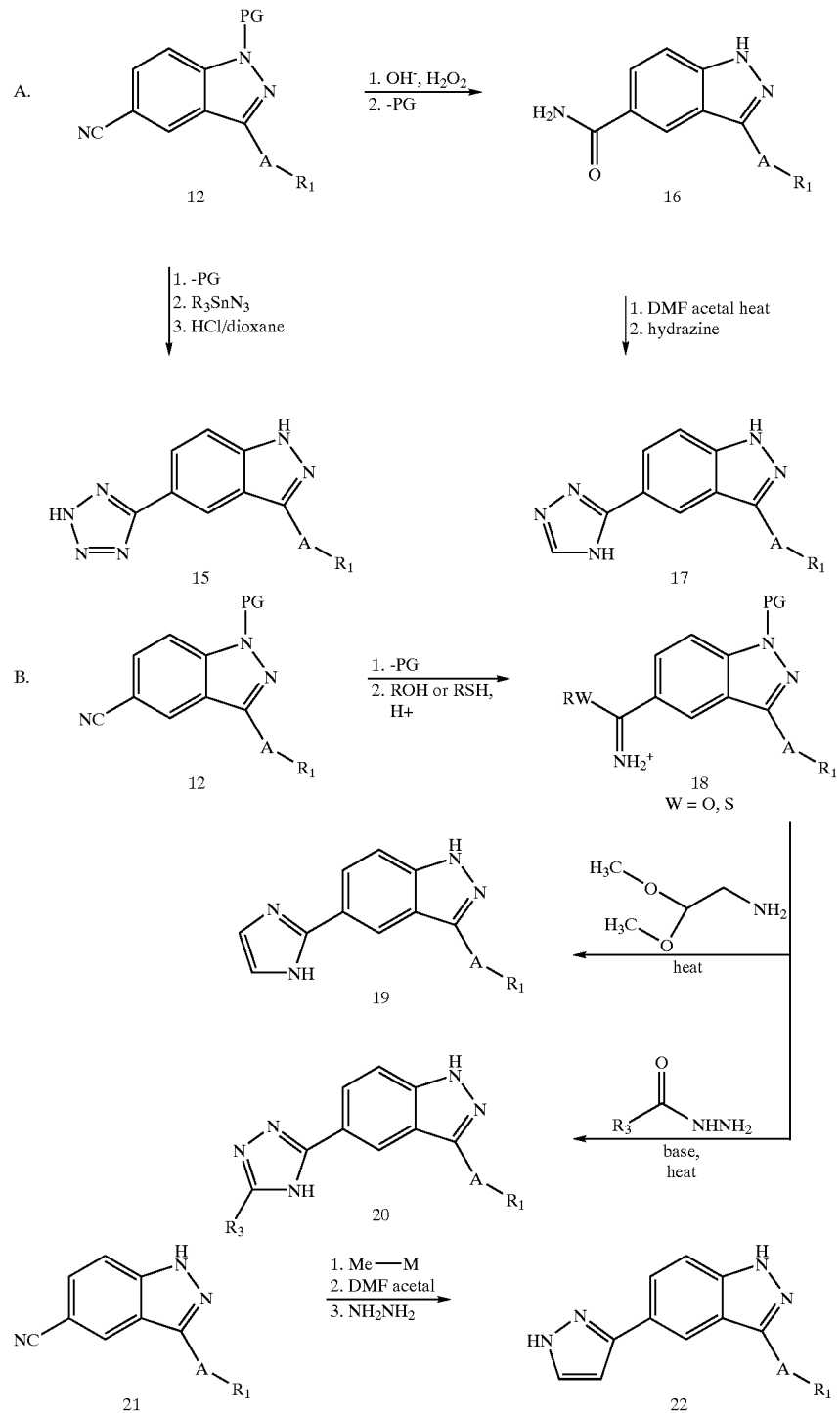

Reaction Scheme 6

Reaction Scheme 6 illustrates the additional embodiment wherein $R_2$ is a five-membered heterocyclic substituent. In Scheme 6A, nitrile 12 is deprotected at N-1 and converted to the tetrazole 15 by use of an electrophilic azide source (e.g., a trialkyl tin such as $(Bu)_3SnN_3$). Nitrile 12 may also be converted to the unsubstituted triazole 17 in four steps. The nitrile is first transformed to the carboxamide by exposure to aqueous base under oxidizing conditions (e.g., NaOH and $H_2O_2$). The N-1 protecting group is removed to give intermediate 16. The carboxamide is heated with DMF acetal and subsequently treated with hydrazine under acidic conditions to give the desired triazole.

Scheme 6B illustrates the synthesis of imidazole and substituted triazole derivatives at $R_2$. Nitrile 12 is deprotected and converted to the imidate or thioimidate by heating in the appropriate alcohol or thiol under acidic conditions to give 18. Subsequent exposure to 1-amino-2,2-dimethoxyethane and gentle heating effects formation of imidazole 19. Alternatively, heating 18 with alkyl, aryl or heterocyclic hydrazides under basic conditions (e.g., in presence of a tertiary organoamine such as triethylamine) results in production of 3-substituted triazole 20.

Pyrazole derivatives maybe synthesized according to Scheme 6C. Nitrile 12 may be deprotected at N-1 to give starting material 21. Treatment of the latter nitrile with a suitable organometallic agent, e.g., methyl lithium, yields a methyl ketone intermediate. Subsequent treatment by heating with DMF acetal followed by exposure to hydrazine gives pyrazole 22.

Scheme 7 depicts alternative routes to 5-triazole derivatives of 1H-indazoles. In scheme 7A nitrile 11 is converted to triazole 23 under conditions similar to those employed in Scheme 6B. A suitable protecting group, e.g., trityl, is incorporated onto the free triazole nitrogen to give 24. A-$R_1$ is then added to position-3 by a boronic acid or other suitable derivative. Finally, the triazole protecting group is removed under, e.g., acidic conditions, to give indazole 17.

In Scheme 7B, starting material 25 is prepared by activation of 13 as, e.g., an acid halide such as chloride. Subsequent reaction with a protected hydrazide followed by removal of protecting groups yields hydrazide 26. By way of example, when PG=acetyl and $PG_2$=t-butyl-oxycarbonyl, the protecting groups are removed by sequential treatment with ammonia followed by acid, e.g., HCl. Indazole 26 is treated with an appropriate imidate to give 27 and converted to triazole 20 by heating in a polar solvent, e.g., DMF.

Scheme 7

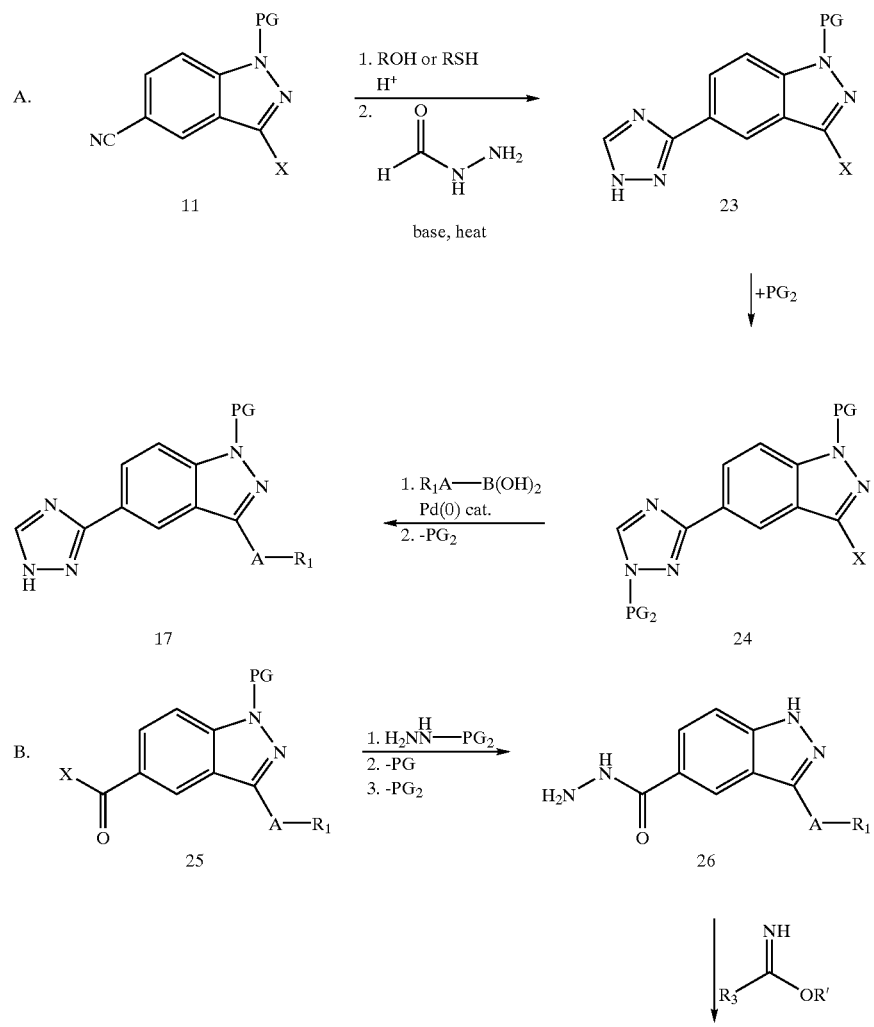

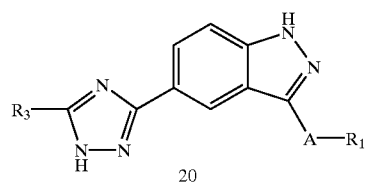 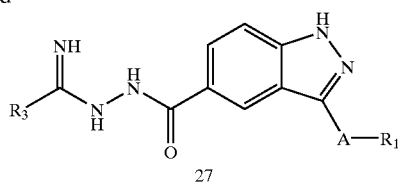

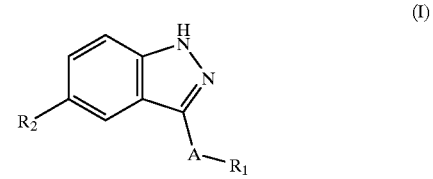

Pharmaceutically acceptable salts of compounds of structure (I) are also within the scope of this invention. To this end, the compound may generally be utilized as the free base. Alternatively, the compounds may be used in the form of acid addition salts. Acid addition salts of the free base amino compounds of the present invention may be prepared by methods well known in the art, and may be formed from organic and inorganic acids. Suitable organic acids include maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Thus, the term "pharmaceutically acceptable salt" of a compound of structure (I) is intended to encompass any and all acceptable salt forms.

Pharmaceutically acceptable salts of this invention may be formed by conventional and known techniques, such as by reacting a compound of this invention with a suitable acid as disclosed above. Such salts are typically formed in high yields at moderate temperatures, and often are prepared by merely isolating the compound from a suitable acidic wash in the final step of the synthesis. The salt-forming acid may dissolved in an appropriate organic solvent, or aqueous organic solvent, such as an alkanol, ketone or ester. On the other hand, if the compound of this invention is desired in the free base form, it may be isolated from a basic final wash step, according to known techniques. For example, a typical technique for preparing hydrochloride salt is to dissolve the free base in a suitable solvent, and dry the solution thoroughly, as over molecular sieves, before bubbling hydrogen chloride gas through it.

The compound of this invention may also exist in various isomeric forms, including configurational, geometric and conformational isomers, as well as existing in various tautomeric forms, particularly those that differ in the point of attachment of a hydrogen atom. As used herein, the term "isomer" is intended to encompass all isomeric forms of a compound, including tautomeric forms of the compound.

As used herein, the term "prodrug" refers to any derivative of indazoles of this invention that are metabolized or otherwise converted into an active form upon introduction into the body of an animal. Prodrugs are well known to those skilled in the art of pharmaceutical chemistry, and provide benefits such as increased adsorption and half-life. Prodrugs of this invention may be formed when, for example, hydroxy groups are esterified or alkylated, or when carboxyl groups are esterified. Those skilled in the art of drug delivery will readily appreciate that the pharmacokinetic properties of indazoles of this invention may be controlled by an appropriate choice of moieties to produce prodrug derivatives.

In another embodiment, the present invention provides a method for treating one or more of a variety of conditions by administering an effective amount of a compound of this invention to a patient in need thereof. In this embodiment, the compounds of this invention have the following structure (I):

including isomers, prodrugs and pharmaceutically acceptable salts thereof,
wherein:

A is a direct bond, $-(CH_2)_a-$, $-(CH_2)_bCH=CH(CH_2)_c-$, or $-(CH_2)_bC\equiv C(CH_2)_c-$;

$R_1$ is aryl, heteroaryl or heterocycle fused to phenyl, each being optionally substituted with one to four substituents independently selected from $R_3$;

$R_2$ is $-R_3$, $-R_4$, $-(CH_2)_bC(=O)R_5$, $-(CH_2)_bC(=O)OR_5$, $-(CH_2)_bC(=O)NR_5R_6$, $-(CH_2)_bC(=O)NR_5(CH_2)_cC(=O)R_6$, $-(CH_2)_bNR_5C(=O)R_6$, $-(CH_2)_bNR_5C(=O)NR_6R_7$, $-(CH_2)_bNR_5R_6$, $-(CH_2)_bOR_5$, $-(CH_2)_bSO_dR_5$ or $-(CH_2)_bSO_2NR_5R_6$;

a is 1, 2, 3, 4, 5 or 6;

b and c are the same or different and at each occurrence independently selected from 0, 1, 2, 3 or 4;

d is at each occurrence 0, 1 or 2;

$R_3$ is at each occurrence independently halogen, hydroxy, carboxy, alkyl, alkoxy, haloalkyl, acyloxy, thioalkyl, sulfinylalkyl, sulfonylalkyl, hydroxyalkyl, aryl, substituted aryl, arylalkyl, substituted arylalkyl, heterocycle, substituted heterocycle, heterocycloalkyl, $-C(=O)OR_8$, $-OC(=O)R_8$, $-C(=O)NR_8R_9$, $-C(=O)NR_8OR_9$, $-SO_2NR_8R_9$, $-NR_8SO_2R$, $-CN$, $-NO_2$, $-NR_8R_9$, $-NR_8C(=O)R_9$, $-NR_8C(=O)(CH_2)_bOR_9$, $-NR_8C(=O)(CH_2)_bR_9$, $-O(CH_2)_bNR_8R_9$, or heterocycle fused to phenyl;

$R_4$ is alkyl, aryl, arylalkyl, heterocycle or heterocycloalkyl, each being optionally substituted with one to four substituents independently selected from $R_3$, or $R_4$ is halogen or hydroxy;

$R_5$, $R_6$ and $R_7$ are the same or different and at each occurrence independently hydrogen, alkyl, aryl, arylalkyl, heterocycle or heterocycloalkyl, wherein each of $R_5$, $R_6$ and $R_7$ are optionally substituted with one to four substituents independently selected from $R_3$; and $R_8$ and $R_9$ are the same or different and at each occurrence independently hydrogen, alkyl, aryl, arylalkyl, heterocycle, or heterocycloalkyl, or $R_8$ and $R_9$ taken together with the atom or atoms to which they are bonded form a heterocycle, wherein each of $R_8$, $R_9$, and $R_8$ and $R_9$ taken together to form a heterocycle are optionally substituted with one to four substituents independently selected from $R_3$.

In one embodiment $R_2$ is $-R_4$, $-(CH_2)_bC(=O)R_5$, $-(CH_2)_bC(=O)OR_5$, $-(CH_2)_bC(=O)NR_5R_6$, —$(CH_2)_bC(=O)NR_5(CH_2)_cC(=O)R_6$, —$(CH_2)_b$NR_5C(=O)R_6$, —$(CH_2)_bNR_5C(=O)NR_6R_7$, —$(CH_2)_bNR_5R_6$, —$(CH_2)_bOR_5$, —$(CH_2)_bSO_dR_5$ or —$(CH_2)_bSO_2NR_5R_6$.

In one embodiment, -A-$R_1$ is phenyl, optionally substituted with one to four substituents independently selected from halogen, alkoxy, —$NR_8C(=O)R_9$, —$C(=O)NR_8R_9$, and —$O(CH_2)_bNR_8R_9$, wherein b is 2 or 3 and wherein $R_8$ and $R_9$ are defined above.

In another embodiment, $R_2$ is —$R_4$, —$(CH_2)_bC(=O)R_5$, —$(CH_2)_bC(=O)OR_5$, —$(CH_2)_bC(=O)NR_5R_6$, —$(CH_2)_bC(=O)NR_5(CH_2)_cC(=O)R_6$, —$(CH_2)_bNR_5C(=O)R_6$, —$(CH_2)_bNR_5C(=O)NR_6R_7$, —$(CH_2)_bNR_5R_6$, —$(CH_2)_bOR_5$, —$(CH_2)_bSO_dR_5$ or —$(CH_2)_bSO_2NR_5R_6$, and b is an integer ranging from 0–4

In another embodiment, $R_2$ is —$(CH_2)_bC(=O)NR_5R_6$, —$(CH_2)_bNR_5C(=O)R_6$, 3-triazolyl or 5-tetrazolyl, wherein b is 0 and wherein $R_8$ and $R_9$ are defined above.

In a preferred embodiment, $R_2$ is 3-triazolyl or 5-tetrazolyl.

In another preferred embodiment:

(a) -A-$R_1$ is phenyl, optionally substituted with one to four substituents independently selected from halogen, alkoxy, —$NR_8C(=O)R_9$, —$C(=O)NR_8R_9$, and —$O(CH_2)_bNR_8R_9$, wherein b is 2 or 3; and (b) $R_2$ is —$(CH_2)_bC(=O)NR_5R_6$, —$(CH_2)_bNR_5C(=O)R_6$, 3-triazolyl or 5-tetrazolyl, wherein b is 0 and wherein $R_8$ and $R_9$ are defined above.

In a more preferred embodiment:

(a) -A-$R_1$ is phenyl, optionally substituted with one to four substituents independently selected from halogen, alkoxy, —$NR_8C(=O)R_9$, —$C(=O)NR_8R_9$, and —$O(CH_2)_bNR_8R_9$, wherein b is 2 or 3; and (b) $R_2$ is 3-triazolyl or 5-tetrazolyl.

In another preferred embodiment, $R_2$ is $R_4$, and $R_4$ is 3-triazolyl, optionally substituted at its 5-position with:

(a) a $C_1$–$C_4$ straight or branched chain alkyl group optionally substituted with a hydroxyl, methylamino, dimethylamino or 1-pyrrolidinyl group; or (b) a 2-pyrrolidinyl group.

In a more preferred embodiment, $R_2$ is $R_4$, and $R_4$ is methyl, n-propyl, isopropyl, 1-hydroxyethyl, 3-hydroxypropyl, methylaminomethyl, dimethylaminomethyl, 1-(dimethylamino)ethyl, 1-pyrrolidinylmethyl or 2-pyrrolidinyl.

Conditions that may be treated by the compounds of this invention, or a pharmaceutical composition containing the same, include any condition which is responsive to JNK inhibition, and thereby benefit from administration of such an inhibitor. Representative conditions in this regard include (but are not limited to) rheumatoid arthritis; rheumatoid spondylitis; osteoarthritis; gout; asthma, bronchitis; allergic rhinitis; chronic obstructive pulmonary disease; cystic fibrosis; inflammatory bowel disease; irritable bowel syndrome; mucous colitis; ulcerative colitis; Crohn's disease; Huntington's disease; gastritis; esophagitis; hepatitis; pancreatitis; nephritis; multiple sclerosis; lupus erythematosus; Type II diabetes; atherosclerosis; restenosis following angioplasty; left ventricular hypertrophy; myocardial infarction; stroke; ischemic damages of heart, lung, gut, kidney, liver, pancreas, spleen and brain; acute or chronic organ transplant rejection; preservation of the organ for transplantation; graft versus host disease; endotoxin shock; multiple organ failure; psoriasis; burn from exposure to fire, chemicals or radiation; eczema; dermatitis; skin graft; ischemia; ischemic conditions associated with surgery or traumatic injury; epilepsy; Alzheimer's disease; Parkinson's disease; immunological response to bacterial or viral infection; cachexia; angiogenic and proliferative dieseases; solid tumor; and cancers of a variety of tissues such as colon, rectum, prostate, liver, lung, bronchus, pancreas, brain, head, neck, stomach, skin, kidney, cervix, blood, larynx, esophagus, mouth, pharynx, urinary bladder, ovary or uterine.

The compounds described herein could also be useful as an adjunct to existing and/or experimental therapies.

The compounds of this invention may be administered to animals (including humans) orally or parenterally in conventional and well known preparations, such as capsules, microcapsules, tablets, granules, powder, troches, pills, suppositories, injections, suspensions and syrups. Suitable formulations in this regard may be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylprrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous sicilic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinyl pyrrolidone or aluminum stearate), a dispersing agent (e.g., hydroxypropylmethylcellulose), a diluent (e.g., water), and/or a base wax (e.g., cocoa buffer, white petrolatum or polyethylene glycol). The compounds of the invention may also be administered by any other convenient route, for example, by infusion or bolus injection, by absorption through epithelial or mucocutaneous linings (e.g., oral mucosa, rectal and intestinal mucosa, etc.) and may be administered together with another biologically active agent. Administration can be systemic or local. Various delivery systems are known, e.g., encapsulation in liposomes, microparticles, microcapsules, capsules, etc., and can be used to administer a compound of the invention. In certain embodiments, more than one compound of the invention is administered to a patient. Methods of administration include but are not limited to intradermal, intramuscular, intraperitoneal, intravenous, subcutaneous, epidural, oral, sublingual, intranasal, intracerebral, intravaginal, transdermal, rectally, by inhalation, or topically, particularly to the ears, nose, eyes, or skin. The preferred mode of administration is left to the discretion of the practitioner, and will depend in-part upon the site of the medical condition. In most instances, administration will result in the release of the compounds of the invention into the bloodstream.

In specific embodiments, it may be desirable to administer one or more compounds of the invention locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of an atherosclerotic plaque tissue.

In certain embodiments, for example, for the treatment of Alzheimer's Disease, it may be desirable to introduce one or more compounds of the invention into the central nervous system by any suitable route, including intraventricular, intrathecal and epidural injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compounds of the invention can be formulated as a suppository, with traditional binders and vehicles such as triglycerides.

In another embodiment, the compounds of the invention can be delivered in a vesicle, in particular a liposome (see Langer, 1990, Science 249:1527–1533; Treat et al, in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.).

In yet another embodiment, the compounds of the invention can be delivered in a controlled release system. In one embodiment, a pump may be used (see Langer, supra; Sefton, 1987, CRC Crit. Ref. Biomed. Eng. 14:201; Buchwald et al., 1980, Surgery 88:507 Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; see also Levy et al., 1985, Science 228:190; During et al, 1989, Ann. Neurol. 25:351; Howard et al., 1989, J. Neurosurg. 71:105). In yet another embodiment, a controlled-Release system can be placed in proximity of the target of the compounds of the invention, e.g., the liver, thus requiring only a fraction of the systemic dose (see, e.g., Goodson, in Medical Applications of Controlled Release, supra, vol. 2, pp. 115–138 (1984)). Other controlled-Release systems discussed in the review by Langer, 1990, Science 249:1527–1533) may be used.

The present compositions will contain a therapeutically effective amount of a compound of the invention, optionally more than one compound of the invention, preferably in purified form, together with a suitable amount of a pharmaceutically acceptable vehicle so as to provide the form for proper administration to the patient.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "vehicle" refers to a diluent, adjuvant, excipient, or carrier with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the compounds of the invention and pharmaceutically acceptable vehicles are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propyleneglycol, water, ethanol and the like. The present compositions, if desired, can also contain minor amounts of wetting or emulsifying agents, or pH buffering agents The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles are described in "Remington's Pharmaceutical Sciences" by E. W. Martin.

In a preferred embodiment, the compounds of the invention are formulated in accordance with routine procedures as a pharmaceutical composition adapted for intravenous administration to human beings. Typically, compounds of the invention for intravenous administration are solutions in sterile isotonic aqueous buffer. Where necessary, the compositions may also include a solubilizing agent. Compositions for intravenous administration may optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound of the invention is to be administered by infusion, it can be dispensed, for example, with an infusion bottle containing sterile pharmaceutical grade water or saline. Where the compound of the invention is administered by injection, an ampoule of sterile water for injection or saline can be provided so that the ingredients may be mixed prior to administration.

Compositions for oral delivery may be in the form of tablets, lozenges, aqueous or oily suspensions, granules, powders, emulsions, capsules, syrups, or elixirs, for example. Orally administered compositions may contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

The dose of a compound of this invention to be administered to a patient, such as a human, is rather widely variable and subject to the judgment of the attending physician. The general range of effective administration rates of the compounds of this invention are from about 0.05 mg/day to about 250 mg/day, and typically from about 0.25 mg/day to 60 mg/day. Of course, it is often practical to administer the daily dose of compound in portions, at various hours of the day. However, in any given case, the amount of compound administered will depend on such factors as the solubility of the active component, the formulation used, subject condition (such as weight), and/or the route of administration.

Further, the effect of the compounds of this invention may be delayed or prolonged by proper formulation. For example, a slowly soluble pellet of the compound may be prepared and incorporated in a tablet or capsule. The technique may be improved by making pellets of several different dissolution rates and filling capsules with a mixture of the pellets. Tablets or capsules may be coated with a film which resists dissolution for a predictable period of time. Even the parenteral preparations may be made long-acting, by dissolving or suspending the compound in oily or emulsified vehicles which allow it to disperse only slowly in the serum.

The following examples are offered by way of illustration, not limitation. (To this end, it should be noted that one or more hydrogen atoms may be omitted from the drawn structures consistent with accepted shorthand notation of such organic compounds, and that one skilled in the art would readily appreciate their presence.)

5. EXAMPLES

Example 1

SYNTHESIS OF 3-(4-METHOXYPHENYL)-1H-INDAZOLE

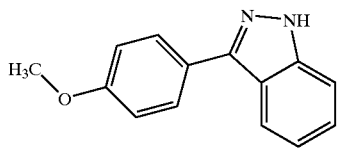

A. 3-Bromo-1H-indazole

To a suspension of 1H-indazole (3.00 g, 25.4 mmol) in 2.0 M sodium hydroxide solution (70 mL) at ambient temperature was added a solution of bromine (3.00 g, 18.8 mmol) in 2.0 M sodium hydroxide solution (30 mL) dropwise. After stirring for 3 hours, to the reaction mixture was added sodium bisulfite (0.1 g), followed by 2.0 N hydrochloric acid solution (80 mL). The precipitates were filtered and washed with water to provide the title compound (3.98 g, 80% yield): mp 136° C.; $^1$H NMR (CDCl$_3$) δ 13.4 (br s, 1H), 7.57 (m, 2H), 7.45 (t, 1H), 7.22 (t, 1H); EI-MS (m/z) 198 [M+2]$^+$, 196 [M]$^+$.

B. 3-(4-Methoxyphenyl)-1H-indazole

A mixture of 3-bromo-1H-indazole (0.20 g, 1.0 mmol), 4-methoxyphenylboronic acid (0.228 g, 1.5 mmol), and tetrakis(triphenylphosphine)palladium(0) (0.228 g, 0.1 mmol) in ethylene glycol dimethyl ether (5 mL) and 2.0 M sodium carbonate solution (6 mL) under nitrogen was heated at 100° C. for 18 hours. It was quenched by water and extracted with chloroform. The extracts were dried over magnesium sulfate, filtered, and concentrated. The residue was then purified by chromatography (SiO$_2$, 15–30% ethyl acetate/hexane) to provide the title compound (0.012 g, 5% yield): $^1$H NMR (CDCl$_3$) δ 10.4 (br s, 1H), 8.01 (d, 1H), 7.92 (d, 2H), 7.46 (m, 2H), 7.22 (m, 1H), 7.06 (d, 2H), 3.89 (s, 3H); EI-MS (m/z) 224 [M]$^+$.

Example 2

SYNTHESIS OF 3-(4-HYDROXYPHENYL)-1H-INDAZOLE

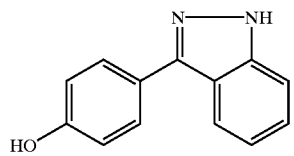

A. 3-Bromo-1-[2-(methoxyethoxy)methyl]-1H-indazole

To a solution of 3-bromo-1H-indazole (6.15 g, 31 mmol) in dried tetrahydrofuran (40 mL) at ambient temperature was added 1.0 M solution of sodium bis(trimethylsilyl)amide in tetrahydrofuran. After stirring 20 minutes, to the mixture was added neat 2-methoxyethoxymethyl chloride (4.36 g, 35 mmol). The reaction mixture was stirred at ambient temperature overnight. It was quenched with water and extracted with chloroform. The extracts were dried over magnesium sulfate, filtered, and concentrated. The residue was then purified by chromatography (SiO$_2$, 15–30% ethyl acetate/hexane) to provide the title compound (6.512 g, 74% yield): EI-MS (m/z) 286 [M+2]$^+$, 284 [M]$^+$.

B. 1-[2-(Methoxyethoxy)methyl]-3 (4-methoxyphenyl)-1H-indazole

A mixture of 3-bromo-1-[2-(methoxyethoxy)methyl]-1H-indazole (0.640 g, 2.2 mmol), 4-methoxyphenylboronic acid (0.456 g, 3.0 mmol), potassium phosphate (2.12 g, 10 mmol), and [1,1'-bis(diphenylphosphino)ferrocene] dichloropalladium(II) complex with dichloromethane (1:1), (0.245 g, 0.3 mmol) in ethylene glycol dimethyl ether (10 mL) under nitrogen was heated to reflux overnight. It was quenched with water and extracted with chloroform. The extracts were dried over magnesium sulfate, filtered, and concentrated. The residue was then purified by chromatography (SiO$_2$, 20–50% ethyl acetate/hexane) to provide the title compound (0.537 g, 78% yield): $^1$H NMR (CDCl$_3$) δ 7.99 (d, 1H), 7.90 (d, 2H), 7.62 (d, 1H), 7.45 (t, 1H), 7.26 (m, 2H), 7.50 (d, 2H), 5.86 (s, 2H), 3.90 (s, 3H), 3.68 (m, 2H), 3.48 (m, 2H), 3.35 (s, 3H); EI-MS (m/z) 312 [M]$^+$.

C. 3-(4-Hydroxyphenyl)-1H-indazole

To a solution of 1-[2-(methoxyethoxy)methyl]-3-(4-methoxyphenyl)-1H-indazole (20.40 g, 1.28 mmol) in dried dichloromethane under nitrogen was added 1.0 M solution of boron tribromide in dichloromethane (4.0 mL, 4.0 mmol). It was stirred at ambient temperature for 18 hours, quenched with saturated sodium bicarbonate solution, and extracted with ethyl acetate. The extracts were dried over magnesium sulfate, filtered, and concentrated. The residue was then purified by chromatography (SiO$_2$, 30–50% ethyl acetate/hexane) to provide the title compound (0.089 g, 33% yield): mp 189–190° C.; $^1$H NMR (CDCl$_3$) δ 10.0 (br s, 1H), 7.97 (d, 1H), 7.87 (d, 2H), 7.51 (d, 1H), 7.43 (t, 1H), 7.26 (m, 2H), 6.99 (d, 2H); EI-MS (m/z) 210 [M]$^+$.

Example 3

SYNTHESIS OF 3-(2-METHOXYPHENYL)-1H-INDAZOLE

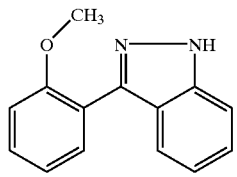

A. 1-[2-(Methoxyethoxmethyl]-3-(2-methoxyphenyl)-1H-indazole

The title compound was prepared as described in Example 2 B, using 2-methoxyphenylboronic acid (0.304 g, 2.0 mmol) (0.235 g, 48% yield): $^1$H NMR (CDCl$_3$) δ 7.74 (d, 1H), 7.49 (m, 3H), 7.32 (t, 1H), 7.04–7.15 (m, 3H), 5.73 (s, 2H), 3.78 (s, 3H), 3.65 (m, 2H), 3.41 (m, 2H), 3.29 (s, 3H); EI-MS (m/z) 312 [M]$^+$.

B. 3-(2-Methoxyphenyl)-1H-indazole

A solution of 1-[2-(methoxyethoxy)methyl]-3-(2-methoxyphenyl)-1H-indazole (0.20 g, 0.64 mmol) in 1,4-dioxane (4 mL) and 6 N hydrochloric acid solution (4 mL) was stirred at ambient temperature for 16 hours. It was neutralized with saturated sodium carbonate solution and extracted with chloroform. The extracts were dried over magnesium sulfate, filtered, and concentrated. The residue was then purified by chromatography (SiO$_2$, 20–40% ethyl acetate/hexane) to provide the title compound (0.061 g, 60% yield): mp 99° C.; $^1$H NMR (CDCl$_3$) δ 10.23 (br s, 1H), 7.79 (d, 1H), 7.68 (d, 1H), 7.37–7.52 (m, 3H), 7.07–7.20 (m, 3H), 3.88 (s, 3H); EI-MS (m/z) 224 [M]$^+$.

Example 4

SYNTHESIS OF 3-(4-FLUOROPHENYL)-1H-INDAZOLE

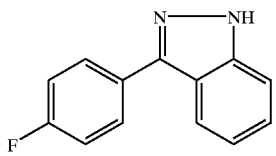

A. 3-(4-Fluorophenyl)-1-[2-(methoxyethoxy)methyl]-1H-indazole

The title compound was prepared as described in Example 2 B, using 4-fluorophenylboronic acid (0.182 g, 1.3 mmol) (0.237 g, 79% yield): $^1$H NMR (CDCl$_3$) δ 7.53–7.79 (m, 4H), 7.10–7.48 (m, 4H), 5.75 (s, 2H), 3.94 (m, 2H), 3.53 (s, 3H); EI-MS (m/z) 300 [M]$^+$.

B. 3-(4-Fluorophenyl)-1H-indazole

The title compound was prepared as described in Example 3 B, using 3-(4-fluorophenyl)-1-[2-(methoxyethoxy)methyl]-1H-indazole (0.20 g, 0.67 mmol) (0.092 g, 65% yield): mp 126° C.; $^1$H NMR (CDCl$_3$) δ 10.14 (br s, 1H), 7.93–8.01 (m, 3H), 7.52 (d, 1H), 7.44 (t, 1H), 7.18–7.28 (m, 3H); EI-MS (m/z) 212 [M]$^+$.

Example 5

SYNTHESIS OF 3-PHENYL-5-TRIFLUOROMETHYL-1H-INDAZOLE

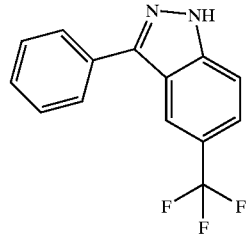

A. 3-Phenyl-5-trifluoromethyl-1H-indazole

A solution of 2-fluoro-5-trifluoromethylbenzophenone (0.828 g, 3.09 mmol) in hydrazine was heated at 130° C. for 3 hours. The reaction mixture stood at ambient temperature overnight and gave white needles. It was filtered and washed with hexane to provide the title compound (0.617 g, 76% yield): mp 152° C.; $^1$H NMR (CDCl$_3$) δ 10.63 (br s, 1H), 8.33 (s, 1H), 7.96 (d, 2H), 7.48–7.67 (m, 5H); EI-MS (m/z) 262 [M]$^+$.

Example 6

SYNTHESIS OF 5-FLUORO-3-PHENYL-1H-INDAZOLE

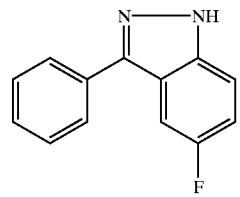

A. 5-Fluoro-3-phenyl-1H-indazole

A solution of 2,5-difluorobenzophenone (0.655 g, 3.0 mmol) and hydrazine (1.0 mL) in dried pyridine (10 mL) was heated at 130° C. for 5 hours and then concentrated and purified by chromatography (SiO$_2$, 15–30% ethyl acetate/hexane) to provide the title compound (0.254 g, 40% yield): mp 124–125° C.; $^1$H NMR (CDCl$_3$) δ 10.89 (br s, 1H), 7.94 (d, 2H), 7.65 (dd, 1H), 7.42–7.54 (m, 3H), 7.33 (dd, 1H), 7.21 (dt, 1H); EL-MS (m/z) 212 [M]$^+$.

Example 7

SYNTHESIS OF 5-NITRO-3-PHENYL-1H-INDAZOLE

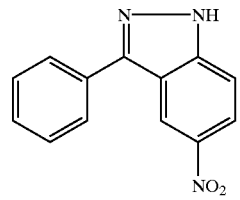

A. 5-Nitro-3-phenyl-1H-indazole

The title compound was prepared as described in Example 6 A, using 2-chloro-5-nitrobenzophenone (1.00 g, 3.8 mmol) (0.823 g, 91% yield): mp 185–186° C.; $^1$H NMR (CDCl$_3$) δ 10.69 (br s, 1H), 9.01 (d, 1H), 8.34 (dd, 1H), 7.97 (d, 2H), 7.49–7.61 (m, 4H); EI-MS (m/z) 239 [M]$^-$.

Example 8

SYNTHESIS OF 5-AMINO-3-PHENYL-1H-INDAZOLE

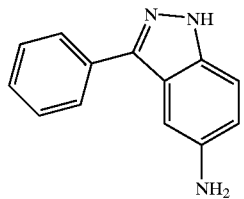

A. 5-Amino-3-phenyl-1H-indazole

A suspension of 5-nitro-3-phenyl-1H-indazole (0.239 g, 1.0 mmol) and palladium (10 wt % on activated carbon, 30 mg) in ethyl acetate (10 mL) was stirred under hydrogen at ambient temperature for 18 hours. It was filtered with celite and washed with ethyl acetate. The filtrate was concentrated and the residue was then purified by chromatography ($SiO_2$, 30–50% ethyl acetate/hexane) to provide the title compound (0.184 g, 88% yield): mp 104° C.; $^1H$ NMR ($CDCl_3$) δ 10.40 (br s, 1H), 7.94 (d, 2H), 7.51 (m, 2H), 7.20–7.42 (m, 3H), 6.90 (m, 1H), 3.6 (br, 2H); EI-MS (m/z) 209 $[M]^+$.

Example 9

SYNTHESIS OF 3-PHENYL-1H-INDAZOLE

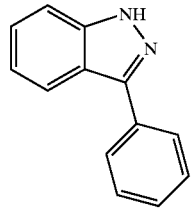

A. 3-Phenyl-1H-indazole

To 2-fluorobenzophenone (1.0 g, 5.0 mmol) was added hydrazine (5 mL) and the reaction was heated to reflux for 3 hours. The reaction was then added to water (100 mL) and extracted with ethyl acetate (3×30 mL). The combined organic layers were dried with sodium sulfate ($Na_2SO_4$) and concentrated to an oil. The subsequent hydrazine adduct was heated with pyridine (20 mL) to 170° C. for 4 days. Pyridine was then removed under vacuum and the resulting oil taken up in water (100 mL) and extracted with ethyl acetate (3×30 mL). The combined ethyl acetate layers were dried ($Na_2SO_4$) and concentrated to give the final compound (650 mg, 67% yield). $^1H$ NMR ($CDCl_3$) δ 10.6 (br s, 1H), 8.04–7.99 (m, 2H), 7.56–7.50 (m, 2H), 7.47–7.33 (m, 2H), 7.29–7.19 (m, 3H); ES-MS (m/z) 195 $[M+1]^-$.

Example 10

SYNTHESIS OF 3-PHENYL-5-(PHENYLMETHOXY)-1H-INDAZOLE

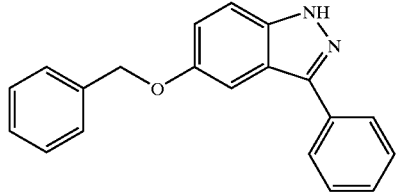

A. Phenyl-N-F2-(phenylcarbonyl)-4-(phenylmethoxy) phenyl]carboxamide

To a solution of N-[4-hydroxy-2-(phenylcarbonyl)phenyl] benzamide (4.0 g, 12.6 mmol) in dimethyl formamide (DMF) (15 mL) was added potassium carbonate ($K_2CO_3$) (large excess) then benzyl bromide (660 μL, 5.5 mmol). The reaction was stirred overnight. It was added to water (100 mL) then extracted with ethyl acetate (3×40 mL). The combined organic layers were dried ($Na_2SO_4$) then concentrated under vacuo to give a solid which was recrystallized with ethyl acetate/hexane to give the title compound (3.24 g, 63% yield, analytical).

B. 2-Amino-5-(phenylmethoxy)phenyl phenyl ketone

A solution of phenyl-N-[2-(phenylcarbonyl)-4-(phenylmethoxy)phenyl]carboxamide (3.24 g, 8.0 mmol) in methanol (20 mL) and 10 N sodium hydroxide (NaOH) (6 mL) was heated to reflux temperature when tetrahydrofuran (THF) (15 mL) was added. The solution was then heated to reflux overnight when the methanol and THF was removed under vacuo. The solution was then added to water (100 mL) and extracted with ethyl acetate (3×40 mL). The combined organic layers were dried ($Na_2SO_4$) and concentrated under vacuo to an oil to isolate the title compound (2.60 g, >100% yield, analytical).

C. 3-Phenyl-5-(phenylmethoxy)-1H-indazole

To a solution of 2-amino-5-(phenylmethoxy)phenyl phenyl ketone (2.6 g, 8.0 mmol) in 6N HCl (70 mL) at 0° C. was added a solution of sodium nitrite ($NaNO_2$) (650 mg, 9.4 mmol) in water (2 mL). To this solution was added methanol and THF to keep it homogeneous. A solution of tin (II) chloride ($SnCl_2$) (5.3 g, 23.6 mmol) in concentrated HCl (20 mL) was then added. The solution was stirred at room temperature overnight. The solid was then filtered and the solution concentrated and chromatographed on silica gel eluting with 20% ethyl acetate in hexane to give the title compound (1.15 g, 48% yield). $^1H$ NMR (DMSO-$d_6$) δ 13.1 (s, 1H), 7.95 (d, 2H), 7.56–7.48 (m, 6H), 7.44–7.3 (m, 4H), 7.14 (d, 1H), 5.12 (s, 2H); ES-MS (m/z) 301 $[M+1]^+$.

Example 11

SYNTHESIS OF 3-PHENYL-1H-INDAZOL-5-OL

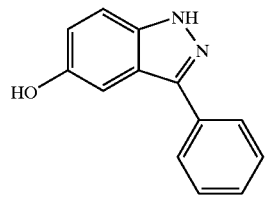

A. 3-Phenyl-1H-indazole-5-ol

To a solution of 5-nitro-3-phenyl-1H-indazole (1.0 g, 4.2 mmol) in ethyl acetate (80 mL) was added palladium on activated carbon (Pd/carbon) then the reaction was subjected to an atmosphere of hydrogen. The reaction was stirred for 3 days when the Pd/carbon was filtered off and the solution concentrated to an oil under vacuo. The oil was then taken up in $H_2SO_4$ (6 mL) and water (60 mL) and the suspension was heated in a bomb to 180° C. for 2 days. The reaction was then cooled to room temperature, quenched with $NaHCO_3$ (100 mL) and extracted with ethyl acetate (3×30 mL). The organic layers were combined and dried ($Na_2SO_4$) and concentrated to recover the title compound (250mg, 28% yield). $^1$H NMR (CDCl$_3$) δ 13.0 (s, 1H), 9.20 (s, 1H), 7.91 (s, 1H), 7.88 (s, 1H), 7.50 (t, 2H), 7.41 (d, 1H), 7.36 (t, 1H), 7.28 (s, 1H), 6.96 (dd, 1H); ES-MS (m/z) 195 [M+1]$^-$.

Example 12

SYNTHESIS OF 5-METHYL-3-PHENYL-1H-INDAZOLE

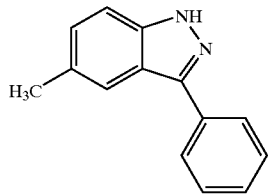

A. 5-Methyl-3-phenyl-1H-indazole

To a solution of 2-amino-5-methylphenyl phenyl ketone (2.0 g, 9.5 mmol) in HCl (45 mL of a 6M solution) at 0° C. was added sodium nitrite (NaNO$_2$) (719 mg, 10.4 mmol) in water (2 mL). The reaction was stirred for 30 min when the homogeneous solution was added dropwise to a solution of SnCl$_2$ (5.88, 26 mmol) in concentrated HCl (15 mL) at room temperature. The reaction was stirred for 30 min when it was filtered. The solid was then taken up in ethyl acetate (80 mL) and saturated sodium bicarbonate (80 mL). The suspension was then filtered and the ethyl acetate layer dried (Na$_2$SO$_4$) and concentrated to give the product (1.59 g, 80% yield). ($^1$H NMR (DMSO-d$_6$) δ 7.96 (d, 2H), 7.85 (br s, 1H), 7.54–7.46 (m, 3H), 7.39 (t, 1H), 7.24 (d, 1H), 2.45 (s, 3H); ES-MS (m/z) 209 [M+1]$^+$.

Example 13

SYNTHESIS OF PHENYL-N-(3-PHENYL(1H-INDAZOL-5-YL))CARBOXAMIDE

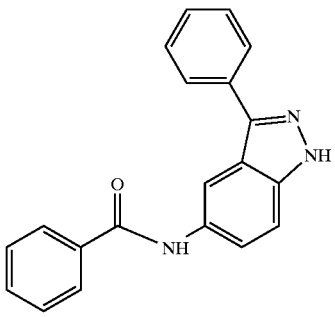

A. Phenyl-N-(3-Phenyl(1H-Indazol-5-yl)Carboxamide

To a mixture of 5-amino-3-phenyl-1H-indazole (190 mg, 0.909 mmol) in acetonitrile (6 mL) was added benzoyl chloride (123 mg, 0.909 mmol). The solution was allowed to reflux for three hours. Triethylamine (3 drops) was added over a period of one hour while reflux continued for an additional hour. The solution was condensed and distilled water was added. The reaction mixture was extracted with ethyl acetate. The organics were dried using sodium sulfate, and condensed to give a solid. The solid was purified using chromatography (SiO$_2$, 30–45% ethyl acetate/hexanes) to give the title compound (20 mg, 8% yield). $^1$H NMR (DMSO-d$_6$) δ 13.40 (br s, 1H), 10.32 (s, 1H), 8.56 (s, 1H), 7.96 (m, 4H), 7.75 (d, 1H), 7.55 (m, 6H), 7.39 (t, 1H); ES-MS (m/z) 314 [M+1]$^+$.

Example 14

SYNTHESIS OF N-(3-PHENYL(1H-INDAZOL-5-YL))-2-PYRIDYLCARBOXAMIDE

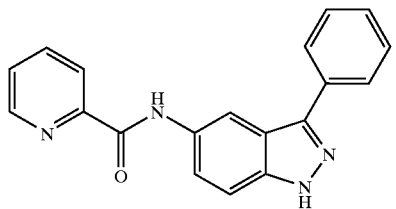

A. N-(1-Acetyl-3-Phenyl(1H-Indazole-5-yl))-2-Pyridylcarboxamide

To a flask containing 1-acetyl-5-amino-3-phenyl-1H-indazole (300 mg, 1.2 mmol) and dichloromethane (10 mL) was added 4-(dimethylamino)pyridine (75 mg, 0.6 mmol) and triethylamine (0.18 mg). The solution was allowed to stir for 10 minutes, then picolinoyl chloride hydrochloride (260 mg, 1.44 mmol) was added. The mixture was stirred at room temperature for 18 hours. The mixture was quenched with water and extracted with ethyl acetate. The extracts were dried using sodium sulfate, filtered, and concentrated to provide the title compound (364 mg, 85% yield). ES-MS (m/z) 357 [M+1]$^+$.

B. N-(3-Phenyl(1H-Indazole-5-yl))-2-Pyridylcarboxamide.

N-(1-acetyl-3-phenyl(1H-indazole-5-yl))-2-pyridylcarboxamide (364 mg, 1.02 mmol) was added to 0.3% ammonia in methanol (7 mL). The mixture was heated to 70° C. for 3 hours. The resulting precipitate was filtered and dried to give the title compound (221 mg, 71% yield). $^1$H NMR (DMSO-d$_6$) δ 13.20 (br s, 1H), 10.75 (s, 1H), 8.72 (d, 2H), 8.16 (d, 1H), 8.05 (m, 1H), 7.94 (t, 3H), 7.66 (m, 1H), 7.53 (q, 3H), 7.38 (t, 1H). ES-MS (m/z) 315 [M+1]$^+$.

Example 15

SYNTHESIS OF METHYL 4-[N-(3-PHENYL-1H-INDAZOL-5-YL) CARBAMOYL]BENZOATE

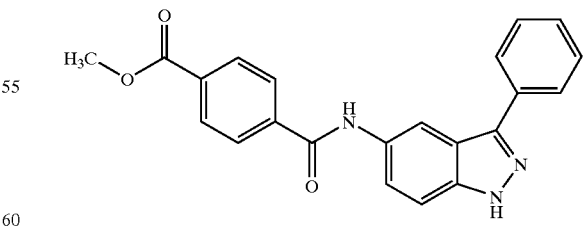

A. Methyl 4-[N-(1-acetyl-3-phenyl-1H-indazol-5-yl)carbamoyl]benzoate

To a flask containing 1-acetyl-5-amino-3-phenyl-1H-indazole (300 mg, 1.2 mmol) was added dichloromethane (10 mL), 4-(dimethylamino)pyridine (75 mg, 0.6 mmol) and triethylamine (180 mg, 1.8 mmol). The mixture was allowed to stir for ten minutes. Terephthalic acid monomethyl ester hydrochloride (285 mg, 1.44 mmol) was then added and stirring continued for 18 hours. The mixture was quenched with 5% sodium bicarbonate and extracted with dichloromethane. The extracts were dried using sodium sulfate, filtered and condensed to give a solid. The solid was recrystallized in ethanol to give the title compound (368 mg, 75%/; yield). ES-MS (m/z) 414 [M+1]+.

B. Methyl 4-[N-(3-Phenyl-1H-Indazol-5-yl)Carbamoyl] Benzoate.

Methyl 4-[N-(3-phenyl-1H-indazol-5-yl)carbamoyl] benzoate (368 mg, 0.890 mmol) was added to a solution of 0.3% ammonia in methanol (18 mL). The mixture was allowed to stir at 70° C. for 3 hours. The resulting precipitate was filtered and dried under vacuum to give the title compound (282 mg, 85% yield). $^1$H NMR (DMSO-d$_6$) δ 13.22 (br s, 1H), 10.50 (s, 1H), 8.55 (s, 1H), 8.09 (s, 4H), 7.91 (d, 2H), 7.75 (d, 1H), 7.52 (m, 3H), 7.39 (m, 1H), 3.88 (s, 3H); ES-MS (m/z) 372 [M+1]+.

Example 16

SYNTHESIS OF 4-[N-(3-PHENYL-1H-INDAZOL-5-YL)CARBAMOYL]BENZOIC ACID

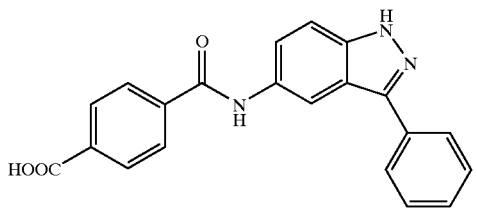

A. 4-[N-(3-phenyl-1H-indazol-5-yl)carbamoyl]benzoic acid

Methyl 4-[N-(3-phenyl-1H-indazole-5-yl)carbamoyl] benzoate (92 mg, 0.247 mmol) was added to a solution of lithium hydroxide (10 mg, 1.23 mmol) in tetrahydrofuran (5 mL) and water (5 mL). The solution was allowed to stir at room temperature for 3 hours. The solution was acidified using a 5% HCl solution. The resulting white precipitate was filtered and dried to provide the title compound (62 mg, 70% yield). $^1$H NMR (DMSO-d$_6$) δ 13.22 (br s, 1H), 10.48 (s, 1H), 8.55 (s, 1H), 8.06 (s, 4H), 7.92 (d, 2H), 7.75 (d, 1H), 7.55 (m, 3H), 7.38 (m, 1H); ES-MS (m/z) 358 [M+1]+.

Example 17

SYNTHESIS OF (2-HYDROXYPHENYL)-N-(3-PHENYL(1H-INDAZOL-5-YL)CARBOXAMIDE

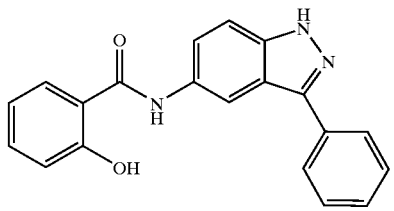

A. 2-[N-(1-acetyl-3-phenyl-1H-indazole-5-yl)carbamoyl] Phenyl Acetate and N-(1-acetyl-3-phenyl-1H-indazole-5-yl) acetamide.

To a solution of 5-amino-3-phenylindazole (330 mg, 1.31 mmol) in dichloromethane (11 mL) was added triethylamine (200 mg) and 4-(dimethylamine)pyridine (79 mg, 0.65 mmol). The solution was allowed to stir for fifteen minutes, then acetyl salicyloyl chloride (311 mg, 1.57 mmol) was added. Stirring under nitrogen continued for 18 hours. The solution was then neutralized using 5% sodium bicarbonate solution and extracted with ethyl acetate. The organic layer was dried with sodium sulfate, filtered and concentrated to give a solid which was purified by chromatography (SiO$_2$, 25–45% ethyl acetate/hexanes, respectively). The resulting two fractions provided the title compounds. First fraction: $^1$H NMR (DMSO-d$_6$) δ 10.62 (s, 1H), 8.54 (s, 1H), 8.33 (d, 2H), 7.94 (m, 3H), 7.61 (m, 5H), 7.39 (m, 1H), 7.24 (d, 1H), 2.76 (s, 3H), 2.16 (s, 3H); ES-MS (m/z) 414 [M+1]+. Second fraction: $^1$H NMR (DMSO-d$_6$) δ 10.23 (s, 1H), 8.47 (s, 1H), 8.29 (d, 1H), 7.93 (d, 2H), 7.73 (d, 1H), 7.60 (m, 3H), 2.74 (s, 3H), 2.05 (s, 3H), ES-MS (m/z) 252 [M+1]+.

B. (2-hydroxyphenyl)-N-(3-phenyl(1H-indazole-5-yl)) carboxamide.

A solution of 2-[N-(1-acetyl-3-phenyl-1H-indazole-5-yl) carbamoyl]phenyl acetate (100 mg, 0.241 mmol) in methanol (11 mL) with 0.3% ammonia was allowed to stir for three hours at reflux temperature. The mixture was then acidified with 5% HCl solution until neutral pH. The resulting solid was filtered, dried and triturated with hexanes to give the title compound (45 mg, 57% yield). $^1$H NMR (DMSO-d$_6$) δ 13.23 (br s, 1H), 11.92 (br s, 1H), 10.47 (s, 1H), 8.45 (s, 1H), 7.96 (m, 3H), 7.51 (m, 6H), 6.95 (d, 2H); ES-MS (m/z) 330 [M+1]+.

Example 18

SYNTHESIS OF N-(3-(PHENYL-1H-INDAZOLE-5-YL))ACETAMIDE

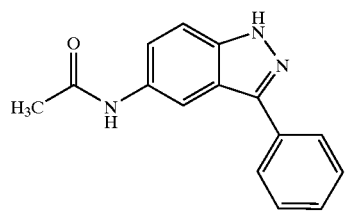

A. 3-(phenyl-11H-indazole-5-yl)acetamide

N-(1-acetyl-3phenyl-1H-indazole-5-yl)acetamide (70 mg, 0.238 mmol) was added to 0.3% ammonia in methanol (10 mL). The solution was heated at 70° C. for 3 hours. The solution was then neutralized using 5% HCl solution. The solution was concentrated and extracted with ethyl acetate. The organics were dried using sodium sulfate, filtered and concentrated to give a white solid. The solid was triturated with diethyl ether and dried under vacuum to give the title compound (35 mg, 59% yield). $^1$H NMR (DMSO-d$_6$) δ 13.13 (br s, 1H), 9.97 (s, 1H), 8.37 (s, 1H), 7.87 (d, 2H), 7.48 (br s, 4H), 7.36 (t, 1H), 2.03 (s, 3H); ES-MS (m/z) 252 [M+1]+.

Example 19

SYNTHESIS OF (4-AMINOPHENYL)-N-(3-PHENYL(1H-INDAZOL-5-YL)) CARLBOXAMIDE

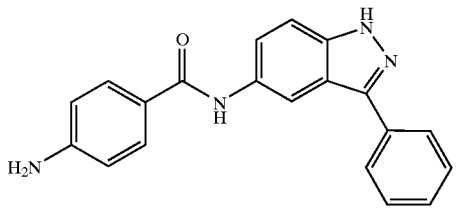

A. N-(1-acetyl-3-phenyl(1H-indazol-5-yl))(4-nitrophenyl) carboxamide

To suspension of 1-acetyl-5-amino-3-phenyl-1H-indazole (250 mg, 1.0 mmol) in dichloromethane (10 mL) was added 4-(dimethylamino)pyridine (60 mg, 0.5 mmol) followed by triethylamine (150 mg, 1.5 mmol). The mixture was allowed to stir for fifteen minutes, then para-nitrobenzoyl chloride (222 mg, 1.2 mmol) was added. The reaction mixture was allowed to stir for 18 hours under nitrogen conditions. It was quenched with 5% sodium bicarbonate and extracted with dichloromethane. The extracts were dried over sodium sulfate, filtered, and condensed to give a precipitate. The precipitate was triturated using hexanes to provide the title compound (295 mg, 74% yield). $^1$H NMR (DMSO-d$_6$) δ 10.83 (s, 1H), 8.63 (s, 1H), 8.38 (m, 3H), 8.20 (d, 2H), 7.99 (m, 3H), 7.60 (m, 3H), 2.76 (s, 3H); ES-MS (m/z) 401 [M+1]$^+$.

B. N-(1-acetyl-3-phenyl(1H-indazol-5-yl)(4-aminophenyl) carboxamide

A suspension of N-(1-acetyl-3-phenyl(1H-indazol-5-yl)) (4-nitrophenyl)carboxamide (246 mg, 0.710 mmol) and palladium on activated carbon (10%, 57 mg) in ethyl acetate (30 mL) was stirred under hydrogen atmosphere at room temperature for 18 hours. The reaction mixture was filtered through celite and combined with ethyl acetate washings. The filtrate was concentrated to give the title compound (246 mg, 94% yield). $^1$H NMR (DMSO-d$_6$) δ 10.04 (s, 1H), 8.61 (s, 1H) 8.31 (d, 1H), 7.99 (m, 2H), 7.64 (m, 4H), 6.58 (d, 2H), 5.78 (s, 2H), 2.76 (s, 3H); ES-MS (m/z) 371 [M+1]$^+$.

C. (4-aminophenyl)-N-(3-phenyl(1H-indazol-5-yl) carboxamide

To a solution of N-(1-acetyl-3-phenyl(1H-indazol-5-yl)) (4-aminophenyl)carboxamide (200 mg, 0.664 mmol) in 0.3% ammonia in methanol (12 mL). After the reaction mixture was stirred at room temperature for 3 hours, the mixture was acidified with 5% HCl. The resulting precipitate was filtered and dried to give the title compound (200 mg, 92% yield). $^1$H NMR (DMSO-d$_6$) δ 13.14 (br s, 1H), 9.84 (s, 1H), 8.52 (s, 1H), 7.95 (d, 2H), 7.75 (m, 3H), 7.54 (m, 3H), 7.39 (t, 1H), 5.74 (br, 2H); ES-MS (m/z) 329 [M+1]$^+$.

Example 20

SYNTHESIS OF (3-AMINOPHENYL)-N-(3-PHENYL(1H-INDAZOL-5-YL))CARBOXAMIDE

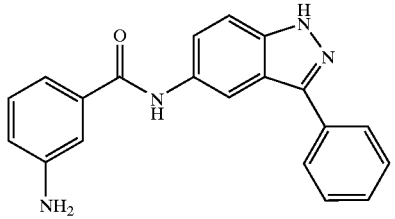

A. N-(1-acetyl-3-phenyl(1H-indazol-5-yl))(3-nitrophenyl) carboxamide

The title compound was prepared as described in Example 19 A, using 3-nitrobenzoylchloride (222 mg, 1.20 mmol) (257 mg, 65% yield). $^1$H NMR (DMSO-d$_6$) δ 10.85 (s, 1H), 8.82 (s, 1H), 8.63 (s, 1H), 8.41 (m, 3H), 8.00 (m, 3H), 7.84 (t, 1H), 7.60 (m, 3H), 2.77 (s, 3H); ES-MS (m/z) 401 [M+1]$^+$.

B. N-(1-acetyl-3-phenyl(1H-indazol-5-yl))(4-aminophenyl) carboxamide

The title compound was prepared as described in Example 19 B (200 mg, 92% yield). $^1$H NMR (DMSO-d$_6$) δ 10.36 (s, 1H), 8.63 (s, 1H), 8.34 (d, 1H), 8.00 (m, 3H), 7.60 (m, 3H), 7.12 (m, 3H), 6.74 (d, 1H), 5.32 (s, 2H), 2.77 (s, 3H); ES-MS (m/z) 371 [M+1]$^+$.

C. (3-aminophenyl)-N-(3-phenyl(1H-indazol-5-yl) carboxamide

The title compound was prepared as described in Example 19 C (172 mg, 88% yield). $^1$H NMR (DMSO-d$_6$) δ 13.18 (br s, 1H), 10.14 (s, 1H), 8.54 (s, 1H), 7.93 (d, 2H), 7.76 (d, 1H), 7.53 (m, 3H), 7.39 (t, 1H), 7.11 (m, 3H), 6.73 (d, 1H), 5.30 (s, 2H); ES-MS (m/z) 329 [M+1]$^+$.

Example 21

SYNTHESIS OF 3-(4-METHOXYPHENYL)-5-NITRO-1H-INDAZOLE

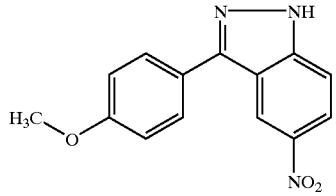

A. 3-bromo-5-nitro-1H-indazole

The title compound was prepared as described in Example 1 A, using 5-nitro-1H-indazole (9.78 g, 60.0 mmol) (13.674 g, 94% yield): $^1$H NMR (DMSO-d$_6$) δ 14.10 (br, 1H), 8.48 (s, 1H), 8.25 (d, 1H), 7.78 (d, 1H); EI-MS (m/z) 243[M+2]$^+$, 241 [M]$^+$.

B. 3-bromo-1-[2-(methoxyethoxy)methyl-5-nitro-1H-indazole

The title compound was prepared as described in Example 2 A, using 3-bromo-5-nitro-1H-indazole (4.84 g, 20.0 mmol) (4.52 g, 68% yield): mp 74° C.; $^1$H NMR (CDCl$_3$) δ 8.64 (d, 1H), 8.37 (dd, 1H), 7.69 (d, 1H), 5.82 (s, 2H), 3.69 (m, 2H), 3.50 (m, 2H), 3.34 (s, 3H); EI-MS (m/z) 231[M+2]+, 329 [M]$^+$.

C. 1-[2-(methoxyethoxy)methyl]-3-(4methoxyphenyl)-5-nitro-1H-indazole

The title compound was prepared as described in Example 2 B, using 3-bromo-1-[2-(methoxyethoxy)methyl]-5-nitro-1H-indazole (0.66 g, 2.0 mmol) and 4-methoxyphenylboronic acid (0.456 g, 3.0 mmol) (0.584 g, 82% yield): mp 65° C.; $^1$H NMR (CDCl$_3$) δ 8.72 (d, 1H), 8.14 (dd, 1H), 7.76 (d, 1H), 7.70 (d, 2H), 7.14 (d, 2H), 5.77 (s, 2H), 3.97 (m, 2H), 3.92 (s, 3H), 3.58 (m, 2H), 3.38 (s, 3H); EI-MS (m/z) 357 [M]$^+$.

D. 3-(4-methoxyphenyl)-5-nitro-1H-indazole

A solution of 1-[2-(methoxyethoxy)methyl]-3-(4-methoxyphenyl)-5-nitro-1 H-indazole (0.51 g, 1.4 mmol) in methanol (10 mL) and 6 N hydrochloric acid solution (10 mL) was heated at 75° C. for 8 hours. After the reaction mixture was cooled to room temperature, a yellow solid was precipitated. It was recrystallized from diethyl ether to provide the title compound (0.270 g, 72% yield): mp 153° C.; $^1$H NMR (CDCl$_3$) δ 10.42 (br s, 1H), 8.99 (d, 1H), 8.33 (dd, 1H), 7.91 (d, 2H), 7.56 (d, 1H), 7.11 (d, 2H); ES-MS (m/z) 269 [M]$^+$.

Example 22

SYNTHESIS OF 5-NITRO-3-[3-(TRIFLUOROMETHYL)PHENYL]-1H-INDAZOLE

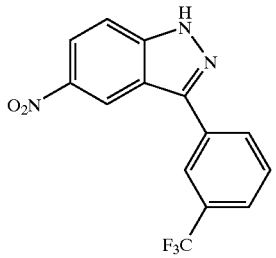

A. 5-Nitro-3-[3-(trifluoromethyl)phenyl]-1H-indazole

The title compound was prepared as described in Example 2 B using 3-trifluoromethylphenyl boronic acid (40 mg, 0.10 mmol) (23 mg, 75% yield). $^1$H NMR (DMSO-d$_6$) δ 8.95 (s, 1H), 8.36 (d, 1H), 8.3 (m, 2H), 7.85–7.8 (m, 3H); ES-MS (m/z) 308 [M+1]$^+$.

Example 23

SYNTHESIS OF 3-(3,4-DIMETHOXYPHENYL)-5-NITRO-1H-INDAZOLE

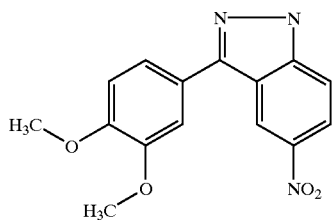

A. 3-(3,4-Dimethoxyphenyl)-1-[2-(methoxyethoxy)methyl]-5-nitro-1H-indazole

The title compound was prepared as described in Example 2 B, using 3-bromo-1-[2-(methoxyethoxy)methyl]-5-nitro-1H-indazole (0.50 g, 1.5 mmol) and 3,4-dimethoxyphenylboronic acid (0.40 g, 2.2 mmol) (0.467 g, 80% yield): $^1$H NMR (CDCl$_3$) δ 8.97 (s, 1H), 8.35 (d, 1H), 7.70 (d, 1H), 7.51 (m, 2H), 7.06 (d, 1H), 5.89 (s, 2h), 4.01 (s, 3H), 4.00 (s, 3H), 3.72 (m, 2H), 3.51 (m, 2H), 3.56 (s, 3H); EI-MS (m/z) 387 [M]$^+$.

B. 3-(3,4-Dimethoxyphenyl)-5-nitro-1H-indazole

The title compound was prepared as described in Example 21 D, using 3(3,4-dimethoxyphenyl)-1-[2-(methoxyethoxy)methyl]-5-nitro-1H-indazole (0.387 g, 1.0 mmol) (0.205 g, 69% yield): mp 172–173° C.; $^1$H NMR (DMSO-d$_6$) δ 13.79 (br, 1H), 8.89 (d, 1H), 8.25 (dd, 1H), 7.77 (d, 1H), 7.57 (dd, 1H), 7.51 (s, 1H), 7.17 (d, 1H), 3.88 (s, 3H), 3.85 (s, 3H); ES-MS (m/z) 300 [M+1]$^+$.

Example 24

SYNTHESIS OF 5-NITRO-3-(3-NITROPHENYL)-1H-INDAZOLE

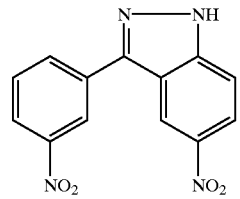

A. 1-[2-(Methoxyethoxy)methyl]-5-nitro-3-(3-nitrophenyl)-1H-indazole

The title compound was prepared as described in Example 2 B, using 3-bromo-1-[2-(methoxyethoxy)methyl]-5-nitro-1H-indazole (0.50 g, 1.5 mmol) and 3-nitrophenylboronic acid (0.376 g, 2.25 mmol) (0.487 g, 87% yield): $^1$H NMR (CDCl$_3$) δ 8.98 (d, 1H), 8.86 (s, 1H), 8.30–8.42 (m, 3H), 7.77 (m, 2H), 5.94 (s, 2H), 3.54 (m, 21H), 3.36 (s, 3H); EI-MS (m/z) 372 [M]$^+$.

B. 5-Nitro-3-(3-nitrophenyl)-1H-indazole

The title compound was prepared as described in Example 21 D, using 1-[2-(methoxyethoxy)methyl]-5-nitro-3-(3-nitrophenyl)-1H-indazole (0.42 g, 1.13 mmol) (0.208 g, 65% yield): mp 249–251° C.; $^1$H NMR (DMSO-d$_6$) δ 14.00 (br s, 1H), 9.00 (s, 1H), 8.73 (s, 1H), 8.51 (d, 1H), 8.30 (m, 2H), 7.85 (m, 2H); ES-MS (m/z) 285 [M+1]$^+$.

Example 25

SYNTHESIS OF 3-NAPHTHYL-5-NITRO-1H-INDAZOLE

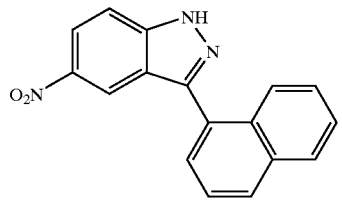

A. 3-Naphthyl-5-nitro-1H-indazole

The title compound was prepared as described in Example 2 B using 1-napthyl boronic acid (117 mg, 0.68 mmol) (90 mg, 46% yield). $^1$H NMR (DMSO-d$_6$) δ 14.09 (s, 1H), 8.52 (s, 1H, 8.27 (dd, 2H), 8.11 (t, 2H) 7.86 (t, 2H), 7.73 (t, 1H), 7.6 (m, 2H); ES-MS (m/z) 290 [M+1]$^+$.

Example 26

SYNTHESIS OF 3-(2-NAPHTHYL)-5-NITRO-1H-INDAZOLE

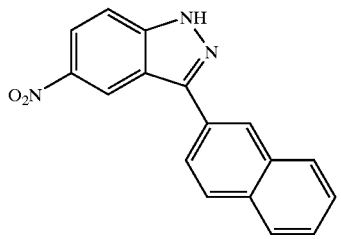

A. 3-(2-Naphthyl)-5-nitro-1H-indazole

The title compound was prepared as described in Example 2 B using 2-napthyl boronic acid (51 mg, 0.68 mmol) (95 mg, 48% yield). $^1$H NMR (DMSO-$d_6$) δ 14.01 (s, 1H), 9.11 (s, 1H), 8.62 (s, 1H) 8.30 (d, 1H), 8.0–8.1 (m, 3H), 8.0 (m, 1H), 7.82 (d, 1H), 7.6 (m, 2H); ES-MS (m/z) 290 [M+1]$^+$.

Example 27

SYNTHESIS OF 3-(5-NITRO-1H-INDAZOL-3-YL)FURAN

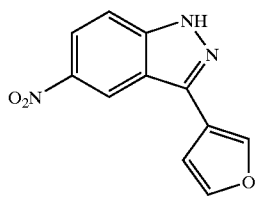

A. 3-(5-Nitro-1H-indazol-3-yl)furan

The title compound was prepared as described in Example 2 B using 3-furan boronic acid (51 mg, 0.45 mmol) (14 mg, 20% yield). HPLC retention time on C18 column, 24.3 min. ES-MS (m/z) 230 [M+1]$^+$.

Example 28

SYNTHESIS OF 3-ETHOXY-1-(5-NITRO(1H-INDAZOL-3-Yl))BENZENE

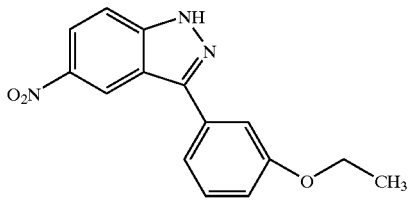

A. 3-Ethoxy-1-(5-nitro(1H-indazol-3-yl))benzene

The title compound was prepared as described in Example 2 B using 3-ethoxyphenyl boronic acid (75 mg, 0.45 mmol) (75 mg, 82% yield). ES-MS (m/z) 284 [M+1]$^+$.

Example 29

SYNTHESIS OF 3-[3-(METHYLETHYL)PHENYL]-5-NITRO-1H-INDAZOLE

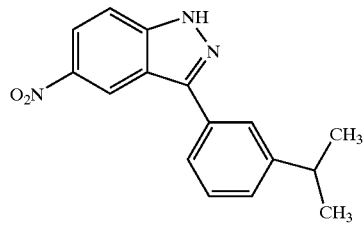

A. 3-[3-(Methylethyl)phenyl]-5-nitro-1H-indazole

The title compound was prepared as described in Example 2 B using 3-isopropylphenyl boronic acid (74 mg, 0.45 mmol) (40 mg, 47% yield). ES-MS (m/z) 282 [M+1]$^+$.

Example 30

SYNTHESIS OF 3-[4-(METHYLETHYL)PHENYL]-5-NITRO-1H-INDAZOLE

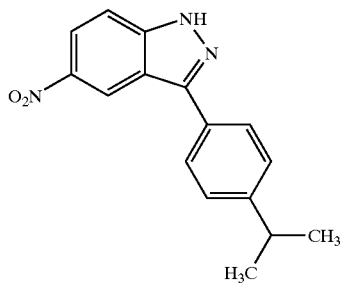

A. 3-[4-(Methylethyl)phenyl-5-nitro-1H-indazole

The title compound was prepared as described in Example 2 B using 4-isopropylphenyl boronic acid (74 mg, 0.45 mmol) (43 mg, 47% yield). ES-MS (m/z) 282 [M+1]$^+$.

Example 31

SYNTHESIS OF 5-NITRO-3-(3-PHENYLPHENYL)-1H-INDAZOLE

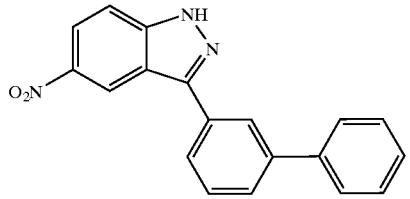

A. 5-Nitro-3-(3-phenylphenyl)-1H-indazole

The title compound was prepared as described in Example 2 B using 3-metabiphenyl boronic acid (89 mg, 0.45 mmol) (50 mg, 53% yield). ES-MS (m/z) 316 [M+1]$^+$.

Example 32

SYNTHESIS OF 5-NITRO-3-(4-PHENYLPHENYL)-1H-INDAZOLE

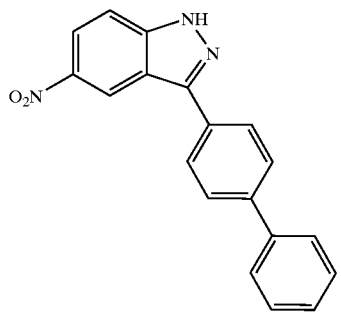

A. 5-Nitro-3-(4-phenylphenyl)-1H-indazole

The title compound was prepared as described in Example 2 B using 3-phenylphenylboronic acid (89 mg, 0.45 mmol) (52 mg, 53% yield). ES-MS (m/z) 316 [M+1]$^+$.

Example 33

SYNTHESIS OF 5-AMINO-3-(3,4-DIMETHOXYPHENYL)-1H-INDAZOLE TRIFLOUROACETATE

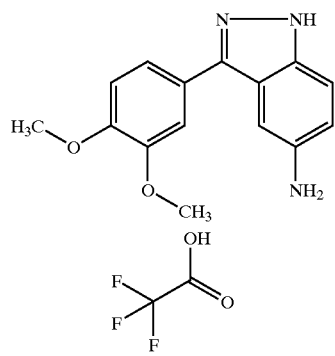

A. 5-Amino-3-(3,4-dimethoxyphenyl)-1H-indazole Trifluoroacetate

A suspension of 3-(3,4-dimethoxyphenyl)-5-nitro-1H-indazole (0.20 g, 0.67 mmol) and palladium (10 wt % on activated carbon, 30 mg) in ethanol (20 mL) with 5 drops of concentrated hydrochloric acid was stirred under hydrogen at ambient temperature for 24 hours. It was filtered with celite and washed with ethanol. The filtrate was concentrated and the residue was purified by preparative HPLC to provide the title compound (0.021 g, 12% yield): mp 150° C. (dec.); $^1$H NMR (DMSO-d$_6$) δ 13.4 (br s, 1H), 9.8 (br s, 2H), 7.96 (s, 1H), 7.68 (d, 1H), 7.46 (m, 2H), 7.32 (d, 1H), 7.13 (d, 1H), 3.87 (s, 3H), 3.83 (s, 3H); ES-MS (m/z) 270 [M+1]$^+$.

Example 34

SYNTHESIS OF 5-AMINO-3-(4-METHOXYPHENYL)-1H-INDAZOLE HYDROCHLORIDE

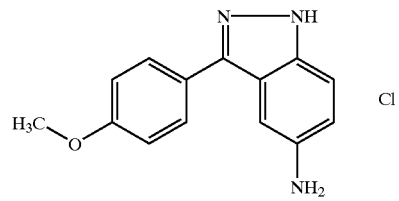

A. 5-Amino-3-(4-methoxyphenyl)-1H-indazole Hydrochloride

The title compound was prepared as described in Example 33 A, using 3-(4-methoxyphenyl)-5-nitro-1H-indazole (0.22 g, 0.8 mmol) (0.121 g, 55% yield): mp 240° C. (dec.); $^1$H NMR (DMSO-d$_6$) δ 13.0 (br s, 1H), 10.45 (br s, 2H), 8.10 (s, 1H), 7.85 (d, 2H), 7.72 (d, 1H), 7.41 (dd, 1H), 7.13 (d, 2H); ES-MS (m/z) 240 [M+1]$^+$.

Example 35

SYNTHESIS OF 3-[3-(TRIFLUOROMETHYL)PHENYL]-1H-INDAZOLE-5-YLAMINE

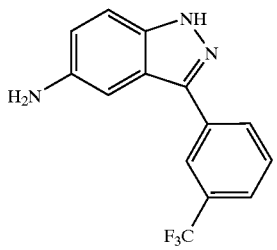

A 3-[3-(Trifluoromethyl)phenyl]-1H-indazole-5-ylamine

The title compound was prepared as described in Example 36 (15 mg, 5% yield). $^1$H NMR (DMSO-d$_6$) δ 13.02 (s, 1H), 8.20 (d, 1H), 8.16 (s, 1H), 7.7–7.68 (m, 2H), 7.34 (d, 1H), 7.11 (s, 1H), 6.86 (d, 1H), 5.0 (br s, 2H); ES-MS (m/z) 278 [M+1]$^+$.

Example 36

SYNTHESIS OF 3-(4-FLUROPHENYL)-1H-INDAZOLE-5-YLAMINE

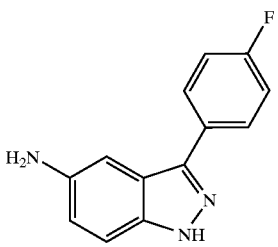

A. 3-(4-Fluorophenyl)-1H-indazole-5-ylamine

To a solution of 1-{[3-(4-fluorophenyl)-5-nitro(1H-indazolyl)]methoxy}-2-methoxyethane (100 mg, 0.29 mmol) in ethanol (30 mL) was added a scoup of Pd/carbon. The reaction was stirred overnight at room temperature under an atmosphere of hydrogen. It was filtered over celite and the solution concentrated to an oil. The oil was taken up in methanol (20 mL) and 6N HCl (20 mL) and the solution was heated to 75° C. for 3 hours. The solution was concentrated under vacuo, added to saturated bicarbonate (100 mL) and extracted with ethyl acetate (3×30 mL). The organic layers were dried (Na$_2$SO$_4$), concentrated to an oil and chromatographed on silica gel, eluting with 50% ethyl acetate/hexane to give the title compound (35 mg, 53% yield). $^1$H NMR (CDCl$_3$) δ 10.1 (br s, 1H), 7.89 (dd, 1H), 7.23–7.16 (m, 4H), 6.91 (dd, 1H), 3.6 (br s, 1H); ES-MS (m/z) 228 [M+1 ]$^+$.

Example 37

SYNTHESIS OF ETHYL[3-(4-FLUOROPHENYL)(1H-INDAZOL-5-Yl)]AMINE

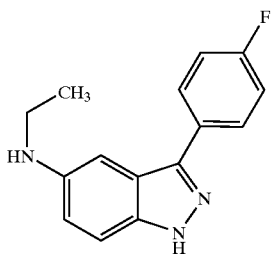

A. Ethyl[3-(4-fluorophenyl)(1H-indazol-5-yl)]amine

To a solution of 1-{[3-(4-fluorophenyl)-5-nitro(1H-indazolyl)]methoxy}-2-methoxyethane (100 mg, 0.29 mmol) in ethanol (30 mL, containing a contaminant of acetaldehyde) was added a scoup of Pd/carbon. The reaction was stirred overnight at room temperature under an atmosphere of hydrogen. It was filtered over celite and the solution concentrated to an oil. The oil was taken up in methanol (20 mL) and 6N HCl (20 mL) and heated to 75° C. for 3 hours. The solution was concentrated under vacuo, added to saturated bicarbonate (100 mL), and extracted with ethyl acetate (3×30 mL). The organic layers were dried (Na$_2$SO$_4$), concentrated to an oil and chromatographed on silica gel, eluting with 50% ethyl acetate/hexane to give the title compound (8 mg, 11% yield). $^1$H NMR (CDCl$_3$) δ 10.4 (br s, 1H), 7.91 (dd, 2H), 7.26–7.17 (m, 3H), 6.99 (s, 1H), 6.84 (dd, 1H), 3.21 (q, 2H), 1.31 (t, 3H); ES-MS (m/z) 256 [M+1]$^+$.

Example 38

SYNTHESIS OF N-[3-(4-FLUOROPHENYL)(1H-INDAZOL-5-YL)](2-METHYLPHENYL)CARBOXAMIDE

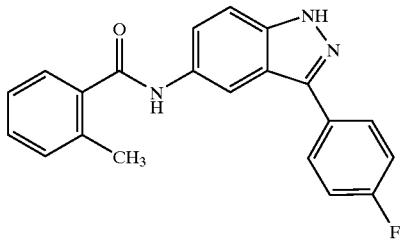

To a solution of 1-{[3-(4-fluorophenyl)-5-amino(1H-indazolyl)]methoxy}-2-methoxyethane (100 mg, 0.32 mmol) in pyridine (3 mL) was added benzoyl chloride (45 μL, 0.38 mmol). The solution was stirred for 12 hours when water (80 mL) was added and the solid filtered. The solid was then taken up in methanol (3 mL) and 6N HCl (3 mL) and heated to 80° C. for 3 hours. Water (80 mL) was then added and the solid filtered and dried to give the title compound (20 mg, 19% yield). $^1$H NMR (DMSO-d$_6$) δ 13.3 (br s, 1H), 10.37 (s, 1H), 8.57 (s, 1H), 8.0–7.9 (m, 5H), 7.78 (d, 1H), 7.6–7.5 (m, 4H), 7.40 (t, 2H); ES-MS (m/z) 332 [M+1]$^+$.

Example 39

SYNTHESIS OF N-[3-(4-FLUOROPHENYL)(1H-INDAZOL-5-YL)](2-METHOXYPHENYL)CARBOXAMIDE

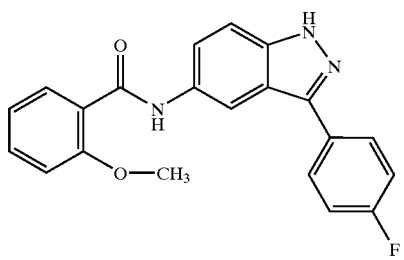

A. N-[3-(4-Fluorophenyl)(1H-indazol-5-yl)](2-methoxyphenyl)carboxamide

The title compound was prepared as described in Example 38 using 2-methoxybenzoyl chloride (73 μL, 0.45 mmol) (45 mg, 39% yield). $^1$H NMR (DMSO-d$_6$) δ 13.2 (br s, 1H), 10.35 (s, 1H), 8.55 (s, 1H), 7.98 (dd, 2H), 7.78 (d, 1H), 7.58 (d, 2H), 7.54 (s, 1H), 7.46 (t, 1H), 7.39 (t, 2H), 7.16 (dd, 1H), 3.85 (s, 3H); ES-MS (m/z) 362 [M+1]$^+$.

Example 40

SYNTHESIS OF N-[3-(4-FLUOROPHENYL)(1H-INDAZOL-5-YL)](4-PHENYLPHENYL)CARBOXAMIDE

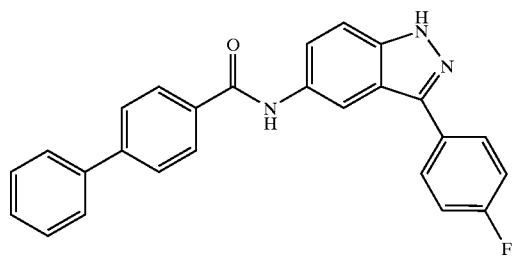

A. N-[3-(4-Fluorophenyl)(1H-indazol-5-yl)]1(4-phenylphenyl)carboxamide

The title compound was prepared as described in Example 38 using 4-phenylbenzoyl chloride (83 mg, 0.45 mmol) (55 mg, 42% yield). $^1$H NMR (DMSO-d$_6$) δ 13.3 (br s, 1H), 10.41 (s, 1H), 8.59 (s, 1H), 8.11 (d, 2H), 7.99 (dd, 2H), 7.8 (m, 3H), 7.77 (d, 3H), 7.60 (d, 1H), 7.52 (t, 2H), 7.44 (d, 1H), 7.39 (d, 1H); ES-MS (m/z) 408 [M+1]$^+$.

Example 41

SYNTHESIS OF BENZO[B]THIOPHEN-2-YL-N-[3-(4-FLUOROPHENYL)(1H-INDAZOL-5-YL)]CARBOXAMIDE

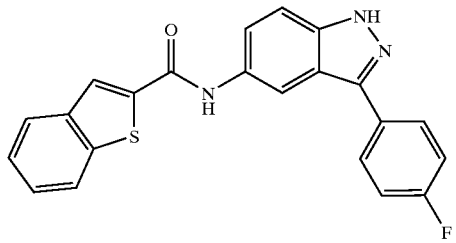

A. Benzor[b]thiophen-2-yl-N-[3-(4-fluorophenyl)(1H-indazol-5-yl)]carboxamide

The title compound was prepared as described in Example 38 using 2-thiophenecarbonyl chloride (75 mg, 0.45 mmol) (48 mg, 39% yield). $^1$H NMR (DMSO-d$_6$) δ 13.3 (br s, 1H), 10.66 (s, 1H), 8.55 (s, 1H), 8.41 (s, 1H), 8.1–7.9 (m, 4 H), 7.80 (d, 1H), 7.63 (d, 1H), 7.50 (m, 2H), 7.41 (t, 2H); ES-MS (m/z) 388 [M+1]$^+$.

Example 42

SYNTHESIS OF [3-(4-(FLUOROPHENYL)(1H-INDAZOL-5-YL)](PHENYLSULFONYL)AMINE

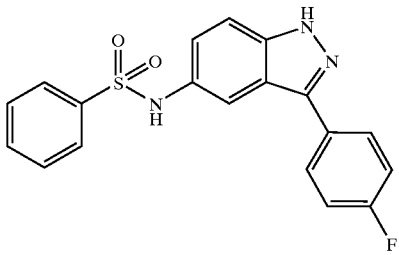

A. [3-(4-Fluorophenyl)(1H-indazol-5-yl)](phenylsulfonyl)amine

The title compound was prepared as described in Example 38 using -phenylsulfonyl chloride (56 μL, 0.45 mmol) (55 mg, 42% yield). $^1$H NMR (DMSO-d$_6$) δ 13.25 (s, 1H), 10.1 (s, 1H), 7.77 (dd, 2H), 7.7–7.6 (m, 2H), 7.6–7.5 (m, 4H), 7.46 (d, 1H), 7.38 (t, 2H), 7.12 (dd, 1H); ES-MS (m/z) 368 [M+1]$^+$.

Example 43

SYNTHESIS OF METHYL 4-{N-[3-(4-(FLUOROPHENYL)-1H-INDAZOL-5-YL]CARBAMOYL}BENZOATE

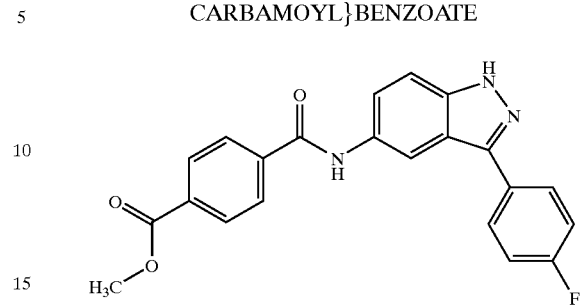

A. Methyl 4-{N-[3-(4-fluorophenyl)-1H-indazol-5-yl]carbamoyl}benzoate

The title compound was prepared as described in Example 38 using methyl 4-carboxybenzoyl chloride (87 mg, 0.45 mmol) (35 mg, 28% yield). $^1$H NMR (DMSO-d$_6$) δ 13.3 (s, 1H), 10.6 (s, 1H), 8.56 (s, 2H), 8.12 (s, 4H), 7.98(dd, 2H), 7.80 (d, 1H), 7.61 (d, 1H), 7.40 (t, 2H), 3.91 (s, 3H); ES-MS (m/z) 390 [M+1]$^+$.

Example 44

SYNTHESIS OF N-[3-(4-FLUOROPHENYL)(1H-INDAZOL-5-YL)]-2-PYRIDYLCARBOXAMIDE

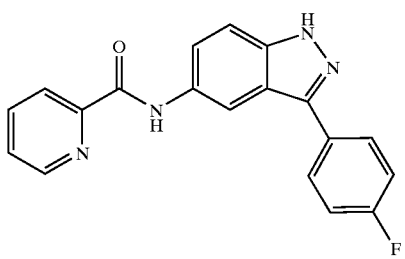

A. N-[3-(4-Fluorophenyl)(H-indazol-5-yl]-2-pyridylcarboxamide

The title compound was prepared as described in Example 38 using pyridine-2-carbonyl chloride hydrochloride (40 μL, 0.45 mmol) (35 mg, 33% yield). $^1$H NMR (DMSO-d$_6$) δ 13.3 (s, 1H), 10.8 (s, 1H), 8.77 (d, 1H), 8.72 (s, 1H), 8.19 (d, 1H), 8.09 (dt, 1H), 8.0–7.9 (m, 3H), 7.7 (t, 1H), 7.59 (d, 1H), 7.40 (t, 2H); ES-MS (m/z) 333 ]M+1]$^+$.

Example 45

SYNTHESIS OF 4-{N-[3-(4-(FLUOROPHENYL)-1H-Indazol-5-YL]CARBAMOYL}BENZOIC ACID

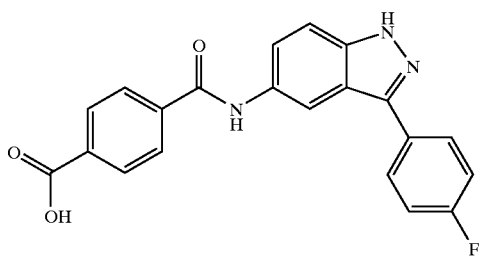

A. 4-{N-[3-(4-Fluorophenyl)-1H-indazol-5-yl]carbamoyl}benzoic acid

The title compound was prepared as described in Example 48 (11 mg, 85% yield). $^1$H NMR (DMSO-d$_6$) δ 13.2 (s, 1H), 10.5 (s, 1H), 8.56 (s, 1H), 8.10 (s, 4H), 7.99 (dd, 1H), 7.8 (d, 1H), 7.61 (d, 1H), 7.40 (t, 2H); ES-MS (m/z) 376 [M+1]$^+$.

Example 46

SYNTHESIS OF CYCLOPROPYL-N-[3-(4-(FLUOROPHENYL)(1H-INDAZOL-5-YL)]CARBOXAMIDE

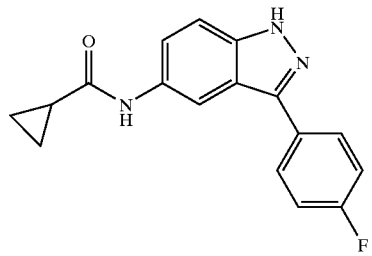

A. Cyclopropyl-N-[3-(4-fluorophenyl)(1H-indazol-5-yl)]carboxamide

The title compound was prepared as described in Example 38 using cyclopropyl carbonyl chloride (40 μL, 0.45 mmol) (35 mg, 33% yield). $^1$H NMR (DMSO-d$_6$) δ 13.2 (br s, 1H), 10.3 (s, 1H), 8.45 (s, 1H), 7.92 (dd, 2H), 7.51 (d, 2H), 7.37 (t, 2H), 1.8 (m, 1H), 0.81 (m, 4H); ES-MS (m/z) 296 [M+1]$^+$.

Example 47

SYNTHESIS OF METHYL 4-{N-[3-(4-(FLUOROPHENYL)(1H-INDAZOL-5-YL)]-N-METHYLCARBAMOYL}BENZOATE

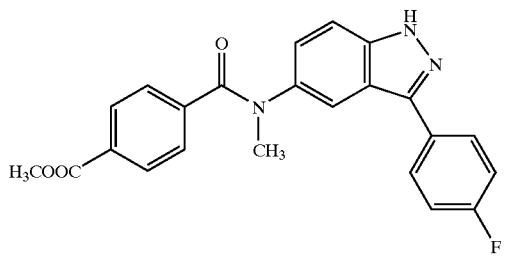

A. Methyl 4-(N-{3-(4-fluorophenyl)-1-[(2-methoxyethoxy)methyl]-1H-indazole-5-yl]carbamoyl)benzoate To a suspension of 1-{3-fluorophenyl)-5-amino(1H-indazoloyl)]methoxy}-2-methoxyethane (1.51 g, 3.17 mmol) in dichloromethane (55 mL) was added triethylamine (4.75 g, 4.75 mmol), and 4-(dimenthylamino)pyridine (193 mg, 1.58 mmol). The solution was allowed to stir for 15 minutes, then terephthalic acid chloride hydrochloride (753 mg, 3.80 mmol) was added. The reaction mixture was allowed to stir for 18 hours. The solution was acidified to pH 8 using 5% HCl and extracted with dichloromethane. The extracts were dried over sodium sulfate, filtered and concentrated. The residue was purified by chromoatography (SiO$_2$, 60% ethyl acetate/hexanes) to provide the title compound (1.36 g, 60% yield). $^1$H NMR (DMSO-d$_6$) δ 10.57 (s, 1H), 8.54 (s, 1H), 8.09 (s, 4H), 7.95 (m, 2H), 7.83 (m, 2H), 5.83 (s, 2H), 3.88 (s, 3H), 3.60 (t, 2H), 3.38 (m, 2H), 3.16 (s, 3H); ES-MS (m/z) 478 [M+1]$^+$.

B. Methyl 4-(N-{3-(fluorophenyl)-1[(2-methoxyethoxy)methyl](1H-indazol-5-yl)}-N-methylcarbamoyl)benzoate To a flask containing Example 47 A (300 mg, 0.628 mmol) in dimethyl formamide (12 mL), was added 1.0 M sodium bis-trimethylsilyl amide (0.753 mL in THF). The solution was stirred for 30 minutes. Methyl Iodide (134 mg, 0.942 mmol) was then added and stirring continued at room temperature for 18 hours. The solution was condensed and water (25 mL) added. The aqueous phase was extracted with ethyl acetate. The extracts were combined, dried over sodium sulfate, filtered and condensed to give an oil. The oil was purified by chromatography (SiO$_2$, 60% ethyl acetate/hexanes) to afford the title compound (220 mg, 74% yield). $^1$H NMR (DMSO-d$_6$) δ 7.90 (m, 3H), 7.69 (m, 3H), 7.43 (br s, 2H), 7.32 (t, 3H), 5.75 (s, 2H), 3.72 (s, 3H), 3.54 (m, 2H), 3.43 (s, 3H), 3.09 (s, 3H); ES-MS (m/z) 492 [M+1]$^+$.

C. Methyl 4-{N-[3-(4-fluorophenyl)(1H-indazol-5-yl)]-N-methylcarbamoyl)}benzoate To a solution containing Example 47 B (229 mg, 0.466 mmol) in methanol (7 mL) was added 6N HCl (7 mL). The reaction mixture was allowed to stir at room temperature for 18 hours. The resulting precipitate was filtered, dried and purified by chromatography (SiO$_2$, 40% ethyl acetate/hexanes) to afford the title compound (100 mg, 53% yield). $^1$H NMR (DMSO-d$_6$) δ 13.26 (s, 1H), 7.86 (s, 3H), 7.71 (br s, 2H), 7.41 (br s, 3H), 7.26 (m, 3H), 3.72 (s, 3H), 3.42 (s, 3H); ES-MS (m/z) 404 [M+1]$^+$.

Example 48

SYNTHESIS OF 4-{N-[3-(FLUOROPHENYL)(1H-INDAZOL-5-YL)]-N-METHYLCARBAMOYL}BENZOIC ACID

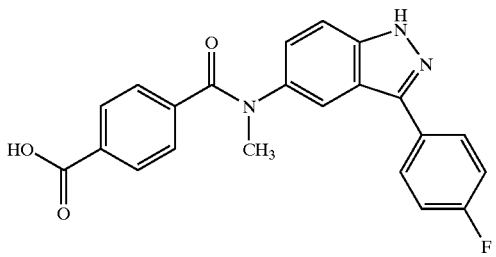

A. 4-{{N-(Fluorophenyl)(1H-indazol-5-yl)}-N-methylcarbamoyl}benzoic acid

To a solution containing Example 47 C (100 mg, 0.250 mmol) in tetrahydrofuran (5 mL) and water (5 mL), was added lithium hydroxide hydrate (52 mg). The solution was allowed to stir at room temperature for 3 hours. The reaction mixture was acidified using 5% HCl. The solution was condensed to afford a solid which was filtered and dried to provide the title compound (93 mg, 89% yield). $^1$H NMR (DMSO-d$_6$) δ 13.28 (br s, 1H), 13.01 (br s, 1H), 7.85 (s, 3H), 7.67 (s, 3H), 7.29 (m, 6H), 3.42 (s, 3H); ES-MS (m/z) 390 [M+1]$^+$.

Example 49

SYNTHESIS OF METHYL 3-{N-[(4-(FLUOROPHENYL)-1H-INDAZOL-5-YL}CARBAMOYL}BENZOATE

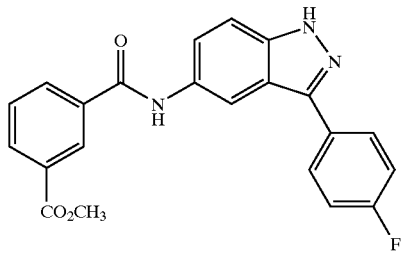

A. Methyl 3-{N-(4-fluorophenyl)-1-perhydro-2H pyran-2-yl-1H-indazol-5-yl]carbamoyl}benzoate To a solution of isophthalic acid monomethyl ester (138 mg, 0.770 mmol) in dimethyl formamide (8 mL) was added 1-ethyl-(3-dimethylamino)carbodiimide hydrochloride (147 mg, 0.770 mmol). The mixture was allowed to stir for 20 minutes, then, 2-[3-(4-fluorophenyl)-5-amino-1H-indazoloyl]perhydro-2H-pyran (200 mg, 0.642 mmol) was added. The reaction mixture was stirred at ambient temperature for 18 hours. The solution was condensed and extracted with water and ethyl acetate. The extracts were dried over sodium sulfate, filtered and condensed to afford the title compound (180 mg, 60% yield). $^1$H NMR (DMSO-$d_6$) δ 10.56 (s, 1H), 8.52 (s, 1H), 8.09 (s, 4H), 7.93 (s, 2H), 7.80 (m, 2H), 7.38 (t, 2H), 5.90 (d, 1H), 3.88 (s, 3H), 3.79 (br s, 1H), 2.05 (br s, 2H), 1.79 (br s, 1H), 1.60 (br s, 2H); ES-MS (m/z) 474 [M+1]$^+$.

B. Methyl 3-{N-[4-fluorophenyl)-1H-indazol-5-yl}carbamoyl}benzoate

The title compound was prepared as described in Example 47 C (140 mg, 94% yield). $^1$H NMR (DMSO-$d_6$) δ 13.22 (br s, 1H), 10.55 (s, 1H), 8.54 (d, 2H), 8.25 (d, 1H), 8.15 (d, 1H), 7.96 (m, 2H), 7.69 (m, 3H), 7.37 (t, 2H), 3.90 (s, 3H); ES-MS (m/z) 390 [M+1]$^+$.

Example 50

SYNTHESIS OF 3-{N-[3-(4-(FLUOROPHENYL)-1H-INDAZOL-5-YL]CARBAMOYL}BENZOIC ACID

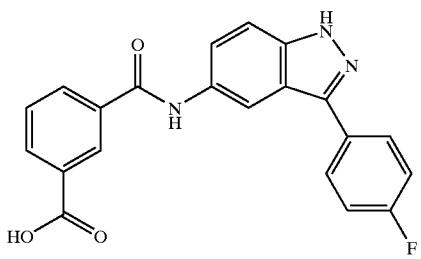

A. 3-{N-[3-(4-Fluorophenyl)-1H-indazol-5-yl]carbamoyl}benzoic acid

The title compound was prepared as in Example 48 A (32 mg, 67% yield). $^1$H NMR (DMSO-$d_6$) δ 13.23 (br s, 2H), 10.52 (s, 1H), 8.53 (d, 2H), 8.21 (d, 1H), 8.11 (d, 1H), 7.95 (m, 2H), 7.66 (m, 3H), 7.37 (m, 2H); ES-MS (m/z) 376 [M+1]$^+$.

Example 51

SYNTHESIS OF N-[3-(4-(FLUOROPHENYL)-(1H-INDAZOL-5-YL)][4-(N-METHYLCARBAMOYL)PHENYL] CARBOXAMIDE

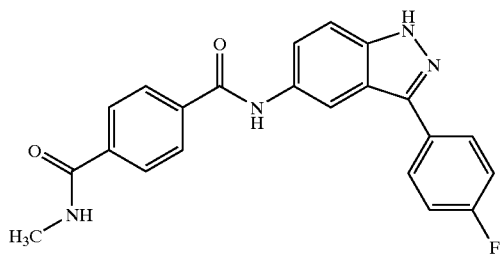

A. N-[3-(4-Fluorophenyl)(1H-indazol-5-yl)][4-(N-methylcarbamoyl) phenyl]carboxamide The product of example 45 (50 mg, 0.128 mmol) in methylamine (40% in water, 3mL) was heated in a sealed tube at 100° C. for two hours. The resulting precipitate was filtered and washed with small portions of ethyl acetate to afford the title compound (33 mg, 67% yield). $^1$H NMR (DMSO-$d_6$) δ 13.22 (br s, 1H), 10.41 (s, 1H), 8.58 (m, 1H), 8.52 (s, 1H), 8.00 (m, 6H), 7.75 (d, 1H), 7.56 (d, 1H), 7.36 (t, 2H), 2.79 (m, 3H); ES-MS (m/z) 389[M+1]$^+$.

Example 52

SYNTHESIS OF 4-{N-[3-(4-(FLUOROPHENYL)-1H-INDAZOL-5-YL) CARBAMOYL}BENZAMIDE

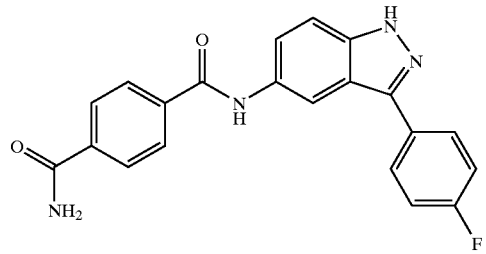

A. 4-{N-[3-(4-Fluorophenyl)-1H-indazol-5-yl]carbamoyl}benzamide

The product of example 45 (195 mg, 0.500 mmol) in concentrated ammonium hydroxide (5 mL) and ammonium chloride (1.00 mg) was heated in a sealed tube at 100° C. for 4 hours. The resulting precipitate was filtered, dried and purified by chromatography (SiO$_2$, 80% ethyl acetate/hexanes) to provide the title compound (25 mg, 13% yield). $^1$H NMR (DMSO-$d_6$) δ 13.24 (br s, 1H), 10.42 (s, 1H), 8.53 (s, 1H), 8.12 (s, 1H), 7.97 (m, 6H), 7.74 (d, 1H), 7.55 (m, 2H), 7.37 (t, 2H); ES-MS (m/z) 375 [M+1]$^+$.

Example 53

SYNTHESIS OF 1,4-{N-[3-(4-METHOXYPHENYL)-1H-INDAZOL-5-YL]CARBAMOYL}BENZOIC ACID

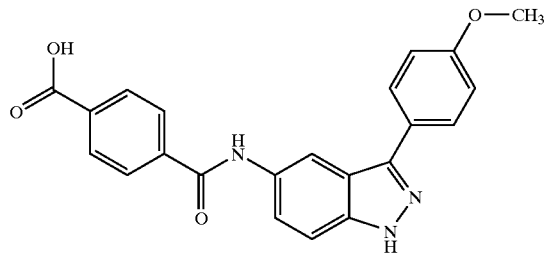

A. 4-Methoxy-1-(5-nitro-1-perhydro-2H-pyran-2-yl(1H-indazol-3-yl))benzene

To a solution of 2-(3-bromo-5-nitro-1H-indazolyl)perhydro-2H-pyran (0.5 g, 1.53 mmol) in ethylene glycol dimethyl ether (10 mL) was added 4-methoxy phenyl boronic acid (0.349 g, 2.3 mmol), [1,1'-bis(diphenylphosphino)-ferrocene] complex with dichloromethane (1:1) (0.177 g, 0.153 mmol) and potassium phosphate (1.62 g, 7.65 mmol). The reaction mixture was heated to reflux temperature for 12 hours. The solvent was then evaporated to dryness and the residue was dissolved in 10 mL of ethyl acetate. The heterogeneous solution was washed 3 times with 5 mL of water and once with 5 mL of brine. The organic layer was dried over $Na_2SO_4$ and evaporated to dryness. The resulting brown solid was adsorbed on silica gel and purified by column chromatography (80:20 hexanes/ethyl acetate) to provide the title compound (0.411 g, 65% yield): ES-MS (m/z) 354 [M+H]$^+$.

B. 3-(4-Methoxyphenyl)-1-perhydro-2H-pyran-2-yl-1H-indazole-5-ylamine

To a solution of 4-methoxy-1-(5-nitro-1-perhydro-2H-pyran-2-yl(1H-indazol-3-yl))benzene (0.411 g, 1.16 mmol) in ethyl acetate (15 mL), purged with nitrogen gas was added 15 mg of palladium on activated carbon (10 wt. %). The flask was purged with hydrogen and the reaction was stirred at room temperature for 6 hours under 1 atm of $H_2$. The catalyst was filtered and washed twice with 5-mL portions of ethyl acetate. The filtrate was concentrated to dryness to afford the title compound (0.347 g, 92% yield): ES-MS (m/z) 324 [M+1]$^+$.

C. Methyl 4-{N-[3-(4-methoxyphenyl)-1H-indazol-5-yl]carbamoyl}benzoate

To a solution of 3-(4-methoxyphenyl)-1-perhydro-2H-pyran-2-yl-1H-indazole-5-ylamine (0.347 g, 1.07 mmol) in tetrahydrofuran (8.5 mL) was added triethyl amine (0.224 mL, 1.605 mmol). The solution was cooled to 0° C. before 4-methoxybenzoyl chloride was added as a solid in one portion (0.234 g, 1.17 mmol). The reaction was stirred at room temperature for 48 hours. The crude reaction mixture was partitioned between water and ethyl acetate. A white solid insoluble in water ethyl acetate or dichloromethane was removed by filtration. The filtrate was evaporated to dryness and purified by chromatography ($SiO_2$, 20–50% ethyl acetate in hexanes). The title compound was isolated as a pale pink solid (0.099 g, 19% yield): ES-MS (m/z) 486 [M+1]$^+$.

D. Methyl 4-{N-[3-(4-methoxyphenyl)-1H-indazol-5-yl]carbamoyl}benzoate

To a solution of methyl 4-{N-[3-(4-methoxyphenyl)-1-perhydro-2H-pyran-2-yl-1H-indazol-5-yl]carbamoyl}benzoate (0.099 g, 0.20 mmol) in anhydrous tetrahydrofuran (5 mL), 6.0N aqueous HCl was added (5 mL). The solution was stirred at room temperature for 48 hours. The reaction mixture was then neutralized with saturated aqueous sodium bicarbonate and the organic layer was extracted with ethyl acetate (10 mL, 3 times). The organic layer was dried over $Na_2SO_4$ and evaporated to dryness to afford the title compound (0.081 g, quantitative yield): ES-MS (m/z) 402 [M+1]$^+$.

E. 4-{N-[3-(4-methoxyphenyl)-1H-indazol-5-yl]carbamoyl}benzoic acid

To a solution of methyl 4-{N-[3-(4-methoxyphenyl)-1H-indazol-5-yl]carbamoyl}benzoate (0.089 g, 0.20 mmol) in THF (3 mL) was added lithium hydroxide monohydrate as a solid in one portion (0.042 g, 1.0 mmol). Water was added to aid solubility (0.5 mL). The reaction was stirred at room temperature for 12 hours. The pH of the solution was adjusted to 8, using 2.0 N NaOH. The aqueous phase was washed with ethyl acetate (2×10 mL). The pH was raised to 5 using 2.0 N aqueous HCl resulting in the precipitation of the title compound as a pink solid that was filtered and washed with small portions of diethyl ether. The compound was further purified by trituration in a 1:1 mixture of diethyl ether and hexanes (0.028 g, 36% yield): $^1$H NMR (DMSO-d$_6$) 13.1 (s, 1H), 10.5 (s, 1H), 8.5 (s, 1H), 8.1 (s, 2H), 7.8 (d, 2H), 7.7 (d, 2H), 7.5 (d, 2H), 3.8 (s, 3H); ES-MS (m/z) 388 [M+1]$^+$.

Example 54

SYNTHESIS OF 4-[N-(3-(4-PYRIDYL)-1H-INDAZOL-5-YL)CARBAMOYL]BENZOIC ACID

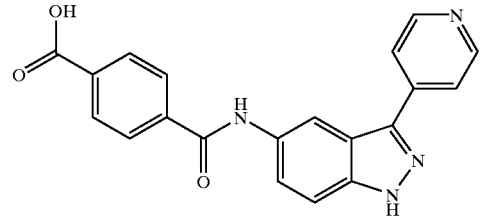

A. 2-(5-Nitro-3-(4-pyridyl)-1H-indazolyl)perhydro-2H-pyran

The title compound was prepared according to the procedure described in example 53 using 2-(3-bromo-5-nitro-1H-indazolyl)perhydro-2H-pyran (0.300 g, 0.92 mmol), 4-pyridyl boronic acid (0.170 g, 1.38 mmol), 1,1'-bis(diphenylphosphino)-ferrocene] complex with dichloromethane (1:1) (0.106 g, 0.092 mmol) and potassium phosphate (0.975 g, 4.6 mmol) (0.200 g, 67% yield): ES-MS (m/z) 325 [M+1]$^+$.

B. 1-Perhydro-2H-pyran-2-yl-3-(4-pyridyl)-1H-Indazole-5-ylamine

The title compound was prepared by hydrogenolysis using 2-(5-nitro-3-(4-pyridyl)-1H-indazolyl)perhydro-2H-pyran (0.200 g, 0.615 mmol), palladium on activated carbon (10 wt. %, 10 mg) under 1 atm of hydrogen (0,158 g, 87% yield): ES-MS (m/z) 295 [M+1]$^+$.

C. Methyl 4-[N-(1-perhydro-2H-pyran-2-yl-3-(4-pyridyl)-1H-indazol-5-yl)carbamoyl]benzoate The title compound was prepared using 1-perhydro-2H-pyran-2-yl-3-(4-pyridyl)-1H-indazole-5-ylamine (0.158 g, 0.54 mmol), 4-methoxybenzoyl chloride (0.215 g, 1.08 mmol), and triethylamine (0.150 mL, 1.08 mmol). After 3 h at room temperature and work-up, the product was isolated and used without further purification (0.158 g, 64% yield): ES-MS (m/z) 457 [M+1]$^+$.

D. Methyl 4-[N-(3-(4-pyridyl)-1H-indazol-5-yl)carbamoyl]benzoate

The title compound was prepared using methyl 4-[N-(1-perhydro-2H-pyran-2-yl-3-(4-pyridyl)-1H-indazol-5-yl)carbamoyl]benzoate (0.158 g, 035 mmol) as a solution in tetrahydrofuran (3 mL) and 6.0 N aqueous HCl (5 mL). The intermediate was isolated and used without further purification (0.129 g, quantitative): ES-MS (m/z) 373 [M+1].

E. 4-[N-(3-(4-pyridyl)-1H-indazol-5-yl)carbamoyl]benzoic acid

The title compound was prepared using methyl 4-[N-(3-(4-pyridyl)-1H-indazol-5-yl)carbamoyl]benzoate (0.129 g, 0.35 mmol) and lithium hydroxide mono hydrate (0.075 g, 1.8 mmol) in tetrahydrofuran (5 mL). The compound was isolated as a beige powder that was washed with small portions of diethyl ether (5 mL). (0.091 g, 70.5% yield) $^1$H NMR (DMSO-$d_6$) 10.2 (s, 1H), 8.5 (m, 3H), 7.9–7.8 (m, 6H), 7.6 (s, 2H); ES-MS (m/z) 359 [M+1]$^+$.

Example 55

SYNTHESIS OF N-[3-(4-(FLUOROPHENYL)(1H-INDAZOL-5-YL)BENZAMIDE

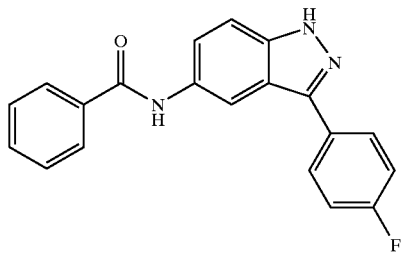

A. N-[3-(4-Fluorophenyl)(1H-indazol-5-yl)]benzamide

To a solution of 1-{[3-(4-fluorophenyl)-5-amino(1H-indazolyl)]methoxy}-2-methoxyethane (100 mg, 0.32 mmol) in pyridine (3 mL) was added benzoyl chloride (45 µL, 0.38 mmol). The solution was stirred for 12 hours when water (80 mL) was added and the solid filtered. The solid was then taken up in methanol (3 mL) and 6N HCl (3 mL) and heated to 80° C. for 3 hours. Water (80 mL) was then added and the solid filtered and dried to give the title compound (20 mg, 19% yield). $^1$H NMR (DMSO-$d_6$) δ 13.3 (br s, 1H), 10.37 (s, 1H), 8.57 (s, 1H), 8.0–7.9 (m, 5H), 7.78 (d, 1H), 7.6–7.5 (m, 4H), 7.40 (t, 2H); ES-MS (m/z) 332 [M+1]$^+$.

Example 56

SYNTHESIS OF [3,4-BIS(TRIFLUOROMETHYL)PHENYL]-N-[3-(4-(FLUOROPHENYL)(1H-INDAZOL-5-YL)]CARBOXAMIDE

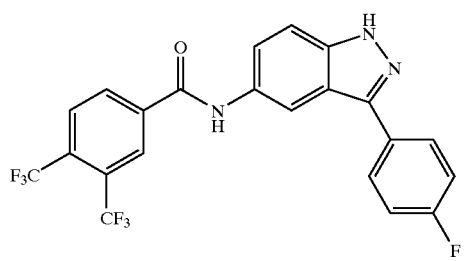

A. [3,5-bis(Trifluoromethyl)phenyl]-N-[3-(4-fluorophenyl)(1H-indazol-5-yl)]carboxamide The title compound was prepared as described in Example 55 A using 3,5-ditrifluoromethylphenylbenzoyl chloride (69 µL, 0.38 mmol) (20 mg, 11% yield). $^1$H NMR (DMSO-$d_6$) δ 13.3 (br s, 1H), 10.79 (s, 1H), 8.68 (s, 2H), 8.53 (s, 1H), 8.40 (s, 1H), 7.99 (dd, 2H), 7.79 (d, 1H), 7.64 (d, 1H), 7.40 (t, 2H); ES-MS (m/z) 468 [M+1]$^+$.

Example 57

SYNTHESIS OF N-[3-(4-(FLUOROPHENYL)(1H-INDAZOL-5-YL)]-2-FURYLCARBOXAMIDE

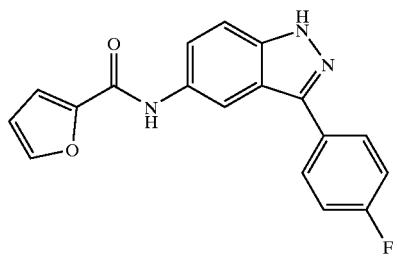

A. N-[3-(4-Fluorophenyl)(1H-indazol-5-yl)1-2-furylcarboxamide

The title compound was prepared as described in Example 55 A using 2-furyl chloride (38 µL, 0.38 mmol) (20 mg, 16% yield). $^1$H NMR (DMSO-$d_6$) δ 13.3 (br s, 1H), 10.32 (s, 1H), 8.51 (s, 1H), 8.0–7.94 (m, 3H), 7.78 (d, 1H), 7.58 (d, 1H), 7.4–7.34 (m, 3H), 7.72 (s, 1H); ES-MS (m/z) 322 [M+1]$^+$.

Example 58

SYNTHESIS OF N-[3-(4-(FLUOROPHENYL)(1H-INDAZOL-5-YL)](3,4-DICHLOROPHENYL)CARBOXAMIDE

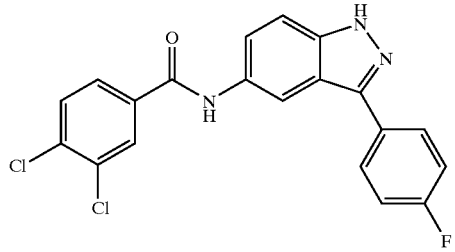

A. N-[3-(4-Fluorophenyl)(1H-Indazol-5-yl)](3,4-Dichlorophenyl)Carboxamide

The title compound was prepared as described in Example 55 A using 3,4-dichlorophenylbenzoyl chloride (80 mg, 0.38 mmol) (20 mg, 11% yield). $^1$H NMR (DMSO-$d_6$) δ 13.3 (br s, 1H), 10.52 (s, 1H), 8.52 (s, 1H), 8.28 (s, 1H), 8.0–7.9 (m, 3H), 7.85 (d, 1H), 7.78 (d, 1H), 7.61 (d, 1H), 7.40 (t, 2H); ES-MS (m/z) 400 [M+1]$^+$.

Example 59

SYNTHESIS OF N-[3-(4-(FLUOROPHENYL)(1H-INDAZOL-5-YL)](2-HYDROXYPHENYL)CARBOXAMIDE

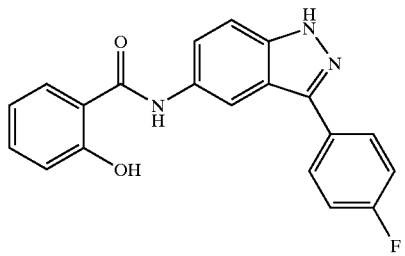

A. N-[3-(4-Fluorophenyl)(1H-indazol-5-yl) 1(2-hydroxyphenyl)carboxamide

The title compound was prepared as described in Example 55 A using 2-(chlorocarbonyl)phenyl acetate (76 mg, 0.38 mmol) (20 mg, 15% yield). $^1$H NMR (DMSO-$d_6$) δ 13.3 (br s, 1H), 12.0 (br s, 1H), 10.53 (s, 1H), 8.47 (s, 1H), 8.0–7.9 (m, 3H), 7.64 (dd, 2H), 7.4–7.3 (m, 3H), 6.9–7.0 (m, 2H); ES-MS (m/z) 348 [M+1]$^+$.

Example 60

SYNTHESIS OF (2-{N-[3-(4-(FLUOROPHENYL)-1H-INDAZOL-5-YL] CARBAMOYL}PHENYL) METHYL BENZOATE

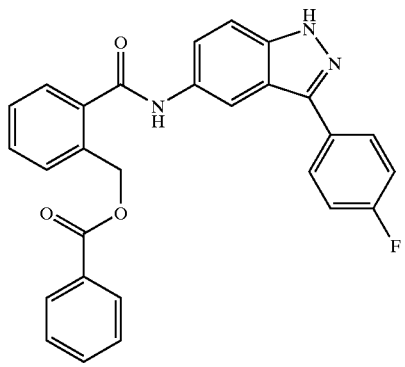

A. (2-[{N-[3-(4-Fluorophenyl)-1H-indazol-5-yl]carbamoyl phenyl)methyl benzoate

The title compound was prepared as described in Example 55 A using (2-(chlorocarbonyl)phenyl)methyl benzoate (105 mg, 0.38 mmol) (11 mg, 15% yield). $^1$H NMR (DMSO-$d_6$) δ 13.2 (br s, 1H), 10.55 (s, 1H), 8.47 (s, 1H), 7.9–7.8 (m, 4H), 7.6–7.5 (m, 7H), 7.4–7.3 (m, 4H), 5.57 (s, 2H); ES-MS (m/z) 466 [M+1]$^+$.

Example 61

SYNTHESIS OF N-[3-(4-(FLUOROPHENYL)(1H-INDAZOL-5-YL)]-4-PYRIDYLCARBOXAMIDE

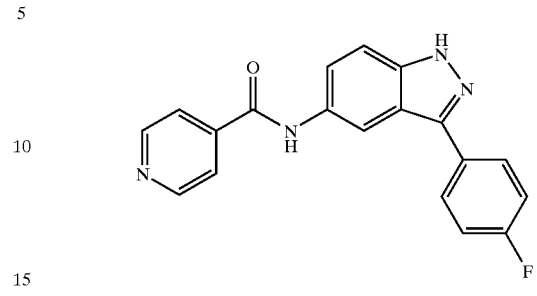

A. N-[3-(4-Fluorophenyl)(1H-indazol-5-yl)]-4-pyridylcarboxamide

The title compound was prepared as described in Example 55 A using pyridine-4-carbonyl chloride hydrochloride (119 mg, 0.67 mmol) (27 mg, 15% yield). $^1$H NMR (CDCl$_3$) δ 13.30 (s, 1H), 10.61 (s, 1H), 8.82 (s, 1H), 8.56 (s, 1H), 8.0–7.9 (m, 4H), 7.78 (d, 1H), 7.62 (d, 1H), 7.40 (t, 2H); ES-MS (m/z) 333 [M+1]$^+$.

Example 62

SYNTHESIS OF N-[3-(4-(FLUOROPHENYL)(1H-INDAZOL-5-YL)]-3-PYRIDYLCARBOXAMIDE

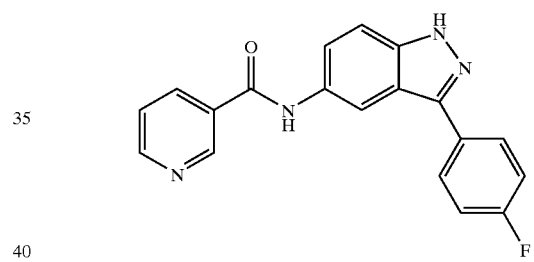

A. N-[3-(4-Fluorophenyl)(1H-indazol-5-yl)]-3-pyridylcarboxamide

The title compound was prepared as described in Example 55 A using pyridine-3-carbonyl chloride hydrochloride (152 mg, 0.86 mmol) (29 mg, 10% yield).). $^1$H NMR (CDCl$_3$) δ 13.28 (s, 1H), 10.55 (s, 1H), 9.17 (s, 1H), 8.78 (d, 1H), 8.57 (s, 1H), 8.34 (d, 1H), 7.99 (dd, 2H), 7.78 (d, 1H), 7.63–7.57 (m, 2H), 7.40 (t, 2H); ES-MS (m/z) 333 [M+1]$^+$.

Example 63

SYNTHESIS OF [3-(4-(FLUOROPHENYL)(1H-INDAZOL-5-YL)](4-PYRIDYLMETHYL)AMINE

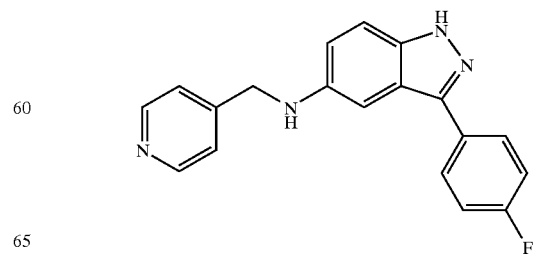

A. [3-(4-Fluorophenyl)(1H-indazol-5-yl)(4-pyridylmethyl)amine

To a solution of N-[3-(4-fluorophenyl)(1H-indazol-5-yl)]-4-pyridylcarboxamide (50 mg, 0.12 mmol) in THF (3 mL) was added lithium aluminum hydride (LAH) (9 mg, 0.24 mmol). The solution was stirred for 3 hours when an additional equivalence of LAH was added. The reaction was stirred for another 3 hours when it was quenched with ethyl acetate and water (100 mL) was added. The layers were separated and the water layer extracted with ethyl acetate (3×30 mL). The combined organic layers were dried (Na$_2$SO$_4$) and concentrated to an oil. The oil was taken up in methanol (10 mL) and 6N HCl (10 mL) and heated to 80° C. for 2 hours when it was quenched with NaHCO$_3$ and extracted with ethyl acetate. The combined organic layers were dried (Na$_2$SO$_4$) and concentrated to afford the title compound (7.5 mg, 20% yield). $^1$H NMR (CDCl$_3$) δ 8.6 (br s, 1H), 7.76 (dd, 2H), 7.35 (d, 2H), 7.24 (d, 2H), 7.15 (t, 2H), 6.9–6.8 (m, 2H), 4.43 (s, 2H); ES-MS (m/z) 319[M+1]$^+$.

Example 64

SYNTHESIS OF [3-(4-(FLUOROPHENYL)(1H-INDAZOL-5-YL)](3-PYRIDYLMETHYL)AMINE

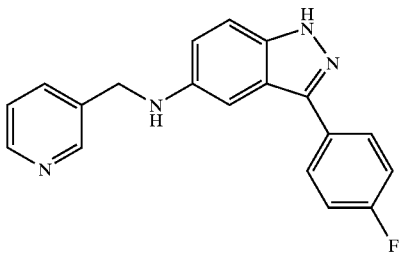

A. [3-(4-Fluorophenyl)(1H-indazol-5-yl)](3-pyridylmethyl)amine

The title compound was prepared as described in Example 63 A using N-[3-(4-fluorophenyl)(1H-indazol-5-yl)]-3-pyridylcarboxamide (126 mg, 0.3 mmol) (8 mg, 8% yield). $^1$H NMR (CDCl$_3$) δ 12.87 (s, 1H), 8.66 (s, 1H), 8.45 (s, 1H), 8.85 (m, 3H), 8.39–8.27 (m, 3H), 6.95 (d, 1H), 6.91 (s, 1H), 6.18 (t, 1H), 4.37 (d, 2H); ES-MS (m/z) 319 [M+1]$^+$.

Example 65

SYNTHESIS OF N-[3-(4-(FLUOROPHENYL)(1H-INDAZOL-5-YL)]-2-THIENYLCARBOXAMIDE

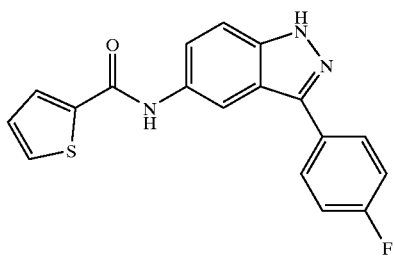

A. N-[3-(4-Fluorophenyl)(1H-indazol-5-yl)]-2-thienylcarboxamide

The title compound was prepared as described in Example 55 A using 2-thiophenecarbonyl chloride (51 µg, 0.47 mmol) (25 mg, 16% yield). $^1$H NMR (DMSO-d$_6$) δ 10.37 (s, 1H), 8.48 (s, 1H), 8.08 (d, 1H), 7.9 (m, 2H) 7.85 (d, 1H), 7.74 (d, 1H), 7.59 (d, 1H), 7.38 (t, 2H), 7.23 (t, 1H); ES-MS (m/z) 338 [M+1]$^+$.

Example 66

SYNTHESIS OF N-[3-(4-(FLUOROPHENYL)(1H-INDAZOL-5-YL)]MORPHOLIN-4-YLCARBOXAMIDE

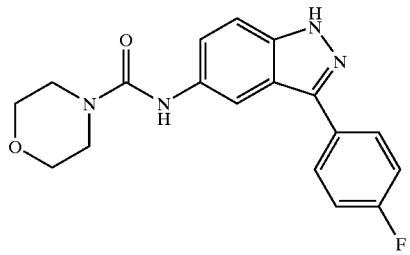

A. N-[3-(4-Fluorophenyl)(1H-indazol-5-yl)]morpholin-4-ylcarboxamide

The title compound was prepared as described in Example 55 A using morpholine-4-carbonyl chloride (45 ,L, 0.38 mmol) (20 mg, 19% yield). $^1$H NMR (DMSO-d$_6$) δ 13.1 (s, 1H), 8.60 (s, 1H), 8.13 (s, 1H), 7.94 (dd, 2H), 7.49 (s, 2H), 7.37 (t, 2H), 3.63 (m, 4H), 3.43 (m, 4H); ES-MS (m/z) 341 [M+1]$^+$.

Example 67

SYNTHESIS OF N-[3-(4-(FLUOROPHENYL)(1H-INDAZOL-5-YL)][(4-(FLUOROPHENYL)AMINO]CARBOXAMIDE

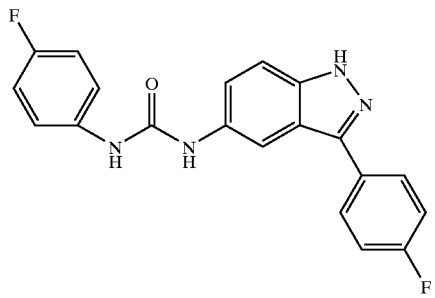

A. N-[3-(4-Fluorophenyl)(1H-indazol-5-yl)][(4-fluorophenyl)amino]carboxamide

To a solution of 3-(4-fluorophenyl)-1-(2-methoxyethoxy)-1H-indazole-5-ylamine (115 mg, 0.36 mmol) in dioxane (5 mL) was added 4-fluorophenyl isocyanate (50 µL, 0.44 mmol). The reaction was stirred overnight at room temperature. It was then filtered and the solid dried in a vaxuum oven. The solid was then taken up in 6N HCl (10 mL) and methanol (10 mL) and heated to 80° C. for 2 hours. The reaction was then cooled to room temperature and quenched with NaHCO$_3$ (100 mL) and extracted with ethyl acetate (3×40 mL). The organic layers were combined and dried with magnesium sulfate (MgSO$_4$) and concentrated to a solid to afford the title compound (25 mg, 19% yield). $^1$H NMR (CDCl$_3$) δ 13.1 (br s, 1H), 9.32 (s, 2H), 8.28 (s, 1H), 7.94 (dd, 2H), 7.52 (d, 1H), 7.48 (dd, 2H), 7.38 (t, 2H), 7.33 (dd, 1H), 7.11 (t, 2H); ES-MS (m/z) 364 [M+1]$^+$.

Example 68

SYNTHESIS OF 3-(4-(FLUOROPHENYL)-1H-INDAZOLE-5-CARBOXAMIDE

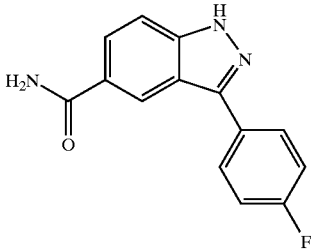

To a solution of 1-acetyl-3-(4-fluorophenyl)-1H-indazole-5-carbonyl chloride (200 mg, 0.63 mmol) in methylene chloride (20 mL) was added saturated ammonium hydroxide (NH$_4$OH). The solution was stirred overnight at room temperature when it was added to water (100 mL) and extracted with ethyl acetate (3×40 mL). The combined organic layers were dried (Na$_2$SO$_4$) and concentrated under vacuo to an oil. The resulting oil was chromatographed on silica gel, eluting with 10% methanol in methylene chloride to give the title compound (115 mg, 72%). $^1$H NMR (DMSO-d$_6$) δ 13.4 (s, 1H), 8.60 (s, 1H), 8.09 (m, 2H), 7.94 (d, 1H), 7.61 (d, 1H), 7.38 (t, 2H); ES-MS (m/z) 256 [M+1]$^+$.

Example 69

SYNTHESIS OF 5-[3-(4-(FLUOROPHENYL)-1H-Indazol-5-Yl]-2H-1,2,3,4-Tetrazole

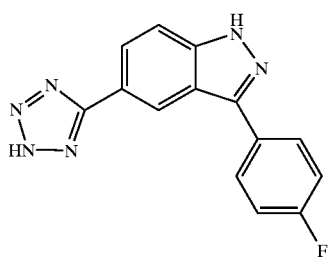

A. 5-[3-(4-Fluorophenyl)-1H-indazol-5-yl]-2H-1,2,3,4-tetrazole

The title compound was prepared as described in Example 73 B. To a solution of the nitrite (300 mg, 1.26 mmol) in toluene (10 mL) was added the azidotributyltin (380 μL, 1.32 mmol). The reaction was then heated to reflux overnight. The solid was isolated by filtration, taken up in a 1:1 solution of THF:concentrated HCl and stirred at room temperature for 4 hours. The product was then extracted with ethyl acetate/water, dried (Na$_2$SO$_4$), and chromatographed on silica gel eluting with 15% methanol in methylene chloride to give the title tetrazole (80 mg, 23% yield). $^1$H NMR (DMSO-d$_6$) δ 13.6 (s, 1H), 8.77 (s, 1H) 8.08–8.13 (m, 3H), 7.83 (d, 1H), 7.45 (t, 2H); ES-MS (m/z) 281 [M+1]$^+$.

Example 70

SYNTHESIS OF 3-[3-(4-(FLUOROPHENYL)-1H-INDAZOL-5-YL]-1H-1,2,4-TRIAZOLE

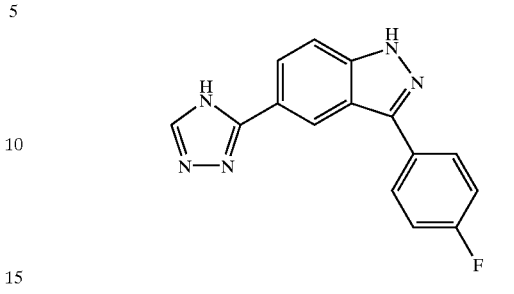

A. 3-[3-(4-Fluorophenyl)-1H-indazol-5-yl]-1H-1,2,4-triazole

The title compound was prepared as described in Example 68. The amide (350 mg, 1.2 mmol) was heated in DMF acetal (40 mL) at 90° C. for 4 hrs. The solvent was then removed under vacuo to give an oil which was taken up in a solution of hydrazine (0.5 mL) in acetic acid (40 mL). The subsequent solution was stirred at room temperature overnight. Water was then added to the reaction and the resulting solid filtered then dried in a vacuum oven. The product was purified by silica gel column chromatography eluting with 15% methanol in methylene chloride to give the title triazole (190 mg, 57% yield). $^1$H NMR (DMSO-d$_6$) δ 13.4 (br s, 1H), 8.67 (s, 1H), 8.4 (br s, 1H), 8.12–8.03 (m, 3H), 7.71 (d, 1H), 7.41 (dt, 2H); ES-MS (m/z) 280 [M+1]$^+$.

Example 71

SYNTHESIS OF 3-(4-(FLUOROPHENYL)-5-IMIDAZOL-2-YL-1H-INDAZOLE

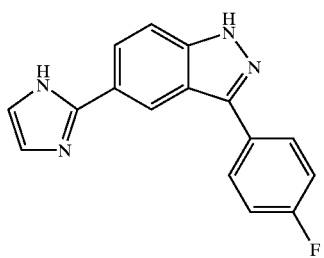

A. 3-(4-Fluorophenyl)-5-imidazol-2-yl-1H-indazole

To a solution of the nitrile (100 mg, 0.31 mmol) in methanol (60 mL) was bubbled in gaseous hydrochloric acid at 0° C. The reaction was stirred at room temperature overnight when it was rotary evaporated to a solid and washed with ether (20 mL). Methanol (60 mL) was added followed by 1-amino-2,2-dimethoxyethane (0.5 mL, excess) and the reaction heated to a gentle reflux overnight. The reaction was then concentrated under vacuo to an oil when H$_2$SO$_4$ (30 mL) was added. The reaction was stirred at room temperature for 4 hrs when it was added to ice and neutralized with potassium carbonate (K$_2$CO$_3$). The aqueous layer was then extracted with ethyl acetate and the subsequent organic layer dried (Na$_2$SO$_4$) and concentrated to an oil. The product was isolated by column chromatography on silica gel eluting with 5% methanol in methylene chloride to give the imidazole (50 mg, 58% yield). $^1$H NMR (DMSO-d$_6$) δ 13.4 (s, 1H), 8.58 (s, 1H), 8.11–8.06 (m, 3H), 7.65 (d, 1H), 7.40 (t, 2H), 7.16 (s, 1H); ES-MS (m/z) 279 [M+1]$^+$.

Example 72

SYNTHESIS OF 3-(4-(FLUOROPHENYL)-5-PYRAZOL-3-Yl-1H-INDAZOLE

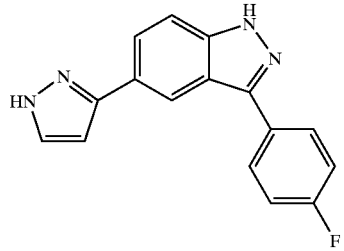

A. 3-(4-Fluorophenyl)-5-pyrazol-3-yl-1H-indazole

To a solution of 3-(4-fluorophenyl)-1-perhydro-2H-pyran-2-yl-1H-indazole-5-carbonitrile (265 mg, 0.82 mmol) in THF (10 mL) at −78° C. was added methyl lithium (1.2 mL of a 1.0 molar solution in THF, 1.2 mmol). The solution was allowed to warm to room temperature over 3 hours when it was worked up with ethyl acetate/water, dried ($Na_2SO_4$), and concentrated under vacuo to give the methyl ketone. The product was then taken up in DMF dimethoxy acetal (30 mL) and heated to 90° C. overnight. The solvent was then removed under vacuo and a solution of hydrazine (1 mL) in acetic acid (40 mL) was added. After stirring at room temperature overnight, the acetic acid was removed under vacuo and the solution neutralized with aqueous $NaHCO_3$, extracted with ethyl acetate, dried ($Na_2SO_4$), and concentrated to an oil. The THP-protected indazole was then isolated after silica gel column chromatography eluting with 40% ethyl acetate in hexane. The solid was taken up in 6N HCl (30 mL) and methanol (30 mL) and stirred at room temperature for 1Hour when the methanol was removed under vacuo and the resulting solution extracted with ethyl acetate/water. The organic layer was then dried ($Na_2SO_4$) and the product isolated after silica gel column chromatography eluting with 50% ethyl acetate in hexane to give the title pyrazole (40 mg, 17% yield). $^1$H NMR (DMSO-$d_6$) δ 13.3 (m, 2H), 12.8 (br s, 1H), 8.4 (br s, 1H), 8.08 (m, 2H), 7.95 (d, 1H), 7.8 (br s, 1H), 7.6 (m, 1H), 7.39 (t, 2H), 6.8 (br s, 1H); ES-MS (m/z) 279 [M+1]$^+$.

Example 73

SYNTHESIS OF 3-(4-(FLUOROPHENYL)-1H-INDAZOLE-5-CARBOXYLIC ACID

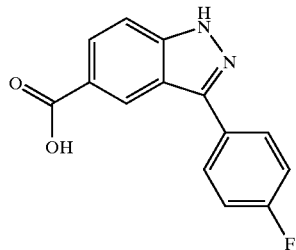

A. 4-Fluoro-3-{(4-fluorophenyl)carbonyl]benzenecarbonitrile

To a flask containing 4-fluorobenzonitrile (10 g, 0.08 mol) dried under vacuum and placed under nitrogen was added anhydrous tetrahydrofuran (200 mL). The flask was placed in a dry ice/acetone bath and cooled to −78° C. A 2 molar solution of lithium diisopropylamide in heptane, tetrahydrofuran and ethylbenzene (20 mL, 0.04 mmol) was added dropwise to the flask. The reaction stirred for two and one half-hours at this temperature. To the flask was added water and the reaction vessel was quickly removed from the cooling bath. The tetrahydrofuran was removed by rotary evaporation and the product was extracted from the reaction using ethyl acetate. The organic layer was washed with brine, dried with magnesium sulfate, filtered and concentrated. After 12 hours a product crystallized. This was triturated with hexane and ether. The procedure was repeated again using an additional amount of 4-fluorobenzonitrile (10 g, 0.08 mol). The crude product from both reactions were combined and purified by column chromatography ($SiO_2$, 5% Ethyl Acetate in Hexane increased to 15% Ethyl Acetate in Hexane) to yield the title compound (9.7 g, 50% yield). $^1$H NMR (DMSO-$d_6$) 8.15–8.2 (m, 2H), 7.9 (m, 2H), 7.65 (t, 1H), 7.4 (t, 2H), ES-MS m/z 244 [M+1]$^+$.

B. 3-(4-Fluorophenyl)-1H-indazole-5-carbonitrile

To a flask containing 4-fluoro-3-{(4-fluorophenyl)carbonyl}benzenecarbonitrile (4.2 g, 0.017 mmol) was added hydrazine monohydrate (15mL) and anhydrous hydrazine (10 mL). In an addition flask the procedure was repeated. Both flasks were allowed to stir overnight exposed to the atmosphere. LCMS confirmed the reactions were complete. To the flasks were added an excess amount of water. The reactions were allowed to stir for two hours. The product of the reactions was collected via a fritted funnel by filtration and combined to yield the title compound. The product was allowed to dry under vacuum and taken on crude into the next step of the synthesis. $^1$H NMR (DMSO-$d_6$) 8.7 (s, 1H), 8.1 (m, 2H), 7.7–7.8 (m, 2H), 7.3–7.4 (t, 2H), ES-MS m/z 238 [M+1]$^+$.

C. 3-(4-Fluorophenyl)-1H-indazole-5-carboxylic acid

To a round bottom flask containing 3-(4-fluorophenyl)-1H-indazole-5-carbonitrile (8.05 g, 0.034 mol) was added acetic acid (250 mL) and concentrated HCl (250 mL). The reaction was heated to reflux temperature for 7.5 hours and then 105° C. for two and one half-hours. The reaction was allowed to stir at room temperature overnight. The reaction was diluted with water and a solid crashed out of solution. The solid was collected by filtration and dried in a low temperature oven to yield the title compound (7.5 g, 86% yield). $^1$H NMR (DMSO-$d_6$) δ 13.6 (br s, 1H), 13.0 (br s, 1H), 8.64 (s, 1H), 8.0–7.9 (m, 3H), 7.68 (d, 1H), 7.42 (t, 2H); ES-MS (m/z) 301 [M+1]$^+$.

Example 74

SYNTHESIS OF Ethyl 3-(4-(FLUOROPHENYL)-1H-INDAZOLE-5-CARBOXYLATE

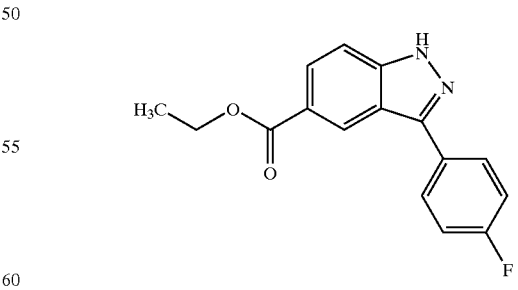

A. Ethyl 3-(4-fluorophenyl)-1H-indazole-5-carboxylate

To a solution of 1-acetyl-3-(4-fluorophenyl)-1H-indazole-5-carbonyl chloride (100 mg, 0.33 mmol) in ethanol (40 mL) was added pyridine (0.5 mL). The reaction was stirred overnight at room temperature when saturated ammonium hydroxide (1 mL) was added. The reaction was stirred overnight when water (150 mL) was added and the solution filtered. The solid was dried to recover the product (100 mg, 100% yield). $^1$H NMR (DMSO-$d_6$) δ 13.6 (s, 1H), 8.62 (s, 1H), 8.03–7.9 (m, 3H), 7.70 (d, 1H), 7.61 (d, 1H), 7.42 (t, 2H); ES-MS (m/z) 285 [M+1]$^+$.

Example 75

SYNTHESIS OF 5-BENZIMIDAZOL-2-YL-3-(4-(FLUOROPHENYL)-1H-INDAZOLE

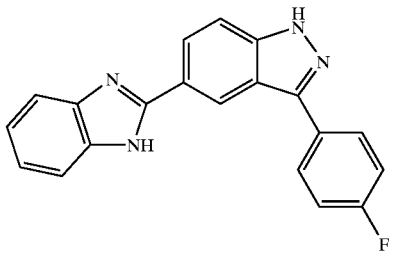

A. 5-Benzimidazol-2-yl-3-(4-fluorophenyl)-1H-indazole

To a solution of 2-nitroaniline (92 mg, 0.67 mmol) in pyridine (4 mL) was added 1-acetyl-3-(4-fluorophenyl)-1H-indazole-5-carbonyl chloride (200 mg, 0.67 mmol). The reaction was stirred at room temperature overnight when water (30 mL) was added and the solid filtered and dried in a vacuum oven (45° C.). The solid was then taken up in ethyl acetate (20 mL)/ethanol (20 mL) and a scoup of palladium on carbon added. The resulting heterogenous solution was then subjected to an atmosphere of hydrogen. After stirring overnight, the solution was filtered and concentrated to an oil under vacuo and taken up in 4 N HCl (80 mL) which was refluxed for 12 hours. The reaction was quenched with saturated NaHCO$_3$ and the product collected as a solid. The pure product was isolated after chromatography on silica gel eluting with 7% methanol in methylene chloride. (37 mg, 17% yield). $^1$H NMR (DMSO-$d_6$) δ 13.6 (br s,1H), 8.86 (s, 1H), 8.29 (d, 1H), 8.16–8.10 (m, 2H), 7.76 (d, 1H), 7.64 (dd, 2H), 7.45 (t, 2H), 7.24 (dd, 2H); ES-MS (m/z) 329 [M+1]$^+$.

Example 76

SYNTHESIS OF [3-(4-(FLUOROPHENYL)(1H-INDAZOL-5-YL)]-N-BENZAMIDE

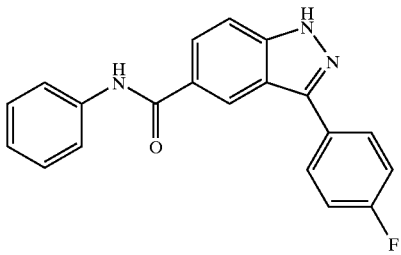

A. [3-(4-Fluorophenyl)(1H-indazol-5-yl)]-N-benzamide

To a solution of 3-(4-fluorophenyl)-1H-indazole-5-carboxylic acid (100 mg, 0.39 mmol) and 1-hydroxybenzotriazole hydrate (63 mg, 0.47 mmol) in DMF (HOBT) (5 20 mL) at 0° C. was added 1-(3-dimethylaminopropyl)-3-ethylcarbodiimide hydrochloride (90 mg, 0.47 mmol). The reaction was stirred at 0° C. for 30 min when aniline (36 mL, 0.39 mmol) was added. The reaction was stirred at room temperature overnight when it was worked up with ethyl acetate/water and chromatographed with silica gel eluting with 45% ethyl acetate/hexane to give the title compound (90 mg, 70% yield). $^1$H NMR (DMSO-$d_6$) δ 13.5 (s, 1H), 10.3 (s, 1H), 8.67 (s, 1H), 8.12 (dd, 2H), 8.0 (d, 1H), 7.78 (d, 2H), 7.69 (d, 1H), 7.4–7.3 (m, 4H), 7.11 (t, 1H); ES-MS (m/z) 332 [M+1]$^+$.

Example 77

SYNTHESIS OF N-[2-(DIMETHYLAMINO)ETHYL][3-(4-(FLUOROPHENYL)(1H-INDAZOL-5-YL)]CARBOXAMIDE

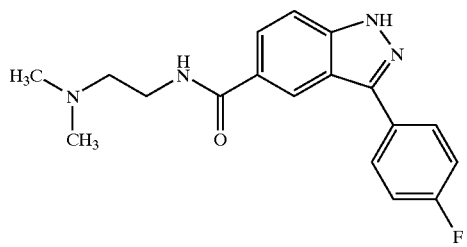

A. N-[2-(Dimethylamino)ethyl]3-(4-fluorophenyl)(1H-indazol-5-yl]carboxamide

The title compound was prepared as described in Example 76 A, using N,N-dimethylethylenediamine (43 μL, 0.39 mmol) and further purified by preparative HPLC (0.100 mg, 79% yield). $^1$H NMR (DMSO-$d_6$) δ13.5 (s, 1H), 8.58 (t, 1H), 8.53 (s, 1H), 8.07 (dd, 2H), 7.9 (d, 1H), 7.63 (d, 1H), 7.42 (t, 2H), 3.4 (m, 2H), 2.4 (t, 2H), 2.22 (s, 6H); ES-MS (m/z) 327 [M+1]$^+$.

Example 78

SYNTHESIS OF ETHYL 1-{[3-(4-(FLUOROPHENYL)-1H-INDAZOL-5-YL]CARBONYL}PIPERIDINE-4-CARBOXYLATE

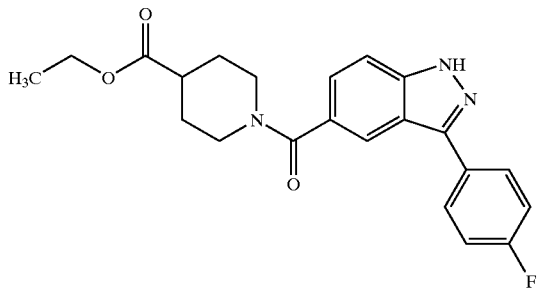

A. Ethyl 1-1[3-(4-fluorophenyl)-1H-indazol-5-yl]carbonyl}piperidine-4-carboxylate The title compound was prepared as described in Example 109 A, using ethyl 4-piperidinecarboxylate (60 μL, 0.39 mmol) and was further purified by preparative HPLC (0.07 mg, 45% yield). $^1$H NMR (DMSO-$d_6$) δ 13.5 (s, 1H), 8.06 (br s, 1H), 8.02 (d, 2H), 7.64 (d, 1H), 7.42 (d, 1H), 7.36 (t, 2H), 4.3 (br s, 1H), 4.08 (q, 2H), 3.75 (br s, 1H), 3.1 (br s, 2H), 2.65 (br s, 1H), 1.9 (br s, 2H), 1.6 (br s, 2H), 1.18 (t, 3H); ES-MS (m/z) 396 [M+1]$^+$.

Example 79

SYNTHESIS OF METHYL 4-{[3-(4-(FLUOROPHENYL)-1H-INDAZOL-5-YL]CARBONYLAMINO}BENZOATE

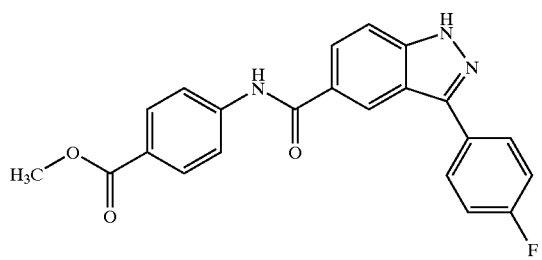

A. Methyl 4-{[3-(4-fluorophenyl)-1H-indazol-5-yl]carbonylamino}benzoate

The title compound was prepared as described in Example 109 A, using methyl 4-aminobenzoate (30 mg, 0.19 mmol) and purified by HPLC (65 mg, 88% yield). 1H NMR (DMSO-$d_6$) δ 13.6 (s, 1H), 10.6 (s, 1H), 8.70 (s, 1H), 8.12 (dd, 2H), 8.0 (d, 1H), 8.0 (s, 4H), 7.70 (d, 1H), 7.41 (t, 2H), 3.84 (s, 3H); ES-MS (m/z) 390 [M+1]$^+$.

Example 80

SYNTHESIS OF 4-{[3-(4-(FLUOROPHENYL)-1H-INDAZOL-5-YL]CARBONYLAMINO}BENZOIC ACID

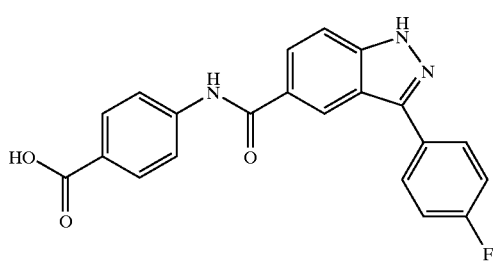

A. 4-{3-(4-Fluorophenyl)-1H-indazol-5-yl]carbonylamino}benzoic acid

To a solution of methyl 4-{[3-(4-fluorophenyl)-1H-indazol-5-yl]carbonylamino}benzoate (112 mg, 0.29 mmol) in methanol (20 mL) and water (20 mL) was added sodium hydroxide (25 mg, 0.64 mmol). The solution was stirred at room temperature for 2 hours when it was acidified and the methanol removed under vacuo. The resulting solid was filtered and dried to recover the product (55 mg, 51%). 1H NMR (DMSO-$d_6$) δ 13.6 (s, 1H), 12.8 (br s, 1H), 10.6 (s, 1H), 8.69 (s, 1H), 8.12 (dd, 2H), 8.0 (d, 1H), 7.94 (s, 4H), 7.70 (d, 1H), 7.41 (t, 2H); ES-MS (m/z) 376 [M+1]$^+$.

Example 81

SYNTHESIS OF 4-{[3-(4-(FLUOROPHENYL)-1H-INDAZOL-5-YL]CARBONYLAMINO}BENZAMIDE

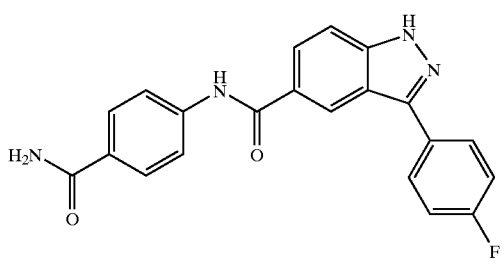

A. 4-{[3-(4-Fluorophenyl)-1H-indazole-5-yl]carbonylamino}benzamide

The title compound was prepared as described in Example 109 A, using 4-aminobenzamide (45 mg, 0.33 mmol) to provide the title compound (25 mg, 20% yield). $^1$H NMR (DMSO-$d_6$) δ 13.7 (s, 1H), 10.5 (s, 1H), 8.68 (s, 1H), 8.12 (dd, 2H), 8.0 (d, 1H), 7.9 (s, 4H), 7.70 (d, 1H), 7.42 (t, 2H), 7.28 (br s, 2H); ES-MS (m/z) 375 [M+1]$^+$.

Example 82

SYNTHESIS OF 1-{[3-(4-(FLUOROPHENYL)-1H-INDAZOL-5-YL]CARBONYL}PIPEREDINE-4-CARBOXYLIC ACID

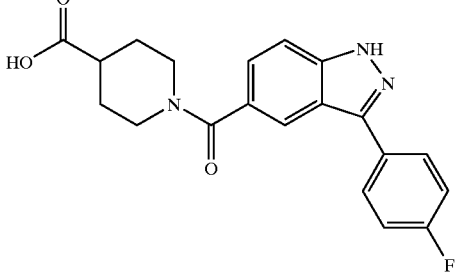

A. 1-{[3-(4-Fluorophenyl)-1H-indazol-5-yl]carbonyl}piperidine-4-carboxylic acid

The title compound was prepared as described in Example 80 A to provide the title compound (55 mg). $^1$H NMR (DMSO-$d_6$) δ 13.5 (br s, 1H), 8.06 (br s, 1H), 8.02 (dd, 2H), 7.64 (d, 1H), 7.42 (d, 1H), 7.36 (t, 2H), 4.3 (br s, 1H), 3.75 (br s, 1H), 3.1 (br s, 2H), 2.5 (br s, 1H), 1.9 (br s, 2H), 1.6 (br s, 2H); ES-MS (m/z) 368 [M+1]$^+$.

Example 83

SYNTHESIS OF [3-(4-(FLUOROPHENYL)(1H-INDAZOL-5-YL)]-N-(2-PYRIDYL) CARBOXAMIDE

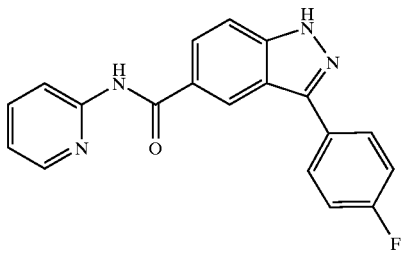

A. [3-(4-Fluorophenyl)(1H-indazol-5-yl)]-N-(2-pyridyl) carboxamide

The title compound was prepared as described in Example 109 A using 2-amninopyridine (75 mg, 0.80 mmol) to provide the title compound (120 mg, 45% yield). $^1$H NMR (DMSO-d$_6$) δ 13.5 (s, 1H), 11.08 (s, 1H), 8.79 (s, 1H), 8.40 (s, 1H), 8.42–8.16 (m, 3H), 8.03 (d, 1H), 7.85 (t, 1H), 7.68(d, 1H), 7.41 (t, 2H), 7.17 (t, 1H); ES-MS (m/z) 333 [M+1]$^+$.

Example 84

SYNTHESIS OF [3-(4-(FLUOROPHENYL)(1H-INDAZOL-5-YL)]-N-(3-PYRIDYL) CARBOXAMIDE

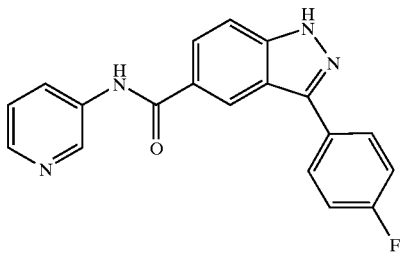

A. [3-(4-Fluorophenyl)(1H-indazol-5-yl)]-N-(3-pyridyl) carboxamide

The title compound (130 mg, 48% yield) was prepared as described in Example 109 A using 3-aminopyridine (75 mg, 0.80 mmol). $^1$H NMR (DMSO-d$_6$) δ 13.6 (s, 1H), 10.5 (s, 1H), 8.95 (s, 1H), 8.71 (s, 1H), 8.33 (s, 1H), 8.21 (d, 1H), 8.11 (t, 2H), 8.02(d, 1H), 7.72 (d, 2H), 7.42 (t, 3H); ES-MS (m/z) 333 [M+1]$^+$.

Example 85

SYNTHESIS OF [3-(4-(FLUOROPHENYL)(1H-INDAZOL-5-YL)]-N-(4-PYRIDYL) CARBOXAMIDE

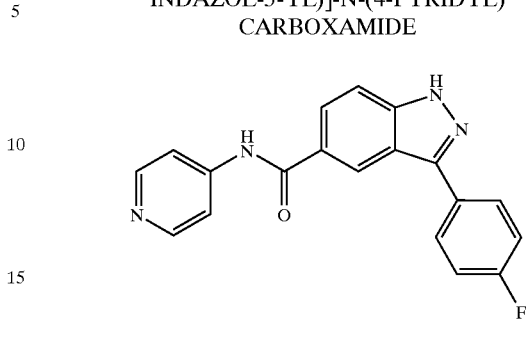

A. [3-(4-Fluorophenyl)(1H-indazol-5-yl)]-N-(4-pyridyl) carboxamide

The title compound (110 mg, 41% yield) was prepared as described in Example 109 A using 4-aminopyridine (75 mg, 0.80 mmol). $^1$H NMR (DMSO-d$_6$) δ 13.6 (s, 1H), 10.7 (s, 1H), 8.69 (s, 1H), 8.49 (br s,2H), 8.11 (dd, 2H), 8.00 (d, 1H), 7.81 (d, 2H), 7.72 (d, 1H), 7.42 (t, 2H); ES-MS (m/z) 333 [M+1]$^+$.

Example 86

SYNTHESIS OF TERT-BUTYL 3-{[3-(4-(FLUOROPHENYL)-1H-INDAZOL-5-YL] CARBONYLAMINO)PROPANOATE

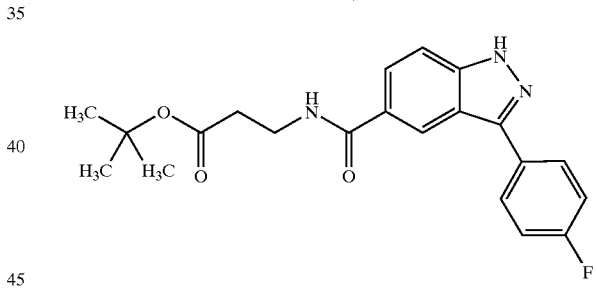

A. tert-butyl 3-{[3-(4-fluorophenyl)-1H-indazol-5-yl] carbonylamino)propanoate

To a suspension of 3-(4-fluorophenyl)-1H-indazole-5-carboxylic acid (200 mg, 0.780 mmol) in dimethyl formamide (10 mL) was added 1-Hydroxybenzotriazole (126 mg, 0.936 mmol) and 4-(dimethylamino)pyridine (114 mg, 0.936 mmol). The mixture was allowed to stir for fifteen minutes. 1-ethyl-(3-dimethylamino)carbodiimide hydrochloride (179 mg, 0.936 mmol) was then added and stirring continued for fifteen additional minutes. H-p-ala-O-t-Bu-hydrochloride (170 mg, 0.936 mmol) was added and stirring continued at ambient temperature for 18 hours. The mixture was condensed and extracted with 5% sodium bicarbonate and ethyl acetate. The extracts were dried over sodium sulfate, filtered, and concentrated to afford the title compound (165 mg, 55%).$^1$H NMR (DMSO-d$_6$) δ 13.43 (s, 1H), 8.65 (s, 1H), 8.47 (s, 1H), 8.02 (m, 2H), 7.85 (d, 2H), 7.59 (d, 1H), 7.36 (m, 2H), 3.46 (q, 4H), 1.37 (s, 9H); ES-MS (m/z) 384 [M+1]$^+$.

Example 87

SYNTHESIS OF [3-(4-(FLUOROPHENYL)(1H-INDAZOL-5-YL)]-N-(3-HYDROXYPHENYL)CARBOXAMIDE

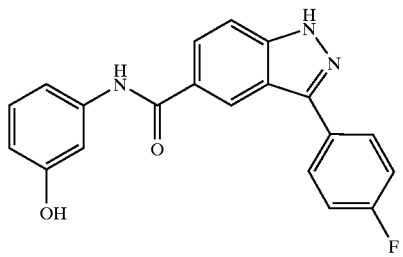

A. [3-(4-Fluorophenyl)(1H-indazol-5-yl)1]-N-(3-hydroxyphenyl)carboxamide

The title compound was prepared as described in Example 86 A, using 3-aminophenol (93.6 mg, 0.858 mmol) to provide the title compound (88 mg, 32%). $^1$H NMR (DMSO-$d_6$) δ 13.49 (br s, 1H), 10.19 (s, 1H), 9.38 (s, 1H), 8.60 (s, 1H), 8.08 (d, 2H), 7.93 (d, 1H), 7.65 (d, 1H), 7.38 (m, 3H), 7.12 (m, 2H), 6.49 (d, 1H); ES-MS (m/z) 348 [M+1]$^+$.

Example 88

SYNTHESIS OF 3-{[3-(4-(FLUOROPHENYL)-1H-INDAZOL-5-YL]CARBONYLAMINO)PROPANOIC ACID

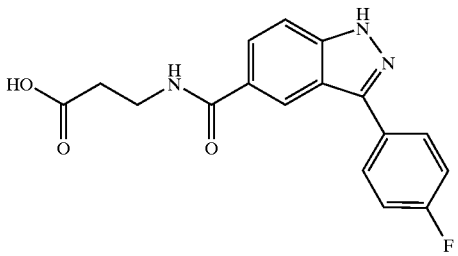

A. 3-{[3-(4-Fluorophenyl)-1H-indazol-5-yl]carbonylamino)propanoic acid

To a solution containing Example 86 (150 mg, 0.391 mmol) in dioxane (2 mL) was added 6N HCl (2 mL). The reaction mixture was allowed to stir at ambient temperature for 18 hours. The solution was quenched with water (30 mL) and the mixture extracted with ethyl acetate. The extracts were dried over sodium sulfate, filtered and condensed to give a solid. The solid was triturated with dichloromethane and hexanes to provide the title compound (94 mg, 73%). $^1$H NMR (DMSO-$d_6$) δ 13.43 (br s, 1H), 12.21 (br s, 1H), 8.68 (m, 1H), 8.50 (s, 1H), 8.03 (m, 2H), 7.86 (d, 1H), 7.59 (d, 1H), 7.37 (t, 2H), 3.47 (q, 2H), 2.52 (m, 2H); ES-MS (m/z) 328 [M+1]$^+$.

Example 89

SYNTHESIS OF [3-(4-(FLUOROPHENYL)(1H-INDAZOL-5-YL)]-N-(3-NITROPHENYL)CARBOXAMIDE

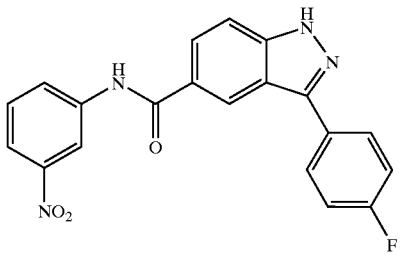

A. [3-(4-Fluorophenyl)(1H-indazol-5-yl)1-N-(3-nitrophenyl)carboxamide

To a solution containing 3-nitroaniline (96 mg, 0.694 mmol) in pyridine (5 mL) was added 1-acetyl-3-(4-fluorophenyl)-1H-indazole-5-carbonyl chloride (200 mg, 0.631 mmol). The reaction mixture was allowed to stir for 18 hours at ambient temperature. Water (30 mL) was then added and the resulting precipitate was filtered and dried to afford the title compound. This precipitate was taken on directly to the next step for deprotection.

To the previous precipitate was added 0.3% ammonia in methanol (10 mL). The solution was brought to 60° C. for three hours. The resulting precipitate was filtered and dried to provide the title compound (140 mg, 60% overall yield). $^1$H NMR (DMSO-$d_6$) δ 13.55 (br s, 1H), 10.76 (s, 1H), 8.78 (s, 1H), 8.70 (s, 1H), 8.20 (m, 1H), 8.11 (m, 2H), 8.00 (m, 2H), 7.68 (m, 2H), 7.40 (m, 2H); ES-MS (m/z) 377 [M+1]$^+$.

Example 90

SYNTHESIS OF TERT-BUTYL-2-{[3-(4-(FLUOROPHENYL)-1H-INDAZOL-5-YL]CARBONYLAMINO}ACETATE

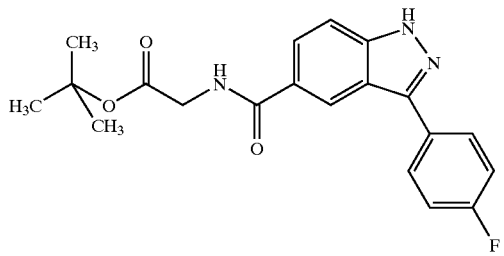

A. tert-butyl 2-{[3-(4-fluorophenyl)-1H-indazol-5-yl]carbonylamino}acetate

The title compound was prepared as described in Example 86 A, using t-butyl glycine (112 mg, 0.858 mmol) (80 mg, 30%). ES-MS (m/z) 370[M+1]$^+$.

Example 91

SYNTHESIS OF 4-{[3-(4-(FLUOROPHENYL)-1H-INDAZOL-5-YL]CARBONYLAMINO}BUTANOIC ACID

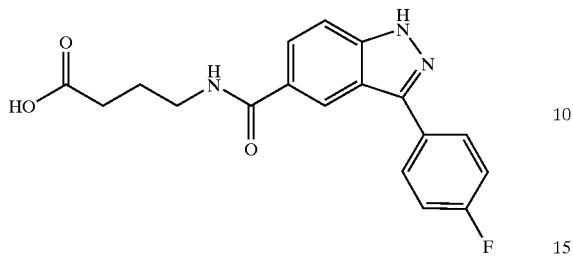

A. Methyl 4-{[1-acetyl-3-(4-fluorophenyl)-1H-Indazol-5-Yl]carbonylamino}butanoate To a solution containing methyl 4-aminobuytrate hydrochloride (106.6 mg, 0.694 mmol) in pyridine (5 mL) was added I-acetyl-3-(4-fluorophenyl)-1H-indazole-5-carbonyl chloride (200 mg, 0.631 mmol). The reaction mixture was allowed to stir at ambient temperature for 18 hours. Water (40 mL) was added to the reaction mixture to afford a precipitate. The precipitate was filtered and dried to provide the title compound. The title compound was taken to the deprotection step. ES-MS (m/z) 398 [M+1]+.

B. Methyl 4-{[3-(4-Fluorophenyl)-1H-Indazol-5-Yl]Carbonylamino]Butanoate

Example 91 A in 0.3% ammonia in methanol (10 mL) was allowed to stir at 60° C. for three hours. Water (40 mL) was added and the resulting solution was extracted with ethyl acetate. The extracts were dried over sodium sulfate, filtered and removed to give a precipitate (50 mg). The title compound was taken to the next step. ES-MS (m/z) 356 [M+1]+.

C. 4-{[3-(4-fluorophenyl)-1H-indazol-5-yl]carbonylamino}butanoic acid

The title compound was prepared as described in Example 48 A (21 mg, 44%). $^1$H NMR (DMSO-d$_6$) δ 13.42 (br s, 1H), 12.02 (br s, 1H), 8.61 (br s, 1H), 8.50 (s, 1H), 8.04 (t, 2H), 7.89 (d, 1H), 7.58 (d, 1H), 7.37 (t, 2H), 2.27 (t, 2H), 1.75 (m, 2H); ES-MS (m/z) 342 [M+1]+.

Example 92

SYNTHESIS OF N-(3-AMINOPHENYL)[3-(4-FLUOROPHENYL)(1H-INDAZOL-5-YL)]CARBOXAMIDE

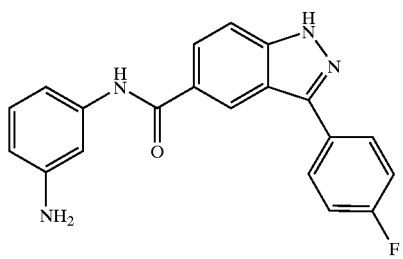

A. [1-Acetyl-3-(4-fluorophenyl)(1H-indazol-5-yl) 1-N-(3-nitrophenyl)carboxamide

The title compound was prepared as described in Example 91 A and was taken on to the next step (quantitative yield). ES-MS (m/z) 419[M+1]+.

B. N-(3-Nitrophenyl)[3-(4-fluorophenyl)(1H-indazol-5-yl)] carboxamide

The title compound was prepared as described in Example 14 B (140 mg). ES-MS (m/z) 377 [M+1]+.

C. N-(3-Aminophenyl)3-(4-fluorophenyl)(1H-indazol-5-yl)]carboxamide

The title compound was prepared as described in Example 19 B (39.5 mg, 33%). $^1$H NMR (DMSO-d$_6$) δ 13.47 (br s, 1H), 10.04 (s, 1H), 8.59 (s, 1H), 8.08 (t, 2H), 7.93 (d, 1H), 7.65 (d, 1H), 7.38 (t, 2H), 7.07 (s, 1H), 6.29 (d, 1H), 5.10 (br s, 2H); ES-MS (m/z) 347 [M+1]+.

Example 93

SYNTHESIS OF 2-{[3-(4-(FLUOROPHENYL)-1H-INDAZOL-5-YL]CARBONYLAMINO}ACETIC ACID

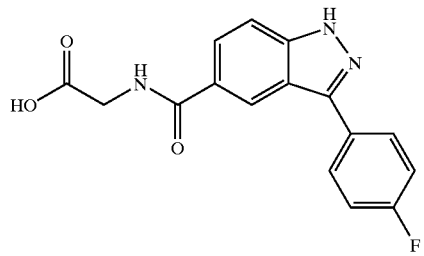

A. 2-{[3-(4-Fluorophenyl)-1H-indazol-5-yl]carbonylamino}acetic acid

Using Example 90 A (169 mg, 0.457 mmol), the title compound was prepared, except that an extraction with ethyl acetate was used to afford the title compound (77 mg, 54%). $^1$H NMR (DMSO-d$_6$) δ 13.47 (br s, 1H), 12.58 (br s, 1H), 8.98 (s, 1H), 8.05 (s, 2H), 7.89 (m, 1H), 7.61 (m, 1H), 7.37 (br s, 2H), 3.93 (s, 2H); ES-MS (m/z) 314 [M+1]+.

Example 94

SYNTHESIS OF 5-{[3-(4-(FLUOROPHENYL)-1H-INDAZOL-5-YL]CARBONYLAMINO}PENTANOIC ACID

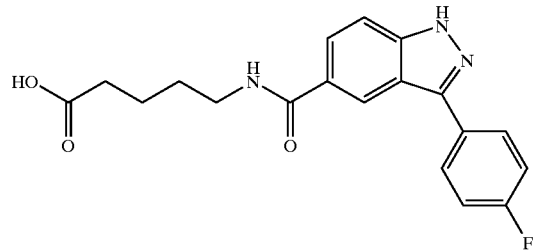

A. Methyl 4-{[1-acetyl-3-(4-Fluorophenyl)-1H-indazol-5-yl]carbonylamino}butyrate The title compound was prepared as described in Example 91 A, using methyl 5-amino valerate ester (91 mg, 0.694 mmol) to afford the title compound (105 mg, 40%).

B. 5-{[3-(4-Fluorophenyl)-1H-indazol-5-yl]carbonylamino}pentanoic acid

The title compound was prepared as described in Example 91 A to afford the title compound (77 mg, 100%). $^1$H NMR (DMSO-d$_6$) δ 13.43 (s, 1H), 12.02 (br s, 1H), 8.58 (s, 1H), 8.50 (s, 1H), 8.02 (s, 2H), 7.87 (d, 1H), 7.58 (d, 1H), 7.37 (t, 2H), 3.57 (s, 1H), 2.23 (m, 2H), 1.53 (m, 4H); ES-MS (m/z) 356 [M+1]+.

Example 95

SYNTHESIS OF 4-({[3-(4-(FLUOROPHENYL)-1H-INDAZOL-5-YL]CARBONYLAMINO}METHYL)BENZOIC ACID

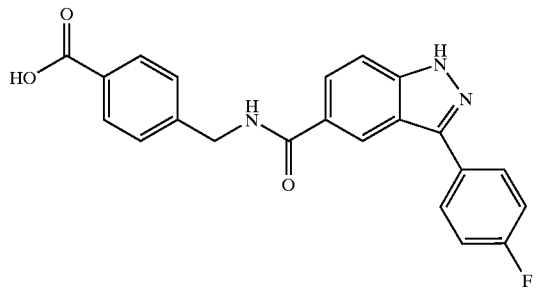

A. Methyl 4-({1-acetyl-3-(4-fluorophenyl)-1H-indazol-5-yl]carbonylamino}methyl benzoate The title compound was prepared as described in Example 91 A, using methyl-4(aminomethyl)benzoate (129 mg, 0.642 mmol) and was taken on to the next step. ES-MS (m/z) 446 [M+1]+.

B. Methyl 4-({[(4-fluorophenyl)-1H-indazol-5-yl] carbonylamino}methyl benzoate

The title compound was prepared as described in Example 14 B, using the title compound from Example 95 A (118 mg, 50% overall). $^1$H NMR (DMSO-$d_6$) δ 13.47 (br s, 1H), 12.86 (br s, 1H), 9.24 (s, 1H), 8.60 (s, 1H), 7.96 (m, 5H), 7.62 (d, 1H), 7.41 (m, 3H), 4.56 (s, 2H); ES-MS (m/z) 390 [M+1]+.

Example 96

SYNTHESIS OF [3-(4-(FLUOROPHENYL)(1H-INDAZOL-5-YL)]-N-(4-PYRIDYLMETHYL)CARBOXAMIDE

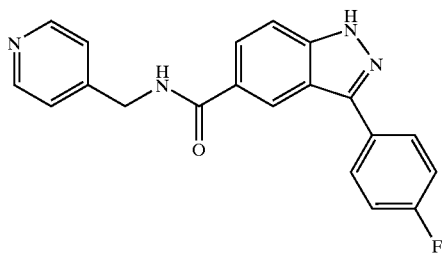

A. [1-Acetyl-3-(4-fluorophenyl)(1H-indazol-5-Yl)]-N-(4-pyridylmethyl)carboxamide The title compound was prepared as described in Example 91 A, using (4-(aminomethyl)pyridine (75 mg, 0.694 mmol), except that the resulting solid was extracted with 5% sodium carbonate solution and ethyl acetate. The extracts were dried over sodium sulfate, filtered and condensed to afford the title compound (130 mg, 53%). ES-MS (m/z) 389 [M+1]+

B. [3-(4-Fluorophenyl)(1H-indazol-5-yl)]-N-(4-pyridylmethyl)carboxamide

The title compound was prepared as described in Example 14 B, except that the resulting solution was extracted with ethyl acetate. The extracts were dried over sodium sulfate, filtered and condensed to afford the title compound after trituration with hexanes (55 mg, 47%). $^1$H NMR (DMSO-$d_6$) δ 13.47 (s, 1H), 9.25 (s, 1H), 8.61 (s, 1H), 8.47 (m, 2H), 7.92 (m, 3H), 7.62 (d, 1H), 7.32 (m, 4H), 4.52 (m, 2H); ES-MS (m/z) 347 [M+1]+.

Example 97

SYNTHESIS OF 2-(4-{[3-(4-(FLUOROPHENYL)-1H-INDAZOL-5-YL]CARBONYLAMINO}PHENYL)ACETIC ACID

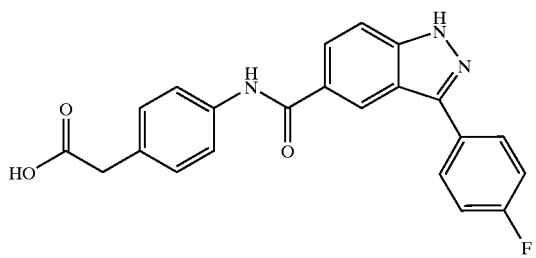

A. Ethyl 2-(4-{[1-acetyl-3-(4-fluorophenyl)-1H-indazol-5-yl]carbonylamino}phenyl)acetate The title compound (115 mg, 46%) was prepared as described in Example 91 A, using ethyl 4-aminophenyl acetate (112 mg, 0.673 mmol). ES-MS (m/z) 460 [M+1]+.

B. Ethyl 2-(4-{[3-(4-fluorophenyl)-1H-indazol-5-yl]carbonylamino}phenyl)acetate

The title compound (25 mg, 27%) was prepared as described in Example 14 B, except that the precipitate was purified using preparative HPLC. It was then taken to the next step. ES-MS (m/z) 418 [M+1]+.

C. 2-(4-{[3-(4-Fluorophenyl)-1-H-indazol-5-yl]carbonylamino}phenyl)acetic acid

The title compound was prepared as described in Example 48 A (6 mg, 26% overall). $^1$H NMR (DMSO-$d_6$) δ 13.50 (s, 1H), 12.30 (br s, 1H), 10.03 (s, 1H), 8.01 (m, 3H), 7.68 (m, 3H), 7.38 (t, 2H), 7.23 (m, 2H), 3.51 (s, 2H), ES-MS (m/z) 390 [M+1]+.

Example 98

SYNTHESIS OF [3-(4-(FLUOROPHENYL)(1H-INDAZOL-5-YL)]-N,N-DIMETHYLCARBOXAMIDE

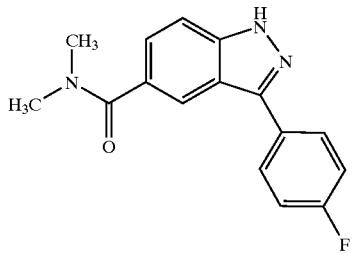

A. [3-(4-Fluorophenyl)(1H-indazol-5-yl)]-N,N-dimethylcarboxamide

The title compound (163 mg, 73%) was prepared as described in Example 91 A, using 2.0 M dimethylamine in THF (1.5 mL) to afford the title compound. $^1$H NMR (DMSO-$d_6$) δ 13.40 (s, 1H), 8.00 (m, 3H), 7.59 (t, 1H), 7.43 (m, 1H), 7.31 (m, 2H), 3.29 (s, 6H); ES-MS (m/z) 284 [M+1]+.

Example 99

SYNTHESIS OF [3-(4-(FLUOROPHENYL)(1H-INDAZOL-5-YL)]-N-METHYLCARBOXAMIDE

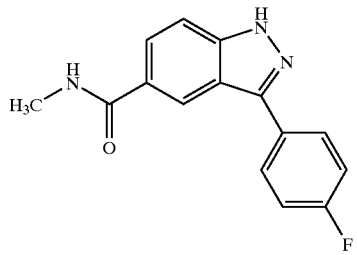

A. [3-(4-Fluorophenyl)(1H-indazol-5-yl)]-N-methylcarboxamide

The title compound was prepared as described in Example 91 A, using 2.0M methylamine in tetrahydrofuran (1.26 mL), except the solution was extracted with 5% sodium carbonate and ethyl acetate. The extracts were dried over sodium sulfate, filtered and condensed to afford a solid. The solid was purified by trituration using dichloromethane and hexanes to afford the title compound (33 mg, 19% yield). $^1$H NMR (DMSO-d$_6$) δ 13.41 (s, 1H), 8.49 (m, 2H), 8.03 (m, 2H), 7.86 (m, 1H). 7.58 (m, 1H), 7.36 (t, 2H), 2.79 (s, 3H); ES-MS (m/z) 270[M+1]$^+$.

Example 100

SYNTHESIS OF N-(3-AMINOETHYL)[3-(4-(FLUOROPHENYL) (1H-INDAZOL-5-YL)] CARBOXAMIDE

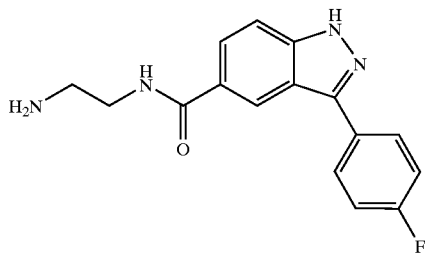

A. N-{2-[(tert-Butoxy)carbonylamino]ethyl} [3-(4-fluorophenyl(1H-indazol-5-yl)]carboxamide The title compound was prepared as described in Example 91 A, using N-(2-aminoethyl)carbamic acid tert-butyl ester (400 mg, 2.52 mmol), except that the reaction mixture was extracted with 5% sodium carbonate and ethyl acetate. The extracts were dried over sodium sulfate, filtered and condensed to afford the title compound. The solid was taken on to the following step without purification. ES-MS (m/z) 399 [M+1]$^+$.

B. N-(3-Aminoethy)[3-(4-fluorophenyl)(1H-indazol-5-yl)]carboxamide

The solid from Example 100 A was dissolved in tetrahydrofuran (3mL) and trifluoroacetic acid (6 mL) and allowed to stir at ambient temperature for 18 hours. The reaction mixture was neutralized and extracted with 5% sodium carbonate and ethyl acetate. The extracts were dried over sodium sulfate, filtered and condensed to afford the title compound (150 mg, 80% overall). ES-MS (m/z) 299 [M+1]$^+$.

Example 101

SYNTHESIS OF N-(3-AMINOPROPYL)[3-(4-(FLUOROPHENYL) (1H-INDAZOL-5-YL)] CARBOXAMIDE

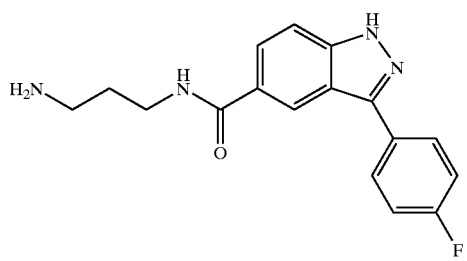

A. N-{3-[(tert-Butoxy)carbonylamino]propyl}[3-(4-fluorophenyl)(1H-indazol-5-yl)carboxamide The title compound was prepared as described in Example 100 A, using N-(2-aminopropyl)carbamic acid tert-butyl ester (430 mg, 2.52 mmol) and was taken on to the next step. ES-MS (m/z) 413 [M+1]$^+$.

B. N-(3-Aminopropyl)[3-(4-fluorophenyl)(1H-indazole-5-yl)]carboxamide

The title compound was prepared as described in Example 100 B (193 mg, 97% overall). $^1$H NMR (DMSO-d$_6$) δ 13.50 (s, 1H), 8.78 (m, 1H), 8.52 (s, 1H), 7.90 (m, 6H), 7.36 (m, 2H), 2.83 (m, 2H), 1.80 (m, 2H), 1.96 (s, 1H), 1.13 (m, 1H); ES-MS (m/z) 313 [M+1]$^+$.

Example 102

SYNTHESIS OF 3-(4-FLUOROPHENYL)(1H-INDAZOL-5-YL) PYRROLIDINYL KETONE

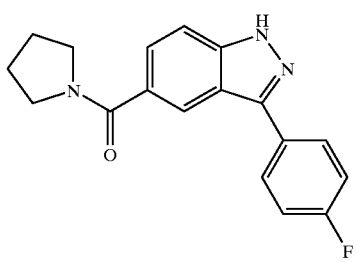

A. 3-(4-Fluorophenyl)(1H-indazol-5-yl)pyrrolidinyl ketone

The title compound was prepared as described in Example 91 A, using pyrrolidine (49.3 mg, 0.694 mmol). After 18 hours of reaction time, ammonium hydroxide (3 drops) was added to the solution. Stirring continued for an additional 2 hours. The reaction mixture was extracted with 5% sodium carbonate and ethyl acetate. The extracts were dried over sodium sulfate, filtered and condensed to give an oil. The oil was purified by trituration with dichloromethane and hexanes to provide the title compound (129 mg, 66% yield). $^1$H NMR (DMSO-d$_6$) δ 13.39 (s, 1H), 8.14 (s, 1H), 8.00 (m, 2H), 7.55 (q, 2H), 7.32 (t, 2H), 3.44 (m, 4H), 1.79 (m, 4H); ES-MS (m/z) 310 [M+1]$^+$.

Example 103

SYNTHESIS OF 3-(4-FLUOROPHENYL)(1H-INDAZOL-5-YL)PIPERAZINYL KETONE

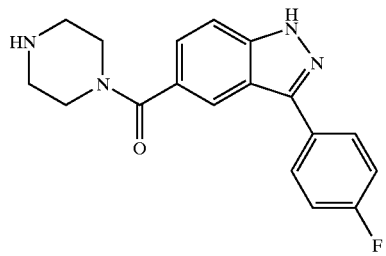

A. tert-Butyl 4-{[1-acetyl-3-(4-fluorophenyl-1H-indazol-5-yl]carbonyl}piperazinecarboxylate The title compound (130 mg, 32%) was prepared as described in Example 100 A, using tert-butyl 1-piperazine carboxylate (129 mg, 0.694 mmol) and trituration with dichloromethane and hexanes. ES-MS (m/z) 482 [M+1]$^+$.

B. 1-Acetyl-3-(4-fluorophenyl)-5-(piperazinylcarbonyl)-1H-indazole

The title compound was prepared as described in Example 100 B, except that the solid was purified by trituration with dichloromethane and hexanes (120 mg). ES-MS (m/z) 367 [M+1]$^+$.

C. 3-(4-Fluorophenyl)(1H-indazol-5-yl)piperazinyl ketone

The title compound was prepared as described in Example 14 B, using 0.3% ammonium hydroxide in methanol (6 mL). The methanol was then removed and the resulting solid was purified by trituration with dichloromethane and hexanes to afford the title compound (24 mg, 23%). $^1$H NMR (DMSO-d$_6$) δ 13.53 (s, 1H), 8.11 (s, 1H), 8.00 (m, 2H), 7.62 (d, 1H), 7.44 (m, 1H), 7.34 (m, 2H), 3.72 (br, 4H), 3.10 (m, 4H); ES-MS (m/z) 325 [M+1]$^+$.

Example 104

SYNTHESIS OF [3-(4-FLUOROPHENYL)(1H-INDAZOL-5-YL)]-N-(PHENYLMETHOXY)CARBOXAMIDE

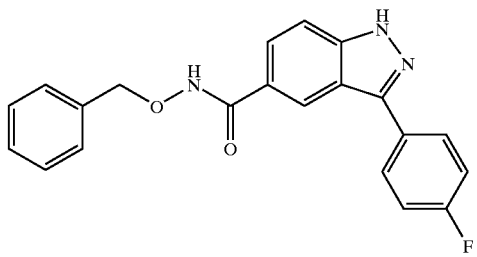

A. [3-(4-Fluorophenyl)(1H-indazol-5-yl)]-N-(phenylmethoxy)carboxamide

The title compound (166 mg, 73%) was prepared as described in Example 102 A, except that an additional drop of ammonium hydroxide was added. ES-MS (m/z) 362 [M+1]$^+$.

Example 105

SYNTHESIS OF [3-(4-FLUOROPHENYL)(1H-INDAZOL-5-YL)]-N-(2-HYDROXYPROPYL)CARBOXAMIDE

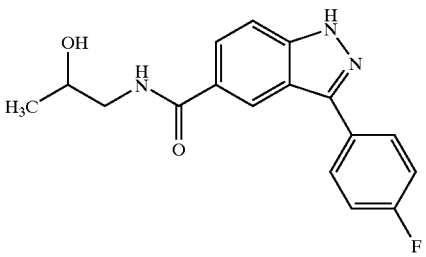

A. [3-(4-Fluorophenyl)(1H-indazol-5-yl)]-N-(2-hydroxypropyl)carboxamide

The title compound (68 mg, 28% yield) was prepared as described in Example 86 A, using 1-amino-2-propanol (64 mg, 0.852 mmol) and triethyl amine (3 drops) in lieu of 4-(dimethylamino)pyridine. ES-MS (m/z) 314[M+1]$^+$.

Example 106

SYNTHESIS OF 3-(4-FLUOROPHENYL)-1H-INDAZOLE-5-CARBOHYDROXAMIC ACID

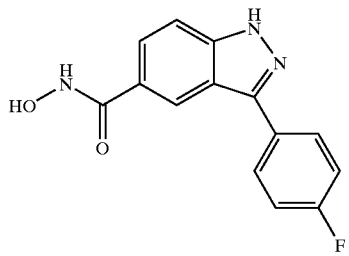

A. 3-(4-fluorophenyl)-1H-indazole-5-carbohydroxamic acid

To a solution containing [3-(4-fluorophenyl)(1H-indazol-5-yl)]-N-phenylmethoxy)carboxamide (140 mg, 0.388 mmol) in ethyl acetate (10 mL) was added palladium on activated carbon (10%, 30 mg). The reaction mixture was stirred at ambient temperature for 18 hours. It was filtered with celite and washed with ethyl acetate. The filtrate was concentrated to give the title compound (35 mg, 33%). ES-MS (m/z) 272 [M+1]$^+$.

Example 107

SYNTHESIS OF N-(2H-1,2,3,4-TETRAZOL-5-YL) [3-(4-FLUOROPHENYL)(1H-INDAZOL-5-YL)]CARBOXAMIDE

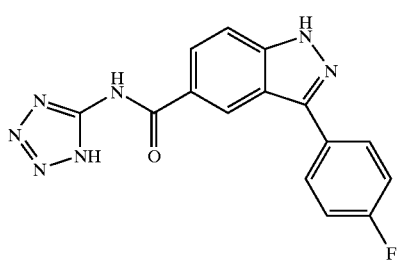

A. N-(2H-1,2,3,4-Tetrazol-5-yl)[3-(4-fluorophenyl)(1H-indazol-5-yl)]carboxamide

The title compound was prepared as described in Example 86 A, except that 4-(dimethylamino)pyridine was omitted, and purified by preparative HPLC (20 mg, 6% yield). $^1$H NMR (DMSO-d$_6$) δ 13.61 (br s, 1H), 12.52 (br s, 1H), 8.89 (s, 1H), 8.06 (m, 3H), 7.71 (d, 1H), 7.40 (t, 2H); ES-MS (m/z) 324 [M+1]$^+$.

Example 108

SYNTHESIS OF {3-(4-FLUOROPHENYL)(1H-INDAZOL-5-YL)}-N-(3-MORPHOLIN-4-YLPROPYL)CARBOXAMIDE

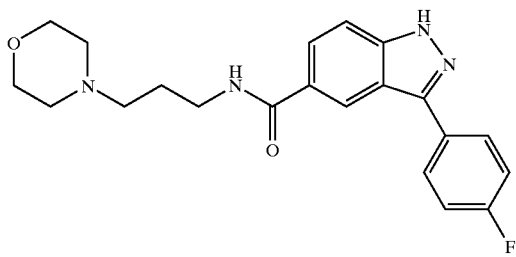

A. 1-Acetyl-3-(4-fluorophenyl)-1H-indazole-5-carboxylic acid

To a flask containing 3-(4-fluorophenyl)-1H-indazole-5-carboxylic acid (5.0 g, 0.02 mol) was added acetic acid (100 mL). The flask was placed under nitrogen and to the flask was added acetic anhydride (5.6 mL, 0.06 mol). The reaction refluxed at 80° C. for three hours. The flask was cooled to room temperature and the reaction was diluted with water. The product was collected by vacuum filtration and rinsed with additional amounts of water to yield the title compound (5.96 g, 100% yield) $^1$H NMR (DMSO-d$_6$) δ 8.6 (s, 1H), 8.45–8.5 (d, 1H), 8.2–8.25 (d, 1H), 8.1 (m, 2H), 7.5 (t, 2H), 2.8 (s, 3H).

B. 1-Acetyl-3-(4-fluorophenyl)-1H-indazole-5-carbonyl chloride

To a flask containing 1-acetyl-3-(4-fluorophenyl)-1H-indazole-5-carboxylic acid (1.5 g, 5.9 mmol) was added dichloromethane (80 mL) and oxalyl chloride (1.02 mL, 11.7 mmol). The reaction was allowed to stir under a nitrogen atmosphere overnight. To the flask was added a catalytic amount of DMF. The reaction was allowed to stir for three hours. TLC indicated reaction was complete. The solvent was removed and a solid formed to yield the title compound (1.57 g, 84% yield).

C. {3-(4-Fluorophenyl)(1H-indazol-5-yl)}-N-(3-morpholin-4-ylpropyl)carboxamide

To a flask containing a solution of 4-(3-Aminopropyl)-morpholine (117 μl, 0.79 mmol) in pyridine (1 mL) was added 1-acetyl-3-(4-fluorophenyl)-1H-indazole-5-carbonyl chloride (230 mg, 0.72 mmol) dissolved in pyridine (5 mL). The reaction was allowed to stir under a nitrogen atmosphere overnight. The reaction was not complete so an additional equivalent of 4-(3-Aminopropyl)-morpholine (100 μl, 0.72 mmol) was added. The reaction was allowed to stir at room temperature overnight. LCMS showed the product formation. Solvent was removed by rotary evaporation. The reaction was treated with water and the product was extracted with ethyl acetate and dichloromethane. The organic layers were combined and washed with saturated aqueous sodium carbonate solution and brine. The organic layer was dried with magnesium sulfate, filtered and concentrated to yield the product. This was purified by semi-preparative HPLC. The product was washed with a sodium bicarbonate solution to remove the TFA salt to yield the title compound (37.3 mg, 13.5% yield). $^1$H NMR (DMSO-d$_6$) δ 8.6 (m, 1H), 8.5 (m, 1H), 8.0 (m, 2H), 7.9 (m, 1H), 7.7 (m, 1H), 7.4 (m, 2H), 3.3 (m, 4H), 3.1 (m, 2H), 2.3 (m, 6H), 1.6 (m, 2H) ES-MS m/z 383 [M+1]$^+$.

Example 109

SYNTHESIS OF [3-(4-FLUOROPHENYL)(1H-INDAZOL-5-YL)]-N-(3-PYRIDYLMETHYL)CARBOXAMIDE

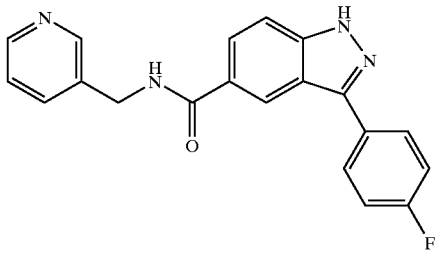

To a flask containing 1-acetyl-3-(4-fluorophenyl)-1H-indazole-5-carbonyl chloride (300 mg, 0.95 mmol) dissolved in pyridine (4 mL) was added 3-aminomethyl pyridine (106 μl, 1.05 mmol). The reaction was allowed to stir under a nitrogen atmosphere overnight. LCMS indicated the reaction was complete. Solvent was removed and water was added to the flask. A solid crashed out of solution that was collected by filtration. The solid was taken up in a 3% ammonia in methanol solution (8 mL) and allowed to reflux at 60° C. for three hours. The reaction was neutralized with 1 N HCl solution and extracted with ethyl acetate. The organic layer was dried with magnesium sulfate, filtered and concentrated to yield the title compound (134 mg, 41% yield). $^1$H NMR (DMSO-d$_6$) δ 13.5 (s, 1H), 9.2 (s, 1H), 8.6 (m, 2H), 8.5 (s, 1H), 8.1 (m, 2H), 7.95 (d, 1H), 7.65 (d, 1H), 7.6 (m, 1H), 7.4 (m, 3H), 4.6 (m, 2H) ES-MS m/z 347 [M+1]$^+$.

Example 110

SYNTHESIS OF N-[((2R)-2-HYDROXYCYCLOHEXYL)METHYL][3-(4-FLUOROPHENYL)(1H-INDAZOL-5-YL)]CARBOXAMIDE

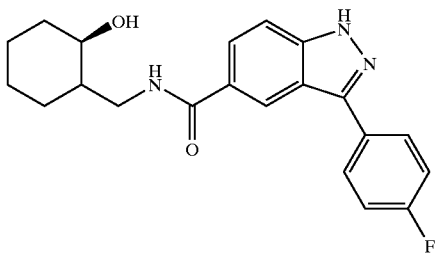

To a flask containing 1-acetyl-3-(4-fluorophenyl)-1H-indazole-5-carbonyl chloride (330 mg, 0.95 mmol) dissolved in pyridine (6 mL) was added trans-2-aminomethyl-1-cyclohexanol (135.6 mg, 1.05 mmol). The reaction was allowed to stir under a nitrogen atmosphere overnight. Solvent was removed and the reaction was extracted with ethyl acetate. The organic phase was washed with a saturated aqueous solution of sodium bicarbonate, dried with magnesium sulfate, filtered and concentrated to yield the crude product. The product was purified by column chromatography (SiO$_2$, 5% methanol in dichloromethane). The compound was taken up in a 3% ammonia in methanol solution (8 mL) and allowed to reflux at 60° C. for three hours. The reaction was neutralized with 1 N HCl solution and extracted with ethyl acetate. The organic layer was dried with magnesium sulfate, filtered and concentrated to yield the title compound (240 mg, 69% yield). $^1$H NMR (DMSO-d$_6$) δ 13.5 (s, 1H), 8.6 (s, 2H), 8.1 (m, 2H), 7.9 (d, 1H), 7.6 (d, 1H), 7.4 (m, 2H), 4.8 (s, 1H), 3.5 (m, 1H), 3.2 (m, 1H), 1.8 (m, 2H), 1.6 (m, 2H), 1.4 (m, 2H), 0.8–1.0 (m, 3H), ES-MS m/z 368 [M+1]$^+$.

Example 111

SYNTHESIS OF [3-(4-FLUOROPHENYL)(1H-INDAZOL-5-YL)]-N-[2-(1-METHYLIMIDAZOL-5-YL)ETHYL]CARBOXAMIDE)

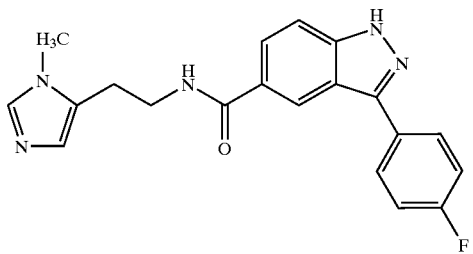

The product was synthesized as described in Example 109 using 1-acetyl-3-(4-fluorophenyl)-1H-indazole-5-carbonyl chloride (142.5 mg, 0.45 mmol) and 3-methylhistamine 100 mg, 0.5 mmol). The product was purified by semipreparative HPLC (20–80% acetonitrile gradient over 30 minutes at 20 mL/min) to yield the title compound (52 mg, 32% yield). $^1$H NMR (DMSO-d$_6$) δ 8.85 (s, 1H), 8.5 (s, 1H), 8.05 (m, 2H), 7.9 (d, 1H), 7.7 (d, 1H), 7.4 (m, 3H), 3.9 (s, 3H), 3.6 (m, 2H), 3.0 (m, 2H). ES-MS m/z 364 [M+1]$^+$.

Example 112

SYNTHESIS OF [3-(4-FLUOROPHENYL)(1H-INDAZOL-5-YL)]-N-(2-PYRIDYLMETHYL)CARBOXAMIDE

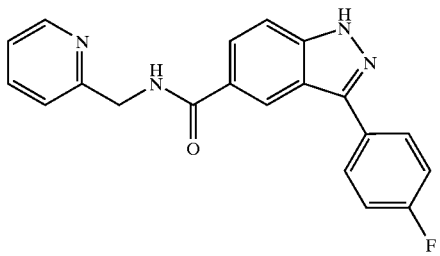

To a flask containing 1-acetyl-3-(4-fluorophenyl)-1H-indazole-5-carbonyl chloride (300 mg, 0.95 mmol) dissolved in pyridine (4 mL) was added 2-aminomethyl pyridine (106 µl, 1.02 mmol). The reaction was allowed to stir under a nitrogen atmosphere overnight. LCMS indicated the reaction was complete. Solvent was removed and water was added to the flask. A solid crashed out of solution that was collected by filtration. The product was purified by column chromatography (SiO$_2$, 5% methanol in dichloromethane). The solid was taken up in 3% ammonia in methanol solution (8 mL) and allowed to reflux at 60° C. for three hours. The reaction was neutralized with 1 N HCl solution and extracted with Ethyl Acetate. The organic layer was dried with magnesium sulfate, filtered and concentrated to yield the title compound (106 mg, 32% yield). $^1$H NMR (DMSO-d$_6$) δ 13.5 (s, 1H), 9.3 (t, 1H), 8.65 (s, 1H), 8.5 (d, 1H), 8.1 (m, 2H), 8.0 (d, 1H), 7.75 (t, 1H), 7.65 (d, 1H), 7.4 (m, 3H), 7.25 (t, 1H), 4.6 (d, 2H), ES-MS m/z 368 [M+1]$^+$.

Example 113

SYNTHESIS OF N-[(TERT-BUTOXY)CARBONYLAMINO][3-(4-FLUOROPHENYL)(1H-INDAZOL-5-YL)]CARBOXAMIDE

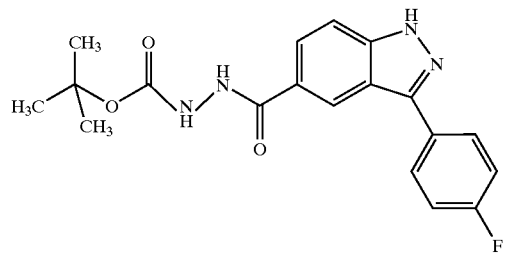

The product was synthesized as described in Example 109 A using 1-acetyl-3-(4-fluorophenyl)-1H-indazole-5-carbonyl chloride (500 mg, 1.58 mmol) and tert-butyl carbazate (230 mg, 1.74 mmol). $^1$H NMR (DMSO-d$_6$) δ 10.35 (s, 1H), 8.95 (s, 1H), 8.4 (s, 1H), 8.1 (m, 2H), 7.9 (d, 1H), 7.65 (d, 1H), 7.4 (t, 2H), 1.3–1.5 (m, 9H), ES-MS m/z 371 [M+1]$^+$.

Example 114

SYNTHESIS OF N-AMINO[3-(4-FLUOROPHENYL)(1H-INDAZOL-5-YL)]CARBOXAMIDE

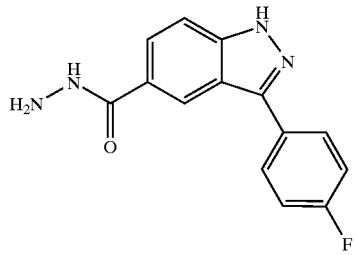

To a flask containing N-[(tert-butoxy)carbonylamino][3-(4-fluorophenyl)(1H-indazol-5-yl)]carboxamide (230 mg, 0.62 mmol) was added 4 N HCl in dioxane (6 mL). The reaction was allowed to stir for four hours. The reaction was treated with 10% sodium hydroxide solution to make the reaction slightly basic. The solvent was removed and the reaction was diluted with water and extracted with ethyl acetate. The organic layer was dried with magnesium sulfate, filtered and concentrated to yield the title compound (153 mg, 91.6% yield). $^1$H NMR (DMSO-d$_6$) δ 13.5 (s, 1H), 9.9 (s, 1H), 8.55 (s, 1H), 8.1 (m, 2H), 7.9 (d, 1H), 7.65 (d, 1H), 7.4 (t, 2H), 4.5 (bs, 1H), 3.6 (s, 1H), ES-MS m/z 271 [M+H]$^+$.

Example 115

N-(2-CARBAMOYLETHYL)[3-(4-FLUOROPHENYL)(1H-INDAZOL-5-YL)]CARBOXAMIDE

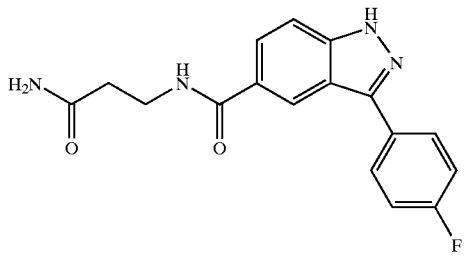

A. Tert-butyl 3-{[1-acetyl-3-(4-fluorophenyl-1H-indazol-5-yl]carbonylamino}propanoate The title compound was prepared as described in Example 91 A, using H-β-Ala-O-tert-butyl hydrochloride (249 mg, 1.90 mmol) and 1-acetyl-3-(4-fluorophenyl)-1H-indazole-5-carbonyl chloride (300 mg, 0.947 mmol). The reaction mixture was extracted with 5% sodium carbonate and ethyl acetate to afford the title compound (115 mg, 28%). ES-MS (m/z) 426[M+1]+.

B. N-(2-carbamoylethyl)[3-(4-fluorophenyl)(1H-indazol-5-yl)]carboxamide

A sealed tube containing tert-butyl 3-{[1-acetyl-3-(4-fluorophenyl)-1H-indazol-5-yl]carbonylamino}propanoate (115 mg, 0.270 mmol) and methanol saturated with ammonium hydroxide (2 mL) was heated to 80° C. for 18 hours. The solution was condensed to give an oil. The oil was dissolved in dimethyl formamide (5 mL) with N—N'-carbonyldiimidazole (110 mg). The solution was allowed to stir for two hours at ambient temperature. Ammonium acetate (160 mg) was added and the reaction mixture was allowed to stir at ambient conditions under nitrogen for 18 hours. The mixture was condensed and extracted with 5% sodium bicarbonate and ethyl acetate. The extracts were dried over sodium sulfate, filtered and condensed to give the title compound (17 mg, 19% yield) after purification by preparative-HPLC. $^1$H NMR (DMSO-$d_6$) δ 8.65 (br s, 1H), 8.47 (s, 1H), 8.00 (m, 2H), 7.84 (d, 1H), 7.59 (d, 1H), 7.43 (br, 1H), 7.35 (t, 2H), 6.84 (s, 1H), 3.45 (m, 2H), 2.39 (m, 2H); ES-MS (m/z) 327[M+1]+.

Example 116

N-(3-CARBAMOYLPROPYL)[3-(4-FLUOROPHENYL)(1H-INDAZOL-5-yl)]CARBOXAMIDE

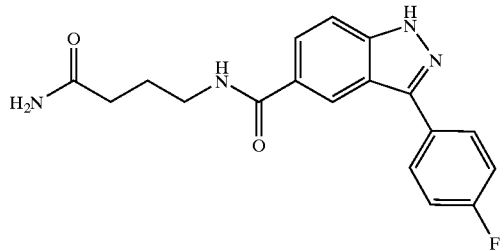

A. Methyl 4-{[1-acetyl-3-(4-fluorophenyl)-1H-indazol-5-yl]carbonylamino}butanoate The title compound was prepared as described in Example 91 A, using methyl 4-amino butyrate hydrochloride (291 mg, 1.90 mmol), except that the solution was extracted with 5% sodium bicarbonate solution and ethyl acetate. The resulting solid was triturated with dichloromethane and hexanes to afford the title compound (95 mg, 25%). ES-MS (m/z) 398[M+1]+.

B. N-(3-carbamoylpropyl)[3-(4-fluorophenyl)(1H-indazole-5-yl)]carboxamide

A sealed glass bomb containing methyl 4-{[1-acetyl-3-(4-fluorophenyl)-1H-indazole-5-yl]carbonylamino}butanoate (95 mg, 0.239 mmol) in methanol with saturated ammonia (7 mL) was heated to 80° C. for 18 hours. The reaction mixture was condensed and the resulting solid was purified by HPLC to afford the title compound (35 mg, 43% yield). $^1$H NMR (DMSO-$d_6$) δ 13.43 (br s, 1H), 8.50 (s, 1H), 8.04 (m, 2H), 7.87 (d, 1H), 7.58 (d, 1H), 7.37 (t, 1H), 7.29 (s, 1H), 6.75 (br s, 1H), 3.75 (m, 2H), 2.09 (t, 2H), 1.73 (t, 2H); ES-MS (m/z) 341[M+1]+.

Example 117

SYNTHESIS OF 5-[3-(4-FLUOROPHENYL)(1H-INDAZOLE-5-YL)]-3-METHYL-4H-1,2,4-TRIAZOLE

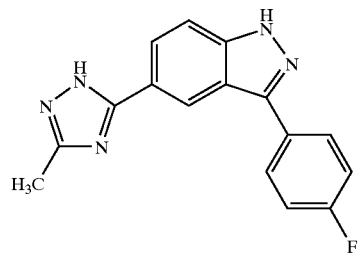

A. [3-(4-Fluorophenyl)inden-5-yl]-N-{(iminoethyl)amino]carboxamide

To a flask containing N-amino[3-(4-fluorophenyl)(1H-indazol-5-yl)]carboxamide (196 mg, 0.73 mmol) under a nitrogen atmosphere was added anhydrous ethanol (3 mL) and triethylamine (0.1 mL, 0.73 mmol). In a separate flask ethyl acetimidate hydrochloride (90 mg, 0.73 mmol) was dissolved in anhydrous ethanol (2 mL) and triethylamine (0.1 mL, 0.73 mmol). The flask containing the N-amino[3-(4-fluorophenyl)(1H-indazole-5-yl)]carboxamide solution was placed on ice while the ethyl acetimidate hydrochloride solution was added dropwise to the chilled flask. The flask was kept at 0° C. for 2 hours and then allowed to stir at room temperature for two days. LC-MS indicated the reaction was complete. The solvent was removed and the compound was taken on crude into the next step of the synthesis. ES-MS m/z 312 [M+H]+.

B. 5-[3-(4-Fluorophenyl)(1H-indazole-5-yl)]-3-methyl-4H-1,2,4-triazole

In a flask containing [3-(4-fluorophenyl)inden-5-yl]-N-{(iminoethyl)amino]carboxamide (81 mg, 0.26 mmol) under a nitrogen atmosphere was added anhydrous dimethylformamide (5 mL). This was heated overnight at 110° C. In an additional flask [3-(4-fluorophenyl)inden-5-yl]-N-{(iminoethyl)amino]carboxamide (105 mg, 0.33 mmol) was heated overnight in anhydrous dimethylformamide (5 mL) at 80° C. The solvents for both reaction were removed and the products combined. The combined product was purified by HPLC (20–100 acetonitrile gradient over 30 minutes at 20 mL/min) to yield the title compound (19 mg, 11% yield). $^1$H NMR (DMSO-d$_6$) δ 13.5 (s, 1H), 8.6 (s, 1H), 8.0–8.08 (m, 3H), 7.7 (d, 1H), 7.42 (t, 2H), 2.5 (s, 3H), ES-MS m/z 294 [M+H]$^+$.

Example 118

SYNTHESIS OF 5-{3-(4-FLUOROPHENYL)(1H-INDAZOLE-5-YL)]-3-(METHYLETHYL)-4H-1,2,4-TRIAZOLE

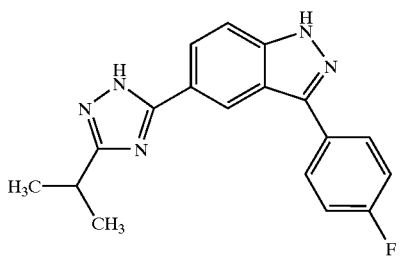

A. Ethoxy[3-(4-fluorophenyl)(1H-indazole-5-yl)]methanimine hydrochloride

To a flask containing 3-(4-fluorophenyl-1H-indazole-5-carbonitrile (200 mg, 0.84 mmol) was added absolute ethanol (15 mL). The flask was placed in an ice bath and into the flask was bubbled hydrochloric acid gas until the solution became saturated. The reaction was allowed to stir under a nitrogen atmosphere overnight. LC-MS showed the reaction was complete. The solvent was removed and left on the pump to dry. The product was taken on crude into the next step of the synthesis ES-MS (m/z) 284.

B. 5-[3-(4-Fluorophenyl)(1H-indazole-5-yl}-3-(methylethyl-4H-1,2,4-triazole

To a flask containing ethoxy[3-(4-fluorophenyl)(1H-indazole-5-yl)]methanimine hydrochloride (106 mg, 0.37 mmol) was added absolute ethanol (2.5 mL) and triethylamine (0.15 mL, 1.11 mmol). The flask was placed on ice and to the flask was added a solution of isobutyric acid hydrazide (37.7 mg, 0.37 mmol) in absolute ethanol was heated at 60° C. for fifteen hours. An additional two equivalents of the isobutyric acid hydrazide (75 mg, 0.74 mmol) and triethylamine (0.2 mL, 1.35 mmol) was added to the reaction and allowed to stir overnight. Reaction was continuing to progress slowly, two equivalents of the isobutyric acid hydrazide (75 mg, 0.74 mmol) and triethylamine (0.2 ml, 1.35 mmol) were added to the reaction and allowed to stir overnight. The reaction was stopped. Solvent was removed by rotary evaporation and the product was purified by HPLC to yield the title compound (53 mg, 45% yield). $^1$H NMR (DMSO-d$_6$) δ 13.5 (s, 1H), 8.6 (s,1H), 8.0–8.1 (m, 3H), 7.7 (m, 1H), 7.35–7.5 (m, 2H), 1.4 (m, 7H), ES-MS (m/z) 322 [M+1]$^+$.

Example 119

SYNTHESIS OF 1-{5-[3-(4-FLUOROPHENYL)-1H-INDAZOLE-5-YL]-4H-1,2,4-TRIAZOL-3-YL}PROPAN-2-OL

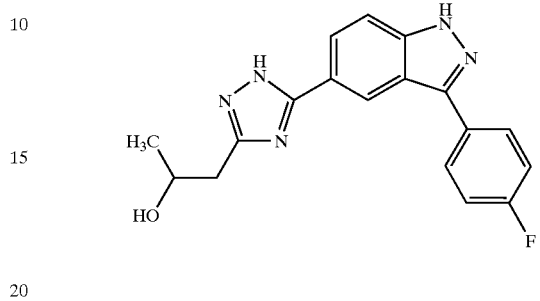

To a sealed tube containing ethoxy[3-(4-fluorophenyl)(1H-indazole-5-yl)]methanimine hydrochloride (300 mg, 0.94 mmol) dissolved in ethanol (15 mL) and triethylamine (0.3 μl, 2.82 mmol) was added a solution of 3-hydroxybutyric acid hydrazide (190 mg, 1.5 mmol) in ethanol. The reaction was sealed and allowed to stir at 70° C. overnight. Solvent was removed and the product was purified via HPLC to yield the title compound. $^1$H NMR (DMSO-d$_6$) δ 8.7 (s, 1H), 8.1 (m, 3H), 7.75 (d, 1H), 7.4 (t, 2H), ES-MS (m/z) 338 [M+1]$^+$.

Example 120

SYNTHESIS OF 5-{3-(4-FLUOROPHENYL)(1H-INDAZOLE-5-YL)]-3-PHENYL-4H-1,2,4-TRIAZOLE

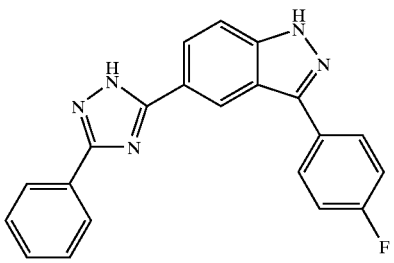

The procedure described in example 119 using ethoxy[3-(4-fluorophenyl)(1H-indazole-5-yl)]methanimine hydrochloride (200 mg, 0.62 mmol), triethylainine (0.25 mL, 1.86 mmol) and benzoic hydrazide (170 mg, 1.25 mmol) was followed to yield the title compound (105 mg, 48% yield). $^1$H NMR (DMSO-d$_6$) δ 13.5 (br s, 1H), 8.74 (s, 1H), 8.0–8.2 (m, 5H), 7.75 (d, 1H), 7.35–7.6 (m, 5H), ES-MS (m/z) 356 [M+1]$^+$.

Example 121

SYNTHESIS OF 2-{5-[3-(4-FLUOROPHENYL)-(1H-INDAZOL-5-YL]-4H-1,2,4-TRIAZOL-3-YL}FURAN

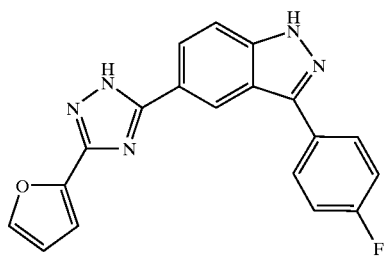

The procedure described in example 119 using ethoxy[3-(4-fluorophenyl)(1H-indazol-5-yl)]methanimine hydrochloride (200 mg, 0.62 mmol), triethylainine (0.25 mL, 1.86 mmol) and 2-furoic acid hydrazide (157.6 mg, 1.25 mmol) was followed to yield the title compound (32 mg, 15% yield). $^1$H NMR (DMSO-d$_6$) δ 14.8 (br s, 1H), 13.5 (s, 1H), 8.7 (s, 1H), 8.0–8.15 (m, 3H), 7.78 (s, 1H), 7.75 (d, 1H), 7.4 (t, 2H), 7.0 (br s, 7.0), 6.65 (s, 1H), ES-MS (m/z) 346 [M+1]$^+$.

Example 122

SYNTHESIS OF 5-[3-(4-FLUOROPHENYL)(1H-INDAZOL-5-YL)]-3-(4-PYRIDYL)-4H-1,2,4-TRIAZOLE

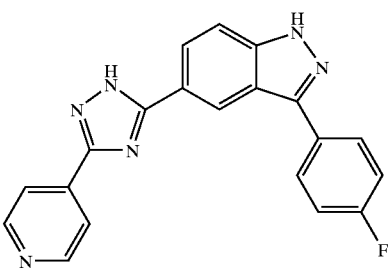

The procedure described in example 119 using ethoxy[3-(4-fluorophenyl)(1H-indazole-5-yl)]methanimine hydrochloride (200 mg, 0.62 mmol), triethylainine (0.25 mL, 1.86 mmol) and isonicotinic acid hydrazide (171.42 mg, 1.25 mmol) was followed to yield the title compound (34 mg, 15% yield). $^1$H NMR (DMSO-d$_6$) δ 13.6 (s, 1H), 8.78–8.82 (m, 3H), 8.05–8.25 (m, 5H), 7.8 (d, 1H), 7.45 (t, 2H), ES-MS (m/z) 357 [M+1]$^-$.

Example 123

SYNTHESIS OF 3-(4-CHLOROPHENYL)-5-[3-(4-FLUOROPHENYL)(1H-INDAZOL-5-YL)]-4H-1,2,4-TRIAZOLE

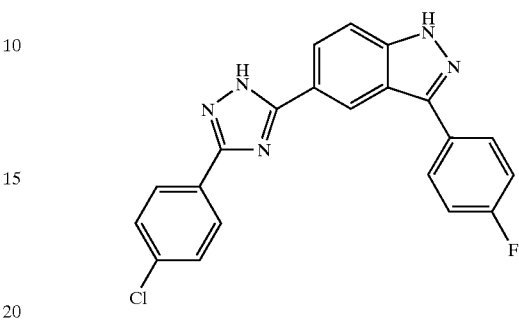

To a sealed tube containing ethoxy[3-(4-fluorophenyl)(1H-indazol-5-yl)]methanimine hydrochloride (300 mg, 0.94 mmol) dissolved in ethanol (15 mL) and triethylamine (0.3 µL, 2.82 mmol) was added 4-chlorobenzoic hydrazide (213 mg, 1.25 mmol). The tube was sealed and allowed to stir at 75° C. overnight. The solvent was removed and the material was purified by HPLC to yield the title compound (46 mg, 19% yield). $^1$H NMR (DMSO-d$_6$) δ 13.5 (s, 1H), 8.75 (s, 1H), 8.0–8.2 (m, 5H), 7.76 (d, 1H), 7.6 (m, 2H), 7.4–7.42 (t, 2H), ES-MS (m/z) 390 [M+1]$^+$.

Example 124

SYNTHESIS OF 5-[3-(4-FLUOROPHENYL)(1H-INDAZOL-5-YL)]-3-PROPYL-4H-1,2,4-TRIAZOLE

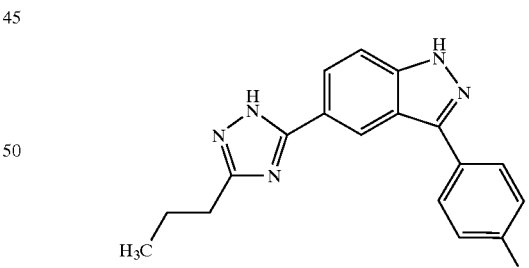

The procedure described in example 123 using ethoxy[3-(4-fluorophenyl)(1H-indazol-5-yl)]methanimine hydrochloride (200 mg, 0.62 mmol), triethylamine (0.25 mL, 1.86 mmol) and butyric acid hydrazide (127.7 mg, 1.25 mmol) was used to prepare the title compound (16 mg, 8% yield). $^1$H NMR (DMSO-d$_6$) δ 13.5 (s,1H), 8.6 (s, 1H), 8.0–8.1 (m, 3H), 7.68–7.7 (d, 1H), 7.42 (t, 2H), 2.7 (t, 2H), 1.75 (m, 2H), 0.95 (t, 3H), ES-MS (m/z) 322 [M+1]$^+$.

Example 125

SYNTHESIS OF 5-[3-(4-FLUOROPHENYL)(1H-INDAZOLE-5-YL)]-3-(4-NITROPHENYL)-4H-1,2,4-TRIAZOLE

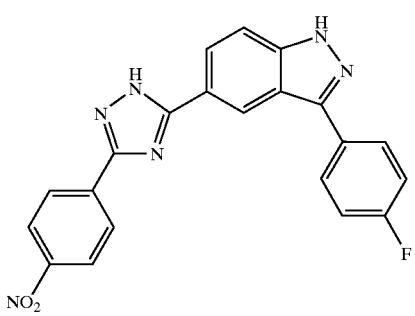

The procedure described in example 123 using ethoxy[3-(4-fluorophenyl)(1H-indazole-5-ylyimethanimine hydrochloride (400 mg, 1.25 mmol), triethylamine (0.5 mL, 3.7 mmol) and 4-nitrobenzoic hydrazide(452 mg, 2.5 mmol) was used to prepare the title compound (167 mg, 33% yield). $^1$H NMR (DMSO-$d_6$) δ 14.9 (bs, 1H), 13.6 (s, 1H), 8.79 (s, 1H), 8.4 (s, 4H), 8.05–8.2 (m, 3H), 7.8 (d, 1H), 7.45 (t, 2H), ES-MS (m/z) 401 [M+1]$^+$.

Example 126

SYNTHESIS OF 1-{5-[3-(4-FLUOROPHENYL)(1H-INDAZOL-5-YL)](4H-1,2,4-TRIAZOL-3-YL)]-4-METHOXYBENZENE

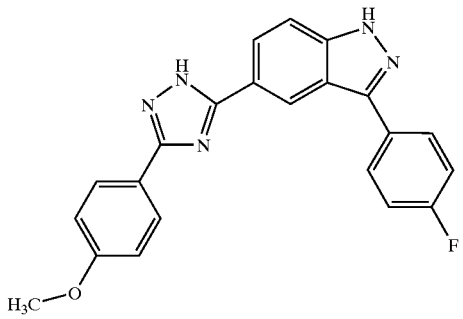

The procedure described in example 123 using ethoxy[3-(4-fluorophenyl)(1H-indazol-5-yl)]methanimine hydrochloride (400 mg, 1.25 mmol), triethylamine (0.5 mL, 3.7 mmol) and 4-methoxy benzhydrazide (415 mg, 2.5 mmol) was used to prepare the title compound (175 mg, 37% yield). $^1$H NMR (DMSO-$d_6$) δ 13.5 (s, 1H), 8.71 (s, 1H), 8.16 (d, 1H), 8.0–8.1 (m, 4H), 7.75 (d, 1H), 7.45 (t, 2H), 7.1 (d, 2H), 3.88 (s, 3H), ES-MS (m/z) 386 [M+1]$^+$.

Example 127

SYNTHESIS OF ETHYL-2-{5-[3-(4-FLUOROPHENYL)-1H-INDAZOL-5-YL]-4H-1,2,4-TRIAZOL-3-YL}ACETATE

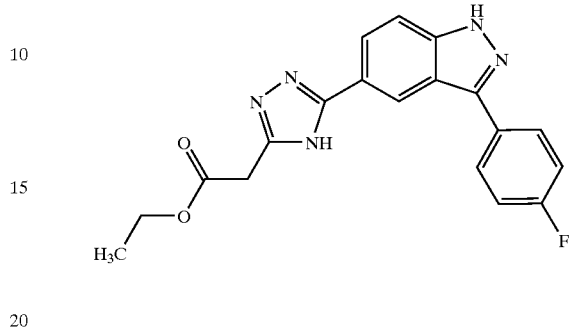

The procedure described in Example 123 using ethoxy[3-(4-fluorophenyl)(1H-indazole5-yl)]methanimine hydrochloride (400 mg, 1.25 mmol), triethylamine (0.5 mL, 3.7 mmol) and 4-methoxy benzhydrazide (415 mg, 2.5 mmol) was used to prepare the title compound (195 mg, 43% yield). $^1$H NMR (DMSO-$d_6$) δ 13.5 (s, 1H), 8.62 (s, 1H), 8.05 (t, 3H), 7.65 (d, 1H), 7.41 (t, 2H), 4.15 (q, 2H), 3.9 (s, 2H), 1.2 (t, 3H), ES-MS (m/z) 366 [M+1]$^+$.

Example 128

SYNTHESIS OF 4-{5-[3-(4-FLUOROPHENYL)-1H-INDAZOL-5-YL]-4H-1,2,4-TRIAZOL-3-YL}PHENYLAMINE

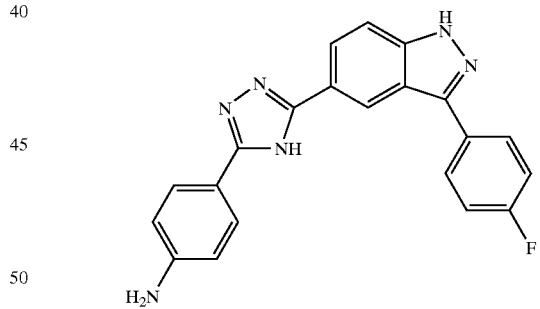

To a flask containing 5-[3-(4-fluorophenyl)(1H-indazol-5-yl)]-3-(4-nitrophenyl)-4H-1,2,4-triazole (60 mg) was added ethyl acetate (15 ml). The flask was evacuated and purged with nitrogen. To the flask was added palladium on carbon catalyst (10 mg). The reaction was placed under a hydrogen atmosphere and allowed to stir overnight. The reaction was filtered through celite and the organic layer was concentrated. The product was purified by HPLC to yield the title compound (15 mg, 26% yield). $^1$H NMR (DMSO-$d_6$) δ 13.5 (s, 1H), 8.65 (s, 1H), 8.1 (d, 1H), 8.05 (t, 2H), 7.77 (d, 2H), 7.7 (d, 1H), 7.4 (t, 2H), 6.7 (d, 2H), ES-MS (m/z) 371 [M+1]$^+$.

Example 129

SYNTHESIS OF 5-[3-(4-FLUOROPHENYL)(1H-INDAZOL-5-YL)]-3-BENZYL-4H-1,2,4-TRIAZOLE

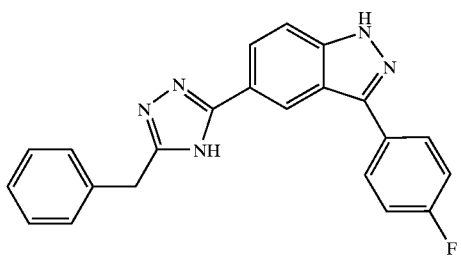

The procedure described in example 123 using ethoxy[3-(4-fluorophenyl)(1H-indazol-5-yl)]methanimine hydrochloride (200 mg, 0.62 mmol), triethylamine (0.25 mL, 1.86 mmol) and phenyl acetic hydrazide (187 mg, 1.25 mmol) was used to prepare the title compound (101 mg, 44% yield). $^1$H NMR (DMSO-d$_6$) δ 8.7 (s, 1H), 8.05 (m, 3H), 7.5 (d, 1H), 7.2–7.5 (m, 7H), 4.15 (s, 2H), ES-MS(m/z) 370 [M+1]$^+$.

Example 130

SYNTHESIS OF 2-[3-(4-FLUOROPHENYL)(1H-INDAZOL-5-YL)]-5-PHENYL-1,3,4-OXADIAZOLE

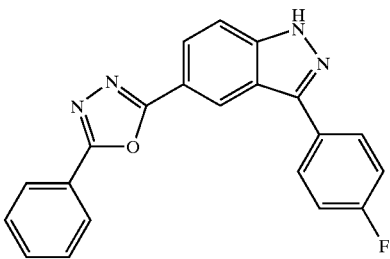

A. 2-[3-(4-Fluorophenyl)(1H-indazol-5-yl)]-5-phenyl-1,3,4-oxadiazole

To a solution of phenyl hydrazide (68 mg, 0.5 mmol) in pyridine (3 mL) was added N-acetyl,3-F-Phenyl-5-carbonyl chloride indazole (150 mg, 0.5 mmol). The solution was stirred overnight at room temperature when water (30 mL) was added and the solid was filtered and dried in a vacuum oven (40° C.). The solid was then taken up in thionyl chloride (20 mL) and refluxed for 3 hours when the solvent was removed. The crude reaction mixture was then chromatographed on silica gel eluting with 15% methanol in methylene chloride to recover the acetylated product. The solid was taken up in methanol (30 mL) and saturated ammonium hydroxide (3 mL) and stirred at room temperature for 3 hours when it was diluted with water (100 mL) and filtered. The title product was then dried in a vacuum oven to give 90 mg of said material (50% yield). $^1$H NMR (DMSO-d$_6$) δ 13.7 (br s, 1H), 8.76 (s, 1H), 8.23–8.14 (m, 3H), 8.10 (t, 2H), 7.83 (d, 1H), 7.68–7.62 (m, 3H), 7.43 (t, 2H); ES-MS (m/z) 357 [M+1]$^+$.

Example 131

SYNTHESIS OF 5-[3-(4-FLUOROPHENYL)(1H-INDAZOL-5-YL)]-2-METHYL-1,3,4-OXADIAZOLE

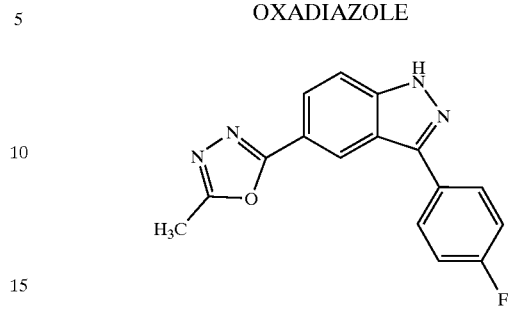

This was a byproduct isolated in the purification of Example 117, 5-[3-(4-fluorophenyl)(1H-indazole-5-yl)]-3-methyl-4H-1,2,4-triazole. $^1$H NMR (DMSO-d$_6$) δ 13.6 (s, 1H), 8.55 (s, 1H), 8.0–8.08 (m, 3H), 7.8 (d, 1H), 7.4 (t, 2H), 2.5 (s, 3H), ES-MS (m/z) 295 [M+1]$^+$.

Example 132

SYNTHESIS OF 3-(4-FLUOROPHENYL)-5-(2-PHENYLETHYNYL)-1H-INDAZOLE

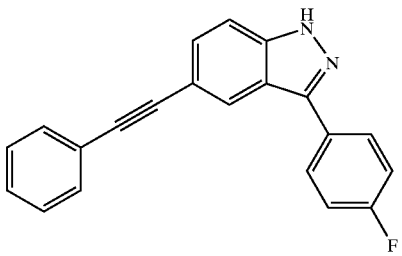

A. 2-Amino-5-bromo-4'-fluorobenzophenone

To neat 4-fluorobenzoyl chloride (50.00 g, 315 mmol) in a flask at 130° C. was added 4-bromoaniline (17.00 g, 100 mmol) in several portions. After it was stirred at 130° C. for 1 hour and the temperature was raised to 190° C., to the reaction mixture was added zinc chloride (11.00 g, 80.7 mmol) in several portions, then it was heated at 220° C. for 22 hours. Once cooled to 180° C., to the mixture was carefully added concentrated sulfuric acid (50 mL), acetic acid (70 mL), water (70 mL), and another portion of sulfuric acid (50 mL). The mixture was heated at 120° C. overnight. It was poured into water (500 mL) and a white solid was precipitated. It was collected by filtration and was dissolved in ethyl acetate and washed with 5% sodium carbonate until pH of the aqueous phase reached 8. The filtrate was basified with sodium carbonate and extracted with ethyl acetate. The combined ethyl acetate layers were dried over magnesium sulfate, filtered, and concentrated. The residue was then purified by chromatography (SiO$_2$, 15–20% ethyl acetate/hexane) to provide the title compound (13.64 g, 46% yield). $^1$H NMR (CDCl$_3$) δ 7.67 (m, 2H), 7.51 (d, 1H), 7.37 (dd, 1H), 7.14–7.20 (m, 2H), 6.65 (d, 1H), 6.02 (br s, 2H); ES-MS (m/z) 296 [M+3]$^+$, 294 [M+1]$^+$.

B. 5-Bromo-3-(4-fluorophenyl)-1H-indazole

To a solution of 2-amino-5-bromo-4'-fluorobenzophenone (13.50 g, 45.9 mmol) in 6 N hydrochloride solution (400 mL) and tetrahydrofuran (500 mL) at −15° C. was slowly dropped a solution of sodium nitrite (4.12 g, 59.7 mmol) in water (20 mL). After stirring for 30 minutes in cold bath, to the reaction mixture was added a solution of tin(II) chloride dihydrate (28.48 g, 126 mmol) in concentrated hydrochloric acid (70 mL) dropwise. A white solid precipitated immediately. After 30 minutes, the white solid was filtered, dissolved in ethyl acetate, and washed with saturated sodium bicarbonate. The filtrate was neutralized with sodium hydroxide and extracted with dichloromethane. The ethyl acetate and dichloromethane layers were combined, dried over magnesium sulfate, and concentrated. Crystallization from ethyl acetate gave the title compound as a white solid (5.266 g). The mother liquor was then purified by chromatography (SiO$_2$, 15–30% ethyl acetate/hexane) to provide another batch of the title compound (3.429 g, total 8.695 g, 65% yield). $^1$H NMR (CDCl$_3$) δ 10.54 (br s, 1H), 8.11 (m, 1H), 7.87–7.92 (m, 2H), 7.50 (m, 1H), 7.34 (d, 1H), 7.20–7.26 (m, 2H); ES-MS (m/z) 293 [M+3]$^+$, 291 [M+1]$^+$.

C. 5-Bromo-3-(4-fluorophenyl)-1-(tetrahydropyran-2-yl)-1H-indazole

To a solution of 5-bromo-3-(4-fluorophenyl)-1H-indazole (8.00 g, 27.48 mmol) in dried tetrahydrofuran (80 mL) under nitrogen at ambient temperature was added 3,4-dihydro-2H-pyran (5.78 g, 68.7 mmol) and p-toluenesulfonic acid monohydrate (1.00 g, 5.26 mmol). The reaction mixture was stirred at room temperature for 24 hours. It was quenched with dichloromethane and washed with 5% sodium carbonate and brine. The dichloromethane layer was dried over magnesium sulfate and concentrated. Crystallization from diethyl ether and hexane provided the title compound (8.47 g, 82% yield). $^1$H NMR (CDCl$_3$) δ 8.07 (t, 1H), 7.86–7.91 (m, 2H), 7.47–7.55 (m, 2H), 7.16–7.26 (m, 2H), 5.74 (dd, 1H), 4.05 (m, 1H), 3.76 (m, 1H), 2.60 (m, 1H), 2.08–2.21 (m, 2H), 1.66–1.83 (m, 3H); ES-MS (m/z) 377 [M+3]$^+$, 375 [M+1]$^+$.

D. 3-(4-Fluorophenyl)-5-(2-phenylethynyl)-1-(tetrahydropyran-2-yl)-1H-indazole

A mixture of 5-bromo-3-(4-fluorophenyl)-1-(tetrahydropyran-2-yl)-1H-indazole (0.375 g, 1.0 mmol), triethylamine (1.5 mL), tri-o-tolylphosphine (0.122 g, 0.4 mmol), tri(dibenzylideneacetone)dipalladium(0) (0.092 g, 0.1 mmol) and phenylacetylene (0.204 g, 2.0 mmol) in dried acetonitrile (10 mL) under nitrogen was heated to reflux overnight. It was quenched with water and extracted with ethyl acetate. The extracts were dried over magnesium sulfate, filtered, and concentrated. The residue was then purified by chromatography (SiO$_2$, 10–15% ethyl acetate/hexane) to provide the title compound (0.127 g, 32% yield). $^1$H NMR (CDCl$_3$) δ 8.16 (t, 1H), 7.93–7.97 (m, 2H), 7.54–7.64 (m, 4H), 7.34–7.37 (m, 3H), 7.21 (t, 2H) 5.77 (dd, 1H), 4.08 (m, 1H), 3.79 (m, 1H), 2.62 (m, 1H), 2.11–2.21 (m, 2H), 1.57–1.83 (m, 3H); ES-MS (m/z) 397 [M+1]$^+$.

E. 3-(4-Fluorophenyl)-5-(2-phenylethynyl)-1H-indazole

To a solution of 3-(4-fluorophenyl)-5-(2-phenylethynyl)-1-(tetrahydropyran-2-yl)-1H-indazole in tetrahydrofuran (15 mL) was added 6 N hydrochloride solution (10 mL) and the mixture was stirred at ambient temperature overnight. After tetrahydrofuran was evaporated, the aqueous phase was neutralized with 5% sodium carbonate and extracted with ethyl acetate. The extracts were dried over magnesium sulfate, filtered, and concentrated. The residue was then purified by chromatography (SiO$_2$, 15–30% ethyl acetate/hexane) to provide the title compound (0.071 g, 90% yield). $^1$H NMR (CDCl$_3$) δ 10.19 (br, 1H), 8.20 (s, 1H), 7.94–7.98 (m, 2H), 7.55–7.61 (m, 3H), 7.48 (dd, 1H), 7.34–7.41 (m, 3H), 7.23 (t, 2H); ES-MS (m/z) 313 [M+1]$^+$.

Example 133

SYNTHESIS OF 5-[(1E)-2-PHENYLVINYL]-3-(4-FLUOROPHENYL)-1H-INDAZOLE

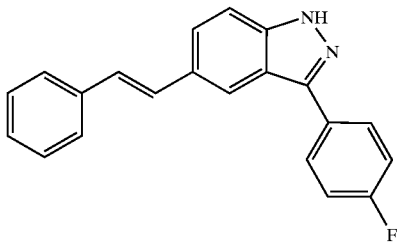

A. 5-[(1E)-2-Phenylvinyl]-3-(4-fluorophenyl)-1-(tetrahydropyran-2-yl)-1H-indazole The title compound was prepared as described in Example 132 D, using styrene (0.208 g, 2.0 mmol) (0.267 g, 67% yield). $^1$H NMR (CDCl$_3$) δ 7.94–7.99 (M, 3H), 7.69 (dd, 1H), 7.62 (d, 1H), 7.55 (d, 1H), 7.53 (d, 1H), 7.37 (t, 2H), 7.19–7.29 (M, 4H), 7.15 (d, 1H), 5.77 (dd, 1H), 4.08 (m, 1H), 3.79 (m, 1H), 2.63 (m, 1H), 1.83–2.21 (m, 2H), 1.57–1.80 (m, 3H); ES-MS (m/z) 399 [M+1]$^+$.

B. 5-[(1E)-2-Phenylvinyl]-3-(4-fluorophenyl)-1H-indazole

The title compound was prepared as described in Example 132.E, using 5-[(1E)-2-phenylvinyl]-3-(4-fluorophenyl)-1-(tetrahydropyran-2-yl)-1H-indazole (0.20 g, 0.5 mmol) (0.124 g, 79% yield). $^1$H NMR (CDCl$_3$) δ 10.1 (br 5, 1H), 7.95–8.02 (m, 3H), 7.72 (dd, 1H), 7.49–7.56 (m, 3H), 7.38 (t, 2H), 7.21–7.30 (m, 4H), 7.15 (d, 1H); ES-MS (m/z) 315 [M+1]$^+$.

Example 134

SYNTHESIS OF 5-[(1E)-2-(2-PYRIDYL)VINYL]-3-(4-FLUOROPHENYL)-1H-INDAZOLE

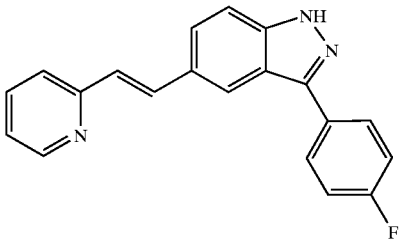

A. 5-[(1E)-2-Pyridylvinyl]-3-(4-fluorophenyl)-1-(tetrahydropyran-2-yl)-1H-indazole The title compound was prepared as described in Example 132.D, using 2-vinylpyridine (0.210 g, 2.0 mmol) (0.305 g, 76% yield). $^1$H NMR (CDCl$_3$) δ 8.61 (d, 1H), 8.09 (d, 1H), 7.94–7.98 (m, 2H), 7.62–7.80 (m, 4H), 7.42 (d,1H), 7.13–7.24 (m, 4H), 5.77 (dd, 1H), 4.08 (m, 1H), 3.79 (m, 1H), 2.63 (m, 1H), 2.10–2.21 (m, 2H), 1.64–1.83 (m, 3H); ES-MS (m/z) 400 [M+1]$^+$.

B. 5-[(1E)-2-Pyridylvinyl]-3-(4-fluorophenyl)-1H-indazole

The title compound was prepared as described in Example 132 E, using 5-[(1E)-2-pyridylvinyl]-3-(4-fluorophenyl)-1-(tetrahydropyran-2-yl)-1H-indazole (0.20 g, 0.5 mmol) (0.149 g, 94% yield). $^1$H NMR (DMSO-d$_6$) δ 13.4 (br s, 1H), 8.76 (d, 1H), 8.53 (t, 1H), 8.35–8.45 (m, 3H), 8.06 (m, 2H), 7.70–7.85 (m, 4H), 7.40 (m, 2H); ES-MS (m/z) 316 [M+1]$^+$.

Example 135

SYNTHESIS OF 4-{(1E)-2-[(3-(4-FLUOROPHENYL)-1H-INDAZOL-5-YL]VINYL}BENZOIC ACID

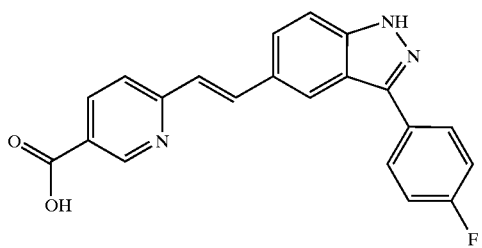

A. 4-{(1E)-2[(3-(4-Fluorophenyl)-1-(tetrahydropyran-2-yl)-1H-indazol-5-yl]vinyl}benzoic Acid The title compound was prepared as described in Example 132 D, using 4-vinylbenzoic acid (0.296 g, 2.0 mmol) (0.284 g, 64% yield). $^1$H NMR (DMSO-d$_6$) δ 12.87 (br s, 1H), 8.25 (s, 1H), 8.07 (m, 2H), 7.94 (m, 3H), 7.84 (d, 1H), 7.74 (d, 2H), 7.63 (d, 1H), 7.40 (m, 3H), 5.94 (d, 1H), 3.92 (m, 1H), 3.81 (m, 1H), 2.47 (m, 1H), 2.06 (m, 2H), 1.78 (m, 3H); ES-MS (m/z) 443 [M+1]$^+$.

B. 4-{(1E)-2[(3-(4-Fluorophenyl)-1H-indazol-5-yl]vinyl}benzoic Acid

The title compound (0.163 g, 91% yield) was prepared as described in Example 132 E, using 4-{(1E)-2-[(3-(4-fluorophenyl)-1-(tetrahydropyran-2-yl)-1H-indazole-5-yl]vinyl}benzoic acid (0.221 g, 0.5 mmol). $^1$H (DMSO-d$_6$) δ 13.35 (br s, 1H), 12.8 (br s, 1H), 8.25 (s, 1H), 8.08 (m, 2H), 7.95 (d, 2H), 7.83 (d, 1H), 7.74 (d, 2H), 7.63 (m, 2H), 7.38 (m, 3H); ES-MS (m/z) 359 [M+1]$^+$.

Example 136

SYNTHESIS OF 5-[(1E)-2-(3-NITROPHENYL)VINYL]-3-(4-FLUOROPHENYL)-1H-INDAZOLE

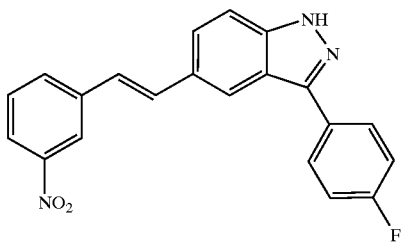

A. 5-[(1E)-2-(3-Nitrophenyl)vinyl]-3-(4-fluorophenyl)-1H-indazole

The title compound (0.134 g, 52% yield) was prepared as described in Example 132 D, using 5-bromo-3-(4-fluorophenyl)-1H-indazole (0.291 g, 1.0 mmol) and 3-nitrostyrene (0.298 g, 2.0 mmol). $^1$H NMR (CDCl$_3$) δ 10.12 (br s, 1H), 8.41 (t, 1H), 8.11 (ddd, 1H), 8.07 (s, 1H), 7.97 (m, 2H), 7.82 (d, 1H), 7.73 (dd, 1H), 7.54 (m, 2H), 7.40 (d, 1H), 7.26 (m, 2H), 7.16 (d, 1H); ES-MS (m/z) 360 [M+1]$^+$.

Example 137

SYNTHESIS OF 5-[(1Z)-2-PHENYLVINYL]-3-(4-FLUOROPHENYL)-1H-INDAZOLE

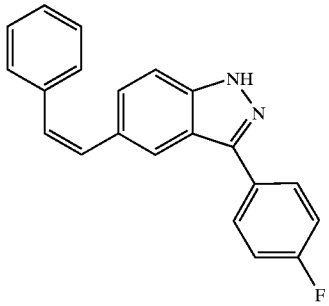

A. 5-[(1Z)-2-Phenylvinyl]-3-(4-fluorophenyl)-1H-indazole

A mixture of 3-(4-fluorophenyl)-5-(2-phenylethynyl)-1H-indazole (0.050 g, 0.16 mmol), quinoline (0.030 g), and palladium (5 wt. % on barium carbonate, 0.015 g) in ethyl acetate (10 mL) was stirred under hydrogen for 5 hours. It was filtered with celite and washed with ethyl acetate. The filtrate was washed with 5% hydrochloric acid solution and brine, dried over magnesium sulfate, filtered, and concentrated. The residue was then purified by chromatography (SiO$_2$, 15–30% ethyl acetate/hexane) and by HPLC to provide the title compound (0.023 g, 46% yield): $^1$H NMR (CDCl$_3$) δ 10.15 (br s, 1H), 7.83 (s, 1H), 7.70 (m, 2H), 7.29 (m, 7H), 7.11 (t, 2H), 6.72 (d, 1H), 6.68 (d, 1H); ES-MS (m/z) 315 [M+1]$^+$.

Example 138

SYNTHESIS OF 5-[(1E)-2-(4-AMINOPHENYL)VINYL]-3-(4-FLUOROPHENYL)-1H-INDAZOLE

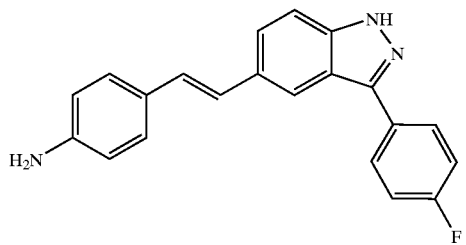

A. 5-[(1E)-2-(4-Aminophenyl)vinyl]-3-(4-fluorophenyl)-1-(tetrahydropyran-2-yl)-1H-indazole The title compound was prepared as described in Example 132 D, using 4-vinylaniline (0.286 g, 2.4 mmol) (0.196 g, 49% yield): $^1$H NMR (CDCl$_3$) δ 7.96 (m, 2H), 7.92 (s, 1H), 7.5 (ddd, 1H), 7.59 (d, 1H), 7.36 (d, 2H), 7.21 (t, 2H), 7.05 (d, 1H), 7.04 (d, 1H), 6.69 (m, 2H), 5.76 (dd, 1H), 4.08 (m, 1H), 3.78 (m, 1H), 3.7 (br, 2H), 2.63 (m, 1H), 2.14 (m, 2H), 1.79 (m, 3H); ES-MS (m/z) 414 [M+1]$^-$.

B. 5-[(1E)-2-(4-Aminophenyl)vinyl]-3-(4-fluorophenyl)-1H-indazole

The title compound was prepared as described in Example 132 E, using 5-[(1E)-2-(4-aminophenyl)vinyl]-3-(4-fluorophenyl)-1-(tetrahydropyran-2-yl)-1H-indazole (0.185 g, 0.45 mmol) (0.094 g, 64% yield): $^1$H NMR (CDCl$_3$) δ 10.1 (br s, 1H), 7.97 (m, 3H), 7.66 (dd, 1H), 7.47 (dd, 1H), 7.37 (m, 2H), 7.23 (m, 2H), 7.05 (m, 2H), 6.71 (m, 2H); ES-MS (m/z) 330 [M+1]$^+$.

Example 139

SYNTHESIS OF 5-[(1E)-2-(4-PYRIDYL)VINYL]-3-(4-FLUOROPHENYL)-1H-INDAZOLE

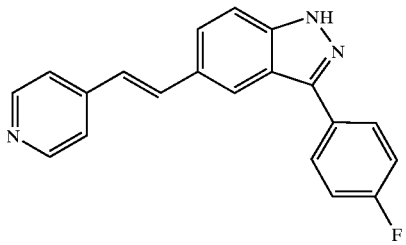

A. 5-[(1E)-2-(4-Pyridyl)vinyl]-3-(4-fluorophenyl)-1-(tetrahydropyran-2-yl)-1H-indazole The title compound (0.284 g, 74% yield) was prepared as described in Example 132 D, using 4-vinylpyridine (0.252 g, 2.4 mmol) (0.284 g, 74% yield). $^1$H NMR (CDCl$_3$) δ 8.58 (dd, 2H), 7.95 (m, 3H), 7.69 (dd, 1H), 7.65 (d, 1H), 7.44 (d, 1H), 7.39 (dd, 2H), 7.22 (m, 2H), 7.04 (d, 1H), 5.78 (dd, 1H), 4.09 (m, 1H), 3.80 (m, 1H), 2.63 (m, 1H), 2.15 (m, 2H), 1.80 (m, 3H); ES-MS (m/z) 400 [M+1]$^+$.

B. 5-[(1E)-2-(4-Pyridyl)vinyl]-3-(4-fluorophenyl)-1H-indazole

The title compound (0.164 g, 79% yield) was prepared as described in Example 132 E, using 5-[(1E)-2-(4-pyridyl)vinyl]-3-(4-fluorophenyl)-1-(tetrahydropyran-2-yl)-1H-indazole (0.265 g, 0.66 mmol). $^1$H NMR (CDCl$_3$) δ 10.3 (br s, 1H), 8.59 (d, 2H), 8.06 (s, 1H), 7.96 (dd, 2H), 7.72 (dd, 1H), 7.54 (d, 1H), 7.46 (d, 1H), 7.40 (d, 2H), 7.25 (t, 2H), 7.04 (d, 1H); ES-MS (m/z) 416 [M+1]$^+$.

Example 140

SYNTHESIS OF (2E)-3-[3-(4-FLUOROPHENYL)-1H-INDAZOL-5-YL]PROP-2-ENOIC ACID

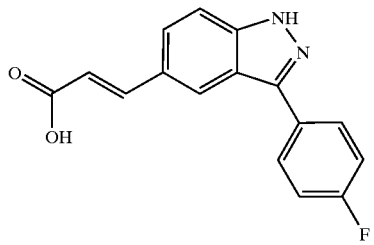

A. Ethyl(2E)-3-[3-(4-Fluorophenyl)-1-(tetrahydropyran-2-yl)-1H-indazol-5-yl]prop-2-enoate The title compound (0.881 g, 74% yield) was prepared as described in Example 132 D, using ethyl acrylate (0.751 g, 7.5 mmol). $^1$H NMR (CDCl$_3$) δ 8.05 (s, 1H), 7.92 (m, 2H), 7.83 (d, 1H), 7.64 (d, 2H), 7.21 (t, 2H), 6.46 (d, 1H), 5.76 (dd, 1H), 4.28 (q, 2H), 4.07 (m, 1H), 3.78 (m, 1H), 2.63 (m, 1H), 2.14 (m, 2H), 1.76 (m, 3H), 1.35 (t, 3H); ES-MS (m/z) 395 [M+1]$^+$.

B. Ethyl (2E)-3-[3-(4-Fluorophenyl)-1H-indazol-5-yl]prop-2-enoate

The title compound (0.602 g, 90% yield) was prepared as described in Example 132 E, using ethyl (2E)-3-[3-(4-fluorophenyl)-1-(tetrahydropyran-2-yl)-1H-indazol-5-yl]prop-2-enoate (0.850 g, 2.15 mmol). $^1$H NMR (CDCl$_3$) δ 10.51 (br s, 1H), 8.09 (s, 1H), 7.93 (m, 2H), 7.84 (d, 1H), 7.65 (d, 1H), 7.49 (d, 1H), 7.24 (t, 2H), 6.47 (d, 1H), 4.29 (q, 2H), 1.36 (t, 3H); ES-MS (m/z) 311 [M+1]$^+$.

C. (2E)-3-[3-(4-Fluorophenyl)-1H-indazol-5-yl]prop-2-enoic Acid

To a solution of ethyl (2E)-3-[3-(4-fluorophenyl)-1H-indazol-5-yl]prop-2-enoate (0.10 g, 0.32 mmol) in tetrahydrofuran (10 mL) was added a solution of lithium hydroxide (0.032 mg, 1.6 mmol) in water (5 mL) and the mixture was stirred at ambient temperature overnight. The reaction mixture was acidified with 6 N hydrochloric acid solution to give a white solid. It was then purified by HPLC to provide the title compound (0.43 g, 48% yield): $^1$H NMR (DMSO-d$_6$) δ 13.45 (br s, 1H), 12.28 (br s, 1H), 8.39 (s, 1H), 8.11 (d, 1H), 8.10 (d, 1H), 7.83 (d, 1H), 7.79 (d, 1H), 7.60 (d, 1H), 7.35 (t, 2H), 6.57 (d, 1H); ES-MS (m/z) 283 [M+1]$^+$.

Example 141

SYNTHESIS OF ETHYL (2E)-3-[3-(4-FLUOROPHENYL)-1H-INDAZOL-5-YL]PROP-2-ENOATE

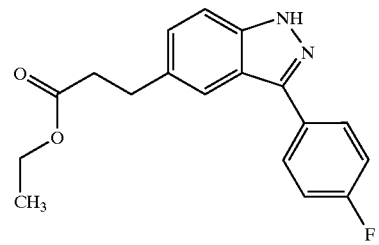

A. Ethyl(2E)-3-[3-(4-Fluorophenyl)-1H-indazol-5-yl]prop-2-enoate

A suspension of ethyl (2E)-3-[3-(4-fluorophenyl)-1H-indazol-5-yl]prop-2-enoate (0.48 g, 1.54 mmol) and palladium (10 wt % on activated carbon, 0.05 g) in ethyl acetate (15 mL) was stirred under hydrogen for 6 hours. It was filtered with celite, washed with ethyl acetate, and concentrated. The residue was then purified by chromatography (SiO$_2$, 30–50% ethyl acetate/hexane) to provide the title compound (0.465 g, 96% yield): $^1$H NMR (CDCl$_3$) δ 10.28 (br s, 1H), 7.92 (m, 2H), 7.78 (s, 1H), 7.42 (d, 1H), 7.29 (d,1H), 7.21 (t, 2H), 4.13 (q, 2H), 3.10 (t, 2H), 2.69 (t, 2H), 1.23 (t, 3H); ES-MS (m/z) 313 [M+1]$^+$.

Example 142

SYNTHESIS OF 3-[3-(4-FLUOROPHENYL)-1H-INDAZOL-5-YL]PROPANOIC ACID

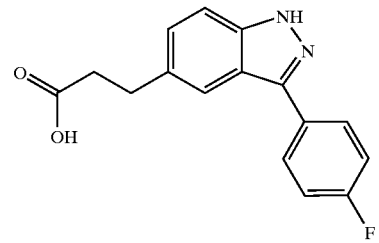

A. 3-[3-(4-Fluorophenyl)-1H-indazol-5-yl]propanoic Acid

The title compound (0.224 g, 62% yield) was prepared as described in Example 140 C, using ethyl (2E)-3-[3-(4-fluorophenyl)-1H-indazol-5-yl]prop-2-enoate (0.40 g, 1.28 mmol). $^1$H NMR (CDCl$_3$) δ 13.15 (br s, 1H), 8.01 (m, 2H), 7.78 (s, 1H), 7.50 (d, 1H), 7.33 (m, 3H), 2.96 (t, 2H), 2.60 (t, 2H); ES-MS (m/z) 285 [M+1]$^+$.

Example 143

SYNTHESIS OF 5-[2-(3-AMINOPHENYL) ETHYL]-3-(4-FLUOROPHENYL)-1H-INDAZOLE

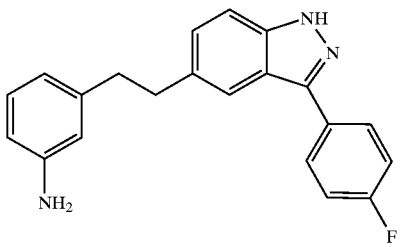

A. 5-[2-(3-Aminophenyl)ethyl]-3-(4-fluorophenyl)-1H-indazole

The title compound (0.051 g, 55% yield) was prepared as described in Example 141 A, using 5-[(1E)-2-(3-Nitrophenyl)vinyl]-3-(4-fluorophenyl)-1H-indazole (0.10 g, 2.78 mmol). $^1$H NMR (CDCl$_3$) δ 9.8 (br s, 1H), 7.88 (m, 2H), 7.69 (s, 1H), 7.43 (d, 1H), 7.18–7.26 (m, 3H), 7.09 (t, 1H), 6.62 (d, 1H), 6.54 (m, 2H), 3.5 (br s, 2H), 3.05 (m, 2H), 2.88 (m, 2H); ES-MS (m/z) 332 [M+1]$^+$.

Example 144

SYNTHESIS OF 4-{2-[3-(4-FLUOROPHENYL)-1H-INDAZOL-5-YL]ETHYL}BENZOIC ACID

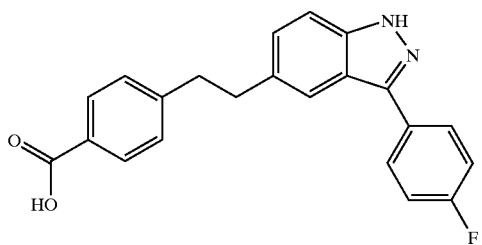

A. 4-{2-[3-(4-Fluorophenyl)-1H-indazol-5-yl]ethyl}benzoic Acid

The title compound (0.044 g, 36% yield) was prepared as described in Example 141 A, using 4-{(1E)-2-[(3-(4-fluorophenyl)-1H-indazol-5-yl]vinyl}benzoic acid (0.120 g, 0.33 mmol) in methanol and it was then purified by HPLC. $^1$H NMR (DMSO-d$_6$) δ 13.13 (br s, 1H), 7.76–7.94 (m, 5H), 7.48 (m, 1H), 7.32 (m, 5H), 3.03 (m, 4H); ES-MS (m/z) 361 [M+1]$^+$.

Example 145

SYNTHESIS OF 3-(4-FLUOROPHENYL)-5-[2-(2-PYRIDYL)ETHYL]-1H-INDAZOLE

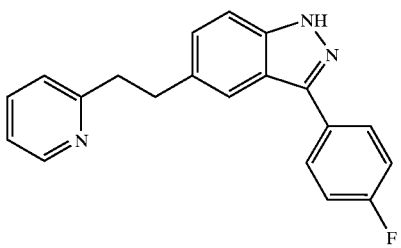

A. 3-(4-Fluorophenyl)-5-[2-(2-pyridyl)ethyl]-1H-indazole

The title compound was prepared as described in Example 141 A, using 5-[(1 E)-2-pyridylvinyl]-3-(4-fluorophenyl)-1H-indazole (0.125 g, 0.4 mmol) in methanol and it was then purified by HPLC (0.060 g, 47% yield): $^1$H NMR (DMSO-d$_6$) δ 13.14 (br s, 1H), 8.52 (d, 1H), 7.95 (m, 2H), 7.79 (s, 1H), 7.69 (ddd, 1H), 7.42 (dd, 1H), 7.22–7.35 (m, 5H), 3.12 (m, 4H); ES-MS (m/z) 318 [M+1]$^+$.

Example 146

SYNTHESIS OF 3-(4-FLUOROPHENYL)-5-(2-PHENYLETHYL)-1H-INDAZOLE

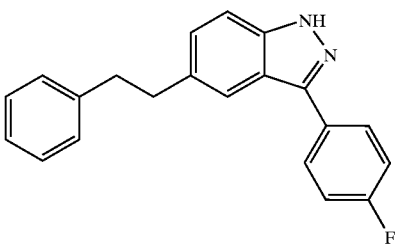

A. 3-(4-Fluorophenyl)-5-(2-phenylethyl)-1H-indazole

The title compound (0.035 g, 35% yield) was prepared as described in Example 141 A, using 5-[(1E)-2-phenylvinyl]-3-(4-fluorophenyl)-1H-indazole (0.10 g, 0.32 mmol). $^1$H NMR (CDCl$_3$) δ 10.0 (br s, 1H), 7.87 (m, 2H), 5 7.66 (m, 1H), 7.43 (dd, 1H), 7.27–7.30 (m, 3H), 7.17–7.24 (m, 5H), 3.08 (m, 2H), 2.98 (m, 2H); ES-MS (m/z) 317 [M+1]$^+$.

Example 147

SYNTHESIS OF 1-[3-(4-FLUOROPHENYL)-1H-INDAZOL-5-YL]-2-PHENYLETHAN-1-OL

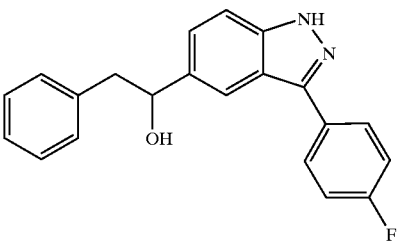

A. 1-[3-(4-Fluorophenyl)-1-(tetrahydrofuran-2-yl)-1H-indazol-5-yl]-2-phenylethan-1-ol To a solution of 5-bromo-3-(4-fluorophenyl)-1-(tetrahydropyran-2-yl)-1H-indazole (0.50 g, 1.0 mmol) in dried tetrahydrofuran (15 mL) under nitrogen at −78° C. was added dropwise a 1.6 M solution of butyl lithium in hexane (1.1 mL, 1.7 mmol). After stirring for 20 minutes, to the reaction mixture was added phenylacetaldehyde (0.228 g, 1.9 mmol). The reaction mixture was stirred additional 1 hour at −78° C. and the temperature was gradually raised to room temperature. It was quenched with water and extracted with dichloromethane. The extracts were dried over magnesium sulfate, filtered, and concentrated. The residue was then purified by chromatography (SiO$_2$, 15–30% ethyl acetate/hexane) to provide the title compound (0.246 g, 44% yield): $^1$H NMR (CDCl$_3$) δ 7.86 (m, 2H), 7.80 (d, 1H), 7.09–7.47 (m, 9H), 6.98 (dd, 1H), 5.70 (dd, 1H), 5.07 (t, 1H), 4.08 (m, 1H), 3.65 (m, 1H), 3.06 (d, 1H), 2.67 (m, 2H), 2.11 (m, 2H), 1.75 (m, 3H); ES-MS (m/z) 417 [M+1]$^+$.

B. 1-[3-(4-Fluorophenyl)-1H-indazol-5-yl]-2-phenylethan-1-ol

The title compound was prepared as described in Example 132 E, using 1-[3-(4-fluorophenyl)-1-(tetrahydropyran-2-yl)-1H-indazol-5-yl]-2-phenylethan-1-ol (0.130 g, 0.31 mmol) to provide the title compound (0.024 g, 23% yield): $^1$H NMR (CDCl$_3$) δ 10.0 (br s, 1H), 7.89 (m, 2H), 7.49 (m, 1H), 7.40 (dd, 1H), 7.27–7.34 (m, 3H), 7.16–7.23 (m, 5H), 7.05 (dd, 1H), 5.07 (dd, 1H), 3.09 (m, 2H); ES-MS (m/z) 333 [M+1]$^+$.

Example 148

SYNTHESIS OF 1-[3-(4-FLUOROPHENYL)-1H-INDAZOL-5-YL]-2-PHENYLETHAN-1-ONE

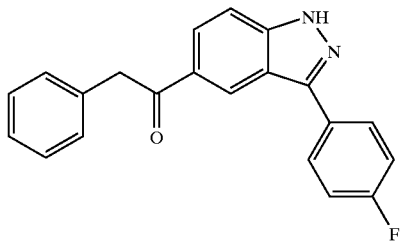

A. 1-[3-(4-Fluorophenyl)-1-(tetrahydropyran-2-yl)-1H-indazol-5-yl]-2-phenylethan-1-one A suspension of 1-[3-(4-fluorophenyl)-1-(tetrahydropyran-2-yl)-1H-indazol-5-yl]-2-phenylethan-1-ol (0.223 g, 0.54 mmol) and pyridinium chlorochromate (1.0 g, 4.6 mmol) in dried dichloromethane (10 mL) under nitrogen was stirred at ambient temperature for 6 hours. It was diluted with dichloromethane and washed with saturated sodium bicarbonate and brine. The organic layer was dried over magnesium sulfate, filtered, and concentrated. The residue was then purified by chromatography (SiO$_2$, 15–30% ethyl acetate/hexane) to provide the title compound (0.112 g, 51% yield): $^1$H NMR (CDCl$_3$) δ 8.62 (d, 1H), 8.10 (dd, 1H), 7.85–7.90 (m, 2H), 7.65 (dd, 1H), 7.19–7.37 (m, 7H), 5.77 (dd, 1H), 4.35 (s, 2H), 4.06 (m, 1H), 3.77 (m, 1H), 2.59 (m, 1H), 2.14 (m, 2H), 1.70 (m, 3H); ES-MS (m/z) 415 [M+1]$^+$.

B. 1-[3-(4-Fluorophenyl)-1H-indazol-5-yl]-2-phenylethan-1-one

The title compound (0.021 g, 27% yield) was prepared as described in Example 132 E, using 1-[3-(4-fluorophenyl)-1-(tetrahydropyran-2-yl)-1H-indazol-5-yl]-2-phenylethan-1-one (0.10 g, 0.24 mmol. $^1$H NMR (CDCl$_3$) δ 10.37 (br s, 1H), 8.67 (d, 1H), 8.12 (dd, 1H), 7.86–7.91 (m, 2H), 7.52 (d, 1H), 7.21–7.38 (m, 7H), 4.37 (s, 2H), 3.09 (m, 2H); ES-MS (m/z) 331 [M+1]$^+$.

Example 149

SYNTHESIS OF 3-(4-METHOXYPHENYL)-1H-INDAZOLE-5-CARBOXAMIDE

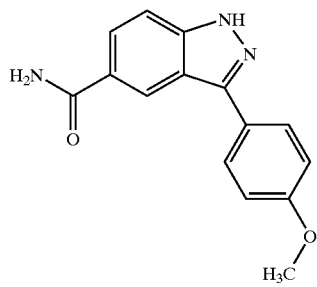

A. 1H-Indazole-5-carbonitrile

To a 1-L beaker was added 20.0 g (150 mmol) of 5-aminoindazole, and 150 g of ice. The mixture was stirred with a magnetic stir bar and cooled on an ice-water bath. To this mixture was added 37.5 mL of concentrated aqueous hydrochloric acid, followed by a solution of 10.5 g (152 mmol, 1.01 equiv.) of sodium nitrite in 30 mL of H$_2$O, dropwise over 15 min. The mixture was vigorously stirred for 30 min. and then carefully neutralized to pH ca. 7.0 with 9.5 g of solid sodium carbonate (Na$_2$CO$_3$). This mixture was transferred to a 1-L separatory funnel, kept cold by the addition of ice, and added dropwise to an ice cooled, magnetically stirred mixture of 16.8 g (188 mmol, 1.24 equiv.) of copper (I) cyanide (CuCN), 24.4 g (498 mmol, 3.32 equiv.) of sodium cyanide (NaCN), 112 mL H$_2$O, and 250 mL of ethyl acetate (EtOAc) in a 2-L erlenmeyer flask over 20 min. Nitrogen gas was evolved from the reaction. The mixture turned dark quickly, and was stirred on ice for 30 min. and then the ice was removed. Stirring was continued for 3.5 h. The mixture was then heated on a hot plate until the internal temperature was 50° C. The reaction was removed from the hot plate and allowed to cool to 35° C., and filtered through filter paper. The layers were separated, and the organic layer was washed with saturated aqueous NaCl, and dried (Na$_2$SO$_4$). The organic layer was poured directly onto a 65 mm column containing 200 g of silica gel and eluted with EtOAc. Fractions of 500 mL were collected, and all product containing fractions were combined and concentrated to give the title compound (19.60 g, 91% yield): ES-MS (m/z) 144 [M+1]$^+$.

B. 3-Bromo-1H-indazole-5-carbonitrile

A 2-L round bottomed flask was charged with 1H-indazole-5-carbonitrile (17.6 g, 123 mmol), 333 mL methanol (MeOH), 333 mL of 2.0 M aq. NaOH, and a solution of bromine (Br$_2$, 54.7 g, 344 mmol, 2.80 equiv.) in 166 mL of 2.0 M aq. NaOH. The mixture was warmed on an oil bath to 40° C. (external temperature) for 6 h, and then cooled to room temperature in a water bath. The pH of the solution adjusted to ca. 5.5 with 103 mL of 4.0 M aq. HCl. The resulting precipitate was collected by filtration, washed with 200 mL of H$_2$O, and dried. The product was purified by chromatography on 265 g of silica gel using 30–40% EtOAc in hexanes. This afforded the title compound (12.83 g, 47% yield): ES-MS (m/z) 222 [M+1]$^+$.

C. 3-Bromo-1-perhydro-2H-pyran-2-yl-1H-indazole-5-carbonitrile

To a solution of 13.67 g (61.56 mmol) of 3-bromo-1H-indazole-5-carbonitrile and 2.06 g (10.8 mmol, 0.175 equiv.) of p-toluenesulfonic acid monohydrate in 247 mL of anhydrous tetrahydrofuran (THF) was added 11.2 mL (123 mmol, 2.00 equiv.) of 3,4-dihydro-2H-pyran. The mixture was refluxed under a nitrogen atmosphere for 14 h. The reaction was quenched with saturated aqueous sodium bicarbonate (sat. aq. NaHCO$_3$). The mixture was extracted twice with EtOAc. The combined organics were washed with 2× sat. aq. NaHCO$_3$, 1× sat. aq. NaCl, and dried over Na$_2$SO$_4$. Chromatography of the crude material on 200 g of silica gel using 30% EtOAc in hexanes afforded the title compound (14.34 g, 76% yield): ES-MS (m/z) 306 [M+1]$^+$.

D. 3-(4-Methoxyphenyl)-1-perhydro-2H-pyran-2-yl-1H-indazole-5-carbonitrile

A flask was charged with 300 mg (0.98 mmol) of 3-bromo-1-perhydro-2H-pyran-2-yl-1H-indazole-5-carbonitrile, 223 mg (1.47 mmol, 1.50 equiv.) of 4-methoxyphenylboronic acid, 80.3 mg (0.098 mmol, 0.100 equiv.) of [1,1'-bis (diphenylphosphino)-ferrocene}dichloropalladiuin (II) complex with dichloromethane (Aldrich), 1.04 g (4.90 mmol, 4.98 equiv.) of powdered potassium phosphate (K$_3$PO$_4$), and 4.90 mL of anhydrous 1,2-dimethoxyethane (DME). The mixture was refluxed under nitrogen for 19 h. The mixture was diluted with CH$_2$Cl$_2$, washed with 2× sat. aq. NaHCO$_3$, and dried (Na$_2$SO$_4$). The crude material was purified by silica gel chromatography using 20–30% EtOAc in hexanes affording the title compound (251 mg, 77% yield): ES-MS (m/z) 334 [M+1]$^+$.

E. 3-(4-Methoxyphenyl)-1H-indazole-5-carbonitrile

A mixture of 251 mg (0.753 mmol) of 3-(4-methoxyphenyl)-1-perhydro-2H-pyran-2-yl-1H-indazole-5-carbonitrile, 5.0 mL of dioxane, and 5.0 mL of 6.0 N aq. HCl was heated at 65° C. for 22 h. The reaction mixture was added to a mixture of 10.0 mL of H$_2$O and 20.0 mL of EtOAc with stirring. The layers were separated and the aqueous layer was extracted with EtOAc. The combined organic layers were added to 60 mL of sat. aq. NaHCO$_3$ with rapid stirring. The layers were separated, and the organic layer was washed with sat. aq. NaHCO$_3$, and dried (Na$_2$SO$_4$). Purification of the crude material by silica gel chromatography using 30–50% EtOAc in hexanes afforded the title compound (129 mg, 71% yield): ES-MS (m/z) 250 [M+1]$^+$.

F. 3-(4-Methoxyphenyl)-1H-indazole-5-carboxamide

A mixture of 20 mg (0.080 mmol) of 3-(4-methoxyphenyl)-1H-indazole-5-carbonitrile, 0.428 mL of 95% denatured ethanol, 0.021 mL of H$_2$O, 0.32 mL of 30% aqueous hydrogen peroxide (aq. H$_2$O$_2$) and 0.032 mL of 6.0 N aq. NaOH (0.192 mmol, 2.4 equiv.) was heated at 50° C. for 3 h, and then acidified to pH=6.0 with 0.052 mL of 6.0 N 10 aq. HCl. The mixture was extracted with 2× EtOAc. The combined organics were washed with 2× sat. aq. NaHCO$_3$, dried (Na$_2$SO$_4$), filtered, and concentrated affording the title compound (8.9 mg, 41.6% yield): $^1$H NMR (CDCl$_3$/DMSO-d$_6$) δ 12.5 (br s, 1H), 8.60 (s, 1H), 7.95 (d, 2H), 7.85 (d, 2H), 7.55 (d, 1H), 7.05 (d, 2H), 3.89 (s, 3H); ES-MS (m/z) 268 [M+1]$^+$.

Example 150

SYNTHESIS OF 3-(4-HYDROXYPHENYL)-1H-INDAZOLE-5-CARBOXAMIDE

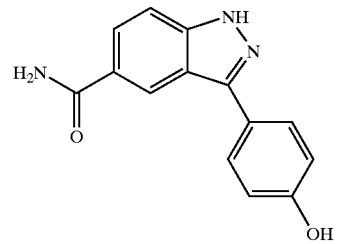

A. 3-(4-Hydroxyphenyl)-1-perhydro-2H-pyran-2-yl-1H-indazole-5-carbonitrile

The title compound (219 mg, 57% yield) was prepared as described in Example 149 D using 4-hydroxybenzeneboronic acid (250 mg, 1.81 mmol). ES-MS (m/z) 320 [M+1]$^+$.

B. 3-(4-Hydroxyphenyl)-1H-indazole-5-carbonitrile

The title compound (520 mg, 82% yield) was prepared as described in Example 149 E using 3-(4-hydroxyphenyl)-1-perhydro-2H-pyran-2-yl-1H-indazole-5-carbonitrile (860 mg, 2.69 mmol). ES-MS (m/z) 236 [M+1]$^+$.

C. 3-(4-Hydroxyphenyl)-1H-indazole-5-carboxamide

The title compound (30 mg, 48% yield) was prepared as described in Example 149 F using 3-(4-hydroxyphenyl)-1H-indazole-5-carbonitrile (60 mg, 0.255 mmol). $^1$H NMR (DMSO-d$_6$) δ 13.22 (s, 1H), 9.67 (s, 1H), 8.56 (s, 1H), 8.1 (br s, 1H), 7.95–7.80 (m, 3H), 7.56 (d, 1H), 7.4 (br, 1H), 6.93 (d, 2H); ES-MS (m/z) 254 [M+1]$^+$.

Example 151

SYNTHESIS OF 3-(2-NAPHTHYL)-1H-INDAZOLE-5-CARBOXAMIDE

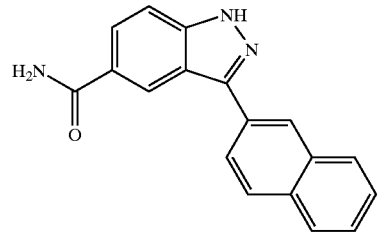

A. 3-(2-Napthyl-1-perhydro-2H-pyran-2-yl-1H-indazole-5-carbonitrile

The title compound (262 mg, 76% yield) was prepared as described in Example 149 D using 2-naphthaleneboronic acid (252 mg, 1.46 mmol. ES-MS (m/z) 354 [M+1]$^+$.

B. 3-(2-Naphthyl)-1H-indazole-5-carbonitrile

The title compound (105 mg, 53% yield) was prepared as described in Example 149 E using 3-(2-naphthyl)-1-perhydro-2H-pyran-2-yl-1H-indazole-5-carbonitrile (262 mg, 0.741 mmol). ES-MS (m/z) 270 [M+1]$^+$.

C. 3-(2-Naphthyl)-1H-indazole-5-carboxamide

The title compound (142 mg, 79% yield) was prepared as described in Example 149 F using 3-(2-naphthyl)-1H-indazole-5-carbonitrile (168 mg, 0.624 mmol). $^1$H NMR (DMSO-d$_6$) δ 13.53 (s, 1H), 8.77 (s, 1H), 8.60 (s, 1H), 8.23 (dd, 2H), 8.16–8.05 (m, 2H), 7.98 (m, 2H), 7.68–7.52 (m, 3H), 7.39 (br s, 1H); ES-MS (m/z) 288 [M+1]$^+$.

Example 152

SYNTHESIS OF METHYL 3-BENZO[B]THIOPHEN-2-YL-1H-INDAZOLE-5-CARBOXYLATE

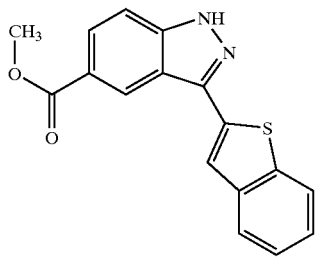

A. 3-Bromo-1-perhydro-2H-pyran-2-yl-1H-indazole-5-carboxamide

The title compound was prepared as described in Example 149 F using 3-bromo-1-perhydro-2H-pyran-2-yl-1H-indazole-5-carbonitrile (1.50 g, 4.92 mmol) to provide the title compound (1.37 g, 86% yield): ES-MS (m/z) 324 [M+1]$^+$.

B. 3-Benzo[b]thiophen-2-yl-1-perhydro-2H-pyran-2-yl-1H-indazole-5-carboxamide

A mixture of 3-bromo-1-perhydro-2H-pyran-2-yl-1H-indazole-5-carboxamide (425 mg, 1.31 mmol), benzo[b]thiophene-2-boronic acid (348 mg, 1.95 mmol, 1.49 equiv.), [1,1'-bis(diphenylphosphino)-ferrocene}dichloropalladium (II) complex with dichloromethane (107 mg, 0.131 mmol, 0.10 equiv.), potassium phosphate (K$_3$PO$_4$, 1.38 g, 6.50 mmol, 4.96 equiv.) and 6.5 mL of DME were refluxed for 18 h and concentrated. Purification by silica gel chromatography using 0–5% MeOH in EtOAc as eluent afforded the title compound (126 mg, 26% yield): ES-MS (m/z) 378 [M+1]$^+$.

C. Methyl 3-benzo[b]thiophen-2-yl-1H-indazole-5-carboxylate

A mixture of 3-benzo[b]thiophen-2-yl-1-perhydro-2H-pyran-2-yl-1H-indazole-5-carboxamide (126 mg, 0.334 mmol), 10.0 mL of MeOH, and 10.0 mL of 6.0 N aq. HCl were heated at 65° C. for 24 h. The reaction mixture was added dropwise to 50 mL of 6.0 N aq. NaOH with stirring. This mixture was extracted with 3× EtOAc and the combined organics were dried (Na$_2$SO$_4$). Purification by silica gel chromatography using 30–40% EtOAc in hexanes afforded the title compound (27.0 mg, 26% yield): $^1$H NMR (DMSO-d$_6$) δ 13.75 (br s, 1H), 8.84 (s, 1H), 8.19 (s, 1H), 8.15–7.95 (m, 3H), 7.74 (d, 1H), 7.45–7.35 (m, 2H), 3.94 (s, 3H); ES-MS (m/z) 378 [M+1]$^+$.

Example 153

SYNTHESIS OF 3-BENZO[B]THIOPHEN-2-YL-1H-INDAZOLE-5-CARBOXYLIC ACID

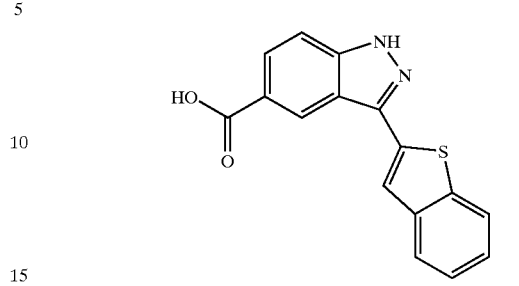

A. 3-Benzo[b]thiophen-2-yl-1H-indazole-5-carboxylic acid

A solution of methyl 3-benzo[b]thiophen-3-yl-1H-indazole-5-carboxylate (20 mg, 0.065 mmol), 5.00 mL of MeOH, and 5.00 mL of 6.0 N aq. NaOH was heated at 85° C. for 2.5 h. The mixture was diluted with 6.0 N aq. NaOH, and extracted with 3× EtOAc. The aqueous layer was then acidified to pH 1.0 with 6.0 N aq. HCl. This mixture was extracted with 3× EtOAc, and the combined organics were dried (Na$_2$SO$_4$), filtered, and concentrated to give the title compound (5 mg, 26% yield): $^1$H NMR (DMSO-d$_6$) δ 13.71 (br s, 1H), 13.0 (very br s, 1H), 8.83 (s, 1H), 8.17 (s, 1H), 8.05–7.95 (m, 3H), 7.70 (d, 2H), 8.50–8.35 (m, 2H); ES-MS (m/z) 295 [M+1]$^+$.

Example 154

SYNTHESIS OF 3-BENZO[B]THIOPHEN-2-YL-1H-INDAZOLE-5-CARBOXAMIDE

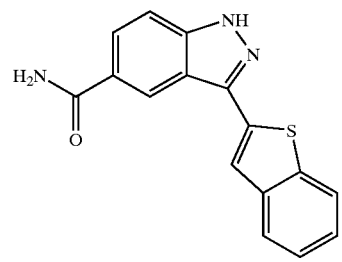

A. 3-Benzo[b]thiophen-2-yl-1-perhydro-2H-pyran-2-yl-1H-indazole-5-carbonitrile

The title compound (397 mg, 110% yield, 85.5% pure by HPLC) was prepared as described in Example 149 D using benzo[b]thiophene-2-boronic acid (348 mg, 1.95 mmol). ES-MS (m/z) 360 [M+1]$^+$.

B. 3-Benzo[b]thiophen-2-yl-1H-indazole-5-carbonitrile

The title compound (153 mg, 50.3% yield) was prepared as described in Example 149 E using 3-benzo[b]thiophen-2-yl-1-perhydro-2H-pyran-2-yl-1H-indazole-5-carbonitrile (397 mg, 1.10 mmol). ES-MS (m/z) 276 [M+1]$^+$.

C. 3-Benzo[b]thiophen-2-yl-1H-indazole-5-carboxamide

The title compound (127 mg, 80.9% yield) was prepared as described in Example 149 F using 3-benzo[b]thiophen-3-yl-1H-indazole-5-carbonitrile (147 mg, 0.534 mmol). $^1$H NMR (DMSO-d$_6$) δ 13.59 (br, 1H), 8.80 (s, 1H), 8.31 (s, 1H), 8.25 (br s, 1H), 8.05–7.90 (m, 3H), 7.65 (d, 1H), 8.50–8.38 (m,3H; ES-MS (m/z) 294 [M+1]$^+$.

Example 155

SYNTHESIS OF 3-Benzo[D]FURAN-2-YL-1H-INDAZOLE-5-CARBOXAMIDE

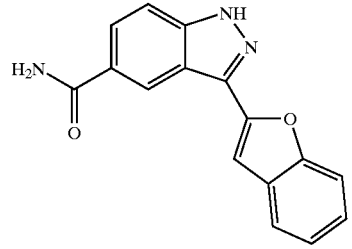

A. 3-Benzo[d]furan-2-yl-1-perhydro-2H-pyran-2-yl-1H-indazole-5-carbonitrile

The title compound (361 mg, 79% yield) was prepared as described in Example 149 D using benzo[b]furan-2-boronic acid (342 mg, 2.11 mmol). ES-MS (m/z) 344 [M+1]$^+$.

B. 3-Benzo[d]furan-2-yl-1H-indazole-5-carbonitrile

The title compound (128 mg, 47% yield) was prepared as described in Example 149 E using 3-benzo[d]furan-2-yl-1-perhydro-2H-pyran-2-yl-1H-indazole-5-carbonitrile (361 mg, 1.05 mmol). ES-MS (m/z) 260 [M+1]$^+$.

C. 3-Benzo[d]furan-2-yl-1H-indazole-5-carboxamide

The title compound (134 mg, 98% yield) was prepared as described in Example 149 F using 3-benzo[d]furan-2-yl-1H-indazole-5-carbonitrile (128 mg, 0.494 mmol). $^1$H NMR (DMSO-d$_6$) δ 8.73 (d, 1H), 8.21 (s, 1H), 7.97 (dd, 1H), 7.70 (dt, 2H), 7.61 (s, 1H), 7.43 (d, 1H), 7.42–7.25 (m, 3H); ES-MS (m/z) 278 [M+1]$^+$.

Example 156

SYNTHESIS OF 3-[3-(METHYLETHYL)PHENYL]-1H-INDAZOLE-5-CARBOXAMIDE

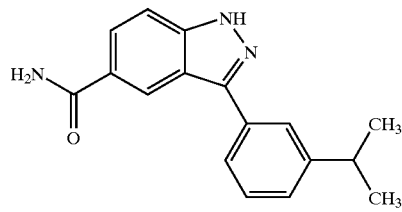

A. 3-[3-(Methylethyl)phenyl]-1H-indazole-5-carboxamide

The title compound (100 mg, 55% yield) was prepared as described in Example 149 F using hydrogen peroxide (2.5 mL). $^1$H NMR (DMSO-d$_6$) δ 13.4 (s, 1H), 8.58 (s, 1H), 8.15 (br s, 1H), 7.92 (d, 1H), 7.88–7.84 (m, 2H), 7.61 (d, 1H), 7.48 (t, 1H), 7.33 (d, 2H), 3.03 (septet, 1H), 1.28 (d, 6H); ES-MS (m/z) 280 [M+1]$^+$.

Example 157

SYNTHESIS OF 3-[4-(DIMETHYLAMINO)PHENYL]-1H-INDAZOLE-5-CARBOXAMIDE

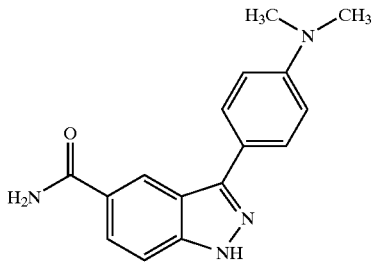

A. 3-[4-(dimethylamino)phenyl]-1-perhydro-2H-pyran-2-yl-1H-indazole-5-carbonitrile The title compound (257 mg, 56.7% yield) was prepared as described in Example 149 D using 4-(N,N-dimethylamino)phenylboronic acid (322 mg, 1.95 mmol). ES-MS (m/z) 347 [M+1]$^+$.

B. 3-[4-(dimethylamino)phenyl]-1H-indazole-5-carbonitrile

The title compound (127 mg, 65.1% yield) was prepared as described in Example 149 E using 3-[4-(dimethylamino)phenyl]-1-perhydro-2H-pyran-2-yl-1H-indazole-5-carbonitrile (257 mg, 0.742 mmol). ES-MS (m/z) 276 [M+1]$^+$.

C. 3-[4-(dimethylamino)phenyl]-1H-indazole-5-carboxamide

A solution of 3-[4-(dimethylamino)phenyl]-1H-indazole-5-carbonitrile (125 mg, 0.476 mmol) in 5.00 mL of concentrated aq. HCl was heated at 47° C. for 1 h, and then added dropwise with stirring to 20 mL of 6.0 N aq. NaOH that was cooled in a water bath. The mixture was extracted with 2× EtOAc, and the combined organics were dried (Na$_2$SO$_4$). Purification by silica gel chromatography using EtOAc as eluent afforded the title compound (69.3 mg, 52.1% yield): $^1$H NMR (DMSO-d$_6$) δ 13.19 (s, 1H), 8.58 (s, 1H), 8.10 (br s, 1H), 7.9S–7.82 (m, 3H), 7.56 (d, 1H), 7.30 (br s, 1H), 6.84 (d, 2H), 2.98 (s, 6H); ES-MS (m/z) 281 [M+1]$^+$.

Example 158

SYNTHESIS OF 3-(3-FURYL)-1H-INDAZOLE-5-CARBOXAMIDE

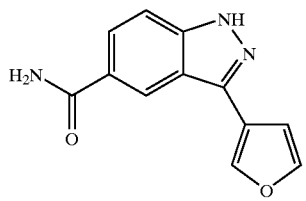

A. 3-(3-Furyl)-1H-indazole-5-carboxamide

The title compound (100 mg, 55% yield) was prepared as described in Example 149 F using hydrogen peroxide (2.5 mL). $^1$H NMR (DMSO-d$_6$) δ 13.3 (s, 1H), 8.57 (s, 1H), 8.54 (s, 1H), 8.14 (br s, 1H), 7.95 (d, 1H), 7.85 (m, 1H), 7.58 (d, 1H), 7.35 (br s, 1H), 7.08 (s, 1H); ES-MS (m/z) 228 [M+1]$^+$.

Example 159

SYNTHESIS OF 3-(2-PHENYLETHYNYL)-1H-INDAZOLE-5-CARBOXAMIDE

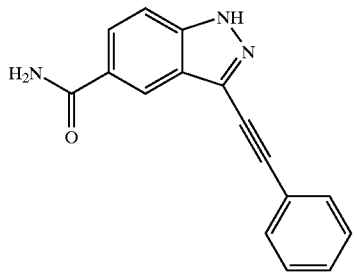

A. 1-Perhydro-2H-pyran-2-yl-3-(2-phenylethynyl-1H-indazole-5-carbonitrile

A mixture of 3-bromo-1-perhydro-2H-pyran-2-yl-1H-indazole-5-carbonitrile (400 mg, 1.31 mmol), 10.0 mL of acetonitrile ($CH_3CN$), diisopropylethylamine (172 mg, 1.33 mmol, 1.01 equiv.), dichlorobis(triphenylphosphine)palladium(II) [$(Ph_3)P_2PdCl_2$, 0.0187 mmol, 0.0143 equiv.), copper (I) iodide (CuI, 13.1 mg, 0.0688 mmol, 0.0525 equiv.), and phenylacetylene (147 mg, 1.44 mmol, 1.10 equiv.) were refluxed for 3 h and concentrated. Purification by silica gel chromatography using 20–30% EtOAc in hexanes afforded the title compound (327 mg, 76.2% yield): ES-MS (m/z) 328 $[M+1]^+$.

B. 3-(2-Phenylethynyl)-1H-indazole-5-carbonitrile

The title compound (77.7 mg, 32.0% yield) was prepared as described in Example 149 E using 1-perhydro-2H-pyran-2-yl-3-(2-phenylethynyl)-1H-indazole-5-carbonitrile (327 mg, 0.999 mmol). ES-MS (m/z) 244 $[M+1]^+$.

C. 3-(2-Phenylethynyl)-1H-indazole-5-carboxamide

The title compound (73.8 mg, 69.0% yield) was prepared as described in Example 149 F using 3-(2–15 phenylethynyl)-1H-indazole-5-carbonitrile (99.4 mg, 0.409 mmol). $^1$H NMR (DMSO-$d_6$) δ 13.72 (s, 1H), 8.43 (br, 1H), 8.19 (br s, 1H), 7.95 (d, 1H), 7.75–7.62 (m, 3H), 7.51–7.45 (m, 3H), 7.41 (br, 1H); ES-MS (m/z) 262 $[M+1]^+$.

Example 160

SYNTHESIS OF 3-{4-[2-(DIMETHYLAMINO)ETHOXY]PHENYL}-1H-INDAZOLE-5-CARBOXAMIDE

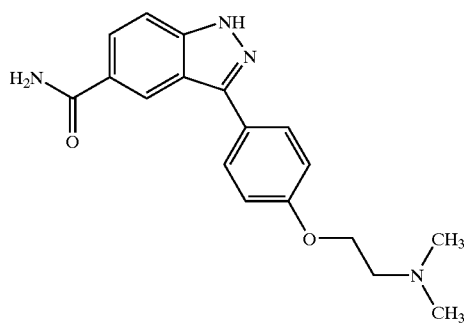

A. 3-{4-[2-(Dimethylamino)ethoxy]phenyl}-1H-indazole-5-carboxamide

A mixture of 3-(4-hydroxyphenyl)-1-perhydro-2H-pyran-2-yl-1H-indazole-5-carbonitrile (400 mg, 1.25 mmol), triphenylphosphine ($Ph_3P$, 656 mg, 2.50 mmol, 2.00 equiv.), 4.00 mL EtOAc, N,N-dimethylethanolamine (223 mg, 2.50 mmol, 2.00 equiv.), and diethyl azodicarboxylate (DEAD, 436 mg, 2.50 mmol, 2.00 equiv.) Was stirred at room temperature for 24 h. The mixture was diluted with EtOAc and washed with 6.0 N aq. HCl. The aqueous layer was extracted with 3× EtOAc and then added to enough 6.0 N aq. NaOH so that the final pH=14.0. This mixture was extracted with 3× EtOAc, and the combined organics were dried ($Na_2SO_4$), filtered, and concentrated. To the crude residue was added 6.00 mL of concentrated aq. HCl. The mixture was heated at 45° C. for 1.25 h. This mixture was then added to 25 mL of 6.0 N aq. NaOH that was stirred and cooled on a water bath. The mixture was extracted with 2× EtOAc, and the combined organics dried ($Na_2SO_4$). Purification by silica gel chromatography using 0.5% triethylamine (TEA) in $CH_2Cl_2$ containing 5–15% MeOH as eluent afforded the title compound (86.6 mg, 21.4% yield): $^1$H NMR (DMSO-$d_6$) δ 13.34 (br s, 1H), 8.59 (s, 1H), 8.17 (br s, 1H), 8.00–7.85 (m, 3H), 7.58 (d, 2H), 7.35 (br s, 1H), 7.10 (d, 2H), 4.13 (t, 2H), 2.66 (t, 2H), 2.24 (s, 6H); ES-MS (m/z) 325 $[M+1]^+$.

Example 161

SYNTHESIS OF 1-(5-(2H-1,2,3,4-TETRAZOL-5-YL)(1H-INDAZOL-3-YL))-2-METHOXYBENZENE

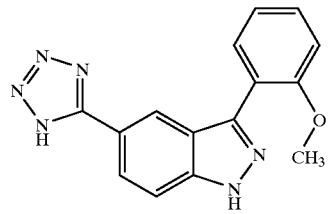

A. 4-Fluoro-3-formylbenzenecarbonitrile

Lithium diisopropyl amide (LDA) (22 mL, 49.56 mmol, 2.0 N commercial solution in heptanes) was added to tetrahydrofuran (50 mL), cooled to 78° C. and under nitrogen. 4-Fluorobenzonitrile was weighed out (5.0 g, 41.3 mmol), placed under nitrogen and dissolved in 25 mL of dry tetrahydrofuran. This solution was added dropwise to the solution of LDA. The resulting solution was stirred at −78° C. for one hour before quenching with 4 mL of dimethylformamide. The temperature was maintained for 10 min before adding 8 mL of acetic acid and 20 mL of distilled water. The crude product was extracted with ethyl acetate. Purification by column chromatography ($SiO_2$, 20% ethyl acetate in hexanes) afforded 4.6 g of pure product as a white solid (74.6% yield).

A second batch of the title compound (3.5 g, 56.8% yield) was prepared 20 using 5 g of benzonitrile (41.3 mmol): $^1$H NMR ($CDCl_3$) δ 10.3 (s, 1H), 8.21 (dd, 1H), 7.91 (d of q, 1H), 7.35 (t, 1H); ES-MS $M^+$ was not detected.

B. 1H-indazole-5-carbonitrile

4-Fluoro-3-formylbenzenecarbonitrile (4.6 g, 30.85 mmol) was suspended in 20 mL of hydrazine mono-hydrate and the reaction mixture was stirred at room temperature for 48 hours. The title compound was isolated by filtration as a white solid, was washed with small portions of distilled water, and was dried in a vacuum (3.6 g, 81% yield).

The same protocol was used to convert 3.5 g of 4-fluoro-3-formylbenzenecarbonitrile to the title compound and resulted in the isolation of 1.9 g of white solid (80% yield): $^1$H NMR ($CDCl_3$) δ 10.45 (br s, 1H), 8.20 (d, 1H), 8.19 (d, 1H), 7.6 (s, 1H); ES-MS 250 $[M+1]^+$.

C. 3-Bromo-1H-indazole-5-carbonitrile

1H-Indazole-5-carbonitrile (5.3 g, 36.8 mmol) was dissolved in methanol (60 mL) and aqueous sodium hydroxide (30 mL). Bromine (7.07 g, 44.4 mmol) in solution in 2.0 N aqueous sodium hydroxide (30 mL) was added with a disposable pipet. The reaction mixture was then heated to 40° C. for 1.5 hours. The reaction was cooled to room temperature and acidified with 6.0 N aqueous hydrochloric acid. The resulting solid was collected by filtration and washed 3 times with 20-mL portions of water. The solid was dried under vacuum for 1 day. The solid was used without further purification. (7.54 g, 92% yield): $^1$H NMR (CDCl$_3$) δ 13.3 (br s, 1H), 8.0 (s, 1H), 7.5 (s, 2H); ES-MS (m/z) 224 [M+1]$^+$.

D. 3-Bromo-1-perhydro-2H-pyran-2-yl-1H-indazole-5-carbonitrile

3-Bromo-1H-indazole-5-carbonitrile (7.0 g, 31.5 mmol) was dissolved in tetrahydrofuran (120 mL). Dihydropyran was added as a solid (7.96 g, 94.6 mmol), followed by p-toluene sulfonic acid (1.80 g, 9.45 mmol). The reaction mixture was stirred at reflux temperature for 8 hours. The reaction was cooled to room temperature. The crude reaction mixture was partitioned between sodium bicarbonate and ethyl acetate. The organic extracts were dried over Na$_2$SO$_4$ and evaporated to dryness. The resulting oil was purified by column chromatography (SiO$_2$, 20% ethyl acetate in hexanes). Traces of residual impurities could be removed by trituration of the product in diethyl ether and hexanes. (6.230 g, 57% yield) $^1$H NMR CDCl$_3$) δ 8.0 (s, 1H), 7.6 (dd, 2H), S.7 (dd, 1H), 4.0 (m, 1H), 3.7 (s, 1H), 2.4 (m, 1H), 2.1 (m, 2H), 1.7 (m, 3H); ES-MS (m/z) 306 [M+1]$^+$.

E. 3-(2-Methoxyphenyl)-1-perhydro-2H-pyran-2-yl-1H-indazole-5-carbonitrile

To a solution of 3-bromo-1-perhydro-2H-pyran-2-yl-1H-indazole-5-carbonitrile (0.600 g, 1.96 mmol), in ethylene glycol dimethyl ether (20 mL) was added 2-methoxyphenyl boronic acid (0.447 g, 2.94 mmol), [1,1'-bis(diphenylphosphino)-ferrocene] complex with dichloromethane (1:1) (0.226 g, 0.196 mmol) and potassium phosphate (2.07 g, 9.8 mmol). The reaction mixture was heated to reflux temperature for 12 hours. The solvent was then evaporated to dryness and the residue was dissolved in 20 mL of ethyl acetate. The heterogeneous solution was washed 3 times with 10 mL of water and once with 10 mL of brine. The organic layer was dried over Na$_2$SO$_4$ and evaporated to dryness. The resulting brown solid was adsorbed on silica gel and purified by column chromatography (85:15 hexanes/ethyl acetate) to provide the title compound (0.539 g, 82.5% yield): ES-MS (m/z) 334 [M+1]$^+$.

F. 3-(2-Methoxyphenyl)-1H-indazole-5-carbonitrile 3-(2-Methoxyphenyl)-1-perhydro-2H-pyran-2-yl-1H-indazole-5-carbonitrile (0.539 g, 2.17 mmol) was dissolved in 10 mL of tetrahydrofuran. Aqueous hydrogen chloride (10 mL, 6.0N) was added and the reaction mixture was stirred at room temperature for 12 hours, then reflux temperature for 7 hours. The pH of the reaction was neutralized using saturated sodium bicarbonate and the crude was extracted with ethyl acetate (3×15 mL). Attempt to purify the crude by column chromatography was unsuccessful: ES-MS (m/z) 250 [M+1]$^+$.

G. 1-(5-(2H-1,2,3,4-Tetrazol-5-yl)(1H-indazol-3-yl))-2-methoxybenzene

To a solution of 3-(2-methoxyphenyl)-1H-indazole-5-carbonitrile in toluene (20 mL) was added azidotributyl tin (0.716 g, 0.591 mL, 2.156 mmol). The reaction mixture was heated to reflux temperature for 18 hours. The solvent was removed under reduced pressure with no heat. The resulting oil was dissolved in tetrahydrofuran (2 mL) and toluene was added (20 mL). Hydrogen chloride was bubbled through the solution for 15 min, which resulted in the precipitation of a white solid. The product was collected by filtration after cooling to 0° C. and was washed with 5 mL portions of toluene. The impure solid was dissolved in 5 mL of aqueous sodium hydroxide (2.0 N) and the aqueous phase was washed with ethyl acetate. The product was precipitated out of the aqueous phase by bubbling hydrogen chloride gas. The solid was collected by filtration and washed with small portions of water. The product was isolated as an off-white solid after drying in a vacuum oven (0.110 g, 0.377 mmol, 20% over 2 steps): $^1$H NMR (DMSO-d$_6$) δ 13.5 (br s, 1H), 8.4 (s, 1H), 8.0 (d, 1H), 7.7 (d, 1H), 7.5 (d, 1H), 7.4 (t, 1H), 7.2 (d, 1H), 7.1 (t, 1H), 3.8 (s, 3H); ES-MS (m/z) 293 [M+1]$^+$.

Example 162

SYNTHESIS OF 5-[3-((1E)-2-PHENYLVINYL)-1H-INDAZOLE-5YL]-2H-1,2,3,4-TETRAZOLE

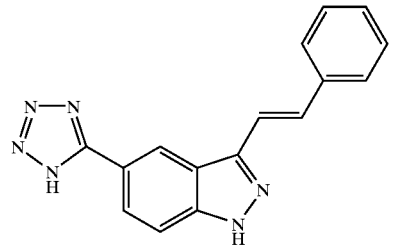

A. 3-((1E)-2-Phenylvinyl)-1-perhydro-2H-pyran-2-yl-1H-indazole-5-carbonitrile

The title compound was prepared as described in Example 161, using 3-bromo-1-perhydro-2H-pyran-2-yl-1H-indazole-5-carbonitrile (0.300 g, 0.98 mmol), in ethylene glycol dimethyl ether (10 mL), trans-phenylethenyl boronic acid (0.217 g, 1.47 mmol), [1,1'-bis(diphenylphosphino)-ferrocene] complex with dichioromethane (1:1) (0.113 g, 0.098 mmol), and potassium phosphate (1.04 g, 4.9 mmol) (0.268 g, 83% yield): ES-MS (m/z) 330 [M+1]$^+$.

B. 3-((1E)-2-Phenylvinyl)-1H-indazole-5-carbonitrile

The title compound was prepared by hydrolyzing 3-((1E)-2-phenylvinyl)-1-perhydro-2H-pyran-2-yl-1H-indazole-5-carbonitrile (0.268 g, 0.815 mmol) in a mixture of 6 mL of tetrahydrofuran and 6 mL of aqueous hydrogen chloride (6.0 N) at room temperature for 12 hours, and reflux temperature for 6 hours. The compound was used without further purification. ES-MS (m/z) 246 [M+1]$^+$.

C. 5-[3-((1E)-2-Phenylvinyl)-1H-indazol-5-yl]-2H-1,2,3,4-tetrazole

The title compound was prepared from 3-((1E)-2-phenylvinyl)-1H-indazole-5-carbonitrile 0.815 mmol, theoretical yield), azidotributyl tin (0.358 g, 0.295 mL, 1.078 mmol) in toluene (10 mL). The product was isolated using the procedure described for compound 161 (0.057 g, 0.198 mmol, 20% over 2 steps): $^1$H NMR (DMSO-d$_6$) 13.5 (br s, 1H), 8.9 (s, 1H), 8.0 (d, 1H), 7.7 (d, 3H), 7.6 (s, 2H), 7.4 (t, 1H), 7.3 (t, 1H); ES-MS (m/z) 289 [M+1]$^+$.

Example 163

SYNTHESIS OF 5-(3-(3-PYRIDYL)-1H-INDAZOL-5-YL)-2H-1,2,3,4-TETRAZOLE

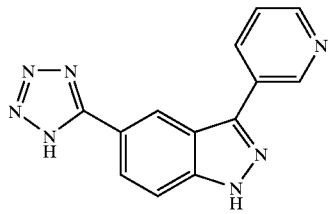

A. 1-Perhydro-2H-pyran-2-yl-3-(3-pyridyl)-1H-indazole-5-carbonitrile

The title compound was prepared as described in Example 161, using 3-bromo-1-perhydro-2H-pyran-2-yl-1H-indazole-5-carbonitrile (0.500 g, 1.63 mmol), in ethylene glycol dimethyl ether (10 mL), 3-pyridyl boronic acid (0.301 g, 2.5 mmol), [1,1'-bis(diphenylphosphino)-ferrocene] complex with dichloromethane (1:1) (0.188 g, 0.163 mmol), and potassium phosphate (1.72 g, 8.15 mmol) (0.304 g, 61% yield): ES-MS (m/z) 305 [M+1]+.

B. 3-(3-Pyridyl)-1H-indazole-5-carbonitrile

The title compound was prepared by hydrolyzing 1-perhydro-2H-pyran-2-yl-3-(3-pyridyl)-1H-indazole-5-carbonitrile (0.147 g, 0.48 mmol) in a mixture of 5 mL of tetrahydrofuran and 5 mL of aqueous hydrogen chloride (6.0N) at room temperature for 12 hours, and reflux temperature for 6 hours. The compound was successfully purified by column chromatography (SiO2, 50% ethyl acetate in hexanes). (0.068 g, 64.5% yield): ES-MS (m/z) 221 [M+1]+.

C. 5-(3-(3-Pyridyl-1H-indazole-5-yl)-2H-1,2,3,4-tetrazole

The title compound was prepared from 3-(3-pyridyl)-1H-indazole-5-carbonitrile (0.068 g, 0.031 mmol), azidotributyl tin (0.116 g, 0.096 mL, 0.32 mmol) in toluene (10 mL). The product was isolated using the procedure described for Example 161 (0.009 g, 0.04 mmol, 12.5% yield): 1H NMR (DMSO-d6) δ 14.0 (br s, 1H), 9.2 (d, 1H), 8.8 (s, 1H), 8.7 (d, 1H), 8.5 (d, 1H), 7.83–7.78 (m, 2H), 7.76–7.64 (m, 1H); ES-MS (m/z) 264 [M+1]+.

Example 164

SYNTHESIS OF 2-(5-(2H-1,2,3,4-TETRAZOL-5-YL)-1H-INDAZOL-3-YL) THIOPHENE

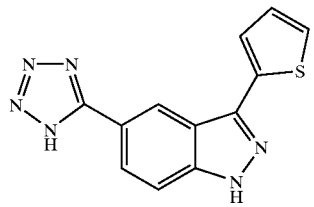

A. 1-Perhydro-2H-pyran-2-yl-3-(2-thienyl)-1H-indazole-5-carbonitrile

The title compound was prepared as described in Example 161, using 3-bromo-1-perhydro-2H-pyran-2-yl-1H-indazole-5-carbonitrile (0.300 g, 0.98 mmol), in ethylene glycol dimethyl ether (10 mL), 2-thiophene boronic acid (0.188 g, 1.46 mmol), [1,1'-bis(diphenylphosphino)-ferrocene] complex with dichloromethane (1:1) (0.113 g, 0.098 mmol), and potassium phosphate (1.03 g, 4.9 mmol) (0.097 g, 32% yield): ES-MS (m/z) 310 [M+1]+.

B. 2-(5-(2H-1,2,3,4-Tetrazo-5-yl)-1H-indazol-3-yl)thiophene

The title compound was prepared from 1-perhydro-2H-pyran-2-yl-3-(2-thienyl)-1H-indazole-5-carbonitrile (0.095 g, 0.307 mmol), azidotributyl tin (0.112 g, 0.093 mL, 0.338 mmol) in toluene (10 mL) as described for the preparation of Example 167. Deprotection was effected by treating a dioxane solution (5 mL) with 8 mL of 4.0 N solution of hydrogen chloride in 1,4-dioxane. The compound was purified by preparative HPLC (10–100% acetonitrile in H2O, 20 min) (0.004 g, 0.015 mmol, 5% yield over 2 steps): 1H NMR (DMSO-d6) δ 13.5 (s, 1H), 8.8 (s, 1H), 8.1 (d, 1H), 7.8 (m, 2H), 7.6 (d, 1H), 7.2 (t, 1H); ES-MS (m/z) 269 [M+1]+.

Example 165

SYNTHESIS OF 5-{3-[4-(METHYLETHYL)PHENYL]-1H-INDAZOL-5-YL}-2H-1,2,3,4-TETRAZOLE

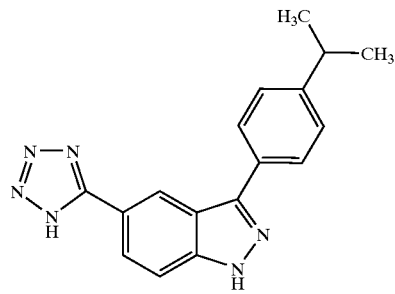

A. 3-[4-(Methylethyl)phenyl]-1-perhydro-2H-pyran-2-yl-1H-indazole-5-carbonitrile The title compound was prepared as described in Example 161, using 3-bromo-1-perhydro-2H-pyran-2-yl-1H-indazole-5-carbonitrile (0.400 g, 1.30 mmol), in ethylene glycol dimethyl ether (10 mL), 4-isopropyl phenyl boronic acid (0.321 g, 1.96 mmol), [1,1'-bis(diphenylphosphino)-ferrocene] complex with dichloromethane (1:1) (0.150 g, 0.130 mmol), and potassium phosphate (1.38 g, 6.5 mmol): (0.364 g, 81% yield): ES-MS (m/z) 346 [M+1]+.

B. 5-{3-[4-(Methylethyl)phenyl]-1H-indazol-5-yl}-2H-1,2,3,4-tetrazole

The title compound was prepared from 3-[4-(methylethyl)phenyl]-1-perhydro-2H-pyran-2-yl-1H-indazole-5-carbonitrile (0.095 g, 0.307 mmol), azidotributyl tin (0.744 g, 0.689 mL, 2.33 mmol) in toluene (10 mL) as described for the preparation of compound 167. Deprotection was effected by treating a dioxane solution (5 mL) with 5 mL of 6.0 N aqueous solution of hydrogen chloride. The solid obtained upon completion of the reaction was partially dissolved in 2.0 N aqueous sodium hydroxide and was extracted in ethyl acetate (4×15 mL). (0.260 g, 0.85 mmol, 80% yield over 2 steps): 1H NMR (DMSO-d6) δ 13.5 (br s, 1H), 8.7 (s, 1H), 8.1 (d, 1H), 7.9 (d, 2H), 7.8 (d, 1H), 7.4 (d, 2H), 3.0 (septet, 1H), 1.3 (d, 6H); ES-MS (m/z) 305 [M+1]+.

Example 166

SYNTHESIS OF 2-(5-(2H-1,2,3,4-TETRAZOL-5-YL)-1H-INDAZOL-3-YL)FURAN

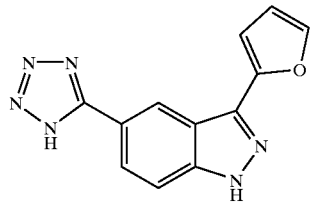

A. 3-(2-Furyl)-1-perhydro-2H-pyran-2-yl-1H-indazole-5-carbonitrile

The title compound was prepared as described in Example 161, using 3-bromo-1-perhydro-2H-pyran-2-yl-1H-indazole-5-carbonitrile (0.300 g, 0.98 mmol), in ethylene glycol dimethyl ether (10 mL), 2-furan boronic acid (0.164 g, 1.46 mmol), [1,1'-bis(diphenylphosphino)-ferrocene] complex with dichloromethane (1:1) (0.113 g, 0.098 mmol), and potassium phosphate (1.03 g, 4.9 mmol) (0.198 g, 69% yield): ES-MS (m/z) 294 [M+1]$^+$.

B. 2-(5-(2H-1,2,3,4-Tetrazol-5-yl)-1H-indazole-3-yl)furan

The title compound was prepared from 3-(2-furyl)-1-perhydro-2H-pyran-2-yl-1H-indazole-5-carbonitrile (0.095 g, 0.307 mmol), azidotributyl tin (0.245 g, 0.202 mL, 0.74 mmol) in toluene (8 mL) as described for the preparation of compound 167. Deprotection was effected by treating a dioxane solution (5 mL) with 8 mL of 4.0N solution of hydrogen chloride in 1,4-dioxane. The compound was purified by preparative HPLC (10–100% acetonitrile in H$_2$O, 20 min) (0.008 g, 0.032 mmol, 4.7% yield over 2 steps): $^1$H NMR (DMSO-d$_6$) δ 13.6 (br s, 1H), 8.8 (s, 1H), 8.1 (d, 1H), 7.9 (d, 1H), 7.8 (d, 1H), 7.1 (d, 1H), 6.7 (dd, 1H); ES-MS (m/z) 253 [M+1]$^+$.

Example 167

SYNTHESIS OF 3-(5-(2H-1,2,3,4-TETRAZOL-5-YL)-1H-INDAZOL-3-YL)PHENYLAMINE

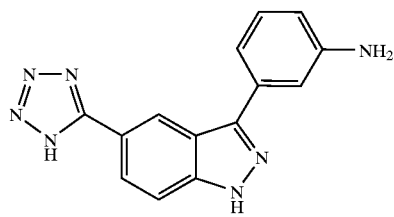

A. 3-(3-Aminophenyl)-1-perhydro-2H-pyran-2-yl-1H-indazole-5-carbonitrile

The title compound was prepared as described in Example 161, using 3-bromo-1-perhydro-2H-pyran-2-yl-1H-indazole-5-carbonitrile (0.300 g, 0.98 mmol), in ethylene glycol dimethyl ether (10 mL), 3-aminophenyl boronic acid (0.227 g, 1.46 mmol), [1,1'-bis(diphenylphosphino)-ferrocene] complex with dichloromethane (1:1) (0.113 g, 0.098 mmol), and potassium phosphate (1.03 g, 4.9 mmol): (0.273 g, 87% yield): ES-MS (m/z) 319 [M+1]$^+$.

B. 3-(5-(2H-1,2,3,4-Tetrazol-5-yl)-1H-indazole-3-yl)phenylamine

The title compound was prepared from 3-(3-aminophenyl)-1-perhydro-2H-pyran-2-yl-1H-indazole-5-carbonitrile (0.273 g, 0.86 mmol), azidotributyl tin (0.314 g, 0.260 mL, 0.95 mmol) in toluene (10 mL). The reaction mixture was heated to reflux temperature for 12 hours resulting in partial conversion to the desired product along with partially and fully deprotected final products. An additional amount of azidotributyl tin was added (0.260 mL) and the reaction was heated to reflux temperature for 18 hours. Toluene was removed under reduced pressure and the crude was dissolved in 5 mL of 1,4-dioxane, 5 mL of 6.0 N aqueous hydrogen chloride, and 2 mL of methanol. The reaction was then heated to 60° C. for 2 days. The reaction was concentrated under reduced pressure and the pH was made basic by adding 2.0 N aqueous NaOH. The aqueous phase was washed with ethyl acetate (3×10 mL). The aqueous phase was then acidified using 6.0 N aqueous hydrogen chloride. The compound was filtered and purified by preparative HPLC (10–100% acetonitrile in H$_2$O, 20 min) (0.050 g, 0.18 mmol, 21% yield over 2 steps): $^1$H NMR (DMSO-d$_6$) δ 13.8 (br s, 1H), 8.9 (s, 1H), 8.1 (d, 1H), 8.0 (d, 2H), 7.8 (d, 1H), 7.6 (t, 1H), 7.3 (d, 1H); ES-MS (m/z) 278 [M+1]$^+$.

Example 168

SYNTHESIS OF 5-(5-(1H-1,2,3,4-TETRAAZOL-5-YL)-1H-INDAZOL-3-YL)-2H-BENZO[D] 1,3-DIOXOLENE

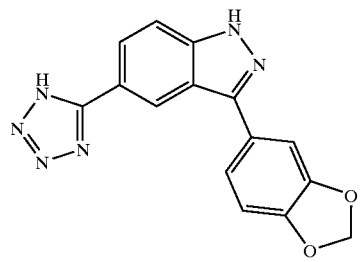

A. 3-(2H-Benzo[d]1,3-dioxolen-5-yl)-1-perhydro-2H-pyran-2-yl-1H-indazole-5-carbonitrile The title compound (1.45 g, 63% yield) was prepared as described in Example 149 D using 3,4-(methylenedioxy)phenylboronic acid (1.64 g, 9.91 mmol). ES-MS (m/z) 348 [M+1]$^+$.

B. 3-(2H-Benzo[d]1,3-dioxolen-5-yl)-1H-indazole-5-carbonitrile

The title compound (790 mg, 78% yield) was prepared as described in Example 149 E using 3-(2H-benzo[d]1,3-dioxolen-5-yl)-1-perhydro-2H-pyran-2-yl-1H-indazole-5-carbonitrile (1.33 g, 3.83 mmol). ES-MS (m/z) 264 [M+1]$^+$.

C. 5-(5-(1H-1,2,3,4-Tetraazol-5-yl)-1H-indazol-3-yl)-2H-benzo[d]1,3-dioxolene

The title compound (360 mg, 41% yield) was prepared as described in Example 170 A using 3-(2H-benzo[d]1,3-dioxolen-5-yl)-1H-indazole-5-carbonitrile (750 mg, 2.85 mmol). $^1$H NMR (DMSO-d$_6$) δ 13.50 (s, 1H), 8.72 (s, 1H), 8.09 (d, 1H), 7.78 (d, 1H), 7.58–7.52 (m, 2H), 7.13 (d, 1H), 6.13 (s, 2H); ES-MS (m/z) 307 [M+1]$^+$.

Example 169

SYNTHESIS OF 3-(5-(2H-1,2,3,4-TETRAZOL-5-YL)-1H-INDAZOL-3-YL)THIOPHENE

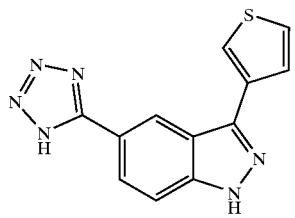

A. 1-Perhydro-2H-pyran-2-yl-3-(3-thienyl)-1H-indazole-5-carbonitrile

The title compound (0.233 g, 38% yield) was prepared as described in Example 161, using 3-bromo-1-perhydro-2H-pyran-2-yl-1H-indazole-5-carbonitrile (0.400 g, 1.30 mmol), in ethylene glycol dimethyl ether (10 mL), 3-thiophene boronic acid (0.251 g, 1.96 mmol), [1,1'-bis(diphenylphosphino)-ferrocene] complex with dichloromethane (1:1) (0.150 g, 0.130 mmol), and potassium phosphate (1.38 g, 6.5 mmol): ES-MS (m/z) 310 [M+1]$^+$.

B. 3-(5-(2H-1,2,3,4-Tetrazol-5-yl)-1H-indazol-3-yl)thiophene

The title compound was prepared from 1-perhydro-2H-pyran-2-yl-3-(3-thienyl)-1H-indazole-5-carbonitrile (0.233 g, 0.75 mmol), azidotributyl tin (0.375 g, 0.310 mL, 1.13 mmol) in toluene (10 mL) as described for the preparation of Example 167. Deprotection was effected by treating a dioxane solution (5 mL) with 5 mL of 6.0N aqueous solution of hydrogen chloride. The solid obtained upon completion of the reaction was partially dissolved in 3 mL of tetrahydrofuran and was precipitated out by adding 20 mL of hexanes (0.108 g, 0.85 mmol, 79% yield over 2 steps): $^1$H NMR (DMSO-d$_6$) δ 13.5 (br s, 1H), 8.8 (s, 1H), 8.2 (t, 1H), 8.1 (dd, 1H), 7.8–7.7 (m, 3H); ES-MS (m/z) 269 [M+1]$^+$.

Example 170

SYNTHESIS OF 5-(3-(2-NAPHTHYL)-1H-INDAZOL-5-YL)-1H-1,2,3,4-TETRAZOLE

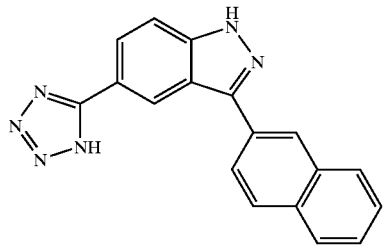

A. 5-(3-(2-naphthyl)-1H-indazol-5-yl)-1H-1,2,3,4-tetrazole

A mixture of 3-(2-naphthyl)-1H-indazole-5-carbonitrile (105 mg, 0.390 mmol), azidotributyltin (Bu$_3$SnN$_3$, 710 mg, 2.14 mmol, 5.49 equiv.), and 4.1 mL toluene was refluxed for 49.5 h and concentrated to an oil. The oil was stirred in 31 mL dioxane and 31 mL 6.0 N aq HCl at room temperature for 4 h. The mixture was partitioned between 6.0 N aq. NaOH and hexanes, and the layers separated. The aqueous layer was extracted with hexanes, and 2× EtOAc, and then filtered. The aqueous layer was acidified to pH ca. 4.0 with 6.0 N aq. HCl. The resulting precipitate was either collected by filtration and dried in a vacuum oven, or extracted with EtOAc, dried (Na$_2$SO$_4$), filtered and concentrated to afford the title compound (78.4 mg, 64.3% yield): $^1$H NMR (DMSO-d$_6$) δ 13.70 (s, 1H), 8.92 (s, 1H), 8.60 (s, 1H), 8.17 (d, 1H), 8.15–8.00 (m, 3H), 7.94 (d, 1H), 7.85 (d, 1H), 7.63–7.58 (m, 2H); ES-MS (m/z) 313 [M+1]$^+$.

Example 171

SYNTHESIS OF 1-(5-(1H-1,2,3,4-TETRAAZOL-5-YL)(1H-INDAZOL-3-YL))-4-METHOXYBENZENE

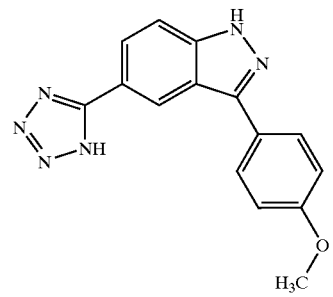

A. 1-(5-(1H-1,2,3,4-Tetraazol-5-yl)(1H-indazol-3-yl)-4-methoxybenzene

The title compound (92.6 mg 72.3% yield) was prepared as described in Example 170 A using 3-(4-methoxyphenyl)-1H-indazole-5-carbonitrile (109 mg, 0.437 mmol). $^1$H NMR (DMSO-d$_6$) δ 13.42 (s, 1H), 8.73 (s, 1H), 8.10 (d, 1H), 7.98 (d, 2H), 7.73 (d, 1H), 7.18 (d, 2H), 3.85 (s, 3H); ES-MS (m/z) 293 [M+1]$^+$.

Example 172

SYNTHESIS OF 1-(5-(1H-1,2,3,4-TETRAAZOL-5-YL)(1H-INDAZOL-3-YL))-4-(2-METHYLPROPOXY)BENZENE

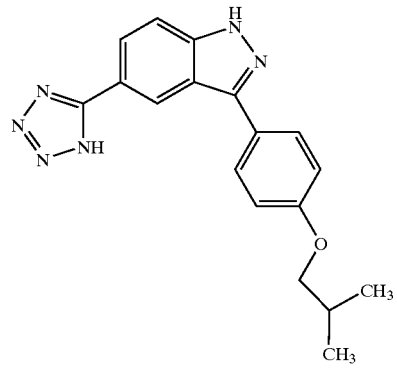

A. 3-[4-(2-Methylpropoxy)phenyl]-1-perhydro-2H-pyran-2-yl-1H-indazole-5-carbonitrile A mixture of 3-(4-hydroxyphenyl)-1-perhydro-2H-pyran-2-yl-1H-indazole-5-carbonitrile (219 mg, 0.686 mmol), potassium carbonate (K$_2$CO$_3$, 568 mg, 4.12 mmol, 6.00 equiv.), 2.00 mL of dimethylformamide (DMF), and 1-bromo-2-methylpropane (Aldrich, 300 mg, 2.18 mmol, 3.20 equiv.) were stirred at room temperature for 2 h, and then heated at 40° C. for 22 h. Additional potassium carbonate (568 mg, 4.12 mmol, 6.00 equiv.), and 1-bromo-2-methylpropane (Aldrich, 300 mg, 2.18 mmol, 3.20 equiv.) were added, and heating continued for another 28 h. The mixture was diluted with EtOAc, washed with 2× sat. aq.

NaHCO$_3$, 2× sat. aq. NaCl, and dried (Na$_2$SO$_4$). Purification by silica gel chromatography using 20% EtOAc in hexanes afforded the title compound (190 mg, 73.6% yield): ES-MS (m/z) 376 [M+1]$^+$.

B. 3-[4-(2-Methylpropoxy)phenyl]-1H-indazole-5-carbonitrile

The title compound was prepared as described in Example 149 E using 3-[4-(2-methylpropoxy)phenyl]-1-perhydro-2H-pyran-2-yl-1H-indazole-5-carbonitrile (186 mg, 0.495 mmol) to provide the title compound (83.7 mg, 58.1% yield): ES-MS (m/z) 292 [M+1]$^+$.

C. 1-(5-(1H-1,2,3,4-Tetraazol-5-yl)(1H-indazole-3-yl))-4-(2-methylpropoxy)benzene The title compound was prepared as described in Example 170.A using 3-[4-5(2-methylpropoxy)phenyl]-1H-indazole-5-carbonitrile (83.7 mg, 0.287 mmol) to provide the title compound (58.2 mg, 60.6% yield): $^1$H NMR (DMSO-d$_6$) δ 13.47 (s, 1H), 8.78 (s, 1H), 8.14 (d, 1H), 7.99 (d, 2H), 7.78 (d, 1H), 7.16 (d, 2H), 3.82 (d, 2H), 2.06 (m, 1H), 1.02 (d, 6H); ES-MS (m/z) 33S [M+1]$^+$.

Example 173

SYNTHESIS OF 5-[3-(4-CHLOROPHENYL)-1H-INDAZOL-5-YL]-2H-1,2,3,4-TETRAZOLE

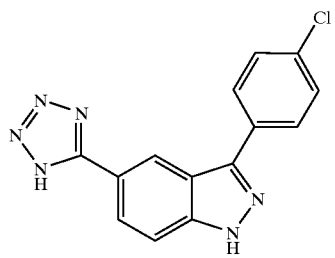

A. 3-(4-Chlorophenyl)-1-perhydro-2H-pyran-2-yl-1H-indazole-5-carbonitrile

The title compound was prepared as described in Example 161, using 3-bromo-1-perhydro-2H-pyran-2-yl-1H-indazole-5-carbonitrile (0.400 g, 1.30 mmol), in ethylene glycol dimethyl ether (10 mL), 4-chlorophenyl boronic acid (0.306 g, 1.96 mmol), [1,1'-bis(diphenylphosphino)-ferrocene] complex with dichloromethane (1:1) (0.150 g, 0.130 mmol), and potassium phosphate (1.38 g, 6.5 mmol): (0.351 g, 80% yield): ES-MS (m/z) 338 [M+1]$^+$.

B. 5-[3-(4-Chlorophenyl)-1H-indazol-5-yl]-2H-1,2,3,4-tetrazole

The title compound was prepared from 3-(4-chlorophenyl)-1-perhydro-2H-pyran-2-yl-1H-indazole-5-carbonitrile (0.351 g, 1.04 mmol), azidotributyl tin (0.351 g, 0.627 mL, 2.29 mmol) in toluene (10 mL) as described for the preparation of compound 167. Deprotection was effected by treating a dioxane solution (5 mL) with 5 mL of 6.0N aqueous solution of hydrogen chloride. Half of the solid obtained upon completion of the reaction was purified by preparatory HPLC (0.054 g, 0.18 mmol, 35% yield over 2 steps) $^1$H NMR (DMSO-d$_6$) 13.7 (s, 1H), 8.8 (s, 1H), 8.1 (t, 3H), 7.8 (d, 1H), 7.6 (t, 2H); ES-MS (m/z) 297 [M+1]$^+$.

Example 174

SYNTHESIS OF 1-(5-(2H-1,2,3,4-TETRAZOL-5-YL)(1H-INDAZOL-3-YL))-3-METHOXYBENZENE

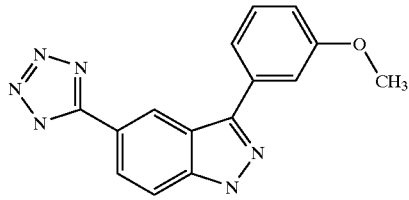

A. 3-(3-Methoxyphenyl-1-perhydro-2H-pyran-2-yl-1H-indazole-5-carbonitrile

The title compound was prepared as described in Example 161, using 3-bromo-1-perhydro-2H-pyran-2-yl-1H-indazole-5-carbonitrile (0.350 g, 1.14 mmol), in ethylene glycol dimethyl ether (10 mL), 3-methoxyphenyl boronic acid (0.260 g, 1.71 mmol), [1,1'-bis(diphenylphosphino)-ferrocene] complex with dichloromethane (1:1) (0.131 g, 0.114 mmol), and potassium phosphate (1.20 g, 5.7 mmol): (0.333 g, 87% yield): ES-MS (m/z) 334 [M+1]$^+$.

B. 1-(5-(2H-1,2,3,4-Tetrazol-5-yl)(1H-indazol-3-yl))-3-methoxybenzene

The title compound was prepared from 3-(3-methoxyphenyl)-1-perhydro-2H-pyran-2-yl-1H-indazole-5-carbonitrile (0.333 g, 1.00 mmol), azidotributyl tin (0.664 g, 0.548 mL, 2.0 mmol) in toluene (10 mL) as described for the preparation of Example 167. Deprotection was effected by treating a dioxane solution (5 mL) with 5 mL of 6.0 N aqueous solution of hydrogen chloride. The solvent was removed under reduced pressure and the crude was extracted into 10 mL of 2.0 N aqueous sodium hydroxide solution. Impurities were washed with ethyl acetate (3×10 mL). The product was collected by filtration after addition of 6.0 N HCl and was washed with small portions of water (0.092 g, 0.18 mmol, 31.5% yield over 2 steps): $^1$H NMR (DMSO-d$_6$) δ 13.6 (br s, 1H), 8.8 (s, 1H), 8.1 (d, 1H), 7.8 (d, 1H), 7.6 (d, 1H), 7.48–7.55 (m, 3H), 7.0 (dd, 1H), 3.9 (s, 3H); ES-MS (m/z) 293 [M+1]$^+$.

Example 175

SYNTHESIS OF 5-(3-(4-PYRIDYL)-1H-INDAZOL-5-YL)-2H-1,2,3,4-TETRAZOLE

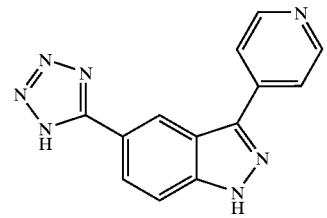

A. 1-Perhydro-2H-pyran-2-yl-3-(4-pyridyl)-1H-indazole-5-carbonitrile

The title compound was prepared as described in Example 161, using 3-bromo-1-perhydro-2H-pyran-2-yl-1H-indazole-5-carbonitrile (0.350 g, 1.14 mmol), in ethylene glycol dimethyl ether (10 mL), 4-pyridyl boronic acid (0.210 g, 1.71 mmol), [1,1'-bis(diphenylphosphino)-ferrocene] complex with dichloromethane (1:1) (0.131 g, 0.114 mmol), and potassium phosphate (1.20 g, 5.7 mmol) (0.164 g, 47% yield): ES-MS (m/z) 306 [M+1]$^+$.

B. 5-(3-(4-Pyridyl)-1H-indazol-5-yl-2H-1,2,3,4-tetrazole

The title compound was prepared from 1-perhydro-2H-pyran-2-yl-3-(4-pyridyl)-1H-indazole-5-carbonitrile (0.164 g, 053 mmol), azidotributyl tin (0.357 g, 0.295 mL, 1.07 mmol) in toluene (5 mL) as described for the preparation of Example 167. Deprotection was effected by treating a methanol solution (5 mL) with 5 mL of 6.0 N aqueous solution of hydrogen chloride. The solvent was removed under reduced pressure and the crude was extracted into 10 mL of 2.0 N aqueous sodium hydroxide solution. Impurities were washed with ethyl acetate (3×10 mL). The product was collected by filtration after addition of 6.0 N HCl and was washed with small portions of water. Further purification was achieved by trituration in 2 mL of methanol and 2 mL of ethyl acetate (0.114 g, 0.43 mmol, 81.7% yield over 2 steps): $^1$H NMR (DMSO-$d_6$) δ 14.2 (d, 1H), 9.1 (s, 1H), 8.8 (d, 2H), 8.3 (d, 2H), 8.2 (d, 1H), 7.9 (d, 1H); ES-MS (m/z) 264 [M+1]$^+$.

Example 176

2-(5-(2H-1,2,3,4-TETRAAZOL-5-YL)-1H-INDAZOL-3-YL)BENZO[B]FURAN

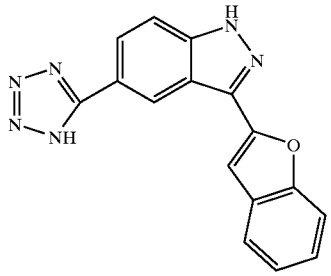

A. 3-benzo[b]furan-2-yl-1-perhydro-2H-pyran-2-yl-1H-indazole-5-carbonitrile

To a flask containing 3-bromo-1-perhydro-2H-pyran-2-yl-1H-indazole-5-carbonitrile (400 mg, 1.30 mmol) in dimethyl glycol ether (15 mL) was added potassium phosphate (2.75 g), [1,1'-bis(diphenylphosphino)-ferrocene] dichloropalladium (II), complex with dichloromethane (1:1) (106 mg, 0.130 mmol), and benzo[b]furan-2-boronic acid (315 mg, 1.95 mmol). The reaction mixture was brought to 90° C. under nitrogen conditions for 18 hours. The mixture was condensed and extracted with water (25 mL) and ethyl acetate. The extracts were dried over sodium sulfate, filtered and concentrated. The residue was then purified by chromatography (SiO$_2$, 20% ethyl acetate/hexanes) to afford the title compound (278 mg, 62%). ES-MS (m/z) 344[M+1]$^+$.

B. 3-benzo[b]furan-2-yl-1H-indazole-5-carbonitrile

To a flask containing 3-benzo[b]furan-2-yl-1-perhydro-2H-pyran-2-yl-1H-indazole-5-carbonitrile (278 mg, 0.8 10 mmol) was added 6N HCl (12 mL) and methanol (12 mL). The solution was brought to 60° C. for 4 hours. The resulting precipitate was filtered and washed with water to provide the title compound (189 mg, 90%). ES-MS (m/z) 260[M+1]$^+$.

C. 2-(5-(2H-1,2,3,4,-tetrazol-5-yl)-1H-indazole-3-yl)benzo[b]furan

To a solution of 3-benzo[b]furan-2-yl1H-indazole-5-carbonitrile (185 mg, 0.713 mmol) in toluene (10 mL) was added tributyl tin azide (0.780 mL). The solution was brought to 110° C. for 18 hours. The solution was cooled and toluene condensed to give an oil. Dioxane (3 mL) and 6 N HCl (3 mL) was added and the solution stirred for 3 hours at ambient temperature. The resulting precipitate was basified using 6 N HCl. The basic aqueous layer was washed with hexanes and ethyl acetate. The aqueous hydroxide solution was filtered through celite and acidified with 6 N HCl to pH 4. The resulting precipitate was filtered and dried to afford the title compound (25 mg, 12% yield). $^1$H NMR (DMSO-$d_6$) δ 13.88 (s, 1H), 8.90 (s, 1H), 8.10 (d, 1H), 7.83 (d, 1H), 7.73 (d, 2H), 7.54 (s, 1H), 7.34 (m, 2H); ES-MS (m/z) 303 [M+1]$^+$.

Example 177

SYNTHESIS OF 2-(5-(2H-1,2,3,4-TETRAZOL-5-YL)-1H-INDAZOL-3-YL)PHENOL

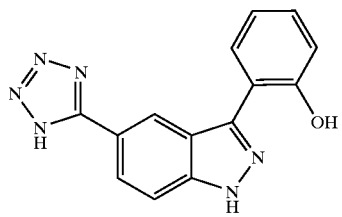

The compound of Example 161 (0.050 g, 0.17 mmol) was suspended in 1 mL of boron tribromide (1.0 M commercial solution in dichloromethane). The reaction mixture was stirred at room temperature in a closed system for 4 days to achieve completion. The product was then collected by filtration and washed with small portions of dichloromethane. Trituration in a few mL of tetrahydrofuran and filtration did not afford satisfactory purity. Final purification by preparative HPLC (30–80% acetonitrile in water, 20 mm) afforded 3 mg of pure product. (6% yield): $^1$H NMR (DMSO-$d_6$) δ 13.6 (s, 1H), 10.3 (s, 1H), 8.7 (s, 1H), 8.1 (d, 1H), 7.8 (t, 2H), 7.3 (t, 1H), 7.08–7.00 (m, 2H); ES-MS (m/z) 279 [M+1]$^+$.

Example 178

SYNTHESIS OF 3-(5-(2H-1,2,3,4-TETRAZOL-5-YL)-1H-INDAZOL-3-YL)PHENOL

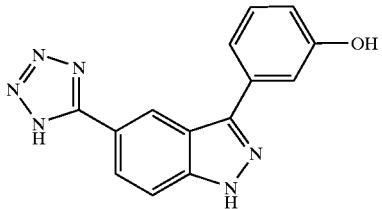

The compound of Example 178 was prepared by deprotection of Example 174 (0.100 g, 0.34 mmol), with 1.5 mL of boron tribromide (1.0 M commercial solution in dichloromethane). The reaction mixture was stirred at room temperature in a closed system for 5 days. The product was then collected by filtration and washed with small portions of dichloromethane. Purification was achieved by preparative HPLC (30–80% acetonitrile in water, 20 min) to afford 71 mg of pure product (75% yield): $^1$H NMR (DMSO-$d_6$) δ 13.6 (br s, 1H), 9.7 (br s, 1H), 8.8 (s, 1H), 8.1 (d, 1H), 7.8 (d, 1H), 7.4 (m, 2H), 7.3 (t, 1H), 6.8 (dt, 1H); ES-MS (m/z) 279 [M+1]$^+$.

Example 179

SYNTHESIS OF 5-[3-(2-PHENYLETHYNYL)-1H-INDAZOL-5-YL]-1H-1,2,3,4-TETRAZOLE

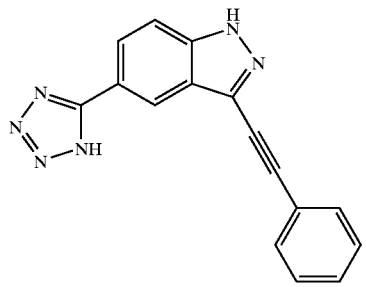

A. 5-[3-(2-Phenylethynyl-1H-indazol-5-yl]-1H-1,2,3,4,4-tetrazole

The title compound (92 mg, 100% yield) was prepared as described in Example 170 A using 3-(2-phenylethynyl)-1H-indazole-5-carbonitrile (77.7 mg, 0.319 mmol). $^1$H NMR (DMSO-d$_6$) δ 13.86 (s, 1H), 8.54 (s, 1H), 8.13 (d, 1H), 7.84 (d, 1H), 7.75–7.69 (m, 2H), 7.52–7.45 (m, 3H); ES-MS (m/z) 287 [M+1]$^+$.

Example 180

SYNTHESIS OF 5-[3-(2-PHENYLETHYL)-1H-INDAZOL-5-YL]-2H-1,2,3,4-TETRAZOLE

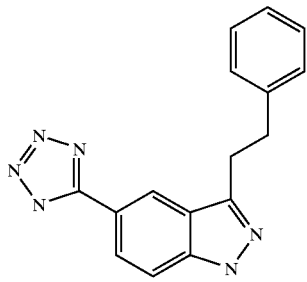

A. 3-((1E)-2-Phenylvinyl)-1-perhydro-2H-pyran-2-yl-1H-indazole-5-carbonitrile

The title compound was prepared as described in example 161, using 3-bromo-1-perhydro-2H-pyran-2-yl-1H-indazole-5-carbonitrile (0.300 g, 0.98 mmol), in ethylene glycol dimethyl ether (10 mL), trans-phenylethenyl boronic acid (0.217 g, 1.47 mmol), [1,1'-bis(diphenylphosphino)-ferrocene] complex with dichloromethane (1:1) (0.113 g, 0.098 mmol), and potassium phosphate (1.04 g, 4.9 mmol) (0.275 g, 85% yield): ES-MS (m/z) 330 [M+1]$^+$.

B. 1-Perhydro-2H-pyran-2-yl-3-(2-phenylethyl)-1H-indazole-5-carbonitrile 3-((1E)-2-Phenylvinyl)-1-perhydro-2H-pyran-2-yl-1H-indazole-5-carbonitrile (0.275 g, 0.83 mmol) was dissolved in ethyl acetate (20 mL). The flask was purged with nitrogen, then hydrogen. To this solution was added palladium on carbon (10 weight %, 14 mg). The mixture was stirred under an atmosphere of hydrogen for 5 hours. The catalyst was filtered and washed with small portions of ethyl acetate (5 mL). The filtrate was concentrated under reduced pressure resulting in the title compound (oil solidified under vacuum) (0.117 g, 84% yield): ES-MS (m/z) 332 [M+1]$^+$.

C. 5-[3-(2-Phenylethyl)-1H-indazol-5-yl]-2H-1,2,3,4-tetrazole

The title compound was prepared as described in Example 167, using 1-perhydro-2H-pyran-2-yl-3-(2-phenylethyl)-1H-indazole-5-carbonitrile (0.117 g, 0.35 mmol), azidotributyl tin (0.353 g, 0.292 mL, 1.06 mmol) in toluene (5 mL). After hydrolysis of the protecting group under acidic conditions, the compound was purified by acid/base extraction. The residue was partitioned between 6.0N NaOH and ethyl acetate. The aqueous phase was then acidified with 6.0 N aqueous hydrogen chloride, to pH 3–4, resulting in the formation of a white precipitate that was collected by filtration, washed with small portions of cold water and dried under vacuum (0.038 g, 37% yield over 2 steps): $^1$H NMR (DMSO-d$_6$) δ 13.05 (br s, 1H), 8.5 (s, 1H), 8.0 (d, 1H), 7.65 (d, 1H), 7.3 (m, 4H), 7.15 (m, 1H), 3.3 (m, 2H), 3.1 (m, 2H); ES-MS (m/z) 291 [M+1]$^+$.

Example 181

SYNTHESIS OF 5-{3-[3-(METHYLETHYL)PHENYL]-1H-INDAZOL-5-YL}-1H-1,2,4-TRIAZOLE

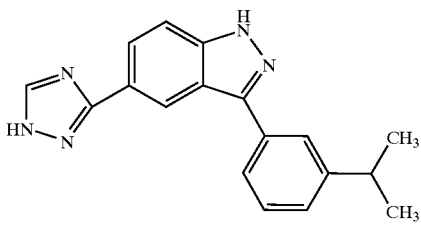

A. 5-{3-[3-(Methylethyl)phenyl]-1H-indazol-5-yl}-1H-1,2,4-triazole

The title compound was prepared as described in Example 184 B (60 mg, 55% yield). $^1$H NMR (DMSO-d$_6$) δ 14.3 (m, 1H), 13.4 (m, 1H), 8.68 (s, 1H), 8.6 (m, 1H), 8.1 (m, 1H), 7.86 (s, 1H), 7.6–7.9 (m, 2H), 7.48 (t, 1H), 7.35 (d, 1H), 3.00 (septet, 1H), 1.29 (d, 6H); ES-MS (m/z) 304 [M+1]$^+$.

Example 182

SYNTHESIS OF 4-(5-(1H-1,2,4-TRIAZOL-5-YL)-1H-INDAZOL-3-YL)PHENOL

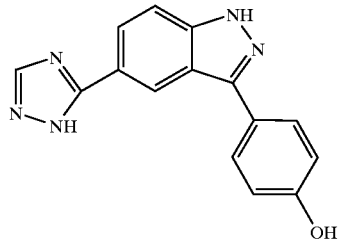

A. 4-(5-(1H-1,2,4-triazol-5-yl)-1H-indazol-3-yl)phenol

A mixture of 3-(4-hydroxyphenyl)-1H-indazole-5-carboxamide (100 mg, 0.425 mmol) and N,N-dimethylformamide dimethyl acetal (10.0 mL, 75.3 mmol, 177 equiv.) was heated at 90° C. for 3 h. The reaction mixture was separated from some dark residue via pipet and concentrated. To the concentrate was added 20 mL of glacial acetic acid (AcOH), and anhydrous hydrazine (357 mg, 11.1 mmol, 26.1 equiv.). The mixture was heated at 90° C. for 2 h. Water (50 mL) was added to the mixture, and the acetic acid was removed on a rotary evaporator. The remaining mixture was extracted with EtOAc. The combined organics were dried (Na$_2$SO$_4$) and purified by prep HPLC to afford the title compound (11.4 mg, 9.7% yield): $^1$H NMR (DMSO-$d_6$) δ 13.25 (br s, 1H), 9.70 (br, 2H), 8.64 (s, 1H), 8.42 (br s, 1H) 8.05 (d, 1H), 7.83 (d, 2H), 7.65 (d, 1H), 6.95 (d, 2H); ES-MS (m/z) 278 [M+1]$^+$.

Example 183

SYNTHESIS OF [4-(5-(1H-1,2,4-TRIAZOL-5-YL)(1H-INDAZOL-3-YL))PHENYL]DIMETHYLAMINE

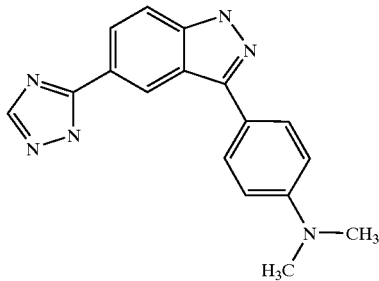

A. [4-(5-(1H-1,2,4-Triazol-5-yl)(1H-indazole-3-yl))phenyl]dimethylamine

A mixture of 3-[4-(dimethylamino)phenyl]-1H-indazole-5-carboxamide (60 mg, 0.214 mmol) and N,N-dimethylformamide dimethyl acetal (10.0 mL, 75.3 mmol, 352 equiv.) was heated at 93° C. for 4.5 h and then concentrated. To the concentrate was added 4.0 mL of glacial acetic acid (AcOH), and anhydrous hydrazine (180 mg, 5.62 mmol, 26.3 equiv.). The mixture was heated at 93° C. for 3 h and concentrated. The residue was partitioned between EtOAc and 6.0 N aq. NaOH and the layers separated. The aqueous layer was extracted with 2×EtOAc and then the pH adjusted between 10–11 with 6.0 N aq. HCl. The resulting precipitate was collected by filtration, washed with H$_2$O, and dried in a vacuum oven to afford the title compound (191 mg, 29.3% yield): $^1$H NMR (DMSO-$d_6$ D$_2$O containing one drop of aqueous HCl) δ 9.30 (s, 1H), 8.89 (s, 1H), 8.27 (d, 2H), 8.12 (d, 1H), 7.96–7.88 (m, 3H), 3.29 (s, 6H); ES-MS (m/z) 305 [M+1]$^+$.

Example 184

SYNTHESIS OF 3-[3-((1E)-2-PHENYLVINYL)-1H-INDAZOL-5-YL]-1H-1,2,4-TRIAZOLE

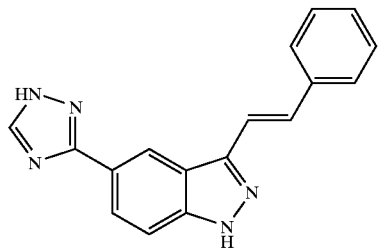

A. 3-((1E)-2-Phenylvinyl)-1-perhydro-2H-pyran-2-yl-1H-indazole-5-carbonitrile

The synthesis of the title compound was performed as described in Example 180.
B. 3-[3-((1E)-2-Phenylvinyl)-1H-indazol-5-yl]-1H-1,2,4-triazole Compound 3-((1E)-2-phenylvinyl)-1-perhydro-2H-pyran-2-yl-1H-indazole-5-carbonitrile (0.126 g, 0.38 mmol) was suspended in 2.50 mL of ethanol and 0.10 mL of water. To this suspension, hydrogen peroxide (30% commercial solution, 3.40 mL), and aqueous sodium hydroxide (6.0 N, 0.320 mL) were added. The reaction mixture was heated to 45° C. for 14 hours. Acidification of the reaction mixture with aqueous hydrogen chloride (6.0 N) to pH 5 resulted in the formation of a white precipitate that was filtered and washed with small portions of water. The product was dried under vacuum. The solid was dissolved in N,N-dimethyl formamide dimethyl acetal (20 mL) and heated to reflux temperature for 2 hours. The white solid formed upon addition of 5 mL of water, was collected, washed with water and dried overnight in a vacuum oven. The solid was dissolved in 20 mL of acetic acid and 1.5 mL of anhydrous hydrazine was added. The solution was heated to 80° C. for 12 hours resulting in the formation of the triazole substituent as well as deprotection of the indazole nitrogen. Solvents were removed under reduced pressure and the title compound was isolated after purification by preparative HPLC (0.040 g, 36% yield over 4 steps): $^1$H NMR (DMSO-$d_6$) δ 8.8 (s, 1H), 8.5 (s, 1H), 8.0 (dd, 1H), 7.7 (d, 2H), 7.6 (d, 1H), 7.55 (d, 1H), 7.5 (d, 1H), 7.4 (t, 1H), 7.3 (t, 1H); ES-MS (m/z) 288 [M+1]$^+$.

Example 185

SYNTHESIS OF {2-[4-(5-(1H-1,2,4-TRIAZOL-5-YL)(1H-INDAZOL-3-YL))PHENOXY]ETHYL}DIMETHYLAMINE

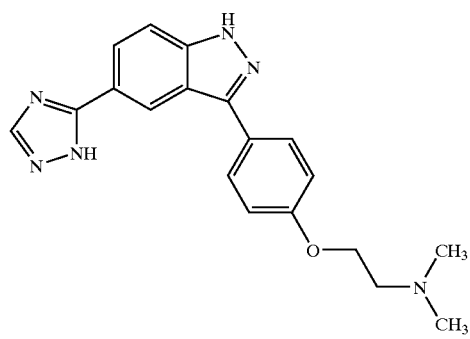

A. {2-[4-(5-(1H-1,2,4-Triazol-5-yl)(1H-indazol-3-yl))phenoxy]ethyl}dimethylamine A mixture of 3-{4-[2-(dimethylamino)ethoxy]phenyl}-1H-indazole-5-carboxamide (79 mg, 0.243 mmol) and N,N-dimethylformamide dimethyl acetal (10.0 mL, 75.3 mmol, 310 equiv.) was heated at 93° C. for 3 h and then concentrated. To the concentrate was added 4.0 mL of glacial acetic acid (AcOH), and anhydrous hydrazine (204 mg, 6.36 mmol, 26.2 equiv.). The mixture was heated at 93° C. for 3 h and concentrated. The residue was partitioned between EtOAc and 6.0 N aq. NaOH and the layers separated. The aqueous layer was extracted with 2×EtOAc and then the pH adjusted between 10–11 with 6.0 N aq. HCl to give maximum cloudiness. The mixture was extracted with 3×EtOAc. The combined organics were dried (Na$_2$SO$_4$), filtered, and concentrated to afford the title compound (73.3 mg, 86.5% yield): $^1$H NMR (DMSO-$d_6$) δ 14.20 (br s, 1H), 13.30 (br s, 1H), 8.65 (s, 1H), 8.37 (br s, 1H), 8.07 (d, 1H), 7.96 (d, 2H), 7.65 (d, 1H), 7.15 (d, 2H), 4.14 (t, 2H), 2.67 (t, 2H), 2.24 (s, 6H); ES-MS (m/z) 349 [M+1]$^+$.

Example 186

SYNTHESIS OF 3-(5-(1H-1,2,4-TRIAZOL-5-YL)-1H-INDAZOL-3-YL)FURAN

A. 3-(5-(1H-1,2,4-Triazol-5-yl)-1H-indazol-3-yl)furan

The title compound was prepared as described in Example 184 B to provide the title compound (60 mg, 55% yield). $^1$H NMR DMSO-d$_6$) δ 14.2 (m, 1H), 13.3 (br s, 1H), 8.59 (br s, 1H), 8.45 (br s, 1H), 8.10 (br s, 1H), 8.07 (br s, 1H), 7.88 (s, 1H), 7.67 (m, 1H), 7.06 (br s, 1H); ES-MS (m/z) 252 [M+1]$^+$.

Example 187

SYNTHESIS OF 1-(5-(1H-1,2,4-TRIAZOL-5-YL)(1H-INDAZOL-3-YL))-4-METHOXYBENZENE

A. 1-(5-(1H-1,2,4-triazol-5-yl)(1H-indazol-3-yl))-4-methoxybenzene

The title compound was prepared as described in Example 185 A using 3-(4-methoxyphenyl)-1H-indazole-5-carboxamide (200 mg, 0.748 mmol) to provide the title compound (166 mg, 76.1% yield): $^1$H NMR (DMSO-d$_6$) δ 13.6 (br s, 1H), 8.73 (s, 1H), 8.22 (s, 1H), 8.05 (d, 1H), 7.95 (d, 2H), 7.63 (d, 1H), 7.13 (d, 2H), 3.84 (s, 3H); ES-MS (m/z) 292 [M+1]$^+$.

Example 188

SYNTHESIS OF 5-(3-NAPHTHYL-1H-INDAZOL-5-YL)-1H-1,2,4-TRIAZOLE

A. 3-Naphthyl-1-perhydro-2H-pyran-2-yl-1H-indazole-5-carbonitrile

The title compound (298 mg, 64.4% yield) was prepared as described in Example 149 D using 1-naphthylboronic acid (336 mg, 1.95 mmol). ES-MS (m/z) 354 [M+1]$^+$.

B. 3-Naphthyl-1H-indazole-5-carbonitrile

The title compound (108 mg, 47.6% yield) was prepared as described in Example 149 E using 3-naphthyl-1-perhydro-2H-pyran-2-yl-1H-indazole-5-carbonitrile (298 mg, 0.843 mmol). ES-MS (m/z) 270 [M+1]$^+$.

C. 3-Naphthyl-1H-indazole-5-carboxamide

The title compound (71.4 mg, 62.1% yield) was prepared as described in Example 149 F using 3-naphthyl-1H-indazole-5-carbonitrile (108 mg, 0.401 mmol). ES-MS (m/z) 288 [M+1]$^+$.

D. 5-(3-Naphthyl-1H-indazole-5-yl)-1H-1,2,4-triazole

The title compound was prepared as described in Example 185 A using 3-naphthyl-1H-indazole-5-carboxamide (71.4 mg, 0.248 mmol). Further purification by prep HPLC afforded the title compound (26.8 mg, 34.7% yield): $^1$H NMR (DMSO-d$_6$) δ 13.58 (br s, 1H), 8.38 (br s, 1H), 8.27–8.22 (m, 2H), 8.17–8.03 (m, 3H), 7.83–7.67 (m, 3H), 7.62–7.52 (m, 2H); ES-MS (m/z) 312 [M+1]$^+$.

Example 189

SYNTHESIS OF 3-(5-(1H-1,2,4-TRIAZOL-3-YL)-1H-INDAZOL-3-YL)THIOPHENE

A. 1-Perhydro-2H-pyran-2-yl-3-(3-thienyl)-1H-indazole-5-carbonitrile

The title compound was prepared according to the procedure described for compound 184, using 3-bromo-1-perhydro-2H-pyran-2-yl-1H-indazole-5-carbonitrile (0.300 g, 0.98 mmol), in ethylene glycol dimethyl ether (10 mL), 3-thiophene boronic acid (0.450 g, 1.47 mmol), [1,1'-bis (diphenylphosphino)-ferrocene] complex with dichloromethane (1:1) (0.113 g, 0.098 mmol), and potassium phosphate (1.04 g, 4.9 mmol) (0.159 g, 52% yield): ES-MS (m/z) 310 [M+H]$^+$.

B. 3-(5-(1H-1,2,4-Triazol-3-yl)-1H-indazol-3-yl)thiophene

Hydrolysis of 1-perhydro-2H-pyran-2-yl-3-(3-thienyl)-1H-indazole-5-carbonitrile (0.159 g, 0.51 mmol) 1-perhydro-2H-pyran-2-yl-3-(3-thienyl)-1H-indazole-5-carboxamide using hydrogen peroxide (30% commercial solution, 5.00 mL) and aqueous sodium hydroxide (6.0 N, 0.400 mL) did not result in satisfactory conversion after 18 hours at 45° C. So the reaction mixture was submitted to THP hydrolysis conditions (4.0N HCl in dioxane, 5 mL, and 6.0 N aqueous HCl, 5 mL; 60° C., 4 hours) before performing the conversion of the nitrile intermediate to the primary amide (4 mL of 30% hydrogen peroxide, 0.2 mL of 6.0 N aqueous sodium hydroxide, 50° C., 2 hours). Precipitation of the intermediate was induced by addition of water. 3-(3-thienyl)-1H-indazole-5-carboxamide was converted to (2E)-2-aza-3-(dimethylamino)-1-(3-(3-Thienyl)(1H-indazol-5-yl))prop-2-en-1-one upon heating a N,N-dimethyl formamide dimethyl acetal (10 mL) to reflux temperature. Cyclization to the final compound was achieved by treating an acetic acid solution of amidine intermediate (10 mL) with 1.0 mL of anhydrous hydrazine at reflux temperature for 2 hours. After aqueous work-up, the title compound was purified by preparative HPLC (15–80% acetonitrile in water) (0.012 g, 9% yield over 4 steps): $^1$H NMR (DMSO-$d_6$) δ 13.3 (br s, 1H), 8.7 (s, 1H), 8.4 (br s, 1H), 7.75–8.1 (m, 2H), 7.7–7.6 (m, 4H); ES-MS (m/z) 268 [M+H]$^+$.

Example 190

SYNTHESIS OF 5-(3-(2-NAPHTHYL)-1H-INDAZOL-5-YL)-1H-1,2,4-TRIAZOLE

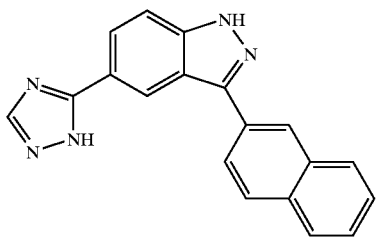

A. 5-(3-(2-Naphthyl-1H-indazol-5-yl)-1H-1,2,4-triazole

The title compound (79.3 mg, 55.4% yield) was prepared as described in Example 185 A using 3-(2-naphthyl)-1H-indazole-5-carboxamide (132 mg, 0.459 mmol). $^1$H NMR (DMSO-$d_6$) δ 13.4–13.2 (m, 1H), 11.99 (s, 0.42H, partial NH), 9.67–8.50 (m, 3H), 8.22–7.97 (m, 5H), 7.79–7.67 (m, 1H), 7.64–7.55 (m, 2H); ES-MS (m/z) 312 [M+1]$^+$.

Example 191

SYNTHESIS OF 3-(5-(1H-1,2,4-TRIAZOL-3-YL)-1H-INDAZOL-3-YL) PHENYLAMINE

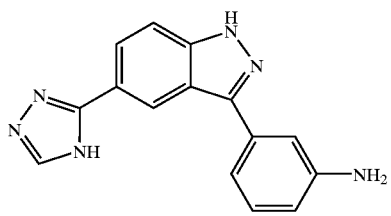

A. 3-(3-Aminophenyl)-1-perhydro-2H-pyran-2-yl-1H-indazole-5-carbonitrile

The title compound (0.420 g, 81% yield) was prepared according to the procedure described for compound 184, using 3-bromo-1-perhydro-2H-pyran-2-yl-1H-indazole-5-carbonitrile (0.500 g, 1.63 mmol), in ethylene glycol dimethyl ether (10 mL), 3-aminophenyl boronic acid (0.380 g, 2.45 mmol), [1,1'-bis(diphenylphosphino)-ferrocene] complex with dichloromethane (1:1) (0.188 g, 0.16 mmol), and potassium phosphate (1.72 g, 8.15 mmol): ES-MS (m/z) 319 [M+H]$^+$.

B. 3-(5-(1H-1,2,4-Triazol-3-yl)-1H-indazol-3-yl) phenylamine

The tetrahydropyran protecting group was removed under acidic conditions using 5 mL of 4.0 N HCl solution in dioxane, and 2.5 mL of aqueous HCl at 60° C. for 2 hours added to 3-(3-aminophenyl)-1-perhydro-2H-pyran-2-yl-1H-indazole-5-carbonitrile (0.220 g, 0.69 mmol). The reaction mixture was neutralized with 2.0 N aqueous sodium hydroxide and extracted with ethyl acetate. After evaporation of the solvent, the residue was dissolved in 4.0 mL of absolute ethanol and reacted with 4.0 mL of 30% commercial hydrogen peroxide solution and 0.2 mL of 6.0 N aqueous sodium hydroxide solution. The reaction mixture was heated to 45° C. for 2 hours. After neutralization and extraction in ethyl acetate, the intermediate was dissolved in 10 mL of dimethoxydimethyl formamide acetal and heated to reflux temperature of the solvent for 2 hours. After evaporation of the solvent, the final cyclization was performed by treating a solution of the precursor in acetic acid (5 mL), with 1 mL of anhydrous hydrazine at 80° C. for 2 hours. The title compound was purified by preparative HPLC (0.011 g, 5% yield over 4 steps): $^1$H NMR (DMSO-$d_6$) 13.4 (br s, 1H), 10.1 (s, 1H), 8.7 (s, 1H), 8.2 (s, 1H), 8.1 (d, 1H), 7.7 (t, 3H), 7.5 (t, 1H); ES-MS (m/z) 319 [M+H]$^+$.

Example 192

SYNTHESIS OF 3-[3-(3,4-DICHLOROPHENYL)-1H-INDAZOL-5-YL]-1H-1,2,4-TRIAZOLE

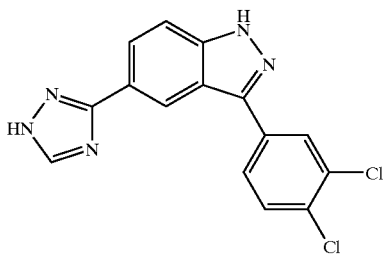

A. 3-(3,4-Dichlorophenyl)-1-perhydro-2H-pyran-2-yl-1H-indazole-5-carbonitrile

The title compound was prepared according to the procedure described in Example 184 using 3-bromo-1-perhydro-2H-pyran-2-yl-1H-indazole-5-carbonitrile (0.300 g, 0.98 mmol), in ethylene glycol dimethyl ether (10 mL), 3,4-dichlorophenyl boronic acid (0.279 g, 1.46 mmol), [1,1'-bis(diphenylphosphino)-ferrocene] complex with dichloromethane (1:1) (0.13 g, 0.098 mmol), and potassium phosphate (1.03 g, 4.9 mmol) (0.249 g, 74% yield): ES-MS (m/z) 372 [M+1]$^+$.

B. 3-[3-(3,4-Dichlorophenyl)-1H-indazol-5-yl]-1H-1,2,4-triazole

The tetrahydropyran protecting group was removed under acidic conditions using 4 mL of 4.0 N HCl solution in dioxane, and 4 mL of aqueous HCl (6.0 N) at 60° C. for 2 hours added to 3-(3,4-dichlorophenyl)-1-perhydro-2H-pyran-2-yl-1H-indazole-5-carbonitrile (0.220 g, 0.69 mmol). The residue was dissolved in 4.0 mL of absolute ethanol and reacted with 4.0 mL of 30% commercial hydrogen peroxide solution and 0.3 mL of 6.0 N aqueous sodium hydroxide solution. The reaction mixture was heated to 80° C. for 1 hour. The intermediate was dissolved in 8 mL of dimethoxydimethyl formamide acetal and heated to reflux temperature of the solvent for 1 Hour. Cyclization to the final compound was achieved by treating an acetic acid solution of the amidine intermediate (10 mL) in the presence of 1.0 mL of anhydrous hydrazine. The title compound was purified by preparative HPLC (0.030 g, 13% yield over 4 steps): $^1$H NMR (DMSO-$d_6$) δ 8.7 (s, 1H), 8.4 (br s, 1H), 8.2 (d, 1H), 8.1 (d, 1H), 8.05 (d, 1H), 7.8 (d, 1H), 7.7 (d, 1H); ES-MS (m/z) 331 [M+1]$^+$.

Example 193

SYNTHESIS OF 3-(5-(1H-1,2,4-TRIAZOL-5-YL)-1H-INDAZOL-3-YL)BENZO[B]THIOPHENE

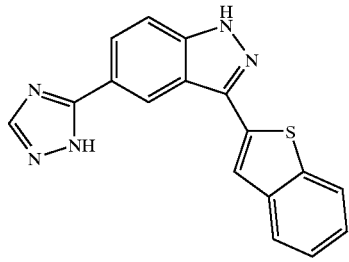

A. 3-(5-(1H-1,2,4-Triazol-5-yl)-1H-indazol-3-yl)benzo[b]thiophene

The title compound was prepared as described in Example 185 A using 3-benzo[b]thiophen-3-yl-1H-indazole-5-carboxamide (112 mg, 0.382 mmol). Further purification by prep HPLC afforded the title compound (32.3 mg, 26.7% yield): $^1$H NMR (DMSO-d$_6$) δ 13.60 (s, 1H), 8.85 (s, 1H), 8.45 (br, 1H), 8.18–8.11 (m, 2H), 8.07–7.98 (m, 2H), 7.75 (d, 1H), 7.50–7.48 (m, 2H); ES-MS (m/z) 318 [M+1]$^+$.

Example 194

SYNTHESIS OF 3-[3-(4-METHYLPHENYL)-1H-INDAZOL-5-YL]-1H-1,2,4-TRIAZOLE

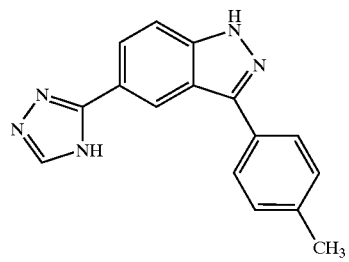

A. 3-Bromo-1-perhydro-2H-pyran-2-yl-1H-indazole-5-carboxamide

To a solution of 3-bromo-1-perhydro-2H-pyran-2-yl-1H-indazole-5-carbonitrile (2.6 g, 8.48 mmol) in 20 mL of ethanol was added 20 mL of commercial solution of hydrogen peroxide (30%) and 1.8 mL of aqueous solution of sodium hydroxide (6.0 N). The suspension was heated to 50° C. for 20 min. The reaction mixture was cooled down and neutralized with 6.0 N aqueous HCl. Further precipitation was observed upon addition of water (20 mL). The solid was collected by filtration, washed with small portions of water and dried in a vacuum oven at 40° C. (2.6 g, 95% yield) $^1$H NMR (CDCl$_3$) δ 8.2 (s, 1H), 8.0 (d, 1H), 7.7 (br s, 1H), 7.6 (d, 1H), 6.4 (br s, 1H), 5.7 (dd, 1H), 4.0 (m, 1H), 3.75 (m, 1H), 2.5 (m, 1H), 2.0 (m, 2H), 1.7 (m, 3H); ES-MS (m/z) 276 [M+H]$^+$.

B. (2E)-2-Aza-3-(Dimethylamino)-1-(3-bromo-1-perhydro-2H-pyran-2-yl-(1H-indazol-5-yl))prop-2-en-1-one 3-Bromo-1-perhydro-2H-pyran-2-yl-1H-indazole-5-carboxamide (2.6 g, 8.04 mmol) and the resulting solution was heated to 80° C. for 2 hours. The solvent was removed under reduced pressure to afford the title compound that was used without further purification: ES-MS (m/z) 379 [M+1]$^+$.

C. 2-(5-(1H-1,2,4-Triazol-3-yl)-3-bromo-1H-indazoyl)perhydro-2H-pyran

To a solution of (2E)-2-aza-3-(dimethylamino)-1-(3-bromo-1-perhydro-2H-pyran-2-yl(1H-indazol-5-yl))prop-2-en-1-one in 25 mL of acetic acid was added 3 mL of anhydrous hydrazine. The solution was heated to 80° C. for 0.5 hour during which the formation of a precipitate and discoloration were observed. Complete precipitation of the product was achieved upon addition of 50 mL of water. The title compound was collected by filtration, washed with small portions of water, and dried in a vacuum oven (40° C.) (2.78 g, quantitative yield): $^1$H NMR (CDCl$_3$) δ 8.3 (d, 1H), 8.1 (d, 1H), 7.6 (d, 1H), 5.7 (d, 1H), 4.0 (m, 1H), 3.75 (m, 1H), 2.5 (m, 1H), 2.0 (m, 2H), 1.7 (m, 3H); ES-MS (m/z) 348 [M+1]$^+$.

D. 2-{3-Bromo-5-[1-(triphenylmethyl)(1,2,4-triazol-3-yl)]-1H-indazoyl}perhydro-2H-pyran To a solution of 2-(5-(1H-1,2,4-triazol-3-yl)-3-bromo-1H-indazoyl)perhydro-2H-pyran in 60 mL in dimethyl formamide, was added triphenylmethyl chloride (3.48 g, 12.5 mmol), and triethyl amine (4.64 mL, 33.32 mmol). The reaction mixture was heated to 80° C. for 12 hours. The solvent was removed under reduced pressure and the crude reaction mixture was partitioned between water and ethyl acetate. The oil resulting from evaporation of the extracts was purified by column chromatography (SiO$_2$, 25% ethyl acetate in hexanes (2.90 g, 61% over 4 steps): $^1$H NMR (CDCl$_3$) δ 8.3 (s, 1H), 8.2 (d, 1H), 7.9 (s, 1H), 7.5 (d, 1H), 7.4–8.1 (m, 15H), 5.68 (dd, 1H), 4.0 (m, 1H), 3.75 (m, 1H), 2.5 (m, 1H), 2.1 (m, 2H), 1.7 (m, 3H); ES-MS (m/z) 592 [M+2]$^+$.

E. 2-{3-(4-Methylphenyl)-5-[1-(trimethylphenyl)(1,2,4-triazol-3-yl)]-1H-indazoyl}perhydro-2H-pyran To a solution of 2-{3-bromo-5-[1-(triphenylmethyl)(1,2,4-triazol-3-yl)]-1H-indazoyl}perhydro-2H-pyran (0.150 g, 0.254 mmol), in ethylene glycol dimethyl ether (3 mL) was added 4-methylphenyl boronic acid (0.052 g, 0.381 mmol), [1,1'-bis(diphenylphosphino)-ferrocene] complex with dichloromethane (1:1) (0.030 g, 0.0254 mmol) and potassium phosphate (0.269 g, 1.27 mmol). The reaction mixture was heated to reflux temperature for 5 hours. The solvent was then evaporated to dryness and the residue was dissolved in 20 mL of ethyl acetate. The heterogeneous solution was washed 3 times with 10 mL of water and once with 10 mL of brine. The organic layer was dried over Na$_2$SO$_4$ and evaporated to dryness. The resulting brown solid was adsorbed on silica gel and purified by column chromatography (85:15 hexanes/ethyl acetate) to provide the title compound (0.130 g, 85% yield): ES-MS (m/z) 602 [M+1]$^+$.

F. 3-[3-(4-Methylphenyl)-1H-indazol-5-yl]-1H-1,2,4-triazole

2-{3-(4-Methylphenyl)-5-[1-(trimethylphenyl)(1,2,4-triazol-3-yl)]-1H-indazoyl}perhydro-2H-pyran (0.130 g, 0.216 mmol) was dissolved in 4 mL of 4.0 N HCl in dioxane and 2 mL of 6.0 N aqueous HCl were added. After 2 hours at room temperature, the reaction mixture was neutralized using aqueous sodium hydroxide (6.0 N) and the product was extracted with ethyl acetate. The extracts were dried under vacuum and dissolved in 5 mL of 6.0 N aqueous sodium hydroxide, side products extracted twice with diethyl ether. The aqueous phase was neutralized with 6.0 N HCl and the product was extracted with ethyl acetate. The crude was purified by preparative HPLC (15–80% acetonitrile in water) (0.024 g, 40% yield): $^1$H NMR (DMSO-d$_6$) δ 13.4 (br s, 1H), 8.7 (s, 1H), 8.4 (br s, 1H), 8.1 (dd, 1H), 7.9 (d, 2H), 7.7 (d, 1H), 7.4 (d, 2H), 7.0 (d, 1H), 2.4 (s, 3H); ES-MS (m/z) 276 [M+]$^+$.

Example 195

SYNTHESIS OF N-[3-(5-(1H-1,2,4-TRIAZOL-3-YL)-1H-INDAZOL-3-YL)PHENYL]ACETAMIDE

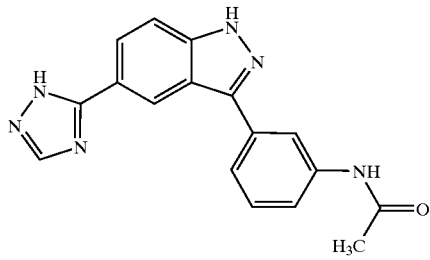

To a solution 3-{1-perhydro-2H-pyran-2-yl-5-[1-(triphenylmethyl)(1,2,4-triazol-3-yl)]-1H-indazole-3-yl}phenylamine (0.200 g, 0.63 mmol), in acetic acid (6.0 mL) was added acetic anhydride (0.178 mL, 1.89 mmol). The reaction mixture was heated to reflux temperature for 12 hours. Water was added (10 mL) and the mixture was neutralized with 2.0 N aqueous sodium hydroxide. The product was extracted with ethyl acetate and concentrated to dryness. The crude oil was dissolved in 4 mL of ethanol and treated with 4 mL of commercial solution of hydrogen peroxide and 0.200 mL of 2.0 N aqueous sodium hydroxide. After 3 hours, the solvent was removed under reduced pressure. The resulting oil was dissolved in 5 mL of dimethoxy dimethyl formamide acetal and the solution was heated to reflux temperature for 3 hours. The solvent was removed under reduced pressure and the residue was dissolved in 10 mL of acetic acid and treated with 1 mL of anhydrous hydrazine. The reaction mixture was heated to reflux temperature for 12 hours. After neutralization with aqueous sodium hydroxide (2.0 N), the crude was extracted with ethyl acetate and purified by preparative HPLC (15–80% acetonitrile in water) (0.040 g, 20% over 5 steps): $^1$H NMR (DMSO-$d_6$) δ 13.4 (br s, 1H), 10.1 (s, 1H), 8.7 (s, 1H), 8.4 (br s, 1H), 8.2 (s, 1H), 8.1 (d, 1H), 7.7 (t, 3H), 7.5 (t, 1H), 2.1 (s, 3H); ES-MS (m/z) 319 [M+1]$^+$.

Example 196

SYNTHESIS OF 5-[3-(3-CHLOROPHENYL)-1H-INDAZOL-5-YL]-1H-1,2,4-TRIAZOLE

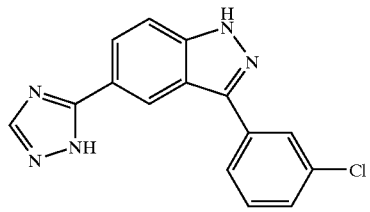

A. 5-[3-(3-Chlorophenyl)-1H-indazol-5-yl]-1H-1,2,4-triazole

The title compound was prepared as described in Example 189 B (55% yield). $^1$H NMR (DMSO-$d_6$) δ 13.7 (br s, 1H), 8.74 (s, 1H), 8.53 (br s, 1H), 8.13 (d, 1H), 8.04–8.01 (m, 2H), 7.75 (d, 1H), 7.64 (t, 1H), 7.53 (d, 1H); ES-MS (m/z) 296 [M+1]$^+$.

Example 197

SYNTHESIS OF 1-[(1E)-2-(5-(1H-1,2,4-TRIAZOL-3-YL)((1H-INDAZOL-3-YL))VINYL]-4-METHOXYBENZENE

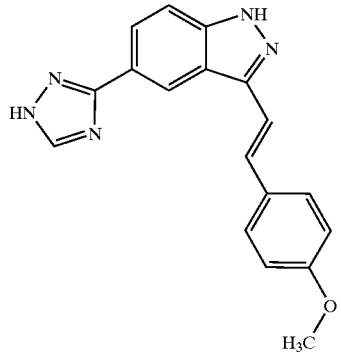

A. 1-((1E)-2-{1-Perhydro-2H-pyran-2-yl-5-[1-(triphenylmethyl)(1,2,4-Triazol-3-yl)](1H-indazole-3-yl)}vinyl-4-methoxybenzene The title compound was prepared according to the procedure described in Example 194 using 2-{3-bromo-5-[1-(triphenylmethyl)(1,2,4-triazol-3-yl)]-1H-indazolyl}perhydro-2H-pyran (0.150 g, 0.254 mmol), in ethylene glycol dimethyl ether (3 mL), trans-4-methoxyphenylethenyl boronic acid (0.067 g, 0.375 mmol), [1,1'-bis(diphenylphosphino)-ferrocene] complex with dichloromethane (1:1) (0.030 g, 0.0254 mmol), and potassium phosphate (0.269 g, 1.27 mmol) (0.105 g, 64% yield): ES-MS (m/z) 644 [M+H]$^+$.

B. 1-[(1E)-2-(5-(1H-1,2,4-Triazol-3-yl)((1H-indazol-3-yl))vinyl]-4-methoxybenzene Hydrolysis was performed by stirring 1-((1E)-2-{1-perhydro-2H-pyran-2-yl-[1-(triphenylmethyl)(1,2,4-triazol-3-yl)](1H-indazol-3-yl)}vinyl-4-methoxybenzene in 4 mL of 4.0 N commercial solution of HCl in dioxane and 2 mL of 6.0 N aqueous HCl at room temperature for 6.5 hours. A mixture of 2 isomers was isolated after purification by preparative HPLC (3% of the minor isomer) (0.014 g, 17.4% yield) $^1$H NMR DMSO-$d_6$) δ 8.8 (s, 1H), 8.55 (s, 1H), 8.15 (d, 1H), 7.7 (t, 3H), 7.5 (d, 2H), 7.0 (d, 2H), 3.8 (s, 3H); ES-MS (m/z) 318 [M+1]$^+$.

Example 198

SYNTHESIS OF 3-{3-[(1E)-2-(4-CHLOROPHENYL)VINYL]-1H-INDAZOL-5-YL}-1H-1,2,4-TRIAZOLE

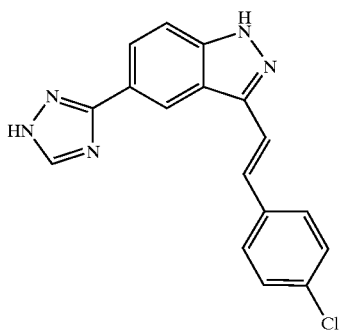

A. 2-{3-[(1 E)-2-(4-Chlorophenyl)vinyl]-5-[1-(triphenylmethyl)(1,2,4-triazol-3-yl)]-1H-indazoyl}perhydro-2H-pyran The title compound was prepared according to the procedure described in Example 194 using 2-{3-bromo-5-[1-(triphenylmethyl)(1,2,4-triazol-3-yl)]-1H-indazolyl}perhydro-2H-pyran (0.160 g, 0.271 mmol), in ethylene glycol dimethyl ether (3 mL), trans-4-chlorophenylethenyl boronic acid (0.074 g, 0.406 mmol), [1,1'-bis(diphenylphosphino)-ferrocene] complex with dichloromethane (1:1) (0.031 g, 0.027 mmol), and potassium phosphate (0.287 g, 1.35 mmol) (0.146 g, 83% yield): ES-MS (m/z) 648 [M+1]⁺.

B. 3-{3-[(1E)-2-(4-Chlorophenyl)vinyl]-1H-indazol-5-yl}-1H-1,2,4-triazole

Hydrolysis was performed by stirring 2-{3-[(1E)-2-(4-chlorophenyl)vinyl]-5-[1-(triphenylmethyl)(1,2,4-triazol-3-yl)]-1H-indazoyl}perhydro-2H-pyran in 4 mL of 4.0 N commercial solution of HCl in dioxane and 2 mL of 6.0 N aqueous HCl, at room temperature for 6.5 hours. The title compound was purified by column chromatography (5% MeOH in dichloromethane) and was isolated as a 98:2 mixture of isomers (0.040 g, 56.6% yield): ¹H NMR (DMSO-d₆) δ 14.4, 14.0 (2s, 1H), 13.4, 13.3 (2s, 11H), 8.7 (m, 1H), 8.1 (m, 2H), 7.8–7.4 (m, 7H); ES-MS (m/z) 322 [M+1]⁺.

Example 199

SYNTHESIS OF 2-(5-(1H-1,2,4-TRIAZOL-5-YL)-1H-INDAZOL-3-YL)BENZO[B]FURAN

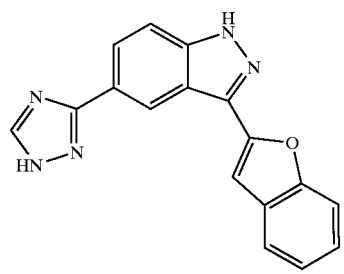

A. 2-(5-(1H-1,2,4-Triazol-5-yl)-1H-indazol-3-yl)benzo[b]furan

The title compound was prepared as described in Example 185 A using 3-benzo[d]furan-2-yl-1H-indazole-5-carboxamide (117 mg, 0.423 mmol). Further purification by prep HPLC afforded the title compound (83 mg, 65% yield) ¹H NMR (DMSO-d₆) δ 13.70 (s, 1H), 8.86 (s, 1H), 8.15 (d, 1H), 7.76 (m, 3H), 7.51 (s, 1H), 7.42–7.29 (m, 3H); ES-MS (m/z) 302 [M+1]⁺.

Example 200

SYNTHESIS OF 1-(5-(1H-1,2,4-TRIAZOL-5-YL)(1H-INDAZOL-3-YL))-4-(METHYLSULFONYL)BENZENE

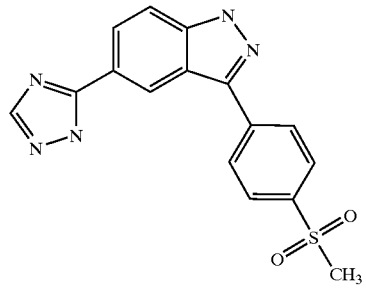

A. 4-Methylthio-1-{1-perhydro-2H-pyran-2-yl-5-[1-(triphenylmethyl)(1,2,4-Triazol-3-yl)](1H-indazole-3-yl)}benzene The title compound was prepared as described in Example 194 E using 4-(methylthio)phenylboronic acid (169 mg, 1.01 mmol) (412 mg, 96.0% yield): ES-MS (m/z) 634 [M+1]⁺.

B. 1-(5-(1H-1,2,4-Triazol-5-yl)(1H-indazol-3-yl))-4-(methylsulfonyl)benzene

A mixture of 4-methylthio-1-{1-perhydro-2H-pyran-2-yl-5-[1-(triphenylmethyl)(1,2,4-triazol-3-yl)](1H-indazol-3-yl)}benzene (200 mg, 0.316 mmol), 1.00 mL CH₂Cl₂, and 3-chloroperoxybenzoic acid (Aldrich, 77% purity, 177 mg, 0.79 mmol based on 77% purity, 2.50 equiv.) was stirred at room temperature for 30 minutes. The reaction was diluted with EtOAc, washed with 2× sat. aq. NaHCO₃, dried (Na₂SO₄, filtered, and concentrated. The crude concentrate was heated in 5.00 mL of MeOH and 5.00 mL of 6.0 N aq. HCl at 65° C. for 17.5 h. The mixture was poured onto 6.0 N aq. NaOH and extracted with 2×EtOAc. The aqueous layer was neutralized to pH=6.0 with 6.0 N aq. HCl, and extracted with 2×EtOAc. The combined organics were dried (Na₂SO₄), filtered, and concentrated. Purification by prep HPLC afforded the title compound (10 mg, 9.4% yield): ¹H NMR (CDCl₃/CD₃OD) δ 8.82–8.73 (m, 1H), 8.42–8.01 (m, 6H), 7.75–7.65 (m, 1H), 3.18 (s, 3H); ES-MS (m/z) 340 [M+1]⁺.

Example 201

SYNTHESIS OF 3-{3-[(1 E)-2-(4-METHYLPHENYL)VINYL]-1H-INDAZOL-5-YL}-1H-1,2,4-TRIAZOLE

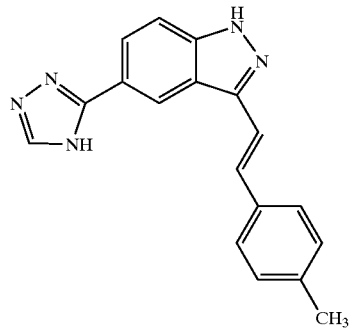

A. 2-{3-[(1E)-2-(4-Methylphenyl)vinyl]-5-[1-(triphenylmethyl)(1,2,4-triazol-3-yl)]-1H-indazoyl}perhydro-2H-pyran The title compound was prepared according to the procedure described in Example 194 using 2-{3-bromo-5-[1-(triphenylmethyl)(1,2,4-triazol-3-yl)]-1H-indazolyl}perhydro-2H-pyran (0.300 g, 0.508 mmol), in ethylene glycol dimethyl ether (5 mL), trans-4-methoxyphenylethenyl boronic acid (0.123 g, 0.762 mmol), [1,1'-bis(diphenylphosphino)-ferrocene] complex with dichloromethane (1:1) (0.059 g, 0.051 mmol), and potassium phosphate (0.538 g, 2.54 mmol) (0.269 g, 84% yield): ES-MS (m/z) 628 [M+1]$^+$.

B. 3-{3-[(1E)-2-(4-Methylphenyl)vinyl]-1H-indazol-5-yl}-1H-1,2,4-triazole

Hydrolysis was performed by stirring 2-{3-[(1E)-2-(4-methylphenyl)vinyl]-5-[1-(triphenylmethyl)(1,2,4-triazol-3-yl)]-1H-indazoyl}perhydro-2H-pyran (0.269 g, 0.42 mmol) in 4 mL of 4.0 N commercial solution of HCl in dioxane and 2 mL of 6.0 N aqueous HCl, at room temperature for 6.5 hours. The title compound was purified by column chromatography (5% MeOH in dichloromethane) and isolated as a 97:3 ratio of 2 isomers (0.103 g, 81% yield): $^1$H NMR (DMSO-d$_6$) δ 8.8 (s, 1H), 8.6 (br s, 1H), 8.1 (d, 1H), 7.6 (m, 3H), 7.5 (d, 2H), 7.0 (d, 2H), 2.34 (s, 3H); ES-MS (m/z) 302 [M+1]$^+$.

Example 202

SYNTHESIS OF 1-(5-(1H-1,2,4-TRIAZOL-5-YL)(1H-INDAZOL-3-YL))-4-(METHYLSULFINYL)BENZENE

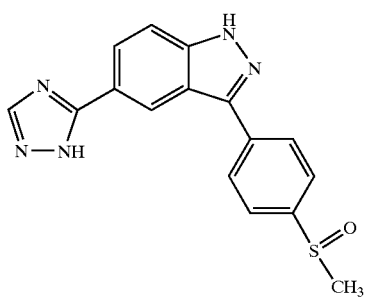

A. 1-(5-(1H-1,2,4-Triazol-5-yl)(1H-indazol-3-yl))-4-(methylsulfinyl)benzene

A mixture of 4-methylthio-1-{1-perhydro-2H-pyran-2-yl-5-[1-(triphenylmethyl)(1,2,4-triazol-3-yl)](1H-indazol-3-yl)}benzene (136 mg, 0.214 mmol), 1.00 mL CH$_2$Cl$_2$, and 3-chloroperoxybenzoic acid (Aldrich, 77% purity, 48.1 mg, 0.214 mmol based on 77% purity, 1.00 equiv.) was stirred at room temperature for 30 minutes. The reaction was diluted with EtOAc, washed with 2× sat. aq. NaHCO$_3$, dried (Na$_2$SO$_4$), filtered, and concentrated. The crude concentrate was heated in 5.00 mL of MeOH and 5.00 mL of 6.0 N aq. HCl at 65° C. for 17.5 h. The mixture was poured onto 6.0 N aq. NaOH and extracted with 2×EtOAc. The aqueous layer was neutralized to pH=6.0 with 6.0 N aq. HCl, and extracted with 2×EtOAc. The combined organics were dried (Na$_2$SO$_4$), filtered, and concentrated. Purification by prep HPLC afforded the title compound (7.2 mg, 10.4% yield): $^1$H NMR (CDCl$_3$/CD$_3$OD) δ 8.78 (s, 1H), 8.45–7.98 (m, 4H), 7.86 (d, 2H), 7.72 (d, 1H), 2.89 (s, 3H); ES-MS (m/z) 324 [M+1]$^+$.

Example 203

SYNTHESIS OF 5-(5-(1H-1,2,4-TRIAZOL-5-YL)-1H-INDAZOL-3-YL)-2H-BENZO[D]1,3-DIOXOLENE

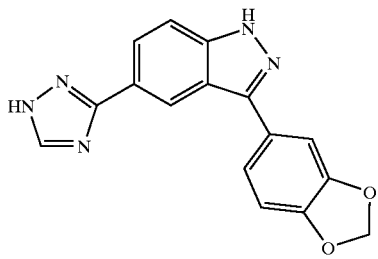

A. 5-{1-Perhydro-2H-pyran-2-yl-5-[1-(triphenylmethyl)(1,2,4-triazol-3-yl)]-1H-indazol-3-yl}-2H-benzo[d]1,3-dioxolene The title compound (168 mg, 52% yield) was prepared as described in Example 194 E using 3,4-(methylenedioxy)phenylboronic acid (134 mg, 0.808 mmol). ES-MS (m/z) 632 [M+1]$^+$.

B. 5-(5-(1H-1,2,4-Triazol-5-yl)-1H-indazol-3-yl)-2H-benzo[d]1,3-dioxolene

The title compound was prepared as described in Example 194 F using 5-{1-perhydro-2H-pyran-2-yl-5-[1-(triphenylmethyl)(1,2,4-triazol-3-yl)]-1H-indazole-3-yl}-2H-benzo[d]1,3-dioxolene (168 mg, 0.267 mmol). Further purification by HPLC afforded the title compound (7 mg, 9% yield): $^1$H NMR (DMSO-d$_6$) δ 13.35 (s, 1H), 8.64 (s, 1H), 8.07 (d, 1H), 7.74–7.37 (m, 4H), 7.13 (d, 1H), 6.12 (s, 2H); ES-MS (m/z) 306 [M+1]$^+$.

Example 204

SYNTHESIS OF 4-(5-(1H-1,2,4-TRIAZOL-5-YL)-1H-INDAZOL-3-YL) PHENYLAMINE

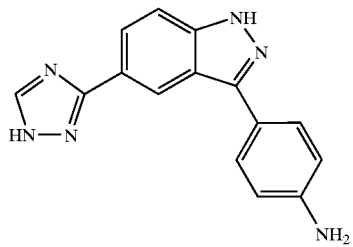

A. 4-(5-(1H-1,2,4-Triazol-5-yl)-1H-indozol-3-yl) phenylamine

The title compound was prepared as described in Example 184 B (40 mg, 28% yield). $^1$H NMR (DMSO-d$_6$) δ 14.2 (m, 1H), 13.1 (br s, 1H), 8.60 (br s, 1H), 8.03 (d, 1H), 7.8–7.5 (m, 4H), 6.71 (d, 2H), 5.33 (s, 2H); ES-MS (m/z) 277 [M+1]$^+$.

Example 205

SYNTHESIS OF 5-{3-[4-(TRIFLUOROMETHYL)PHENYL]-1H-INDAZOL-5-YL}-1H-1,2,4-TRIAZOLE

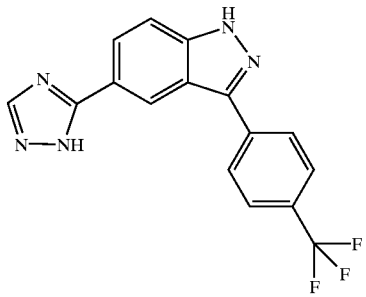

A. 5-{3-[4-(Trifluoromethyl)phenyl]-1H-indazol-5-yl}-1H-1,2,4-triazole

A mixture of 2-{3-bromo-5-[1-(triphenylmethyl)(1,2,4-triazol-3-yl)]-1H-indazolyl}perhydro-2H-pyran (300 mg, 0.508 mmol), 4-trifluoromethylphenylboronic acid (144 mg, 0.758 mmol, 1.49 equiv.), [1,1'-bis(diphenylphosphino)ferrocene}dichloropalladium (II) complex with dichloromethane (Aldrich), 41.5 mg (0.0508 mmol, 0.100 equiv.), 2.53 mL of anhydrous DME, and powdered potassium phosphate ($K_3PO_4$, 535 mg, 2.52 mmol, 4.96 equiv.) were refluxed for 5 days. The reaction was diluted with $CH_2Cl_2$, washed with 2x sat. aq. $NaHCO_3$, dried ($Na_2SO_4$), filtered, and concentrated. The crude material was purified by silica gel using 30–40% EtOAc in hexanes. To the purified material was added 5.00 mL of MeOH, and 5.00 mL of 6.0 N aq. HCl. The mixture was heated at 60° C. for 24 h. The reaction mixture was filtered. The solid was further purified by silica gel chromatography using EtOAc affording the title compound (69.3 mg). Further purification by prep HPLC afforded the title compound (18.9 mg, 11.3% yield): $^1$H NMR (CDCl$_3$/CD$_3$OD) δ 8.74 (s, 1H), 8.41–7.97 (m, 4H), 7.78 (d, 2H), 7.66 (d, 1H); ES-MS (m/z) 330 [M+1]$^+$.

Example 206

SYNTHESIS OF [3-(5-(1H-1,2,4-TRIAZOL-3-YL)(1H-INDAZOL-3-YL))PHENYL](METHYLSULFONYL)AMINE

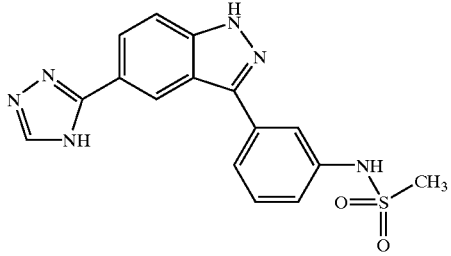

A. 3-{1-Perhydro-2H-pyran-2-yl-5-[1-(triphenylmethyl(1,2,4-triazol-3-yl)]-1H-indazol-3-yl}phenyl amine To a solution of 2-{3-bromo-5-[1(triphenylmethyl)(1,2,4-triazol-3-yl)]-1H-indazolyl}perhydro-2H-pyran (1.0 g, 1.69 mmol) in ethylene glycol dimethyl ether, (20 mL), 3-aminophenyl boronic acid was added as a solid (0.393 g, 2.53 mmol), followed by [1,1'-bis(diphenylphosphino)ferrocene] complex with dichloromethane (1:1) (0.196 g, 0.169 mmol), and potassium phosphate (1.79 g, 8.45 mmol). The reaction mixture was heated to reflux temperature of the solvent for 12 h. The crude reaction mixture was partitioned between ethyl acetate and water. The organic extracts were dried over $Na_2SO_4$. The desired product was isolated as a beige solid after column chromatography purification (SiO$_2$, 25–50% ethyl acetate in hexanes) (0.801 g, 79% yield): ES-MS (m/z) 603 [M+1]$^+$.

B. (Methylsulfonyl)(3-{1-perhydro-2H-pyran-2-yl-5-[1-(triphenylmethyl)(1,2,4-triazol-3-yl)](1H-indazol-3-yl)}phenylamine To a solution of 3-{1-perhydro-2H-pyran-2-yl-5-[1-(triphenylmethyl)(1,2,4-triazol-3-yl)]-1H-indazol-3-yl}phenylamine (0.125 g, 0.207 mmol), in tetrahydrofuran (5 mL), were added, methane sulfonyl chloride (0.036 g, 0.315 mmol, 0.025 mL) and triethyl amine (0.107 g, 1.06 mmol, 0.147 mL). The reaction mixture was stirred at room temperature for 12 hours. After evaporation of the solvent, the residue was dissolved in 10 mL of ethyl acetate and was washed 3 times with water (5 mL). The crude was used without further purification (0.140 g, 99% yield): ES-MS (mlz) 681 [M+1]$^+$.

C. [3-(5-(1H-1,2,4-Triazol-3-yl)(1H-indazol-3-yl))phenyl](methylsulfonyl)amine

Hydrolysis was performed by stirring (methylsulfonyl)(3-{1-perhydro-2H-pyran-2-yl-5-[1-(triphenylmethyl)(1,2,4-triazol-3-yl)](1H-indazol-3-yl)}phenyl)amine (0.140 g, 0.205 mmol) in 4 mL of 4.0 N commercial solution of HCl in dioxane and 2 mL of 6.0 N aqueous HCl, at room temperature for 18 hours. The title compound was purified by preparative HPLC (15–80% acetonitrile in water) (0.052 g, 71% yield): $^1$H NMR (DMSO-d$_6$) δ 13.5 (br s, 1H), 10.0 (s, 1H), 8.7 (s, 1H), 8.4 (br s, 1H), 8.1 (d, 1H), 7.9 (s, 1H), 7.7 (dd, 2H), 7.5 (dd, 1H), 7.3 (d, 1H), 3.06 (s, 3H); ES-MS (m/z) 355 [M+1]$^+$.

Example 207

N-[3-(5-(1H-1,2,4-TRIAZOL-3-YL)(1H-INDAZOL-3-YL))PHENYL]-2-METHOXYACETAMIDE

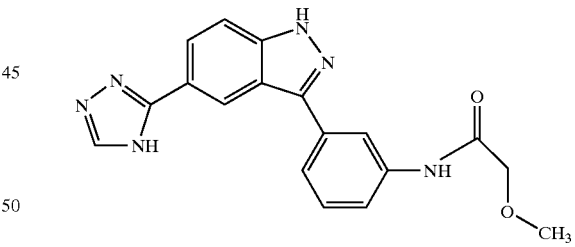

A. 2-Methoxy-N-(3-{1-perhydro-2H-pyran-2-yl-5-[1-(triphenylmethyl)(1,2,4-triazol-3-yl)](1 H-indazol-3-yl)}phenyl)acetamide To a solution of 3-{1-perhydro-2H-pyran-2-yl-5-[1-(triphenylmethyl)(1,2,4-triazol-3-yl)]-1H-indazol-3-yl}phenylamine (0.125 g, 0.207 mmol), in tetrahydrofuran (5 mL), were added, 2-methoxy acetyl chloride (0.034 g, 0.315 mmol, 0.025 mL) and triethylamine (0.107 g, 1.06 mmol, 0.147 mL). The reaction mixture was stirred at room temperature for 12 hours. After evaporation of the solvent, the residue was dissolved in 10 mL of ethyl acetate and was washed 3 times with water (5 mL). The crude was used without further purification (0.141 g, 99% yield): ES-MS (m/z) 675 [M+1]$^+$.

B. N-[3-(5-(1H-1,2,4-Triazol-3-yl)(1H-indazol-3-yl))phenyl]-2-methoxyacetamide

Hydrolysis was performed by stirring 2-methoxy-N-(3-{1-perhydro-2H-pyran-2-yl-5-[1-(triphenylmethyl)(1,2,4-triazol-3-yl)](1H-indazol-3-yl)}phenyl)acetamide (0.141 g, 0.207mmol) in 4 mL of 4.0 N commercial solution of HCl in dioxane and 2 mL of 6.0N aqueous HCl, at room temperature for 18 hours. The title compound was purified by preparative HPLC (15–80% acetonitrile in water) (0.033 g, 46% yield) $^1$H NMR (DMSO-d$_6$) δ 13.5 (br s, 1H), 10.0 (s, 1H), 8.7 (s, 1H), 8.4 (br s, 1H), 8.3 (s, 1H), 8.1 (d, 1H), 7.8 (d, 1H), 7.7 (d, 2H), 7.5 (dd, 1H), 4.06 (s, 2H), 3.4 (s, 3H); ES-MS (m/z) 349 [M+1]$^+$.

Example 208

SYNTHESIS OF N-[3-(5-(1H-1,2,4-TRIAZOL-3-YL)(1H-INDAZOL-3-YL))PHENYL]-2-PHENYLACETAMIDE

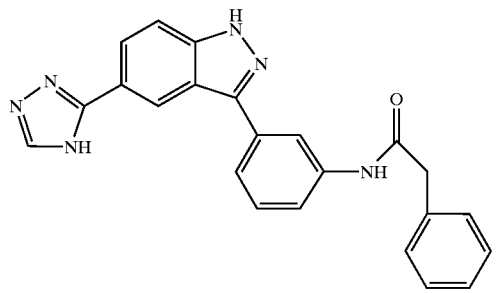

A. N-(3-{1-perhydro-2H-pyran-2-yl-5-[1-(triphenylmethyl)(1,2,4-triazol-3-yl)](1H-indazol-3-yl)phenyl)2-phenylacetamide To a solution of 3-{1-perhydro-2H-pyran-2-yl-5-[1-(triphenylmethyl)(1,2,4-triazol-3-yl)]-1H-indazol-3-yl}phenylamine (0.125 g, 0.207 mmol), in tetrahydrofuran (5 mL), were added, phenyl acetyl chloride (0.049 g, 0.315 mmol, 0.025 mL) and triethyl amine (0.107 g, 1.06 mmol, 0.147 mL). The reaction mixture was stirred at room temperature for 12 hours. After evaporation of the solvent, the residue was dissolved in 10 mL of ethyl acetate and was washed 3 times with water (5 mL). The crude was used without further purification (0.186 g, 99% yield): ES-MS (m/z) 721 [M+1]$^+$.

B. N-[3-(5-(1H-1,2,4-Triazol-3-yl)(1H-indazol-3-yl))phenyl]-2-phenylacetamide

Hydrolysis was performed by stirring N-(3-{1-perhydro-2H-pyran-2-yl-5-[1-(triphenylmethyl)(1,2,4-triazol-3-yl)](1H-indazol-3-yl)}phenyl)2-phenylacetamide (0.186 g, 0.207 mmol) in 4 mL of 4.0 N commercial solution of HCl in dioxane and 2 mL of 6.0 N aqueous HCl, at room temperature for 18 hours. The title compound was purified by preparative HPLC (0.039 g, 48% yield): $^1$H NMR (DMSO-d$_6$) δ 13.4 (br s, 1H), 10.4 (s, 1H), 8.7 (s, 1H), 8.4 (br s, 1H), 8.2 (s, 1H), 8.1 (dd, 1H), 7.7–7.6 (m, 3H), 7.5 (t, 1H), 7.4–7.2 (m, 4H); ES-MS (m/z) 395 [M+1]$^+$.

Example 209

SYNTHESIS OF N-[3-(5-(1H-1,2,4-TRIAZOL-3-YL)(1H-INDAZOL-3-YL))PHENYL]-2-FURYLCARBOXAMIDE

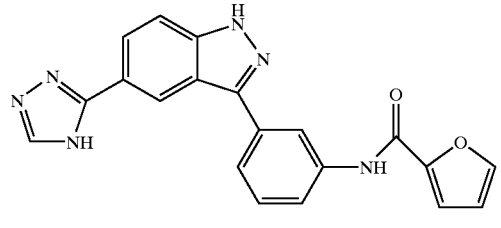

A. 2-Furyl-N-(3-{1-perhydro-2H-pyran-2-yl-5-1-(triphenylmethyl)(1,2,4-triazol-3-yl)](1H-indazol-3-yl)}phenyl)carboxamide To a solution of 3-{1-perhydro-2H-pyran-2-yl-5-[1-(triphenylmethyl)(1,2,4-triazol-3-yl)]-1H-indazol-3-yl}phenylamine (0.125 g, 0.207 mmol), in tetrahydrofuran (5 mL), were added, 2-furoyl chloride (0.041 g, 0.315 mmol, 0.031 mL) and triethyl amine (0.107 g, 1.06 mmol, 0.147 mL). The reaction mixture was stirred at room temperature for 12 hours. After evaporation of the solvent, the residue was dissolved in 10 mL of ethyl acetate and was washed 3 times with water (5 mL). The crude was used without further purification (0.150 g, 99% yield): ES-MS (m/z) 697 [M+1]$^+$.

B. N-[3-(5-(1H-1,2,4-Triazol-3-yl)(1H-indazol-3-yl))phenyl]-2-furylcarboxamide

Hydrolysis was performed by stirring 2-furyl-N-(3-{1-perhydro-2H-pyran-2-yl-5-[1-(triphenylmethyl)(1,2,4-triazol-3-yl)](1H-indazol-3-yl)}phenyl)carboxamide (0.150 g, 0.207 mmol) in 4 mL of 4.0 N commercial solution of HCl in dioxane and 2 mL of 6.0 N aqueous HCl, at room temperature for 18 hours. The title compound was purified by preparative HPLC (15–80% acetonitrile in water) (0.050 g, 50% yield): $^1$H NMR (DMSO-d$_6$) δ 8.8 (s, 1H), 8.6 (s, 1H), 8.3 (s, 1H), 8.0 (d, 1H), 7.8–7.7 (m, 4H), 7.5 (t, 1H), 7.3 (d, 1H), 6.6 (m, 1H); ES-MS (m/z) 371 [M+1]$^+$.

Example 210

SYNTHESIS OF 5-[3-(2-PHENYLETHYNYL)-1H-INDAZOL-5-YL]-1H-1,2,4-TRIAZOLE

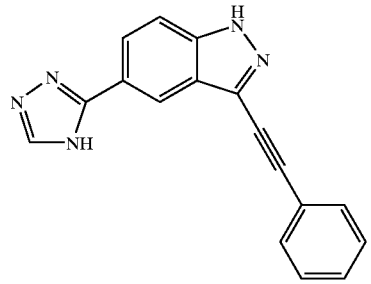

A. 5-[3-(2-phenylethynyl)-1H-indazol-5-yl]-1H-1,2,4-triazole

The title compound was prepared as described in Example 185 A using 3-(2-phenylethynyl)-1H-indazole-5-carboxamide (73.8 mg, 0.282 mmol). Further purification by prep HPLC afforded the title compound (11.7 mg, 14.6% yield): $^1$H NMR (DMSO-d$_6$) δ 13.71 (br, 1H), 8.46 (s. and br s, 2H), 8.12 (d, 1H), 7.78–7.65 (in, 3H), 7.51–7.47 (m, 3H); ES-MS (m/z) 286 [M+1]$^+$.

Example 211

SYNTHESIS OF N-[3-(5-(1H-1,2,4-TRIAZOL-3-YL)(1H-INDAZOL-3-YL))PHENYL]-3-PYRIDYLCARBOXAMIDE

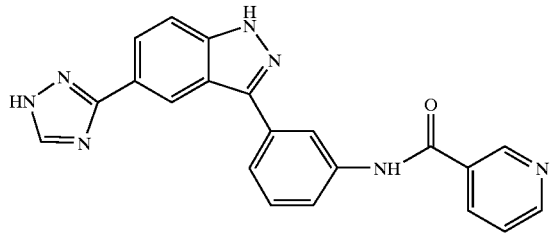

A. N-[3-{1-Perhydro-2H-pyran-2-yl-5-[1-(triphenylmethyl)(1,2,4-triazol-3-yl)](1H-indazol-3-yl)}phenyl)-3-pyridylcarboxamide To a solution of 3-{1-perhydro-2H-pyran-2-yl-5-[1-(triphenylmethyl)(1,2,4-triazol-3-yl)]-1H-indazol-3-yl}phenylamine (0.250 g, 0.415 mmol), in tetrahydrofuran (5 mL), were added, nicotinoyl chloride-hydrochloride (0.148 g, 0.83 mmol), triethyl amine (0.210 g, 2.07 mmol, 0.289 mL), and 2 mL of dimethyl formamide. The reaction mixture was stirred at room temperature for 12 hours. After evaporation of the solvent, the residue was dissolved in 10 mL of ethyl acetate and was washed 3 times with water (5 mL). The crude was used without further purification. ES-MS (m/z) 708 [M+1]$^+$.

B. N-[3-(5-(1H-1,2,4-Triazol-3-yl)(1H-indazol-3-yl))phenyl]-3-pyridylcarboxamide Hydrolysis was performed by stirring N-[3-{1-perhydro-2H-pyran-2-yl-5-[1-(triphenylmethyl)(1,2,4-triazol-3-yl)](1H-indazol-3-yl)}phenyl)-3-pyridylcarboxamide in 4 mL of 4.0 N commercial solution of HCl in dioxane and 2 mL of 6.0 N aqueous HCl, at room temperature for 18 hours. The title compound was purified by preparative HPLC and neutralized with aqueous sodium hydroxide (0.046 g, 29% yield over 2 steps): $^1$H NMR (DMSO-d$_6$) δ 8.8 (s, 1H), 8.6 (s, 1H), 8.3 (s, 1H), 8.0 (d, 1H), 7.8–7.7 (m, 4H), 7.5 (t, 1H), 7.3 (d, 1H), 6.6 (m, 1H); ES-MS (m/z) 382 [M+1]$^+$.

Example 212

SYNTHESIS OF 5-[3-(4-FLUOROPHENYL)(1H-INDAZOL-5-YL)]-3-(3-PYRIDYL)-4H-1,2,4-TRIAZOLE

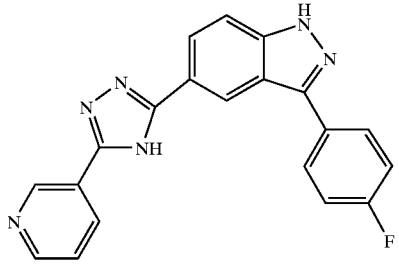

The procedure described in Example 123 using ethoxy[3-(4-fluorophenyl)(1H-indazol-5-yl)]methylanimine hydrochloride (200 mg, 0.62 mmol), triethylamine (0.25 ml, 1.86 mmol), and nicotinic hydrazide (171.4 mg, 1.25 mmol) was used to prepare the title compound (124 mg, 56% yield). $^1$H NMR (DMSO-d$_6$) δ 9.45 (s, 1H), 9.05 (d, 1H), 8.8 (m, 2H), 8.18 (d, 1H), 8.0–8.1 (m, 3H), 7.75 (d, 1H), 7.33 (t, 2H), ES-MS m/z 357 [M+H]$^+$.

Example 213

SYNTHESIS OF 4-{5-[3-(4-FLUOROPHENYL)-1H-INDAZOL-5-YL]-4H-1,2,4-TRIAZOL-3-YL}PHENOL

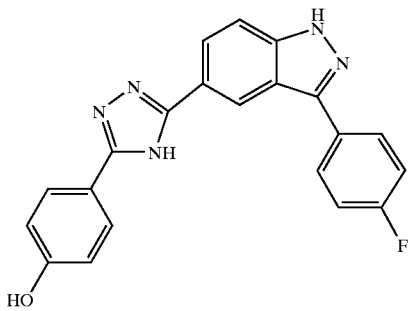

To a round bottom flask containing 1-{5-[3-(4-fluorophenyl)(1H-indazol-5-yl)](4H-1,2,4-triazol-3-yl)]-4-methoxybenzene (100 mg, 0.26 mmol) was added anhydrous dichloromethane (2 ml). The flask, under a nitrogen atmosphere, was placed in an ice/salt bath. To the flask was added boron tribromide (1.3 ml, 1.3 mmol). The reaction was allowed to stir at 0° C. for one hour and at room temperature for an additional four hours. The reaction was quenched with water and the solvent was removed. The product was extracted from the reaction mixture with ethyl acetate. The organic layer was dried with magnesium sulfate, filtered and concentrated. The product was purified by semipreparative HPLC (20–80% acetonitrile over 30 minutes) to yield the title compound (18 mg, 18.7% yield). $^1$H NMR (DMSO-d$_6$) δ 13.5 (s, 1H), 9.95 (s, 1H), 8.65 (s, 1H), 8.1 (m, 3H), 7.95 (m, 2H), 7.78 (d, 1H), 7.4 (m, 2H), 6.85 (m, 2H), ES-MS m/z 372 [M+H]$^+$.

Example 214

SYNTHESIS OF 2-{5-[3-(4-FLUOROPHENYL)1H-INDAZOL-5-YL]-4H-1,2,4-TRIAZOL-3-YL}ACETIC ACID

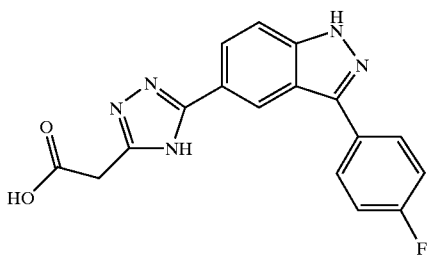

To a round bottom flask containing ethyl 2-{5-[-(4-fluorophenyl)-1H-indazol-5-yl]-4H-1,2,4-triazol-3-yl}acetate (100 mg, 0.27 mmol) was added ethanol (1.5 ml), and the compound was dissolved in the solvent. To the flask was added 10% NaOH solution, and the reaction was allowed to stir for three hours. The compound was soluble in the aqueous layer so the solvent was removed. The compound was taken up in methanol and the solution was filtered. The organic layer was concentrated and the product was purified by semipreparative HPLC (20–80% acetonitrile over 30 minutes) to yield the title compound (24 mg, 26% yield). $^1$H NMR (DMSO-d$_6$) δ 13.5 (s, 1H), 8.6 (s, 1H), 8.0–8.1 (in, 3H), 7.66 (d, 1H), 7.42 (m, 2H), 2.6 (s, 2H), ES-MS m/z 338 [M+H]$^+$.

Example 215

SYNTHESIS OF 1-{5-{3-(4-FLUOROPHENYL) 1H-INDAZOL-5-YL}-4H-1,2,4-TRIAZOL-3-YL}ETHAN-1-OL

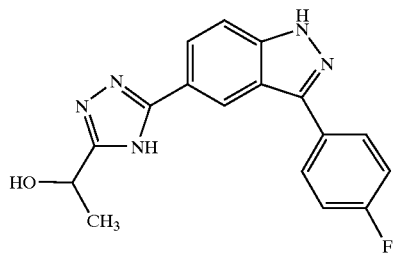

To a round bottom flask was added ethanol (12 ml), hydrazine monohydrate (0.61 ml, 0.0127 mol), and methyl lactate (1.8 ml, 0.019 mol). This was allowed to heat at 60° C. for three hours, then to 75° C. for three hours, and left to stir at room temperature overnight. Solvent and excess methyl lactate were removed under reduced pressure and the reaction mixture was diluted with additional ethanol. To the flask was bubbled in gaseous hydrochloric acid, a solid formed in solution. This was collected by filtration and washed with ethanol to yield N-amino-2-hydroxypropanamide. To a round bottom flask was added ethoxy[3-(4-fluorophenyl)(1H-indazol-5-yl)]methylanimine hydrochloride (200 mg, 0.62 mmol), triethylamine (0.25 mL, 1.86 mmol), and N-amino-2-hydroxypropanamide (150 mg, 1.25 mmol). This was taken up in anhydrous ethanol (10 mL) and sodium sulfate was added to the reaction mixture. The reaction was allowed to stir at 75° C. overnight while under a nitrogen atmosphere. The solvent was removed and the material was purified by semipreparative HPLC (20–80% acetonitrile over 30 minutes) to yield the title compound (30 mg, 15% yield). $^1$H NMR (DMSO-d$_6$) δ 13.4 (s, 1H), 8.6 (s, 1H), 8.0–8.1 (m, 3H), 7.65 (d, 1H), 7.4 (t, 2H), 4.9 (m, 1H), 1.5 (d, 3H), ES-MS m/z 324 [M+H]$^+$.

Example 216

SYNTHESIS OF N-[3-(5-(2H-1,2,3,4-TETRAZOL-5-YL)(1H-INDAZOL-3-YL))PHENYL]-2-METHOXYACETAMIDE

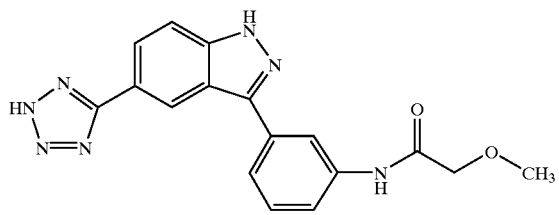

A. 2-(5-(2H-1,2,3,4-Tetrazol-5-yl)-3-bromo-1H-indazolyl)perhydro-2H-pyran

To a solution of 3-bromo-1-perhydro-2H-pyran-2-yl-1H-indazole-5-carbonitrile (1.0 g, 3.27 mmol), in toluene (30 mL), was added tributyltin (2.270 mL, 8.2 mmol). The reaction mixture was heated to reflux temperature of the solvent for 8 hours. Volatile materials were removed under reduced pressure. The oily residue was dissolved in 20 mL of toluene and hydrogen chloride gas was bubbled through the solution for 20 min resulting in the formation of a suspension. The pH of the reaction was adjusted to 5 and the product was extracted with ethyl acetate (0.560 g, 48.5% yield): ES-MS (m/z) 350 [M+H]$^+$.

B. 2-{3-Bromo-5-[2-(triphenylmethyl)(1,2,3,4-tetrazol-5-yl)]-1H-indazolyl}perhydro-2H-pyran To a solution of 2-(5-(2H-1,2,3,4-tetrazol-5-yl)-3-bromo-1H-indazolyl)perhydro-2H-pyran (0.554 g, 1.59 mmol) in dimethyl formamide (5 mL) was added triphenylmethyl chloride (0.662 g, 2.38 mmol), and triethyl amine (1.110 mL, 7.95 mmol). The reaction was heated to reflux temperature for 3.5 hours and maintained at room temperature overnight. The solvent was removed under reduced pressure. The resulting solid was dissolved in 20 mL of ethyl acetate and was washed with 10 ml-portions of water. The title compound was purified by column chromatography (SiO$_2$, 20% ethyl acetate in hexanes) (0.754 g, 70%): ES-MS (m/z) mass not detected.

C. 3-{1-Perhydro-2H-pyran-2-yl-5-[2-(triphenylinethyl)(1,2,3,4-tetrazol-5-yl)]-1H-indazol-3-yl}phenylamine The title compound was prepared according to the procedure described in example 209A using 2-{3-bromo-5-[2-(triphenylmethyl)(1,2,3,4-tetrazol-5-yl)]-1H-indazolyl}perhydro-2H-pyran (0.754 g, 1.27 mmol) in ethylene glycol dimethyl ether (12 mL), 3-aminophenyl boronic acid (0.296 g, 1.91 mmol), [1,1'-bis (diphenylphosphino)-ferrocene] complex with dichloromethane (1:1) (0.147 g, 0.127 mmol), and potassium phosphate (1.35 g, 6.35 mmol). It was isolated after chromatographic purification using 25% ethyl acetate in hexanes (0.246 g, 32% yield): ES-MS (m/z) 604 [M+H]$^+$.

D. 2-Methoxy-N-(3-{1-perhydro-2H-pyran-2-yl-5-[2-(triphenylmethyl)(1,2,3,4-tetrazol-5-yl)](1H-indazol-3-yl)}phenyl)acetamide To a solution of 3-{1-perhydro-2H-pyran-2-yl-5-[2-(triphenylmethyl)(1,2,3,4-tetrazol-5-yl)]-1H-indazol-3-yl}phenylamine (0.246 g, 0.407 mmol) in tetrahydrofiran (4 mL) was added 2-methoxyacetyl chloride (0.056 mL, 0.61 mmol) and triethyl amine (0.284 mL, 2.035 mmol). The reaction mixture was stirred overnight at room temperature before being partitioned between ethyl acetate and water. The product was purified by column chromatography (40% ethyl acetate in hexanes) (0.104 g, 38% yield): ES-MS (m/z) M+ was not detected.

E. N-[3-(5-(2H-1,2,3,4-Tetrazol-5-yl)(1H-indazol-3-yl))phenyl]-2-methoxyacetamide 2-Methoxy-N-(3-{1-perhydro-2H-pyran-2-yl-5-[2-(triphenylinethyl)(1,2,3,4-tetrazol-5-yl)](1H-indazol-3-yl)}phenyl)acetamide was dissolved in 3 mL of 4.0 N hydrogen chloride solution in dioxane. Aqueous hydrogen chloride solution (1.0 mL, 6.0 N) was added and the solution was stirred at room temperature for 48 hours. The pH of the reaction mixture was made basic using 2.0 N aqueous sodium hydroxide and organic impurities were extracted with ethyl acetate. The pH of the aqueous phase was then adjusted to 4–5 using aqueous hydrochloric acid and the crude compound was extracted with ethyl acetate. The title compound was purified by preparative HPLC (15–80% acetonitrile in water) (0.025 g, 48% yield): $^1$H NMR (DMSO-d$_6$) δ 13.6 (s, 1H), 9.9 (s, 1H), 8.8 (s, 1H), 8.4 (s, 1H), 8.07 (d, 1H), 7.82 (d, 1H), 7.74 (d, 1H), 7.5 (t, 1H), 5.7 (s, 2H), 4.4 (s, 3H); ES-MS (m/z) 350 [M+H]$^+$.

Example 217

SYNTHESIS OF 1-{5-[3-(4-FLUOROPHENYL)-1H-INDAZOL-5-YL}-4H-1,2,4-TRIAZOL-3-YL)PROPAN-2-OL

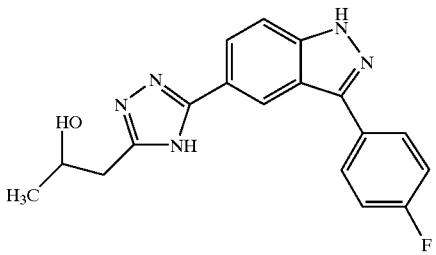

To a flask was added ethyl-3-hydroxybutyrate (2.46 mL, 0.019 mmol), hydrazine monohydrate (0.61 mL, 0.0127 mmol) and ethanol (12 mL). This was allowed to stir under a nitrogen atmosphere at 75° C. overnight. Gaseous hydrochloric acid was bubbled into the reaction and a solid crashed out of solution that was collected by filtration. This compound was determined to be N-amino-3-hydroxybutanamide. To a round bottom flask was added ethoxy[3-(4-fluorophenyl)(1H-indazol-5-yl)]methylanimine hydrochloride (200 mg, 0.62 mmol), triethylamine (0.25 mL, 1.86 mmol), and N-amino-3-hydroxybutanamide (175 mg, 1.25 mmol). This was taken up in anhydrous ethanol (10 mL) and sodium sulfate was added to the reaction mixture. The reaction was allowed to stir at 75° C. overnight while under a nitrogen atmosphere. The solvent was removed and the material was purified by semipreparative HPLC (20–80% acetonitrile over 30 minutes) to yield the title compound (60 mg, 28% yield). $^1$H NMR (DMSO-$d_6$) δ 13.5 (s, 1H), 8.6 (s, 1H), 8.05 (m, 3H), 7.7 (d, 1H), 7.4 (t, 2H), 4.1 (m, 1H), 2.85 (d, 2H), 1.15 (d, 3H); ES-MS m/z 338 [M+H]$^+$.

Example 218

SYNTHESIS OF 1-[3-(4-FLUOROPHENYL)-1H-INDAZOL-5-YL]ETHAN-1-ONE

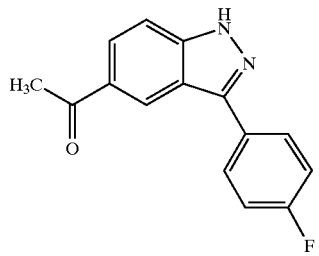

A. 1-[3-(4-Fluorophenyl)-1-perhydro-2H-pyran-2-yl-1H-indazol-5-yl]ethan-1-one

To a solution of 3-(4-fluorophenyl)-1-perhydro-2H-pyran-2-yl-1H-indazole-5-carbonitrile (215 mg, 0.67 mmol) in THF (10 mL) at −78° C. was added methyl lithium (1.0 mL of a 1.0 molar solution, 1.0 mmol). The reaction was allowed to warm to room temperature over 3 hours when it was quenched with water (80 mL) and extracted with ethyl acetate (3×30 mL). The combined ethyl acetate layers were dried (Na$_2$SO$_4$) and concentrated to an oil. The product was recovered from the crude by chromatography on silica gel eluting with 20% ethyl acetate/hexane to give 100 mg of a white solid (44% yield). ES-MS (m/z) 339 [M+1]$^+$.

B. 1-[3-(4-fluorophenyl)-1H-indazol-5-yl]ethan-1-one

To a solution of 1-[3-(4-fluorophenyl)-1-perhydro-2H-pyran-2-yl-1H-indazol-5-yl]ethan-1-one (100 mg, 0.30 mmol) in methanol (30 mL) was added 6 N HCl (30 mL). The solution was stirred at room temperature for 4.5 hours when the methanol was removed under vacuo and the solution made basic with saturated Na$_2$CO$_3$. The suspension was then filtered and the product dried to give the title compound (83 mg, 100% yield). $^1$H NMR (DMSO-$d_6$) δ 8.64 (s, 1H), 8.1 (m, 2H), 7.97 (d, 1H), 7.67 (d, 1H), 7.40 (t, 2H), 2.69 (s, 3H); ES-MS (m/z) 255 [M+1]$^+$.

Example 219

SYNTHESIS OF 2-(5-(1H-1,2,3,4-TETRAZOL1-5-YL)-1H-INDAZOL-3-YL)BENZO[B]THIOPHENE

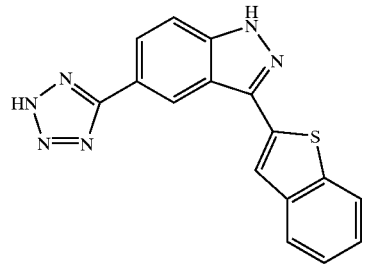

A. 2-(5-(1H-1,2,3,4-Tetraazol-5-yl)-1H-indazol-3-yl)benzo[b]thiophene

The title compound was prepared as described in Example 170.A using 3-benzo[b]thiophen-2-yl-1H-indazole-5-carbonitrile (294 mg, 1.07 mmol) (19.5 mg, 5.7% yield): $^1$H NMR (DMSO-$d_6$) δ 13.72 (s, 1H), 8.95 (s, 1H), 8.21 (s, 1H), 8.13 (d, 1H), 8.03(d, 1H), 7.98 (d, 1H), 7.86 (d, 1H), 7.48–7.39 (m, 2H); ES-MS (m/z) 319 [M+1]$^+$.

Example 220

SYNTHESIS OF 1-(5-(1H-1,2,3,4-TETRAAZOL-5-YL)(1H-INDAZOL-3-YL))-4-(2-MORPHOLIN-4-YLETHOXY)BENZENE

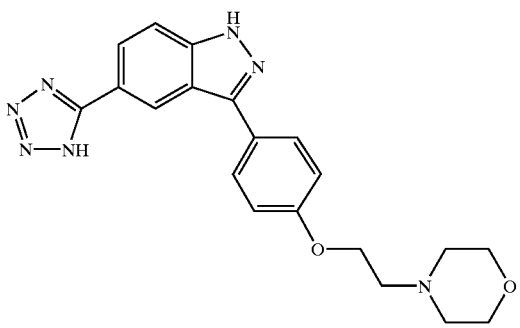

A. 3-[4-(2-Morpholin-4-yl-ethoxy)phenyl]-1H-indazole-5-carbonitrile

A mixture of 3-(4-hydroxyphenyl)-1-perhydro-2H-pyran-2-yl-1H-indazole-5-carbonitrile (400 mg, 1.25 mmol), triphenylphosphine (Ph$_3$P, 1.31 g, 5.00 mmol, 4.00 equiv.), 4.00 mL THF, 4-(2-hydroxyethyl)morpholine (656 mg, 5.00 mmol, 4.00 equiv.), and diethyl azodicarboxylate (DEAD, 871 mg, 5.00 mmol, 4.00 equiv.) were stirred at room temperature for 5 days. The reaction was diluted with EtOAc and washed with 2×6.0 N aq. HCl. The combined aqueous layers were extracted with 2×EtOAc. The acidic aqueous layer was allowed to stand at room temperature for 5 h, and then added to enough 6.0 N aq. NaOH such that the final pH>12.0. The aqueous layer was extracted with EtOAc. The organic layer was dried (Na$_2$SO$_4$), filtered and concentrated. Purification by silica gel chromatography using 0–5% MeOH in EtOAc as eluent afforded an oil. Sonication of the oil in 15 mL of 10% EtOAc/hexane gave a precipitate. This mixture was diluted with 18 mL of hexanes, sonicated, and filtered affording the title compound (310 mg, 71.1% yield: ES-MS (m/z) 349 [M+1]$^+$.

B. 1-(5-(1H-1,2,3,4-Tetraazol-5-yl)(1H-indazol-3-yl))-4-(2-morpholin-4-ylethoxy)benzene A mixture of 3-[4-(2-morpholin-4-ylethoxy)phenyl]-1H-indazole-5-carbonitrile (290 mg, 0.832 mmol), azidotributyltin (Bu$_3$SnN$_3$, 1.56 g, 4.70 mmol, 5.65 equiv.), and 9.0 mL toluene was refluxed for 17.5 h and concentrated to an oil. To the oil was added 6.5 mL of dioxane and 6.5 mL of 6.0 N aq. HCl. The mixture was stirred at room temperature for 4 h and then added to 25 mL of 6.0 N aq. NaOH. The mixture was extracted with 3× hexanes, and 3×Et$_2$O. The aqueous layer was filtered to remove particulates. The pH was adjusted with 6.0 N aq. HCl to give maximum visual turbidity (approximately pH 5.0–5.5) and then the mixture was extracted with 2×EtOAc. The combined organics were dried (Na$_2$SO$_4$), filtered, and concentrated. The product was triturated in 5% EtOAc in hexanes. Filtration and drying of the solid afforded the title compound (29.0 mg, 8.90% yield): $^1$H NMR (CDCl$_3$/CD$_3$OD) δ 8.75 (s, 1H), 8.08 (d, 1H), 7.95 (d, 2H), 7.70 (m, 1H), 7.13 (d, 2H), 4.30 (t, 2H), 3.85–3.79 (m, 4H), 3.07 (t, 2H), 2.89–2.80 (m, 4H); ES-MS (m/z) 392 [M+1]$^+$.

Example 221

SYNTHESIS OF 4-[3-(4-FLUOROPHENYL)-1H-INDAZOLE-5-YL]PYRIMIDINE-2-YLAMINE

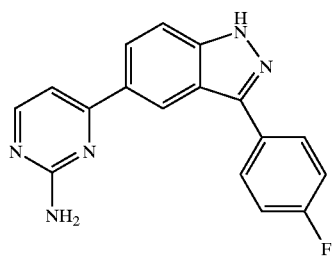

A solution of 1-[3-(4-fluorophenyl)-1H-indazol-5-yl] ethan-1-one (73 mg, 0.29 mmol) in dimethoxy DMF acetal (25 mL) was heated to 90° C. overnight. The solution was then concentrated to an oil under vacuo when methanol (10 mL), guanidine (55 mg, 0.57 mmol), and NaOMe (290 μL of a 2 N solution, 0.58 mmol) was added. The reaction was then heated in a sealed tube to 120° C. overnight. The reaction was then acidified with trifluoroacetic acid then subjected to preparative HPLC (CH$_3$CN/water 0.1% TFA) to recover the final compound (3 mg, 3% yield). $^1$H NMR (DMSO-d$_6$) δ 13.5 (br s, 1H), 8.78 (s, 1H), 8.35 (d, 1H), 8.19 (d, 1H), 8.06 (dd, 2H), 7.72 (d, 1H), 7.53 (d, 1H), 7.38 (t, 2H); ES-MS (m/z) 306 [M+1]$^+$.

Example 222

SYNTHESIS OF N-[3-(5-2H-1,2,3,4-TETRAZOL-5-YL)(1H-INDAZOL-3-YL))PHENYL]2-PHENOXYPROPANAMIDE

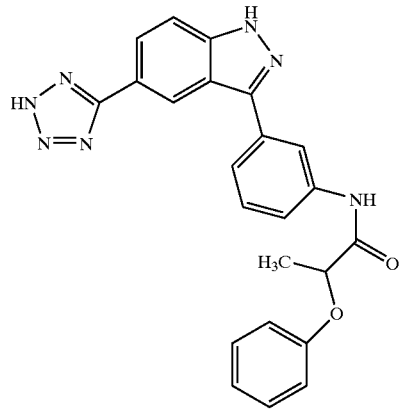

A. 3-(3-aminophenyl)-1-perhydro-2H-pyran-2-yl-1H-indazole-5-carbonitrile

The title compound was prepared as described in example 161 using 3-bromo-1-perhydro-2H-pyran-2-yl-1H-indazole-5-carbonitrile (1.7 g, 5.55 mmol), in ethylene glycol dimethyl ether (60 mL), 3-amino boronic acid (1.72 g, 11.10 mmol), [1,1'-bis(diphenylphosphino)-ferrocene] complex with dichloromethane (1:1) (0.641 g, 0.555 mmol), and potassium phosphate (5.89 g, 27.75 mmol). A second batch was prepared using 3-bromo-1-perhydro-2H-pyran-2-yl-1H-indazole-5-carbonitrile (2.0 g, 6.53 mmol), in ethylene glycol dimethyl ether (70 mL), 3-amino boronic acid (2.025 g, 13.06 mmol), [1,1'-bis(diphenylphosphino)-ferrocene] complex with dichloromethane (1:1) (0.755 g, 0.653 mmol), and potassium phosphate (6.92 g, 32.65 mmol). The crude compounds were combined and purified by column chromatography using 30% ethyl acetate in hexanes (3.2 g, 82% yield): ES-MS (m/z) 319 [M+H]$^+$.

B. N-[3-(5-Cyano-1-perhydro-2H-pyran-2-yl-(1H-indazole-3-yl)phenyl]-2-phenoxypropanamide To a solution of 3-(3-aminophenyl)-1-perhydro-2H-pyran-2-yl-1H-indazole-5-carbonitrile (0.300 g, 0.94 mmol) in dichloromethane (10 mL) was added 2-phenoxy propionic acid (0.172 g, 1.034 mmol) and 1-(3-dimethylaminopropyl)-3-ethylcarbodiimide hydrochloride (0.216 g, 1.13 mmol). After overnight reaction at room temperature, the reaction mixture was partitioned between dichloromethane and water. The organic phase was dried over sodium sulfate and evaporated to dryness. The title compound was purified by column chromatography (SiO$_2$, 25% ethyl acetate in hexanes) (0.370 g, 84%): ES-MS (m/z) 489 [M+Na], 467 [M+H]$^+$.

C. N-[3-(5-2H-1,2,3,4-Tetrazol-5-yl)(1H-indazole-3-yl)) phenyl]2-phenoxypropanamide To a solution of N-[3-(5-cyano-1-perhydro-2H-pyran-2-yl(1H-indazole-3-yl))phenyl]-2-phenoxypropanamide (0.370 g, 0.79 mmol) in toluene (10 mL) was added azidotributyltin (0.952 mL, 3.48 mmol). The reaction mixture was stirred overnight at reflux temperature of the solvent. Volatile materials were removed under reduced pressure. The oily residue was dissolved in 20 mL of toluene and HCl gas was bubbled through the solution for 20 min. The suspension was stirred at room temperature for 12 hours. The solid was decanted and washed 3 times with small portions of toluene. The crude product was purified by preparatory HPLC (15–80% acetonitrile in water) (0.107 g, 32% yield over 2 steps): $^1$H NMR (CD$_3$OD) δ 8.7 (s, 1H), 8.2 (s, 1H), 8.1 (d, 1H), 7.8 (t, 1H), 7.7 (d, 2H), 7.5 (t, 1H), 7.3 (t, 2H), 7.0 (d, 2H), 6.9 (t, 1H), 1.6 (d, 3H); ES-MS (m/z) 426 [M+H]$^+$.

Example 223

SYNTHESIS OF 3-(3,4-DIMETHOXYPHENYL)-1H-INDAZOLE-5-CARBOXAMIDE

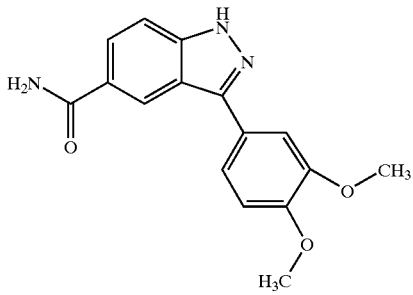

A. 3-(3,4-Dimethoxyphenyl)-1-perhydro-2H-pyran-2-yl-1H-indazole-5-carbonitrile

To a solution of 3-bromo-1-perhydro-2H-pyran-2-yl-1H-indazole-5-carbonitrile (1.0 g, 0.327 mmol) in ethylene glycol dimethylether (35 mL) was added 3,4-dimethoxyphenyl boronic acid (892 mg, 4.9 mmol), potassium phosphate (6.9 g, 33 mmol), and [1,1'-bis(diphenylphosphino)-ferrocene] complex with dichloromethane (1:1) (267 mg, 0.33 mmol). The reaction was heated to reflux for 12 hours when the solvent was removed under vacuo and the crude reaction mixture subjected to chromatography on silica gel eluting with 25% ethyl acetate/hexane to give the title compound (550 mg, 46% yield). ES-MS (m/z) 364 [M+1]$^+$.

B. 3-(3,4-Dimethoxyphenyl)-1H-indazole-5-carbonitrile

To a solution of 3-(3,4-dimethoxyphenyl)-1-perhydro-2H-pyran-2-yl-1H-indazole-5-carbonitrile (550 mg, 1.51 mmol) in methanol (30 mL) was added 6 N HCl (30 mL). The solution was stirred at room temperature for 3 hours when water (80 mL) was added and the suspension filtered to give after drying, the title compound (390 mg, 93% yield). ES-MS (m/z) 280 [M+1]$^+$.

C. 3-(3,4-Dimethoxyphenyl)-1H-indazole-5-carboxamide

To a solution of 3-(3,4-dimethoxyphenyl)-1H-indazole-5-carbonitrile (200 mg, 0.72 mmol) in ethanol (3.5 mL) was added 6 N NaOH (0.5 mL) followed by H$_2$O$_2$ (2.0 mL of a 30% solution). The solution was heated to 45° C. for 1 Hour when water (80 mL) was added and the pH adjusted to <1 with 3 N HCl. The reaction was then filtered and the product dried to give the title compound (180 mg, 61 mmol, 84% yield). $^1$H NMR (DMSO-d$_6$) δ 13.3 (s, 1H), 8.59 (s, 1H), 8.12 (br s, 1H), 7.92 (d, 1H), 7.6–7.5 (m, 2H), 7.52 (s, 1H), 7.3 (br s, 1H), 7.13 (d, 1H), 3.87 (s, 3H), 3.84 (s, 3H); ES-MS (m/z) 298 [M+1]$^+$.

Example 224

SYNTHESIS OF N-[3-(5-(2H-1,2,3,4-TETRAZOL-5-YL)(1H-INDAZOL-3-YL))PHENYL]-3-PIPRERIDYLPROPANAMIDE

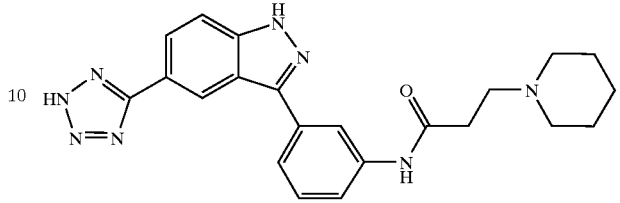

A. N-[3-(-5-Cyano-1-perhydro-2H-pyran-2-yl(1H-indazol-3-yl))phenyl]-3-piperidylpropanamide The title compound was prepared as described in example 222B using 3-(3-aminophenyl)-1-perhydro-2H-pyran-2-yl-1H-indazole-5-carbonitrile (0.300 g, 0.94 mmol) in dichloromethane (10 mL), 1-piperidinepropionic acid (0.162 g, 1.034 mmol) and 1-(3-dimethylaminopropyl)-3-ethylcarbodiimide hydrochloride (0.216 g, 1.13 mmol). The product was used without chromatographic purification (0.362 g, 84%): ES-MS (m/z) 458 [M+H]$^+$.

B. N-[3-(5-(2H-1,2,3,4-Tetrazol-5-yl)(1H-indazol-3-yl))phenyl]-3-piperidylpromanamide The title compound was prepared according to the procedure described for the preparation of compound 222 C using N-[3-(5-cyano-1-perhydro-2H-pyran-2-yl(1H-indazol-3-yl))phenyl]-3-piperidylpropanamide (0.362 g, 0.74 mmol) in toluene (8 mL) and azidotributyltin (0.477 mL, 1.74 mmol). The product was purified by preparatory HPLC (15–80% acetonitrile in water) (0.077 g, 25% yield over 2 steps): $^1$H NMR (CD$_3$OD) δ 8.7 (s, 1H), 8.2 (s, 1H), 8.1 (d, 1H), 7.78 (d, 1H), 7.74 (d, 2H), 7.64 (d, 1H), 7.5 (s, 1H), 3.2 (t, 2H), 3.0 (br s, 4H), 2.8 (t, 2H), 1.8 (quint, 4H), 1.6 (m, 2H); ES-MS (m/z) 417 [M+H]$^+$.

Example 225

SYNTHESIS OF N-[3-(5-(2H-1,2,3,4-TETRAZOL-5-yl)(1H-INDAZOL-3-YL))PHENYL]-2-FURYLCARBOXAMIDE

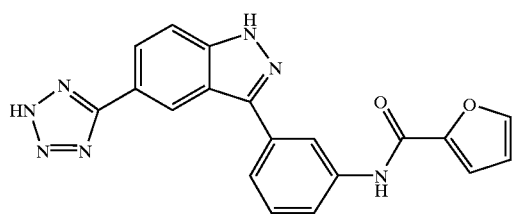

A. N-[3-(5-Cyano-1-perhydro-2H-pyran-2-yl(1H-indazol-3-yl))phenyl]-2-Furylcarboxamide To a solution of 3-(3-aminophenyl)-1-perhydro-2H-pyran-2-yl-1H-indazole-5-carbonitrile (0.300 g, 0.94 mmol) in tetrahydrofuran (10 mL), was added 2-furoyl chloride (0.139 mL, 1.41 mmol) and triethyl amine (0.655 mL, 4.7 mmol). After stirring at room temperature overnight, the reaction mixture was concentrated under reduced pressure and the residue was partitioned between ethyl acetate and water. The organic phase was dried under vacuum and the title product was purified by column chromatography (SiO$_2$, 20–30% ethyl acetate in hexanes) (0.370 g, 95%): ES-MS (m/z) 413 [M+H]$^+$.

B. N-[3-(5-(2H-1,2,3,4-Tetrazol-5-yl)(1H-indazol-3-yl))phenyl]-2-furylcarboxamide The title compound was prepared according to the procedure described for the preparation of compound 222C using N-[3-(5-cyano-1-perhydro-2H-pyran-2-yl(1H-indazole-3-yl))phenyl]-2-furylcarboxamide (0.370 g, 0.89 mmol) in toluene (8 mL) and azidotributyltin (1.08 mL, 3.94 mmol). The product was purified by preparatory HPLC (15–80% acetonitrile in water) (0.042 g, 13% yield over 2 steps): $^1$H NMR (CD$_3$OD) δ 8.8 (s, 1H), 8.4 (t, 1H), 8.1 (dd, 1H), 7.8–7.7 (m, 4H), 7.5 (t, 1H), 7.3 (dd, 1H), 6.67 (dd, 1H); ES-MS (m/z) 372 [M+H]$^+$.

Example 226

SYNTHESIS OF 1-(5-(1H-1,2,3,4-TETRAAZOL-5-yl)(1H-INDAZOL-3-YL))-3-(2-MORPHOLIN-4-YLETHOXY)BENZENE

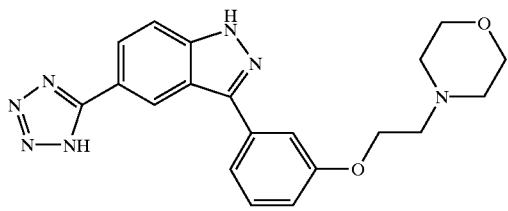

A. 1-(5-(1H-1,2,3,4-Tetraazol-5-yl-)(1H-indazol-3-yl))-3-(2-morpholin-4-ylethoxy)benzene A mixture of 3-(3-hydroxyphenyl)-1-perhydro-2H-pyran-2-yl-1H-indazole-5-carbonitrile (400 mg, 1.25 mmol), triphenylphosphine (Ph$_3$P, 1.31 g, 5.00 mmol, 4.00 equiv.), 4.00 mL THF, 4-(2-hydroxyethyl)morpholine (656 mg, 5.00 mmol, 4.00 equiv.), and diethyl azodicarboxylate (DEAD, 871 mg, 5.00 mmol, 4.00 equiv.) were stirred at room temperature for 3 days. The reaction was diluted with EtOAc and washed with 2×6.0 N aq. HCl. The combined aqueous layers were extracted with 2×EtOAc. The acidic aqueous layer was allowed to stand at room temperature for 5 h, and then added to enough 6.0 N aq. NaOH such that the final pH>12.0. The aqueous layer was extracted with EtOAc. The organic layer was dried (Na$_2$SO$_4$), filtered and concentrated. Purification by silica gel chromatography using 0–5% MeOH in EtOAc as eluent afforded an oil. A mixture of the oil (1.25 mmol), azidotributyltin (Bu$_3$SnN$_3$, 2.35 g, 7.08 mmol, 5.66 equiv.), and 13.5 mL toluene was refluxed for 17.5 h and concentrated to an oil. To the oil was added 6.5 mL of dioxane and 6.5 mL of 6.0 N aq. HCl. The mixture was stirred at room temperature for 4 h and then added to 25 mL of 6.0 N aq. NaOH. The mixture was extracted with 3× hexanes, and 3×Et$_2$O. The aqueous layer was filtered to remove particulates. The pH was adjusted with 6.0 N aq. HCl to give maximum visual turbidity (approximately pH 5.0–5.5) and the mixture was extracted with 2×EtOAc. The combined organics were dried (Na$_2$SO$_4$), filtered, and concentrated. Purification by silica gel chromatography using 0–20% MeOH in EtOAc as eluents afforded the title compound (43.1 mg, 8.82% yield): $^1$H NMR (DMSO-d$_6$) δ 13.54 (s, 1H), 8.72 (s, 1H), 8.10 (d, 1H), 7.77 (d, 1H), 7.61 (d, 1H), 7.52–7.45 (m, 2H), 7.06 (d, 1H), 4.23 (t, 2H), 3.65–3.56 (m, 4H), 2.82 (t, 2H), 2.52–2.45 (m, 4H); ES-MS (m/z) 392 [M+1]$^+$.

Example 227

SYNTHESIS OF ETHYL 3-{5-{3-(4-FLUOROPHENYL)-1H-INDAZOL-5-YL]-4H-1,2,4-TRIAZOL-3-yl}PROPANOATE

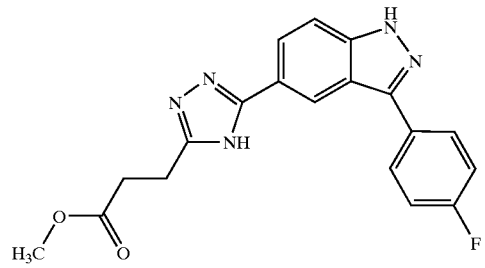

To a round bottom flask under a nitrogen atmosphere containing tert-butyl carbazate (1.0 g, 0.008 mol) was added dichloromethane (16 mL) and triethylamine (1.06 mL, 0.008 mol). The flask was placed in an ice bath and to the reaction was added ethyl glytaryl chloride (1.38 mL, 0.0088 mol). The reaction was allowed to stir at room temperature overnight. Solvent was removed and the material was taken up in anhydrous ethanol. Gaseous hydrochloric acid was bubbled into the reaction and a solid crashed out of solution that was collected by filtration. This compound was determined to be ethyl 3-(N-aminocarbamoyl)propanoate. To a round bottom flask was added ethoxy[3-(4-fluorophenyl)(1H-indazol-5-yl)]methylamine hydrochloride (200 mg, 0.62 mmol), triethylamine (0.25 mL, 1.86 mmol), and 3-(N-aminocarbamoyl)propanoate (243 mg, 1.25 mmol). This was taken up in anhydrous ethanol (10 mL) and molecular sieves were added to the reaction mixture. The reaction was allowed to stir at 75° C. overnight while under a nitrogen atmosphere. The solvent was removed and the material was purified by preparative HPLC (30–100% acetonitrile over 20 minutes) to yield the title compound (38 mg, 16% yield). Retention time 9.764 minutes 20–100% ODS 1 mL/min; ES-MS m/z 380 [M+H]$^+$.

Example 228

SYNTHESIS OF ETHYL-4-{5-[3-(4-FLUOROPHENYL)-1H-INDAZOL-5-YL}-4H-1,2,4-TRIAZOL-3-YL}BUTANOATE

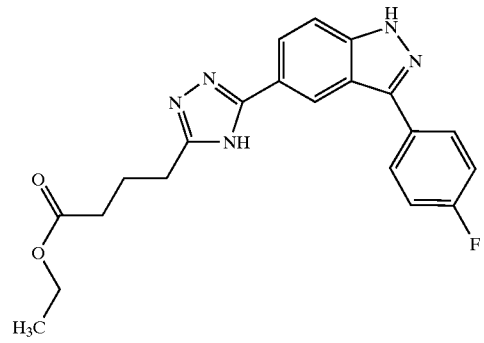

To a round bottom flask under a nitrogen atmosphere containing tert-butyl carbazate (5.0 g, 0.044 mmol) was added dichloromethane (50 mL) and triethylamine (5 mL, 0.04 mmol). The flask was placed in an ice bath and to the reaction was added ethyl succinyl chloride (6.22 mL, 0.044 mmol). The reaction was allowed to stir at room temperature overnight. Solvent was removed and the material was taken up in anhydrous ethanol. Gaseous hydrochloric acid was bubbled into the reaction and a solid crashed out of solution that was collected by filtration. This compound was determined to be ethyl 4-(N-aminocarbamoyl)butanoate. To a round bottom flask was added ethoxy[3-(4-fluorophenyl)(1H-indazol-5-yl)]methylanimine hydrochloride (200 mg, 0.62 mmol), triethylamine (0.25 mL, 1.86 mmol), and 3-(N-aminocarbamoyl)propanoate (260 mg, 1.25 mmol). This was taken up in anhydrous ethanol (10 mL) and molecular sieves were added to the reaction mixture. The reaction was allowed to stir at 75° C. overnight while under a nitrogen atmosphere. The solvent was removed and the material was purified by preparative HPLC (30–100% acetonitrile over 20 minutes) to yield the title compound (9 mg, 3.7% yield). Retention time 9.8 minutes 20–100% ODS 1 mL/min; ES-MS m/z 394 [M+H]$^+$.

Example 229

SYNTHESIS OF 4-(5-(2H-1,2,3,4-TETRAAZOL-5-YL)(1H-INDAZOL-3-YL))-1,2-DIMETHOXYBENZENE

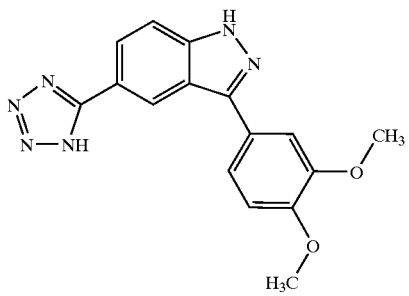

To a solution of 3-(3,4-dimethoxyphenyl)-1H-indazole-5-carbonitrile (190 mg, 0.68 mmol) in toluene (10 mL) was added tributyltin azide (930 µL, 3.4 mmol). The solution was heated to reflux for 12 hours when 3 N NaOH (80 mL) was added and the solution extracted with ethyl acetate (2×20 mL). The aqueous layer was then acidified with 4 N HCl to pH<1 and extracted with ethyl acetate (3×30 mL). The combined organic layers were dried (Na$_2$SO$_4$) and concentrated to an oil. After remaining at room temperature for 14 hours, the product crystallized from solution to recover, after filtration and drying, the title compound (115 mg, 53% yield). $^1$H NMR (DMSO-d$_6$) δ 13.4 (s, 1H), 8.70 (s, 1H), 8.04 (d, 1H), 7.75 (d, 1H), 7.54 (d, 1H), 7.49 (s, 1H), 7.12 (d, 1H), 3.85 (s, 3H), 3.81 (s, 3H); ES-MS (m/z) 323 [M+1]$^+$.

Example 230

SYNTHESIS OF N-[3-(5-(2H-1,2,3,4-TETRAZOL-5-YL)(1H-INDAZOL-3-YL))PHENYL]-3-METHOXYPROPANAMIDE

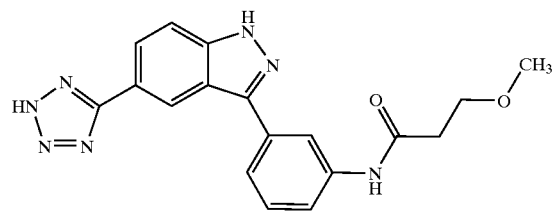

A. N-{3-(5-Cyano-1-perhydro-2H-pyran-2-yl(1H-indazol-3-yl))phenyl]-3-methoxypropanamide The title compound was prepared as described in example 222B using 3-(3-aminophenyl)-1-perhydro-2H-pyran-2-yl-1H-indazole-5-carbonitrile (0.300 g, 0.94 mmol) in dichloromethane (10 mL), 3-methoxypropionic acid (0.097 mL, 1.034 mmol), and 1-(3-dimethylaminopropyl)-3-ethylcarbodiimide hydrochloride (0.216 g, 1.13 mmol). The product was used without chromatographic purification (0.437 g, quantitative yield): ES-MS (m/z) 405 [M+H]$^+$.

B. N-[3-(5-(2H-1,2,3,4-Tetrazol-5-yl)(1H-indazol-3-yl))phenyl]-3-fumethoxypropanamide The title compound was prepared according to the procedure described for the preparation of compound 222 C using N-[3-(5-cyano-1-perhydro-2H-pyran-2-yl(1H-indazol-3-yl))phenyl]-3-methoxypropanamide (0.437 g, 0.94 mmol) in toluene (8 mL) and azidotributyltin (1.13 mL, 4.13 mmol). The product was purified by preparatory HPLC (15–80% acetonitrile in water) (0.189 g, 55% yield over 3 steps): $^1$H NMR (CD$_3$OD) δ 10.06 (s, 1H), 8.7 (s, 1H), 8.2 (s, 1H), 8.09 (dd, 1H), 7.77 (d, 1H), 7.74 (d, 1H), 7.67 (d, 1H), 7.5 (t, 1H), 3.76 (t, 2H), 3.38 (s, 3H), 2.68 (t, 2H); ES-MS (m/z) 364 [M+H]$^+$.

Example 231

SYNTHESIS OF N-[3-(5-(2H-1,2,3,4-TETRAZOL-5-YL)(1H-INDAZOL-3-YL))PHENYL]-3-PYRIDYLCARBOXAMIDE

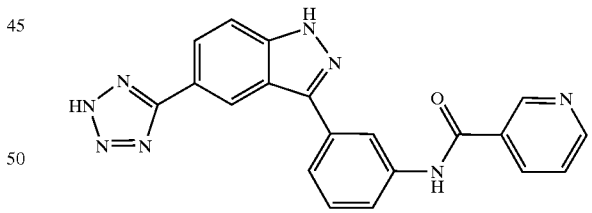

A. N-[3-(5-Cyano-1-perhydro-2H-pyran-2-yl(1H-indazol-3-yl))phenyl]-3-pyridylcarboxamide The title compound was prepared according to the procedure described in 225A, using 3-(3-aminophenyl)-1-perhydro-2H-pyran-2-yl-1H-indazole-5-carbonitrile (0.300 g, 0.94 mmol), nicotinoyl chloride hydrochloride (0.334 mL, 1.88 mmol), and triethyl amine (0.655 mL, 4.7 mmol). The title product was purified by column chromatography (SiO$_2$, 5% methanol in dichloromethane) (0.215 g, 54% yield): ES-MS (m/z) 424 [M+H]$^+$.

B. N-[3-(5-(2H-1,2,3,4-Tetrazol-5-yl)(1H-indazol-3-yl))phenyl]-3-pyridylcarboxamide The title compound was prepared according to the procedure described for the preparation of compound 222 C using N-[3-(5-Cyano-1-perhydro-2H-pyran-2-yl(1H-indazol-3-yl))phenyl]-3-pyridylcarboxamide (0.215 g, 0.508 mmol) in toluene (6 mL) was added azidotributyltin (0.612 mL, 2.23 mmol). The product was purified by preparatory HPLC (15–80% acetonitrile in water) (0.035 g, 18% yield over 2 steps): $^1$H NMR (CD$_3$OD) δ 9.1 (s, 1H), 8.8 (s, 1H), 8.7 (d, 1H), 8.4 (d, 1H), 8.2 (s, 1H), 8.1 (d, 1H), 8.0 (d, 1H), 7.9 (d, 1H), 7.6–7.5 (m, 4H); ES-MS (m/z) 383 [M+H]$^+$.

Example 232

SYNTHESIS OF 3-(3-AMINOPHENYL)-1H-INDAZOLE-5-CARBOXAMIDE

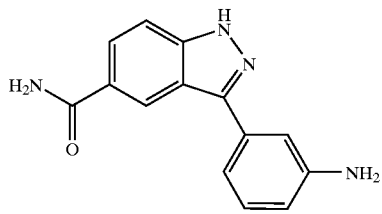

A. N-[3-(5-Cyano-1-perhydro-2H-pyran-2-yl(1H-indazol-3-yl)phenyl]-2-Methoxyacetamide The title compound was prepared using 3-(3-aminophenyl)-1-perhydro-2H-pyran-2-yl-1H-indazole-5-carbonitrile (0.150 g, 0.47 mmol) in tetrahydrofuran (5 mL), 2-methoxy acetyl chloride (0.086 mL, 0.94 mmol) and triethyl amine (0.327 mL, 2.35 mmol). The crude product was isolated after partition of the reaction mixture between ethyl acetate and water. The yield was not calculated: ES-MS (m/z) 391 [M+H]$^+$.

B. 3-[3-(2-Methoxyacetamino)phenyl]-1-perhydro-2H-pyran-2-yl-1H-indazole-5-carboxamide To a solution of N-[3-(5-cyano-1-perhydro-2H-pyran-2-yl(1H-indazole-3-yl))phenyl]-2-methoxyacetamide in 4 mL of ethanol, was added 4 mL of 30% wt. commercial solution of hydrogen peroxide and 0.200 mL of 6.0 N aqueous sodium hydroxide solution. The reaction was heated to 60° C. for 2 hours. The reaction mixture was acidified with a few drops of 6.0 N aqueous hydrogen chloride solution and the product was further precipitated upon addition of 20 mL of water. The intermediate was isolated by filtration, washed 3 times with 5 mL portions of water and dried in a vacuum oven overnight. The yield was not calculated: ES-MS (m/z) 409 [M+H]$^+$.

C. 3-(3-Aminophenyl)-1H-indazole-5-carboxamide

Intermediate 3-[3-(2-Methoxyacetamino)phenyl]-1-perhydro-2H-pyran-2-yl-1H-indazole-5-carboxamide was dissolved in 5 mL of methanol and hydrogen chloride gas was bubbled through the solution for 20 min. The resulting suspension was stirred at room temperature for 3 hours. The pH of the reaction mixture was made basic through the addition of sodium bicarbonate and the crude product was extracted with ethyl acetate. The title compound was isolated after purification by preparative HPLC (15–80% acetonitrile in water) (0.043 g, 36% over 3 steps): $^1$H NMR (CD$_3$OD) δ 8.6 (s, 1H), 7.9 (dd, 1H), 7.6 (d, 1H), 7.3–7.2 (m, 3H), 6.8 (dt, 1H); ES-MS (m/z) 253 [M+H]$^+$.

Example 233

SYNTHESIS OF 3-{5-[3-(4-FLUOROPHENYL)-1H-INDAZOL-5-yl]-4H-1,2,4-TRIAZOL-3-yl}PROPANOIC ACID

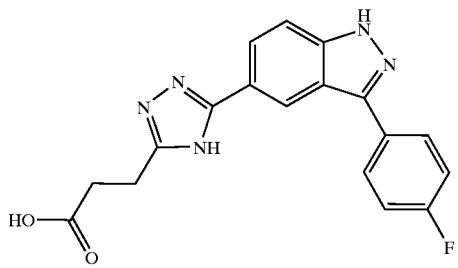

To a flask containing ethyl 3-{5-{3-(4-fluorophenyl)-1H-indazole-5-yl]-4H-1,2,4-triazol-3-yl}propanoate (37mg, 0.1 mmol) was added lithium hydroxide monohydrate (8.2 mg, 0.2 mmol). This was taken up in tetrahydrofuran and allowed to stir under a nitrogen atmosphere overnight. The reaction was acidified slightly. The product was found to be soluble in both the aqueous and organic layers. The layers were concentrated and the product was purified by semi-preparative HPLC (20–80% acetonitrile with 0.1% formic acid over 30 minutes). The fractions containing the compound were concentrated to yield the title compound (11 mg, 32% yield). $^1$H NMR (DMSO-d$_6$) δ 13.5 (s, 1H), 8.6 (s, 1H), 8.0 (m, 3H), 7.6 (d, 1H), 7.4 (t, 2H), 2.95 (m, 2H), 2.7 (m, 2H); ES-MS m/z 352 [M+H]$^+$.

Example 234

SYNTHESIS OF 3-(2H-BENZO[D]1,3-DIOXOLEN-5-YL)-1H-INDAZOLE-5-CARBOXAMIDE

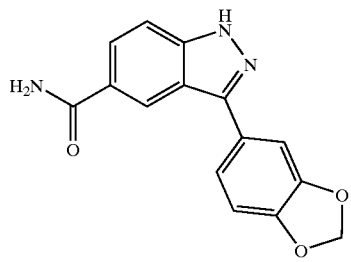

A. 3-(2H-Benzo[d]1,3-dioxolen-5-yl)-1H-indazole-5-carboxamide

The title compound was prepared as described in Example 149 F using 3-(2H-benzo[d]1,3-dioxolen-5-yl)-1H-indazole-5-carbonitrile (256 mg, 0.97 mmol) to provide the title compound (169 mg, 62% yield): $^1$H NMR (DMSO-d$_6$) δ 13.33 (s,1H), 8.56 (s, 1H), 8.16 (s, 1H), 7.92 (d, 1H), 7.60–7.53 (m, 3H), 7.32 (s, 1H), 7.09 (d, 1H), 6.11 (s, 2H); ES-MS (m/z) 282 [M+1]$^+$.

Example 235

SYNTHESIS OF 5-METHYL-3-(4-FLUOROPHENYL)-1H-INDAZOLE

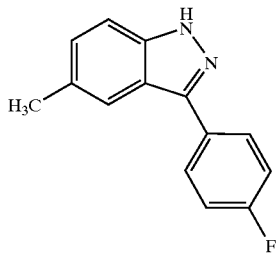

The title compound was prepared as described in Example 12 A using 2-amino-5-methylphenyl 4-fluorophenyl ketone (4.61 g, 20.1 mmol) (2.5 mg, 60% yield). $^1$H NMR (DMSO-$d_6$) δ 13.1 (s, 1H), 8.04–7.98 (m, 2H), 7.83 (br s, 1H), 7.48 (d, 1H), 7.37–7.3 (m, 3H), 7.24 (d, 1H), 2.45 (s, 3H); ES-MS (m/z) 227 [M+1]$^+$.

Example 236

SYNTHESIS OF {3-[4-(5-(1H-1,2,3,4-TETRAZO-5-YL)(1H-INDAZOL-3-YL))PHENOXY]PROPYL}DIMETHYLAMINE

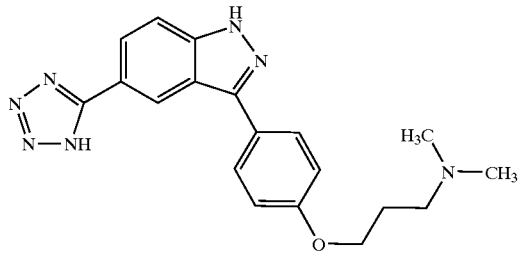

A. 3-{4-[3-(dimethylamino)propoxy]phenyl}-1H-indazole-5-carbonitrile

Triphenylphosphine (1.31 g, 5.00 mmol), THF (4.00 mL), 3-N,N-dimethylaminopropanol (0.592 mL, 5.00 mmol) and diethylazodicarboxylate (0.788 mL, 5.00 mmol) were added to 3-(4-hydroxyphenyl)-1-perhydro-2H-pyran-2-yl-1H-indazole-5-carbonitrile (0.400 g, 1.25 mmol). The mixture was stirred at ambient temperature for 15.5 h and poured into aqueous 6 N hydrochloric acid (30 mL). After stirring at ambient temperature for 4 h, the mixture was extracted with ethyl acetate (3x). The aqueous fraction was added to aqueous 6 N NaOH (30 mL) and the pH adjusted to 11. The solution was extracted with ethyl acetate (3x) and the organic fractions were combined and dried over anhydrous sodium sulfate, filtered and evaporated. Purification by flash chromatography on silica gel pretreated with 2% triethylamine/hexanes followed by 0–20% ethyl acetate/hexanes, sonication of the product in ethyl acetate (3 mL), addition of hexanes (20 mL) and filtration gave the title compound (0.206 g, 51% yield). ES-MS (m/z) 321 [M+1]$^+$.

B. {3-[4-(5-(1H-1,2,3,4-Tetrazo-5-yl)(1H-indazol-3-yl))phenoxy]propyl}dimethylamine 3-{4-[3-(Dimethylamino)propoxy]phenyl}-1H-indazole-5-carbonitrile (0.206 g, 0.643 mmol) and tri-n-butyltin azide (0.967 mL, 3.53 mmol) were refluxed for 19 h in toluene (6.77 mL) saturated with anhydrous hydrochloric acid. The mixture was concentrated, then dioxane (6.5 mL) and aqueous 6 N hydrochloric acid (6.5 mL) were added. The mixture was stirred at ambient temperature for 4 h and then added to concentrated ammonium hydroxide (30 mL). Extraction with hexanes (3x) followed by extraction with ether (3x) gave a crude solid which was filtered. Methanol was added to the filtrate and the solid product collected. This step was repeated. The remaining filtrate was taken up in dimethyl sulfoxide/methanol and the resulting solid collected. The combined solids were purified by preparative HPLC (30–80% water/acetonitrile) and gave the title compound (0.154 g, 69% yield) as the trifluoroacetic acid salt. $^1$H NMR (CD$_3$OD) δ 8.77 (m, 1H), 8.09 (dd, 1H), 8.00 (m, 2H), 7.77 (dd, 1H), 7.17 (m, 2H), 4.20 (t, 2H), 3.39 (t, 2H), 2.95 (s, 6H), 2.25 (m, 2H). ES-MS (m/z) 364 [M+1]$^+$.

Example 237

SYNTHESIS OF {3-[3-(5-(1H-1,2,3,4-TETRAZOL-5-YL)(1H-INDAZOL-3-YL))PHENOXY]PROPYL}DIMETHYLAMINE

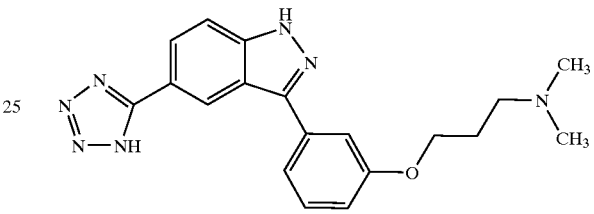

A. 3-(3-hydroxyphenyl)-1-perhydro-2H-pyran-2-yl-1H-indazole-5-carbonitrile

To a stirred solution of 3-bromo-1-perhydro-2H-pyran-2-yl-1H-indazole-5-carbonitrile (1.47 g, 4.82 mmol) in dimethoxyethane (24.0 mL) was added 3-hydroxyphenylboronic acid (1.60 g, 7.27 mmol), dichloro[1,1'-bis(diphenylphosphino) ferrocene]palladium (0.396 g, 0.485 mmol), and potassium phosphate (5.12 g, 24.1 mmol) and the mixture was heated at reflux for 48 h. The mixture was diluted with dichloromethane. The organic extracts were washed with saturated sodium bicarbonate, dried over anhydrous sodium sulfate, filtered and evaporated. Purification of the residue by column chromatography with 20–50% ethyl acetate/hexanes furnished the product (1.31 g, 85% yield). ES-MS (m/z) 320 [M+1]$^+$.

B. 3-{3-[3-(dimethylamino)propoxy]phenyl}-1H-indazole-5-carbonitrile

Triphenylphosphine (1.31 g, 5.00 mmol), tetrahydrofuran (4.00 mL), 3-N,N-dimethylaminopropanol (0.592 mL, 5.00 mmol) and diethylazodicarboxylate (0.788 mL, 5.00 mmol) were added to 3-(3-hydroxyphenyl)-1-perhydro-2H-pyran-2-yl-1H-indazole-5-carbonitrile 3-(3-hydroxyphenyl)-1-perhydro-2H-pyran-2-yl-1H-indazole-5-carbonitrile (0.400 g, 1.25 mmol). The mixture was stirred at ambient temperature for 15.5 h and poured into aqueous 6 N hydrochloric acid (30 mL). After stirring at ambient temperature for 4 h, the mixture was extracted with ethyl acetate (3x). The aqueous fraction was added to aqueous 6 N sodium hydroxide (30 mL) and the pH adjusted to 11. The solution was extracted with ethyl acetate (3x) and the organic fractions were combined and dried over anhydrous sodium sulfate, filtered and evaporated. Purification by flash chromatography on silica gel pretreated with 2% triethylamine/hexanes followed by 0–20% ethyl acetate/hexanes elution, sonication of the product in ethyl acetate (3 mL), addition of hexanes (20 mL) and filtration gave the title compound (0.225 g, 56% yield). ES-MS (m/z) 321 [M+1]$^+$.

C. {3-[3-(5-(1H-1,2,3,4-Tetrazo-5-yl)(1H-indazol-3-yl))phenoxy]propyl}dimethyl amine 3-{3-[3-(Dimethylamino)propoxy]phenyl}-1H-indazole-5-carbonitrile (0.225 g, 0.702 mmol) and tri-n-butyltin azide (1.06 mL, 3.87 mmol) were heated to reflux temperature for 19 h in toluene (7.42 mL) saturated with anhydrous hydrochloric acid. The mixture was concentrated then dioxane (6.5 mL) and aqueous 6 N hydrochloric acid (6.5 mL) were added. The mixture was stirred at ambient temperature for 4 h and poured into concentrated ammonium hydroxide (30 mL). Extraction with hexanes (3×) followed by extraction with ether (3×) gave a crude solid which was filtered. The filtrate was taken up in methanol and solid product collected. This step was repeated. The remaining filtrate was taken up in dimethyl sulfoxide/methanol and the resulting solid collected. The combined solids were purified by preparative HPLC (30–80% water/acetonitrile) and gave the title compound (0.170 g, 67% yield) as the trifluoroacetic acid salt. $^1$H NMR (CD$_3$OD) δ 8.76 (m, 1H), 8.06 (dd, 1H), 7.76 (dd, 1H), 7.63 (dt, 1H), 7.58 (m,1H), 7.50 (m, 1H), 7.06 (m, -H), 4.25 (t, 2H), 3.41 (m, 2H), 3.00 (s, 6H), 2.30 (m,2H). ES-MS (m/z) 364 [M+1]$^+$.

Example 238

SYNTHESIS OF {3-[3-(5-(1H-1,2,4-TRIAZOL-5-YL)(1H-INDAZOL-3-YL))PHENOXY]PROPYL}DIMETHYLAMINE

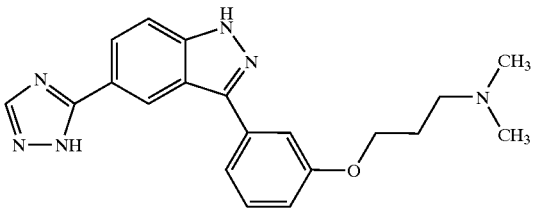

A. 3-{1-Perhydro-2H-pyran-2-yl-5-[1-(triphenylmethyl)(1,2,4-triazol-3-yl)]-1H-indazol-3-yl}phenol To a stirred solution of 2-{3-bromo-5-[1-(triphenylmethyl)(1,2,4-triazol-3-yl)]-1H-indazoyl}perhydro-2H-pyran (3.22 g, 5.46 mmol) in dimethoxyethane (27.1 mL) was added 3-hydroxy phenylboronic acid (1.81 g, 8.22 mmol), dichloro[1,1'-bis(diphenylphosphino) ferrocene]palladium (0.447 g, 0.485 mmol), and potassium phosphate (5.78 g, 27.2 mmol) and the mixture was heated at reflux for 48 h. The mixture was diluted with dichloromethane. The organic extracts were washed with saturated sodium bicarbonate, dried over anhydrous sodium sulfate, filtered and evaporated. Purification of the residue by column chromatography with 20–50% ethyl acetate/hexanes furnished the product (3.16 g, 96% yield). ES-MS (m/z) 362 [M+1(-Tr)]$^+$.

B. {3-[3-(5-(1H-1,2,4-triazol-5-yl)(1H-indazol-3-yl))phenoxy]propyl}dimethylamine Triphenylphosphine (0.694 g, 2.65 mmol), tetrahydrofuran (2.12 mL), 3-N,N-dimethylaminopropanol (0.314 mL, 2.65 mmol) and diethylazodicarboxylate (0.418 mL, 2.65 mmol) were added to 3-{1-perhydro-2H-pyran-2-yl-5-[1-(triphenylmethyl)(1,2,4-triazol-3-yl)]-1H-indazol-3-yl}phenol (0.400 g, 0.662 mmol). The mixture was stirred at ambient temperature for 23 h and poured into aqueous 6 N hydrochloric acid (30 mL). After stirring at ambient temperature for 4 h, the mixture was extracted with ether (3×). The aqueous fraction was added to aqueous 6N sodium hydroxide (30 mL) and the pH adjusted to 11. The solution was extracted with ethyl acetate (3×) and the organic fractions were combined and dried over anhydrous sodium sulfate, filtered and evaporated. The residue was purified by flash chromatography on silica pretreated with 2% triethylamine/hexanes followed by 0–20% ethyl acetate/hexanes elution and gave the title compound (0.0681 g, 28% yield). $^1$H NMR (CD$_3$OD) δ 8.72 (m, 1H), 8.35 (s, 1H), 8.10 (dd, 1H), 7.68 (dd, 1H), 7.60 (dt, 1H), 7.54 (m, 1H), 7.46 (t, 1H), 7.02 (m, 1H), 4.18 (t, 2H), 2.63 (m, 2H), 2.33 (s, 6H), 2.07 (m, 2H). ES-MS (m/z) 363 [M+1]$^+$.

Example 239

SYNTHESIS OF {2-[3-(5-(1H-1,2,4-TRIAZOL-5-YL)(1H-INDAZOL-3-YL))PHENOXY]ETHYL}DIMETHYLAMINE

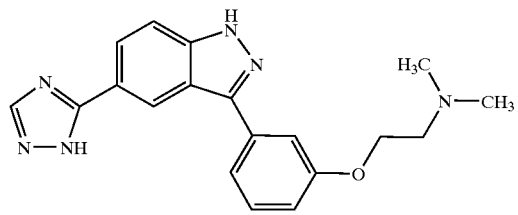

A. 3-{1-Perhydro-2H-pyran-2-yl-5-[1-(triphenylmethyl)(1,2,4-triazol-3-yl)]-1H-indazol-3-yl}phenol To a stirred solution of 2-{3-bromo-5-[1-(triphenylmethyl)(1,2,4-triazol-3-yl)]-1H-indazoyl}perhydro-2H-pyran (3.22 g, 5.46 mmol) in dimethoxyethane (27.1 mL) was added 3-hydroxy phenylboronic acid (1.81 g, 8.22 mmol), dichloro[1,1'-bis(diphenylphosphino) ferrocene]palladium (0.447 g, 0.485 mmol), and potassium phosphate (5.78 g, 27.2 mmol) and the mixture was heated at reflux for 48 h. The mixture was diluted with dichloromethane. The organic extracts were washed with saturated sodium bicarbonate, dried over anhydrous sodium sulfate, filtered and evaporated. Purification of the residue by column chromatography with 20–50% ethyl acetate/hexanes furnished the product (3.16 g, 96% yield). ES-MS (m/z) 362 [M+1(-Tr)]$^+$.

B. {2-[3-(5-(1H-1,2,4-Triazol-5-yl)(1H-indazol-3-yl))phenoxy]ethyl}dimethylamine Triphenylphosphine (0.694 g, 2.65 mmol), tetrahydrofuran (2.12 mL), 2-N,N-dimethylaminoethanol (0.266 mL, 2.65 mmol) and diethylazodicarboxylate (0.418 mL, 2.65 mmol) were added to 3-{1-perhydro-2H-pyran-2-yl-5-[1-(triphenylmethyl)(1,2,4-triazol-3-yl)]-1H-indazol-3-yl}phenol (0.400 g, 0.662 mmol). The mixture was stirred at ambient temperature for 23 h and poured into aqueous 6 N hydrochloric acid (30 mL). After stirring at ambient temperature for 4 h, the mixture was extracted with ether (3×). The aqueous fraction was added to aqueous 6 N sodium hydroxide (30 mL) and the pH adjusted to 11. The solution was extracted with ethyl acetate (3×) and the organic fractions were combined and dried over anhydrous sodium sulfate, filtered and evaporated. The residue was purified by flash chromatography on silica pretreated with 2% triethylamine/hexanes followed by 0–20% ethyl acetate/hexanes elution and gave the title compound (0.0878 g, 38% yield). $^1$H NMR (CD$_3$OD) δ 8.73 (m, 1H), 8.35 (br s, 1H), 8.10 (dd, 1H), 7.68 (dd, 1H), 7.63 (dt, 1H), 7.58 (m, 1H), 7.48 (t, 1H), 7.60 (m, 1H), 4.25 (t, 2H), 2.75 (t, 2H), 2.40 (s, 6H). ES-MS (m/z) 349 [M+1]$^+$.

Example 240

SYNTHESIS OF 1-(5-(1H-1,2,4-TRIAZOL-5-YL)(1H-INDAZOL-3-YL))-3-(2-MORPHOLIN-4-YL-ETHOXY)BENZENE

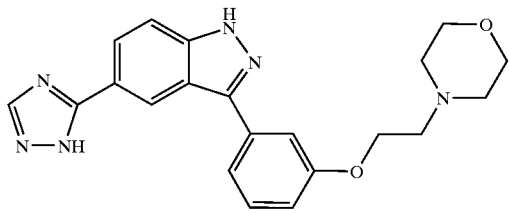

A. 3-{1-perhydro-2H-pyran-2-yl-5-[1-(triphenylmethyl)(1,2,4-triazol-3-yl)]-1H-indazol-3-yl}phenol To a stirred solution of 2-{3-bromo-5-[1-(triphenylmethyl)(1,2,4-triazol-3-yl)]-1H-indazoyl}perhydro-2H-pyran (3.22 g, 5.46 mmol) in dimethoxyethane (27.1 mL) was added 3-hydroxyphenylboronic acid (1.81 g, 8.22 mmol), dichloro [1,1'-bis(diphenylphosphino) ferrocene]palladium (0.447 g, 0.485 mmol), and potassium phosphate (5.78 g, 27.2 mmol) and the mixture was heated at reflux for 48 h. The mixture was diluted with dichloromethane. The organic extracts were washed with saturated sodium bicarbonate, dried over anhydrous sodium sulfate, filtered and evaporated. Purification of the residue by column chromatography with 20–50% ethyl acetate/hexanes furnished the product (3.16 g, 96% yield). ES-MS (m/z) 362 [M+1(–Tr)]⁺.

B. 1-(5-(1H-1,2,4-triazol-5-yl)(1H-indazol-3-yl))-3-(2-Morpholin-4-ylethoxy)benzene Triphenylphosphine (0.694 g, 2.65 mmol), tetrahydrofuran (2.12 mL), 2-morpholinoethanol (0.321 mL, 2.65 mmol) and diethylazodicarboxylate (0.418 mL, 2.65 mmol) were added to 3-{1-perhydro-2H-pyran-2-yl-5-[1-(triphenylmethyl)(1,2,4-triazol-3-yl)]-1H-indazol-3-yl}phenol (0.400 g, 0.662 mmol). The mixture was stirred at ambient temperature for 23 h and poured into aqueous 6 N hydrochloric acid (30 mL). After stirring at ambient temperature for 4 h, the mixture was extracted with ether (3×). The aqueous fraction was added to aqueous 6 N sodium hydroxide (30 mL) and the pH adjusted to 11. The solution was extracted with ethyl acetate (3×) and the organic fractions were combined and dried over anhydrous sodium sulfate, filtered and evaporated. The residue was purified by flash chromatography on silica gel pretreated with 2% triethylamine/hexanes followed by 0–20% ethyl acetate/hexanes and gave the title compound (0.0774 g, 30% yield). ¹H NMR (CD₃OD) δ 8.72 (m, 1H), 8.36 (br s, 1H), 8.10 (dd, 1H), 7.68 (d, 1H), 7.62 (dt, 1H), 7.56 (t, 1H), 7.46 (t, 1H), 7.04 (m, 1H), 4.28 (t, 2H), 3.72 (t, 4H), 2.89 (t, 2H), 2.65 (t, 4H). ES-MS (m/z) 391 [M+1]⁺.

Example 241

SYNTHESIS OF {2-[3-(5-(1H-1,2,3,4-TETRAZOL-5-YL)(1H-INDAZOL-3-YL))PHENOXY]ETHYL}DIMETYLAMINE

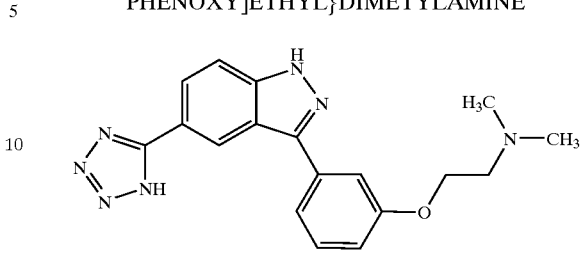

A. 3-(3-Hydroxyphenyl)-1-perhydro-2H-pyran-2-yl-1H-indazole-5-carbonitrile

To a stirred solution of 3-bromo-1-perhydro-2H-pyran-2-yl-1H-indazole-5-carbonitrile (1.47 g, 4.82 mmol) in dimethoxyethane (24.0 mL) was added 3-hydroxyphenylboronic acid (1.60 g, 7.27 mmol), dichloro [1,1'-bis(diphenylphosphino) ferrocene]palladium (0.396 g, 0.485 mmol), and potassium phosphate (5.12 g, 24.1 mmol) and the mixture was heated at reflux for 48 h. The mixture was diluted with dichloromethane. The organic extracts were washed with saturated sodium bicarbonate, dried over anhydrous sodium sulfate, filtered and evaporated. Purification of the residue by column chromatography with 20–50% ethyl acetate/hexanes furnished the product (1.31 g, 85% yield). ES-MS (m/z) 320 [M+1]⁺.

B. 3-{4-[2-(Dimethylamino)ethoxy]phenyl}-1H-indazole-5-carbonitrile

Triphenylphosphine (1.31 g, 5.00 mmol), tetrahydrofuran (4.00 mL), 2-N,N-dimethylaminoethanol (0.503 mL, 5.00 mmol) and diethylazodicarboxylate (0.788 mL, 5.00 mmol) were added to 3-(3-hydroxyphenyl)-1-perhydro-2H-pyran-2-yl-1H-indazole-5-carbonitrile (0.400 g, 1.25 mmol). The mixture was stirred at ambient temperature for 15.5 h and poured into aqueous 6 N hydrochloric acid (30 mL). After stirring at ambient temperature for 4 h, the mixture was extracted with ethyl acetate (3×). The aqueous fraction was added to aqueous 6 N sodium hydroxide (30 mL) and the pH adjusted to 11. The solution was extracted with ethyl acetate (3×) and the organic fractions were combined and dried over anhydrous sodium sulfate, filtered and evaporated. Purification by flash chromatography on silica pretreated with 2% triethylamine/hexanes followed by 0–20% ethyl acetate/hexanes, sonication of the product in ethyl acetate (3 mL), addition of hexanes (20 mL) and filtration gave the title compound (0.177 g, 41% yield). ES-MS (m/z) 307 [M+1]⁺.

C. Synthesis of {2-[3-(5-(1H-1,2,3,4-tetrazo-5-yl)(1H-indazol-3-yl))phenoxy]ethyl}dimethylamine 3-{4-[2-(Dimethylamino)ethoxy]phenyl}-1H-indazole-5-carbonitrile (0.177 g, 0.578 mmol) and tri-n-butyltin azide (0.869 mL, 3.17 mmol) were refluxed for 17 h in toluene (6.08 mL) saturated with anhydrous hydrochloric acid. The mixture was concentrated then dioxane (6.5 mL) and aqueous 6 N hydrochloric acid (6.5 mL) were added. The mixture was stirred at ambient temperature for 4 h and then added to concentrated ammonium hydroxide (30 mL). Extraction with hexanes (3×) followed by extraction with ether (2×) gave a crude solid which was filtered. Methanol was added to the filtrate and solid product collected. This step was repeated. The remaining filtrate was taken up in dimethyl sulfoxide/methanol and the resulting solid collected. The combined solids were purified by preparative HPLC (30–80% water/acetonitrile) and gave the title compound (0.0376 g, 19% yield) as the mono trifluoroacetic acid salt. $^1$H NMR (CD$_3$OD) δ 8.80 (m, 1H), 8.60 (dd, 1H), 7.78 (dd, 1H), 7.72 (dd, 1H), 7.65 (m, 1H), 7.55 (m, 1H), 7.15 (m, 1H), 4.49 (t, 2H), 3.66 (t, 2H), 3.03 (s, 6H). ES-MS (m/z) 350 [M+1]$^+$.

Example 242

SYNTHESIS OF 1-(5-(1H-1,2,4-TRIAZOL-5-YL)(1H-INDAZOL-3-YL))-3-(2-PYRROLIDINYLETHOXY)BENZENE

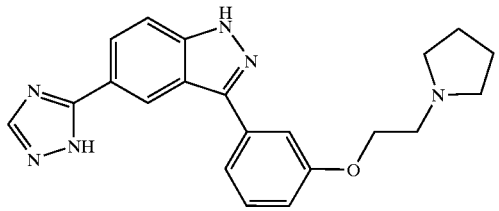

A. 3-[1-Perhydro-2H-pyran-2-yl-5-[1-(triphenylmethyl)(1,2,4-triazol-3-yl)]-1H-indazol-3-yl}phenol To a stirred solution of 2-{3-bromo-5-[1-(triphenylmethyl)(1,2,4-triazol-3-yl)]-1H-indazoyl}perhydro-2H-pyran (3.22 g, 5.46 mmol) in dimethoxyethane (27.1 mL) was added 3-hydroxy phenylboronic acid (1.81 g, 8.22 mmol), dichloro[1,1'-bis(diphenylphosphino) ferrocene]palladium (0.447 g, 0.485 mmol), and potassium phosphate (5.78 g, 27.2 mmol) and the mixture was heated at reflux for 48 h. The mixture was diluted with dichloromethane. The organic extracts were washed with saturated sodium bicarbonate, dried over anhydrous sodium sulfate, filtered and evaporated. Purification of the residue by column chromatography with 20–50% ethyl acetate/hexanes furnished the product (3.16 g, 96% yield). ES-MS (m/z) 362 [M+1(-Tr)]$^+$.

B. 1-(5-(1H-1,2,4-Triazol-5-yl)(1H-indazol-3-yl))-3-(2-pyrrolidinylethoxy)benzene Triphenylphosphine (0.694 g, 2.65 mmol), tetrahydrofuran (2.12 mL), pyrrolidinylethanol (0.310 mL, 2.65 mmol) and diethylazodicarboxylate (0.418 mL, 2.65 mmol) were added to 3-{1-perhydro-2H-pyran-2-yl-5-[1-(triphenylmethyl)(1,2,4-triazol-3-yl)]-1H-indazol-3-yl}phenol (0.400 g, 0.662 mmol). The mixture was stirred at ambient temperature for 23 h and poured into aqueous 6 N hydrochloric acid (30 mL). After stirring at ambient temperature for 4 h, the mixture was extracted with ether (3×). The aqueous fraction was added to aqueous 6 N sodium hydroxide (30 mL) and the pH adjusted to 11. The solution was extracted with ethyl acetate (3×) and the organic fractions were combined and dried over anhydrous sodium sulfate, filtered and evaporated. The residue was purified by flash chromatography on silica pretreated with 2% triethylamine/ethyl acetate followed by 0–20% methanol/ethyl acetate. The desired fractions were concentrated, dissolved in ethyl acetate, washed with aqueous sodium bicarbonate, dried over anhydrous sodium sulfate, filtered and evaporated which gave the title compound (0.114 g, 46% yield). $^1$H NMR (CD$_3$OD) δ 8.72 (s, 1H), 8.34 (s, 1H), 8.09 (dd, 1H), 7.67 (d, 1H), 7.62 (d, 1H), 7.57 (m, 1H), 7.47 (t, 1H), 7.04 (m, 1H), 4.26 (t, 2H), 3.02 (t, 2H), 2.73 (m, 4H), 1.87 (m, 4H). ES-MS (m/z) 375 [M+1]$^+$.

Example 243

SYNTHESIS OF 1-(5-(1H-1,2,4-TRIAZOL-5-YL)(1H-INDAZOL-3-YL))-3-(2-PIPERIDYLETHOXY)BENZENE

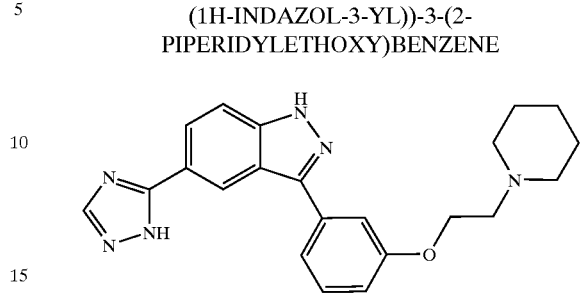

A. 3-{1-Perhydro-2H-pyran-2-yl-5-[1-(triphenylmethyl)(1,2,4-triazol-3-yl)]-1H-indazol-3-yl}phenol To a stirred solution of 2-{3-bromo-5-[1-(triphenylmethyl)(1,2,4-triazol-3-yl)]-1H-indazoyl}perhydro-2H-pyran (3.22 g, 5.46 mmol) in dimethoxyethane (27.1 mL) was added 3-hydroxy phenylboronic acid (1.81 g, 8.22 mmol), dichloro[1,1'-bis(diphenylphosphino) ferrocene]palladium (0.447 g, 0.485 mmol), and potassium phosphate (5.78 g, 27.2 mmol) and the mixture was heated at reflux for 48 h. The mixture was diluted with dichloromethane. The organic extracts were washed with saturated sodium bicarbonate, dried over anhydrous sodium sulfate, filtered and evaporated. Purification of the residue by column chromatography with 20–50% ethyl acetate/hexanes furnished the product (3.16 g, 96%, yield). ES-MS (m/z) 362 [M+1(-Tr)]$^+$.

B. 1-(5-(1H-1,2,4-triazol-5-yl)(1H-indazol-3-yl))-3-(2-piperidylethoxy)benzene

Triphenylphosphine (0.694 g, 2.65 mmol), tetrahydrofuran (2.12 mL), 2-piperidylethanol (0.352 mL, 2.65 mmol) and diethylazodicarboxylate (0.418 mL, 2.65 mmol) were added to 3-{1-perhydro-2H-pyran-2-yl-5-[1-(triphenylmethyl)(1,2,4-triazol-3-yl)]-1H-indazol-3-yl}phenol (0.400 g, 0.662 mmol). The mixture was stirred at ambient temperature for 23 h and poured into aqueous 6 N hydrochloric acid (30 mL). After stirring at ambient temperature for 4 h, the mixture was extracted with ether (3×). The aqueous fraction was added to aqueous 6 N sodium hydroxide (30 mL) and the pH adjusted to 11. The solution was extracted with ethyl acetate (3×) and the organic fractions were combined and dried over anhydrous sodium sulfate, filtered and evaporated. The residue was purified by flash chromatography on silica pretreated with 2% triethylamine/ethyl acetate elution followed by 0–20% methanol/ethyl acetate. The desired fractions were concentrated, dissolved in ethyl acetate, washed with aqueous sodium bicarbonate, dried over anhydrous sodium sulfate, filtered and evaporated which gave the title compound (0.124 g, 48% yield). $^1$H NMR (CD$_3$OD) δ 8.72 (m, 1H), 8.34 (s, 1H), 8.10 (dd, 1H), 7.67 (dd, 1H), 7.62 (dt, 1H), 7.58 (m, 1H), 7.47 (t, 1H), 7.04 (m, 1H), 4.27 (t, 2H), 2.89 (t, 2H), 2.63 (m, 4H), 1.68 (m, 4H), 1.51 (m, 2H). ES-MS (m/z) 389 [M+1]$^+$.

Example 244

SYNTHESIS OF 1-{2-[3-(5-(1H-1,2,4-TRIAZOL-5-YL)-1H-INDAZOL-3-YL)PHENOXY]ETHYL}PYRROLIDIN-2-ONE

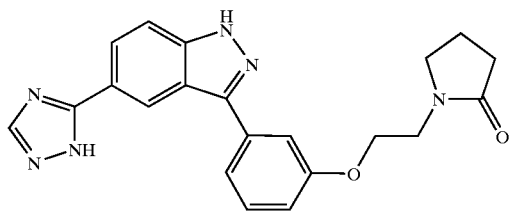

A. 3-{1-Perhydro-2H-pyran-2-yl-5-[1-(triphenylmethyl)(1,2,4-triazol-3-yl)]-1H-indazol-3-yl}phenol To a stirred solution of 2-{3-bromo-5-[1-(triphenylmethyl)(1,2,4-triazol-3-yl)]-1H-indazoyl}perhydro-2H-pyran (3.22 g, 5.46 mmol) in dimethoxyethane (27.1 mL) was added 3-hydroxy phenylboronic acid (1.81 g, 8.22 mmol), dichloro[1,1'-bis(diphenylphosphino) ferrocene]palladium (0.447 g, 0.485 mmol), and potassium phosphate (5.78 g, 27.2 mmol) and the mixture was heated at reflux for 48 h. The mixture was diluted with dichloromethane. The organic extracts were washed with saturated sodium bicarbonate, dried over anhydrous sodium sulfate, filtered and evaporated. Purification of the residue by column chromatography with 20–50% ethyl acetate/hexanes furnished the product (3.16 g, 96%, yield). ES-MS (m/z) 362 [M+1(−Tr)]+.

B. 1-{2-[3-(5-(1H-1,2,4-triazol-5-yl)-1H-indazol-3-yl)phenoxy]ethyl}pyrrolidin-2-one Triphenylphosphine (0.694 g, 2.65 mmol), tetrahydrofuran (2.12 mL), 1-(2-hydroxyethyl)pyrrolidin-2-one (0.299 mL, 2.65 mmol) and diethylazodicarboxylate (0.418 mL, 2.65 mmol) were added to 3-{1-perhydro-2H-pyran-2-yl-5-[1-(triphenylmethyl)(1,2,4-triazol-3-yl)]-1H-indazol-3-yl}phenol (0.400 g, 0.662 mmol). The mixture was stirred at ambient temperature for 23 h and poured into aqueous 6N hydrochloric acid (25 mL). After stirring at ambient temperature for 4 h, the mixture was extracted with ether (3x). The aqueous fraction was added to aqueous 6N sodium hydroxide (25 mL) and the pH adjusted to 11. The solution was extracted with ethyl acetate (3x) and the organic fractions were combined and dried over anhydrous sodium sulfate, filtered and evaporated. The residue was purified by flash chromatography on silica pretreated with 2% triethylamine/ethyl acetate followed by 0–15% methanol/ethyl acetate. The desired fractions were concentrated, dissolved in ethyl acetate, washed with aqueous sodium bicarbonate, dried over anhydrous sodium sulfate, filtered and evaporated to give the title compound (0.0768 g, 30% yield). $^1$H NMR (CD$_3$OD) δ 13.41 (br s, 1H), 8.65 (s, 1H), 8.10 (d, 1H), 7.70 (d, 1H), 7.60 (d, 1H), 7.50 (m, 2H), 7.05 (m, 1H), 4.20 (t, 2H), 3.60 (t, 2H), 3.50 (t, 2H), 2.25 (t, 2H), 1.95 (m, 2H). ES-MS (m/z) 389 [M+1]+.

Example 245

SYNTHESIS OF 1-(5-(1H-1,2,4-TRIAZOL-5-YL)(1H-INDAZOL-3-YL))-3-(2-PIPERAZINYLETHOXY)BENZENE

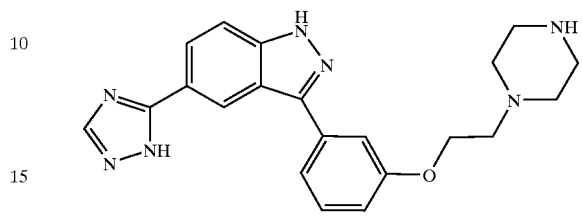

A. 3-{1-Perhydro-2H-pyran-2-yl-5-[1-(triphenylmethyl)(1,2,4-triazol-3-yl]-1H-indazol-3-yl}phenol To a stirred solution of 2-{3-bromo-5-[1-(triphenylmethyl)(1,2,4-triazol-3-yl)]-1H-indazoyl}perhydro-2H-pyran (3.22 g, 5.46 mmol) in dimethoxyethane (27.1 mL) was added 3-hydroxy phenylboronic acid (1.81 g, 8.22 mmol), dichloro[1,1'-bis(diphenylphosphino) ferrocene]palladium (0.447 g, 0.485 mmol), and potassium phosphate (5.78 g, 27.2 mmol) and the mixture was heated at reflux for 48 h. The mixture was diluted with dichloromethane. The organic extracts were washed with saturated sodium bicarbonate, dried over anhydrous sodium sulfate, filtered and evaporated. Purification of the residue by column chromatography with 20–50% ethyl acetate/hexanes furnished the product (3.16 g, 96%, yield). ES-MS (m/z) 362 [M+1(−Tr)]+.

B. 1-(5-(1H-1,2,4-Triazol-5-yl)(1H-indazol-3-yl))-3-(2-piperazinylethoxy)benzene Triphenylphosphine (0.694 g, 2.65 mmol), tetrahydrofuran (2.12 mL), 2-(tert-butyloxycarbonyl)piperazinylethanol (0.610 g, 2.65 mmol) and diethylazodicarboxylate (0.418 mL, 2.65 mmol) were added to 3-{1-perhydro-2H-pyran-2-yl-5-[1-(triphenylmethyl)(1,2,4-triazol-3-yl)]-1H-indazol-3-yl}phenol (0.400 g, 0.662 mmol). The mixture was stirred at ambient temperature for 23 h and poured into aqueous 6N hydrochloric acid (25 mL). After stirring at ambient temperature for 4 h, the mixture was extracted with ether (3x). The aqueous fraction was added to aqueous 6 N sodium hydroxide (25 mL) and the pH adjusted to 11. The solution was extracted with ethyl acetate (3x) and the organic fractions were combined and dried over anhydrous sodium sulfate, filtered and evaporated. The residue was purified by preparative HPLC (5–70% acetonitrile/water). The desired fractions were concentrated, dissolved in ethyl acetate, washed with aqueous sodium bicarbonate, dried over anhydrous sodium sulfate, filtered and evaporated to give the title compound (0.132 g, 52% yield) as the bis-trifluoroacetic acid salt. $^1$H NMR (D$_2$O) δ 8.26 (s, 1H), 8.12 (s, 1H), 7.61 (d, 1H), 7.37 (d, 1H), 7.31 (m, 2H), 7.19 (m, 1H), 6.90 (m, 1H), 4.35 (m, 2H), 3.62 (m, 6H), 3.52 (m, 4H). ES-MS (m/z) 390 [M+1]+.

Example 246

SYNTHESIS OF 1-(5-(1H-1,2,4-TRIAZOL-5-YL) (1H-INDAZOL-3-YL))-3-(3-PIPERDYLPROPOXY)BENZENE

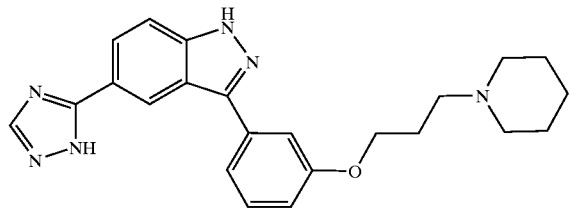

A. 3-{1-perhydro-2H-pyran-2-yl-5-[1-(triphenylmethyl)(1,2,4-triazol-3-yl)]-1H-indazol-3-yl}phenol To a stirred solution of 2-{3-bromo-5-[1-(triphenylmethyl)(1,2,4-triazol-3-yl)]-1H-indazoyl}perhydro-2H-pyran (3.22 g, 5.46 mmol) in dimethoxyethane (27.1 mL) was added 3-hydroxyphenylboronic acid (1.81 g, 8.22 mmol), dichloro [1,1'-bis(diphenylphosphino) ferrocene]palladium (0.447 g, 0.485 mmol), and potassium phosphate (5.78 g, 27.2 mmol) and the mixture was heated at reflux for 48 h. The mixture was diluted with dichloromethane. The organic extracts were washed with saturated sodium bicarbonate, dried over anhydrous sodium sulfate, filtered and evaporated. Purification of the residue by column chromatography with 20–50% ethyl acetate/hexanes furnished the product (3.16 g, 96%, yield). ES-MS (m/z) 362 [M+1(−Tr)]+.

B. 1-(5-(1H-1,2,4-Triazol-5-yl)(1H-indazol-3-yl))-3-(3-piperidylpropoxy)benzene

Triphenylphosphine (0.694 g, 2.65 mmol), tetrahydrofuran (2.12 mL), 3-piperidylpropanol (0.379 mL, 2.65 mmol) and diethylazodicarboxylate (0.418 mL, 2.65 mmol) were added to 3-{1-perhydro-2H-pyran-2-yl-5-[1-(triphenylmethyl)(1,2,4-triazol-3-yl)]-1H-indazol-3-yl}phenol (0.400 g, 0.662 mmol). The mixture was stirred at ambient temperature for 24 h and poured into aqueous 6 N hydrochloric acid (25 mL). After stirring at ambient temperature for 4 h, the mixture was extracted with ether (3×). The aqueous fraction was added to aqueous 6 N sodium hydroxide (25 mL) and the pH adjusted to 11. The solution was extracted with ethyl acetate (3×) and the organic fractions were combined and dried over anhydrous sodium sulfate, filtered and evaporated. The residue was purified by flash chromatography on silica pretreated with 2% triethylamine/ethyl acetate followed by 0–20% methanol/ethyl acetate elution. The desired fractions were concentrated, dissolved in ethyl acetate, washed with aqueous sodium bicarbonate, dried over anhydrous sodium sulfate, filtered and evaporated to give the title compound (0.0847 g, 32% yield). 1H NMR (CD3OD) δ 8.71 (m, 1H), 8.34 (s, 1H), 8.10 (dd, 1H), 7.67 (dd, 1H), 7.60 (dt, 1H), 7.53 (m, 1H), 7.45 (t, 1H), 7.01 (m, 1H), 4.14 (t, 2H), 2.61 (m, 2H), 2.53 (s, 4H), 2.05 (m, 2H), 1.65 (m, 4H), 1.50 (m, 2H). ES-MS (m/z) 403 [M+1]+.

Example 247

SYNTHESIS OF 4-{2-[3-(5-(1H-1,2,4-TRIAZOL-5-YL)(1H-INDAZOL-3-YL))PHENOXY]ETHYL}-1-ACETYLPIPERAZINE

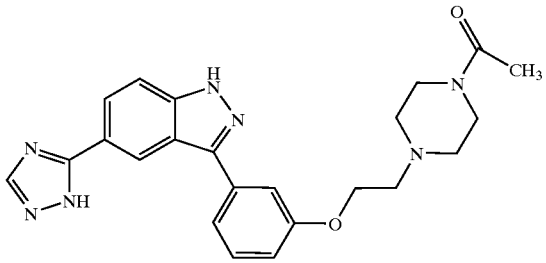

A. 3-{1-Perhydro-2H-pyran-2-yl-5-[1-(triphenylmethyl)(1,2,4-triazol-3-yl)]-1H-indazol-3-yl}phenol To a stirred solution of 2-{3-bromo-5-[1-(triphenylmethyl)(1,2,4-triazol-3-yl)]-1H-indazoyl}perhydro-2H-pyran (3.22 g, 5.46 mmol) in dimethoxyethane (27.1 mL) was added 3-hydroxyphenylboronic acid (1.81 g, 8.22 mmol), dichloro [1,1'-bis(diphenylphosphino) ferrocene]palladium (0.447 g, 0.485 mmol), and potassium phosphate (5.78 g, 27.2 mmol) and the mixture was heated at reflux for 48 h. The mixture was diluted with dichloromethane. The organic extracts were washed with saturated sodium bicarbonate, dried over anhydrous sodium sulfate, filtered and evaporated. Purification of the residue by column chromatography with 20–50% ethyl acetate/hexanes furnished the product (3.16 g, 96% yield). ES-MS (m/z) 362 [M+1(−Tr)]+.

B. 1-(5-(1H-1,2,4-Triazol-3-yl)(1H-indazol-3-yl))-3-(2-piperazinylethoxy)benzene Triphenylphosphine (0.694 g, 2.65 mmol), tetrahydrofuran (2.12 mL), tert-butylcarboxypiperazinylethanol (0.610 g, 2.65 mmol) and diethylazodicarboxylate (0.418 mL) were added to 3-{1-perhydro-2H-pyran-2-yl-5-[1-(triphenylmethyl)(1,2,4-triazol-3-yl)]-1H-indazol-3-yl}phenol (0.400 g, 1.25 mmol). The mixture was stirred at ambient temperature for 21h and poured into aqueous 6N hydrochloric acid (30 mL). After stirring at ambient temperature for 4h, the mixture was extracted with ethyl acetate (3×). The aqueous fraction was added to aqueous 6N sodium hydroxide (30 mL) and the pH adjusted to 11. The solution was extracted with ethyl acetate (3×) and the organic fractions were combined and dried over anhydrous sodium sulfate, filtered and evaporated. The residue was stirred with trifluoracetic acid (3.0 mL) at ambient temperature for 70 min. Purification by preparative HPLC (5–70% acetonitrile/water) gave the title compound (0.132 g, 27% yield). ES-MS (m/z) 390 [M+1]+.

C. 4-{2-[3-(5-(1H-1,2,4-Triazol-5-yl)(1H-indazol-3-yl))phenoxy]ethyl}-1-acetylpiperazine 1-(5-(1H-1,2,4-triazol-3-yl)(1H-indazol-3-yl))-3-(2-piperazinylethoxy)benzene (0.066 g, 0.169 mmol) was stirred with pyridine (0.50 mL, 6.18 mmol), triethylamine (0.10 mL, 0.717 mmol) and acetic anhydride (0.10 mL, 1.06 mmol) at ambient temperature. After 2 h, ammonium hydroxide (0.50 mL) was added and the mixture stirred for 1 h. The mixture was evaporated and gave the title compound (0.0064 g, 9% yield). 1H NMR (CD3OD) δ 8.71 (s, 1H), 8.35 (s, 1H), 8.08 (dd, 1H), 7.66 (d, 1H), 7.61 (dt, 1H), 7.55 (m, 1H), 7.44 (t, 1H), 7.01 (m, 1H), 4.25 (t, 2H), 3.58 (dt, 4H), 2.85 (t, 2H), 2.60 (dt, 4H), 2.08 (s, 3H). ES-MS (m/z) 432 [M+1]+.

Example 248

SYNTHESIS OF N-{2-[3-(5-(1H-1,2,4-TRIAZOL-5-YL)(1H-INDAZOL-3-YL))PHENOXY]ETHYL}(PHENYLMETHOXY)CARBOXAMIDE

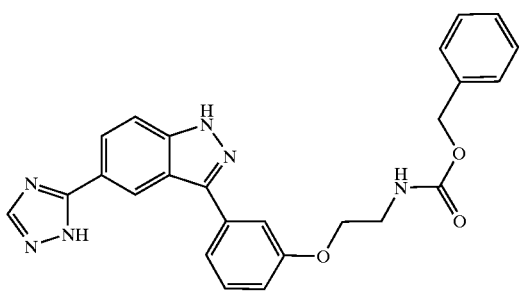

A. 3-{1-perhydro-2H-pyran-2-yl-5-[1-(triphenylmethyl)(1,2,4-triazol-3-yl)]-1H-indazol-3-yl}phenol To a stirred solution of 2-{3-bromo-5-[1-(triphenylmethyl)(1,2,4-triazol-3-yl)]-1H-indazoyl}perhydro-2H-pyran (3.22 g, 5.46 mmol) in dimethoxyethane (27.1 mL) was added 3-hydroxy phenylboronic acid (1.81 g, 8.22 mmol), dichloro[1,1'-bis(diphenylphosphino) ferrocene]palladium (0.447 g, 0.485 mmol), and potassium phosphate (5.78 g, 27.2 mmol) and the mixture was heated at reflux for 48 h. The mixture was diluted with dichloromethane. The organic extracts were washed with saturated sodium bicarbonate, dried over anhydrous sodium sulfate, filtered and evaporated. Purification of the residue by column chromatography with 20–50% ethyl acetate/hexanes furnished the product (3.16 g, 96%, yield). ES-MS (m/z) 362 [M+1(–Tr)]$^+$.

B. N-{2-[3-(5-(1H-1,2,4-triazol-5-yl)(1H-indazol-3-yl))phenoxy]ethyl}(phenylmethoxy)carboxamide Triphenylphosphine (0.694 g, 2.65 mmol), tetrahydrofuran (2.12 mL), N-(carbonylbenzyloxy)aminoethanol (0.517 g, 2.65 mmol) and diethylazodicarboxylate (0.418 mL, 2.65 mmol) were added to 3-{1-perhydro-2H-pyran-2-yl-5-[1-(triphenylmethyl)(1,2,4-triazol-3-yl)]-1H-indazol-3-yl}phenol (0.400 g, 0.662 mmol). The mixture was stirred at room temperature for 23 h and poured into aqueous 6 N hydrochloric acid (25 mL). After stirring at ambient temperature for 4 h, the mixture was extracted with ether (3x). The aqueous fraction was added to aqueous 6 N sodium hydroxide (25 mL) and the pH adjusted to 11. The solution was extracted with ethyl acetate (3x) and the organic fractions were combined and dried over anhydrous sodium sulfate, filtered and evaporated. The residue was purified by flash chromatography on silica pretreated with 2% triethylamine/ethyl acetate followed by 50–100% ethyl acetate/hexanes. The desired fractions were washed with aqueous sodium bicarbonate and extracted with ethyl acetate which gave the title compound (0.127 g, 42% yield) contaminated with triphenylphosphine oxide. The desired compound was further purified by preparative HPLC (30–80% acetonitrile/water). $^1$H NMR (CD$_3$OD) δ 8.71 (br s, 1H), 8.08 (br s, 1H), 7.67 (br s, 1H), 7.61 (d, 1H), 7.56 (s, 1H), 7.45 (t, 1H), 7.30 (m, 5H), 7.03 (m, 1H), 5.08 (s, 2H), 4.16 (t, 2H), 3.57 (t, 2H). ES-MS (m/z) 455 [M+1]$^+$.

Example 249

SYNTHESIS OF 2-[3-(5-(1H-1,2,4-TRIAZOL-5-YL)-1H-INDAZOL-3-YL)PHENOXY]ETHYLAMINE

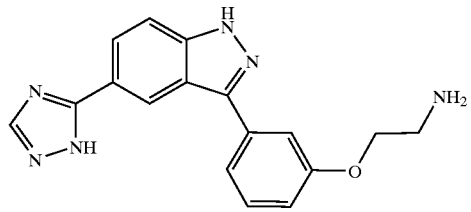

A. 2-[3-(5-(1H-1,2,4-Triazol-5-yl)-1H-indazol-3-yl)phenoxy]ethylamine

N-{2-[3-(5-(1H-1,2,4-triazol-5-yl)(1H-indazol-3-yl))phenoxy]ethyl}(phenylmethoxy)carboxamide (0.056 g, 0.123 mmol) was treated with formic acid (2 mL), methanol (0.088 mL) and 10% palladium on carbon (0.060 g) under nitrogen for 3 h. The mixture was filtered though Celite and concentrated. The residue was taken up in aqueous 6 N hydrochloric acid and extracted with ether (3x). The aqueous layer was adjusted to pH 11 and extracted with dichloromethane. The organic fractions were dried over anhydrous sodium sulfate, filtered and evaporated. The residue was purified by preparative HPLC (30–80% acetonitrile/water) and gave the title compound (0.0062 g, 16% yield) as the mono trifluoroacetic acid salt. $^1$H NMR (CD$_3$OD) δ 8.77 (d, 1H), 8.54 (s, 1H), 8.12 (dd, 1H), 7.73 (m, 1H), 7.70 (m, 1H), 7.65 (m, 1H), 7.54 (t, 1H), 7.13 (m, 1H), 4.38 (t, 2H), 3.44 (t, 2H). ES-MS (m/z) 321 [M+1]$^+$.

Example 250

SYNTHESIS OF 1-(5-(1H-1,2,4-TRIAZOL-5-YL)(1H-INDAZOL-3-YL))-3-(2-CYCLOHEXYLETHOXY)BENZENE

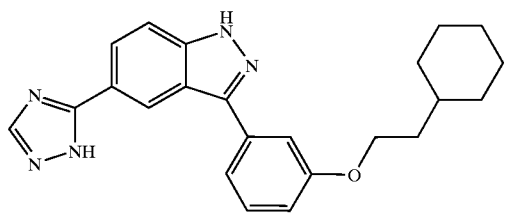

A. 3-{1-Perhydro-2H-pyran-2-yl-5-[1-(triphenylmethyl)(1,2,4-triazol-3-yl)]-1H-indazol-3-yl}phenol To a stirred solution of 2-{3-bromo-5-[1-(triphenylmethyl)(1,2,4-triazol-3-yl)]-1H-indazoyl}perhydro-2H-pyran (3.22 g, 5.46 mmol) in dimethoxyethane (27.1 mL) was added 3-hydroxyphenylboronic acid (1.81 g, 8.22 mmol), dichloro[1,1'-bis(diphenylphosphino) ferrocene]palladium (0.447 g, 0.485 mmol), and potassium phosphate (5.78 g, 27.2 mmol) and the mixture was heated at reflux for 48 h. The mixture was diluted with dichloromethane. The organic extracts were washed with saturated sodium bicarbonate, dried over anhydrous sodium sulfate, filtered and evaporated. Purification of the residue by column chromatography with 20–50% ethyl acetate/hexanes furnished the product (3.16 g, 96%, yield). ES-MS (m/z) 362 [M+1(–Tr)]$^+$.

B. 1-(5-(1H-1,2,4-Triazol-5-yl)(1H-indazol-3-yl))-3-(2-cyclohexylethoxy)benzene

Triphenylphosphine (0.951 g, 3.63 mmol), tetrahydrofuran (2.90 mL), 1-(cyclohexyl)ethanol (0.506 mL, 3.63 mmol) and diethylazodicarboxylate (0.573 mL, 3.63 mmol) were added to 3-{1-perhydro-2H-pyran-2-yl-5-[1-(triphenylmethyl)(1,2,4-triazol-3-yl)]-1H-indazol-3-yl}phenol (0.547 g, 0.906 mmol). The mixture was stirred at room temperature for 23 h and poured into aqueous 6 N hydrochloric acid (25 mL). After stirring at ambient temperature for 4 h, the mixture was extracted with ether (3×). The aqueous fraction was added to aqueous 6 N sodium hydroxide (25 mL) and the pH adjusted to 11. The solution was extracted with ethyl acetate (3×) and the organic fractions were combined and dried over anhydrous sodium sulfate, filtered and evaporated. The residue was purified by preparative HPLC (30–80% acetonitrile/water) and gave an oil. A small amount of this oil was purified by flash chromatography (50–100% ethyl acetate/hexanes). The desired fractions were washed with aqueous sodium bicarbonate and extracted with ethyl acetate which gave the title compound (18.4 mg, 52% yield) as a white foam. $^1$H NMR (CDCl$_3$) δ 8.71 (s, 1H), 8.20 (br s, 1H), 8.08 (br s, 1H), 7.65 (d, 1H), 7.59 (dt, 1H), 7.52 (m, 1H), 7.44 (t, 1H), 7.42 (s, 1H), 4.14 (t, 2H), 3.36 (m, 1H), 1.74 (m, 6H), 1.55 (m, 1H), 1.26 (m, 3H), 1.01 (m, 2H). ES-MS (m/z) 388 [M+1]$^+$.

Example 251

SYNTHESIS OF 1-(5-(1H-1,2,4-TRIAZOL-5-YL)(1H-INDAZOL-3-YL))-3-(2-AZAPERHYROEPINYLETHOXY)BENZENE

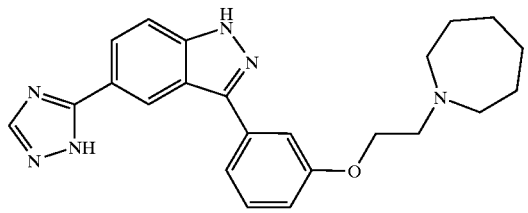

A. 3-{1-Perhydro-2H-pyran-2-yl-5-[1-(triphenylmethyl)(1,2,4-triazol-3-yl)]-1H-indazol-3-yl}phenol To a stirred solution of 2-{3-bromo-5-[1-(triphenylmethyl)(1,2,4-triazol-3-yl)]-1H-indazoyl}perhydro-2H-pyran (3.22 g, 5.46 mmol) in dimethoxyethane (27.1 mL) was added 3-hydroxy phenylboronic acid (1.81 g, 8.22 mmol), dichloro[1,1'-bis(diphenylphosphino)ferrocene]palladium (0.447 g, 0.485 mmol), and potassium phosphate (5.78 g, 27.2 mmol) and the mixture was heated at reflux for 48 h. The mixture was diluted with dichloromethane. The organic extracts were washed with saturated sodium bicarbonate, dried over anhydrous sodium sulfate, filtered and evaporated. Purification of the residue by column chromatography with 20–50% ethyl acetate/hexanes furnished the product (3.16 g, 96%, yield). ES-MS (m/z) 362 [M+1(-Tr)]$^+$.

B. 1-(5-(1H-1,2,4-Triazol-5-yl(1H-indazol-3-yl))-3-(2-azaperhydroepinyl ethoxy)benzene Triphenylphosphine (0.694 g, 2.65 mmol), tetrahydrofuran (2.12 mL), 2-azaperhydroepinylethanol (0.380 mL, 2.65 mmol) and diethylazodicarboxylate (0.418 mL, 2.65 mmol) were added to 3-{1-perhydro-2H-pyran-2-yl-5-[1-(triphenylmethyl)(1,2,4-triazol-3-yl)]-1H-indazol-3-yl}phenol (0.400 g, 0.662 mmol). The mixture was stirred at ambient temperature for 24 h and poured into aqueous 6 N hydrochloric acid (25 mL). After stirring at ambient temperature for 4 h, the mixture was extracted with ether (3×). The aqueous fraction was added to aqueous 6 N sodium hydroxide (25 mL) and the pH adjusted to 11. The solution was extracted with ethyl acetate (3×) and the organic fractions were combined and dried over anhydrous sodium sulfate, filtered and evaporated. The residue was purified by flash chromatography on silica pretreated with 2% triethylamine/ethyl acetate followed by 0–20% methanol/ethyl acetate. The desired fractions were washed with aqueous sodium bicarbonate, extracted with ethyl acetate and evaporated and gave the title compound (0.0948 g, 36% yield). $^1$H NMR (CD$_3$OD) δ 8.73 (m, 1H), 8.35 (s, 1H), 8.09 (dd, 1H), 7.68 (dd, 1H), 7.25 (dt, 1H), 7.57 (m, 1H), 7.48 (t, 1H), 7.04 (m, 1H), 4.26 (t, 2H), 3.07 (t, 2H), 2.91 (t, 4H), 1.70 (m, 8H). ES-MS (m/z) 403 [M+1]$^+$.

Example 252

SYNTHESIS OF N-[4-(5-(1H-1,2,4-TRIAZOL-5-YL)(1H-INDAZOL-3-YL))PHENYL]-2-FURYL CAROXAMIDE

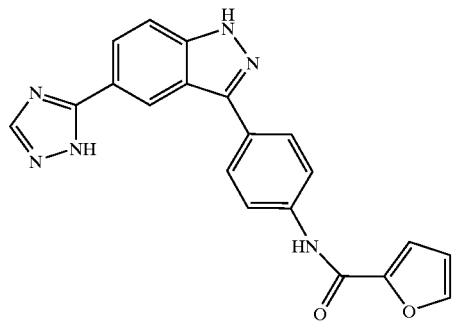

A. 4-{1-perhydro-2H-pyran-2-yl-5-[1-(triphenylmethyl)(1,2,4-triazol-3-yl)] 1H-indazol-3-yl}phenylamine To a stirred solution of 2-{3-bromo-5-[1-(triphenylmethyl)(1,2,4-triazol-3-y])]-1H-indazoyl}perhydro-2H-pyran) (3.22 g, 5.46 mmol) in dimethoxyethane (27.1 mL) was added 4-aminophenylboronic acid (1.80 g, 8.22 mmol), dichloro[1,1'-bis(diphenylphosphino) ferrocene]palladium (0.447 g, 0.485 mmol), and potassium phosphate (5.78 g, 27.2 mmol) and the mixture was heated at reflux for 48 h. The mixture was diluted with dichloromethane. The organic extracts were washed with saturated sodium bicarbonate, dried over anhydrous sodium sulfate, filtered and evaporated. Purification of the residue by column chromatography with 50–75% ethyl acetate/hexanes furnished the product (3.01 g, 91% yield). $^1$H NMR (DMSO-d$_6$) δ 8.54 (s, 1H), 8.20 (s, 1H), 8.00 (d, 1H), 7.79 (d, 1H), 7.62 (d, 2H), 7.42 (m, 10H), 7.18 (m, 7H), 6.73 (d, 2H), 5.85 (dd, 1H), 3.90 (m,1H), 3.76 (m, 1H), 2.50 (m, 2H), 2.05 (m, 2H), 1.60 (m, 2H).

B. N-[4-(5-(1H-1,2,4-Triazol-5-yl)(1H-indazol-3-yl))phenyl]-2-furyl carboxamide

To a solution of 4-{1-perhydro-2H-pyran-2-yl-5-[1-(triphenylmethyl)(1,2,4-triazol-3-yl)]1H-indazol-3-yl}phenylamine (0.300 g, 0.498 mmol) was added tetrahydrofuran (4.50 mL), triethylamine (0.345 mL, 2.48 mmol), and 2-furoyl chloride (0.058 mL, 0.735 mmol). The mixture was stirred for 16 h at ambient temperature and poured into saturated sodium bicarbonate (50 mL). The aqueous layer was extracted with ethyl acetate. The combined organic extracts were washed with saturated sodium bicarbonate, dried over anhydrous sodium sulfate, filtered and evaporated. Purification by preparative HPLC (30–80% acetonitrile/water) followed by washing with saturated sodium bicarbonate and extraction with ethyl acetate gave the title compound (0.0086 g, 5% yield). $^1$H NMR (DMSO-$d_6$) δ 8.75 (d, 1H), 8.10 (m, 6H), 7.74 (m, 1H), 7.39 (d, 1H), 6.75 (m, 1H). ES-MS (m/z) 371 [M+1]$^+$.

Example 253

SYNTHESIS OF [3-(5-(1H-1,2,4-TRIAZOL-5-YL)(1H-INDAZOL-3-YL))PHENYL]-N-BENZYL CAROXAMIDE

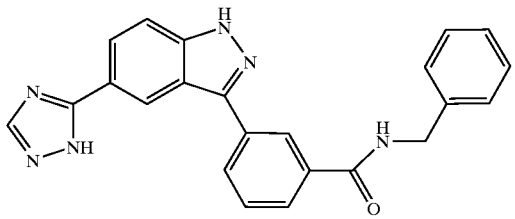

A. Methyl 3-{1-perhydro-2H-pyran-2-yl-5-[1-(triphenylmethyl)(1,2,4-triazol-3-yl)1-1H-indazol-3-yl}benzoate To a stirred solution of 2-{3-bromo-5-[1-(triphenylmethyl)(1,2,4-triazol-3-yl)]-1H-indazoyl}perhydro-2H-pyran (5.92 g, 10.04 mmol) in dimethoxyethane (49.9 mL) was added 3-(carboxymethyl)phenylboronic acid (2.72 g, 15.11 mmol), dichloro[1,1'-bis(diphenylphosphino) ferrocene]palladium (0.822 g, 1.01 mmol), and potassium phosphate (10.64 g, 50.1 mmol) and the mixture was heated at reflux for 60 h. The mixture was diluted with dichloromethane. The organic extracts were washed with saturated sodium bicarbonate, dried over anhydrous sodium sulfate, filtered and evaporated. Purification of the residue by column chromatography with 20–75% ethyl acetate/hexanes furnished the product (6.05 g, 94% yield). $^1$H NMR (CDCl$_3$) δ 8.70 (d, 2H), 8.20 (m, 2H), 8.07 (d, 1H), 7.95 (s, 1H), 7.65 (d, 1H), 7.58 (t, 1H), 7.33 (m, 10H), 7.22 (m, 7H), 5.78 (d, 1H), 3.82 (s, 3H).

B. (3-{1-Perhydro-2H-pyran-2-yl-5-[1-(triphenylmethyl)(1,2,4-triazol-3-yl)](1H-indazol-3-yl)phenyl)-N-benzylcarboxamide To a stirred solution of methyl 3-{1-perhydro-2H-pyran-2-yl-5-[1-(triphenylmethyl)(1,2,4-triazol-3-yl)]-1H-indazol-3-yl}benzoate (0.400 g, 0.619 mmol) in a tetrahydrofuran/water mixture (2.50 mL/1.00 mL) was added lithium hydroxide monohydrate (0.0780 g, 1.86 mmol) and the mixture heated at 60° C. for 21 h. To this mixture was added tetrahydrofuran (2.00 mL), benzylamine (0.203 mL, 1.86 mmol), 1-hydroxybenzotriazole hydrate (0.251 g, 1.86 mmol) and 1-(3-dimethylaminopropyl)-3-ethylcarbodiimide hydrochloride (0.356 g, 1.86 mmol). This mixture was stirred for 18 h at ambient temperature. After the mixture was extracted with ethyl acetate (2×), the combined organic extracts were washed with aqueous saturated sodium bicarbonate, followed by brine, dried over anhydrous sodium sulfate, filtered and evaporated. Purification of the residue by flash chromatography with 30–60% ethyl acetate/hexanes gave the title compound (0.232 g, 78% yield). ES-MS (m/z) 479 [M+1(−Tr)]$^+$.

C. [3-(5-(1H-1,2,4-triazol-5-yl)(1H-indazol-3-yl))phenyl]-N-benzyl carboxamide

To a stirred solution of (3-{1-perhydro-2H-pyran-2-yl-5-[1-(triphenylmethyl)(1,2,4-triazol-3-yl)](1H-indazol-3-yl)}phenyl)-N-benzylcarboxamide (0.232 g, 0.322 mmol) was added dioxane (10.0 mL) and aqueous 6 N hydrochloric acid (10.0 mL) and the mixture heated at 50° C. for 24 h. The mixture was cooled and aqueous 6 N sodium hydroxide (20 mL). Neutralization of the aqueous layer to pH=7 with aqueous 6 N hydrochloric acid followed by extraction with ethyl acetate, drying of the organic extracts over anhydrous sodium sulfate, filtration and evaporation gave crude product. Purification by preparative HPLC (15–80% acetonitrile/water) followed by washing with saturated sodium bicarbonate and extraction with ethyl acetate gave the title compound (0.0230 g, 18% yield). $^1$HNMR(CD$_3$OD) δ 8.78 (s, 1H), 8.49 (t, 1H), 8.21 (dt, 1H), 8.11 (brd, 1H), 7.93 (dt, 1H), 7.69 (t, 1H), 7.65 (d, 1H), 7.40 (dd, 2H), 7.32 (m, 2H), 7.24 (m, 1H), 4.64 (s, 2H). ES-MS (m/z) 395 [M+1]$^+$.

Example 254

SYNTHESIS OF N-{2-[3-(5-(1H-1,2,4-TRIAZOL-5-YL)(1H-INDAZOL-3-YL)PHENOXY]ETHYL}ACETAMIDE

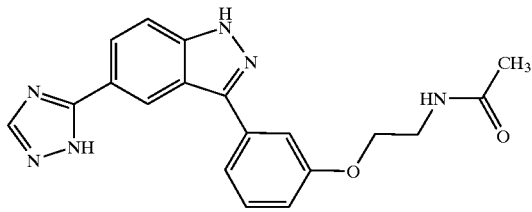

A. 3-{1-Perhydro-2H-pyran-2-yl-5-[1-(triphenylmethyl)(1,2,4-triazol-3-yl)]-1H-indazol-3-yl}phenol To a stirred solution of 2-{3-bromo-5-[1-(triphenylmethyl)(1,2,4-triazol-3-yl)]-1H-indazoyl}perhydro-2H-pyran (3.22 g, 5.46 mmol) in dimethoxyethane (27.1 mL) was added 3-hydroxy phenylboronic acid (1.81 g, 8.22 mmol), dichloro[1,1'-bis(diphenylphosphino) ferrocene]palladium (0.447 g, 0.485 mmol), and potassium phosphate (5.78 g, 27.2 mmol) and the mixture was heated at reflux for 48 h. The mixture was diluted with dichloromethane. The organic extracts were washed with saturated sodium bicarbonate, dried over anhydrous sodium sulfate, filtered and evaporated. Purification of the residue by column chromatography with 20–50% ethyl acetate/hexanes furnished the product (3.16 g, 96% yield). ES-MS (m/z) 362 [M+1(−Tr)]$^+$.

B. N-{2-[3-(5-(1H-1,2,4-Triazol-5-yl)(1H-indazol-3-yl)phenoxy]ethyl}acetamide

Triphenylphosphine (0.694 g, 2.65 mmol), tetrahydrofuran (2.12 mL), 2-N-acetylaminoethanol (0.387 g, 2.65 mmol) and diethylazodicarboxylate (0.418 mL, 2.65 mmol) were added to 3-{1-perhydro-2H-pyran-2-yl-5-[1-(triphenylmethyl)(1,2,4-triazol-3-y])]-1H-indazol-3-yl}phenol (0.400 g, 0.662 mmol). The mixture was stirred at ambient temperature for 24 h and poured into aqueous 6 N hydrochloric acid (25 mL). After stirring at ambient temperature for 4 h, the mixture was extracted with ether (3×). The aqueous fraction was added to aqueous 6 N sodium hydroxide (25 mL) and the pH adjusted to 11. The solution was extracted with ethyl acetate (3×) and the organic fractions were combined and dried over anhydrous sodium sulfate, filtered and evaporated. The residue was purified by flash chromatography on silica pretreated with 2% triethylamine/ethyl acetate followed by 5–10% methanol/ethyl acetate elution. The desired fractions were concentrated, dissolved in ethyl acetate, washed with aqueous sodium bicarbonate, dried over anhydrous sodium sulfate, filtered and evaporated which gave the title compound (0.0088 g, 4% yield). $^1$H NMR (CD$_3$OD) δ 8.72 (s, 1H), 8.40 (br s, 1H), 8.09 (d, 1H), 7.67 (d, 1H), 7.61 (dt, 1H), 7.56 (m, 1H), 7.45 (t, 1H), 7.03 (m, 1H), 4.15 (t, 2H), 3.61 (t, 2H), 1.98 (s, 3H). ES-MS (m/z) 363 [M+1]$^+$.

Example 255

SYNTHESIS OF 5-[3-(2-CHLOROPHENYL)-1H-INDAZOL-3-yl]-1H-1,2,4-TRIAZOLE

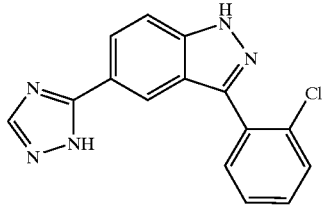

A. 2-{3-(2-Chlorophenyl)-5-[1-(triphenylmethyl)(1,2,4-triazol-3-yl)]-1H-indazolyl}perhydro-2H-pyran To a stirred solution of 2-{3-bromo-5-[1-(triphenylmethyl)(1,2,4-triazol-3-yl)]-1H-indazoyl}perhydro-2H-pyran (0.400 g, 0.619 mmol) in dimethoxyethane (3.36 mL) was added 2-chlorophenylboronic acid (0.160 g, 1.02 mmol), dichloro[1,1'-bis(diphenylphosphino) ferrocene]palladium (0.0554 g, 0.068 mmol), and potassium phosphate (0.718 g, 3.38 mmol) and the mixture was heated at reflux for 60 h. The mixture was diluted with dichloromethane. The organic extracts were washed with saturated sodium bicarbonate, dried over anhydrous sodium sulfate, filtered and evaporated. Purification of the residue by column chromatography with 30–40% ethyl acetate/hexanes furnished the product (0.327 g, 85% yield). ES-MS (m/z) 622 [M+1]$^+$.

B. Synthesis of 5-[3-(2-chlorophenyl)-1H-indazol-3-yl]-1H-1,2,4-triazole

To a stirred solution of 2-{3-(2-chlorophenyl)-5-[1-(triphenylmethyl)(1,2,4-triazol-3-yl)]-1H-indazolyl}perhydro-2H-pyran (0.328 g, 0.527 mmol) was added dioxane (10.0 mL) and aqueous 6 N hydrochloric acid (10.0 mL) and the mixture heated at 60° C. for 24 h. The mixture was cooled and aqueous 6 N sodium hydroxide (20 mL). Neutralization of the aqueous layer to pH 7 with aqueous 6 N hydrochloric acid followed by extraction with ethyl acetate, drying of the organic extracts over anhydrous sodium sulfate, filtration and evaporation gave crude product. Purification of the crude product by preparative HPLC (15–80% acetonitrile/water) followed by washing with saturated sodium bicarbonate and extraction with ethyl acetate gave the title compound (0.0388 g, 25% yield). $^1$H NMR (CD$_3$OD) δ 8.31 (s, 1H), 8.10 (d, 1H), 7.70 (d, 1H), 7.62 (m, 2H), 7.48 (m, 2H). ES-MS (m/z) 296 [M+1]$^+$.

Example 256

SYNTHESIS OF [3-(5-(1H-1,2,4-TRIAZOL-5-YL)(1H-INDAZOL-3-YL))PHENYL]-N-(2,2-DIMETHYLPROPYL)CARBOXAMIDE

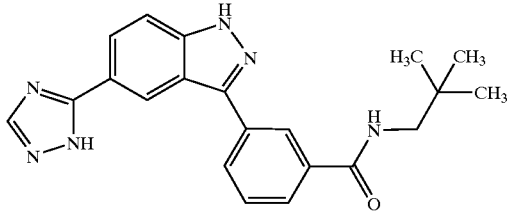

A. Methyl 3-{1-perhydro-2H-pyran-2-yl-5-[1-(triphenylmethyl)(1,2,4-triazol-3-yl)]-1H-indazol-3-yl}benzoate To a stirred solution of 2-{3-bromo-5-[1-(triphenylmethyl)(1,2,4-triazol-3-yl)]-1H-indazoyl}perhydro-2H-pyran (5.92 g, 10.04 mmol) in dimethoxyethane (49.9 mL) was added 3-(carboxymethyl)phenylboronic acid (2.72 g, 15.11 mmol), dichloro[1,1'-bis(diphenylphosphino) ferrocene]palladium (0.822 g, 1.01 mmol), and potassium phosphate (10.64 g, 50.1 mmol) and the mixture was heated at reflux for 60 h. The mixture was diluted with dichloromethane. The organic extracts were washed with saturated sodium bicarbonate, dried over anhydrous sodium sulfate, filtered and evaporated. Purification of the residue by column chromatography with 20–75% ethyl acetate/hexanes furnished the product (6.05 g, 94% yield). $^1$H NMR (CDCl$_3$) δ 8.70 (d, 2H), 8.20 (m, 2H), 8.07 (d, 1H), 7.95 (s, 1H), 7.65 (d, 1H), 7.58 (t, 1H), 7.33 (m, 10H), 7.22 (m, 7H), 5.78 (d, 1H), 3.82 (s, 3H).

B. N-(2,2-Dimethylpropyl)(3-{1-perhydro-2H-pyran-2-yl-5-[1-(triphenyl methyl)(1,2,4-triazol-3-yl)](1H-indazol-3-yl}phenyl)carboxamide To a stirred solution of methyl 3-{1-perhydro-2H-pyran-2-yl-5-[1-(triphenylmethyl)(1,2,4-triazol-3-yl)]-1H-indazol-3-yl}benzoate (0.431 g, 0.667 mmol) in a tetrahydrofuran/water mixture (2.70 mL/1.62 mL) was added lithium hydroxide monohydrate (0.0840 g, 2.00 mmol) and the mixture heated at 60° C. for 21 h. To this mixture was added tetrahydrofuran (2.16 mL), 2,2-dimethylpropyl amine (0.174 g, 2.00 mmol), 1-hydroxybenzotriazole hydrate (0.270 g, 2.00 mmol) and 1-(3-dimethylaminopropyl)-3-ethylcarbodiimide hydrochloride (0.384 g, 2.00 mmol). This reaction mixture was stirred for 67 h at ambient temperature. The mixture was extracted with ethyl acetate (2×). The combined organic extracts were washed with an aqueous saturated sodium bicarbonate solution, washed with brine, dried over anhydrous sodium sulfate, filtered and evaporated. Purification of the residue by flash chromatography with 40–60% ethyl acetate/hexanes gave the title compound (0.337 g, 72% yield). ES-MS (m/z) 459 [M+1(–Tr)]$^+$.

C. [3-(5-(1H-1,2,4-triazol-5-yl)(1H-indazol-3-yl))phenyl]-N-(2,2-dimethylpropyl)carboxamide To a stirred solution of N-(2,2-dimethylpropyl)(3-{1-perhydro-2H-pyran-2-yl-5-[1-(triphenyl methyl)(1,2,4-triazol-3-yl)](1H-indazol-3-yl)}phenyl)carboxamide (0.337 g, 0.481 mmol) was added dioxane (4.0 mL) and aqueous 6 N hydrochloric acid (4.0 mL) and the mixture heated at 60° C. for 4 h. The mixture was cooled and poured into aqueous saturated sodium bicarbonate (50 mL). The aqueous layer was extracted with ethyl acetate. The combined organic extracts were washed with saturated sodium bicarbonate, dried over anhydrous sodium sulfate, filtered and evaporated. Addition of ethyl acetate (5 mL) initiated crystal growth and the ethyl acetate layer was pipetted off. Filtration of the crystals and washing with hexanes gave the title compound (0.0381 g, 21% yield). $^1$H NMR (CD$_3$OD) δ 8.80 (s, 1H), 8.60 (br t, 1H), 8.45 (t, 1H), 8.20 (dt, 1H), 8.12 (br d, 1H), 7.89 (dt, 1H), 7.70 (d, 1H), 7.67 (t, 1H), 3.27 (s, 2H), 1.01 (s, 9H). ES-MS (m/z) 375 [M+1]$^+$.

Example 257

SYNTHESIS OF [3-(5-(1H-1,2,4-TRIAZOL-5-YL)(1H-INDAZOL-3-YL))PHENYL]-N-(CYCLOPROPYLMETHYL)CARBOXAMIDE

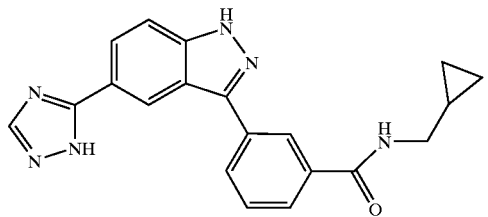

A. Methyl 3-{1-perhydro-2H-pyran-2-yl-5-[1-(triphenylmethyl)(1,2,4-triazol-3-yl)]-1H-indazol-3-yl-benzoate To a stirred solution of 2-{3-bromo-5-[1-(triphenylmethyl)(1,2,4-triazol-3-yl)]-1H-indazoyl}perhydro-2H-pyran (5.92 g, 10.04 mmol) in dimethoxyethane (49.9 mL) was added 3-(carboxymethyl)phenylboronic acid (2.72 g, 15.11 mmol), dichloro[1,1'-bis(diphenylphosphino) ferrocene]palladium (0.822 g, 1.01 mmol), and potassium phosphate (10.64 g, 50.1 mmol) and the mixture was heated at reflux for 60 h. The mixture was diluted with dichloromethane. The organic extracts were washed with saturated sodium bicarbonate, dried over anhydrous sodium sulfate, filtered and evaporated. Purification of the residue by column chromatography with 20–75% ethyl acetate/hexanes furnished the product (6.05 g, 94% yield). $^1$H NMR (CDCl$_3$) δ 8.70 (d, 2H), 8.20 (m, 2H), 8.07 (d, 1H), 7.95 (s, 1H), 7.65 (d, 1H), 7.58 (t, 1H), 7.33 (m, 10H), 7.22 (m, 7H), 5.78 (d, 1H), 3.82 (s, 3H).

B. N-(Cyclopropylmethyl)(3-{1-perhydro-2H-pyran-2-yl-5-[1-(triphenylmethyl)(1,2,4-triazol-3-yl)](1H-indazol-3-yl)}phenyl)carboxamide To a stirred solution of methyl 3-{1-perhydro-2H-pyran-2-yl-5-[1-(triphenylmethyl) (1,2,4-triazol-3-yl)]-1H-indazol-3-yl}benzoate (0.431 g, 0.667 mmol) in a tetrahydrofuran/water mixture (2.70 mL/1.62 mL) was added lithium hydroxide monohydrate (0.0840 g, 2.00 mmol) and the mixture heated at 60° C. for 21 h. To this mixture was added tetrahydrofuran (2.00 mL), cyclopropylmethyl amine (0.161 mL, 1.86 mmol), 1-hydroxybenzotriazole hydrate (0.251 g, 1.86 mmol) and 1-(3-dimethylaminopropyl)-3-ethylcarbodiimide hydrochloride (0.356 g, 1.86 mmol). This reaction mixture was stirred for 67 h at ambient temperature. The mixture was extracted with ethyl acetate (2×). The combined organic extracts were washed with an aqueous saturated solution of sodium bicarbonate, followed by brine, dried over anhydrous sodium sulfate, filtered and evaporated. Purification of the residue by flash chromatography with 40–100% ethyl acetate/hexanes gave the title compound (0.241 g, 53% yield). ES-MS (m/z) 443 [M+1(−Tr)]$^+$.

C. Synthesis of [3-(5-(1H-1,2,4-triazol-5-yl)(1H-indazol-3-yl))phenyl]-N-(cyclopropylmethyl)carboxamide To a stirred solution of N-(Cyclopropylmethyl)(3-{1-perhydro-2H-pyran-2-yl-5-[1-(triphenylmethyl) (1,2,4-triazol-3-yl)](1H-indazol-3-yl)}phenyl)carboxamide (0.241 g, 0.352 mmol) was added dioxane (4.0 mL) and aqueous 6 N hydrochloric acid (4.0 mL) and the mixture heated at 50° C. for 4 h. The mixture was cooled and poured into aqueous saturated sodium bicarbonate (50 mL). The aqueous layer was extracted with ethyl acetate. The combined organic extracts were washed with saturated sodium bicarbonate, dried over anhydrous sodium sulfate, filtered and evaporated. Addition of ethyl acetate (5 mL) initiated crystal growth and the ethyl acetate phase was pipetted off. The crystals were filtered. Purification by preparative HPLC (30–80% acetonitrile/water) gave the title compound (0.0682 g, 54% yield). $^1$H NMR (CD$_3$OD) δ 8.79 (s, 1H), 8.45 (m, 1H), 8.19 (dt, 1H), 8.11 (d, 1H), 7.90 (dt, 1H), 7.69 (d, 1H), 7.66 (t, 1H), 3.30 (m, 2H), 1.18 (m, 1H), 0.55 (m, 2H), 0.32 (m, 2H). ES-MS (m/z) 359 [M+1]$^+$.

Example 258

SYNTHESIS OF [3-(5-(1H-1,2,4-TRIZOL-5-YL)(1H-INDAZOL-3-YL))PHENYL]-N-(3-PYRIDYLMETHYL)CARBOXAMIDE

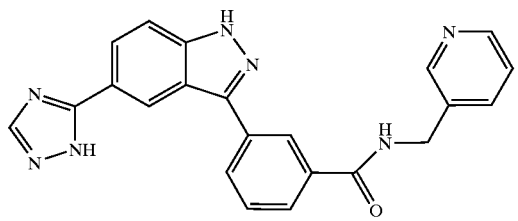

A. Methyl 3-{1-perhydro-2H-pyran-2-yl-5-[1-(triphenylmethyl)(1,2,4-triazol-3-yl)]-1H-indazol-3-yl}benzoate To a stirred solution of 2-{3-bromo-5-[1-(triphenylmethyl)(1,2,4-triazol-3-yl)]-1H-indazoyl}perhydro-2H-pyran (5.92 g, 10.04 mmol) in dimethoxyethane (49.9 mL) was added 3-(carboxymethyl)phenylboronic acid (2.72 g, 15.11 mmol), dichloro[1,1'-bis(diphenylphosphino) ferrocene]palladium (0.822 g, 1.01 mmol), and potassium phosphate (10.64 g, 50.1 mmol) and the mixture was heated at reflux for 60 h. The mixture was diluted with dichloromethane. The organic extracts were washed with saturated sodium bicarbonate, dried over anhydrous sodium sulfate, filtered and evaporated. Purification of the residue by column chromatography with 20–75% ethyl acetate/hexanes furnished the product (6.05 g, 94% yield). $^1$H NMR (CDCl$_3$) δ 8.70 (d, 2H), 8.20 (m, 2H), 8.07 (d, 1H), 7.95 (s, 1H), 7.65 (d, 1H), 7.58 (t, 1H), 7.33 (m, 10H), 7.22 (m, 7H), 5.78 (d, 1H), 3.82 (s, 3H).

B. (3-{1-perhydro-2H-pyran-2-yl-5-[1-(triphenylmethyl)(1,2,4-triazol-3-yl)](1H-indazol-3-yl)}phenyl)-N-(3-Pyridylmethyl)carboxamide To a stirred solution of methyl 3-{1-perhydro-2H-pyran-2-yl-5-[1-(triphenylmethyl) (1,2,4-triazol-3-yl)]-1H-indazol-3-yl}benzoate (0.431 g, 0.667 mmol) in a tetrahydrofuran/water mixture (2.70 mL/1.62 mL) was added lithium hydroxide monohydrate (0.0840 g, 2.00 mmol) and the mixture heated at 60° C. for 21 h. To this mixture was added tetrahydrofuran (2.00 mL), 3-pyridylmethylamine (0.189 mL, 1.86 mmol), 1-hydroxybenzotriazole hydrate (0.251 g, 1.86 mmol) and 1-(3-dimethylaminopropyl)-3-ethylcarbodiimide hydrochloride (0.356 g, 1.86 mmol). This reaction mixture was stirred for 67 h at ambient temperature. The mixture was extracted with ethyl acetate (2×). The combined organic extracts were washed with an aqueous saturated solution of sodium bicarbonate, followed by brine, dried over anhydrous sodium sulfate, filtered and evaporated. Purification of the residue by flash chromatography with 5% methanol/ethyl acetate gave the title compound (0.242 g, 50% yield). ES-MS (m/z) 480 [M+1 (−Tr)]⁺.

C. Synthesis of [3-(5-(1H-1,2,4-triazol-5-yl)(1H-indazol-3-yl))phenyl]-N-(3-pyridylmethyl)carboxamide To a stirred solution of (3-{1-perhydro-2H-pyran-2-yl-5-[1-(triphenylmethyl)(1,2,4-triazol-3-yl)](1H-indazol-3-yl)}phenyl)-N-(3-pyridylmethyl)carboxamide (0.242 g, 0.335 mmol) was added dioxane (4.0 mL) and aqueous 6 N hydrochloric acid (4.0 mL) and the mixture heated at 50° C. for 4 h. The mixture was cooled and poured into aqueous saturated sodium bicarbonate (50 mL). The aqueous layer was extracted with ethyl acetate. The combined organic extracts were washed with saturated sodium bicarbonate, dried over anhydrous sodium sulfate, filtered and evaporated. Addition of ethyl acetate (5 mL) initiated crystal growth and the ethyl acetate phase was pipetted off. The crystals were filtered. Purification by preparative HPLC (5–70% acetonitrile/water) followed by washing with saturated sodium bicarbonate and extraction with ethyl acetate gave the title compound (0.0230 g, 17% yield). ¹H NMR (CD₃OD) δ 8.79 (s, 1H), 8.60 (m, 1H), 8.49 (m, 1H), 8.44 (dd, 1H), 8.22 (dt, 1H), 8.10 (d, 1H), 7.93 (m, 2H), 7.69 (m, 2H), 7.43 (m, 1H), 4.67 (s, 1H). ES-MS (m/z) 396 [M+1]⁺.

Example 259

SYNTHESIS OF [3-(5-(1H-1,2,4-TRIAZOL-5-YL)(1H-INDAZOL-3-YL))PHENYL]-4-METHYL PIPERAZINYL KETONE

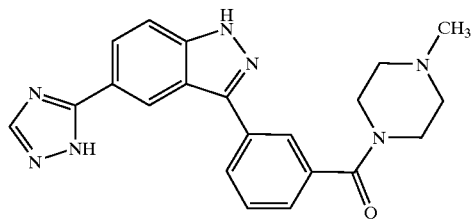

A. Methyl 3-{1-perhydro-2H-pyran-2-yl-5-[1-(triphenylmethyl)(1,2,4-triazol-3-yl)]-1H-indazol-3-yl}benzoate To a stirred solution of 2-{3-bromo-5-[1-(triphenylmethyl)(1,2,4-triazol-3-yl)]-1H-indazoyl}perhydro-2H-pyran (5.92 g, 10.04 mmol) in dimethoxyethane (49.9 mL) was added 3-(carboxymethyl) phenylboronic acid (2.72 g, 15.11 mmol), dichloro[1,1'-bis(diphenylphosphino) ferrocene]palladium (0.822 g, 1.01 mmol), and potassium phosphate (10.64 g, 50.1 mmol) and the mixture was heated at reflux for 60 h. The mixture was diluted with dichloromethane. The organic extracts were washed with saturated sodium bicarbonate, dried over anhydrous sodium sulfate, filtered and evaporated. Purification of the residue by column chromatography with 20–75% ethyl acetate/hexanes furnished the product (6.05 g, 94% yield). ¹H NMR (CDCl₃) δ 8.70 (d, 2H), 8.20 (m, 2H), 8.07 (d, 1H), 7.95 (s, 1H), 7.65 (d, 1H), 7.58 (t, 1H), 7.33 (m, 10H), 7.22 (m, 7H), 5.78 (d, 1H), 3.82 (s, 3H).

B. Synthesis of [3-(5-(1H-1,2,4-triazol-5-yl)(1H-indazol-3-yl))phenyl]-4-methyl piperazinyl ketone To a stirred solution of methyl 3-{1-perhydro-2H-pyran-2-yl-5-[1-(triphenylmethyl)(1,2,4-triazol-3-yl)]-1H-indazol-3-yl}benzoate (0.800 g, 1.24 mmol) in a tetrahydrofuran/water mixture (5.0 mL/2.0 mL) was added lithium hydroxide monohydrate (0.156 g, 3.72 mmol) and the mixture heated at 52° C. for 17 h. To this mixture was added tetrahydrofuran (4.0 mL), 1-hydroxybenzotriazole hydrate (0.502 g, 3.72 mmol) and N-methylpiperazine (0.413 mL, 3.72 mmol) and this reaction mixture was stirred for 10 h at ambient temperature. Additional 1-hydroxybenzotriazole hydrate (0.356 g, 2.64 mmol) and N-methylpiperazine (0.206 mL, 1.86 mmol) were added and the mixture stirred for an additional 63 h at ambient temperature. The mixture was poured into aqueous 6 N hydrochloric acid and the mixture stirred for 24 h at room temperature. The solids were removed by filtration and the filtrate was extracted with ether (2×). The aqueous layer was adjusted to pH 10 with aqueous 6 N sodium hydroxide and extracted with ethyl acetate. The organic extracts were dried over anhydrous sodium sulfate, filtered and evaporated. Purification by preparative HPLC (5–70% acetonitrile/water) followed by washing with saturated sodium bicarbonate and extraction with ethyl acetate gave the title compound (0.140 g). ¹H NMR (CD₃OD) δ 8.73 (s, 1H), 8.36 (s, 1H), 8.16 (dt, 1H), 8.10 (dd, 1H), 8.06 (m, 1H), 7.68 (dd, 1H), 7.66 (t, 1H), 7.49 (dt, 1H), 3.83 (br s, 2H), 3.60 (br s, 2H), 2.54 (br d, 4H), 2.34 (s, 3H). ES-MS (m/z) 388 [M+1]⁺.

Example 260

SYNTHESIS OF [3-(5-(1H-1,2,4-TRIAZOL-5-YL)(1H-INDAZOL-3-YL))PHENYL]-N-[(4-FLUOROPHENYL)METHYL]CARBOXAMIDE

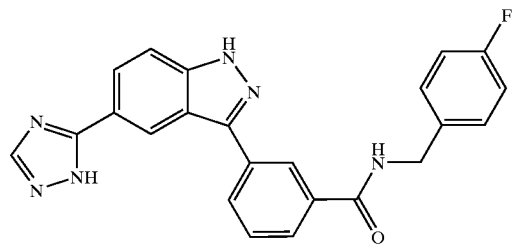

A. Methyl 3-{1-perhydro-2H-pyran-2-yl-5-[1-(triphenylmethyl)(1,2,4-triazol-3-yl)]-1H-indazol-3-yl}benzoate To a stirred solution of 2-{3-bromo-5-[1-(triphenylmethyl)(1,2,4-triazol-3-yl)]-1H-indazoyl}perhydro-2H-pyran (5.92 g, 10.04 mmol) in dimethoxyethane (49.9 mL) was added 3-(carboxymethyl) phenylboronic acid (2.72 g, 15.11 mmol), dichloro[1,1'-bis(diphenylphosphino) ferrocene]palladium (0.822 g, 1.01 mmol), and potassium phosphate (10.64 g, 50.1 mmol) and the mixture was heated at reflux for 60 h. The mixture was diluted with dichloromethane. The organic extracts were washed with saturated sodium bicarbonate, dried over anhydrous sodium sulfate, filtered and evaporated. Purification of the residue by column chromatography with 20–75% ethyl acetate/hexanes furnished the product (6.05 g, 94% yield). ¹H NMR (CDCl₃) δ 8.70 (d, 2H), 8.20 (m, 2H), 8.07 (d, 1H), 7.95 (s, 1H), 7.65 (d, 1H), 7.58 (t, 1H), 7.33 (m, 10H), 7.22 (m, 7H), 5.78 (d, 1H), 3.82 (s, 3H).

B. N-[(4-Fluorophenyl)methyl](3-{1-perhydro-2H-pyran-2-yl-5-[1-(triphenylmethyl)(1,2,4-triazol-3-yl)](1H-indazol-3-yl)}phenyl)carboxamide To a stirred solution of methyl 3-{1-perhydro-2H-pyran-2-yl-5-[1-(triphenylmethyl)(1,2,4-triazol-3-yl)]-1H-indazol-3-yl}benzoate (0.431 g, 0.667 mmol) in a tetrahydrofuran/water mixture (2.70 mL/1.62 mL) was added lithium hydroxide monohydrate (0.0840 g, 2.00 mmol) and the mixture heated at 60° C. for 21 h. To this mixture was added tetrahydrofuran (2.00 mL), 4-fluorobenzylamine (0.212 mL, 1.86 mmol), 1-hydroxybenzotriazole hydrate (0.251 g, 1.86 mmol) and 1-(3-dimethylaminopropyl)-3-ethylcarbodiimide hydrochloride (0.356 g, 1.86 mmol). This reaction mixture was stirred for 18 h at ambient temperature. The mixture was extracted with ethyl acetate (2×). The combined organic extracts were washed with aqueous saturated sodium bicarbonate, followed by brine, dried over anhydrous sodium sulfate, filtered and evaporated. Purification of the residue by flash chromatography with 30–60% ethyl acetate/hexanes gave the title compound (0.423 g, 86% yield). ES-MS (m/z) 497 [M+1(−Tr)]⁺.

C. [3-(5-(1H-1,2,4-triazol-5-yl)(1H-indazol-3-yl))phenyl]-N-[(4-fluorophenyl)methyl]carboxamide To a stirred solution of N-[(4-fluorophenyl)methyl](3-{1-perhydro-2H-pyran-2-yl-5-[1-(triphenylmethyl) (1,2,4-triazol-3-yl)](1H-indazol-3-yl)}phenyl)carboxamide (0.423 g, 0.573 mmol) was added dioxane (4.0 mL) and aqueous 6 N hydrochloric acid (4.0 mL) and the mixture heated at 50° C. for 5.5 h. The mixture was cooled and poured into saturated sodium bicarbonate (50 mL). The aqueous layer was extracted with ethyl acetate. The combined organic extracts were washed with saturated sodium bicarbonate, dried over anhydrous sodium sulfate, filtered and evaporated. Addition of ethyl acetate (5 mL) initiated crystal growth and the ethyl acetate phase was pipetted off. The crystals were filtered. Purification by preparative HPLC (30–80% acetonitrile/water) followed by washing with saturated sodium bicarbonate and extraction with ethyl acetate gave the title compound (0.0723 g, 31% yield). ¹H NMR (CD₃OD) δ 8.78 (s, 1H), 8.49 (t, 1H), 8.22 (dt, 1H), 8.13 (d, 1H), 7.94 (dt, 1H), 7.70 (d, 1H), 7.68 (t, 1H), 7.43 (m, 2H), 7.07 (m, 2H), 4.60 (s, 2H). ES-MS (m/z) 413 [M+1]⁺.

Example 261

SYNTHESIS OF [3-(5-(1H-1,2,4-TRIAZOL-5-yl)(1H-INDAZOL-3-YL))PHENYL]-N-INDAN-2-YLCARBOXAMIDE

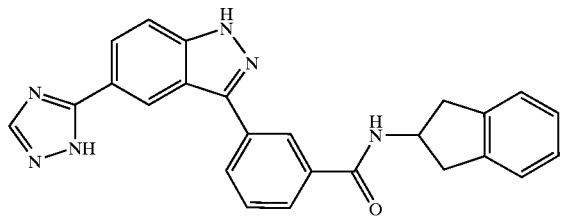

A. Methyl 3-{1-perhydro-2H-pyran-2-yl-5-[1-(triphenylmethyl)(1,2,4-triazol-3-yl)]-1H-indazol-3-yl}benzoate To a stirred solution of 2-{3-bromo-5-[1-(triphenylmethyl)(1,2,4-triazol-3-yl)]-1H-indazoyl}perhydro-2H-pyran (5.92 g, 10.04 mmol) in dimethoxyethane (49.9 mL) was added 3-(carboxymethyl)phenylboronic acid (2.72 g, 15.11 mmol), dichloro[1,1'-bis(diphenylphosphino) ferrocene]palladium (0.822 g, 1.01 mmol), and potassium phosphate (10.64 g, 50.1 mmol) and the mixture was heated at reflux for 60 h. The mixture was diluted with dichloromethane. The organic extracts were washed with saturated sodium bicarbonate, dried over anhydrous sodium sulfate, filtered and evaporated. Purification of the residue by column chromatography with 20–75% ethyl acetate/hexanes furnished the product (6.05 g, 94% yield). ¹H NMR (CDCl₃) δ 8.70 (d, 2H), 8.20 (m, 2H), 8.07 (d, 1H), 7.95 (s, 1H), 7.65 (d, 1H), 7.58 (t, 1H), 7.33 (m, 10H), 7.22 (m, 7H), 5.78 (d, 1H), 3.82 (s, 3H).

B. N-Indan-2-yl(3-{1-perhydro-2H-pyran-2-yl-5-[1-(triphenylmethyl)(1,2,4-triazol-3-yl)](1H-indazol-3-yl)}phenyl)carboxamide To a stirred solution of methyl 3-{1-perhydro-2H-pyran-2-yl-5-[1-(triphenylmethyl)(1,2,4-triazol-3-yl)]-1H-indazol-3-yl}benzoate (0.400 g, 0.619 mmol) in a tetrahydrofuran/water mixture (2.50 mL/1.00 mL) was added lithium hydroxide monohydrate (0.0780 g, 1.86 mmol) and the mixture heated at 60° C. for 21 h. To this mixture was added tetrahydrofuran (2.00 mL), 2-aminoindane (0.316 g, 1.86 mmol), 1-hydroxybenzotriazole hydrate (0.251 g, 1.86 mmol) and 1-(3-dimethylaminopropyl)-3-ethylcarbodiimide hydrochloride (0.356 g, 1.86 mmol). This mixture was stirred for 18 h at ambient temperature. After the mixture was extracted with ethyl acetate (2×), the combined organic extracts were washed with aqueous saturated sodium bicarbonate, followed by brine, dried over anhydrous sodium sulfate, filtered and evaporated. Purification of the residue by flash chromatography with 30–60% ethyl acetate/hexanes gave the title compound (0.342 g, 74% yield). ES-MS (m/z) 505 [M+1(−Tr)]⁺.

C. [3-(5-(1H-1,2,4,-triazol-5-yl)(1H-indazol-3-yl))phenyl]-N-indan-2-ylcarboxamide To a stirred solution of N-indan-2-yl(3-{1-perhydro-2H-pyran-2-yl-5-[1-(triphenylmethyl)(1,2,4-triazol-3-yl)](1H-indazol-3-yl)}phenyl)carboxamide (0.342 g, 0.458 mmol) was added dioxane (4.0 mL) and aqueous 6 N hydrochloric acid (4.0 mL) and the mixture heated at 50° C. for 5.5 h. The mixture was cooled and poured into saturated sodium bicarbonate (50 mL). The aqueous layer was extracted with ethyl acetate. The combined organic extracts were washed with saturated sodium bicarbonate, dried over anhydrous sodium sulfate, filtered and evaporated. Addition of ethyl acetate (5 mL) initiated crystal growth and the ethyl acetate phase was pipetted off. The crystals were filtered. Purification by preparative HPLC (30–80% acetonitrile/water) followed by washing with saturated sodium bicarbonate and extraction with ethyl acetate gave the title compound (0.0414 g, 22% yield). ¹H NMR (CD₃OD) δ 8.79 (s, 1H), 8.50 (m, 1H), 8.21 (d, 1H), 8.13 (d, 1H), 7.91 (d, 1H), 7.69 (m, 2H), 7.25 (m, 2H), 7.17 (m, 2H), 4.83 (m, 1H), 3.34 (dd, 2H), 3.07 (dd, 2H). ES-MS (m/z) 421 [M+1]⁺.

Example 262

SYNTHESIS OF [3-(5-(1H-1,2,4-TRIAZOL-5-YL)(1H-INDAZOL-3-YL))PHENYL]-N-((1R)INDANYL)CARBOXAMIDE

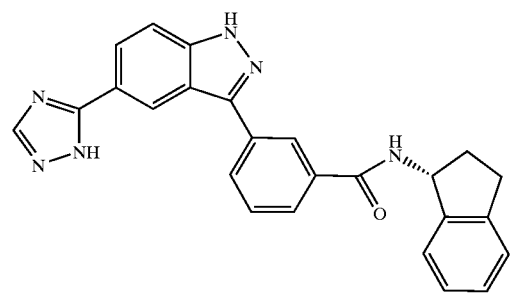

A. Methyl 3-{1-perhydro-2H-pyran-2-yl-5-[1-(triphenylmethyl)(1,2,4-triazol-3-yl)]-H-indazol-3-yl}benzoate To a stirred solution of 2-{3-bromo-5-[1-(triphenylmethyl)(1,2,4-triazol-3-yl)]-1H-indazoyl}perhydro-2H-pyran (5.92 g, 10.04 mmol) in dimethoxyethane (49.9 mL) was added 3-(carboxymethyl) phenylboronic acid (2.72 g, 15.11 mmol), dichloro[1,1'-bis (diphenylphosphino) ferrocene]palladium (0.822 g, 1.01 mmol), and potassium phosphate (10.64 g, 50.1 mmol) and the mixture was heated at reflux for 60 h. The mixture was diluted with dichloromethane. The organic extracts were washed with saturated sodium bicarbonate, dried over anhydrous sodium sulfate, filtered and evaporated. Purification of the residue by column chromatography with 20–75% ethyl acetate/hexanes furnished the product (6.05 g, 94% yield). $^1$H NMR (CDCl$_3$) δ 8.70 (d, 2H), 8.20 (m, 2H), 8.07 (d, 1H), 7.95 (s, 1H), 7.65 (d, 1H), 7.58 (t, 1H), 7.33 (m, 10H), 7.22 (m, 7H), 5.78 (d, 1H), 3.82 (s, 3H).

B. N-((1R)Indanyl)(3-{1-perhydro-2H-pyran-2-yl-5-[1-(triphenylmethyl)(1,2,4-triazol-3-yl)](1H-indazol-3-yl)} phenyl)carboxamide To a stirred solution of methyl 3-{1-perhydro-2H-pyran-2-yl-5-[1-(triphenylmethyl)(1,2,4-triazol-3-yl)]-1H-indazol-3-yl}benzoate (0.400 g, 0.619 mmol) in a tetrahydrofuran/water mixture (2.50 mL/1.00 mL) was added lithium hydroxide monohydrate (0.0780 g, 1.86 mmol) and the mixture heated at 60° C. for 21 h. To this mixture was added tetrahydrofuran (2.00 mL), (R)-(−)-1-aminoindane (0.239 mL, 1.86 mmol), 1-hydroxybenzotriazole hydrate (0.251 g, 1.86 mmol) and 1-(3-dimethylaminopropyl)-3-ethylcarbodiimide hydrochloride (0.356 g, 1.86 mmol). This mixture was stirred for 18 h at ambient temperature. After the mixture was extracted with ethyl acetate (2×), the combined organic extracts were washed with aqueous saturated sodium bicarbonate, followed by brine, dried over anhydrous sodium sulfate, filtered and evaporated. Purification of the residue by flash chromatography with 30–60% ethyl acetate/hexanes gave the title compound (0.292 g, 63% yield). ES-MS (m/z) 505 [M+1(−Tr)]$^+$.

C. [3-(5-(1H-1,2,4-Triazol-5-yl)(1H-indazol-3-yl)phenyl]-N-((1R)indanyl)carboxamide To a stirred solution of N-((1R)indanyl)(3-{1-perhydro-2H-pyran-2-yl-5-[1-(triphenylmethyl)(1,2,4-triazol-3-yl)] (1H-indazol-3-yl)}phenyl)carboxamide (0.292 g, 0.391 mmol) was added dioxane (4.0 mL) and aqueous 6 N hydrochloric acid (4.0 mL) and the mixture heated at 60° C. for 18 h. The mixture was cooled and poured into saturated sodium bicarbonate (50 mL). The aqueous layer was extracted with ethyl acetate. The combined organic extracts were washed with saturated aqueous sodium bicarbonate, dried over anhydrous sodium sulfate, filtered and evaporated. Addition of ethyl acetate (5 mL) initiated crystal growth and the ethyl acetate phase was pipetted off. The crystals were filtered. Purification by preparative HPLC (30–80% acetonitrile/water) followed by washing with saturated sodium bicarbonate and extraction with ethyl acetate gave the title compound (0.0150 g, 9% yield). $^1$H NMR (CD$_3$OD) δ 8.80 (s, 1H), 8.55 (s, 1H), 8.23 (d, 1H), 8.13 (d, 1H), 7.96 (dd, 1H), 7.70 (m, 2H), 7.36 (m, 1H), 7.28 (m, 1H), 7.23 (m, 2H), 5.67 (t, 1H), 3.08 (m, 1H), 2.92 (m, 1H), 2.60 (m, 2H), 2.08 (m, 1H). ES-MS (m/z) 421 [M+1]$^+$.

Example 263

SYNTHESIS OF [3-(5-(1H-1,2,4-TRIAZOL-5-YL) (1H-INDAZOL-3-YL))PHENYL]-N-((1S) INDANYL)CARBOXAMIDE

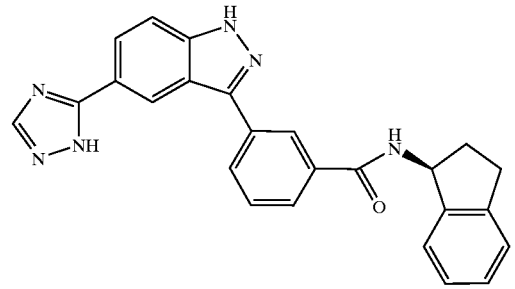

A. Methyl 3-{1-perhydro-2H-pyran-2-yl-5-[1-(triphenylmethyl)(1,2,4-triazol-3-yl]-1H-indazol-3-yl}benzoate To a stirred solution of 2-{3-bromo-5-[1-(triphenylmethyl)(1,2,4-triazol-3-yl)]-1H-indazoyl}perhydro-2H-pyran (5.92 g, 10.04 mmol) in dimethoxyethane (49.9 mL) was added 3-(carboxymethyl) phenylboronic acid (2.72 g, 15.11 mmol), dichloro[1,1'-bis (diphenylphosphino) ferrocene]palladium (0.822 g, 1.01 mmol), and potassium phosphate (10.64 g, 50.1 mmol) and the mixture was heated at reflux for 60 h. The mixture was diluted with dichloromethane. The organic extracts were washed with saturated sodium bicarbonate, dried over anhydrous sodium sulfate, filtered and evaporated. Purification of the residue by column chromatography with 20–75% ethyl acetate/hexanes furnished the product (6.05 g, 94% yield). $^1$H NMR (CDCl$_3$) δ 8.70 (d, 2H), 8.20 (m, 2H), 8.07 (d, 1H), 7.95 (s, 1H), 7.65 (d, 1H), 7.58 (t, 1H), 7.33 (m, 10H), 7.22 (m, 7H), 5.78 (d, 1H), 3.82 (s, 3H).

B. N-((1S)Indanyl)(3-{1-perhydro-2H-pyran-2-yl-5-[1-(triphenyl methyl)(1,2,4-triazol-3-yl)](1H-indazol-3-yl)} phenyl)carboxamide To a stirred solution of methyl 3-{1-perhydro-2H-pyran-2-yl-5-[1-(triphenylmethyl)(1,2,4-triazol-3-yl)]-1H-indazol-3-yl}benzoate (0.400 g, 0.619 mmol) in a tetrahydrofuran/water mixture (2.50 mL/1.00 mL) was added lithium hydroxide monohydrate (0.0780 g, 1.86 mmol) and the mixture heated at 60° C. for 21 h. To this mixture was added tetrahydrofuran (2.00 mL), (S)-(+)-1-aminoindane (0.239 mL, 1.86 mmol), 1-hydroxybenzotriazole hydrate (0.251 g, 1.86 mmol) and 1-(3-dimethylaminopropyl)-3-ethylcarbodiimide hydrochloride (0.356 g, 1.86 mmol). This mixture was stirred for 18 h at ambient temperature. After the mixture was extracted with ethyl acetate (2×), the combined organic extracts were washed with aqueous saturated sodium bicarbonate, followed by brine, dried over anhydrous sodium sulfate, filtered and evaporated. Purification of the residue by flash chromatography with 30–60% ethyl acetate/hexanes gave the title compound (0.277 g, 60% yield). ES-MS (m/z) 505 [M+1(−Tr)]$^+$.

C. [3-(5-(1H-1,2,4-Triazol-5-yl)(1H-indazol-3-yl))phenyl]-N-((1S)indanyl)carboxamide To a stirred solution of N-((1S)indanyl)(3-{1-perhydro-2H-pyran-2-yl-5-[1-(triphenyl methyl)(1,2,4-triazol-3-yl)] (1H-indazol-3-yl)}phenyl)carboxamide (0.277 g, 0.371 mmol) was added dioxane (4.0 mL) and aqueous 6 N hydrochloric acid (4.0 mL) and the mixture heated at 50° C. for 5.5 h. The mixture was cooled and poured into saturated sodium bicarbonate (50 mL). The aqueous layer was extracted with ethyl acetate. The combined organic extracts were washed with saturated sodium bicarbonate, dried over anhydrous sodium sulfate, filtered and evaporated. Addition of ethyl acetate (5 mL) initiated crystal growth and the ethyl acetate phase was pipetted off. The crystals were filtered. Purification by preparative HPLC (30–80% acetonitrile/water) followed by washing with saturated sodium bicarbonate and extraction with ethyl acetate gave the title compound (0.0133 g, 9% yield). $^1$H NMR (CD$_3$OD) δ 8.81 (s, 1H), 8.54 (m, 1H), 8.39 (br s, 1H), 8.24 (d, 1H), 8.13 (d, 1H), 7.96 (m, 1H), 7.70 (m, 2H), 7.37 (m, 1H), 7.27 (m, 1H), 7.22 (m, 2H), 5.70 (t, 1H), 3.09 (m, 1H), 2.93 (m, 1H), 2.61 (m, 2H), 2.09 (m, 1H). ES-MS (m/z) 421 [M+1]$^+$.

Example 264

SYNTHESIS OF [3-(5-(1H-1,2,4-TRIAZOL-5-YL)(1H-INDAZOL-3-YL))PHENYL]-N-((1S,2R)-2-HYDROXYINDANYL)CARBOXAMIDE

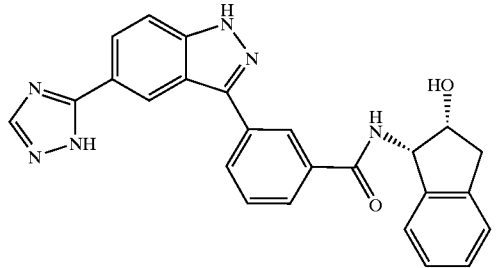

A. Methyl 3-{1-perhydro-2H-pyran-2-yl-5-[1-(triphenylmethyl)(1,2,4-triazol-3-yl)]-1H-indazol-3-yl}benzoate To a stirred solution of 2-{3-bromo-5-[1-(triphenylmethyl)(1,2,4-triazol-3-yl)]-1H-indazoyl}perhydro-2H-pyran (5.92 g, 10.04 mmol) in dimethoxyethane (49.9 mL) was added 3-(carboxymethyl)phenylboronic acid (2.72 g, 15.11 mmol), dichloro[1,1'-bis(diphenylphosphino) ferrocene]palladium (0.822 g, 1.01 mmol), and potassium phosphate (10.64 g, 50.1 mmol) and the mixture was heated at reflux for 60 h. The mixture was diluted with dichloromethane. The organic extracts were washed with saturated sodium bicarbonate, dried over anhydrous sodium sulfate, filtered and evaporated. Purification of the residue by column chromatography with 20–75% ethyl acetate/hexanes furnished the product (6.05 g, 94% yield). $^1$H NMR (CDCl$_3$) δ 8.70 (d, 2H), 8.20 (m, 2H), 8.07 (d, 1H), 7.95 (s, 1H), 7.65 (d, 1H), 7.58 (t, 1H), 7.33 (m, 10H), 7.22 (m, 7H), 5.78 (d, 1H), 3.82 (s, 3H).

B. N-((1S,2R)-2-hydroxyindanyl)(3-{1-perhydro-2H-pyran-2-yl-5-[1-(triphenylmethyl)(1,2,4-triazol-3-yl)]1H-indazol-3-yl})phenyl)carboxamide To a stirred solution of methyl 3-{1-perhydro-2H-pyran-2-yl-5-[1-(triphenylmethyl) (1,2,4-triazol-3-yl)]-1H-indazol-3-yl}benzoate (0.400 g, 0.619 mmol) in a tetrahydrofuran/water mixture (2.50 mL/1.00 mL) was added lithium hydroxide monohydrate (0.0780 g, 1.86 mmol) and the mixture heated at 60° C. for 21 h. To this mixture was added tetrahydrofuran (2.00 mL), (1S,2R)-(−)-cis-1-amino-2-indanol (0.277 g, 1.86 mmol), 1-hydroxybenzotriazole hydrate (0.251 g, 1.86 mmol) and 1-(3-dimethylaminopropyl)-3-ethylcarbodiimide hydrochloride (0.356 g, 1.86 mmol). This mixture was stirred for 18 h at ambient temperature. After the mixture was extracted with ethyl acetate (2×), the combined organic extracts were washed with aqueous saturated sodium bicarbonate, followed by brine, dried over anhydrous sodium sulfate, filtered and evaporated. Purification of the residue by flash chromatography with 40–100% ethyl acetate/hexanes gave the title compound (0.342 g, 72% yield). ES-MS (m/z) 521 [M+1(−Tr)]$^+$.

C. [3-(5-(1H-1,2,4-triazol-5-yl)(1H-indazol-3-yl))phenyl]-N-((1S,2R)-2-hydroxyindanyl)carboxamide To a stirred solution of N-((1S,2R)-2-hydroxyindanyl)(3-{1-perhydro-2H-pyran-2-yl-5-[1-(triphenyl methyl)(1,2,4-triazol-3-yl)](1H-indazol-3-yl)}phenyl)carboxamide (0.342 g, 0.448 mmol) was added 4.0M hydrochloric acid in dioxane (10.0 mL) and the mixture stirred at ambient temperature for 20 h. The mixture was cooled and poured into saturated sodium bicarbonate (50 mL). The aqueous layer was extracted with ethyl acetate. The combined organic extracts were washed with saturated sodium bicarbonate, dried over anhydrous sodium sulfate, filtered and evaporated. Addition of ethyl acetate (5 mL) initiated crystal growth and the ethyl acetate was pipetted off. The crystals were filtered. Purification by preparative HPLC (30–80% acetonitrile/water) followed by washing with saturated sodium bicarbonate and extraction with ethyl acetate gave the title compound (0.0233 g, 12% yield). $^1$H NMR (CD$_3$OD) δ 8.82 (s, 1H), 8.58 (s, 1H), 8.24 (d, 1H), 8.12 (br d, 1H), 8.00 (d, 1H), 7.01 (t, 2H), 7.37 (d, 1H), 7.30 (d, 1H), 7.24 (m, 2H), 5.63 (m, 1H), 4.74 (m, 1H), 3.26 (m, 1H), 3.05 (1H). ES-MS (m/z) 437 [M+1]$^+$.

Example 265

SYNTHESIS OF [3-(5-(1H-1,2,4-TRIAZOL-5-YL)(1H-INDAZOL-3-YL))PHENYL]-N-((2S,1R)-2-HYDROXYINDANYL)CARBOXAMIDE

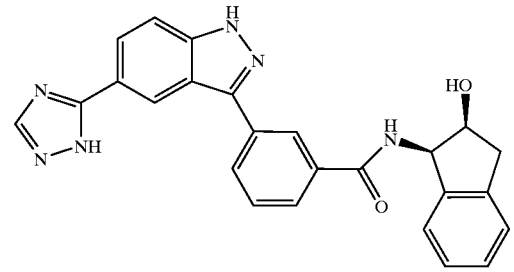

A. Methyl 3-{1-perhydro-2H-pyran-2-yl-5-[1-(triphenylmethyl)(1,2,4-triazol-3-yl)]-1H-indazol-3-yl}benzoate To a stirred solution of 2-{3-bromo-5-[1-(triphenylmethyl)(1,2,4-triazol-3-yl)]-1H-indazoyl}perhydro-2H-pyran (5.92 g, 10.04 mmol) in dimethoxyethane (49.9 mL) was added 3-(Carboxymethyl)phenylboronic acid (2.72 g, 15.11 mmol), dichloro[1,1'-bis(diphenylphosphino) ferrocene]palladium (0.822 g, 1.01 mmol), and potassium phosphate (10.64 g, 50.1 mmol) and the mixture was heated at reflux for 60 h. The mixture was diluted with dichloromethane. The organic extracts were washed with saturated sodium bicarbonate, dried over anhydrous sodium sulfate, filtered and evaporated. Purification of the residue by column chromatography with 20–75% ethyl acetate/hexanes furnished the product (6.05 g, 94% yield). $^1$H NMR (CDCl$_3$) δ 8.70 (d, 2H), 8.20 (m, 2H), 8.07 (d, 1H), 7.95 (s, 1H), 7.65 (d, 1H), 7.58 (t, 1H), 7.33 (m, 10H), 7.22 (m, 7H), 5.78 (d, 1H), 3.82 (s, 3H).

B. N-((1R,2S)-2-Hydroxyindanyl)(3-{1-perhydro-2H-pyran-2-yl-5-[1-(triphenylmethyl)(1,2,4-triazol-3-yl)](1H-indazol-3-yl)}phenyl)carboxamide To a stirred solution of methyl 3-{1-perhydro-2H-pyran-2-yl-5-[1-(triphenylmethyl)(1,2,4-triazol-3-yl)]-1H-indazol-3-yl}benzoate (0.400 g, 0.619 mmol) in a tetrahydrofuran/water mixture (2.50 mL/1.00 mL) was added lithium hydroxide monohydrate (0.0780 g, 1.86 mmol) and the mixture heated at 60° C. for 21 h. To this mixture was added tetrahydrofuran (2.00 mL), (1R,2S)-(+)-cis-1-amino-2-indanol (0.277 g, 1.86 mmol), 1-hydroxybenzotriazole hydrate (0.251 g, 1.86 mmol) and 1-(3-dimethylaminopropyl)-3-ethylcarbodiimide hydrochloride (0.356 g, 1.86 mmol). This mixture was stirred for 18 h at ambient temperature. After the mixture was extracted with ethyl acetate (2×), the combined organic extracts were washed with aqueous saturated sodium bicarbonate, followed by brine, dried over anhydrous sodium sulfate, filtered and evaporated. Purification of the residue by flash chromatography with 40–100% ethyl acetate/hexanes gave the title compound (0.339 g, 72% yield). ES-MS (m/z) 521 [M+1(–Tr)]+

C. [3-(5-(1H-1,2,4-triazol-5-yl)(1H-indazol-3-yl))phenyl]-N-((2S,1R)-2-hydroxyindanyl)carboxamide To a stirred solution of N-((1R,2S)-2-hydroxyindanyl)(3-{1-perhydro-2H-pyran-2-yl-5-[1-(triphenyl methyl)(1,2,4-triazol-3-yl)](1H-indazol-3-yl)}phenyl)carboxamide (0.339 g, 0.444 mmol) was added 4.0 M hydrochloric acid in dioxane (10.0 mL) and the mixture stirred at ambient temperature for 20 h. The mixture was cooled and poured into saturated sodium bicarbonate (50 mL). The aqueous layer was extracted with ethyl acetate. The combined organic extracts were washed with saturated sodium bicarbonate, dried over anhydrous sodium sulfate, filtered and evaporated. Addition of ethyl acetate (5 mL) initiated crystal growth and the ethyl acetate phase was pipetted off. The crystals were filtered. Purification by preparative HPLC (30–80% acetonitrile/water) followed by washing with saturated sodium bicarbonate and extraction with ethyl acetate gave the title compound (0.0440 g, 23% yield). $^1$H NMR (CD$_3$OD) δ 8.82 (s, 1H), 8.58 (s, 1H), 8.24 (d, 1H), 8.12 (d, 1H), 8.00 (d, 1H), 7.70 (t, 2H), 7.37 (d, 1H), 7.27 (m, 3H), 5.63 (d, 1H), 4.74 (m, 1H), 3.26 (dd, 1H), 3.05 (dt, 1H). ES-MS (m/z) 437 [M+1]+

Example 266

SYNTHESIS OF [3-(5-(1H-1,2,4-TRIAZOL-5-YL)(1H-INDAZOL-3-YL))PHENYL]-N-(1-METHYL-1-PHENYLETHYL)CARBOXAMIDE

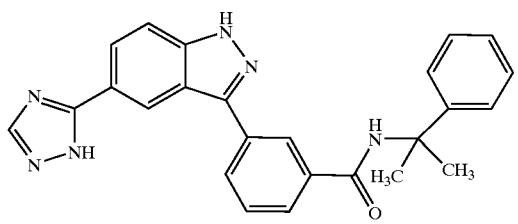

A. Methyl 3-{1-perhydro-2H-pyran-2-yl-5-[1-(triphenylmethyl)(1,2,4-triazol-3-yl)]-1H-indazol-3-yl}benzoate To a stirred solution of 2-{3-bromo-5-[1-(triphenylmethyl)(1,2,4-triazol-3-yl)]-1H-indazoyl}perhydro-2H-pyran (5.92 g, 10.04 mmol) in dimethoxyethane (49.9 mL) was added 3-(carboxymethyl)phenylboronic acid (2.72 g, 15.11 mmol), dichloro[1,1'-bis(diphenylphosphino) ferrocene]palladium (0.822 g, 1.01 mmol), and potassium phosphate (10.64 g, 50.1 mmol) and the mixture was heated at reflux for 60 h. The mixture was diluted with dichloromethane. The organic extracts were washed with saturated sodium bicarbonate, dried over anhydrous sodium sulfate, filtered and evaporated. Purification of the residue by column chromatography with 20–75% ethyl acetate/hexanes furnished the product (6.05 g, 94% yield). $^1$H NMR (CDCl$_3$) δ 8.70 (d, 2H), 8.20 (m, 2H), 8.07 (d, 1H), 7.95 (s, 1H), 7.65 (d, 1H), 7.58 (t, 1H), 7.33 (m, 10H), 7.22 (m, 7H), 5.78 (d, 1H), 3.82 (s, 3H).

B. N-(1-methyl-1-phenylethyl)(3-{1-perhydro-2H-pyran-2-yl-5-[1-(triphenylmethyl)(1,2,4-triazol-3-yl)](1H-indazol-3-yl)}phenyl)carboxamide To a stirred solution of methyl 3-{1-perhydro-2H-pyran-2-yl-5-[1-(triphenylmethyl) (1,2,4-triazol-3-yl)]-1H-indazol-3-yl}benzoate (0.400 g, 0.619 mmol) in a tetrahydrofliran/water mixture (2.50 mL/1.00 mL) was added lithium hydroxide monohydrate (0.0780 g, 1.86 mmol) and the mixture heated at 60° C. for 21 h. To this mixture was added tetrahydrofuran (2.00 mL), cumylamine (0.270 mL, 1.86 mmol), 1-hydroxybenzotriazole hydrate (0.251 g, 1.86 mmol) and 1-(3-dimethylaminopropyl)-3-ethylcarbodiimide hydrochloride (0.356 g, 1.86 mmol). This mixture was stirred for 18 h at ambient temperature. After the mixture was extracted with ethyl acetate (2×), the combined organic extracts were washed with aqueous saturated sodium bicarbonate, followed by brine, dried over anhydrous sodium sulfate, filtered and evaporated. Purification of the residue by flash chromatography with 40–100% ethyl acetate/hexanes gave the title compound (0.376 g, 81% yield). ES-MS (m/z) 507 [M+1(–Tr)]+

C. [3-(5-(1H-1,2,4-Triazol-5-yl)(1H-indazol-3-yl))phenyl]-N-(1-methyl-1-phenylethyl)carboxamide To a stirred solution of (0.376 g, 0.502 mmol) was added 4.0 M hydrochloric acid in dioxane (10.0 mL) and the mixture stirred at ambient temperature for 20 h. The mixture was cooled and poured into saturated aqueous sodium bicarbonate (50 mL). The aqueous layer was extracted with ethyl acetate. The combined organic extracts were washed with saturated sodium bicarbonate, dried over anhydrous sodium sulfate, filtered and evaporated. Addition of ethyl acetate (5 mL) initiated crystal growth and the ethyl acetate phase was pipetted off. The crystals were filtered. Purification by preparative HPLC (30–80% acetonitrile/water) followed by washing with saturated aqueous sodium bicarbonate and extraction with ethyl acetate gave the title compound (0.0686 g, 32% yield). $^1$H NMR (CD$_3$OD) δ 8.77 (m, 1H), 8.43 (t, 1H), 8.21 (dt, 1H), 8.12 (d, 1H), 7.88 (d, 1H), 7.68 (m, 2H), 7.48 (m, 2H), 7.31 (m, 2H), 7.20 (m, 1H), 1.80 (s, 6H). ES-MS (m/z) 423 [M+1]+

Example 267

SYNTHESIS OF [3-(5-(1H-1,2,4-TRIAZOL-5-YL)(1H-INDAZOL-3-YL))PHENYL]-N-(TERT-BUTYL)CARBOXAMIDE

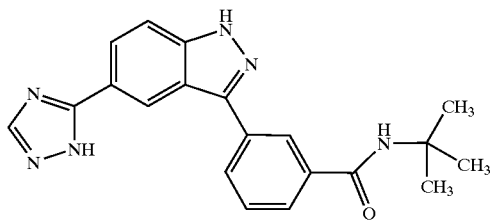

A. Methyl 3-{1-perhydro-2H-pyran-2-yl-5-[1-(triphenylmethyl)(1,2,4-triazol-3-yl)]-1H-indazol-3-yl}benzoate

193

To a stirred solution of 2-{3-bromo-5-[1-(triphenylmethyl)(1,2,4-triazol-3-yl)]-1H-indazoyl}perhydro-2H-pyran (5.92 g, 10.04 mmol) in dimethoxyethane (49.9 mL) was added 3-(carboxymethyl) phenylboronic acid (2.72 g, 15.11 mmol), dichloro[1,1'-bis(diphenylphosphino) ferrocene]palladium (0.822 g, 1.01 mmol), and potassium phosphate (10.64 g, 50.1 mmol) and the mixture was heated at reflux for 60 h. The mixture was diluted with dichloromethane. The organic extracts were washed with saturated sodium bicarbonate, dried over anhydrous sodium sulfate, filtered and evaporated. Purification of the residue by column chromatography with 20–75% ethyl acetate/hexanes furnished the product (6.05 g, 94% yield). $^1$H NMR (CDCl$_3$) δ 8.70 (d, 2H), 8.20 (m, 2H), 8.07 (d, 1H), 7.95 (s, 1H), 7.65 (d, 1H), 7.58 (t, 1H), 7.33 (m, 10H), 7.22 (m, 7H), 5.78 (d, 1H), 3.82 (s, 3H).

B. N-(tert-Butyl)(3-{1-perhydro-2H-pyran-2-yl-5-[1-(triphenylmethyl)(1,2,4-triazol-3-yl)](1H-indazol-3-yl)}phenyl)carboxamide To a stirred solution of methyl 3-{1-perhydro-2H-pyran-2-yl-5-[1-(triphenylmethyl) (1,2,4-triazol-3-yl)]-1H-indazol-3-yl}benzoate (0.400 g, 0.619 mmol) in a tetrahydrofuran/water mixture (2.50 mL/1.00 mL) was added lithium hydroxide monohydrate (0.0780 g, 1.86 mmol) and the mixture heated at 60° C. for 21 h. To this mixture was added tetrahydrofuran (2.00 mL), tert-butylamine (0.195 mL, 1.86 mmol), 1-hydroxybenzotriazole hydrate (0.251 g, 1.86 mmol) and 1-(3-dimethylaminopropyl)-3-ethylcarbodiimide hydrochloride (0.356 g, 1.86 mmol). This mixture was stirred for 18 h at ambient temperature. After the mixture was extracted with ethyl acetate (2×), the combined organic extracts were washed with aqueous saturated sodium bicarbonate, followed by brine, dried over anhydrous sodium sulfate, filtered and evaporated. Purification of the residue by flash chromatography with 40–100% ethyl acetate/hexanes gave the title compound (0.334 g, 78% yield). ES-MS (m/z) 445 [M+1(−Tr)]−

C. [3-(5-(1H-1,2,4-triazol-5-yl)(1H-indazol-3-yl))phenyl]-N-(tert-butyl)carboxamide To a stirred solution of N-(tert-butyl)(3-{1-perhydro-2H-pyran-2-yl-5-[1-(triphenylmethyl)(1,2,4-triazol-3-yl)](1H-indazol-3-yl)}phenyl)carboxamide (0.334 g, 0.486 mmol) was added 4.0 M hydrochloric acid in dioxane (10.0 mL) and the mixture was stirred at ambient temperature for 20 h. The mixture was cooled and poured into saturated aqueous sodium bicarbonate (50 mL). The aqueous layer was extracted with ethyl acetate. The combined organic extracts were washed with saturated sodium bicarbonate, dried over anhydrous sodium sulfate, filtered and evaporated. Addition of ethyl acetate (5 mL) initiated crystal growth and the ethyl acetate phase was pipetted off. The crystals were filtered. Purification by preparative HPLC (30–80% acetonitrile/water) followed by washing with saturated sodium bicarbonate and extraction with ethyl acetate gave the title compound (0.0964 g, 55% yield). $^1$H NMR (CD$_3$OD) δ 8.77 (m, 1H), 8.37 (m, 1H), 8.35 (br s, 1H), 8.16 (d, 1H), 8.11 (d, 1H), 7.82 (d, 1H), 7.69 (d, 1H), 7.64 (t, 1H), 1.51 (s, 9H). ES-MS (m/z) 361 [M+1]$^+$

194

Example 268

SYNTHESIS OF [3-(5-(1H-1,2,4-TRIAZOL-5-YL)(1H-INDAZOL-3-YL))PHENYL]-N-((1R)-1-PHENYLETHYL)CARBOXAMIDE

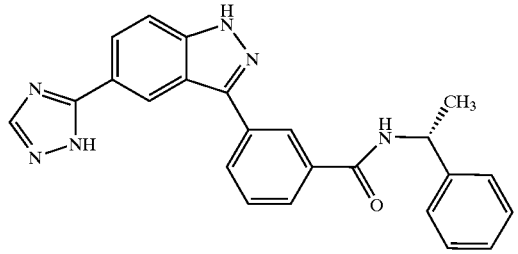

A. Methyl 3-{1-perhydro-2H-pyran-2-yl-5-[1-(triphenylmethyl)(1,2,4-triazol-3-yl)]-1H-indazol-3-yl}benzoate To a stirred solution of 2-{3-bromo-5-[1-(triphenylmethyl)(1,2,4-triazol-3-yl)]-1H-indazoyl}perhydro-2H-pyran (5.92 g, 10.04 mmol) in dimethoxyethane (49.9 mL) was added 3-(carboxymethyl) phenylboronic acid (2.72 g, 15.11 mmol), dichloro[1,1'-bis(diphenylphosphino)ferrocene]palladium (0.822 g, 1.01 mmol), and potassium phosphate (10.64 g, 50.1 mmol) and the mixture was heated at reflux for 60 h. The mixture was diluted with dichloromethane. The organic extracts were washed with saturated sodium bicarbonate, dried over anhydrous sodium sulfate, filtered and evaporated. Purification of the residue by column chromatography with 20–75% ethyl acetate/hexanes furnished the product (6.05 g, 94% yield). $^1$H NMR (CDCl$_3$) δ 8.70 (d, 2H), 8.20 (m, 2H), 8.07 (d, 1H), 7.95 (s, 1H), 7.65 (d, 1H), 7.58 (t, 1H), 7.33 (m, 10H), 7.22 (m, 7H), 5.78 (d, 1H), 3.82 (s, 3H).

B. N-((1R)-1-Phenylethyl)(3-{1-perhydro-2H-pyran-2-yl-5-[1-(triphenylmethyl)(1,2,4-triazol-3-yl)](1H-indazol-3-yl)}phenyl)carboxamide To a stirred solution of methyl 3-{1-perhydro-2H-pyran-2-yl-5-[1-(triphenylmethyl)(1,2,4-triazol-3-yl)]-1H-indazol-3-yl}benzoate (0.400 g, 0.619 mmol) in a tetrahydrofuran/water mixture (2.50 mL/1.00 mL) was added lithium hydroxide monohydrate (0.0780 g, 1.86 mmol) and the mixture heated at 60° C. for 21 h. To this mixture was added tetrahydrofuran (2.00 mL), (R)-(+)-α-methylbenzyl amine (0.240 mL, 1.86 mmol), 1-hydroxybenzotriazole hydrate (0.251 g, 1.86 mmol) and 1-(3-dimethylaminopropyl)-3-ethylcarbodiimide hydrochloride (0.356 g, 1.86 mmol). This mixture was stirred for 18 h at ambient temperature. After the mixture was extracted with ethyl acetate (2×), the combined organic extracts were washed with aqueous saturated sodium bicarbonate, followed by brine, dried over anhydrous sodium sulfate, filtered and evaporated. Purification of the residue by flash chromatography with 30–60% ethyl acetate/hexanes gave the title compound (0.393 g, 86% yield). ES-MS (m/z) 493 [M+1(−Tr)]$^+$ C. [3-(5-(1H-1,2,4-Triazol-5-yl)(1H-indazol-3-yl)phenyl]-N-((1R)-1-phenylethyl)carboxamide To a stirred solution of N-((1R)-1-phenylethyl)(3-{1-perhydro-2H-pyran-2-yl-5-[1-(triphenylmethyl)(1,2,4-triazol-3-yl)](1H-indazol-3-yl)}phenyl)carboxamide (0.393 g, 0.535 mmol) was added 4.0 M hydrochloric acid in dioxane (10.0 mL) and the mixture stirred at ambient temperature for 16 h. The mixture was cooled and poured into saturated sodium bicarbonate (50 mL). The aqueous layer was extracted with ethyl acetate. The combined organic extracts were washed with saturated sodium bicarbonate, dried over anhydrous sodium sulfate, filtered and evaporated. Addition of ethyl acetate (5 mL) initiated crystal growth and the ethyl acetate phase was pipetted off. The crystals were filtered. Purification by preparative HPLC (30–80% acetonitrile/water) followed by washing with saturated sodium bicarbonate and extraction with ethyl acetate gave the title compound (0.0860 g, 39% yield). $^1$H NMR (CD$_3$OD) δ 8.81 (s, 1H), 8.51 (t, 1H), 8.23 (dd, 1H), 8.13 (br d, 1H), 7.93 (d, 1H), 7.70 (m, 2H), 7.47 (m, 2H), 7.35 (m, 2H), 7.25 (m, 1H), 5.28 (q, 1H), 1.59 (d, 3H). ES-MS (m/z) 409 [M+1]$^+$ Example 269

SYNTHESIS OF 1-(5-(1H-1,2,4-TRIAZOL-5-YL) (1H-INDAZOL-3-YL))-3-(2-PIPERIDYLETHOXY)BENZENE

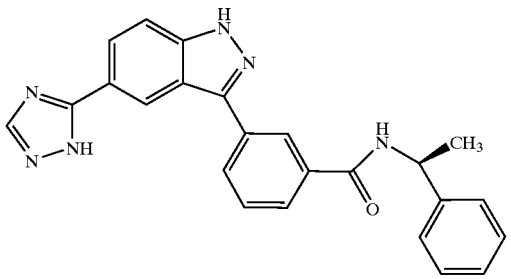

A. Methyl 3-{1-perhydro-2H-pyran-2-yl-5-[1-(triphenylmethyl)(1,2,4-triazol-3-yl)]-1H-indazol-3-yl}benzoate To a stirred solution of 2-{3-bromo-5-[1-(triphenylmethyl)(1,2,4-triazol-3-yl)]-1H-indazoyl}perhydro-2H-pyran (5.92 g, 10.04 mmol) in dimethoxyethane (49.9 mL) was added 3-(carboxymethyl)phenylboronic acid (2.72 g, 15.11 mmol), dichloro[1,1'-bis(diphenylphosphino) ferrocene]palladium (0.822 g, 1.01 mmol), and potassium phosphate (10.64 g, 50.1 mmol) and the mixture was heated at reflux for 60 h. The mixture was diluted with dichloromethane. The organic extracts were washed with saturated sodium bicarbonate, dried over anhydrous sodium sulfate, filtered and evaporated. Purification of the residue by column chromatography with 20–75% ethyl acetate/hexanes furnished the product (6.05 g, 94% yield). $^1$H NMR (CDCl$_3$) δ 8.70 (d, 2H), 8.20 (m, 2H), 8.07 (d, 1H), 7.95 (s, 1H), 7.65 (d, 1H), 7.58 (t, 1H), 7.33 (m, 1OH), 7.22 (m, 7H), 5.78 (d, 1H), 3.82 (s, 3H).

B. N-((1S)-1-phenylethyl)(3-{1-perhydro-2H-pyran-2-yl-5-[1-(triphenylmethyl)(1,2,4-triazol-3-yl)](1H-indazol-3-yl)}phenyl)carboxamide To a stirred solution of methyl 3-{1-perhydro-2H-pyran-2-yl-5-[1-(triphenylmethyl)(1,2,4-triazol-3-yl)]-1H-indazol-3-yl}benzoate (0.400 g, 0.619 mmol) in a tetrahydrofuran/water mixture (2.50 mL/1.00 mL) was added lithium hydroxide monohydrate (0.0780 g, 1.86 mmol) and the mixture heated at 60° C. for 21 h. To this mixture was added tetrahydrofuran (2.00 mL), (S)-(−)-α-methylbenzylamine (0.240 mL, 1.86 mmol), 1-hydroxybenzotriazole hydrate (0.251 g, 1.86 mmol) and 1-(3-dimethylaminopropyl)-3-ethylcarbodiimide hydrochloride (0.356 g, 1.86 mmol). This mixture was stirred for 18 h at ambient temperature. After the mixture was extracted with ethyl acetate (2×), the combined organic extracts were washed with aqueous saturated sodium bicarbonate, followed by brine, dried over anhydrous sodium sulfate, filtered and evaporated. Purification of the residue by flash chromatography with 30–60% ethyl acetate/hexanes gave the title compound (0.368 g, 81% yield). ES-MS (m/z) 493 [M+1(−Tr)]$^+$ C. [3-(5-(1H-1,2,4-Triazol-5-yl)(1H-indazol-3-yl))phenyl]-N-((1S)-1-phenylethyl)carboxamide To a stirred solution of (0.368 g, 0.501 mmol) was added 4.0 M hydrochloric acid in dioxane (10.0 mL) and the mixture stirred at ambient temperature for 16 h. The mixture was cooled and poured into saturated sodium bicarbonate (50 mL). The aqueous layer was extracted with ethyl acetate. The combined organic extracts were washed with saturated aqueous sodium bicarbonate, dried over anhydrous sodium sulfate, filtered and evaporated. Addition of ethyl acetate (5 mL) initiated crystal growth and the ethyl acetate phase was pipetted off. The crystals were filtered. Purification by preparative HPLC (30–80% acetonitrile/water) followed by washing with saturated sodium bicarbonate and extraction with ethyl acetate gave the title compound (0.0884 g, 43% yield). $^1$H NMR (CD$_3$OD) δ 8.80 (s, 1H), 8.51 (s, 1H), 8.23 (d, 1H), 8.12 (br d, 1H), 7.93 (d, 1H), 7.69 (q, 2H), 7.46 (d, 2H), 7.35 (t, 2H), 7.51 (t, 1H), 5.28 (q, 1H), 1.59 (d, 3H). ES-MS (m/z) 409 [M+1]$^+$ Example 270

SYNTHESIS OF [3-(5-(1H-1,2,4-TRIAZOL-5-YL) (1H-INDAZOL-3-YL))PHENYL-ISOINDOLIN-2-YL KETONE

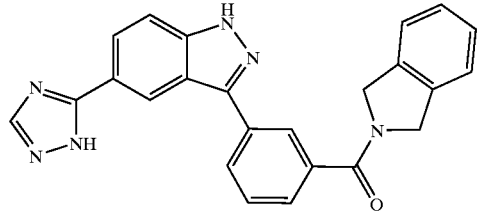

A. Methyl 3-{1-perhydro-2H-pyran-2-yl-5-[1-(triphenylmethyl)(1,2,4-triazol-3-yl)]-1H-indazol-3-yl}benzoate To a stirred solution of 2-{3-bromo-5-[1-(triphenylmethyl)(1,2,4-triazol-3-yl)]-1H-indazoyl}perhydro-2H-pyran (5.92 g, 10.04 mmol) in dimethoxyethane (49.9 mL) was added 3-(carboxymethyl)phenylboronic acid (2.72 g, 15.11 mmol), dichloro[1,1'-bis(diphenylphosphino) ferrocene]palladium (0.822 g, 1.01 mmol), and potassium phosphate (10.64 g, 50.1 mmol) and the mixture was heated at reflux for 60 h. The mixture was diluted with dichloromethane. The organic extracts were washed with saturated sodium bicarbonate, dried over anhydrous sodium sulfate, filtered and evaporated. Purification of the residue by column chromatography with 20–75% ethyl acetate/hexanes furnished the product (6.05 g, 94% yield). $^1$H NMR (CDCl$_3$) δ 8.70 (d, 2H), 8.20 (m, 2H), 8.07 (d, 1H), 7.95 (s, 1H), 7.65 (d, 1H), 7.58 (t, 1H), 7.33 (m, 1OH), 7.22 (m, 7H), 5.78 (d, 1H), 3.82 (s, 3H).

B. Isoindolin-2-yl 3-{1-perhydro-2H-pyran-2-yl-5-[1-(triphenylmethyl)(1,2,4-triazol-3-yl)](1H-indazol-3-yl)}phenyl ketone To a stirred solution of methyl 3-{1-perhydro-2H-pyran-2-yl-5-[1-(triphenylmethyl)(1,2,4-triazol-3-yl)]-1H-indazol-3-yl}benzoate (0.400 g, 0.619 mmol) in a tetrahydrofuran/water mixture (2.50 mL/1.00 mL) was added lithium hydroxide monohydrate (0.0780 g, 1.86 mmol) and the mixture heated at 60° C. for 21 h. To this mixture was added tetrahydrofuran (2.00 mL), isoindoline (0.211 mL, 1.86 mmol), 1-hydroxybenzotriazole hydrate (0.251 g, 1.86 mmol) and 1-(3-dimethylaminopropyl)-3-ethylcarbodiimide hydrochloride (0.356 g, 1.86 mmol). This mixture was stirred for 18 h at ambient temperature. After the mixture was extracted with ethyl acetate (2×), the combined organic extracts were washed with aqueous saturated sodium bicarbonate, followed by brine, dried over anhydrous sodium sulfate, filtered and evaporated. Purification of the residue by flash chromatography with 30–70% ethyl acetate/hexanes gave the title compound (0.240 g, 53% yield). ES-MS (m/z) 491 [M+1(-Tr)]$^+$ C. [3-(5-(1H-1,2,4-Triazol-5-yl)(1H-indazol-3-yl))phenyl-isoindolin-2-yl ketone To a stirred solution of isoindolin-2-yl 3-{1-perhydro-2H-pyran-2-yl-5-[1-(triphenylmethyl)(1,2,4-triazol-3-yl)](1H-indazol-3-yl)}phenyl ketone (0.240 g, 0.327 mmol) was added 4.0 M hydrochloric acid in dioxane (10.0 mL) and the mixture stirred at ambient temperature for 20 h. The mixture was cooled and poured into saturated sodium bicarbonate (50 mL). The aqueous layer was extracted with ethyl acetate. The combined organic extracts were washed with saturated sodium bicarbonate, dried over anhydrous sodium sulfate, filtered and evaporated. Addition of ethyl acetate (5 mL) initiated crystal growth and the ethyl acetate phase was pipetted off. The crystals were filtered. Purification by preparative HPLC (30–80% acetonitrile/water) followed by washing with saturated sodium bicarbonate and extraction with ethyl acetate gave the title compound (0.0458 g, 34% yield). $^1$H NMR (CD$_3$OD) δ 8.74 (s, 1H), 8.50 (br s, 1H), 8.23 (s, 1H), 8.19 (m, 1H), 8.10 (br s, 1H), 7.68 (m, 3H), 7.37 (d, 1H), 7.26 (m, 3H), 5.00 (s, 2H), 4.93 (s, 2H). ES-MS (m/z) 407 [M+1]$^+$ Example 271

SYNTHESIS OF [3-(5-(1H-1,2,4-TRIAZOL-5-YL)(1H-INDAZOL-3-YL))PHENYL]-N-[2-(DIMETHYLAMINO)ETHYL]CARBOXAMIDE

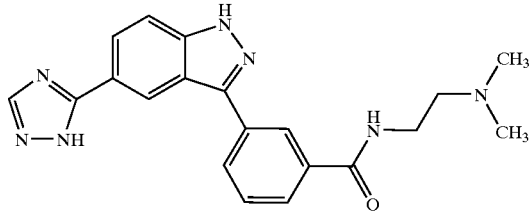

A. Methyl 3-[1-perhydro-2H-pyran-2-yl-5-[1-(triphenylmethyl)(1,2,4-triazol-3-yl]-1H-indazol-3-yl}benzoate To a stirred solution of 2-{3-bromo-5-[1-(triphenylmethyl)(1,2,4-triazol-3-yl)]-1H-indazoyl}perhydro-2H-pyran (5.92 g, 10.04 mmol) in dimethoxyethane (49.9 mL) was added 3-(carboxymethyl)phenylboronic acid (2.72 g, 15.11 mmol), dichloro[1,1'-bis(diphenylphosphino) ferrocene]palladium (0.822 g, 1.01 mmol), and potassium phosphate (10.64 g, 50.1 mmol) and the mixture was heated at reflux for 60 h. The mixture was diluted with dichloromethane. The organic extracts were washed with saturated sodium bicarbonate, dried over anhydrous sodium sulfate, filtered and evaporated. Purification of the residue by column chromatography with 20–75% ethyl acetate/hexanes furnished the product (6.05 g, 94% yield). $^1$H NMR (CDCl$_3$) δ 8.70 (d, 2H), 8.20 (m, 2H), 8.07 (d, 1H), 7.95 (s, 1H), 7.65 (d, 1H), 7.58 (t, 1H), 7.33 (m, 10H), 7.22 (m, 7H), 5.78 (d, 1H), 3.82 (s, 3H).

B. [3-(5-(1H-1,2,4-triazol-5-yl)(1H-indazol-3-yl)phenyl]-N-[2-(dimethylamino)ethyl]carboxamide To a stirred solution of methyl 3-{1-perhydro-2H-pyran-2-yl-5-[1-(triphenylmethyl)(1,2,4-triazol-3-yl)]-1H-indazol-3-yl}benzoate (0.400 g, 0.619 mmol) in a tetrahydrofuran/water mixture (2.50 mL/1.00 mL) was added lithium hydroxide monohydrate (0.0780 g, 1.86 mmol) and the mixture heated at 60° C. for 21 h. To this mixture was added tetrahydrofuran (2.00 mL), N,N-dimethylaminoethyl amine (0.204 mL, 1.86 mmol), 1-hydroxybenzotriazole hydrate (0.251 g, 1.86 mmol) and 1-(3-dimethylaminopropyl)-3-ethylcarbodiimide hydrochloride (0.356 g, 1.86 mmol). This mixture was stirred for 18 h at ambient temperature. To this solution was added 6.0 M hydrochloric acid in dioxane (25.0 mL) and the mixture stirred at ambient temperature for 24 h. The mixture was cooled and poured into saturated aqueous sodium bicarbonate (50 mL). The aqueous layer was extracted with ethyl acetate. The combined organic extracts were washed with saturated sodium bicarbonate, dried over anhydrous sodium sulfate, filtered and evaporated. Addition of ethyl acetate (5 mL) initiated crystal growth and the ethyl acetate phase was pipetted off. The crystals were filtered. Purification by preparative HPLC (30–80% acetonitrile/water) followed by washing with saturated sodium bicarbonate and extraction with ethyl acetate gave the title compound (0.0719 g, 31% yield). $^1$H NMR (CD$_3$OD) δ 8.82 (m, 1H), 8.51 (t, 1H), 8.36 (s, 1H), 8.22 (dt, 1H), 8.14 (dd, 1H), 7.93 (dt, 1H), 7.72 (dd, 1H), 7.67 (t, 1H), 3.59 (t, 2H), 2.65 (t, 2H), 2.35 (s, 6H). ES-MS (m/z) 376 [M+1]$^+$ Example 272

SYNTHESIS OF 1-(5-(1H-1,2,4-TRIAZOL-5-YL)(1H-INDAZOL-3-YL))-3-(2-PIPERIDYLETHOXY)BENZENE

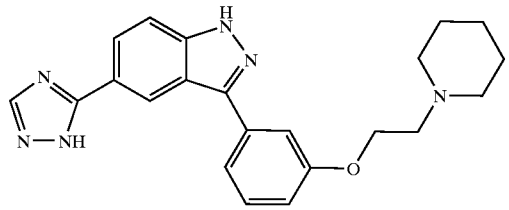

A. 3-{1-perhydro-2H-pyran-2-yl-5-[1-(triphenylmethyl)(1,2,4-triazol-3-yl)]-1H-indazol-3-yl}phenol To a stirred solution of 2-{3-bromo-5-[1-(triphenylmethyl)(1,2,4-triazol-3-yl)]-1H-indazoyl}perhydro-2H-pyran (3.22 g, 5.46 mmol) in dimethoxyethane (27.1 mL) was added 3-hydroxy phenylboronic acid (1.81 g, 8.22 mmol), dichloro[1,1'-bis(diphenylphosphino) ferrocene]palladium (0.447 g, 0.485 mmol), and potassium phosphate (5.78 g, 27.2 mmol) and the mixture was heated at reflux for 48 h. The mixture was diluted with dichloromethane. The organic extracts were washed with saturated sodium bicarbonate, dried over anhydrous sodium sulfate, filtered and evaporated. Purification of the residue by column chromatography with 20–50% ethyl acetate/hexanes furnished the product (3.16 g, 96%, yield). ES-MS (m/z) 362 [M+1(-Tr)]$^+$ B. 1-(5-(1H-1H-1,2,4-triazol-5-yl)(1H-indazol-3-yl))-3-(2-piperidylethoxy)benzene Triphenylphosphine (0.210 g, 0.801 mmol), tetrahydrofuran (0.62 mL), 1-piperidineethanol (0.683 mL, 5.14 mmol) and diethylazodicarboxylate (0.806 mL, 5.12 mmol) were added to 3-{1-perhydro-2H-pyran-2-yl-5-[1-

(triphenylmethyl)(1,2,4-triazol-3-yl)]-1H-indazol-3-yl}phenol (0.654 g, 1.08 mmol). The mixture was stirred at ambient temperature for 23 h and poured into aqueous 6 N hydrochloric acid (30 mL). After stirring at ambient temperature for 4 h, the mixture was extracted with ether (3×). The aqueous fraction was added to aqueous 6 N sodium hydroxide (30 mL) and the pH adjusted to 11. The solution was extracted with ethyl acetate (3×) and the organic fractions were combined and dried over anhydrous sodium sulfate, filtered and evaporated. Purification by preparative HPLC (5–70% acetonitrile/water) followed by washing with saturated sodium bicarbonate and extraction with ethyl acetate gave the title compound (0.248 g, 59% yield). $^1$H NMR (CD$_3$OD) δ 8.72 (m, 1H), 8.35 (s, 1H), 8.09 (m, 1H), 7.64 (m, 2H), 7.56 (s, 1H), 7.50 (m, 1H), 7.04 (m, 1H), 4.26 (s, 2H), 2.87 (s, 2H), 2.62 (s, 4H), 1.65 (s, 4H), 1.50 (s, 2H). ES-MS (m/z) 389 [M+1]$^+$ Example 273

SYNTHESIS OF [3-(5-(1H-1,2,4-TRIAZOL-5-YL)(1H-INDAZOL-3-YL))PHENYL]-N-(1R)INDANYL BENZENE

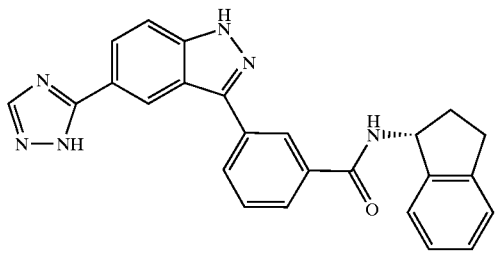

A. Methyl 3-{1-perhydro-2H-pyran-2-yl-5-[1-(triphenylmethyl)(1,2,4-triazol-3-yl)]-1H-indazol-3-yl}benzoate To a stirred solution of 2-{3-bromo-5-[1-(triphenylmethyl)(1,2,4-triazol-3-yl)]-1H-indazoyl}perhydro-2H-pyran (5.92 g, 10.04 mmol) in dimethoxyethane (49.9 mL) was added 3-(carboxymethyl)phenylboronic acid (2.72 g, 15.11 mmol), dichloro[1,1'-bis(diphenylphosphino) ferrocene]palladium (0.822 g, 1.01 mmol), and potassium phosphate (10.64 g, 50.1 mmol) and the mixture was heated at reflux for 60 h. The mixture was diluted with dichloromethane. The organic extracts were washed with saturated sodium bicarbonate, dried over anhydrous sodium sulfate, filtered and evaporated. Purification of the residue by column chromatography with 20–75% ethyl acetate/hexanes furnished the product (6.05 g, 94% yield). $^1$H NMR (CDCl$_3$) δ 8.70 (d, 2H), 8.20 (m, 2H), 8.07 (d, 1H), 7.95 (s, 1H), 7.65 (d, 1H), 7.58 (t, 1H), 7.33 (m, 10H), 7.22 (m, 7H), 5.78 (d, 1H), 3.82 (s, 3H).

B. N-((1R)Indanyl)(3-{1-perhydro-2H-pyran-2-yl-5-[1-(triphenylmethyl)(1,2,4-triazol-3-yl)](1H-indazol-3-yl)}phenyl)carboxamide To a stirred solution of methyl 3-{1-perhydro-2H-pyran-2-yl-5-[1-(triphenylmethyl)(1,2,4-triazol-3-yl)]-1H-indazol-3-yl}benzoate (0.600 g, 0.929 mmol) in a tetrahydrofuran/water mixture (3.75 mL/1.50 mL) was added lithium hydroxide monohydrate (0.117 g, 2.79 mmol) and the mixture heated at 60° C. for 21 h. To this mixture was added tetrahydrofuran (2.00 mL), (R)-(-)-1-aminoindane (0.358 mL, 2.79 mmol), 1-hydroxybenzotriazole hydrate (0.376 g, 2.79 mmol) and 1-(3-dimethylaminopropyl)-3-ethylcarbodiimide hydrochloride (0.534 g, 2.79 mmol). This mixture was stirred for 18 h at ambient temperature. After the mixture was extracted with ethyl acetate (2×), the combined organic extracts were washed with aqueous saturated sodium bicarbonate, followed by brine, dried over anhydrous sodium sulfate, filtered and evaporated. Purification of the residue by flash chromatography with 30–60% ethyl acetate/hexanes gave the title compound (0.625 g, 90% yield). ES-MS (m/z) 505 [M+1(–Tr)]$^+$ C. [3-(5-(1H-1,2,4-triazol-5-yl)(1H-indazol-3-yl))phenyl]-N-((1R)indanyl)benzene To a stirred solution of N-((1R)indanyl)(3-{1-perhydro-2H-pyran-2-yl-5-[1-(triphenylmethyl)(1,2,4-triazol-3-yl)](1H-indazol-3-yl)}phenyl)carboxamide (0.625 g, 0.837 mmol) was added 4.0 M hydrochloric acid in dioxane (15.0 mL) and the mixture stirred at ambient temperature for 18 h. The mixture was cooled and poured into saturated sodium bicarbonate (50 mL). The aqueous layer was extracted with ethyl acetate. The combined organic extracts were washed with saturated sodium bicarbonate, dried over anhydrous sodium sulfate, filtered and evaporated. Addition of ethyl acetate (5 mL) initiated crystal growth and the ethyl acetate phase was pipetted off. The crystals were filtered. Purification by preparative HPLC (30–80% acetonitrile/water) followed by washing with saturated sodium bicarbonate and extraction with ethyl acetate gave the title compound (0.1442 g, 41% yield). $^1$H NMR (CD$_3$OD) δ 8.81 (s, 1H), 8.57 (t, 1H), 8.24 (dt, 1H), 8.13 (br d, 1H), 7.97 (dt, 1H), 7.70 (m, 2H), 7.37 (m, 1H), 7.28 (m, 1H), 7.22 (m, 2H), 5.69 (t, 1H), 3.09 (m, 1H), 2.92 (m, 1H), 2.60 (m, 2H), 2.10 (m, 1H). ES-MS (m/z) 421 [M+1]$^+$ Example 274

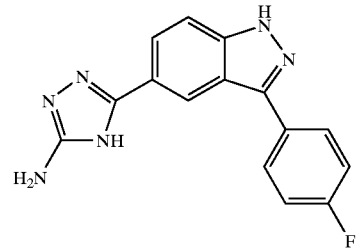

SYNTHESIS OF 5-[3-(4-FLUOROPHENYL)-1H-INDAZOL-5-yl]-4H-1,2,4-TRIAZOLE-3-YL-AMINE

A. N-Amino [3-(4-fluorophenyl)(1H-indazol-5-yl)]carboxamide

To a solution containing tert-butyl carbazate (0.79 g, 0.006 mol) in pyridine (30 mL) was added 1-acetyl-3-(4-fluorophenyl)-1H-indazole-5-carbonyl chloride (1.7 g, 0.005 mol). The reaction mixture was allowed to stir at ambient temperature for 18 hours. Solvent was removed and water was added to the mixture. The reaction was extracted with ethyl acetate. Some 1-acetyl-3-(4-fluorophenyl)-1H-indazole-5-carboxylic acid was isolated. The reaction mixture was treated with an equivalent of tert-butyl carbazate and 1-(3-dimethylaminopropyl)-3-ethylcarbodiimide hydrochloride in dichloromethane and allowed to stir overnight. The reaction was extracted with ethyl acetate. The product was taken up in a solution of 0.3% ammonia in methanol (~50 mL) and allowed to stir overnight. The reaction mixture was extracted with dichloromethane, dried with magnesium sulfate, and concentrated. The material was purified by silica gel chromatography using 2% methanol in dichloromethane. The product was taken up in ethanol and gaseous hydrochloric acid was bubbled into solution. A solid precipitated out and was collected by filtration. This material was dried to provide the title compound (0.91g, 56% yield). ES-MS (m/z) 271 [M+1]+.

B. 5-[3-(4-Fluorophenyl)-1H-indazol-5-yl]-4H-1,2,4-triazole-3-yl-amine

To a solution of N-amino[3-(4-fluorophenyl)(1H-indazol-5-yl)]carboxamide (440 mg, 1.6 mmol) and 3,5-dimethylpyrazole (321 mg, 1.6 mmol) in water (~15 mL) was added triethylamine (0.21 mL, 1.6 mmol). The reaction was heated to reflux overnight. The solvent was removed and the crude reaction mixture was taken up in butanol with molecular sieves. The reaction was heated to reflux overnight. The molecular sieves were removed and the solution concentrated. The crude mixture was purified by preparative HPLC. The material was taken up in ethyl acetate and washed with aqueous sodium bicarbonate. The organic layer was dried with magnesium sulfate, filtered and concentrated to yield the title compound (0.022 g, 4.6% yield). $^1$H NMR (DMSO-$d_6$) δ 13.5 (s, 1H), 12.0 (s, 1H), 8.5 (s, 1H), 8.0 (m, 3H), 7.7 (d, 1H), 7.4 (m, 2H), 6.1 (s, 2H), ES-MS (m/z) 295 [M+1]+.

Example 275

SYNTHESIS OF {5-[3-(4-FLUOROPHENYL)-1H-INDAZOL-5-YL]-4H-[1,2,4]-TRIAZOL-3-YLMETHYL}-DIMETHYL-AMINE

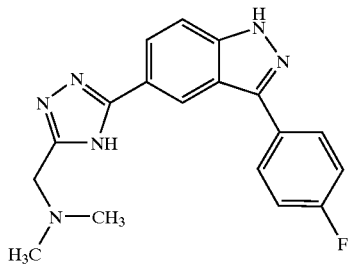

A. N-Amino-2-(dimethylamino)acetamide

A solution of tert-butyl carbazate (376 mg, 2.86 mmol) and N,N-dimethyl glycine hydrochloride (400 mg, 2.86 mmol) in dichloromethane (~5 mL) was allowed to stir in a nitrogen environment at ambient temperature overnight. Solvent was removed. The material was taken up in ethanol and gaseous hydrochloric acid was bubbled into solution. A precipitate crashed out of solution that was collected and determined to be the desired product by NMR. (247 mg, 56% yield). $^1$H NMR (DMSO-$d_6$) 4.1 (s, 2H), 2.9 (s, 6H)

B. {5-[3-(4-Fluoro-phenyl)-1H-indazol-5-yl]-4H-[1,2,4]triazol-3-ylmethyl}-dimethyl-amine To a solution of ethoxy[3-(4-fluorophenyl)(1H-indazol-5-yl)]methanimine hydrochloride (200 mg, 0.62 mmol), N-amino-2-(dimethylamino)acetamide (147.5 mg, 0.95 mmol), and molecular sieves in ethanol was added triethylamine (0.25 mL, 1.86 mmol). The reaction was allowed to stir under a nitrogen atmosphere at 75° C. overnight. The reaction was filtered using a fritted funnel and the filtrate was concentrated. This was purified by semi-prepartive HPLC. The material was taken up in ethyl acetate and washed with aqueous sodium bicarbonate. This organic layer was dried with magnesium sulfate, filtered and concentrated to yield the title compound (192 mg, 23% yield). $^1$H NMR (CD$_3$OD) δ 8.7 (s, 1H), 8.0–8.1 (m, 3H), 7.7 (d, 1H), 7.25 (t, 2H), 4.5 (s, 2H), 3.0 (s, 6H), ES-MS (m/z) 337 [M+1]+.

Example 276

SYNTHESIS OF (3-BENZO[D]FURAN-2-YL(1H-INDAZOL-5-YL))-N-(METHYLETHYL) CARBOXAMIDE

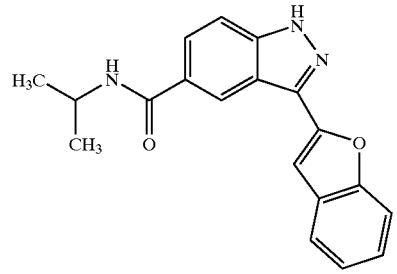

A. Ethyl 3-Benzo[d]furan-2-yl-1-perhydro-2H-pyran-2-yl-1H-indazole-5-carboxylate A solution of ethyl 3-bromo-1-perhydro-2H-pyran-2-yl-1H-indazole-5-carboxylate (500 mg, 1.41 mmol), 2-benzofuran boronic acid (454 mg, 2.82 mmol), [1,1'-bis(diphenylphosphino)-ferrocene]dichloropalladium (II) complex with dichloromethane(163 mg, 0.141 mmol), and potassium phosphate (1.5 g, 7.05 mmol) in ethylene glycol dimethyl ether (12 mL) was allowed to stir under a nitrogen atmosphere at 90° C. overnight. The reaction was extracted with ethyl acetate and purified by silica gel chromatography to yield the title compound (2.0 g, 90% yield). ES-MS (m/z) 391 [M+1]+.

B. 3-Benzo[d]furan-2-yl-1-perhydro-2H-pyran-2-yl-1H-indazole-5-carboxylic acid

To a solution of ethyl-3-benzo[d]furan-2-yl-1-perhydro-2H-pyran-2-yl-1H-indazole-5-carboxylate (500 mg, 1.2 mmol) in a solution of tetrahydrofuran, methanol, and water (2:1:1) (4 mL) was added sodium hydroxide (200 mg, 5 mmol). The reaction was allowed to reflux overnight at 65° C. The solution was neutralized with 1 N HCl and extracted with ethyl acetate to yield the title compound (350 mg, 40% yield). ES-MS (m/z) 363 [M+1]+.

C. (3-Benzo[d]furan-2-yl-1-perhydro-2H-pyran-2-yl(1H-indazol-5-yl))-N-(methylethyl)carboxamide To solution of 3-benzo[d]furan-2-yl-1-perhydro-2H-pyran-2-yl-1H-indazole-5-carboxylic acid (190 mg, 0.52 mmol) and 1-(3-dimethylaminopropyl)-3-ethylcarboimide hydrochloride (109.3 mg, 0.57 mmol) in dimethylformamide was added isopropylamine (48 μL, 0.57 mmol) and the mixture allowed to stir under a nitrogen atmosphere for two days. An additional 2 equivalents of isopropylamine was added to the reaction and allowed to stir for another day. Solvent was removed and the reaction was extracted with ethyl acetate. The crude material was purified by preparative HPLC to yield the title compound (209 mg, 81% yield). ES-MS (m/z) 404 [M+1]+.

D. (3-Benzo[d]furan-2-yl(1H-indazol-5-yl))-N-(methylethyl)carboxamide (3-Benzo[d]furan-2-yl-1-perhydro-2H-pyran-2-yl(1H-indazol-5-yl))-N-(methylethyl)carboxamide (170 mg, 0.41 mmol) was taken up in a solution of 4 N HCl in dioxane and allowed to stir overnight. The reaction was neutralized to pH 7 and extracted with ethyl acetate. The organic layer was dried, filtered, and concentrated to yield the crude material which was purified by semi-preprative HPLC to yield the title compound (9 mg, 7% yield). $^1$H NMR (DMSO-$d_6$) δ 13.8 (s, 1H), 8.7 (s, 1H), 8.4 (d, 1H), 8.0 (d, 1H), 7.6–7.8 (m, 4H), 7.4 (m, 2H), 4.2 (m, 1H), 3.2 (d, 1H), 1.2 (d, 6H)

Example 277

SYNTHESIS OF (3-BENZO[D]FURAN-2-yl(1H-INDAZOL-5-YL))-N-(2-METHOXYETHYL)CARBOXAMIDE

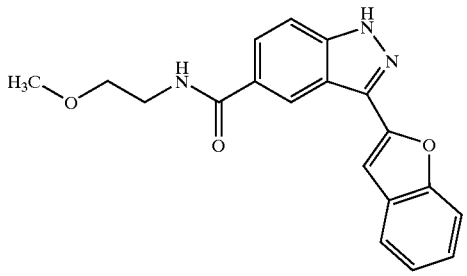

A. (3-Benzo[d]furan-2-yl(1H-indazol-5-yl))-N-(2-methoxyethyl)carboxamide

To a solution of 3-benzo[d]furan-2-yl-1-perhydro-2H-pyran-2-yl-1H-indazole-5-carboxylic acid (218 mg, 0.60 mmol) in N,N-dimethylformamide was added O-benzotriazol-1-yl-N,N,N',N'-tetramethyluronium hexafluorophosphate (250 mg, 0.66 mmol). After stirring for 4 hours the solvent was removed and the material was extracted with ethyl acetate, and the extracts were washed with 1 N HCl, and saturated aqueous sodium carbonate. The organic layer was dried, filtered, and concentrated. The material was taken up in a solution of 4 N HCl in dioxane and stirred for four hours. The reaction was neutralized to pH 7 and extracted with ethyl acetate. The organic layer was dried with magnesium sulfate, filtered, and concentrated. The crude product was purified by semi-preprative HPLC. The product was taken up in ethyl acetate and washed with aqueous sodium bicarbonate (45 mg, 35% yield). $^1$H NMR (DMSO-$d_6$) δ 13.8 (s, 1H), 8.8 (m, 1H), 8.0 (d, 1H), 7.6–7.8 (m, 4H), 7.4 (m, 2H), 3.5 (s, 4H), 3.3 (s, 3H), ES-MS (m/z) 336 [M+1]$^+$.

Example 278

SYNTHESIS OF (3-BENZO[D]FURAN-2-yl(1H-INDAZOL-5-YL))-N-[2-(DIMETHYLAMINO)ETHYL]CARBOXAMIDE

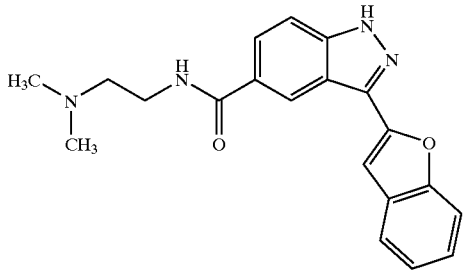

A. (3-Benzo[d]furan-2-yl(1H-indazol-5-yl))-N-[2-(dimethylamino)ethyl]carboxamide The title compound was prepared as described in Example 277 using of 3-benzo[d]furan-2-yl-1-perhydro-2H-pyran-2-yl-1H-indazole-5-carboxylic acid (250 mg, 0.70 mmol), O-benzotriazol-1-yl-N,N,N',N'-tetramethyluronium hexafluorophosphate (292 mg, 0.77 mmol) and N,N-dimethyl ethylene diamine (153 µL, 1.4 mmol); (243 mg, 37% yield). $^1$H NMR (DMSO-$d_6$) δ 13.8 (s, 1H), 8.7 (m, 2H), 8.0 (d, 1H), 7.6–7.8 (m, 4H), 7.4 (m, 2H), 3.3–3.6 (m, 4H), 2.3 (s, 6H), ES-MS (m/z) 349 [M+1]+.

Example 279

SYNTHESIS OF (3-BENZO[D]FURAN-2-yl(1H-INDAZOL-5-YL))-N-[4-(DIMETHYLAMINO)BUTYL]CARBOXAMIDE

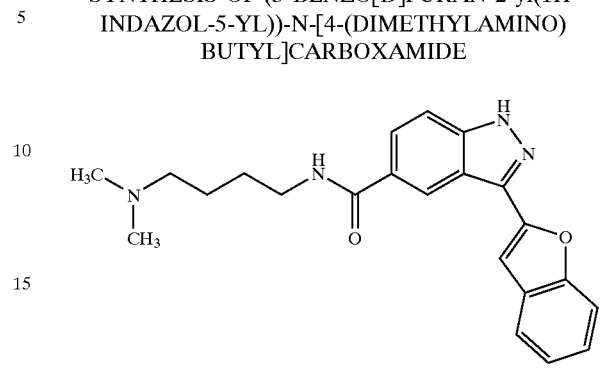

A. (3-Benzo[d]furan-2-yl(1H-indazol-5-yl))-N-[4-(dimethylamino)butyl]carboxamide The title compound was prepared as described in Example 277 using of 3-benzo[d]furan-2-yl-1-perhydro-2H-pyran-2-yl-1H-indazole-5-carboxylic acid (210 mg, 0.58 mmol), O-benzotriazol-1-yl-N,N,N',N'-tetramethyluronium hexafluorophosphate (242 mg, 0.63 mmol) and 4-dimethylaminobutyl amine (139 mg, 1.2 mmol); (67 mg, 30% yield). $^1$H NMR (DMSO-$d_6$) δ 13.8 (s, 1H), 8.7 (m, 2H), 8.0 (d, 1H), 7.6–7.8 (m, 4H), 7.4 (m, 2H), 3.3–3.6 (m, 4H), 2.3 (s, 6H), ES-MS (m/z) 377 [M+1]$^+$.

Example 280

SYNTHESIS OF (3-BENZO[D]FURAN-2-YL(1H-INDAZOL-5-YL))-N-[3-(DIMETHYLAMINO)PROPYL]CARBOXAMIDE

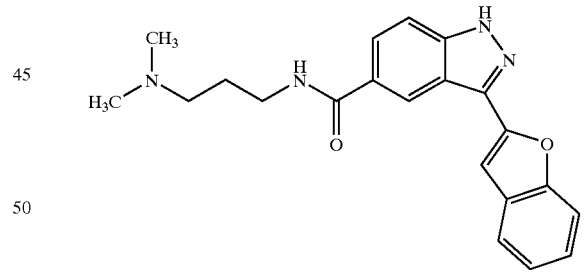

A. (3-Benzo[d]furan-2-yl(1H-indazol-5-yl))-N-[3-(dimethylamino)propyl]carboxamide The title compound was prepared as described in Example 277 using of 3-benzo[d]furan-2-yl-1-perhydro-2H-pyran-2-yl-1H-indazole-5-carboxylic acid (250 mg, 0.7 mmol), O-Benzotriazol-1-yl-N,N,N',N'-tetramethyluronium hexafluorophosphate (292 mg, 0.77 mmol) and 3-dimethylaminopropyl amine (176 µL, 1.4 mmol); (87 mg, 34% yield). $^1$H NMR (DMSO-$d_6$) δ 13.8 (s, 1H), (8.7–8.8 (m, 2H), 8.0 (d, 1H), 7.6–7.8 (m, 4H), 7.3–7.5 (m, 2H), 2.3 (s, 2H), 1.75 (m, 2H), ES-MS (m/z) 363 [M+1]+.

Example 281

SYNTHESIS OF (3-BENZO[D]FURAN-2-YL(1H-INDAZOL-5-YL))-N-(2-METHYLPROPYL) CARBOXAMIDE

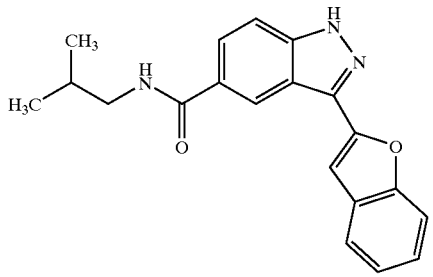

A. (3-Benzo[d]furan-2-yl(1H-indazol-5-yl))-N(2methylpropyl)carboxamide

The title compound was prepared as described in Example 277 using of 3-benzo[d]furan-2-yl-1-perhydro-2H-pyran-2-yl-1H-indazole-5-carboxylic acid (200 mg, 0.55 mmol), O-benzotriazol-1-yl-N,N,N',N'-tetramethyluronium hexafluorophosphate (231 mg, 0.61 mmol) and isobutylamine (60 µL, 0.61 mmol); (71 mg, 19% yield). $^1$H NMR (DMSO-$d_6$) δ 13.8 (s, 1H), 8.7–8.8 (m, 2H), 8.0 (d, 1H), 7.6–7.8 (m, 4H), 7.3–7.5 (m, 2H), 3.2 (m, 2H), 2.0 (m, 1H), 1.0 (d, 6H), ES-MS (m/z) 334 [M+1]+.

Example 282

SYNTHESIS OF (3-BENZO[D]FURAN-2-YL(1H-INDAZOL-5-YL))-N-METHYLCARBOXAMIDE

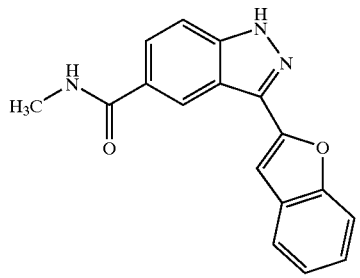

A (3-Benzo[d]furan-2-yl(1H-indazol-5-yl))-N-methylcarboxamide

The title compound was prepared as described in Example 277 using of 3-benzo[d]furan-2-yl-1-perhydro-2H-pyran-2-yl-1H-indazole-5-carboxylic acid (300 mg, 0.82 mmol), O-benzotriazol-1-yl-N,N,N',N'-tetramethyluronium hexafluorophosphate (341 mg, 0.9 mmol) and methylamine (45 mL, 0.9 mmol); (15 mg, 6% yield). RT 7.164 20–100% ODS at 1 mL/min method, ES-MS (m/z) 292 [M+1]+.

Example 283

SYNTHESIS OF 1-({5-[3-(4-FLUOROPHENYL)-1H-INDAZOL-5-YL]-4H-1,2,4-TRIAZOL-3-YL}METHYL)PIPERIDIN-4-OL

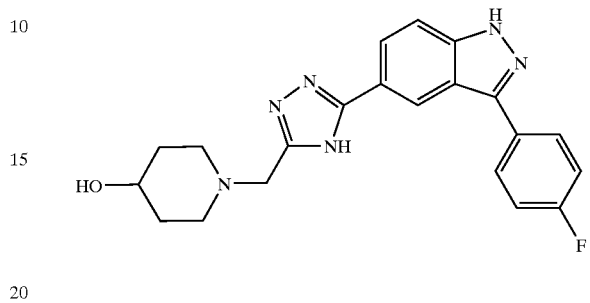

N-Amino-2-(4-hydroxypiperidyn)acetamide

To a solution of 4-hydroxypiperidine (1.1 g, 0.011 mol) and potassium carbonate (1.52 g, 0.011 mol) in acetonitrile (~20 mL) was added methylbromoacetate (0.93 mL, 0.01 mol) and the mixture was stirred in a nitrogen atmosphere overnight. The solvent was removed and the material was taken up in methanol. Gaseous hydrochloric acid was bubbled into solution. The methanol was removed and the material was taken up in tetrahydrofuran and sonicated. A solid was collected using a fritted funnel. The solid was taken up in ethyl acetate. Sodium carbonate was added to the solution and allowed to stir for one hour. The sodium carbonate was removed by filtration and the organic layer was concentrated. A solution of the crude material was made using anhydrous ethanol (~1 mL) and hydrazine (0.167 mL, 5.34 mmol). This was placed in a sealed tube and was heated to 85° C. for 3 hours. The solvent was removed to yield the title compound (0.875 g, 50% yield). $^1$H NMR (DMSO-$d_6$) δ 8.8 (s, 1H), 4.6 (s, 1H), 4.2 (s, 2H), 2.8 (s, 2H), 2.6 (m, 2H), 2.0 (m, 2H), 1.6 (m, 2H), 1.4 (m, 2H).

B. 1-({5-[3-(4-Fluorophenyl)-1H-indazol-5-yl]-4H-1,2,4-triazol-3-yl}methyl)piperidin-4-ol A solution of ethoxy[3-(4-fluorophenyl)(1H-indazol-5-yl)]methanimine hydrochloride (521 mg, 1.63 mmol), N-amino-2-(4-hydroxypiperidyl)acetamide (850 mg, 4.9 mmol), and sodium methoxide (1.2 mL, 4.9 mmol) in methanol (~8 mL) was taken up in a sealed tube and allowed to stir at room temperature for 25 minutes and then heated at 95° C. overnight. The reaction was acidified with hydrochloric acid to neutral pH. The product was extracted using ethyl acetate. The material was concentrated and purified by semipreprative HPLC. The purified material was taken up in ethyl acetate and washed with an aqueous solution of sodium bicarbonate to yield the title compound (47 mg, 7% yield). $^1$H NMR (DMSO-$d_6$) δ 13.4 (br s, 1H), 8.6 (s, 1H), 8.0 (m, 3H), 7.6 (m, 1H), 7.4 (t, 2H), 3.6–3.8 (m, 2H), 3.4 (m, 2H), 3.2 (d, 1H), 2.4 (m, 2H), 2.0 (s, 4H)H, ES-MS (m/z) 393 [M+1]+.

Example 284

SYNTHESIS OF 1-ACETYL-4-({5-[3-(4-FLUOROPHENYL)(1H-INDAZOL-5-YL)](4H-1,2,4-TRIAZOL-3-YL)}METHYL)PIPERAZINE

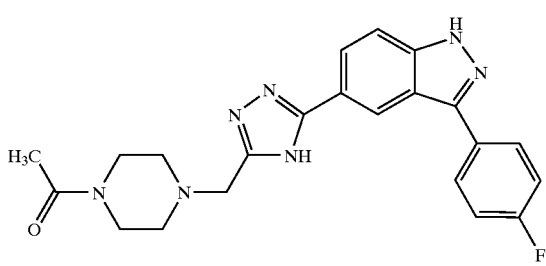

A. 2-(4-Acetylpiperazinyl)-N-Aminoacetamide

The procedure described for Example 283 A was followed using methyl bromoacetate (1.5 g, 0.01 mol), 1-acetyl piperazine (1.4 g, 0.011 mol), and potassium carbonate (1.52 g, 0.011 mol). After one day, an additional 0.3 equivalent of methyl bromoacetate was added to the reaction. The crude material was taken up in approximately 152 mL of ethanol and hydrazine was added to the solution (0.25 mL, 0.008 mol). This was heated in a sealed tube at 85° C. for 4 hours. The solvent was removed to yield the title compound (1.6 g, 80% yield). $^1$H NMR (DMSO-d$_6$) δ 9.0 (s, 1H), 4.2 (br s, 2H), 3.5 (m, 4H), 2.9 (s, 2H), 2.4 (m, 4H), 2.0 (s, 3H).

B. 1-Acetyl-4-({5-[3-(4-Fluorophenyl)(1H-indazol-5-yl)](4H-1,2,4-triazol-3-yl)}methyl)piperazine The procedure described for Example 283 B was followed using ethoxy[3-(4-fluorophenyl)(1H-indazol-5-yl)]methanimine hydrochloride (600 mg, 1.88 mmol), 2-(4-acetylpiperazinyl)-N-aminoacetamide (1.12 g, 5.64 mmol), sodium methoxide (1.3 mL, 5.64 mmol), and methanol (8 mL) to yield the title compound (41 mg, 5% yield). $^1$H NMR (DMSO-d$_6$) δ 13.8 (s, 1H), 8.6 (s, 1H), 8.0 (m, 5H), 7.6 (m, 2H), 7.4 (t, 3H), 4.6 (m, 2H), ES-MS (m/z) 420 [M+1]+.

Example 285

SYNTHESIS OF N-[3-(5-(2H-1,2,3,4-TETRAZOL-5-YL)(1H-INDAZOL-3-YL))PHENYL](2S)-2-HYDROXYPROPANAMIDE

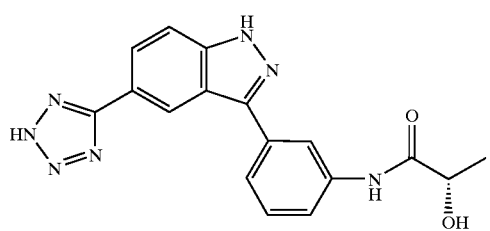

The title compound was isolated during the purification of the compound described in Example 286 (0.024 g, 6.5% yield over 2 steps): $^1$H NMR (CD$_3$OD) δ 8.76 (s, 1H), 8.28 (t, 1H), 8.1 (dd, 1H), 7.8–7.7 (m, 3H), 7.53 (t, 1H), 4.31 (q, 1H), 1.47 (d, 3H); ES-MS (m/z) 350 [M+H]+.

Example 286

SYNTHESIS OF (1S)-1-{N-[3-(5-(2H-1,2,3,4-TETRAZOL-5-YL)(1H-INDAZOL-3-YL))PHENYL]CARBAMOYL}ETHYL ACETATE

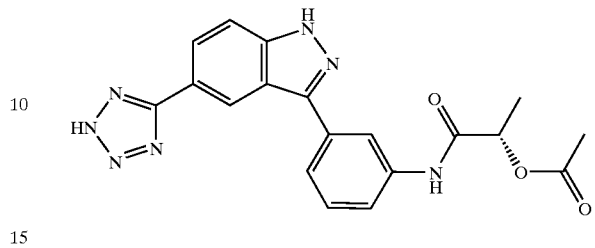

A. (1S)-1-{N-[3-(5-Cyano-1-perhydro-2H-pyran-2-yl(1H-indazol-3-yl))phenyl]carbamoyl}ethyl acetate To a solution of 3-(3-aminophenyl)-1-perhydro-2H-pyran-2-yl-1H-indazole-5-carbonitrile (0.400 g, 1.25 mmol) in dichloromethane (50 mL), was added (S)-(−)-2-acetoxy propionic acid (0.128 mL, 1.38 mmol) and 1-(3-dimethylaminopropyl)-3-ethyl carbodiimide hydrochloride (EDCI) (0.287 g, 1.5 mmol). After overnight reaction at room temperature, 0.6 equivalent of carboxylic acid and EDCI were added. After 12 hours at room temperature, the reaction was complete. The reaction mixture was partitioned between dichloromethane and water. The organic phase was dried under vacuum and the title product was used in the subsequent step without further purification (0.460 g, 85% yield): ES-MS (m/z) 433 [M+H]+.

B. (1S)-1-{N-[3-(5-(2H-1,2,3,4-Tetrazol-5-yl)(1H-indazolL-3-yl))phenyl]carbamoyl}ethyl acetate The title compound was prepared according to the procedure described for the preparation of Example 222 C using (1S)-1-{N-[3-(5-cyano-1-perhydro-2H-pyran-2-yl(1H-indazol-3-yl))phenyl]carbamoyl}ethyl acetate (0.460 g, 1.064 mmol) in toluene (10 mL) and azidotributyltin (1.28 mL, 4.68 mmol). A partial deprotection of the hydroxy group was observed upon hydrolysis of the tin substituent under acidic conditions (HCl gas bubbled through the toluene solution). The 2 components were separated by preparative HPLC (30–90% acetonitrile in water) (0.170 g, 41% yield over 2 steps). About 24 mg of impure hydroxy derivative were isolated: $^1$H NMR (CD$_3$OD) δ 8.7 (s, 1H), 8.2 (t, 1H), 8.1 (dd, 1H), 7.8–7.7 (m, 4H), 7.5 (t, 1H), 5.16 (q, 1H), 2.1 (s, 3H), 1.55 (d, 3H); ES-MS (m/z) 392 [M+H]+.

Example 287

SYNTHESIS OF 3-[3-(3-PYRIDYLCARBONYLAMINO)PHENYL]-1H-INDAZOLE-5-CARBOXAMIDE

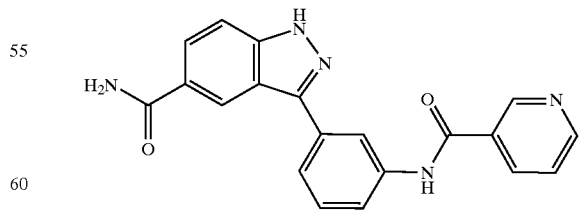

A. 1-Perhydro-2H-pyran-2-yl-3-[3-(3-pyridylcarbonylamino)phenyl]-1H-indazole-5-carboxamide To a solution of 3-(3-aminophenyl)-1-perhydro-2H-pyran-2-yl-1H-indazole-5-carbonitrile (0.150 g, 0.47 mmol) in tetrahydrofuran (5 mL), was added nicotinoyl chloride hydrochloride (0.167 mg, 0.94 mmol) and triethyl amine (0.327 mL, 2.35 mmol). After stirring at room temperature overnight, the crude mixture was partitioned between ethyl acetate and water. The crude compound was isolated as a gummy solid. The yield was not calculated: ES-MS (m/z) 424 [M+H]+.

B. 3-[3-(3-Pyridylcarbonylamino)phenyl]-1H-indazole-5-carboxamide

Precursor, 1-perhydro-2H-pyran-2-yl-3-[3-(3-pyridylcarbonylamino) phenyl]-1H-indazole-5-carboxamide, was dissolved in ethanol (4 mL). Hydrogen peroxide (4 mL, 30% wt) was added to the solution followed by 0.200 mL of 6.0 N NaOH aqueous solution. The suspension turned white upon heating to 60° C. for 3.5 h. The reaction could not be driven to completion even after addition of excess reagent. The reaction mixture was neutralized. A white precipitate formed upon addition of water. The solid was collected by filtration and dried in a vacuum oven at 40° C. overnight. A suspension of this solid in 10 mL of toluene was cooled to 0° C. HCl gas was bubbled through the suspension for 10 min before stirring the flask content at room temperature for 2 hours. The desired product was purified using preparatory HPLC (0.049 g, 30% yield over 3 steps): 1H NMR (CD3OD) 9.2 (d, 1H), 8.77 (dd, 1H), 8.7 (s, 1H), 8.4 (s, 1H), 8.39 (dt, 1H), 7.9–7.8 (m, 3H), 7.6–7.5 (m, 4H); ES-MS (m/z) 358 [M+H]+.

Example 288

N-[3-(5-(1H-1,2,4-TRIAZOL-3-YL)(1H-INDAZOL-3-YL))PHENYL]-3-PIPERIDYLPROPANAMIDE

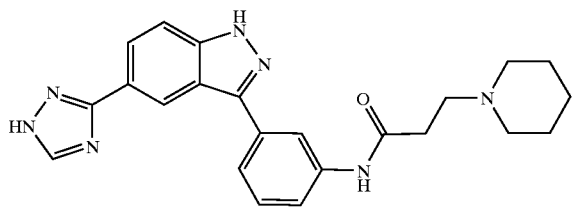

A. N-(3-{1-Perhydro-2H-pyran-2-yl-5-[1-(triphenylmethyl)(1,2,4-triazol-3-yl)](1H-indazol-3-yl}phenyl)-3-piperidylpropanamide To a solution of 3-piperidyl propanoic acid (0.125 g, 0.796 mmol) in 7 mL of dichloromethane was added 1-(3-dimethylaminopropyl)-3-ethyl carbodiimide hydrochloride (0.190 g, 0.99 mmol). After 10 min at room temperature, 3-{1-perhydro-2H-pyran-2-yl-5-[1-(triphenylmethyl)(1,2,4-triazol-3-yl)]-1H-indazol-3-yl}phenylamine (0.200 g, 0.59 mmol) was then added as a solid followed by 2 mL of dimethyl formamide. The reaction mixture was stirred at room temperature overnight. The completion of the reaction mixture was achieved after reacting an additional equivalent of reagents and stirring at room temperature for 24 hours. The crude mixture was partitioned between water and dichloromethane. The crude was not purified (yield not calculated). ES-MS (m/z) 742 [M+H]+.

B. N-[3-(5-(1H-1,2,4-triazol-3-yl)(1H-indazol-3-yl))phenyl]-3-piperidylpropanamide N-(3-{1-perhydro-2H-pyran-2-yl-5-[1-(triphenylmethyl)(1,2,4-triazol-3-yl)](1H-indazol-3-yl)}phenyl)-3-piperidylpropanamide was 4 mL of 4.0 N HCl in 1,4-dioxane. The reaction mixture was stirred at room temperature overnight. After neutralization with a saturated aqueous solution of NaHCO3, the crude reaction mixture was evaporated to dryness and purified by preparative HPLC (0.106 g, 38% yield over 2 steps): 1H NMR (CD3OD) δ 8.73 (br s, 1H), 8.35 (br s, 1H), 8.17 (t, 1H), 8.1 (dd, 1H), 7.7–7.6 (m, 3H), 7.5 (t, 1H), 2.8 (t, 2H), 2.66 (t, 2H), 2.58 (br s, 4H), 1.65 (m, 4H), 1.5 (m, 2H); ES-MS (m/z) 416 [M+H]+.

Example 289

N-[3-(5-(1H-1,2,4-TRIAZOL-3-YL)(1H-INDAZOL-3-YL))PHENYL]-2-HYDROXYPROPANAMIDE

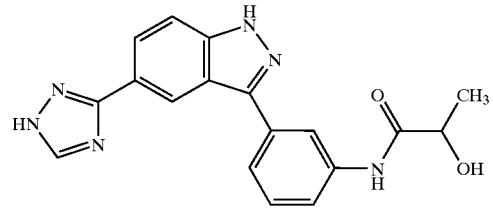

A. [N-(3-[1-Perhydro-2H-pyran-2-yl-5-[1-(triphenylmethyl)(1,2,4-triazol-3-yl)](1H-indazol-3-yl)}phenyl)carbamoyl]ethylacetate To a solution of 3-{1-perhydro-2H-pyran-2-yl-5-[1-(triphenylmethyl)(1,2,4-triazol-3-yl)]-1H-indazol-3-yl}phenylamine (0.502 g, 0.83 mmol), in dichloromethane (9 mL), were added, 2-acetoxy propionic acid (0.100 mL, 0.916 mmol) and 1-(3-dimethylaminopropyl)-3-ethyl carbodiimide hydrochloride (0.191 g, 0.996 mmol). The addition of 1.2 equivalents of acid and coupling agent was necessary to drive the reaction to completion after 48 h at room temperature. The crude reaction mixture was partitioned between dichloromethane and water. The crude was used without further purification and the yield was not calculated (0.141 g, 99% yield): ES-MS (m/z) 717 [M+H]+.

B. N-[3-(5-(1H-1,2,4-Triazol-3-yl)(1H-indazol-3-yl))phenyl]-2-hydroxypropanamide The intermediate, [N-(3-{1-perhydro-2H-pyran-2-yl-5-[1-(triphenylmethyl)(1,2,4-triazol-3-yl)](1H-indazol-3-yl)}phenyl)carbamoyl]ethylacetate, was suspended in 20 mL of toluene and HCl gas was bubbled through the reaction mixture for 15 min. The heterogeneous reaction was stirred at room temperature overnight. The solid was collected by filtration and was washed with small portions of toluene. The title compound was purified by preparative HPLC (30–90% acetonitrile in water) (0.072 g, 27% yield over two steps) 1H NMR (CD3OD) δ 8.7, 8.5 (br s, 1H), 8.2, 8.1 (s, 2H), 7.87 (d, 1H), 7.7 (br d, 1H), 7.5 (t, 1H), 4.2 (q, 1H), 1.47 (d, 3H); ES-MS (m/z) 349 [M+H]+.

Example 290

3-[3-(2-METHOXYACETYLAMINO)PHENYL]-1H-INDAZOLE-5-CARBOXAMIDE

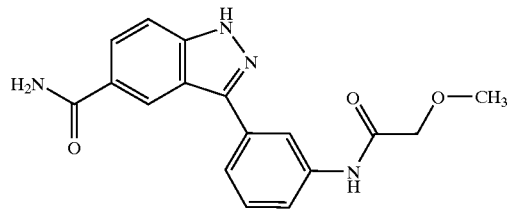

A. 3-Bromo-1-perhydro-2H-pyran-2-yl-1H-indazole-5-carboxamide

To a solution of 3-bromo-1-perhydro-2H-pyran-2-yl-1H-indazole-5-carbonitrile (2.7 g, 8.82 mmol), in ethanol (20 mL), was added 20 mL of a 30% commercial solution of hydrogen peroxide and 2.8 mL of 6.0 N aqueous NaOH solution. The reaction mixture was stirred at room temperature. After 3 hours, the reaction mixture was acidified with 6.0 N HCl aqueous solution. Water was added to aid precipitation. The solid was collected by filtration and was washed with small portions of water. The solid was dried under vacuum (2.77 g, 97% yield): ES-MS (m/z) 325 [M+H]$^+$.

B. 3-(3-Aminophenyl)-1-perhydro-2H-pyran-2-yl-1H-indazole-5-carboxamide

To a solution of 3-bromo-1-perhydro-2H-pyran-2-yl-1H-indazole-5-carboxamide (0.500 g, 1.54 mmol) in 15 mL of ethylene glycol dimethyl ether, was added 3-aminophenyl boronic acid (0.358 g, 2.31 mmol), [1,1'-bis(diphenylphosphino)-ferrocene] complex with dichloromethane (1:1) (0.178 g, 0.098 mmol), and potassium phosphate (1.63 g, 7.7 mmol). The reaction mixture was heated to reflux temperature of the solvent for 18 hours. The solvent was then removed under reduced pressure and the crude was partitioned between ethyl acetate and water. The title compound was purified by column chromatography (SiO$_2$, 6% MeOH in CH$_2$Cl$_2$) (0.457 g, 88% yield): ES-MS (m/z) 337 [M+H]$^+$.

C. 3-[3-(2-Methoxyacetylamino)phenyl]-1-perhydro-2H-pyran-2-yl-1H-indazole-5-carboxamide To a solution of 3-(3-aminophenyl)-1-perhydro-2H-pyran-2-yl-1H-indazole-5-carboxamide in tetrahydrofuran (6 mL), was added 2-methoxyacetyl chloride (0.065 mL, 0.713 mmol) followed by triethyl amine (0.414 mL, 2.97 mmol). A small volume of dimethyl formamide was added to aid solubility (1 mL). The reaction mixture was stirred at room temperature for 2 hours. The solvent was removed under reduced pressure and he crude was partitioned between ethyl acetate and water. The crude product was isolated as an oily yellow residue (yield not calculated): ES-MS (m/z) 409 [M+H]$^+$.

D. 3-[3-(2-Methoxyacetylamino)phenyl]-1H-indazole-5-carboxamide

Through a suspension of 3-[3-(2-methoxyacetylamino)phenyl]-1-perhydro-2H-pyran-2-yl-1H-indazole-5-carboxamide in toluene (10 mL), HCl gas was bubbled for 20 min. After 6 hours at room temperature, the reaction was complete. The pH of the reaction mixture was neutralized using a saturated aqueous NaHCO$_3$ solution before the solvent was removed under reduced pressure. The title compound was isolated as a white solid after purification by preparative HPLC (30–100% acetonitrile/water) (0.078 g, 40.5% yield): $^1$H NMR (CD$_3$OD) δ 8.63 (dd, 1H), 8.19 (t, 1H), 7.94 (dd, 1H), 7.74 (td, 2H), 7.60 (dd, 1H), 7.49 (t, 1H), 4.06 (s, 2H), 3.49 (s, 3H); ES-MS (m/z) 325 [M+H]$^+$.

Example 291

3-[3-(4-PIPERIDYLCARBOXYAMINO)PHENYL]-1H-INDAZOLE-5-CARBOXAMIDE

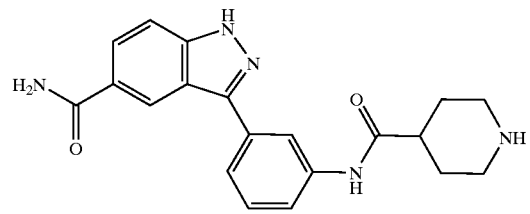

A. tert-Butyl 4-{N-[3-(5-cyano-1-perhydro-2H-pyran-2-yl-1H-indazol-3-yl)phenyl]carbamoyl}piperidinecarboxylate A solution of 1-[(tert-butyl)oxycarbonyl]piperidine-4-carboxylic acid (0.317 g, 1.38 mmol) in 12 mL of dichloromethane was added 1-(3-dimethylaminopropyl)-3-ethyl carbodiimide hydrochloride (EDCI) (0.287 g, 1.5 mmol) The solution was stirred at room temperature for 10 min before 3-(3-aminophenyl)-1-perhydro-2H-pyran-2-yl-1H-indazole-5-carbonitrile (0.400 g, 1.25 mmol) was added as a solid. (A small volume of dichloromethane was used to rinse the flask containing the core). The reaction was stirred at room temperature for 12 hours. Even after addition of 0.5 equivalent of carboxylic acid and EDCI, the reaction could not be driven to completion. The crude mixture was partitioned between water and dichloromethane. The crude was isolated as a brown oil. The yield was not calculated.

B. tert-Butyl 4-{N-[3-(5-carbamoyl-1-perhydro-2H-pyran-2-yl-1H-indazol-3-yl)phenyl]carbamoyl}piperidinecarboxylate To a solution of tert-butyl 4-{N-[3-(5-cyano-1-perhydro-2H-pyran-2-yl-1H-indazol-3-yl)phenyl]carbamoyl}piperidinecarboxylate in 3 mL of ethanol, was added 3 mL of 30% commercially available H$_2$O$_2$ solution followed by 0.280 mL of 6.0 N aqueous NaOH solution. Within 30 min, the formation of an abundant white precipitate was observed. The mixture was acidified using a 6.0 N aqueous solution of HCl. Upon addition of water (20 mL), the formation of a precipitate was observed. The solid was collected by filtration, washed with small portions of water and dried in a vacuum oven overnight. The desired product was isolated as a pure white solid (0.277 g, 40% over 2 steps): ES-MS (m/z) 548 [M+H]$^+$.

C. 3-[3-(4-Piperidylcarboxyamino)phenyl]-1H-indazole-5-carboxamide tert-Butyl 4-{N-[3-(5-carbamoyl-1-perhydro-2H-pyran-2-yl-1H-indazol-3-yl)phenyl]carbamoyl}piperidinecarboxylate was suspended in 10 mL of toluene and HCl gas was bubbled through for 15 min. The reaction mixture was stirred at room temperature overnight. The solvent was removed under reduced pressure after neutralization. Purification was performed by preparatory HPLC. (0.015 g, 8% yield): $^1$H NMR (CD$_3$OD) δ 8.59 (dd, 1H), 7.91 (d, 1H), 7.56 (d, 1H), 7.29–7.20 (m, 3H), 6.73 (dt, 1H), 3.61 (t, 2H), 3.36 (s, 3H), 3.33 (t, 2H); ES-MS (m/z) 311 [M+H]$^+$.

Example 292

(1S)-1-{N-[3-(5-CARBAMOYL(1H-INDAZOL-3-YL))PHENYL]CARBAMOYL}ETHYL ACETATE

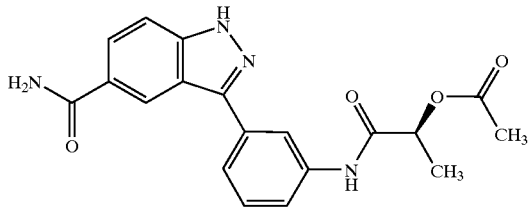

A. (1S)-1-{N-[3-(5-Carbamoyl-1-perhydro-2H-pyran-2-yl (1H-indazol-3-yl))phenyl]carbamoyl}ethyl acetate A solution of (S)-2-acetyl propionic acid (0.118 g, 0.89 mmol) in 82 mL of dichloromethane was added 1-(3-dimethylaminopropyl)-3-ethyl carbodiimide hydrochloride (EDCI) (0.212 g, 1.11 mmol). The solution was stirred at room temperature for 10 min before 3-(3-aminophenyl)-1-perhydro-2H-pyran-2-yl-1H-indazole-5-carboxamide (0.250 g, 0.74 mmol) was added as a solid. (A small volume of dichloromethane was used to rinse the flask containing the core). The reaction was stirred at room temperature for 12 hours. The reaction mixture was partitioned between water and dichloromethane. The crude product was isolated as a brown oil and the yield was not calculated. ES-MS (m/z) 451 [M+H]+.

B. (1S)-1-{N-[3-(5-Carbamoyl (1H-indazol-3-yl))phenyl] carbamoyl}ethyl acetate

In a suspension of (1S)-1-{N-[3-(5-carbamoyl-1-perhydro-2H-pyran-2-yl(1H-indazol-3-yl))phenyl]carbamoyl}ethyl acetate in 20 mL of toluene was bubbled HCl gas for 20 min. The reaction was then stirred at room temperature overnight. The mixture was neutralized with an aqueous saturated solution of NaHCO3 and was concentrated to dryness under reduced pressure. After preparatory HPLC purification, the desired product was still contaminated with de-acetylated product. The mixture was dissolved in 10 mL of tetrahydrofuran and 2 mL of 2.0 N aqueous NaOH were added. After stirring at room temperature for 12 hours, the ratio was close to 1:1. The 2 species were separated via preparatory HPLC (0.043 g, 16% over 3 steps): 1H NMR (DMSO d6) δ 13.47 (s, 1H), 10.25 (s, 1H), 8.6 (s, 1H), 8.2 (s, 1H), 8.1 (br s, 1H), 7.94 (dd, 1H), 7.76 (dt, 2H), 7.6 (d, 1H), 7.5 (t, 1H), 7.34 (br s, 1H), 5.07 (q, 1H), 2.1 (s, 32H), 1.46 (d, 3H); ES-MS (m/z) 367 [M+H]+.

Example 293

3-{3-[(2-METHOXYETHYL)AMINO]PHENYL}-1H-INDAZOLE-5-CARBOXAMIDE

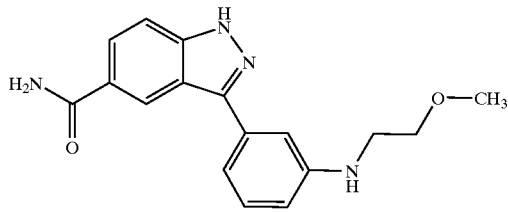

A. 3-{3-[(2-Methoxyethyl)amino]phenyl}-1-perhydro-2H-pyran-2-yl-1H-indazole-5-carboxamide A solution of 3-(3-aminophenyl)-1-perhydro-2H-pyran-2-yl-1H-indazole-5-carboxamide (0.200 g, 0.59 mmol) in 6 mL of dimethylformamide was prepared. An excess of K2CO3 was added as a solid (200 mg) followed by 2-bromo-1-methoxyethane (0.062 mL, 0.65 mmol). The reaction was warmed to 40° C. for 12 hours, then 60° C. for 4 hours. Only a conversion of about 50% was observed, and at that point, some degree of decomposition. The reaction mixture was diluted with water and the crude product was extracted with ethyl acetate. Purification using column chromatography (4% MeOH in CH2Cl2) was not satisfactory but the enriched fractions were carried on to the next step. The yield was not calculated; ES-MS (m/z) 395 [M+H]+.

B. 3-{3-[(2-Methoxyethyl)amino]phenyl}-1H-indazole-5-carboxamide

In a suspension of 3-{3-[(2-methoxyethyl)amino]phenyl}-1-perhydro-2H-pyran-2-yl-1H-indazole-5-carboxamide in 20 mL of toluene was bubbled HCl gas for 20 min. The mixture was then stirred at room temperature overnight. The mixture was neutralized with an aqueous saturated solution of NaHCO3 and was concentrated to dryness under reduced pressure. After 2 preparatory HPLC purifications, a small amount of pure material was isolated. (0.015 g, 8% over 2 steps): 1H NMR (CD3OD) δ 8.59 (dd, 1H), 7.91 (d, 1H), 7.56 (ds, 1H), 7.29–7.20 (m, 3H), 6.73 (dt, 1H), 3.61 (t, 2H), 3.36 (s, 3H), 3.334 (t, 2H); ES-MS (m/z) 311 [M+H]+.

Example 294

3-[3-(3-PIPERIDYLPROPANOYLAMINO) PHENYL]-1H-INDAZOLE-5-CARBOXAMIDE

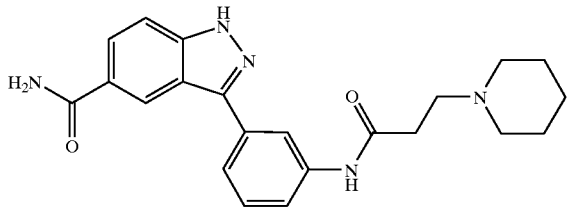

A. 1-Perhydro-2H-pyran-2-yl-3-[3-(3-piperidylpropanoylamino)phenyl]-1H-indazole-5-carboxamide To a solution of 3-piperidylpropanoic acid (0.102 g, 0.65 mmol) in 6 mL of dichloromethane was added 1-(3-dimethylaminopropyl)-3-ethyl carbodiimide hydrochloride (EDCI) (0.135 g, 0.71 mmol). After 10 min at room temperature, 3-(3-aminophenyl)-1-perhydro-2H-pyran-2-yl-1H-indazole-5-carboxamide (0.200 g, 0.59 mmol) was then added as a solid followed by 2 mL of dimethyl formamide. The reaction mixture was stirred at room temperature overnight. The crude mixture was partitioned between water and ethyl acetate. The crude was not purified (yield not calculated). ES-MS (m/z) 476 [M+H]+.

B. 3-[3-(3-Piperidylpropanoylamino)phenyl]-1H-indazole-5-carboxamide

1-Perhydro-2H-pyran-2-yl-3-[3-(3-piperidylpropanoylamino)phenyl]-1H-indazole-5-carboxamide was suspended in 20 mL of toluene and HCl gas was bubbled through for 15 min. The reaction mixture became gummy and was stirred at room temperature overnight. The supernatant solution was decanted and the residue was purified by preparatory HPLC. (0.017 g, 7% yield over 2 steps): 1H NMR (DMSO d6) δ 13.48 (s, 1H), 10.38 (s, 1H), 8.62 (s, 1H), 8.1 (s, 1H), 7.94 (dd, 1H), 7.94 (dd, 1H), 7.73 (d, 1H), 7.62 (d, 1H), 7.48 (t, 1H), 7.36 (br s, 1H), 2.65 (m, 2H), 2.5 (m, 2H), 2.4 (br s, 4H), 1.52 (m, 4H), 1.40 (m, 2H); ES-MS (m/z) 392 [M+H]+.

Example 295

3-[3-(2-FURYLCARBONYLAMINO)PHENYL]-1H-INDAZOLE-5-CARBOXAMIDE

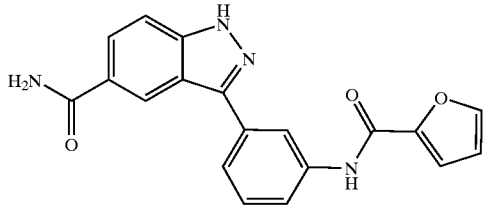

A. 3-[3-(2-Furylcarbonylamino)phenyl]-1-perhydro-2H-pyran-2-yl-1H-indazole-5-carboxamide To a solution of 3-(3-aminophenyl)-]-perhydro-2H-pyran-2-yl-1H-indazole-5-carboxamide (0.200 g, 0.59 mmol) in 6 mL of tetrahydrofuran was added 2-furanoic acid chloride (0.064 mL, 0.65 mmol), followed by triethyl amine (0.091 mL, 0.65 mmol). The reaction was stirred at room temperature overnight. The crude mixture was partitioned between water and ethyl acetate. The extracts were concentrated to dryness. The crude was not purified (yield not calculated). ES-MS (m/z) 431 [M+H]+.

B. 3-[3-(2-Furylcarbonylamino)phenyl]-1H-indazole-5-carboxamide

3-[3-(2-Furylcarbonylamino)phenyl]-1-perhydro-2H-pyran-2-yl-1H-indazole-5-carboxamide was suspended in 10 mL of toluene and HCl gas was bubbled through for 15 min. The reaction mixture was stirred at room temperature overnight. After neutralization with aqueous NaHCO$_3$, the reaction mixture was evaporated to dryness and purified by preparatory HPLC. (0.111 g, 54% yield): $^1$H NMR (DMSO d$_6$) δ 13.5 (br s, 1H), 10.3 (s, 1H), 8.64 (s, 1H), 8.4 (s, 1H), 8.11 (br s, 1H), 7.97 (s, 1H), 7.92 (t, 2H), 7.8 (d, 1H), 7.6 (d, 1H), 7.52 (t, 1H), 7.39 (d, 1H), 7.36 (s, 1H), 6.7 (t, 1H); ES-MS (m/z) 347 [M+H]+.

Example 296

N-[3-(5-(1H-1,2,4-TRIAZOL-3-YL)(1H-INDAZOL-3-YL))PHENYL]-2-(DIMETHYLAMINO)ACETAMIDE

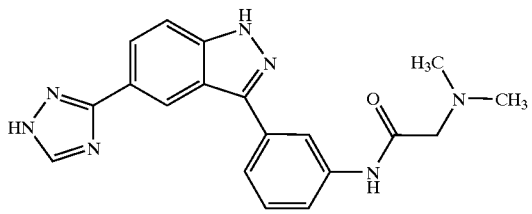

A. 2-(Dimethylamino)-N-(3-{1-perhydro-2H-pyran-2-yl-5-[1-(triphenylmethyl)(1,2,4-triazol-3-yl)](1H-indazol-3-yl)}phenyl)acetamide To a solution of 2-(dimethylamino)acetic acid hydrochloride (0.077 g, 0.55 mmol) in 5 mL of dichloromethane was added 1-(3-dimethylaminopropyl)-3-ethyl carbodiimide hydrochloride (EDCI) (0.105 g, 0.55 mmol) and triethyl amine (0.077 mL, 0.55 mmol). The reaction was stirred at room temperature for 10 min before 3-{1-perhydro-2H-pyran-2-yl-5-[1-(triphenylmethyl)(1,2,4-triazol-3-yl)]-1H-indazol-3-yl}phenylamine (0.300 g, 0.498 mmol), dissolved in 1 mL of dichloromethane was added to the solution. The reaction was stirred at room temperature overnight. Further conversion was promoted by reacting an additional equivalent of reagents and stirring at room temperature for 12 hours. The reaction mixture was then partitioned between water and dichloromethane. The crude material that was obtained from evaporation of the extracts was not purified further. (Yield not calculated) ES-MS (m/z) 688 [M+H]+.

B. N-[3-(5-(1H-1,2,4-Triazol-3-yl)(1H-indazol-3-yl))phenyl]-2-(dimethylamino)acetamide 2-(dimethylamino)-N-(3-{1-perhydro-2H-pyran-2-yl-5-[1-(triphenylmethyl)(1,2,4-triazol-3-yl)](1H-indazol-3-yl)}phenyl)acetamide was dissolved in 4 mL of 4.0 N HCl in 1,4-dioxane and the reaction was stirred at room temperature for 3 hours. After neutralization with aqueous NaHCO$_3$, the reaction mixture was evaporated to dryness and purified by preparatory HPLC. (0.023 g, 13% yield over 2 steps): $^1$H NMR (CD$_3$OD) δ 8.7 (d, 1H), 8.32 (br s, 1H), 8.17 (t, 1H), 8.05 (dd, 1H), 7.7 (t, 2H), 7.6 (dd, 1H), 7.4 (t, 1H), 3.18 (s, 2H), 2.38 (s, 6H); ES-MS (m/z) 362 [M+H]+.

Example 297

N-[3-(5-(1H-1,2,4-TRIAZOL-3-YL)-1H-INDAZOL-3-YL)PHENYL]BUTANAMIDE

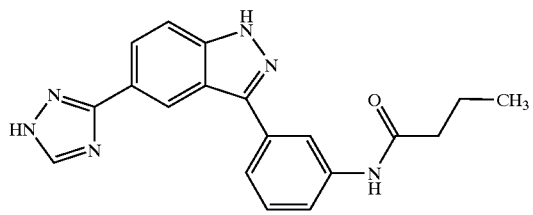

A. N-(3-{1-Perhydro-2H-pyran-2-yl-5-[1-(triphenylmethyl)(1,2,4-triazol-3-yl)]-1H-indazol-3-yl}phenyl)butanamide To a solution of 3-{1-perhydro-2H-pyran-2-yl-5-[1-(triphenylmethyl)(1,2,4-triazol-3-yl)]-1H-indazol-3-yl}phenylamine (0.200 g, 0.33 mmol) in 4 mL of tetrahydrofuran was added butanoyl chloride (0.052 mL, 0.49 mmol) followed by triethyl amine (0.230 mL, 0.167 mmol). The reaction was stirred at room temperature for 15 hours. The reaction mixture was partitioned between water and ethyl acetate. The residue was not purified (yield not calculated). ES-MS (m/z) 673 [M+H]+.

B. N-[3-(5-(1H-1,2,4-Triazol-3-yl)-1H-indazol-3-yl)phenyl]butanamide

N-(3-{1-Perhydro-2H-pyran-2-yl-5-[1-(triphenylmethyl)(1,2,4-triazol-3-yl)]-1H-indazol-3-yl}phenyl)butanamide was dissolved in 4 mL of 4.0 N HCl in 1,4-dioxane and the reaction was stirred at room temperature for 3 hours. After neutralization with aqueous NaHCO$_3$, the reaction mixture was evaporated to dryness and purified by preparatory HPLC. (0.031 g, 27% yield over 2 steps): $^1$H NMR (CD$_3$OD) 8.75 (br s, 1H), 8.25 (br s, 1H), 8.1 (br s, 1H), 7.7–7.6 (m, 3H), 7.5 (t, 1H), 2.4 (t, 2H), 1.72 (sextet, 2H), 1.0 (t, 3H); ES-MS (m/z) 362 [M+H]+.

Example 298

2E-N-[3-(5-(1H-1,2,4-TRIAZOL-3-YL)(1H-INDAZOL-3-YL))PHENYL]-3-PHENYLPROP-2-ENAMIDE

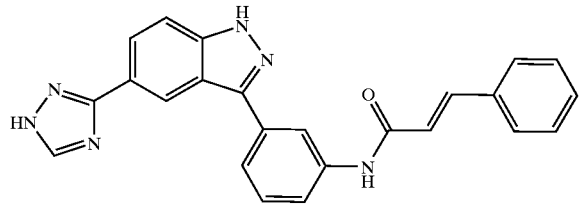

A. (2E)-N-(3-{1-Perhydro-2H-pyran-2-yl-5-[1-(triphenylmethyl)(1,2,4-triazol-3-yl)](1H-indazol-3-yl)}phenyl)-3-phenylprop-2-enamide To a solution of 3-{1-perhydro-2H-pyran-2-yl-5-[1-(triphenylmethyl)(1,2,4-triazol-3-yl)]-1H-indazol-3-yl}phenylamine (0.150 g, 0.248 mmol) in 2.5 mL of tetrahydrofuran was added (2E)-3-phenylprop-2-enoyl chloride (0.062 g, 0.372 mmol) followed by triethyl amine (0.173 mL, 1.24 mmol). The reaction was stirred at room temperature for 2 hours. The reaction mixture was partitioned between water and ethyl acetate. The residue was not purified (yield not calculated). ES-MS (m/z) 733 [M+H]$^+$.

B. 2E-N-[3-(5-(1H-1,2,4-Triazol-3-yl)(1H-indazol-3-yl))phenyl]-3-phenylprop-2-enamide (2E)-N-(3-{1-Perhydro-2H-pyran-2-yl-5-[1-(triphenylmethyl)(1,2,4-triazol-3-yl)](1H-indazol-3-yl)}phenyl)-3-phenylprop-2-enamide was dissolved in 4 mL of 4.0 N HCl in 1,4-dioxane and the reaction was stirred at room temperature overnight. After neutralization with aqueous NaHCO$_3$, the compound precipitated out of solution. The solid was collected by filtration and was purified by preparative HPLC. (0.036 g, 33% yield over 2 steps): $^1$H NMR (CD$_3$OD) δ 8.7 (s, 1H), 8.3 (br s, 1H), 8.1 (br d, 1H), 7.8–7.6 (m, 6H), 7.54 (t, 1H), 7.45–7.4 (m, 3H), 6.85 (d, 1H); ES-MS (m/z) 407 [M+H]$^+$.

Example 299

N-[3-(5-(1H-1,2,4-TRIAZOL-3-YL)(1H-INDAZOL-3-YL))PHENYL]-2-PHENOXYPROPANAMIDE

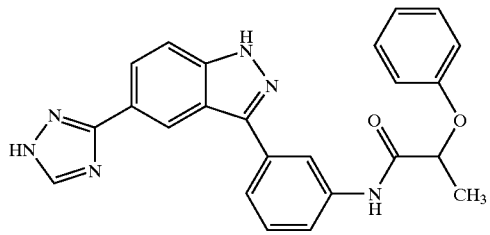

A. N-(3-{1-Perhydro-2H-pyran-2-yl-5-[1-(triphenylmethyl)(1,2,4-triazol-3-yl)](1H-indazol-3-yl)}phenyl)-2-phenoxypropanamide To a solution of 2-phenoxypropanoic acid (0.045 g, 0.274 mmol) in 2.5 mL of dichloromethane was added 1-(3-dimethylaminopropyl)-3-ethyl carbodiimide hydrochloride (EDCI) (0.057 g, 0.298 mmol). The reaction was stirred at room temperature for 10 min before 3-{1-perhydro-2H-pyran-2-yl-5-[1-(triphenylmethyl)(1,2,4-triazol-3-yl)]-1H-indazol-3-yl}phenylamine (0.150 g, 0.248 mmol) dissolved in 1 mL of dichloromethane, was added to the solution. The reaction was stirred at room temperature for 3 hours. The reaction mixture was then partitioned between water and dichloromethane. The crude material that was obtained from evaporation of the extracts was not purified further. (Yield not calculated) ES-MS (m/z) 751 [M+H]$^+$.

B. N-[3-(5-(1H-1,2,4-Triazol-3-yl)(1H-indazol-3-yl))phenyl]-2-phenoxypropanamide N-(3-{1-Perhydro-2H-pyran-2-yl-5-[1-(triphenylmethyl)(1,2,4-triazol-3-yl)](1H-indazol-3-yl)}phenyl)-2-phenoxypropanamide was dissolved in 4 mL of 4.0 N HCl in 1,4-dioxane and the reaction was stirred at room temperature overnight. After neutralization with aqueous NaHCO$_3$, the reaction mixture was evaporated to dryness and purified by preparative HPLC. (0.062 g, 59% yield over 2 steps): $^1$H NMR (CD$_3$OD) δ 8.73 (s, 1H), 8.17 (t, 1H), 8.1 (d, 1H), 7.8–7.67 (m, 3H), 7.51 (t, 1H), 7.34–7.27 (m, 2H), 7.06–6.95 (m, 3H), 4.87 (q, 1H), 1.68 (d, 3H); ES-MS (m/z) 425 [M+H]$^+$.

Example 300

3-{3-[2-(DIMETHYLAMINO)ACETYLAMINO]PHENYL}-1H-INDAZOLE-5-CARBOXAMIDE

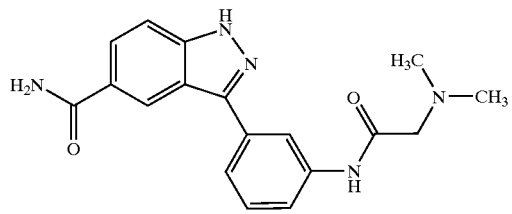

A. 3-{3-[2-(Dimethylamino)acetylamino]phenyl}-1-perhydro-2H-pyran-2-yl-1H-indazole-5-carboxamide To a solution of 2-(dimethylamino)acetic acid hydrochloride (0.091 g, 0.649 mmol) in 6 mL of dichloromethane was added 1-(3-dimethylaminopropyl)-3-ethyl carbodiimide hydrochloride (EDCI) (0.135 g, 0.708 mmol) and triethyl amine (0.090 mL, 0.649 mmol). The reaction was stirred at room temperature for 10 min before 3-(3-aminophenyl)-1-perhydro-2H-pyran-2-yl-1H-indazole-5-carboxamide (0.200 g, 0.59 mmol) dissolved in 1 mL of dichloromethane, was added to the solution. Dimethyl formamide (2 mL) was added to aid solubility. Additional reagent (1 equivalent) was necessary to drive the reaction to completion. The reaction mixture was then partitioned between water and dichloromethane. The crude material that was obtained from evaporation of the extracts was not purified further. (Yield not calculated) ES-MS (m/z) 422 [M+H]$^+$.

B. 3-{3-[2-(Dimethylamino)acetylamino]phenyl}-1H-indazole-5-carboxamide

3-{3-[2-(Dimethylamino)acetylamino]phenyl}-1-perhydro-2H-pyran-2-yl-1H-indazole-5-carboxamide was suspended in toluene (10 mL) and HCl gas was bubbled through the suspension for 15 min. The reaction was then stirred at room temperature overnight. After neutralization with aqueous NaHCO$_3$, the reaction mixture was evaporated to dryness and purified by preparatory HPLC. (0.027 g, 13.5% yield over 2 steps): $^1$H NMR (CD$_3$OD) 8.66 (s, 1H), 8.22 (t, 1H), 7.97 (dd, 1H), 7.75 (t, 2H), 7.63 (d, 2H), 7.51 (t, 1H), 3.21 (s, 2H), 2.41 (s, 6H); ES-MS (m/z) 338 [M+H]$^+$.

Example 301

N-[3-(5-(1H-1,2,4-TRIAZOL-3-YL)(1H-INDAZOL-3-yl))PHENYL]-3,3-DIMETHYLBUTANAMIDE

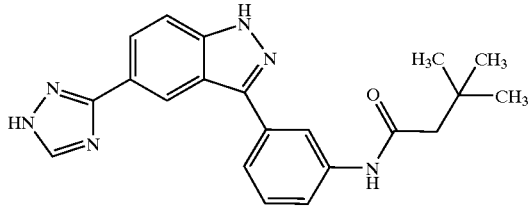

A. 3,3-Dimethyl-N-(3-{1-Perhydro-2H-pyran-2-yl-5-[1-(triphenylmethyl)(1,2,4-triazol-3-yl)](1H-indazol-3-yl}phenyl)butanamide To a solution of 3-{1-Perhydro-2H-pyran-2-yl-5-[1-(triphenylmethyl)(1,2,4-triazol-3-yl)]-1H-indazol-3-yl}phenylamine (0.150 g, 0.248 mmol) in 2.5 mL of tetrahydrofuran was added 3,3-dimethylbutanoyl chloride (0.050 g, 0.372 mmol) followed by triethyl amine (0.173 mL, 1.24 mmol). The reaction was stirred at room temperature for 3 hours. The reaction mixture was partitioned between water and ethyl acetate. The residue was not purified (yield not calculated). ES-MS (m/z) 701 [M+H]$^+$.

B. N-[3-(5-(1H-1,2,4-Triazol-3-yl)(1H-indazol-3-yl))phenyl]-3,3-dimethylbutanamide 3,3-Dimethyl-N-(3-{1-perhydro-2H-pyran-2-yl-5-[1-(triphenylmethyl)(1,2,4-triazol-3-yl)](1H-indazol-3-yl)} phenyl)butanamide was dissolved in 4 mL of 4.0 N HCl in 1,4-dioxane and the reaction was stirred at room temperature overnight. After neutralization with aqueous NaHCO$_3$, the reaction mixture was evaporated to dryness and was purified by preparative HPLC (0.027 g, 29% yield over 2 steps): $^1$H NMR (CD$_3$OD) δ 8.73 (s, 1H), 8.15 (s, 1H), 8.10 (d, 1H), 7.75 (t, 2H), 7.69 (d, 1H), 7.51 (t, 1H), 2.30 (s, 2H), 1.12 (t, 9H); ES-MS (m/z) 375 [M+H]$^+$.

Example 302

N-[3-(5-(1H-1,2,4-TRIAZOL-3-YL)(1H-INDAZOL-3-YL))PHENYL] CYCLOPROPYLCARBOXAMIDE

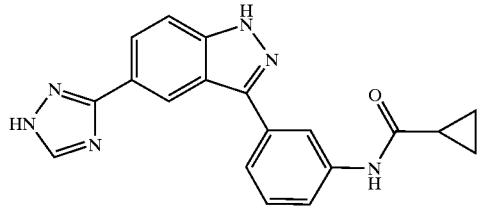

A. Cyclopropyl-N-(3-{1-perhydro-2H-pyran-2-yl-5-[1-(triphenylmethyl)(1,2,4-triazol-3-yl)](1H-indazol-3-yl)} phenyl)carboxamide To a solution of cyclopropanecarboxylic acid (0.024 g, 0.274 mmol) in 2.5 mL of dichloromethane was added 1-(3-dimethylaminopropyl)-3-ethyl carbodiimide hydrochloride (EDCI) (0.057 g, 0.298 mmol). The reaction was stirred at room temperature for 10 min before 3-{1-perhydro-2H-pyran-2-yl-5-[1-(triphenylmethyl)(1,2,4-triazol-3-yl)]-H-indazol-3-yl}phenylamine (0.150 g, 0.248 mmol), dissolved in 1 mL of dichloromethane was added to the solution. The reaction was stirred at room temperature for 2 days while 2 additions of one equivalent of reagents were necessary. The reaction mixture was then partitioned between water and dichloromethane. The crude material that was obtained from evaporation of the extracts was not purified further. (Yield not calculated) ES-MS (m/z) 672 [M+2H]$^+$.

B. N-[3-(5-(1H-1,2,4-Triazol-3-yl)(1H-indazol-3-yl))phenyl]cyclopropylcarboxamide Cyclopropyl-N-(3-{1-perhydro-2H-pyran-2-yl-5-[1-(triphenylmethyl)(1,2,4-triazol-3-yl)](1H-indazol-3-yl)} phenyl)carboxamide was dissolved in 4 mL of 4.0 N HCl in 1,4-dioxane and the reaction was stirred at room temperature overnight. After neutralization with aqueous NaHCO$_3$, the reaction mixture was evaporated to dryness and purified by preparative HPLC. (0.026 g, 30% yield over 2 steps): $^1$H NMR (DMSO d$_6$) δ 8.75 (s, 1H), 8.36 (br s, 1H), 8.24 (s, 1H), 8.12 (d, 1H), 7.76–7.72 (m, 3H), 7.5 (t, 1H), 1.83 (m, 1H), 0.97–0.84 (m, 4H); ES-MS (m/z) 345.

Example 303

N-[3-(5-(1H-1,2,4-TRIAZOL-3-YL)(1H-INDAZOL-3-YL))PHENYL]-2-INDOL-3-YL-2-OXOACETAMIDE

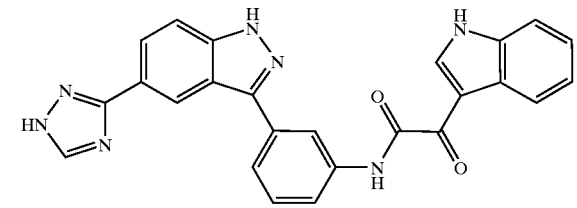

A. 2-Indol-3-yl-2-oxo-N-(3-{1-perhydro-2H-pyran-2-yl-5-[1-(triphenylmethyl)(1,2,4-triazol-3-yl)](1H-indazol-3-yl)} phenyl)acetamide To a solution of 3-{1-perhydro-2H-pyran-2-yl-5-[1-(triphenylmethyl)(1,2,4-triazol-3-yl)]-1H-indazol-3-yl}phenylamine (0.150 g, 0.248 mmol) in 2.5 mL of tetrahydrofuran was added 2-indol-3-yl-2-oxoacetyl chloride (0.103 g, 0.496 mmol), followed by triethyl amine (0.173 mL, 1.24 mmol). The reaction was stirred at room temperature overnight. The reaction mixture was then partitioned between ethyl acetate and water. The crude material that was obtained from evaporation of the extracts was not purified further. (Yield not calculated) ES-MS (m/z) 774 [M+H]$^+$.

B. N-[3-(5-(1H-1,2,4-Triazol-3-yl)(1H-indazol-3-yl))phenyl]-2-indol-3-yl-2-oxoacetamide 2-Indol-3-yl-2-oxo-N-(3-{1-perhydro-2H-pyran-2-yl-5-[1-(triphenylmethyl)(1,2,4-triazol-3-yl)](1H-indazol-3-yl)} phenyl)acetamide was dissolved in 4 mL of 4.0 N HCl in 1,4-dioxane and the reaction was stirred at room temperature overnight. After neutralization with aqueous NaHCO$_3$, the reaction mixture was evaporated to dryness and purified by preparative HPLC. (0.018 g, 16% yield over 2 steps): $^1$H NMR (CD$_3$OD) δ 11.93 (s, 1H), 10.53 (s, 1H), 8.95 (s, 1H), 8.86 (s, 1H), 8.55 (s, 1H), 8.52 (s, 1H), 8.41 (dd, 1H), 8.14 (dd, 1H), 8.0 (d, 1H), 7.89 (d, 1H), 7.75 (d, 1H), 7.64–7.54 (m, 2H), 7.34–7.30 (m, 2 H); ES-MS (m/z) 449.

Example 304

N-[3-(5-(1H-1,2,4-TRIAZOL-3-YL)(1H-INDAZOL-3-YL))PHENYL](6-CHLORO(3-PYRIDYL))CARBOXAMIDE

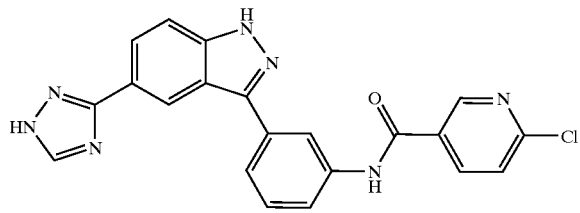

A. 6-Chloro(3-pyridyl))-N-(3-{1-perhydro-2H-pyran-2-yl-5-[1-(triphenylmethyl)(1,2,4-triazol-3-yl)](1H-indazol-3-yl)} phenyl)carboxamide To a solution of 3-{1-perhydro-2H-pyran-2-yl-5-[1-(triphenylmethyl)(1,2,4-triazol-3-yl)]-1H-indazol-3-yl}phenylamine (0.150 g, 0.248 mmol) in 2.5 mL of tetrahydrofuran was added 6-chloropyridine-3-carbonyl chloride (0.087 g, 0.496 mmol), followed by triethyl amine (0.173 mL, 1.24 mmol). The reaction was stirred at room temperature overnight. The reaction mixture was then partitioned between ethyl acetate and water. The crude material that was obtained from evaporation of the extracts was not purified further. (Yield not calculated) ES-MS (m/z) 743 [M+H]$^+$.

B. N-[3-(5-(1H-1,2,4-Triazol-3-yl)(1H-indazol-3-yl))phenyl](6-chloro(3-pyridyl))carboxamide 6-Chloro(3-pyridyl))-N-(3-{1-perhydro-2H-pyran-2-yl-5-[1-(triphenylmethyl)(1,2,4-triazol-3-yl)](1H-indazol-3-yl)} phenyl)carboxamide was dissolved in 4 mL of 4.0 N HCl in 1,4-dioxane and the reaction was stirred at room temperature overnight. After neutralization with aqueous NaHCO$_3$, the reaction mixture was evaporated to dryness and purified by preparative HPLC. Upon neutralization of the fractions, the title compound precipitated out as a white solid that was collected by filtration, washed with water and dried in a vacuum oven. (0.019 g, 18% yield over 2 steps): $^1$H NMR (CD$_3$OD) δ 9.00 (d, 1H), 8.77 (s, 1H), 8.40 (dd, 1H), 8.20 (br s, 1H), 8.15 (dd, 1H), 8.03 (s, 1H), 7.9 (d, 1H), 7.8 (d, 1H), 7.65–7.54 (m, 3H); ES-MS (m/z) 416.

Example 305

N-[3-(5-(1H-1,2,4-TRIAZOL-3-YL)(1H-INDAZOL-3-YL))PHENYL]CYCLOPENTYLCARBOXAMIDE

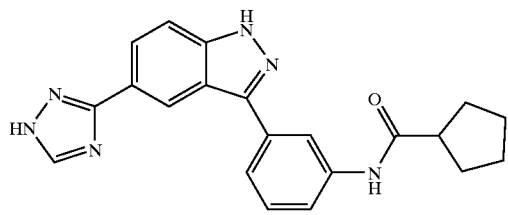

A. Cyclopentyl-N-(3-{1-perhydro-2H-pyran-2-yl-5-[1-(trimethylmethyl)(1,2,4-triazol-3-yl)](1H-indazol-3-yl)}phenyl)carboxamide To a solution of 3-{1-perhydro-2H-pyran-2-yl-5-[1-(triphenylmethyl)(1,2,4-triazol-3-yl)]-1H-indazol-3-yl}phenylamine (0.150 g, 0.248 mmol) in 2.5 mL of tetrahydrofuran was added cyclopentanecarbonyl chloride (0.060 mL, 0.496 mmol), followed by triethyl amine (0.173 mL, 1.24 mmol). Completion of the reaction necessitated the addition of 2 more equivalents of reagents and a total reaction time of 48 hours at room temperature. The reaction mixture was then partitioned between ethyl acetate and water. The crude material that was obtained from evaporation of the extracts was not purified further. (Yield not calculated) ES-MS (m/z) 699 [M+H]$^+$.

B. N-[3-(5-(1H-1,2,4-triazol-3-yl)(1H-indazol-3-yl))phenyl]cyclopentylcarboxamide Cyclopentyl-N-(3-{1-perhydro-2H-pyran-2-yl-5-[1-(triphenylmethyl)(1,2,4-triazol-3-yl)](1H-indazol-3-yl)} phenyl)carboxamide was dissolved in 4 mL of 4.0 N HCl in 1,4-dioxane and the reaction was stirred at room temperature overnight. After neutralization with aqueous NaHCO$_3$, the reaction mixture was evaporated to dryness and purified by preparative HPLC. (0.043 g, 46% yield over 2 steps): $^1$H NMR (CD$_3$OD) δ 8.73 (s, 1H), 8.36 (br s, 1H), 8.17 (s, 1H), 8.10 (d, 1H), 7.76–7.67 (m, 3H), 7.5 (t, 1H), 2.85 (quintet, 1H), 2.04–1.63 (m, 8H); ES-MS (m/z) 373.

Example 306

N-[3-(5-(1H-1,2,4-TRIAZOL-3-YL)(1H-INDAZOL-3-YL))PHENYL]METHANE CARBOXYLIC ACID

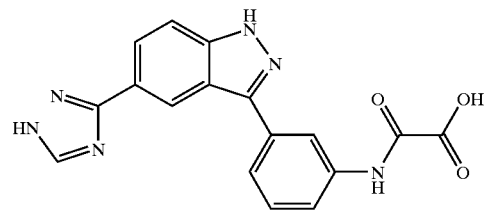

A. Methyl[N-(3-{1-perhydro-2H-pyran-2-yl-5[1-(triphenylmethyl)(1,2,4-triazol-3-yl)]-1H-indazol-3-yl}phenyl)carbamoyl]formate To a solution of 3-{1-perhydro-2H-pyran-2-yl-5-[1-(triphenylmethyl)(1,2,4-triazol-3-yl)]-1H-indazol-3-yl}phenylamine (0.150 g, 0.248 mmol) in 2.5 mL of tetrahydrofuran was added methyl(chlorocarbonyl)formate (0.068 g, 0.496 mmol), followed by triethyl amine (0.173 mL, 1.24 mmol). The reaction was stirred at room temperature overnight. The reaction mixture was then partitioned between ethyl acetate and water. The crude material that was obtained from evaporation of the extracts was not purified further. (Yield not calculated) ES-MS (m/z) 689 [M+H]$^+$.

B. N-[3-(5-(1H-1,2,4-triazol-3-yl)(1H-indazol-3-yl))phenyl]methane carboxylic acid Methyl[N-(3-{1-perhydro-2H-pyran-2-yl-5[1-(triphenylmethyl)(1,2,4-triazol-3-yl)]-1H-indazol-3-yl}phenyl)carbamoyl]formate was dissolved in 4 mL of 4.0 N HCl in 1,4-dioxane and the reaction was stirred at room temperature overnight. These conditions effected deprotection of the triazole and indazole but also hydrolysis of the ester. After neutralization with aqueous NaHCO$_3$, the reaction mixture was evaporated to dryness and purified by preparative HPLC. The pH of the fraction was adjusted to 4 to allow extraction of the pure product in ethyl acetate (0.011 g, 12% yield over 2 steps): $^1$H NMR (CD$_3$OD) δ 8.77 (br s, 1H), 8.43 (br s, 1H), 8.37 (br s, 1H), 8.10 (d, 1H), 7.86 (br s, 2H), 7.70 (d, 1H), 7.57 (t, 1H); ES-MS (m/z) 349 [M+H]$^+$.

Example 307

N-[3-(5-(1H-1,2,4-TRIAZOL-3-YL)(1H-INDAZOL-3-YL))PHENYL]BENZO[b]THIOPHEN-2-CARBOXAMIDE

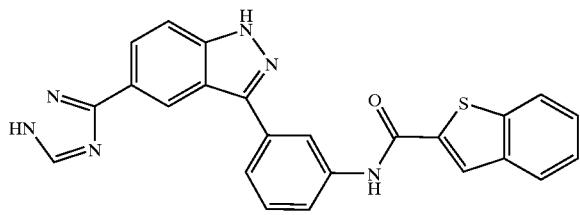

A. Benzo[b]thiophen-2-yl-[N-(3-{1-perhydro-2H-pyran-2-yl-5-[1-(triphenylmethyl)(1,2,4-triazol-3-yl)](1H-indazol-3-yl)}phenyl)carboxamide To a solution of 3-{1-perhydro-2H-pyran-2-yl-5-[1-(triphenylmethyl)(1,2,4-triazol-3-yl)]-1H-indazol-3-yl}phenylamine (0.150 g, 0.248 mmol) in 2.5 mL of tetrahydrofuran was added 2-benzo[b]thiophene-2-carbonyl chloride (0.098 g, 0.496 mmol), followed by triethyl amine (0.173 mL, 1.24 mmol). The reaction was stirred at room temperature overnight. The reaction mixture was then partitioned between ethyl acetate and water. The crude material that was obtained from evaporation of the extracts was not purified further. (Yield not calculated) ES-MS (m/z) 763 [M+H]$^+$.

B. N-[3-(5-(1H-1,2,4-Triazol-3-yl)(1H-indazol-3-yl))phenyl]benzo[b]thiophen-2-carboxamide Benzo[b]thiophen-2-yl-[N-(3-{1-perhydro-2H-pyran-2-yl-5-[1-(triphenylmethyl)(1,2,4-triazol-3-yl)](1H-indazol-3-yl)}phenyl)carboxamide was dissolved in 4 mL of 4.0 N HCl in 1,4-dioxane and the reaction was stirred at room temperature for 3 days. Monitoring of the reaction showed that the removal of the THP group required a reaction time longer than usual. After neutralization with aqueous NaHCO$_3$, the reaction mixture was concentrated, extracted with ethyl acetate and the product was purified by preparative HPLC. (0.027 g, 25% yield over 2 steps): $^1$H NMR (CD$_3$OD) δ 8.81 (s, 1H), 8.38 (t, 1H). 8.27 (s, 1H), 8.12 (d, 1H), 7.99–7.92 (m, 3H), 7.85 (d, 1H), 7.70 (d, 1H), 7.59 (t, 1H), 7.50–7.40 (m, 2H); ES-MS (m/z) 437.

Example 308

N-[3-(5-(1H-1,2,4-TRIAZOL-3-YL)(1H-INDAZOL-3-YL))PHENYL]-2-PYRIDYLCARBOXAMIDE

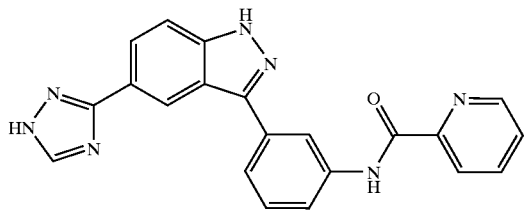

A. [N-(3-{1-perhydro-2H-pyran-2-yl-5-[1-(triphenylmethyl)(1,2,4-triazol-3-yl)(1H-indazol-3-yl)}phenyl)-2-pyridylcarboxamide To a solution of 3-{1-perhydro-2H-pyran-2-yl-5-[1-(triphenylmethyl)(1,2,4-triazol-3-yl)]-1H-indazol-3-yl}phenylamine (0.150 g, 0.248 mmol) in 2.5 mL of tetrahydrofuran was added pyridine-2-carbonyl chloride (0.089 g, 0.496 mmol), followed by triethyl amine (0.173 mL, 1.24 mmol). The reaction was stirred at room temperature overnight. The reaction mixture was then partitioned between ethyl acetate and water. The crude material that was obtained from evaporation of the extracts was not purified further. (Yield not calculated) ES-MS (m/z) 708 [M+H]$^+$.

B. N-[3-(5-(1H-1,2,4-Triazol-3-yl)(1H-indazol-3-yl)phenyl]-2-pyridylcarboxamide

[N-(3-{1-perhydro-2H-pyran-2-yl-5-[1-(triphenylmethyl)(1,2,4-triazol-3-yl)](1H-indazol-3-yl)}phenyl)-2-pyridylcarboxamide was dissolved in 4 mL of 4.0 N HCl in 1,4-dioxane and the reaction was stirred at room temperature overnight. After neutralization with aqueous NaHCO$_3$, the crude product was extracted with ethyl acetate and purified by preparative HPLC. (0.037 g, 39% yield over 2 steps): $^1$H NMR (CD$_3$OD) δ 8.81 (s, 1H), 8.76 (dt, 1H), 8.55 (t, 1H), 8.45 (br s, 1H), 8.25 (dt, 1H), 8.12 (dd, 1H), 8.09 (td, 1H), 8.00 (dt, 1H), 7.85 (dt, 2H), 7.73 (d, 1H), 7.65 (ddd, 1H), 7.59 (t, 1H); ES-MS (m/z) 382 [M+H]$^+$.

Example 309

N-[3-(5-(1H-1,2,4-TRIAZOL-3-YL)(1H-INDAZOL-3-YL))PHENYL]-3-FURYLCARBOXAMIDE

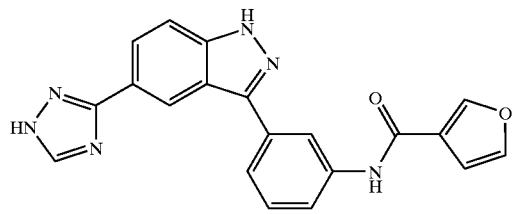

A. 3-Furyl-N-(3-{1-perhydro-2H-pyran-2-yl-5[1-(triphenylmethyl)(1,2,4-triazol-3-yl)](H-indazol-3-yl)}phenyl)carboxamide To a solution of furan-3-carboxylic acid (0.056 g, 0.496 mmol) in 2.5 mL of dichloromethane, was added 1-(3-dimethylaminopropyl)-3-ethyl carbodiimide hydrochloride (EDCI) as a solid (0.105 g, 0.546 mmol). The solution was stirred at room temperature for 10 min before 3-{1-perhydro-2H-pyran-2-yl-5-[1-(triphenylmethyl)(1,2,4-triazol-3-yl)]-1H-indazol-3-yl}phenylamine (0.150 g, 0.248 mmol) dissolved in 1 mL of dichloromethane, was added. The reaction was stirred at room temperature overnight. The reaction mixture was then partitioned between dichloromethane and water. The crude material that was obtained from evaporation of the extracts was not purified further. (Yield not calculated) ES-MS (m/z) 697 [M+H]$^+$.

B. N-[3-(5-(1H-1,2,4-Triazol-3-yl)(1H-indazol-3-yl)phenyl]-3-furylcarboxamide

3-Furyl-N-(3-{1-perhydro-2H-pyran-2-yl-5[1-(triphenylmethyl)(1,2,4-triazol-3-yl)](1H-indazol-3-yl)}phenyl)carboxamide was dissolved in 4 mL of 4.0 N HCl in 1,4-dioxane and the reaction was stirred at room temperature overnight. After neutralization with aqueous NaHCO$_3$, the crude product was extracted in ethyl acetate and was purified by preparative HPLC. (0.034 g, 37% yield over 2 steps): $^1$H NMR (CD$_3$OD) δ 8.79 (s, 1H), 8.28 (d, 2H), 7.88 (d, 1H), 7.81 (d, 1H), 7.70 (d, 1H), 7.65 (t, 1H), 7.55 (t, 1H), 7.01 (d, 1H); ES-MS (m/z) 371.

Example 310

N-[3-(5-(1H-1,2,4-TRIAZOL-3-YL)(1H-INDAZOL-3-YL))PHENYL]-2-HYDROXY-2-PHENYLACETAMIDE

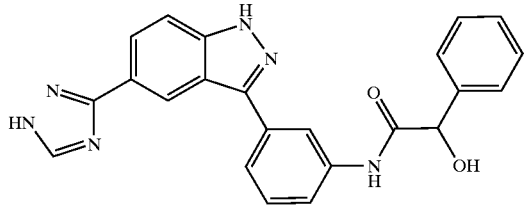

A. N-(3-{1-Perhydro-2H-pyran-2-yl-5-[1-(triphenylmethyl)(1,2,4-triazol-3-yl](1H-indazol-3-yl)}phenyl)carbamoyl]phenylmethyl acetate To a solution of 3-{1-perhydro-2H-pyran-2-yl-5-[1-(triphenylmethyl)(1,2,4-triazol-3-yl)]-1H-indazol-3-yl}phenylamine (0.150 g, 0.248 mmol) in 2.5 mL of tetrahydrofuran was added 3-acetoxy phenyl acetyl chloride (0.105 g, 0.496 mmol), followed by triethyl amine (0.173 mL, 1.24 mmol). The reaction was stirred at room temperature overnight. The reaction mixture was then partitioned between ethyl acetate and water. The crude material that was obtained from evaporation of the extracts was not purified further. (Yield not calculated) ES-MS (m/z) 779 [M+H]$^+$.

B. N-[3-(5-(1H-1,2,4-triazol-3-yl)(1H-indazol-3-yl))phenyl]-2-Hydroxy-2-phenylacetamide N-(3-{1-Perhydro-2H-pyran-2-yl-5-[1-(triphenylmethyl)(1,2,4-triazol-3-yl)](1H-indazol-3-yl)}phenyl)carbamoyl]phenylmethyl acetate was dissolved in 4 mL of 4.0 N HCl in 1,4-dioxane and the reaction was stirred at room temperature overnight. Monitoring of the reaction showed that these conditions effected a clean deprotection of triazole and indazole. After neutralization with aqueous NaHCO$_3$, the intermediate was extracted in ethyl acetate and purified by preparative HPLC. (0.060 g) This intermediate was then dissolved in 3 mL of MeOH and the solution was treated with 0.5 mL of saturated aqueous NaHCO$_3$ solution. After 2 hours at room temperature, the reaction mixture was neutralized with 2.0 N HCl aqueous solution and the desired product was purified by preparatory HPLC (0.030 g, 30% yield over 3 steps): $^1$H NMR (CD$_3$OD) δ 8.73 (br s, 1H), 8.58 (br s, <1H), 8.2 (br s, 1H), 8.0 (br s, <1H), 7.78 (d, 2H), 7.68 (br s, 1H), 7.59–7.49 (m, 3H), 7.41–7.29 (m, 3H), 5.21 (s, 1H); ES-MS (m/z) 411 [M+H]$^+$.

Example 311

N-[3-(5-(1H-1,2,4-TRIAZOL-3-YL)(1H-INDAZOL-3-YL))PHENYL]ISOXAZOL-5-YLCARBOXAMIDE

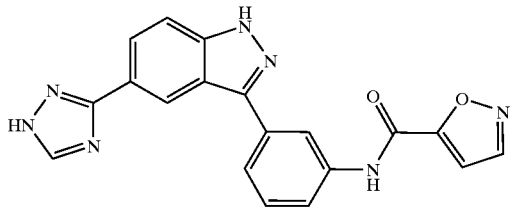

A. Isoxazol-5-yl-N-(3-{1-perhydro-2H-pyran-2-yl-5[1-(triphenylmethyl)(1,2,4-triazol-3-yl)](1H-indazol-3-yl)}phenyl)carboxamide To a solution of 3-{1-perhydro-2H-pyran-2-yl-5-[1-(triphenylmethyl)(1,2,4-triazol-3-yl)]-1H-indazol-3-yl}phenylamine (0.150 g, 0.248 mmol) in 2.5 mL of tetrahydrofuran was added isoxazole-5-carbonyl chloride (0.066 g, 0.496 nimol), followed by triethyl amine (0.173 mL, 1.24 mmol). The reaction was stirred at room temperature overnight. The reaction mixture was then partitioned between ethyl acetate and water. The crude material that was obtained from evaporation of the extracts was not purified further. (Yield not calculated) ES-MS (m/z) 698 [M+H]$^+$.

B. N-[3-(5-(1H-1,2,4-triazol-3-yl)(1H-indazol-3-yl))phenyl]Isoxazol-5-ylcarboxamide Isoxazol-5-yl-N-(3-{1-perhydro-2H-pyran-2-yl-5[1-(triphenylmethyl)(1,2,4-triazol-3-yl)](1H-indazol-3-yl)}phenyl)carboxamide was dissolved in 4 mL of 4.0 N HCl in 1,4-dioxane and the reaction was stirred at room temperature overnight. After neutralization with aqueous NaHCO$_3$, the crude product was extracted in ethyl acetate and purified by preparative HPLC (0.005 g, 5% yield over 2 steps): $^1$H NMR (CD$_3$OD) 8.65 (t, 1H), 8.73 (s, 1H), 8.45 (s, 1H), 8.38 (br s, <1H), 8.10 (d, 1H), 7.92 (d, 1H), 7.82 (d, 1H), 7.58 (t, 1H), 7.32 (d, 1H); ES-MS (m/z) 372 [M+H]$^+$.

Example 312

N-[3-(5-(1H-1,2,4-TRIAZOL-3-YL)(1H-INDAZOL-3-YL))PHENYL]-2-(2-FURYL)-2-OXOACETAMIDE

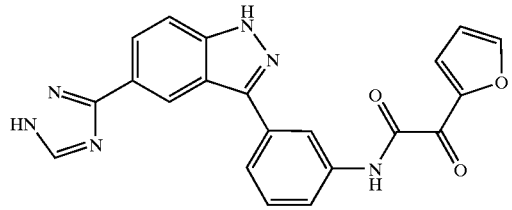

A. 2-(2-Furyl)-2-oxo-N-(3-{1-perhydro-2H-pyran-2-yl-5[1-(triphenylmethyl)(1,2,4-triazol-3-yl)](1H-indazol-3-yl)}phenyl)acetamide To a solution of 2-(2-furyl)-2-oxoacetic acid (0.070 g, 0.496 mmol) in 2.0 mL of dichloromethane, was added 1-(3-dimethylaminopropyl)-3-ethyl carbodiimide hydrochloride (EDCI) as a solid (0.098 g, 0.510 mmol). The solution was stirred at room temperature for 15 min before 3-{1-perhydro-2H-pyran-2-yl-5-[1-(triphenylmethyl)(1,2,4-triazol-3-yl)]-1H-indazol-3-yl}phenylamine (0.150 g, 0.248 mmol), dissolved in 1 mL of dichloromethane was added. The reaction was stirred at room temperature overnight. The reaction mixture was then partitioned between dichloromethane and water. The crude material that was obtained from evaporation of the extracts was not purified further. (Yield not calculated) ES-MS (m/z) 725 [M+H]'.

B. N-[3-(5-(1H-1,2,4-Triazol-3-yl)(1H-indazol-3-yl)]phenyl-2-(2-furyl)-2-oxoacetamide 2-(2-Furyl)-2-oxo-N-(3-{1-perhydro-2H-pyran-2-yl-5[1-(triphenylmethyl)(1,2,4-triazol-3-yl)](1H-indazol-3-yl)}phenyl)acetamide was dissolved in 4 mL of 4.0 N HCl in 1,4-dioxane and the reaction was stirred at room temperature for 4 h. After neutralization with aqueous NaHCO$_3$, the crude product was extracted in ethyl acetate and purified by preparative HPLC (0.0048 g, 5% yield over 2 steps): $^1$H NMR (CD$_3$OD) δ 8.80 (s, 1H), 8.43 (d, 1H), 8.11 (br s, 1H), 8.10 (d, 1H), 8.01 (s, 1H), 7.94 (d, 1H), 7.87 (d, 1H), 7.72 (br d, 1H), 7.58 (t, 1H), 6.77 (dt, 1H); ES-MS (m/z) 399.

Example 313

N-[3-(5-(1H-1,2,4-TRIAZOL-3-YL)(1H-INDAZOL-3-YL))PHENYL]-2-OXO-2-PHENYLACETAMIDE

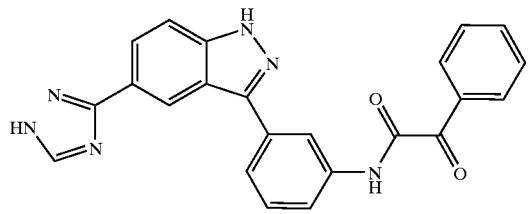

A. 2-Oxo-N-(3-{1-perhydro-2H-pyran-2-yl-5[1-(triphenylmethyl)(1,2,4-triazol-3-yl)](1H-indazol-3-yl)}phenyl)-2-phenylacetamide To a solution of 2-oxo-2-phenylacetic acid (0.074 g, 0.498 mmol) in 2.0 mL of dichloromethane, was added 1-(3-dimethylaminopropyl)-3-ethyl carbodiimide hydrochloride (EDCI) as a solid (0.098 g, 0.510 mmol). The solution was stirred at room temperature for 10 min before 3-{1-perhydro-2H-pyran-2-yl-5-[1-(triphenylmethyl)(1,2,4-triazol-3-yl)]-1H-indazol-3-yl}phenylamine (0.150 g, 0.248 mmol), dissolved in 1 mL of dichloromethane was added. After 2 days at room temperature, the reaction was not complete. Another 2 equivalents of EDCI were added to the mixture, driving the reaction to completion within 12 hours. The reaction mixture was then partitioned between dichloromethane and water. The crude material that was obtained from evaporation of the extracts was not purified further. (Yield not calculated) ES-MS (m/z) 735 [M+H]⁺.

B. N-[3-(5-(1H-1,2,4-Triazol-3-yl)(1H-indazol-3-yl))phenyl]-2-oxo-2-phenylacetamide 2-Oxo-N-(3-{1-perhydro-2H-pyran-2-yl-5[1-(triphenylmethyl)(1,2,4-triazol-3-yl)](1H-indazol-3-yl)}phenyl)-2-phenylacetamide was dissolved in 4 mL of 4.0 N HCl in 1,4-dioxane and the reaction was stirred at room temperature for 4 h. After neutralization with aqueous NaHCO₃, the crude product was extracted in ethyl acetate and purified by preparative HPLC (0.014 g, 14% yield over 2 steps): ¹H NMR (CD₃OD) δ 8.80 (s, 1H), 8.39 (t, 1H), 8.21 (m, 2H), 8.13 (d, 1H), 7.94 (dt, 1H), 7.89 (dt, 1H), 7.82–7.69 (m, 3H), 7.64–7.57 (m, 3H); ES-MS (m/z) 409 [M+H]⁺.

Example 314

N-[3-(5-(1H-1,2,4-TRIAZOL-3-YL)(1H-INDAZOL-3-YL))PHENYL]PENTANAMIDE

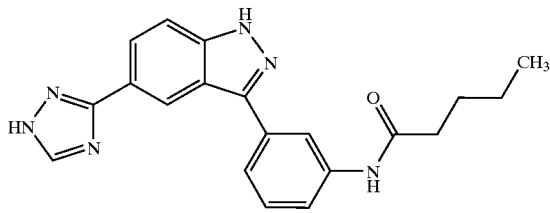

A. N-(3-{1-Perhydro-2H-pyran-2-yl-5[1-(triphenylmethyl)(1,2,4-triazol-3-yl)]1H-indazol-3-yl}phenyl)pentanamide To a solution of 3-{1-perhydro-2H-pyran-2-yl-5-[1-(triphenylmethyl)(1,2,4-triazol-3-yl)]-1H-indazol-3-yl}phenylamine (0.150 g, 0.248 mmol) in 2.5 mL of tetrahydrofuran was added pentanoyl chloride (0.060 g, 0.496 mmol), followed by triethyl amine (0.173 mL, 1.24 mmol). The reaction was stirred at room temperature for 2 hours. The reaction mixture was then partitioned between ethyl acetate and water. The crude material that was obtained from evaporation of the extracts was not purified further. (Yield not calculated) ES-MS (m/z) 687 [M+H]⁺.

B. N-[3-(5-(1H-1,2,4-Triazol-3-yl)(1H-indazol-3-yl))phenyl]pentanamide

N-(3-{1-Perhydro-2H-pyran-2-yl-5[1-(triphenylmethyl)(1,2,4-triazol-3-yl)]-1H-indazol-3-yl}phenyl)pentanamide was dissolved in 4 mL of 4.0 N HCl in 1,4-dioxane and the reaction was stirred at room temperature for 4 h. After neutralization with aqueous NaHCO₃, the crude product was extracted in ethyl acetate and purified by preparative HPLC (0.046 g, 51.5% yield over 2 steps): ¹H NMR (CD₃OD) δ 8.65 (t, 1H), 8.23 (br s, 1H), 8.07 (t, 1H), 8.0 (dd, 1H), 7.66 (dd, 2H), 7.60 (dd, 1H), 7.41 (t, 1H), 2.34 (t, 2H), 1.63 (quintet, 2H), 1.35 (sextet, 2H), 0.90 (t, 3H); ES-MS (m/z) 361 [M+H]⁺.

Example 315

N-[3-(5-(1H-1,2,4-TRIAZOL-3-YL)(1H-INDAZOL-3-YL))PHENYL]-4-PYRIDYLCARBOXAMIDE

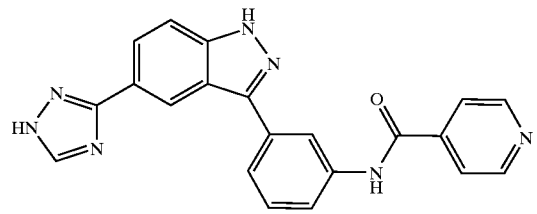

A. N-(3-{1-Perhydro-2H-pyran-2-yl-5-[1-(triphenylmethyl)(1,2,4-triazol-3-yl)]-1H-indazol-3-yl)}-4-pyridylcarboxamide To a solution of 3-{1-perhydro-2H-pyran-2-yl-5-[1-(triphenylmethyl)(1,2,4-triazol-3-yl)]-1H-indazol-3-yl}phenylamine (0.150 g, 0.248 mmol) in 2.5 mL of tetrahydrofuran was added pyridine-4-carbonyl chloride hydrochloride (0.088 g, 0.496 mmol), followed by triethyl amine (0.173 mL, 1.24 mmol). The reaction was stirred at room temperature for 2 hours. The reaction mixture was then partitioned between ethyl acetate and water. The crude material that was obtained from evaporation of the extracts was not purified further. (Yield not calculated) ES-MS (m/z) 708 [M+H]⁺.

B. N-[3-(5-(1H-1,2,4-Triazol-3-yl)(1H-indazol-3-yl))phenyl]-4-pyridylcarboxamide N-(3-{1-Perhydro-2H-pyran-2-yl-5-[1-(triphenylmethyl)(1,2,4-triazol-3-yl)]-1H-indazol-3-yl)}-4-pyridylcarboxamide was dissolved in 4 mL of 4.0 N HCl in 1,4-dioxane and the reaction was stirred at room temperature for 4 h. After neutralization with aqueous NaHCO₃, the crude product was extracted in ethyl acetate and purified by preparative HPLC (0.007 g, 7.5% yield over 2 steps): ¹H NMR (CD₃OD) δ 8.71 (br s, 1H), 8.68 (dt, 2H), 8.25 (br s, 1H), 8.01 (br d, 1H), 7.89–7.83 (m, 3H), 7.77 (d, 1H), 7.62 (d, 1H), 7.50 (t, 1H); ES-MS (m/z) 382 [M+H]⁺.

Example 316

N-[3-(5-(1H-1,2,4-TRIAZOL-3-YL)(1H-INDAZOL-3-YL))PHENYL]-2-CYCLOHEXYLACETAMIDE

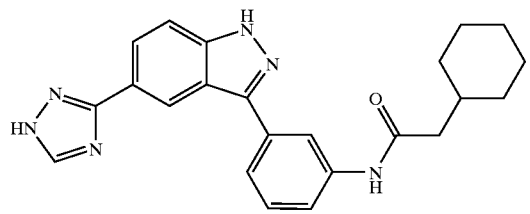

A. 2-Cyclohexyl-N-(3-{1-perhydro-2H-pyran-2-yl-5-[1-(triphenylmethyl)(1,2,4-triazol-3-yl)](1H-indazol-3-yl)}phenyl)acetamide To a solution of 2-cyclohexylacetic acid (0.071 g, 0.498 mmol) in 2.0 mL of dichloromethane, was added 1-(3-dimethylaminopropyl)-3-ethyl carbodiimide hydrochloride (EDCI) as a solid (0.105 g, 0.548 mmol). The solution was stirred at room temperature for 10 min before 3-{1-perhydro-2H-pyran-2-yl-5-[1-(triphenylmethyl)(1,2,4-triazol-3-yl)]-1H-indazol-3-yl}phenylamine (0.150 g, 0.248 mmol), dissolved in 1 mL of dichloromethane was added. The reaction was stirred at room temperature overnight. The reaction mixture was then partitioned between dichloromethane and water. (Yield not calculated) ES-MS (m/z) 727 [M+H]$^+$.

B. N-[3-(5-(1H-1,2,4-Triazol-3-yl)(1H-indazol-3-yl))phenyl]-2-cyclohexylacetamide 2-Cyclohexyl-N-(3-{1-perhydro-2H-pyran-2-yl-5-[1-(triphenylmethyl)(1,2,4-triazol-3-yl)](1H-indazol-3-yl)}phenyl)acetamide was dissolved in 4 mL of 4.0 N HCl in 1,4-dioxane and the reaction was stirred at room temperature overnight. After neutralization with aqueous NaHCO$_3$, the crude product was extracted in ethyl acetate and purified by preparative HPLC (0.034 g, 34% yield over 2 steps): $^1$H NMR (CD$_3$OD) δ 8.75 (s, 1H), 8.38 (br s, 2H), 8.20 (s, 1H), 8.10 (d, 1H), 7.76 (td, 2H), 7.70 (d, 1H), 7.51 (t, 1H), 2.30 (d, 2H), 1.90 (m, 1H), 1.78 (m, 4H), 1.3 (m, 4H), 1.07 (m, 2H); ES-MS (m/z) 401 [M+H]$^+$.

Example 317

N-[3-(5-(1H-1,2,4-TRIAZOL-3-YL)(1H-INDAZOL-3-YL))PHENYL]-3-PROPANAMIDE

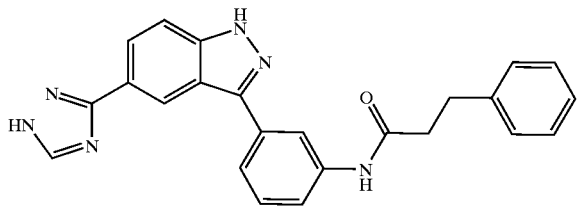

A. N-(3-{1-Perhydro-2H-pyran-2-yl-5-[1-(triphenylmethyl)(1,2,4-triazol-3-yl)](1H-indazol-3-yl)}phenyl)-3-phenylpropanamide To a solution of 3-{1-perhydro-2H-pyran-2-yl-5-[1-(triphenylmethyl)(1,2,4-triazol-3-yl)]-1H-indazol-3-yl}phenylamine (0.150 g, 0.248 mmol) in 2.5 mL of tetrahydrofuran was added 3-phenyl propanoyl chloride (0.084 g, 0.498 mmol), followed by triethyl amine (0.173 mL, 1.24 mmol). The reaction was stirred at room temperature for 2 hours. The reaction mixture was then partitioned between ethyl acetate and water. (Yield not calculated) ES-MS (m/z) 735 [M+H]$^+$.

B. N-[3-(5-(1H-1,2,4-Triazol-3-yl)(1H-indazol-3-yl))phenyl]-3-propanamide

N-(3-{1-Perhydro-2H-pyran-2-yl-5-[1-(triphenylmethyl)(1,2,4-triazol-3-yl)](1H-indazol-3-yl)}phenyl)-3-phenylpropanamide was dissolved in 4 mL of 4.0 N HCl in 1,4-dioxane and the reaction was stirred at room temperature overnight. After neutralization with aqueous NaHCO$_3$, the crude product was extracted in ethyl acetate and purified by preparative HPLC (0.049 g, 48% yield over 2 steps): $^1$H NMR (CD$_3$OD) δ 8.73 (s, 1H), 8.40 (br s, 2H), 8.16 (s, 1H), 8.10 (d, 1H), 7.77–7.67 (m, 3H), 7.50 (t, 1H), 7.28 (d, 4H), 7.18 (sextet, 1H); ES-MS (m/z) 409.

Example 318

N-[3-(5-(1H-1,2,4-TRIAZOL-3-YL1H-INDAZOL-3-YL))PHENYL]-2-(4-FLUOROPHENYL)ACETIC ACID

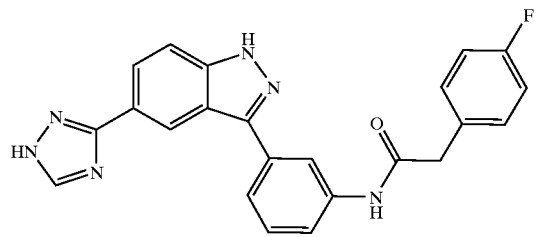

A. 2-(4-Fluorophenyl)-N-(3-{1-perhydro-2H-pyran-2-yl-5-[1-(triphenylmethyl)(1,2,4-triazol-3-yl)](1H-indazol-3-yl)}phenyl)acetamide To a solution of 2-(4-fluorophenyl)acetic acid (0.102 g, 0.66 mmol) in 3.0 mL of dichloromethane, was added 1-(3-dimethylaminopropyl)-3-ethyl carbodiimide hydrochloride (EDCI) as a solid (0.140 g, 0.726 mmol). The solution was stirred a t room temperature for 10 min before 3-{1-perhydro-2H-pyran-2-yl-5-[1-(triphenylmethyl)(1,2,4-triazol-3-yl)]-1H-indazol-3-yl}phenylamine (0.200 g, 0.330 mmol), dissolved in 2 mL of dichloromethane was added. The reaction was stirred at room temperature overnight. The reaction mixture was then partitioned between dichloromethane and water. (Yield not calculated) ES-MS (m/z) 739 [M+H]$^+$.

B. N-[3-(5-(1H-1,2,4-Triazol-3-yl)(1H-indazol-3-yl))phenyl]-2-(4-fluorophenyl)acetic acid 2-(4-Fluorophenyl)-N-(3-{1-perhydro-2H-pyran-2-yl-5-[1-(triphenylmethyl)(1,2,4-triazol-3-yl)](1H-indazol-3-yl)}phenyl)acetamide was dissolved in 4 mL of 4.0 N HCl in 1,4-dioxane and the reaction was stirred at room temperature overnight. After neutralization with aqueous NaHCO$_3$, the crude product was extracted in ethyl acetate and purified by preparative HPLC (0.065 g, 64% yield over 2 steps): $^1$H NMR (CD$_3$OD) δ 8.72 (s, 1H), 8.35 (br s, 1H), 8.17 (t, 1H), 8.10 (dd, 1H), 7.75 (m, 2H), 7.68 (d, 1H), 7.42–7.38 (m, 2H), 7.73 (s, 2H); ES-MS (m/z) 413.

Example 319

N-[3-(5-(1H-1,2,4-TRIAZOL-3-YL)(1H-INDAZOL-3-YL))PHENYL](2R)-2-HYDROXY-2-PHENYLACETAMIDE

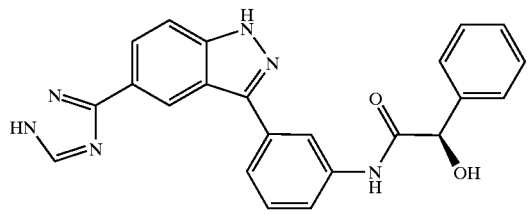

A. (1R)[N-(3-{1-Perhydro-2H-pyran-2-yl-5-[1-(triphenylmethyl)(1,2,4-triazol-3-yl)](1H-indazol-3-yl)}phenyl)carbamoyl]phenylmethyl acetate To a solution of (R)-2-acetoxy-2-phenylacetic acid (0.097 g, 0.498 mmol) in 2.0 mL of dichloromethane, was added 1-(3-dimethylaminopropyl)-3-ethyl carbodiimide hydrochloride (EDCI) as a solid (0.100 g, 0.520 mmol). The solution was stirred at room temperature for 10 min before 3-{1-perhydro-2H-pyran-2-yl-5-[1-(triphenylmethyl)(1,2,4-triazol-3-yl)]-1H-indazol-3-yl}phenylamine (0.150 g, 0.248 mmol), dissolved in 1 mL of dichloromethane, was added. The reaction was stirred at room temperature for 2 hours. The reaction mixture was then partitioned between dichloromethane and water. (Yield not calculated) ES-MS (m/z) 779 [M+H]$^+$.

B. N-[3-(5-(1H-1,2,4-Triazol-3-yl)(1H-indazol-3-yl))phenyl](2R)-2-hydroxy-2-phenylacetamide (1 R)[N-(3-{1-Perhydro-2H-pyran-2-yl-5-[1-(triphenylmethyl)(1,2,4-triazol-3-yl)](1H-indazol-3-yl)}phenyl)carbamoyl]phenylmethyl acetate was dissolved in 4 mL of 4.0 N HCl in 1,4-dioxane and the reaction was stirred at room temperature overnight. Monitoring of the reaction showed that the alcohol functionality had been partially deprotected under these conditions. After neutralization with aqueous NaHCO$_3$ after 48 hours, the crude product was extracted in ethyl acetate. The residue was then dissolved in 2 mL of MeOH and the solution was treated with 0.5 mL of aqueous saturated K$_2$CO$_3$ solution. After 2 hours at room temperature, deprotection was complete. The reaction mixture was neutralized and the crude product extracted with ethyl acetate and purified by preparative HPLC (0.036 g, 35% yield over 3 steps): $^1$H NMR (CD$_3$OD) δ 8.74, 8.55 (s, 1H), 8.22 (br s, 1H), 8.10 (br s, 2H), 7.78 (dt, 2H), 7.68 (br s, 1H), 7.58 (d, 2H), 7.51 (t, 1H), 7.382–7.30 (m, 3H), 5.21 (s, 1H); ES-MS (m/z) 411 [M+H]$^+$.

Example 320

N-[3-(5-(1H-1,2,4-TRIAZOL-3-YL)(1H-INDAZOL-3-YL))PHENYL](2S)-2-HYDROXY-2-PHENYLACETAMIDE

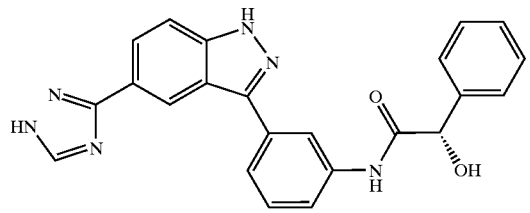

Example 320 was prepared according to the procedure described for Example 319 using (2S)-2-acetyloxy-2-phenyl acetic acid (0.021 g, 20% yield over 3 steps): $^1$H NMR (CD$_3$OD) δ 8.74, 8.55 (s, 1H), 8.22 (br s, 1H), 8.10 (br s, 2H), 7.78 (dt, 2H), 7.68 (br s, 1H), 7.58 (d, 2H), 7.51 (t, 1H), 7.382–7.30 (m, 3H), 5.21 (s, 1H); ES-MS (m/z) 411 [M+H]$^+$.

Example 321

(2-{3-[3-(4-FLUOROPHENYL)(1H-INDAZOL-5-YL)](1H-1,2,4-TRIAZOL-5-YL)}ETHYL)DIMETHYLAMINE

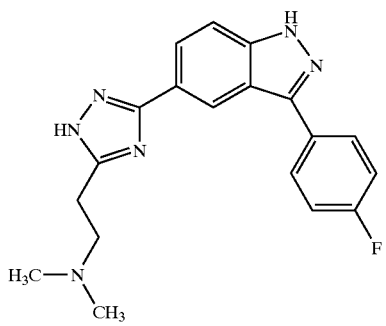

A. N-Amino-3-(dimethylamino)propanamide

To a solution of methyl 3-(dimethylamino)propanoate (1.0 g, 7.62 mmol) in 1 mL of anhydrous ethanol was added anhydrous hydrazine (0.370 mL, 7.62 mmol). The solution was heated to reflux temperature overnight. The solvent was then removed under reduced pressure. (quantitative yield): $^1$H NMR (CDCl$_3$) δ 9.49 (br s, 1H), 3.88 (br s, 2H), 2.53–2.52 (m, 2H), 2.44–2.36 (m, 2H), 2.24 (s, 6H); ES-MS (m/z) 132 [M+H]$^+$.

B. Ethoxy[3-(4-fluorophenyl)(1H-indazol-5-yl)]methanimine hydrochloride

A solution of 3-(4-fluorophenyl)-1H-indazole-5-carbonitrile (0.500 g, 2.10 mmol) in 25 mL of ethanol was cooled to 0° C. HCl gas was bubbled through the solution for 15 min. The resulting suspension was stirred at room temperature for 24 hours. When completion of the reaction was reached, the solvent was removed under reduced pressure. ES-MS (m/z) 284 [M+H]$^+$.

C. (2-{3-[3-(4-Fluorophenyl)(1H-indazol-5-yl)](1H-1,2,4-triazol-5-yl)}ethyl)dimethyl A 0.148 M solution of sodium ethoxide in ethanol was prepared by dissolving 0.155 g of sodium in 32.25 mL of anhydrous ethanol. A solution of ethoxy[3-(4-fluorophenyl)(1H-indazol-5-yl)]methanimine (0.200 g, 0.62 mmol) under nitrogen in NaOEt in ethanol (12.5 mL) was prepared. An excess of N-amino-3-(dimethylamino)propanamide (0.163 g, 1.24 mmol) was added, dissolved in 1 mL of ethanol. After 2 hours at reflux temperature, a mixture of 3-(4-fluorophenyl)-1H-indazole-5-carbonitrile and product was observed. No further conversion was obtained after addition of excess base and imidate. The reaction was worked up by partitioning the crude between water and ethyl acetate. The extracts were purified by preparatory HPLC (0.010 g, 4.6% yield): $^1$H NMR (CD$_3$OD) δ 8.69 (s, 1H), 8.08–8.02 (m, 3H), 7.69 (d, 1H), 7.30 (t, 2H), 4.90 (t, 2H), 3.18 (t, 2H), 2.73 (s, 6H); ES-MS (m/z) 351 [M+H]$^+$.

Example 322

3-[3-(4-FLUOROPHENYL)(1H-INDAZOL-5-YL)]-
5-(PIPERIDYLMETHYL)-1H-1,2,4-TRIAZOLE

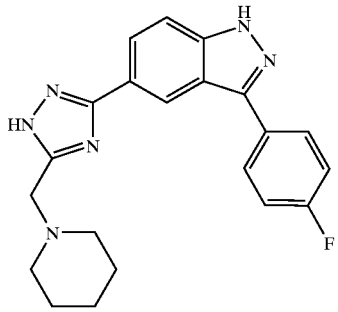

A. N-Amino-2-piperidylacetamide

To a solution of methyl 2-piperidylacetate (1.082 mL, 5.84 mmol) in 1 mL of anhydrous ethanol was added anhydrous hydrazine (0.283 mL, 5.84 mmol). The solution was heated to reflux temperature overnight. The solvent was then removed under reduced pressure and the product was isolated as a gummy white solid in a quantitative yield and was used without further purification: ES-MS (m/z) 158 [M+H]$^+$.

B. 3-[3-(4-Fluorophenyl)(1H-indazol-5-yl)]-5-(piperidylmethyl)-1H-1,2,4-triazole A suspension of ethoxy[3-(4-fluorophenyl)(1H-indazol-5-yl)]methanimine hydrochloride (0.250 g, 0.78 mmol) in 10 mL of anhydrous ethanol was prepared and cooled to 0° C. A freshly prepared solution of NaOEt in ethanol (1.17 mL, 1.0 M) was added followed by 2 equivalents of N-amino-2-piperidylacetamide (0.245 g, 1.56 mmol) as a solid. The reaction mixture was heated to reflux temperature overnight. No further conversion was observed upon addition of excess N-amino-2-piperidylacetamide and sodium ethoxide. The reaction was quenched by addition of water and the crude product was extracted with ethyl acetate. The residue was purified by preparative HPLC (0.047 g, 16% yield): $^1$H NMR (CD$_3$OD) δ 8.71 (d, 1H), 8.11–8.02 (m, 3H), 7.67 (d, 1H), 7.29 (t, 2H), 3.73 (s, 2H)) 2.56 (m, 4H), 1.65 (m, 4H), 1.48 (m, 2H); ES-MS (m/z) 377 [M+H]$^+$.

Example 323

DIETHYL({3-[3-(4-FLUOROPHENYL)(1H-INDAZOL-5-YL)](1H-1,2,4-TRIAZOL-5-YL)}METHYL)AMINE

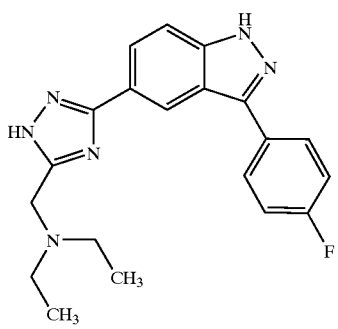

A. N-Amino-2-(diethylamino)acetamide

To a solution of methyl 2-(diethylamino)acetate (4.167 mL, 27.55 mmol) in 4 mL of anhydrous ethanol was added anhydrous hydrazine (1.336 mL, 27.55 mmol). The solution was heated to reflux temperature overnight. The solvent was then removed under reduced pressure and the product was isolated as an oil in a quantitative yield and was used without further purification: $^1$H NMR (CDCl$_3$) δ 8.3 (br s, 1H), 3.83 (br s, 2H), 3.08 (s, 2H), 2.51 (q, 4H), 1.00 (t, 6H); ES-MS (m/z) 146 [M+H]$^+$.

B. Diethyl({3-[3-(4-fluorophenyl)(1H-indazol-5-yl)(1H-1,2,4-triazol-5-yl)}methyl)amine A suspension of ethoxy[3-(4-fluorophenyl)(1H-indazol-5-yl)]methanimine hydrochloride (0.400 g, 1.25 mmol) in 4 mL of anhydrous ethanol was prepared and cooled to 0° C. An excess of a commercial solution of sodium methoxide in methanol (0.858 mL, 4.37 M)) was added followed by 3 equivalents of N-amino-2-(diethylamino)acetamide (0.545 g, 3.75 mmol) as a solid. The reaction mixture was heated to reflux temperature in a sealed tube for 2 days. The reaction was then quenched with water, the pH adjusted to neutral and the crude product extracted with ethyl acetate. The residue was purified by preparative HPLC (0.052 g, 11% yield): $^1$H NMR (CD$_3$OD) δ 8.70 (s, 1H), 8.11–8.02 (m, 3H), 7.67 (d, 1H), 7.29 (td, 2H), 3.8 (s, 1H), 2.68 (q, 4H), 1.15 (t, 3H); ES-MS (m/z) 365 [M+H]$^+$.

Example 324

4-({3-[3-(4-FLUOROPHENYL)(1H-INDAZOL-5-YL)]-1H-1,2,4-TRIAZOL-5-YL}METHYL) MORPHOLINE

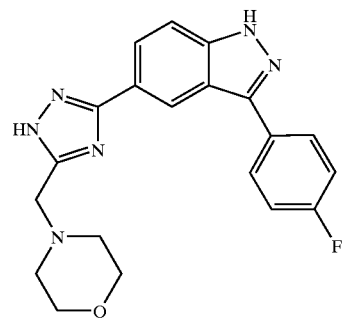

A. N-Amino-2-morpholin-4-ylacetamide

To a solution of methyl 2-morpholin-4-ylacetate (1.0 g, 6.28 mmol) in 1 mL of anhydrous ethanol was added anhydrous hydrazine (0.305 mL, 6.28 mmol). The solution was heated to reflux temperature overnight. The solvent was then removed under reduced pressure and the product was isolated as a solid in a quantitative yield and was used without further purification: $^1$H NMR (CDCl$_3$) δ8.11 (br s, 1H), 3.87 (br s, 2H), 3.71 (t, 4H), 3.09 (s, 6H), 2.53 (t, 4H); ES-MS (m/z) 160 [M+H]$^+$.

B. 4-({3-[3-(4-Fluorophenyl)(1H-indazol-5-yl)]-1H-1,2,4-triazol-5-yl}methyl)morpholine A suspension of ethoxy[3-(4-fluorophenyl)(1H-indazol-5-yl)]methanimine hydrochloride (0.300 g, 0.94 mmol) in 4 mL of anhydrous ethanol was prepared and cooled to 0° C. An excess of a freshly prepared solution of sodium methoxide in methanol (1.41 mL, 2.0 M)) was added followed by 3 equivalents of N-amino-2-morpholin-4-ylacetamide (0.449 g, 2.82 mmol) as a solid. The reaction mixture was heated to reflux temperature in a sealed tube for 2 days. The reaction was then quenched with water, the pH adjusted to neutral and the crude product extracted with ethyl acetate. The components of the crude mixture were separated by preparative HPLC (title compound: 0.017 g, 5% yield): $^1$H NMR (CD$_3$OD) δ 8.71 (d, 1H), 8.08–8.03 (m, 3H), 7.68 (d, 1H), 7.3 (t, 2H), 3.73 (m, 6H), 2.59 (m, 4H); ES-MS (m/z) 379 [M+H]$^+$.

Example 325

4-({5-[3-(4-FLUOROPHENYL)-1H-INDAZOL-5-YL]-1,3,4-OXADIAZOL-2-YL}METHYL)MORPHOLINE

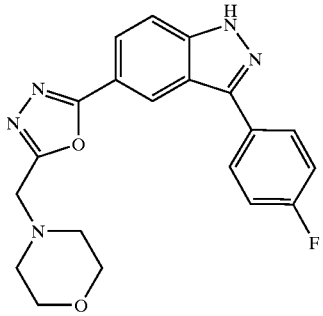

The title compound was isolated during the purification of Example 324 (0.053 g, 4.8% yield): $^1$H NMR (CD$_3$OD) δ 8.68 (d, 1H), 8.13–8.03 (m, 3H), 7.79 (d, 1H), 7.35 (t, H), 3.71 (s, 4H), 3.69 (t, 4H), 2.62 (t, 4H); ES-MS (m/z) 380 [M+H]$^+$.

Example 326

1-({3-[3-(4-FLUOROPHENYL)-1H-INDAZOL-5-YL]-1H-1,2,4-TRIAZOL-5-YL}METHYL)PYRROLIDINE-2-ONE

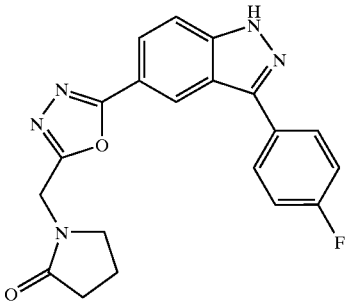

A. N-Amino-2-(2-oxopyrrolidinyl)acetamide

To a solution of methyl 2-(2-oxopyrrolidinyl)acetate (0.884 mL, 6.36 mmol) in 1 mL of anhydrous ethanol was added anhydrous hydrazine (0.308 mL, 6.36 mmol). The solution was heated to reflux temperature overnight. The solvent was then removed under reduced pressure and the product was isolated as a solid in a quantitative yield and was used without further purification: $^1$H NMR (CDCl$_3$) δ 8.17 (br s, 1H), 3.94 (s, 2H), 3.55 (t, 2H), 2.43 (t, 2H), 2.10 (quintet, 2H); ES-MS (m/z) 158 [M+H]$^+$.

B. 1-({3-[3-(4-Fluorophenyl)-1H-indazol-5-yl]-1H-1,2,4-triazol-5-yl}methyl)pyrrolidine-2-one A suspension of ethoxy[3-(4-fluorophenyl)(1H-indazol-5-yl)]methanimine hydrochloride (0.300 g, 0.94 mmol) and N-amino-2-(2-oxopyrrolidinyl)acetamide (0.442 g, 2.81 mmol) in 4 mL of anhydrous methanol was prepared. An excess of a commercial solution of sodium methoxide in methanol (0.643 mL, 4.37 M) was added. Upon adding the basic solution, the reaction mixture became clear then cloudy. After an hour, the temperature was raised to reflux temperature and was maintained for 48 hours. The reaction was then quenched with water, the pH adjusted to neutral and the crude product extracted with ethyl acetate. The title compound was purified by preparative HPLC (0.118 g, 34% yield): $^1$H NMR (CD$_3$OD) δ 8.68 (s, 1H), 8.07–8.02 (m, 3H), 7.68 (d, 1H), 7.29 (t, 2H), 4.66 (s, 2H), 3.53 (t, 2H), 2.47 (t, 2H), 2.10 (quintet, 2H); ES-MS (m/z) 377 [M+H]$^+$.

Example 327

({3-[3-(4-FLUOROPHENYL)(1H-INDAZOL-5-YL)](1H-1,2,4-TRIAZOL-5-YL)}METHYL)METHYLAMINE

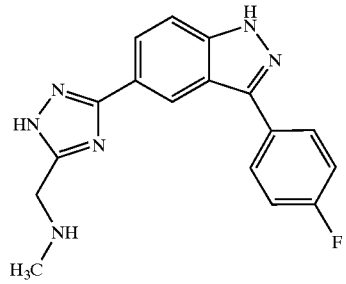

A. N-Amino-2-(methylamino)acetamide

To a suspension of methyl 2-(methylamino)acetate hydrochloride (2.0 g, 14.33 mmol) in 10 mL of anhydrous ethanol was added an excess of potassium carbonate (0.300 g). After 30 min at room temperature, the solution was filtered and transferred to a sealed tube. Anhydrous hydrazine was added (0.695 mL, 14.33 mmol) and the solution was heated to reflux temperature overnight. The solvent was removed under reduced pressure. The product was isolated as an oil and was used without further purification: $^1$H NMR (CDCl$_3$) δ 8.1 (br s, 1H), 2.8 (br s, 2H), 2.87 (s, 2H), 1.76 (s, 3H); ES-MS (m/z) 104 [M+H]$^+$.

B. ({3-[3-(4-Fluorophenyl)(1H-indazol-5-yl)](1H-1,2,4-triazol-5-yl)}methyl)methylamine A suspension of ethoxy[3-(4-fluorophenyl)(1H-indazol-5-yl)]methanimine hydrochloride (0.300 g, 0.94 mmol) and N-amino-2-(methylamino)acetamide (0.290 g, 2.81 mmol) in 4 mL of anhydrous methanol was prepared. An excess of a commercial solution of sodium methoxide in methanol (0.643 mL, 4.37 M) was added. After an hour, the temperature was raised to reflux and was maintained for 48 hours although no further conversion was observed after 24 hours. The reaction was then quenched with water, the pH adjusted to neutral and the crude product extracted with ethyl acetate.

The title compound was purified by preparative HPLC (0.034 g, 11% yield): $^1$H NMR (CD$_3$OD) δ 8.71 (s, 1H), 8.11–8.03 (m, 3H), 7.69 (d, 1H), 7.3 (t, 2H), 3.95 (s, 2H), 2.49 (s, 3H); ES-MS (m/z) 323 [M+H]$^+$.

Example 328

({3-[3-(4-FLUOROPHENYL)(1H-INDAZOL-5-YL)](1H-1,2,4-TRIAZOL-5-YL)}ETHYL)DIMETHYLAMIDE

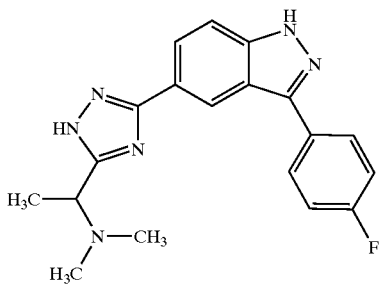

A. N-Amino-2-(dimethylamino)propanamide

Two equivalents of a 2.0 N commercial solution of dimethylamine in THF (36.0 mL, 35.91 mmol) were added to methyl 2-bromopropanoate (2.672 mL, 23.94 mmol), followed by one equivalent of potassium carbonate (5.0 g, 36.1 mmol). The heterogeneous mixture was stirred at room temperature overnight. The solution was filtered and transferred into a sealed tube. Anhydrous hydrazine was added (1.161 mL, 23.94 mmol). The reaction mixture was heated to reflux temperature overnight. The white precipitate that formed was filtered and the solution was concentrated. The title compound was used without further purification: $^1$H NMR (DMSO d$_6$) δ 8.91 (br s, 1H), 3.56 (br s, 2H), 2.89 (q, 1H), 2.15 (s, 6H), 1.06 (d, 3H); ES-MS (m/z) 132 [M+H]$^+$.

B. ({3-[3-(4-Fluorophenyl)(1H-indazol-5-yl)](1H-1,2,4-triazol-5-yl) ethyl)dimethylamine To a suspension of ethoxy[3-(4-fluorophenyl)(1H-indazol-5-yl)]methanimine hydrochloride (0.400 g, 1.25 mmol) in 3 mL of anhydrous methanol was added 3.5 equivalents of N-amino-2-(dimethylamino)propanamide (0.575 g, 4.38 mmol) in 2 mL of anhydrous methanol followed by 3.5 equivalents of commercial solution of sodium methoxide in methanol (1.0 mL, 4.37 M). After an hour, the temperature was raised to reflux temperature and was maintained for 48 hours although no further conversion was observed after 24 hours The reaction was then quenched with water, the pH adjusted to neutral and the crude product extracted with ethyl acetate. The title compound was purified by preparative HPLC (0.036 g, 8% yield): $^1$H NMR (CD$_3$OD) δ 8.71 (s, 1H), 8.12–8.03 (m, 3H), 7.68 (d, 1H), 7.29 (t, 2H), 3.93 (q, 2H), 2.32 (s, 6H), 1.55 (d, 3H); ES-MS (m/z) 351 [M+H]$^+$.

Example 329

(2R)-N-[3-(5-{5-[(DIMETHYLAMINO)METHYL](1H-1,2,4-TRIAZOL-3-YL)}(1H-INDAZOL-3-YL))PHENYL]-2-HYDROXY-2-PHENYLACETAMIDE

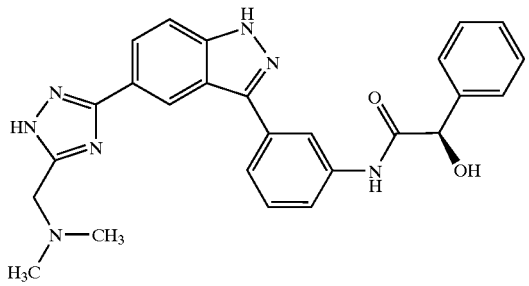

A. (1R)-{N-[3-(5-Cyano-1-perhydro-2H-pyran-2-yl(1H-indazol-3-yl))phenyl]carbamoyl}phenylmethyl acetate To a solution of R-2-acetoxy propionic acid (1.22 g, 6.28 mmol) in dichloromethane was added 1-(3-dimethylaminopropyl)-3-ethyl carbodiimide hydrochloride (EDCI) (1.26 g, 6.59 mmol). The solution was stirred at room temperature for 10 min before 3-(3-aminophenyl)-1-perhydro-2H-pyran-2-yl-1H-indazole-5-carbonitrile (1.0 g, 3.14 mmol) was added as a solid. The reaction was maintained at room temperature overnight. The crude was partitioned between water and dichloromethane. The organic extracts were purified by column chromatography (30–35% ethyl acetate in hexanes) (1.0 g, 64% yield): $^1$H NMR (CDCl$_3$) δ 8.36 (s, 1H), 8.04 (s, 1H), 7.97 (s, 1H), 7.71–7.26 (m, 1H), 6.24 (s, 1H), 5.78 (d, 1H), 4.06 (d, 1H), 3.78 (m, 1H), 2.59 (m, 1H), 2.28–2.1 (m, 4H), 1.78–1.62 (m, 6H); ES-MS (m/z) 495 [M+H]$^+$.

B. (2R)-N-{3-[5-(Ethoxyiminomethyl)(1H-indazol-3-yl)]phenyl}-2-hydroxy-2-phenylacetamide hydrochloride A solution of (1R)-{N-[3-(5-cyano-1-perhydro-2H-pyran-2-yl(1H-indazol-3-yl))phenyl]carbamoyl}phenylmethyl acetate (1.0 g, 2.02 mmol) in 20 mL of ethanol was cooled to 0° C. before HCl gas was bubbled through it for 10 min. The reaction mixture was then stirred at room temperature overnight, resulting in deprotection of the hydroxy substituent as well as formation of the imidate. Ethanol was removed under reduced pressure and the residue was triturated in diethyl ether. The titled product was collected by filtration and isolated as a fine yellow solid that was dried in a vacuum oven for 2 hours (0.860 g, 94% yield): ES-MS (m/z) 415 [M+H]$^+$.

C. (2R)-N-[3-(5-{5-[(Dimethylamino)methyl](1H-1,2,4-triazol-3-yl)}(1H-indazol-3-yl))phenyl]-2-hydroxy-2-phenylacetamide To a suspension of (2R)-N-{3-[5-(ethoxyiminomethyl)(1H-indazol-3-yl)]phenyl}-2-hydroxy-2-phenylacetamide hydrochloride (0.500 g, 1.11 mmol) in methanol (10 mL) were added 3 equivalents of N-amino-2-(dimethylamino)acetamide (0.390 g, 3.33 mmol) and 2.5 equivalents of sodium methoxide in methanol (0.635 mL, 4.3 M). After stirring at room temperature for 1H, the reaction mixture was heated to 95° C. for 48 hours. The reaction was then quenched with water, the pH adjusted to neutral and the crude product extracted with ethyl acetate. The title compound was purified by preparative HPLC (0.050 g, 9% yield): $^1$H NMR (CD$_3$OD) δ 8.72 (s, 1H), 8.23 (s, 1H), 8.08 (d, 1H), 7.89 (d, 2H), 7.68 (d, 1H), 7.58 (d, 2H), 7.51 (t, 1H), 7.40–7.32 (m, 3H), 5.21 (s, 1H), 3.71 (s, 2H), 2.37 (s, 6H); ES-MS (m/z) 468 [M+H]$^+$.

Example 330

N-[3-(5-{5-[(DIMETHYLAMINO)METHYL](1H-1,2,4-TRIAZOL-3-YL)}(1H-INDAZOL-3-YL))PHENYL]-3,3-DIMETHYLBUTANAMIDE

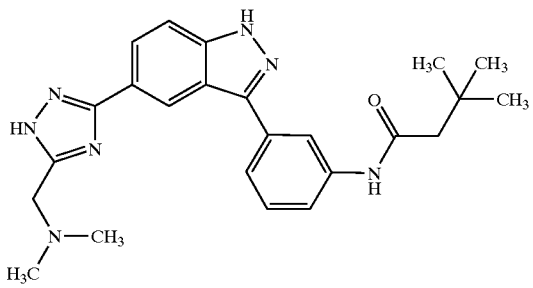

A. N-[3-(5-Cyano-1-perhydro-2H-pyran-2-yl(1H-indazol-3-yl)phenyl]-3,3-dimethylbutanamide The title compound was prepared from 3-(3-aminophenyl)-1-perhydro-2H-pyran-2-yl-1H-indazole-5-carbonitrile (0.700 g, 2.2 mmol), and 3,3-dimethylbutanoyl chloride (0.458 mL, 3.3 mmol) in 22 mL of tetrahydrofuran at room temperature for 12 hours. The product was isolated as an off-white solid after column chromatography (35% ethyl acetate in hexanes) (0.600 g, 65% yield): $^1$H NMR (CDCl$_3$) δ 8.38 (s, 1H), 7.98 (br s, 1H), 7.74–7.72 (m, 2H), 7.64–7.59 (m, 2H), 7.5–7.45 (m, 1H), 5.8 (d, 1H), 4.05 (m, 1H), 3.77 (m, 1H), 2.60 (m, 1H), 2.28 (s, 2H), 2.05 (m, 2H), 1.74 (m, 3H), 1.62 (br, s, 2H), 1.13 (s, 9H); ES-MS (m/z) 319 [M+H]$^+$.

B. N-{3-[5-(Ethoxyiminomethyl)(1H-indazol-3-yl)]phenyl}-3,3-dimethylbutanamide hydrochloride The title compound was prepared according to the procedure described in Example 329 B using N-[3-(5-cyano-1-perhydro-2H-pyran-2-yl(1H-indazol-3-yl))phenyl]-3,3-dimethylbutanamide (0.800 g, 1.92 mmol) in 50 mL of ethanol. The title compound was isolated after trituration in diethyl ether as a pale yellow solid (0.810 g, quantitative yield); ES-MS (m/z) 379 [M+H]$^+$.

C. N-[3-(5-{5-[(Dimethylamino)methyl](1H-1,2,4-triazol-3-yl)}(1H-indazol-3-yl))phenyl]-3,3-dimethylbutanamide The title compound was prepared according to the procedure described in Example 329 C using N-{3-[5-(ethoxyiminomethyl)(1H-indazol-3-yl)]phenyl}-3,3-dimethylbutanamide hydrochloride (0.360 g, 0.87 mmol), N-amino-2-(dimethylamino)acetamide (0.304 g, 2.60 mmol) and sodium methoxide in methanol (0.398 mL, 4.37 M). The title compound was isolated after purification by preparative HPLC (0.093 g, 25% yield): $^1$H NMR (CD$_3$OD) δ 8.72 (s, 1H), 8.16 (t, 1H), 8.08 (dt, 1H), 7.75 (dt, 2H), 7.66 (d, 1H), 7.50 (t, 1H), 3.71 (s, 2H), 2.37 (s, 6H), 2.30 (s, 2H), 1.12 (s, 9H); ES-MS (m/z) 432 [M+H]$^+$.

Example 331

3-[3-(4-FLUOROPHENYL)(1H-INDAZOL-5-YL)]-5-(PYRROLIDINYLMETHYL)-1H-1,2,4-TRIAZOLE

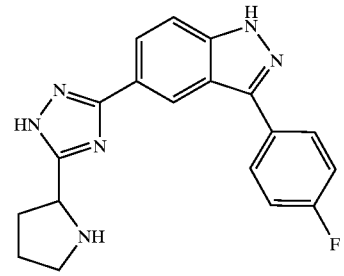

A. N-Aminopyrrolidin-2-ylcarboxamide

To a solution of methyl pyrrolidine-2-carboxylate hydrochloride (1.5 g, mmol) was added potassium carbonate (1.0 g). After stirring at room temperature for 1 h, the free base was isolated by filtration and reacted with one equivalent of hydrazine at reflux temperature overnight. The resulting hydrazide was isolated after removal of the solvent under reduced pressure as a pale yellow oil and was used without further purification: $^1$H NMR (DMSO d$_6$) δ 3.57 (dd, 1H), 2.94–2.79 (m, 2H), 2.01–1.88 (m, 1H), 1.70–1.59 (m, 3H); ES-MS (m/z) 130 [M+H]$^+$.

B. 3-[3-(4-Fluorophenyl)(1H-indazol-5-yl)]-5-(pyrrolidinylmethyl)-1H-1,2,4-triazole A suspension of ethoxy[3-(4-fluorophenyl)(1H-indazol-5-yl)]methanimine hydrochloride (0.500 g, 1.56 mmol) and N-aminopyrrolidin-2-ylcarboxamide (0.606 g, 4.69 mmol) in 4 mL of anhydrous methanol was prepared. An excess of a commercial solution of sodium methoxide in methanol (0.727 mL, 4.37 M) was added. After 2 h, the temperature was raised to reflux and was maintained for 48 hours. The analysis of the mixture showed the formation of the corresponding oxodiazole occurring as a side reaction. The reaction was then quenched with water, the pH adjusted to neutral and the crude product extracted with ethyl acetate. The title compound was purified by preparative HPLC (0.030 g, 5% yield): $^1$H NMR (CD$_3$OD) δ 8.69 (t, 1H), 8.10–8.02 (m, 3H), 7.68 (d, 1H), 7.05 (t, 2H), 4.52 (t, 1H), 3.17 (m, 2H), 2.39–1.99 (m, 4H), 2.37 (s, 6H), 2.30 (s, 2H), 1.12 (s, 9H); ES-MS (m/z) 349 [M+H]$^+$.

Example 332

N-[3-(5-{5-[(DIMETHYLAMINO)METHYL](1H-1,2,4-TRIAZOL-3-YL)}(1H-INDAZOL-3-YL))PHENYL]-3-METHYLBUTANAMIDE

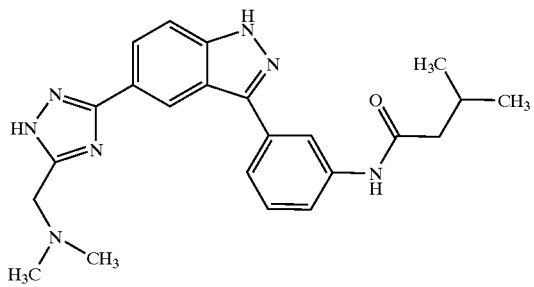

A. N-[3-(5-Cyano-1-perhydro-2H-pyran-2-yl(1H-indazol-3-yl))phenyl]-3,3-dimethylbutanamide The title compound was prepared according to the procedure described in Example 330 A, using 3-(3-aminophenyl)-1-perhydro-2H-pyran-2-yl-1H-indazole-5-carbonitrile (1.0 g, 3.0 mmol), and 3,3-dimethylbutanoyl chloride (0.550 mL, 4.5 mmol) in 30 mL of tetrahydrofuran. The product was isolated as an off-white solid after column chromatography (35% ethyl acetate in hexanes) (0.720 g, 60% yied); ES-MS (m/z) 403 [M+H]$^+$.

B. N-{3-[5-(Ethoxyiminomethyl)(1H-indazol-3-yl)]phenyl}-3-methylbutanamide hydrochloride The title compound was prepared according to the procedure described in Example 329 B using N-[3-(5-cyano-1-perhydro-2H-pyran-2-yl(1H-indazol-3-yl))phenyl]-3,3-dimethylbutanamide (0.720 g, 1.79 mmol) in 50 mL of ethanol. The title compound was isolated after trituration in diethyl ether as a pale yellow solid (0.710 g, quantitative yield); ES-MS (m/z) 365 [M+H]$^+$.

C. N-[3-(5-{5-[(Dimethylamino)methyl](1H-1,2,4-triazol-3-yl)}(1H-indazol-3-yl))phenyl]-3-methylbutanamide The title compound was prepared according to example Example 329 C using N-{3-[5-(ethoxyiminomethyl)(1H-indazol-3-yl)]phenyl}-3-methylbutanamide hydrochloride (0.400 g, 0.997 mmol), N-amino-2-(dimethylamino)acetamide (0.350 g, 2.99 mmol) and sodium methoxide in methanol (0.348 mL, 4.37 M). The title compound was isolated after purification by preparative HPLC (0.074 g, 18% yield): $^1$H NMR (CD$_3$OD) δ 8.73 (s, 1H), 8.19 (s, 1H), 8.08 (d, 1H), 7.75 (t, 2H), 7.69 (d, 1H), 7.51 (t, 1H), 3.81 (s, 2H), 2.45 (s, 6H), 2.3 (d, 2H), 2.21 (m, 1H), 1.04 (d, 6H); ES-MS (m/z) 418 [M+H]$^+$.

Example 333

N-[3-(5-{5-[(DIMETHYLAMINO)METHYL](1H-1,2,4-TRIAZOL-3-YL)}(1H-INDAZOL-3-YL))PHENYL]-3-PYRIDYLCARBOXAMIDE

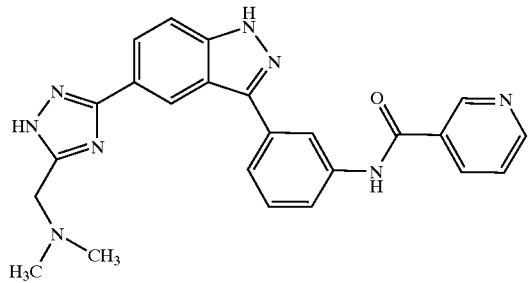

A. N-[3-(5-Cyano-1-perhydro-2H-pyran-2-yl(1H-indazol-3-yl)phenyl]-3-methylbutanamide The title compound was prepared according to the procedure described in Example 330 A, using 3-(3-aminophenyl)-1-perhydro-2H-pyran-2-yl-1H-indazole-5-carbonitrile (1.0 g, 3.0 mmol), and pyridine-3-carbonyl chloride (1.07 g, 6.0 mmol) in 30 mL of tetrahydrofuran and 1 mL of dimethyl formamide. The product was isolated as an off-white solid after column chromatography (2.5–5% methanol in dichloromethane) (0.600 g, 47% yield):); ES-MS (m/z) 424 [M+H]$^+$.

B. N-{3-[5-(Ethoxyiminomethyl)(1H-indazol-3-yl)]phenyl}-3-pyridylcarboxamide hydrochloride The title compound was prepared according to the procedure described in Example 329 B using N-[3-(5-cyano-1-perhydro-2H-pyran-2-yl(1H-indazol-3-yl))phenyl]-3-methylbutanamide (0.860 g, 2.00 mmol) in 50 mL of ethanol but completion of the reaction required re-saturation of the solution 3 times and an overall reaction time of one week. The title compound was isolated after trituration in diethyl ether as a pale yellow solid (0.920 g, quantitative yield); ES-MS (m/z) 386 [M+H]$^+$.

C. N-[3-(5-{5-[(Dimethylamino)Methyl](1H-1,2,4-triazol-3-yl)}(1H-indazol-3-yl))phenyl]-3-pyridylcarboxamide The title compound was prepared according to example Example 329 C using N-{3-[5-(ethoxyiminomethyl)(1H-indazol-3-yl)]phenyl}-3-pyridylcarboxamide hydrochloride (0.400 g, 0.873 mmol), N-amino-2-(dimethylamino)acetamide (0.306 g, 2.62 mmol) and sodium methoxide in methanol (0.609 mL, 4.37 M). The title compound was isolated after purification by preparative HPLC (0.037 g, 10% yield): $^1$H NMR (CD$_3$OD) δ 9.16 (dd, 1H), 8.79 (d, 1H), 8.75 (dd, 1H), 8.43 (dt, 1H), 8.39 (s, 1H), 8.09 (dd, 1H), 7.89–7.83 (m, 2H), 7.72 (d, 1H), 7.65–7.56 (m, 2H), 4.06 (br s, 2H), 2.61 (br s, 6H); ES-MS (m/z) 439 [M+H]$^+$.

Example 334

SYNTHESIS OF 3-[3-(2-PHENYLACETYLAMINO)PHENYL]-1H-INDAZOLE-5-CARBOXAMIDE

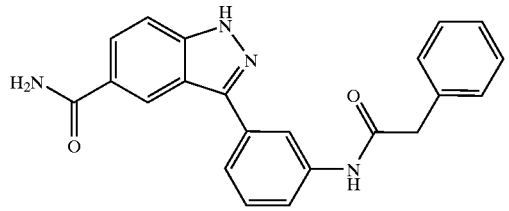

Following Example 290, reaction of 3-(3-aminophenyl)-1-perhydro-2H-pyran-2-yl-1H-indazole-5-carboxamide (250 mg, 0.74 mmol) with phenylacetic acid (0.15 g, 0.89 mmol) and EDCI (0.21 g, 1.11 mmol) furnished 32 mg (12% yield) of the title compound as a white solid. $^1$H NMR (DMSOd$_6$) δ 13.2 (br s, 1H), 10.4 (s, 1H), 8.6 (s, 1H), 8.2 (bs, 1H), 8.1 (m, 1H), 7.9 (dd, 1H), 7.8–7.5 (m, 2H), 7.6 (dd, 1H), 7.5 (t, 1H), 7.4–7.3 (m, 3H), 7.3–7.2 (m, 1H), 3.7 (s, 2H); ES-MS (m/z) 371 [M+H]$^+$.

Example 335

SYNTHESIS OF 3-{3-[2-(4-METOXYPHENYL)ACETYLAMINO]PHENYL}-1H-INDAZOLE-5-CARBOXAMIDE

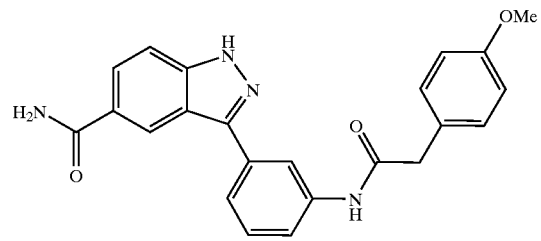

Following Example 290, the reaction of 3-(3-aminophenyl)-1-perhydro-2H-pyran-2-yl-1H-indazole-5-carboxamide (250 mg, 0.74 mmol) with 4-methoxyphenylacetic acid (0.15 g, 0.89 mmol) and EDCI (0.21 g, 1.11 mmol) furnished 27 mg (11% yield) of the title compound. $^1$H NMR (DMSOd$_6$) δ 13.2 (br s, 1H), 10.3 (s, 1H), 8.6 (s, 1H), 8.2 (s, 1H), 8.1 (bs, 1H), 7.9 (d, 1H), 7.7 (m, 2H), 7.6 (d, 1H), 7.5 (t, 1H), 7.4–7.1 (m, 2H), 6.9 (d, 1H), 3.7 (s, 3H), 3.6 (s, 2H); ES-MS (m/z) 401 [M+H]$^+$.

Example 336

SYNTHESIS OF 3-{3-[2-(2-METHYL-1,3-THIAZOL-5-YL)ACETYLAMINO]PHENYL}-1H-INDAZOLE-5-CARBOXAMIDE

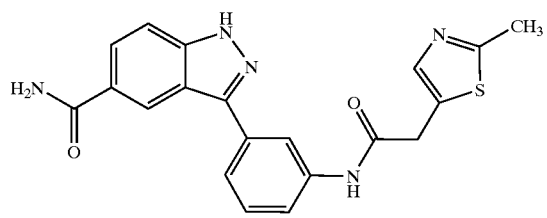

Following Example 290, the reaction of 3-(3-aminophenyl)-1-perhydro-2H-pyran-2-yl-1H-indazole-5-carboxamide (250 mg, 0.74 mmol) with 2-(2-methyl-1,3-thiazol-4-yl)acetic acid (0.14 g, 0.89 mmol) and EDCI (0.21 g, 1.11 mmol) furnished 32 mg (11% yield) of the title compound. $^1$H NMR (DMSOd$_6$) δ 13.2 (br s, 1H), 10.4 (s, 1H), 8.6 (s, 1H), 8.3 (br s, 1H), 8.1 (br s, 1H), 7.9 (d, 1H), 7.8–7.7 (m, 2H), 7.6 (d, 1H), 7.5 (t, 1H), 7.3 (br s. 1H), 7.3 (s, 1H), 3.8 (s, 2H), 2.6 (s, 3H); ES-MS (m/z) 392 [M+H]$^+$.

Example 337

SYNTHESIS OF 3-[3-(OXOLAN-3YLCARBONYLAMINO)PHENYL]-1H-INDAZOLE-5-CARBOXAMIDE

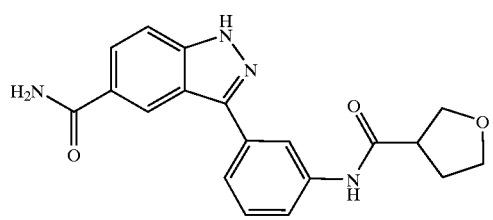

Following Example 290, the reaction of 3-(3-aminophenyl)-1-perhydro-2H-pyran-2-yl-1H-indazole-5-carboxamide (250 mg, 0.74 mmol) with tetrahydro-3-furoic acid (0.10 g, 0.89 mmol) and EDCI (0.21 g, 1.11 mmol) furnished 40 mg (15% yield) of the title compound. $^1$H NMR (DMSOd$_6$) δ 13.2 (br s, 1H), 10.2 (s, 1H), 8.6 (s, 1H), 8.2 (s, 1H), 8.1 (s, 1H), 7.7 (t, 1H), 7.6 (d, 1H), 7.5 (t, 1H), 7.4 (s, 1H), 3.9 (m, 1H), 3.82–3.68 (m, 2H), 3.3–3.1 (m, 2H), 2.2–2.0 (m, 2H); ES-MS (m/z) 351 [M+H]$^+$.

Example 338

SYNTHESIS OF 3-[3-(2-(3-THIENYL)ACETYLAMINO)PHENYL]-1H-INDAZOLE-5-CARBOXAMIDE

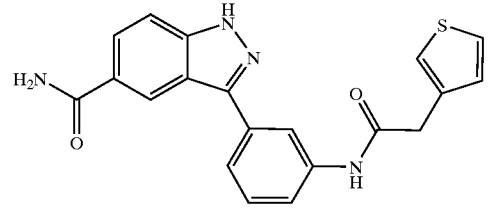

Following Example 290, the reaction of 3-(3-aminophenyl)-1-perhydro-2H-pyran-2-yl-1H-indazole-5-carboxamide (250 mg, 0.74 mmol) with 3-thiopheneacetic acid (0.13 g, 0.89 mmol) and EDCI (0.21 g, 1.11 mmol) furnished 13 mg (5% yield) of the title compound. $^1$H NMR (DMSOd$_6$) δ 13.4 (br s, 1H), 10.2 (s, 1H), 8.6 (s, 1H), 8.2 (s, 1H), 8.1 (br s, 1H), 7.92 (d, 1H), 7.8–7.7 (m, 2H), 7.6 (d, 1H), 7.54–7.44 (m, 2H), 7.35 (m, 2H), 7.14 (m, 1H), 3.7 (s, 2H); ES-MS (m/z) 377 [M+H]$^+$.

Example 339

SYNTHESIS OF 3-[3-(2-THIENYLCARBONYLAMINO)PHENYL]-1H-INDAZOLE5-CARBOXAMIDE

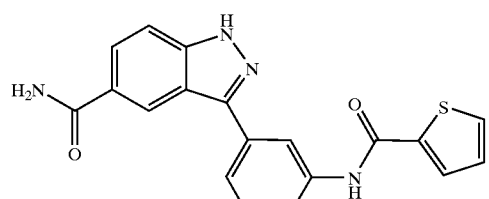

Following Example 290, the reaction of 3-(3-aminophenyl)-1-perhydro-2H-pyran-2-yl-1H-indazole-5-carboxamide (200 mg, 0.56 mmol) with 2-thiophenecarboxylic acid (0.92 g, 0.71 mmol) and EDCI (0.17 g, 0.89 mmol) furnished 56 mg (26% yield) of the title compound. $^1$H NMR (DMSOd$_6$) δ 13.2 (br s, 1H), 10.4 (s, 1H), 8.6 (s, 1H), 8.4 (br s, 1H), 8.1 (br s, 1H), 8.0 (d, 1H), 7.94–7.86 (m, 2H), 7.8 (d, 1H), 7.6 (d, 1H), 7.5 (t, 1H), 7.3 (br s, 1H), 7.2 (t, 1H); ES-MS (m/z) 363 [M+H]$^+$.

Example 340

SYNTHESIS OF 3-[3-(2-(4-PYRIDYL)ACETYLAMINO)PHENYL]-1H-INDAZOLE5-CARBOXAMIDE

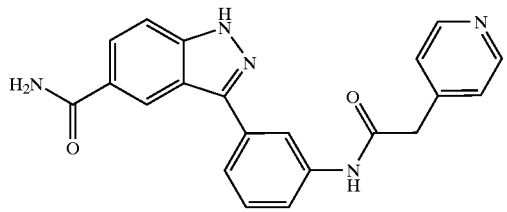

Following Example 290, the reaction of 3-(3 aminophenyl)-1-perhydro-2H-pyran-2-yl-1H-indazole-5-carboxamide (250 mg, 0.74 mmol) with 4-pyridylacetic acid hydrochloride (0.15 g, 0.89 mmol) and EDCI (0.21 g, 1.11 mmol) furnished 12 mg (4% yield) of the title compound. $^1$H NMR (DMSOd$_6$) δ 13.2 (br s, 1H), 10.2 (s, 1H), 8.6 (s, 1H), 8.5 (dd, 1H), 8.2 (s, 1H), 8.1 (br s, 1H), 7.9 (d, 1H), 7.75 (m, 2H), 7.6 (d, 1H), 7.5 (t, 1H), 7.4–7.1 (m, 2H), 3.8 (s, 2H); ES-MS (m/z) 372 [M+H]$^+$.

Example 342

SYNTHESIS OF 3-{3-[2-(4-FLUOROPHENYL)ACETYLAMINO]PHENYL}-1H-INDAZOLE-5-CARBOXAMIDE

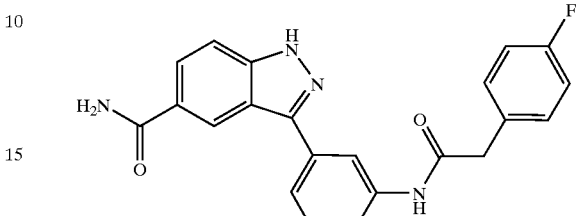

Following Example 290, the reaction of 3-(3-aminophenyl)-1-perhydro-2H-pyran-2-yl-1H-indazole-5-carboxamide (200 mg, 0.56 mmol) with 4-fluorophenylacetic acid (0.11 g, 0.71 mmol) and EDCI (0.17 g, 0.89 mmol) furnished 52 mg (23% yield) of the title compound. $^1$H NMR (DMSOd$_6$) δ 13.2 (br s, 1H), 10.2 (s, 1H), 8.6 (s, 1H), 8.23 (s, 1H), 8.1 (br s, 1H), 7.9 (dd, 1H), 7.73 (m, 1H), 7.6 (d, 1H), 7.5 (t, 1H), 7.47–7.34 (m, 3H), 7.17 (m, 2H), 3.7 (s, 2H); ES-MS (m/z) 389 [M+H]$^+$.

Example 341

SYNTHESIS OF 3-[3-(2-(2-PYRIDYL)ACETYLAMINO)PHENYL]-1H-INDAZOLE5-CARBOXAMIDE

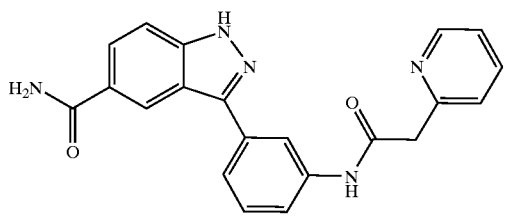

Following Example 290, the reaction of 3-(3-aminophenyl)-1-perhydro-2H-pyran-2-yl-1H-indazole-5-carboxamide (200 mg, 0.56 mmol) with 2-pyridylacetic acid hydrochloride (0.12 g, 0.71 mmol) and EDCI (0.17 g, 0.89 mmol) furnished 22 mg (10% yield) of the title compound. $^1$H NMR (DMSOd$_6$) δ 13.4 (br s, 1H), 10.4 (s, 1H), 8.6 (s, 1H), 8.5 (dd, 1H), 8.2 (br s, 1H), 8.1 (s, 1H), 7.9 (d, 1H), 7.75 (m, 2H), 7.6 (d, 1H), 7.45 (m, 2H), 7.35–7.2 (m, 2H), 3.8 (s, 2H); ES-MS (m/z) 372 [M+H]$^+$.

Example 343

SYNTHESIS OF 3-[3-[(CYCLOPROPYLCARBONYLAMINO)PHENYL]-1H-INDAZOLE5-CARBOXAMIDE

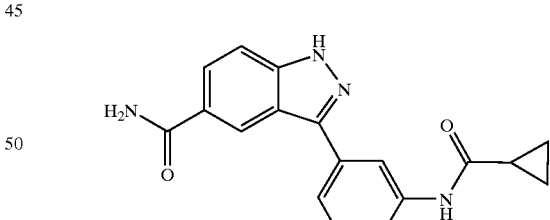

Following Example 290, the reaction of 3-(3-aminophenyl)-1-perhydro-2H-pyran-2-yl-1H-indazole-5-carboxamide (600 mg, 1.79 mmol) with cyclopropanecarboxylic acid (0.43 mL, 0.46 g, 5.4 mmol) and EDCI (1.06 g, 5.4 mmol) furnished 140 mg (26% yield) of the title compound. $^1$H NMR (DMSOd$_6$) δ 13.4 (br s, 1H), 10.4 (s, 1H), 8.6 (s, 1H), 8.2 (s, 1H), 8.1 (br s, 1H), 7.9 (dd, 1H), 7.75 (m, 2H), 7.6 (d, 1H), 7.5 (t, 1H), 7.35 (s, 1H), 1.9–1.68 (m, 1H), 0.8 (m, 4H); ES-MS (m/z) 321 [M+H]$^+$.

Example 344

SYNTHESIS OF 3-{3-[(3-HYDROXYPHENYL)CARBONYLAMINO]PHENYL}-1H-INDAZOLE5-CARBOXAMIDE

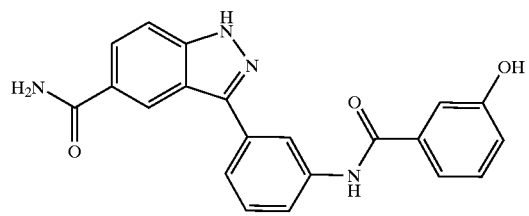

Following Example 290, the reaction of 3-(3-aminophenyl)-1-perhydro-2H-pyran-2-yl-1H-indazole-5-carboxamide (200 mg, 0.56 mmol) with 3-hydroxybenzoic acid (0.098 g, 0.71 mmol) and EDCI (0.17 g, 0.89 mmol) furnished 7 mg (3% yield) of the title compound. $^1$H NMR (DMSOd$_6$) δ 13.4 (br s, 1H), 10.4 (s, 1H), 9.9 (s, 1H), 8.6 (s, 1H), 8.4 (s, 1H), 8.1 (br s, 1H), 7.9 (m, 2H), 7.75 (m, 1H), 7.6 (d, 1H), 7.5 (t, 1H), 7.4 (m, 1H), 7.38–7.28 (m, 2H), 6.8 (m, 1H); ES-MS (m/z) 373 [M+H]$^+$.

Example 345

SYNTHESIS OF 3-{3-[2-(2,4-DICHLOROPHENYL)ACETYLAMINO]PHENYL}-1H-INDAZOLE5-CARBOXAMIDE

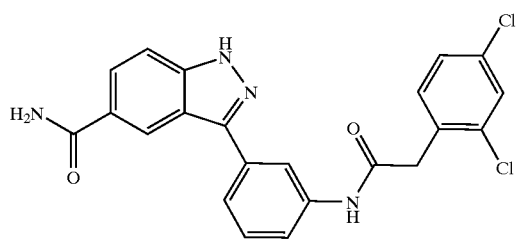

Following Example 290, the reaction of 3-(3-aminophenyl)-1-perhydro-2H-pyran-2-yl-1H-indazole-5-carboxamide (200 mg, 0.56 mmol) with 2,4-dichlorophenylacetic acid (0.15 g, 0.71 mmol) and EDCI (0.17 g, 0.89 mmol) furnished 8 mg (3% yield) of the title compound. $^1$H NMR (DMSOd$_6$) δ 13.4 (br s, 1H), 10.4 (s, 1H), 8.6 (s, 1H), 8.2 (s, 1H), 8.1 (br s, 1H), 7.9 (dd, 1H), 7.75 (m, 2H), 7.64–7.58 (m, 2H), 7.52–7.4 (m, 2H), 7.35 (s, 1H), 3.9 (s, 2H); ES-MS (m/z) 439 [M]$^+$.

Example 346

SYNTHESIS OF 3-(3-{2-[4-(TRIFLUOROMETHYL)PHENYL]ACETYLAMINO}PHENYL)-1H-INDAZOLE-5-CARBOXAMIDE

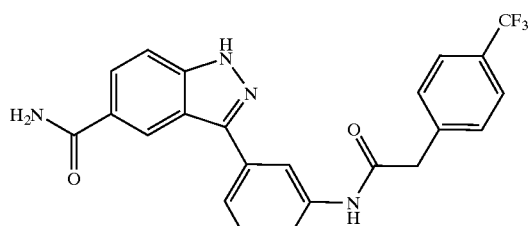

Following Example 290, the reaction of 3-(3-aminophenyl)-1-perhydro-2H-pyran-2-yl-1H-indazole-5-carboxamide (200 mg, 0.56 mmol) with 4-(trifluoromethyl)phenylacetic acid (0.15 g, 0.71 mmol) and EDCI (0.17 g, 0.89 mmol) furnished 28 mg (11% yield) of the title compound. $^1$H NMR (DMSOd$_6$) δ 10.4 (s, 1H), 8.6 (s, 1H), 8.22 (s, 1H), 8.1 (br s, 1H), 7.9 (dd, 1H), 7.8–7.68 (m, 3H), 7.6 (m, 3H), 7.5 (t, 1H), 7.35 (s, 1H), 7.17 (m, 2H), 3.8 (s, 2H); ES-MS (m/z) 439 [M+H]$^+$.

Example 347

SYNTHESIS OF 3-(3-{2-[4-(DIMETHYLAMINO)PHENYL]ACETYLAMINO}PHENYL)-1H-INDAZOLE-5-CARBOXAMIDE

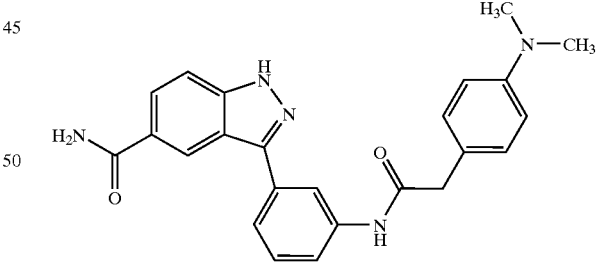

Following Example 290, the reaction of 3-(3-aminophenyl)-1-perhydro-2H-pyran-2-yl-1H-indazole-5-carboxamide (200 mg, 0.56 mmol) with 4-(dimethylamino)phenylacetic acid (0.13 g, 0.71 mmol) and EDCI (0.17 g, 0.89 mmol) furnished 33 mg (13% yield) of the title compound. $^1$H NMR (DMSO-d$_6$) δ 10.4 (s, 1H), 8.6 (s, 1H), 8.15 (s, 1H), 8.1 (br s, 1H), 7.9 (dd, 1H), 7.75 (m, 2H), 7.6 (d, 1H), 7.45 (t, 1H), 7.35 (br s, 1H), 7.18 (m, 2H), 6.68 (d, 2H), 3.5 (s, 2H), 2.9 (s, 6H); ES-MS (m/z) 414 [M+H]$^+$.

Example 348

SYNTHESIS OF 3-{3-[2-(2-CHLORO-4-FLUOROPHENYL) ACETYLAMINO]PHENYL}-1H-INDAZOLE-5-CARBOXAMIDE

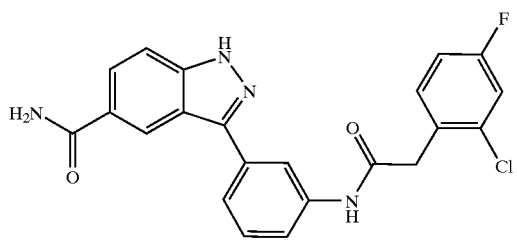

Following Example 290, the reaction of 3-(3-aminophenyl)-1-perhydro-2H-pyran-2-yl-1H-indazole-5-carboxamide (200 mg, 0.56 mmol) with 2-chloro-4-fluorophenylacetic acid (0.13 g, 0.71 mmol) and EDCI (0.17 g, 0.89 mmol) furnished 38 mg (14% yield) of the title compound. $^1$H NMR (DMSO-d$_6$) δ 10.4 (s, 1H), 8.6 (s, 1H), 8.1 (br s, 1H), 7.9 (dd, 1H), 7.75 (m, 2H), 7.65 (d, 1H), 7.52–7.4 (m, 3H), 7.35 (s, 1H), 7.2 (m, 1H), 3.9 (s, 2H); ES-MS (m/z) 423 [M]$^+$.

Example 349

SYNTHESIS OF 3-{3-[2-(4-CHLOROPHENYL) ACETYLAMINO]PHENYL}-1H-INDAZOLE5-CARBOXAMIDE

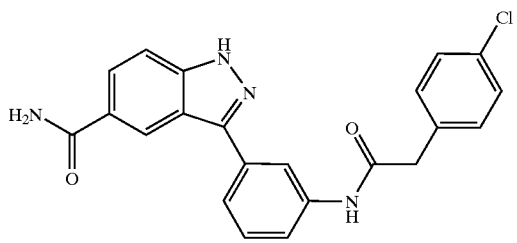

Following Example 290, the reaction of 3-(3-aminophenyl)-1-perhydro-2H-pyran-2-yl-1H-indazole-5-carboxamide (200 mg, 0.56 mmol) with 4-fluorophenylacetic acid (0.11 g, 0.71 mmol) and EDCI (0.17 g, 0.89 mmol) furnished 35 mg (14% yield) of the title compound. $^1$H NMR (DMSOd6) δ 10.4 (s, 1H), 8.6 (s, 1H), 8.2 (s, 1H), 8.1 (br s, 1H), 7.9 (dd, 1H), 7.75 (m, 2H), 7.6 (d, 1H), 7.5 (t, 1H), 7.45–7.3 (m, 4H), 7.17 (m, 2H), 3.7 (s, 2H); ES-MS (m/z) 405 [M+H]$^+$.

Example 350

SYNTHESIS OF 3-[3-(3-PHENYLPROPANOYLAMINO)PHENYL]-1H-INDAZOLE5-CARBOXAMIDE

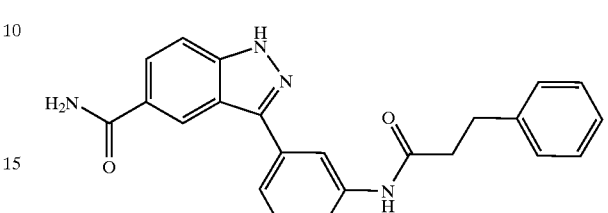

Following Example 290, the reaction of 3-(3-aminophenyl)-1-perhydro-2H-pyran-2-yl-1H-indazole-5-carboxamide (200 mg, 0.56 mmol) with hydrocinnamic acid (0.11 g, 0.71 mmol) and EDCI (0.17 g, 0.89 mmol) furnished 31 mg (13% yield) of the title compound. $^1$H NMR (DMSO-d$_6$) δ 13.4 (s, 1H), 10.2 (s, 1H), 8.6 (s, 1H), 8.2 (s, 1H), 8.1 (br s, 1H), 7.9 (d, 1H), 7.75 (m, 2H), 7.6 (d, 1H), 7.5 (t, 1H), 7.4–7.1 (m, 5H), 2.95 (t, 2H), 2.68 (t, 2H); ES-MS (m/z) 385 [M+H]$^+$.

Example 351

SYNTHESIS OF 3-{3-[3-(4-FLUOROPHENYL) PROPANOYLAMINO]PHENYL}-1H-INDAZOLE5-CARBOXAMIDE

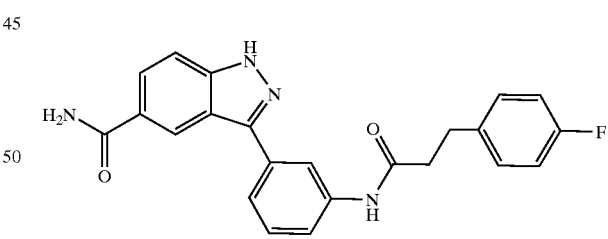

Following Example 290, the reaction of 3-(3-aminophenyl)-1-perhydro-2H-pyran-2-yl-1H-indazole-5-carboxamide (200 mg, 0.56 mmol) with 3-(4-fluorophenyl) propanoic acid (0.12 g, 0.71 mmol) and EDCI (0.17 g, 0.89 mmol) furnished 22 mg (9% yield) of the title compound. $^1$H NMR (DMSO-d$_6$) δ 13.4 (s, 1H), 10.2 (s, 1H), 8.6 (s, 1H), 8.25 (s, 1H), 8.15 (br s, 1H), 7.9 (dd, 1H), 7.75 (m, 2H), 7.6 (d, 1H), 7.45 (t, 1H), 7.4–7.3 (m, 3H), 7.2–7.1 (m, 2H), 2.85 (t, 2H), 2.65 (t, 2H); ES-MS (m/z) 403 [M+H]$^+$.

Example 352

SYNTHESIS OF 3-{3-[2-(3,4-DIFLUOROPHENYL) ACETYLAMINO]PHENYL}-1H-INDAZOLE-5-CARBOXAMIDE

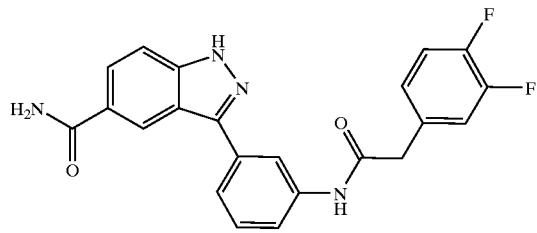

Following Example 290, the reaction of 3-(3-aminophenyl)-1-perhydro-2H-pyran-2-yl-1H-indazole-5-carboxamide (200 mg, 0.56 mmol) with 3,4-difluorophenylacetic acid (0.12 g, 0.71 mmol) and EDCI (0.17 g, 0.89 mmol) furnished 25 mg (10% yield) of the title compound. $^1$H NMR (DMSO-d$_6$) δ 13.4 (s, 1H), 10.4 (s, 1H), 8.6 (s, 1H), 8.2 (s, 1H), 8.1 (br s, 1H), 7.9 (d, 1H), 7.75 (m, 2H), 7.6 (d, 1H), 7.52–7.3 (m, 4H), 7.2 (m, 1H), 3.7 (s, 2H); ES-MS (m/z) 407 [M+H]$^+$.

Example 353

SYNTHESIS OF 3-{3-[2-(2-FLUOROPHENYL)ACETYLAMINO]PHENYL}-1H-INDAZOLE-5-CARBOXAMIDE

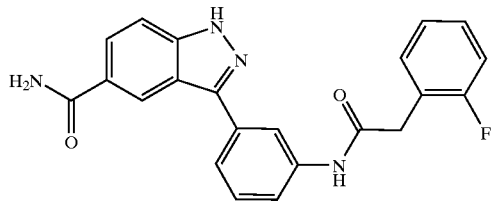

Following Example 290, the reaction of 3-(3-aminophenyl)-1-perhydro-2H-pyran-2-yl-1H-indazole-5-carboxamide (200 mg, 0.56 mmol) with 2-fluorophenylacetic acid (0.11 g, 0.71 mmol) and EDCI (0.17 g, 0.89 mmol) furnished 30 mg (12%) of the title compound. $^1$H NMR (DMSO-d$_6$) δ 10.4 (s, 1H), 8.6 (s, 1H), 8.2 (br s, 1H), 7.9 (dd, 1H), 7.75 (m, 2H), 7.6 (d, 1H), 7.45 (t, 1H), 7.45–7.29 (m, 3H), 7.25–7.15 (m, 2H), 3.8 (s, 2H); ES-MS (m/z) 389 [M+H]$^+$.

Example 354

SYNTHESIS OF 3-[3-(2-PHENYLPROPANOYLAMINO)PHENYL}-1H-INDAZOLE5-CARBOXAMIDE

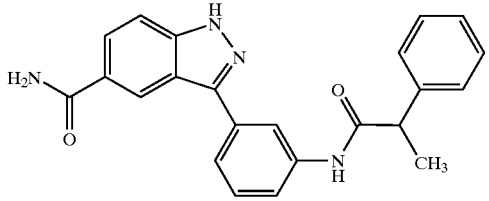

Following Example 290, the reaction of 3-(3-aminophenyl)-1-perhydro-2H-pyran-2-yl-1H-indazole-5-carboxamide (200 mg, 0.56 mmol) with 2-phenylpropionic acid (97 μL, 0.11 g, 0.71 mmol) and EDCI (0.17 g, 0.89 mmol) furnished 40 mg (17% yield) of the title compound. $^1$H NMR (DMSO-d$_6$) δ 13.5 (s, 1H), 10.3 (s, 1H), 8.6 (s, 1H), 8.2 (br s, 1H), 8.35 (br s, 1H), 7.94 (dd, 1H), 7.7 (m, 2H), 7.6 (d, 1H), 7.5–7.3 (m, 5H), 7.25 (m, 1H), 3.8 (s, 1H), 1.4 (d, 3H); ES-MS (m/z) 385 [M+H]$^+$.

Example 355

SYNTHESIS OF 3-[3-(2-PIPERIDYLETHOXY)PHENYL}-1H-INDAZOLE-5-CARBOXAMIDE

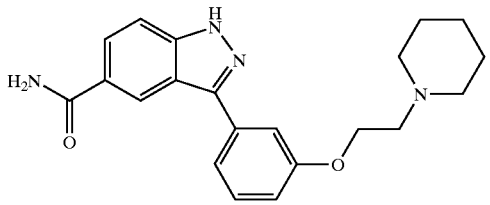

A. 3-(3-Hydroxyphenyl)-1-perhydro-2H-pyran-2-yl-1H-indazole-5-carbonitrile

3-Bromo-1-perhydro-2H-pyran-2-yl-1H-indazole-5-carbonitrile (7.9 g, 24.2 mmol), 3-hydroxyphenylboronic acid (5 g, 36.3 mmol), Pd(dppf)Cl$_2$ (1.97 g, 2.42 mmol) and K$_3$PO$_4$ (25.62 g, 120.8 mmol) were refluxed in 90 mL DME for 24 h. The reaction was cooled and diluted with EtOAc. The reaction mixture was filtered through a celite pad and the filtrate was washed with water, brine, dried (Na$_2$SO$_4$) and filtered. The filtrate was concentrated and the residue purified by column chromatography using 20–75% EtOAc in hexanes to provide 5.4 g (74% yield) of the title compound. $^1$H NMR (DMSO-d$_6$) δ 10.4 (s, 1H), 8.6 (s, 1H), 7.9 (dd, 2H), 7.4 (m, 3H), 6.8 (dd, 1H), 6.0 (m, 1H), 3.95–3.7 (m, 2H), 2.45 (m, 2H), 2.05 (m, 2H), 1.6 (m, 2H); ES-MS (m/z) 320 [M+H]$^+$.

B. 3-[3-(2-Piperidylethoxy)phenyl]-1-perhydro-2H-pyran-2-yl-1H-indazole-5-carbonitrile 3-(3-Hydroxyphenyl)-1-perhydro-2H-pyran-2-yl-1H-indazole-5-carbonitrile (1.0 g, 3.13 mmol), 1-(2-chloroethyl)piperidine monohydrochloride (0.87 g, 4.70 mmol) and K$_2$CO$_3$ (1.3 g, 9.40 mmol) were heated in DMF at 80° C. for 18 h. The reaction was cooled and partitioned between EtOAc and water. The organic layer was washed with water, brine, dried (Na$_2$SO$_4$) and filtered. The filtrate was concentrated and the residue purified by chromatography using 20–50% EtOAc in hexanes to furnish 1.2 g (89% yield) of the title compound. ES-MS (m/z) 431 [M]$^+$.

C. 3-[3-(2-Piperidylethoxy)phenyl]-1-perhydro-2H-pyran-2-yl-1H-indazole-5-carboxamide 3-[3-(2-Piperidylethoxy)phenyl]-1-perhydro-2H-pyran-2-yl-1H-indazole-5-carbonitrile (0.67 g, 1.6 mmol) was dissolved in 2 mL EtOH and the solution was cooled to 0° C. Aqueous 6 N NaOH solution (1.04 mL, 0.25 g, 6.2 mmol) and aqueous 30% $H_2O_2$ (0.7 mL, 0.21 g, 6.2 mmol) were added to the reaction mixture. The reaction mixture was warmed to room temperature and stirred for 1.5 h. The reaction was quenched by addition of 6 N HCl. The resultant solution was neutralized by addition of saturated aqueous solution of sodium bicarbonate. The solution was extracted with EtOAc, the organic layer was washed with water, brine, dried ($Na_2SO_4$) and filtered. The filtrate was concentrated to 0.61 g (87%) of the title compound obtained as a yellow solid. ES-MS (m/z) 449 $[M+H]^+$.

D. 3-[3-(2-Piperidylethoxy)phenyl]-1H-indazole-5-carboxamide

3-[3-(2-Piperidylethoxy)phenyl]-1-perhydro-2H-pyran-2-yl-1H-indazole-5-carboxamide (0.61 g, 1.4 mmol) was suspended in 10 mL of 4 M HCl in dioxane and the suspension was stirred at room temperature for 18 h. The reaction was quenched with saturated aqueous solution of $NaHCO_3$ and extracted with EtOAc. The organic layer was dried ($Na_2SO_4$) and filtered. The filtrate was concentrated and purification of the residue by preparative HPLC (20–80% acetonitrile in water) furnished 65 mg (13% yield) of the title compound. $^1$H NMR (DMSO-$d_6$) δ 13.4 (br s, 1H), 8.6 (s, 1H), 8.2 (s, 1H), 7.94 (dd, 1H), 7.62 (m, 2H), 7.5 (m, 1H), 7.45 (t, 1H), 7.32 (br s, 1H), 7.05 (dd, 1H), 4.18 (t, 2H), 2.7 (m, 2H), 2.5 (m, 4H), 1.5 (m, 4H), 1.4 (m, 2H); ES-MS (m/z) 365 $[M+H]^+$.

Example 356

SYNTHESIS OF N-ETHYL-3-{[3-(4-FLUOROPHENYL)(1H-INDAZOL-5-YL)]CARBONYLAMINO}PROPANAMIDE

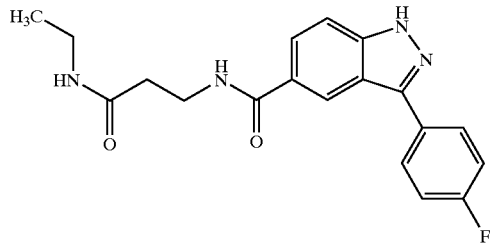

A. N-Ethyl-3-{[3-(4-fluorophenyl)(1H-indazol-5-yl)carbonylamino}propanamide

To a solution containing Example 88 (0.200 g, 0.611 mmol) in tetrahydrofuran (5 mL) was added 1-hydroxybenzotriazole hydrate (0.247 g, 1.83 mmol) followed by 1-(3-dimethylaminopropyl)-3-ethylcarbodiimide hydrochloride (0.351 g, 1.83 mmol), ethylamine (0.915 mL, 1.83 mmol) and N,N-dimethylformamide (2 mL). The solution was stirred for 3 h at room temperature. Water (40 mL) was added and the reaction mixture was extracted with ethyl acetate. The combined organic layers were dried over anhydrous sodium sulfate, filtered and evaporated. The residue was purified by preparative HPLC (10–90% acetonitrile/water). The pure fractions were basified with ammonium hydroxide, evaporated at reduced pressure, diluted with water and filtered which gave the title compound (0.128 g, 59% yield): $^1$H NMR (DMSO-$d_6$) δ 13.43 (s, 1H), 8.68 (t, 1H), 8.52 (s, 1H), 8.07 (AB quartet, 2H), 7.90 (dd, 2H), 7.62 (d, 1H), 7.39 (t, 2H), 3.07 (m, 2H), 2.50 (m, 2H), 2.38 (t, 2H), 0.99 (t, 3H); ES-MS (m/z) 355 $[M+1]^+$.

Example 357

SYNTHESIS OF [3-(5-{5-[(DIMETHYLAMINO)METHYL](1H-1,2,4-TRIAZOL-3-YL)}(1H-INDAZOL-3-YL))PHENYL]-N-[(4-FLUOROPHENYL)METHYL]CARBOXAMIDE

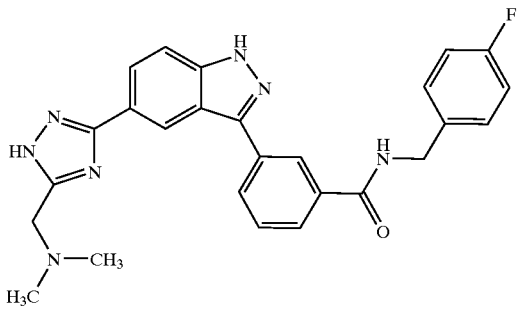

Methyl 3-(5-cyano-1-perhydro-2H-pyran-2-yl-1H-indazol-3-yl)benzoate (10 g, 27.6 mmol) and LiOH.$H_2O$ (3.5 g, 82.8 mmol) were stirred in a mixture of 200 mL THF+80 mL water at room temperature for 18 h. The THF was removed under reduced pressure and the pH of the resulting suspension was adjusted to pH 4 by the addition of 1M HCl. The mixture was extracted with EtOAc, the organic layer dried ($Na_2SO_4$) and filtered. The filtrate was concentrated to a yellow solid which was redissolved in dichloromethane. Addition of hexanes precipitated 6.9 g (72%) of the title compound as a white solid. $^1$H NMR (DMSO-$d_6$) δ 11.5 (bs, 1H), 8.65 (d, 2H), 8.35 (d, 2H), 8.14 (m, 1H), 8.01 (m, 1H), 7.79 (m, 2H), 6.0 (d, 1H), 3.9 (m, 2H), 2.15 (d, 1H), 1.9–1.6 (m, 4H); ES-MS (m/z) 349 $[M+H]^+$.

A. [3-(5-Cyano-1-perhydro-2H-pyran-2-yl(1H-indazol-3-yl))phenyl]-N-[(4-fluorophenyl)methyl]carboxamide The reaction of 3-(5-cyano-1-perhydro-2H-pyran-2-yl-1H-indazol-3-yl)benzoic acid (1.0 g, 2.87 mmol), HOBT (1.16 g, 8.62 mmol), EDCI (1.64 g, 8.62 mmol) and 4-fluorobenzylamine (0.98 mL, 1.07 g, 8.62 mmol) furnished 1.2 g (90% yield) of the title compound. ES-MS (m/z) 455 $[M]^+$.

B. [3-(5-{5-[(Dimethylamino)methyl](1H-1,2,4-triazol-3-yl)}-1-perhydro-2H-pyran-2-yl(1H-indazol-3-yl))phenyl-N-[(4-fluorophenyl)methyl]carboxamide A solution of [3-(5-cyano-1-perhydro-2H-pyran-2-yl-1H-indazol-3-yl))phenyl]-N-(4-fluorophenyl)methyl]carboxamide (1.0 g, 2.2 mmol), N-amino-2-(diemthylamino)acetamide (0.77 g, 6.59 mmol) and NaOMe (1.9 mL of 25% by weight solution in MeOH, 0.47 g, 8.79 mmol) was heated in 10 mnL MeOH in a sealed tube at 100° C. for 30 hours. The reaction mixture was concentrated to an oil which was purified by column chromatography (10–50% MeOH in EtOAc) to furnish 0.42 g (34%) of the title compound. ES-MS (m/z) 554 $[M+H]^+$.

C. [3-(5-{5-[(Dimethylamino)methyl](1H-1,2,4-triazol-3-yl)}(1H-indazol-3-yl))phenyl]-N-[(4-fluorophenyl)methyl]carboxamide

[3-(5-{5-[(Dimethylamino)methyl](1H-1,2,4-triazol-3-yl)}-1-perhydro-2H-pyran-2-yl(1H-indazol-3-yl))phenyl-N-[(4-fluorophenyl)methyl]carboxamide (0.42 g, 0.76 mmol) was suspended in 8 mL of 4 M HCl in dioxane solution. 10 mL toluene was added and the suspension was stirred at room temperature for 18 h. The reaction was quenched with saturated aqueous NaHCO$_3$ solution and then concentrated under reduced pressure. The residue was taken up in DMSO and filtered. Purification by preparative HPLC (15–80% acetonitrile in water) furnished 50 mg (14% yield) of the title compound. $^1$H NMR (DMSOd$_6$) δ 14.0 (s, 1H), 13.4 (s, 1H), 9.3 (t, 1H), 8.55 (br s, 1H), 8.5 (s, 1H), 8.15 (m, 2H), 7.95 (d, 1H), 7.8–7.6 (m, 2H), 7.4 (m, 2H), 7.2 (m, 2H), 4.5 (d, 2H), 3.6 (s, 2H), 2.45 (s, 6H); ES-MS (m/z) 470 [M+H]$^+$.

Example 358

SYNTHESIS OF [3-(5-{5-[(DIMETHYLAMINO)METHYL](1H-1,2,4-TRIAZOL-3YL)}(1H-INDAZOL-3-YL))PHENYL]-N-[(tert-BUTYL)METHYL]CARBOXAMIDE

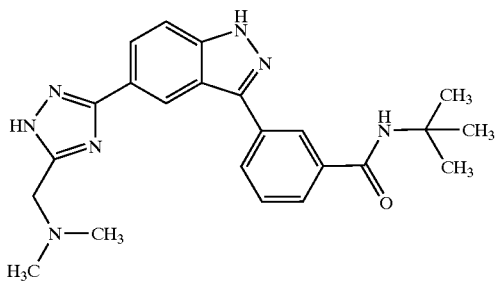

A. N-(tert-Butyl)[3-(5-cyano-1-perhydro-2H-pyran-2-yl (1H-indazol-3-yl))phenyl]carboxamide Following Example 357, the reaction of 3-(5-cyano-1-perhydro-2H-pyran-2-yl-1H-indazol-3-yl)benzoic acid (0.8 g, 2.3 mmol), HOBT (1.16 g, 8.62 mmol), EDCI (1.64 g, 8.62 mmol) and tert-butylamine (0.73 mL, 0.5 g, 6.9 mmol) furnished 0.72 g (74% yield) of the title compound. ES-MS (m/z) 403 [M+H]$^+$.

B. [3-(5-{5-[(Dimethylamino)methyl](1H-1,2,4-triazol-3-yl)}-1-perhydro-2H-pyran-2-yl(1H-indazol-3-yl))phenyl-N-(tert-butyl)carboxamide A solution of [3-(5-cyano-1-perhydro-2H-pyran-2-yl-1H-indazol-3-yl)phenyl]-N-(4-fluorophenyl)methyl]carboxamide (0.4 g, 0.99 mmol), N-amino-2-(diemthylamino)acetamide (0.35 g, 2.98 mmol) and NaOMe (0.64 mL of 25% by weight solution in MeOH, 0.16 g, 2.98 mmol) was heated in 4 mL MeOH in a sealed tube at 100° C. for 36 hours. The reaction mixture was concentrated to an oil which was purified by column chromatography (10–50% MeOH in EtOAc) to furnish 0.3 g (60% yield) of the title compound. ES-MS (m/z) 502 [M+H]$^+$.

C. [3-(5-{5-[(Dimethylamino)methyl](1H-1,2,4-triazol-3-yl)}(1H-indazol-3-yl))phenyl]-N-[(tert-butyl)methyl]carboxamide

[3-(5-{5-[(dimethylamino)methyl](1H-1,2,4-triazol-3-yl)}-1-perhydro-2H-pyran-2-yl(1H-indazol-3-yl))phenyl-N-(tert-butyl)carboxamide (0.3 g, 0.59 mmol) was suspended in 10 mL of 4M in HCl dioxane solution. Toluene (10 mL) was added and the suspension was stirred at room temperature for 18 h. The reaction was quenched with saturated aqueous NaHCO$_3$ solution and then concentrated under reduced pressure. The residue was taken up in DMSO and filtered. Purification by preparative HPLC (15–80% acetonitrile in water) furnished 30 mg (12% yield) of the title compound. $^1$H NMR (DMSOd$_6$) δ 13.4 (s, 1H), 8.65 (br s, 1H), 8.38 (s, 1H), 8.1 (m, 2H), 7.98 (s, 1H), 7.85 (s, 1H), 7.75–7.6 (m, 2H), 3.4 (s, 2H), 2.4 (s, 6H), 1.4 (s, 9H); ES-MS (m/z) 418 [M+H]$^+$.

Example 359

SYNTHESIS OF N-((1R)INDANYL)[3-(5-{5-[(DIMETHYLAMINO)METHYL](1H-1,2,4-TRIAZOL-3-YL)}(1H-INDAZOL-3-YL))PHENYL]CARBOXAMIDE

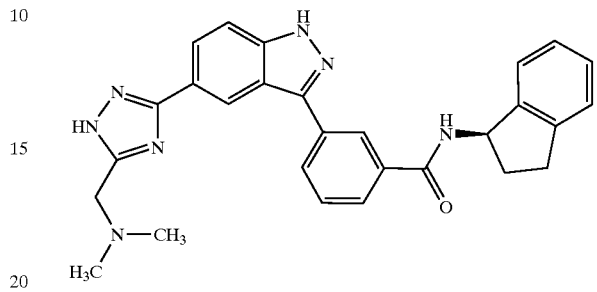

A. N-((1R)Indanyl))[3-(5-cyano-1-perhydro-2H-pyran-2-yl (1H-indazol-3-yl))phenyl]carboxamide Following Example 357, the reaction of 3-(5-cyano-1-perhydro-2H-pyran-2-yl-1H-indazol-3-yl)benzoic acid (0.6 g, 1.72 mmol), HOBT (0.7 g, 5.2 mmol), EDCI (0.99 g, 5.2 mmol) and tert-butylamine (0.66 mL, 0.68 g, 5.2 mmol) furnished 0.45 g (56% yield) of the title compound. ES-MS (m/z) 463 [M]$^+$.

B. N-((1R)Indanyl)[3-(5-{5-[(dimethylamino)methyl](1H-1,2,4-triazol-3-yl)}-1-perhydro-2H-pyran-2-yl(1H-indazol-3-yl))phenyl]carboxamide A solution of N-((1R)indanyl))[3-(5-cyano-1-perhydro-2H-pyran-2-yl(1H-indazol-3-yl))phenyl]carboxamide (0.45 g, 0.97 mmol), N-amino-2-(diemthylamino)acetamide (0.34 g, 2.91 mmol) and NaOMe (0.63 mL of 25% by weight solution in MeOH, 0.16 g, 2.91 mmol) was heated in 28 mL MeOH in a sealed tube at 100° C. for 39 hours. The reaction mixture was concentrated to an oil which was purified by column chromatography (10–50% MeOH in EtOAc) to furnish 0.39 g (71% yield) of the title compound. ES-MS (m/z) 562 [M+H]$^+$.

C. N-((1R)indanyl)[3-(5-{5-[(dimethylamino)methyl](1H-1,2,4-triazol-3-yl)}(1H-indazol-3-yl))phenyl]carboxamide N-((1R)indanyl)[3-(5-{5-[(dimethylamino)methyl](1H-1,2,4-triazol-3-yl)}-1-perhydro-2H-pyran-2-yl(1H-indazol-3-yl))phenyl]carboxamide (0.39 g, 0.69 mmol) was suspended in 10 mL of 4 M in HCl dioxane solution. The suspension was stirred at room temperature for 4 h. The reaction was quenched with saturated aqueous NaHCO$_3$ solution and then concentrated under reduced pressure. The residue was taken up in DMSO and filtered. Purification by preparative HPLC (15–80% acetonitrile in water) furnished 39 mg (12% yield) of the title compound. $^1$H NMR (DMSOd$_6$) δ 13.6 (s, 1H), 9.01 (m, 1H), 8.65 (br s, 1H), 8.45 (s, 1H), 8.2–7.95 (m, 3H), 7.67 (m, 2H), 7.22 (m, 4H), 5.6 (q, 1H), 3.4 (s, 2H), 3.0 (m, 2H), 2.4 (s, 6H), 2.4–2.0 (m,2H); ES-MS (m/z) 478 [M+H]$^+$.

Example 360

SYNTHESIS OF ({3-[3-(4-METHOXYPHENYL)(1H-INDAZOL-5-YL)](1H-1,2,4-TRIAZOL-5-YL)}METHYL)DIMETHYLAMINE

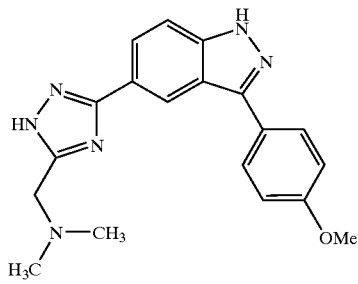

A. 3-(4-Methoxyphenyl)-1-perhydro-2H-pyran-2-yl-1H-indazole-5-carbonitrile

A mixture of 3-bromo-1-perhydro-2H-pyran-2-yl-1H-indazole-5-carbonitrile (5.0 g, 16.3 mmol), 4-methoxyphenylboronic acid (3.7 g, 24.5 mmol), Pd(dppf)Cl$_2$ (1.33 g, 1.63 mmol) and K$_3$PO$_4$ (17.31 g, 81.66 mmol) in 120 mL DME was refluxed for 24 h. The reaction was cooled and diluted with EtOAc. The mixture was filtered through a celite pad and the filtrate was washed with water, brine, dried (Na$_2$SO$_4$) and filtered. Removal of solvent in vacuo followed by chromatographic purification of the residue (10–50% EtOAc in hexanes) furnished 4 g (73% yield) of the title compound as a white solid. ES-MS (m/z) 334 [M+H]$^+$.

B. ({3-[3-(4-Methoxyphenyl)-1-perhydro-2H-pyran-2-yl(1H-indazol-5-yl)](1H-1,2,4-triazol-5-yl)}methyl)dimethylamine A solution of 3-(4-methoxyphenyl)-1-perhydro-2H-pyran-2-yl-1H-indazole-5-carbonitrile (0.8 g, 2.4 mmol), N-amino-2-(diemthylamino)acetamide (0.84 g, 7.2 mmol) and NaOMe (1.6 mL of 25% by weight solution in MeOH, 0.39 g, 7.2 mmol) was heated in 28 mL MeOH in a sealed tube at 100° C. for 36 hours. The reaction mixture was concentrated to an oil which was purified by column chromatography (10–50% MeOH in EtOAc) to furnish 0.57 g (55% yield) of the title compound. ES-MS (m/z) 433 [M+H]$^+$.

C. ({3-[3-(4-Methoxyphenyl)(1H-indazol-5-yl)](1H-1,2,4-triazol-5-yl)}methyl)dimethylamine ({3-[3-(4-methoxyphenyl)-1-perhydro-2H-pyran-2-yl(1H-indazol-5-yl)](1H-1,2,4-triazol-5-yl)}methyl)dimethylamine (0.57 g, 1.32 mmol) was suspended in 10 mL of 4 M in HCl dioxane solution. Toluene (10 mL) was added and the suspension was stirred at room temperature for 18 h. The reaction was quenched with saturated aqueous NaHCO$_3$ solution and then concentrated under reduced pressure. The residue was taken up in DMSO and filtered. Purification by preparative HPLC (15–80% acetonitrile in water) furnished 92 mg (20% yield) of the title compound. $^1$H NMR (DMSOd$_6$) δ 14.0 (s, 1H), 13.2 (s, 1H), 8.6 (s, 1H), 8.05 (dd, 1H), 7.95 (m, 2H), 7.65 (d, 1H), 7.14 (m, 2H), 3.8 (s, 3H), 3.6 (s, 2H), 2.2 (s, 6H); ES-MS (m/z) 349 [M+H]$^+$.

Example 361

SYNTHESIS OF {[3-(3-(2H-BENZO[d]1,3-DIOXOLEN-5-YL))(1H-INDAZOL-5-YL)](1H-1,2,4-TRIAZOL-5-YL)}METHYL}DIMETHYLAMINE

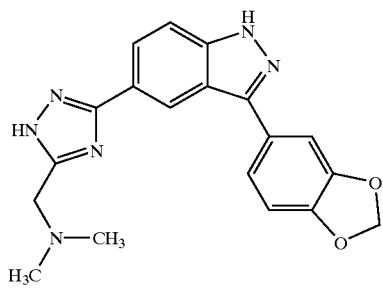

A. 3-(2H-Benzo[d]1,3-dioxolen-5-yl)-1-perhydro-2H-pyran-2-yl-1H-indazole-5-carbonitrile A mixture of 3-bromo-1-perhydro-2H-pyran-2-yl-1H-indazole-5-carbonitrile (5.0 g, 16.3 mmol), 3,4-methylenedioxyphenylboronic acid (4.07 g, 24.5 mmol), Pd(dppf)Cl$_2$ (1.33 g, 1.63 mmol) and K$_3$PO$_4$ (17.31 g, 81.66 mmol) in 85 mL DME was refluxed for 24 h. The reaction was cooled and diluted with EtOAc. The mixture was filtered through a celite pad and the filtrate was washed with water, brine, dried (Na$_2$SO$_4$) and filtered. Removal of solvent in vacuo followed by chromatographic purification of the residue (10–50% EtOAc in hexanes) furnished 4 g (70% yield) of the title compound as a white solid. ES-MS (m/z) 348 [M+H]$^+$.

B. {[3-(3-(2H-Benzo[d]1,3-dioxolen-5-yl)-1-perhydro-2H-pyran-2-yl(1H-indazol-5-yl))(1H-1,2,4-triazol-5-yl)]methyl}dimethylamine A solution of 3-(2H-benzo[d]1,3-dioxolen-5-yl)-1-perhydro-2H-pyran-2-yl-1H-indazole-5-carbonitrile (0.5 g, 1.44 mmol), N-amino-2-(diemthylamino)acetamide (0.5 g, 4.31 mmol) and NaOMe (1.2 mL of 25% by weight solution in MeOH, 0.31 g, 5.75 mmol) was heated in 25 mL MeOH in a sealed tube at 100° C. for 36 hours. The reaction mixture was concentrated to an oil which was purified by column chromatography (10–50% MeOH in EtOAc) to furnish 0.5 g (64% yield) of the title compound. ES-MS (m/z) 447 [M+H]$^+$.

C. {[3-(3-(2H-Benzo[d]1,3-dioxolen-5-yl) (1H-indazol-5-yl)](1H-1,2,4-triazol-5-yl)}methyl}dimethylamine {[3-(3-(2H-Benzo[d]1,3-dioxolen-5-yl)-1-perhydro-2H-pyran-2-yl(1H-indazol-5-yl))(1H-1,2,4-triazol-5-yl)]methyl}dimethylamine (0.5 g, 1.12 mmol) was suspended in 10 mL of 4 M in HCl dioxane solution. Toluene (10 mL) was added and the suspension was stirred at room temperature for 18 h. The reaction was quenched with saturated aqueous NaHCO$_3$ solution and then concentrated under reduced pressure. The residue was taken up in DMSO and filtered. Purification by preparative HPLC (15–80% acetonitrile in water) furnished 47 mg (11% yield) of the title compound. $^1$H NMR (DMSOd$_6$) δ 14.0 (br s, 1H), 13.4 (s, 1H), 8.6 (s, 1H), 8.1 (d, 1H), 7.65 (d, 1H), 7.5 (s, 2H), 7.15 (d, 1H), 6.1 (s, 2H), 3.4 (s, 2H), 2.2 (s, 6H); ES-MS (m/z) 363 [M+H]$^+$.

Example 362

SYNTHESIS OF [3-(4-FLUOROPHENYL)(1H-INDAZOL-5-YL)]-N-(3-METHOXYPROPYL) CARBOXAMIDE

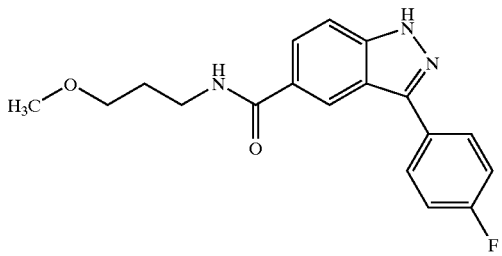

A. [3-(4-Fluorophenyl)(1H-indazol-5-yl)-N-(3-methoxypropyl)carboxamide

The title compound was prepared as described in Example 68. To a solution of 1-acetyl-3-(4-fluorophenyl)-1H-indazole-5-carbonyl chloride (0.200 g, 0.632 mmol) in pyridine (4 mL) was added 2-methoxypropylamine (0.274 mL, 3.16 mmol). The solution was stirred for 3 h at room temperature. Water (40 mL) was added and the reaction mixture was extracted with ethyl acetate. The combined organic layers were washed with aqueous 1 N hydrochloric acid, dried over anhydrous sodium sulfate, filtered and evaporated. The residue was purified by preparative HPLC (10–90% acetonitrile/water). The pure fractions were basified with ammonium hydroxide, evaporated at reduced pressure, diluted with water and filtered to give the title compound (0.073 g, 35% yield): $^1$H NMR (DMSO-$d_6$) δ 13.42 (br s, 1H), 8.60 (t, 1H), 8.53 (s, 1H), 8.07 (AB quartet, 2H), 7.92 (dd, 1H), 7.62 (d, 1H), 7.40 (t, 2H), 3.40 (t, 2H), 3.34 (m, 2H), 3.25 (s, 3H), 1.79 (m, 2H); ES-MS (m/z) 328 [M+1]$^+$.

Example 363

SYNTHESIS OF 3-[3-(4-FLUOROPHENYL)-1H-INDAZOL-5-YL]-1,2,4-OXADIAZOLIN-5-ONE

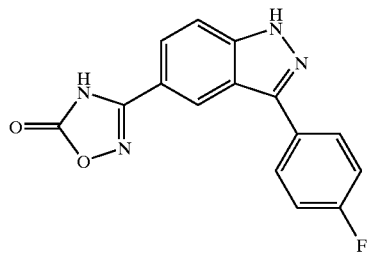

A. [3-(4-Fluorophenyl)-1-perhydro-2H-pyran-2-yl(1H-indzaol-5-yl)](hydroxyimino)methylamine 3-(4-Fluorophenyl)-1-perhydro-2H-pyran-2-yl-1H-indazole-5-carbonitrile (400 mg, 1.25 mmol), hydroxylamine hydrochloride (434 mg, 6.25 mmol) and K$_2$CO$_3$ (864 mg, 6.25 mmol) in ethanol (7.0 mL) was placed in a screw-top pressure tube and heated in a 100° C. oil bath for 16 h. The reaction mixture was filtered through a sintered glass funnel while hot, washed with hot ethanol and concentrated in vacuo to give the desired product (283 mg, 64%) as an off white solid. ES-MS (m/z) 355 [M+H$^+$]$^+$.

B. 2-Amino-1-aza-2-[3-(4-phenyl)-1-perhydro-2H-pyran-2-yl(1H-indazol-5-yl)]vinyl ethoxyformate To a slurry of [3-(4-fluorophenyl)-1-perhydro-2H-pyran-2-yl(1H-indzaol-5-yl)](hydroxyimino)methylamine (125 mg, 0.35 mmol) in anhydrous chloroform (1.5 mL, 30.85 mmol) was added triethylamine (64 mL, 0.46 mmol) and ethyl chloroformate (38 mL, 0.39 mmol) at ambient temperature. After stirring for 2 h the reaction mixture was diluted with dichloromethane, washed with brine, dried over MgSO4 and concentrated in vacuo to give the desired product as a pale solid which was used without further purification for the next step.

C. 3-[3-(4-Fluorophenyl)-1-perhydro-2H-pyran-2-yl-1H-indazol-5-yl]-1,2,4-oxadiazolin-5-one 2-Amino-1-aza-2-[3-(4-phenyl)-1-perhydro-2H-pyran-2-yl(1H-indazol-5-yl)]vinyl ethoxyformate, obtained from the previous reaction, and anhydrous toluene (3.0 mL) was placed in a screw-top pressure tube and heated in a 135° C. oil bath for 15 h. The reaction mixture was cooled, diluted with hot methanol, filtered through a sintered glass funnel and concentrated in vacuo to give a dark brown residue. Purification of the residue by flash chromatography on silica gel eluting with 10% methanol in dichloromethane gave the desired product (88 mg, 66% for two steps) as a tan solid. ES-MS (m/z) 381 [M+H$^+$]$^+$.

D. 3-[3-(4-Fluorophenyl)-1H-indazol-5-yl]-1,2,4-oxadiazolin-5-one

To a solution of 3-[3-(4-fluorophenyl)-1-perhydro-2H-pyran-2-yl-1H-indazol-5-yl]-1,2,4-oxadiazolin-5-one (88 mg, 0.23 mmol) in dioxane (4.0 mL) was added 6 N HCl (4.0 mL) at ambient temperature. After stirring for 16 h an additional amount of dioxane (1.0 mL) was added and the reaction mixture was gently heated in a 60° C. oil bath for 4 h after which an additional amount of 6 N HCl (1.0 mL) and several drops of methanol were added and after an additional 4 h of heating the reaction was stopped by slowly pouring into vigorously stirred aqueous 6 N NaOH (6.0 mL). The solution was adjusted to pH=8 with the addition of 4 N HCl and extracted with ethyl acetate. The organic layer was washed with brine, dried over MgSO$_4$ and concentrated in vacuo to give a pale orange solid which was purified by flash chromatography on silica gel eluting with 10% methanol in dichloromethane to give a pale yellow solid which was dissolved in a minimum amount of methanol and precipitated with ethyl ether and hexanes to afford the desired product as a pale powder (13 mg, 19% yield) $^1$H NMR (DMSO-$d_6$): δ 13.6 (s, 1H), 13.0 (br s, 1H), 8.5 (s, 1H), 8.1–8.0 (m, 2H), 7.8 (q, 2H), 7.3 (t, 2H); ES-MS (m/z) 297 [M+H]$^+$.

Example 364

SYNTHESIS OF (5-[3-(4-FLUOROPHENYL)-1H-INDAZOL-5-YL]-1H-1,2,4-TRIAZOL-3-YL) METHAN-1-OL

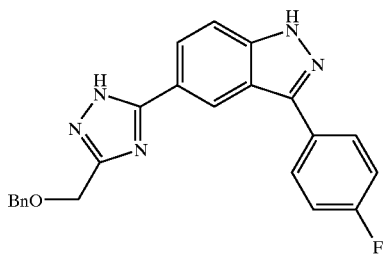

A. (5-[3-(4-Fluorophenyl)(1H-indazol-5-yl)](1H-1,2,4-triazol-3-yl))(phenylmethoxy)methane To a suspension of ethoxy[3-(4-fluorophenyl)(1H-indazol-5-yl)]methanimine.2HCl (307 mg, 0.96 mmol) and N-amino-2-(phenylmethoxy)acetamide (259 mg, 1.44 mmol) in anhydrous methanol (3.0 mL) in a screw-top pressure tube was added freshly prepared sodium methoxide (615 μL of a 3.12 M solution in methanol). The tube was sealed and heated in a 90° C. oil bath for 17 h. The reaction was cooled, evaporated to dryness and partitioned between ethyl acetate and satd. NH$_4$Cl. The organic layer was separated, washed with brine, dried over MgSO$_4$ and concentrated in vacuo to give an oily brown residue. Purification by flash chromatography on silica gel eluting with 5% methanol in dichloromethane (R$_f$=0.43) gave a pale solid (155 mg) which was re-chromatographed using 30% hexanes in ethyl acetate to remove traces of color.

B. (5-[3-(4-Fluorophenyl)-1H-indazol-5-yl]-1H-1,2,4-triazol-3-yl)methan-1-ol

A solution of (5-[3-(4-fluorophenyl)(1H-indazol-5-yl)](1H-1,2,4-triazol-3-yl))(phenylmethoxy)methane, obtained from the previous reaction, was hydrogenated at 60 psi in methanol (20 mL) over Pd(OH)$_2$ on carbon (200 mg, 25% w/w) for 20 h. The reaction was filtered through a Celite pad, washed with methanol and concentrated in vacuo to give a residue which was purified by flash chromatography on silica gel with 10% methanol in dichloromethane then 20% methanol in dichloromethane. Fractions containing the desired product were pooled and evaporated to give a pale solid which was washed with ethyl ether to afford the title compound (35 mg, 12% yield for two steps) $^1$H NMR (DMSO-d$_6$w/100 μL CD$_3$CO$_2$D) δ 8.6 (s, 1H), 8.0–7.9 (m, 3H), 7.6 (d, 1H), 7.3 (t, 2H), 4.6 (s, 2H); ES-MS (m/z) 310 [M+H]$^+$.

Example 365

SYNTHESIS OF [3-(5-(3-[(DIMETHYLAMINO)METHYL](1H-1,2,4-TRIAZOL-5-YL))(1H-INDAZOL-3-YL))PHENYL]-N-(2-PIPERIDYLETHYL)CARBOXAMIDE

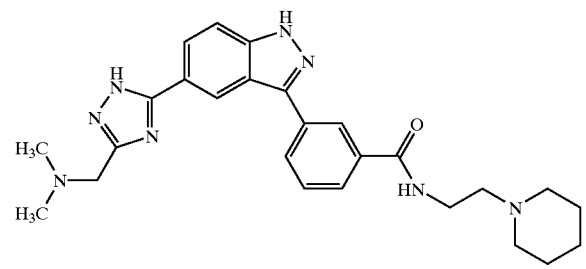

A. [3-(5-Cyano-1-perhydro-2H-pyran-2-yl(1H-indazol-3-yl))phenyl]-N-(2-piperidylethyl)carboxamide HOBT (1.74 g, 12.93 mmol) was added in one portion to a solution of 3-(5-cyano-1-perhydro-2H-pyran-2-yl-1H-indazol-3-yl)benzoic acid (1.50 g, 4.31 mmol) in anhydrous THF (50.0 mL) and anhydrous DMF (20.0 mL) at ambient temperature. After 30 min EDAC.HCl (2.47 g, 12.93 mmol) and 1-(2-aminoethyl)piperidine (1.84 mL, 12.93 mmol) was added and the resultant mixture was stirred for 20 h. The reaction mixture was partitioned between ethyl acetate and water, washed with brine, dried over Na$_2$SO$_4$ and concentrated in vacuo during which the product began to precipitate as a colorless solid. Hexanes were added and the desired product was collected by vacuum filtration (1.8 g, 91% yield) ES-MS (m/z) 458 [M+H]$^+$.

B. (3-[5-(Ethoxyiminomethyl)(1H-indazol-3-yl)]phenyl)-N-(2-piperidylethyl)carboxamide.3HCl Anhydrous hydrogen chloride gas was bubbled into a suspension of [3-(5-cyano-1-perhydro-2H-pyran-2-yl(1H-indazol-3-yl))phenyl]-N-(2-piperidylethyl)carboxamide (952 mg, 2.08 mmol) in anhydrous ethanol (70 mL) at 0° C. for 10 min. The reaction mixture was sealed, stirred at ambient temperature for several days and the bulk of the ethanol was removed in vacuo to give an off-white solid. The solid was suspended in anhydrous ethyl ether, filtered under a blanket of nitrogen, washed with copious amounts of ethyl ether, collected and dried under vacuum to give the desired product as a hygroscopic solid (1.07 g, 97% yield) ES-MS (m/z) 421 [M+H]$^+$(HCl salt not detected).

C. [3-(5-(3-[(dimethylamino)methyl](1H-1,2,4-triazol-5-yl))(1H-indazol-3-yl))phenyl]-N-(2-piperidylethyl)carboxamide To a suspension of (3-[5-(ethoxyiminomethyl)(1H-indazol-3-yl)]phenyl)-N-(2-piperidylethyl)carboxamide.3HCl (412 mg, 0.78 mmol) and N-amino-2-(dimethylamino)acetamide (275 mg, 2.35 mmol) in anhydrous methanol (5.0 mL) in a screw-top pressure tube was added sodium methoxide (626 mL of a 25% w/w in methanol). The tube was sealed, heated in a 105° C. oil bath for 48 h and then concentrated to dryness. Purification of the residue by preparatory TLC using 40% ethyl acetate in methanol gave the desired product after precipitation from methanol/ethyl acetate with ethyl ether (12 mg, 3% yield) $^1$H NMR (DMSO-d$_6$) δ 13.7 (br s, 1H), 8.7 (br s, 2H), 8.4 (s, 1H), 8.1–8.0 (m, 2H), 7.85 (br d, 1H), 7.7–7.6 (m, 2H), 3.6 (s, 2H), 3.5–3.3 (m, 2H), 2.5–2.2 (m, 6H), 2.2 (s, 6H), 1.6–1.3 (m, 6H); ES-MS (m/z) 473 [M+H]$^+$.

Example 366

SYNTHESIS OF ([5-(3-BENZO[D]FURAN-2-YL(1H-INDAZOL-5-YL))(1H-1,2,4-TRIAZOL-3-YL)]METHYL)DIMETHYLAMINE

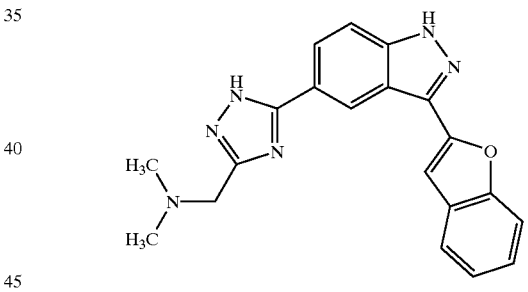

A. 3-Benzo[d]furan-2-yl-1-perhydro-2H-pyran-2-yl-1H-indazole-5-carbonitrile

3-Bromo-1-(tetrahydro-2-pyranyl)-1H-indazole-5-carbonitrile (1.00 g, 3.27 mmol), 2-benzofuranboronic acid (795 mg, 4.90 mmol), Pd(dppf)Cl$_2$.CH$_2$Cl$_2$ (266 mg) and potassium phosphate (3.47 g, 16.35 mmol) in 1,2-dimethoxyethane (16.0 mL) was placed into a screw-top pressure tube and heated in a 95° C. oil bath for 21 h. The reaction mixture was cooled and partitioned between dichloromethane and water. The organic layer was separated, washed with satd. NaHCO$_3$, brine, dried over MgSO$_4$ and concentrated in vacuo to give a residue which was purified by flash chromatography on silica gel with 30% ethyl acetate in hexane (R=0.49) to afford the desired product (167 mg, 15% yield) as a pale orange foam.

B. ([5-(3-Benzo[d]furan-2-yl-1-perhydro-2H-pyran-2-yl(1H-indazol-5-yl))(1H-1,2,4-triazol-3-yl)]methyl)dimethylamine To a suspension of 3-benzo[d]furan-2-yl-1-perhydro-2H-pyran-2-yl-1H-indazole-5-carbonitrile (167 mg, 0.49 mmol) and N-amino-2-(dimethylamino)acetamide (171 mg, 1.46 mmol) in anhydrous methanol (1.0 mL) in a screw-top pressure tube was added sodium methoxide (445 μL of a 25% w/w in methanol). The tube was sealed and heated in a 100° C. oil bath for 21 h. An additional amount of N-amino-2-(dimethylamino) acetamide (171 mg, 1.46 mmol) was added and the reaction heated for an additional 2 days. The reaction was cooled, evaporated to dryness and partitioned between ethyl acetate and satd. ammonium chloride. The organic layer was separated, washed with brine, dried over MgSO$_4$ and concentrated in vacuo to give a yellow solid. Purification of the residue by flash chromatography on silica gel using 5% methanol in dichloromethane then 20% methanol in dichloromethane gave the desired product (15 mg, 7% yield) as a pale yellow foam. ES-MS (m/z) 443 [M+H]$^+$.

C. ([5-(3-Benzo[d]furan-2-yl(1H-indazol-5-yl))(1H-1,2,4-triazol-3-yl)]methyl)dimethylamine ([5-(3-Benzo[d]furan-2-yl-1-perhydro-2H-pyran-2-yl(1H-indazol-5-yl))(1H-1,2,4-triazol-3-yl)]methyl)dimethylamine (15 mg, 0.034 mmol) in anhydrous HCl (5.0 mL of a 4 N solution in 1,4-dioxane) was vigorously stirred at ambient temperature for 18 h. The reaction mixture was neutralized with the slow addition of satd. NaHCO$_3$ and extracted with ethyl acetate. The organic layer was washed with brine, dried over MgSO$_4$ and concentrated in vacuo to give a solid which was redissolved in a minimum amount of ethyl acetate and precipitated with hexanes to give the desired product as an off-white powder. The product was further purified by preparatory HPLC using a 30–80% acetonitrile/water gradient with 0.1% CF$_3$CO$_2$H. Fractions containing the desired product were pooled and evaporated to give a pale yellow solid which was partitioned between ethyl acetate and satd. NaHCO$_3$. The organic layer was separated, washed with brine, dried over MgSO$_4$ and concentrated in vacuo to give a solid which was dissolved in a minimum amount of methanol/ethyl acetate and precipitated with hexanes. The solid was collected, washed with ethyl ether/hexanes and dried under vacuum to afford the desired product as a pale solid (5.0 mg, 41% yield) $^1$H NMR (DMSO-d$_6$) δ 8.9 (s, 1H), 8.14 (dd, 1H), 7.8–7.6 (m, 3H), 7.46 (s, 1H), 7.4–7.26 (m, 2H), 4.65 (s, 2H), 1.85 (s, 6H); ES-MS (m/z) 359 [M+H]$^+$.

Example 367

SYNTHESIS OF [3-(5-(3-[(DIMETHYLAMINO)METHYL](1H-1,2,4-TRIAZOL-5-YL))(1H-INDAZOL-3-YL))PHENYL]-N-BENZAMIDE

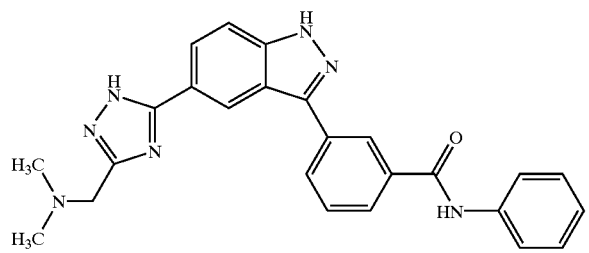

A. [3-(5-Cyano-1-perhydro-2H-pyran-2-yl(1H-indazol-3-yl))phenyl]-N-benzamide

HOBT (931 mg, 6.88 mmol) was added in one portion to a solution of 3-(5-cyano-1-perhydro-2H-pyran-2-yl-1H-indazol-3-yl)benzoic acid (800 mg, 2.30 mmol) in anhydrous THF (20.0 mL) at ambient temperature. After 30 min EDAC.HCl (1.32 g, 6.88 mmol), aniline (628 μL, 7.48 mmol) and anhydrous DMF (10.0 mL) was added. After stirring overnight, volatile materials were removed under reduced pressure and the residue was partitioned between ethyl acetate and water. The organic layer was separated, washed with brine, dried over MgSO$_4$ and concentrated in vacuo to give a solid which was precipitated from ethyl acetate and methanol with hexanes to give the desired product (799 mg, 82% yield) as a tan powder. ES-MS (m/z) 423 [M+H]$^+$.

B. (3-[5-(Ethoxyiminomethyl)(1H-indazol-3-yl)]phenyl)-N-benzamide.2HCl

Anhydrous hydrogen chloride gas was bubbled into a suspension of [3-(5-cyano-1-perhydro-2H-pyran-2-yl(1H-indazol-3-yl))phenyl]-N-benzamide (620 mg, 1.47 mmol) in anhydrous ethanol (30 mL) at 0° C. for 10 min. The reaction mixture was sealed, stirred at ambient temperature for several days and the bulk of the ethanol was removed in vacuo to give an off-white solid. The solid was suspended in anhydrous ethyl ether, filtered, washed with copious amounts of ethyl ether, collected and dried under vacuum to give the desired product as an off-white solid (599 mg, 89% yield). $^1$H NMR (DMSO-d$_6$) δ 12.1 (br s, 1H), 11.1 (br s, 1H), 10.55 (s, 1H), 9.2 (s, 1H), 8.6 (s, 1H), 8.3 (d, 3H), 8.1 (t, 2H), 7.9–7.6 (5H), 7.45 (t, 2H), 7.1 (t, 1H), 4.65 (q, 2H), 1.5 (t, 3H).

C. [3-(5-(3-[(dimethylamino)methyl](1H-1,2,4-triazol-5-yl))(1H-indazol-3-yl))phenyl]-N-benzamide To a suspension of (3-[5-(ethoxyiminomethyl)(1H-indazol-3-yl)]phenyl)-N-benzamide.2HCl (250 mg, 0,55 mmol) and N-amino-2-(dimethylamino)acetamide (192 mg, 1.64 mmol) in anhydrous methanol (3.0 mL) in a screw-top pressure tube was added sodium methoxide (314 μL of a 25% w/w in methanol). The tube was sealed, heated in a 100° C. oil bath for 48 h and concentrated to dryness. Purification of the residue by preparatory TLC using 50% ethyl acetate in methanol gave the desired product which was further purified by precipitation from methanol with ethyl acetate and ether to give the title compound (47 mg, 20%) as an off-white powder $^1$H NMR (DMSO-d$_6$) δ 10.45 (br s, 1H), 8.65 (s, 1H), 8.55 (s, 1H), 8.2 (d, 1H), 8.1 (d, 1H), 8.0 (d, 1H), 7.8 (d, 2H), 7.75–7.65 (m, 2H), 7.35 (t, 2H), 7.1 (t, 1H), 3.55 (s, 2H), 2.2 (s, 6H); ES-MS (m/z) 438 [M+H]$^+$.

Example 368

SYNTHESIS OF [3-(5-(3-[(DIMETHYLAMINO)METHYL](1H-1,2,4-TRIAZOL-5-YL))(1H-INDAZOL-3-YL))PHENYL]-N-(4-FLUOROPHENYL)CARBOXAMIDE.2HCl

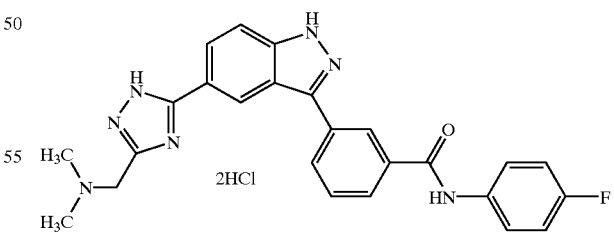

A. [3-(5-Cyano-1-perhydro-2H-pyran-2-yl(1H-indazol-3-yl)phenyl]-N-(4-fluorophenyl)carboxamide The title compound was prepared according to the procedure of Example 367 A using the following amounts of reagents: 3-(5-cyano-1-perhydro-2H-pyran-2-yl-1H-indazol-3-yl)benzoic acid (2.65 g, 7.63 mmol), 4-fluoroaniline (2.20 mL, 23.22 mmol), HOBT (3.1 g, 22.95 mmol), EDAC.HCl (4.4 g, 22.95 mmol), anhydrous THF (50.0 mL) and anhydrous DMF (15.0 mL) (2.99 g, 89% yield) as a yellow solid. ES-MS (m/z) 441 [M+H]⁺.

B. (3-[5-(Ethoxyiminomethyl)(1H-indazol-3-yl)]phenyl)-N-(4-fluorophenyl)carboxamide.2HCl The title compound was prepared according to the procedure of Example 367 B using [3-(5-cyano-1-perhydro-2H-pyran-2-yl(1H-indazol-3-yl))phenyl]-N-(4-fluorophenyl)carboxamide (2.99 g, 6.79 mmol) in anhydrous ethanol (500 mL) with a reaction time of 5 days at ambient temperature to afford the desired compound (2.37 g, 74%) as a yellow solid. ES-MS (m/z) 403 [M+H]⁺ (HCl salt not detected).

C. [3-(5-(3-[(dimethylamino)methyl](1H-1,2,4-triazol-5-yl))(1H-indazol-3-yl))phenyl]-N-(4-fluorophenyl)carboxamide.2HCl Prepared according to the procedure of Example 367 C using (3-[5-(ethoxyiminomethyl)(1H-indazol-3-yl)]phenyl)-N-(4-fluorophenyl)carboxamide.2HCl (1.50 g, 3.15 mmol), N-amino-2-(dimethylamino) acetamide (1.2 g, 10.33 mmol) and sodium methoxide (1.8 mL of a 25% w/w in methanol) in anhydrous methanol (20.0 mL) with a reaction time of 1.5 days. Purification by flash chromatography on silica gel using 50% methanol in ethyl acetate afforded a solid which was dissolved in anhydrous methanol and treated with anhydrous hydrogen chloride gas for 10 min at 0° C. After stirring at ambient temperature for 5 min anhydrous ethyl acetate was added to precipitate the desired product which was collected on a sintered glass funnel, washed with methanol and ethyl acetate and dried under vacuum to give the title compound (267 mg, 50% yield) as a light yellow solid ¹H NMR (DMSO-d₆) δ 13.5 (br s, 1H), 10.5 (s, 1H), 8.5 (s, 1H), 8.2 (br d, 1H), 8.1 (d, 1H), 8.0 (d, 1H), 7.84 (dd, 2H), 7.75–7.6 (m, 2H), 7.2 (t, 2H), 3.6 (bs, 2H), 2.2 (s, 6H), ES-MS (m/z) 456 [M+H]⁺.

Example 369

SYNTHESIS OF [3-(5-(3-[(DIMETHYLAMINO)METHYL](1H-1,2,4-TRIAZOL-5-YL))(1H-INDAZOL-3-YL))PHENYL]-N-INDAN-2-YL-CARBOXAMIDE

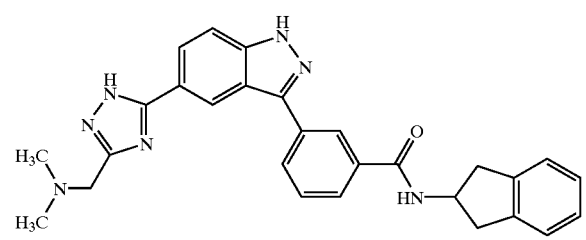

A. [3-(5-Cyano-1-perhydro-2H-pyran-2-yl(1H-indazol-3-yl)]phenyl-N-indan-2-ylcarboxamide The title compound was prepared in a similar fashion to that of Example 367 A using the following amounts of reagents: 3-(5-cyano-1-perhydro-2H-pyran-2-yl-1H-indazol-3-yl)benzoic acid (800 mg, 2.29 mmol), 2-aminoindan hydrochloride (652 mg, 3.84 mmol), HOBT (931 mg, 6.89 mmol), EDAC.HCl (1.32 g, 6.89 mmol) and triethylamine (535 gL, 3.85 mmol) in anhydrous THF (20.0 mL) and anhydrous DMF (7.0 mL). Precipitation from methanol and ethyl acetate with hexanes afforded the desired compound (824 mg, 78% yield) as an off-white powder ¹H NMR (DMSO-d₆) δ 8.87 (d, 1H), 8.7 (s, 1H), 8.39 (s, 1H), 8.16 (d, 1H), 8.02 (d, 1H), 7.94 (d, 1H), 7.84 (dd, 1H), 7.62 (t, 1H), 7.3–7.1 (m, 4H), 6.02 (dd, 1H), 4.78–4.7 (m,1H), 3.9–3.7 (m, 2H), 3.27 (dd, 2H), 2.98 (dd, 2H), 2.1–1.5 (m, 6H).

B. (3-[5-(Ethoxyiminomethyl)(1H-indazol-3-yl)]phenyl)-N-indan-2-ylcarboxamide.2HCl The title compound was prepared according to the procedure of Example 367 B using [3-(5-cyano-1-perhydro-2H-pyran-2-yl(1H-indazol-3-yl))phenyl]-N-indan-2-ylcarboxamide (820 mg, 1.77 mmol) in anhydrous ethanol (40 mL) with a reaction time of 19 h to afford the desired compound (870 mg, 98% yield) as a pale yellow powder. ¹H NMR (DMSO-d₆) δ 12.27 (br s, 1H), 11.2 (br s, 1H), 9.1 (s, 1H), 9.07 (d, 1H), 8.52 (s, 1H), 8.26 (d, 1H), 7.98 (t, 2H), 7.80 (d, 1H), 7.64 (t, 1H), 7.24–7.10 (m, 4H), 4.8–4.7 (m, 1H), 4.64 (q, 2H), 3.24 (dd, 2H), 3.06 (dd, 2H), 1.5 (t, 3H).

C. [3-(5-(3-[(dimethylamino)methyl](1H-1,2,4-triazol-5-yl))(1H-indazol-3-yl)) phenyl]-N-indan-2-ylcarboxamide The title compound was prepared according to the procedure of Example 367 C using (3-[5-(ethoxyiminomethyl)(1H-indazol-3-yl)]phenyl)-N-indan-2-ylcarboxamide.2HCl (360 mg, 0.72 mmol), N-amino-2-(dimethylamino) acetamide (254 mg, 2.17 mmol) and sodium methoxide (415 μL of a 25% w/w in methanol) in anhydrous methanol (4.0 mL) with a reaction time of 48 h. Purification of the residue by preparatory TLC using 50% ethyl acetate in methanol gave the desired product which was further purified by precipitation from methanol and ethyl acetate with hexanes and ethyl ether to give the title compound (86 mg, 25% yield) as a colorless powder ¹H NMR (DMSO-d₆) δ 13.9 (br s, 1H), 13.4 (br s, 1H), 8.85 (d, 1H), 8.6 (br s, 1H), 8.45 (s, 1H), 8.1–8.0 (m, 2H), 7.7–7.6 (m, 2H), 7.3–7.1 (m, 4H), 4.8–4.7 (m, 1H), 3.6 (br s, 2H), 3.25 (dd, 2H), 3.0 (dd, 2H), 2.2 (s, 6H); ES-MS (m/z) 478 [M+H]⁺.

Example 370

SYNTHESIS OF [3-(5-(3-[(DIMETHYLAMINO)METHYL](1H-1,2,4-TRIAZOL-5-YL))(1H-INDAZOL-3-YL))PHENYL]-N-CYCLOPROPYLCARBOXAMIDE

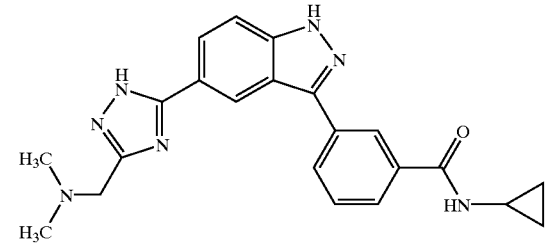

A. [3-(5-Cyano-1-perhydro-2H-pyran-2-yl(1H-indazol-3-yl))phenyl]-N-cyclopropylcarboxamide The title compound was prepared according to the procedure of Example 367 A using the following amounts of reagents: 3-(5-cyano-1-perhydro-2H-pyran-2-yl-1H-indazol-3-yl) benzoic acid (600 mg, 1.73 mmol), cyclopropyl amine (358 μL, 5.17 mmol), HOBT (700 mg, 5.20 mmol), EDAC.HCl (1.00 g, 5.20 mmol), anhydrous THF (15.0 mL) and anhydrous DMF (4.0 mL) to give a pale solid (528 mg, 79% yield). ES-MS (m/z) 387 [M+H]⁺.

B. N-cyclopropyl(3-[5-(ethoxyiminomethyl)(1H-indazol-3-yl)]phenyl)carboxamide.2HCl

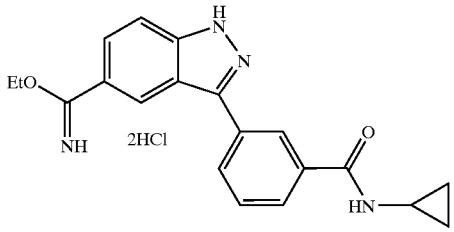

Prepared according to the procedure of Example 367 B using [3-(5-cyano-1-perhydro-2H-pyran-2-yl(1H-indazol-3-yl))phenyl]-N-cyclopropylcarboxamide (528 mg, 1.37 mmol) in anhydrous ethanol (50.0 mL) with a reaction time of 23 h to give a pale powder (520 mg, 90% yield). ES-MS (m/z) 349 [M+H]$^+$(HCl salt not detected).

C. [3-(5-(3-[(dimethylamino)methyl](1H-1,2,4-triazol-5-yl))(1H-indazol-3-yl))phenyl]-N-cyclopropylcarboxamide The title compound was prepared according to the procedure of Example 367 C using N-cyclopropyl(3-[5-(ethoxyiminomethyl)(1H-indazol-3-yl)]phenyl)carboxamide.2HCl (377 mg, 0.89 mmol), N-amino-2-(dimethylamino) acetamide (315 mg, 2.69 mmol) and sodium methoxide (515 μL of a 25% w/w in methanol) in anhydrous methanol (5.0 mL) with a reaction time of 24 h. Purification of the residue by flash chromatography on silica gel with 50% methanol in ethyl acetate gave the desired product as a light orange solid. Further purification by preparatory TLC using 50% methanol in ethyl acetate afforded the title compound (145 mg, 40% yield) as an off-white powder. $^1$H NMR (DMSO-d$_6$) δ 8.8 (br d, 1H), 8.7 (s, 1H), 8.4 (s, 1H), 8.14–8.05 (m, 2H), 7.84 (d, 1H), 7.7–7.6 (m, 2H), 3.55 (s, 2H), 2.92–2.85 (m, 1H), 2.2 (s, 6H); ES-MS (m/z) 402 [M+H]$^+$.

Example 371

SYNTHESIS OF [3-(5-(3-[(DIMETHYLAMINO)METHYL](1H-1,2,4-TRIAZOL-5-YL))(1H-INDAZOL-3-YL))PHENYL]-N-CYCLOBUTYLCARBOXAMIDE.2HCL

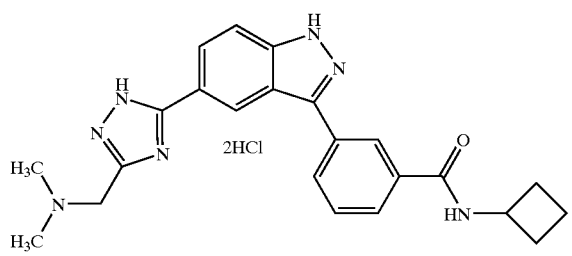

A. [3-(5-Cyano-1-perhydro-2H-pyran-2-yl(1H-indazol-3-yl))phenyl]-N-cyclobutylcarboxamide The title compound was prepared in a similar fashion to that of Example 367 A using the following amounts of reagents: 3-(5-cyano-1-perhydro-2H-pyran-2-yl-1H-indazol-3-yl)benzoic acid (800 mg, 2.29 mmol), cyclobutyl amine (738 μL, 8.64 mmol), HOBT (1.17 g, 8.70 mmol), EDAC.HCl (1.67 g, 8.70 mmol) in anhydrous THF (25.0 mL) and anhydrous DMF (7.0 mL). Precipitation from methanol and ethyl acetate with hexanes afforded the desired compound (826 mg, 72% yield) as an off-white powder. ES-MS (m/z) 401 [M+H]$^+$.

B. N-cyclobutyl(3-[5-(ethoxyiminomethyl)(1H-indazol-3-yl)]phenyl)carboxamide.2HCl The title compound was prepared according to the procedure of Example 367 B using [3-(5-cyano-1-perhydro-2H-pyran-2-yl(1H-indazol-3-yl))phenyl]-N-cyclobutylcarboxamide (826 mg, 2.06 mmol) in anhydrous ethanol (65.0 mL) with a reaction time of 48 h to afford the desired compound (709 mg, 79% yield) as an off-white powder. $^1$H NMR (DMSO-d$_6$) δ 12.3 (br s, 1H), 11.2 (br s, 1H), 9.14 (s, 1H), 9.02 (d, 1H), 8.49 (s, 1H), 8.25 (d, 1H), 7.96 (dd, 2H), 7.80 (d, 1H), 7.63 (t, 1H), 4.65 (q, 2H), 4.55–4.40 (m, 1H), 2.3–2.1 (m, 4H), 1.75–1.55 (m, 2H), 1.5 (t, 3H).

C. [3-(5-(3-[(dimethylamino)methyl](1H-1,2,4-triazol-5-yl))(1H-indazol-3-yl))phenyl]-N-cyclobutylcarboxamide.2HCl The title compound was prepared according to the procedure of Example 367C using N-cyclobutyl(3-[5-(ethoxyiminomethyl)(1H-indazol-3-yl)]phenyl)carboxamide.2HCl (460 mg, 1.06 mmol), N-amino-2-(dimethylamino) acetamide (372 mg, 3.17 mmol) and sodium methoxide (608 μL of a 25% w/w in methanol) in anhydrous methanol (7.0 mL) with a reaction time of 44 h. Purification of the residue by flash chromatography on silica gel with 50% methanol in ethyl acetate gave the desired product as a pale yellow solid. The residue was dissolved in a minimum amount of anhydrous methanol and excess 1.0 N HCl in anhydrous ethyl ether was added dropwise to precipitate the desired product as the bis-hydrochloride salt. The product was collected and dried under vacuum to afford the title compound (27 mg, 5% yield) as a light yellow powder. $^1$H NMR (DMSO-d$_6$) δ 10.6 (br s, 1H), 8.89 (d, 1H), 8.84 (s, 1H), 8.4 (s, 1H), 8.17 (d, 1H), 8.12 (d, 1H), 7.91 (d, 1H), 7.76 (d, 1H), 7.63 (t, 1H), 4.5–4.4 (m, 1H), 4.44 (s, 2H), 2.83 (s, 6H), 2.23–2.0 (m, 4H), 1.72–1.62 (m, 2H); ES-MS (m/z) 416 [M+H]$^+$ (HCl salt not detected).

Example 372

N-[4-(5-(2H-1,2,3,4-TETRAZO-5-YL)(1H-INDAZOL-3-YL))PHENYL]-3-PYRIDYLCARBOXAMIDE

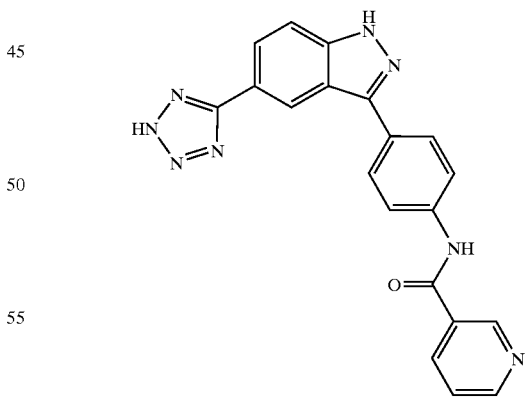

A. 3-(4-Aminophenyl)-1-perhydro-2H-pyran-2-yl-1H-indazole-5-carbonitrile

The title compound was prepared as described in Example 308, using 3-bromo-1-perhydro-2H-pyran-2-yl-1H-indazole-5-carbonitrile (2.102 g, 6.86 mmol), in ethylene glycol dimethyl ether (35 mL), 4-(4,4,5,5-tetramethyl-1,3,2-dioxaborolan-2-yl)aniline (2.274 g, 10.38 mmol), [1,1'-bis(diphenylphosphino-ferrocene] complex with dichloromethane (1:1) (0.573 g, 0.70 mmol) and potassium phosphate (7.337 g, 34.56 mmol) (0.416 g, 19% yield): ES-MS (m/z) 319 [M+1]+.

B. N-[4-(5-Cyano-1-perhydro-2H-pyran-2-yl(1H-indazol-3-yl))phenyl]-3-pyridylcarboxamide

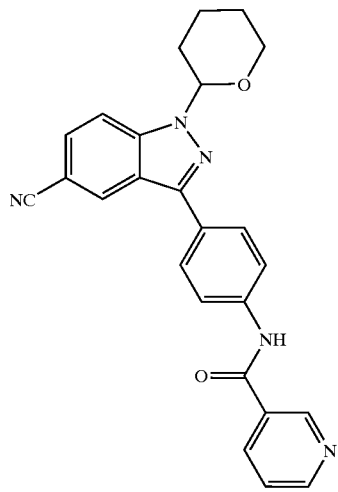

To a solution of 3-(4-aminophenyl)-1-perhydro-2H-pyran-2-yl-1H-indazole-5-carbonitrile (0.459 g, 1.44 mmol) in tetrahydrofuran (15 mL) was added nicotinoyl chloride hydrochloride (0.386 g, 2.17 mmol) and triethyl amine (1.00 mL, 7.17 mmol). The reaction mixture was stirred overnight at room temperature before being partitioned between ethyl acetate and water. The crude product was taken up in ethyl acetate and washed with saturated aqueous NaHCO$_3$ and partitioned. The aqueous layer was extracted twice with ethyl acetate, organics were combined, dried with Na$_2$SO$_4$, filtered, and volatile materials removed. The crude was used without further purification (0.433 g, 71% yield): ES-MS (m/z) 424.0 [M+1]+.

C. N-[4-(5-(2H-1 2,3,4-Tetrazol-5-yl)(1H-indazol-3-yl))phenyl]-3-pyridylcarboxamide

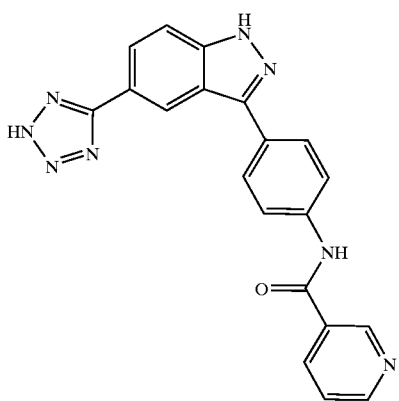

The titled compound was prepared from N-[4-(5-cyano-1-perhydro-2H-pyran-2-yl(1H-indazol-3-yl))phenyl]-3-pyridylcarboxamide (0.433 g, 1.02 mmol), azidotributyl tin (1.54 mL, 5.62 mmol) in toluene (10.5 mL) and heated to 115° C. overnight. The volatile materials were removed after allowing the reaction to cool to room temperature to yield a brown oil. This crude product was taken up in toluene (35 mL) and hydrogen chloride was bubbled through the solution until the solution was saturated with the gas. The reaction was allowed to stir overnight at room temperature. The product was isolated using the procedure described in Example 161.C (0.062 g, 16% yield): $^1$H NMR (DMSO-d$_6$) 13.30 (br s, 1H), 10.71 (s, 1H), 9.16 (d, 1H), 8.77 (dd, 1H), 8.62 (s, 1H), 8.37 (d, 1H), 8.10 (dd, 1H), 8.01 (m, 4H), 7.59 (m, 2H); ES-MS (m/z) 383.0 [M+1]+.

Example 373

1-(5-(1H-1,2,4-TRIAZOL-3-YL)(1H-INDAZOL-3-YL)-3-(2-METHOXYETHOXY)BENZENE

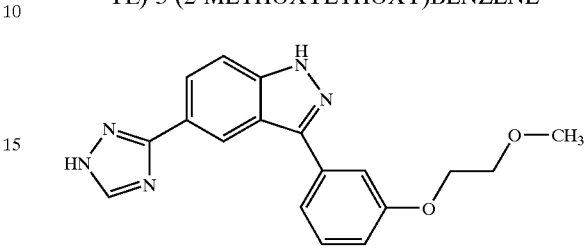

A. 1-(5-(1H-1,2,4-Triazol-3-yl)-1-perhydro-2H-pyran-2-yl(1H-indazol-3-yl))-3-(2-methoxyethoxy)benzene The title compound was prepared from 3-(5-(1H-1,2,4-triazol-3-yl)-1-perhydro-2H-pyran-2-yl-1H-indazol-3-yl)phenol (0.401 g, 0.66 mmol), triphenyl phosphine (0.709 g, 2.70 mmol), diethyl azodicarboxylate (0.43 mL, 2.70 mmol), 2-methoxyethanol (0.21 mL, 2.70 mmol) in tetrahydrofuran (2.6 mL) and was allowed to stir at room temperature overnight. The product was diluted with ethyl acetate and washed with sodium bicarbonate (saturated aqueous). These layers were partitioned and the aqueous layer was extracted with ethyl acetate (2×). Organic fractions were combined, dried with sodium sulfate, filtered, and condensed. The compound was successful purified by column chromatography (SiO$_2$, 30% ethyl acetate in hexanes). The crude intermediate was used without further purification: ES-MS (m/z) 420 [M+1]+.

B. 1-(5-(1H-1,2,4-Triazol-3-yl)(1H-indazol-3-yl)-3-(2-methoxyethoxy)benzene

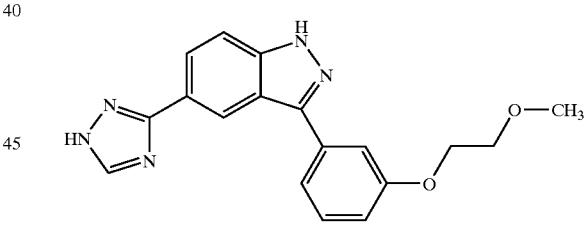

1-(5-(1H-1,2,4-triazol-3-yl)-1-perhydro-2H-pyran-2-yl(1H-indazol-3-yl))-3-(2-methoxyethoxy)benzene was subjected to 6 N hydrochloride solution (aqueous) (10 mL) and methanol (10 mL), and allowed to stir at 50° C. overnight. The reaction was allowed to cool to room temperature, and basified to a pH~14 with 6 N sodium hydroxide solution (aqueous). This solution was extracted with ethyl acetate (3×), and then acidified to a pH~2 using 6 N hydrochloride solution (aqueous). The acidic solution was extracted with ethyl acetate (3×), and organic fractions combined. The organics were washed with sodium bicarbonate (saturated aqueous), dried with sodium sulfate, filtered, and condensed. The compound was purified by preparative HPLC (15–80% acetonitrile in H$_2$O, 30 min.) (0.014 g, 6% yield over 2 steps): $^1$H NMR (CD$_3$OD) δ 8.71 (d, 1H), 8.45 (s, 1H), 8.07 (dd, 1H), 7.67 (dd, 1H), 7.59 (d, 1H), 7.55 (m, 1H), 7.45 (t, 1H), 7.03 (dd, 1H), 4.22 (m, 2H), 3.79 (m, 2H), 3.43 (s, 3H), 2.75 (br s, 1H); ES-MS (m/z) 383 [M+]+.

Example 374

1-(5-(1H-1,2,4-TRIAZOL-3-YL)(1H-INDAZOL-3-YL)-3-(3-PYRYDYLMETHOXY)BENZENE

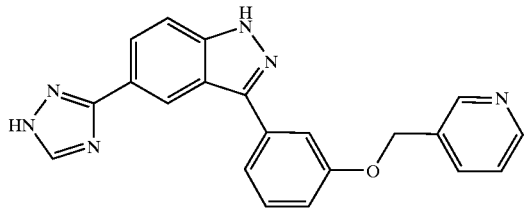

The title compound was prepared from 3-(5-(1H-1,2,4-triazol-3-yl)-1-perhydro-2H-pyran-2-yl-1H-indazol-3-yl)phenol (0.394 g, 0.65 mmol), triphenyl phosphine (0.685 g, 2.61 mmol), diethyl azodicarboxylate (0.41 mL, 2.61 mmol), 3-pyridylcarbinol (0.26 mL, 2.67 mmol) in tetrahydrofuran (2.5 mL) and was allowed to stir at room temperature overnight. To this mixture 6 N hydrogen chloride (20 mL) was added and allowed to stir at room temperature for 5 hours. This reaction was extracted with diethyl ether (3×), basified to pH~11 with 6 N sodium hydroxide (aqueous), extracted with ethyl acetate (3×). The organic fractions were combined and dried with sodium sulfate, filtered, and condensed. The compound was purified by column chromatography (SiO$_2$, 100% ethyl acetate in hexanes to 95% ethyl acetate in 5% methanol) and preparative HPLC (15–80% acetonitrile to H$_2$O, 30 min.) (0.028 g, 12% yield over 2 steps): $^1$H NMR (CD$_3$OD) δ 8.72 (m, 2H), 8.51 (dd, 1H), 8.11 (br s, 1H), 8.03 (dd, 1H), 7.68 (m, 3H), 7.50 (m, 2H), 7.13 (ddd, 1H), 5.30 (s, 2H); ES-MS (m/z) 369 [M+1]$^+$.

Example 375

3-(5-(1H-1,2,4-TRIAZOL-3-YL)-1H-INDAZOL-3-YL)BENZOIC ACID

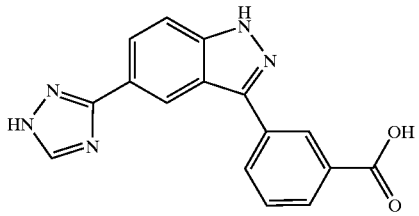

A. Methyl 3-{1-perhydro-2H-pyran-2-yl-5-[1-(triphenylmethyl)(1,2,4-triazol-3-yl]-1H-indazol-3-yl}benzoate The title compound was prepared using 2-{3-bromo-5-[1-(triphenylmethyl)(1,2,3-triazol-3-yl)]-1H-indazolyl}perhydro-2H-pyran (2.019 g, 3.42 mmol), in ethylene glycol dimethyl ether (17 mL), 4-(4,4,5,5-tetramethyl-1,3,2-dioxaborolan-2-yl)aniline (0.880 g, 4.89 mmol), [1,1'-bis(diphenylphosphino_-ferrocene] complex with dichloromethane (1:1) (0.281 g, 0.34 mmol) and potassium phosphate (3.581 g, 16.87 mmol) (1.988 g, 90% yield): ES-MS (m/z) 646.6 [M+1]$^+$.

B. 3-(5-(1H-1,2,4-Triazol-3-yl)-1H-indazol-3-yl)benzoic acid

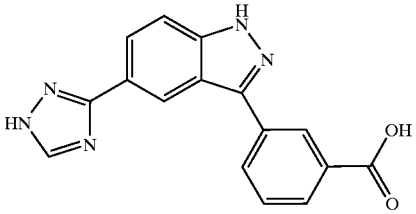

The title compound was prepared using methyl 3-{1-perhydro-2H-pyran-2-yl-5-[1-(triphenylmethyl)(1,2,4-triazol-3-yl)]-1H-indazol-3-yl}benzoate (0.125 g, 0.19 mmol), 6 N sodium hydroxide (aqueous) (3 mL), and methanol (3 mL) heated at 60° C. for 6 hours. The reaction was allowed to cool to room temperature, and extracted with diethyl ether (2×). The aqueous fraction was dropwise added to a 6 N hydrochloride solution (aqueous) to form a white precipitate, which is filtered and dried in a vacuum oven (0.018 g, 30% yield): $^1$H NMR (DMSO-d$_6$) δ 8.91 (m, 2H), 8.60 (s, 1H), 8.36 (d, 1H), 8.16 (d, 1H), 8.02 (d, 1H), 7.75 (m, 2H); ES-MS (m/z) 306 [M+1]$^+$.

Example 376

N-[4-(5-(1H-1,2,4-TRIAZOL-3-YL)(1H-INDAZOL-3-YL))PHENYL]-2-(3-PYRIDYL)ACETAMIDE

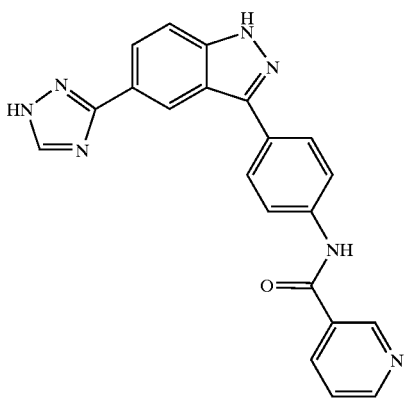

To a solution of 4-{1-perhydro-2H-pyran-2-yl-5-[1-(triphenylmethyl)(1,2,4-triazol-3-yl)]-1H-INDAZOL-3-yl}phenylamine (0.306 g, 0. 51 mmol) in tetrahydrofuran (4.5 mL) was added nicotinoyl chloride hydrochloride (0.409 g, 0.79 mmol) and triethylamine (0.35 mL, 2.52 mmol). The reaction mixture was stirred overnight at room temperature, and quenched with methanol (0.20 mL). This mixture was washed with sodium bicarbonate (aqueous) and extracted with ethyl acetate (3×). The organic fractions were combined, dried with magnesium sulfate, filtered, and condensed resulting in a crude solid (0.346 g) that was used without further purification. This solid was dissolved in 6 N hydrochloride solution (aqueous) (5 mL) and 1,4-dioxane (5 mL) and allowed to stir at room temperature overnight. The reaction was quenched by adding the reaction mixture dropwise to a solution of sodium bicarbonate (saturated aqueous) to form a precipitate, which was filtered and dried in a vacuum oven overnight. (0.109 g, 56% yield): $^1$H NMR (DMSO-d$_6$) δ 9.12 (d, 1H), 8.78 (dd, 1H), 8.72 (s, 1H), 8.34

(dt,1H), 8.29 (s, 1H), 8.04 (m, 5H), 7.68 (d, 1H), 7.60 (ddd, 1H); ES-MS (m/z) 382 [M+1]$^+$.

Example 377

N-[4-(5-(1H-1,2,4-TRIAZOL-3-YL)(1H-INDAZOL-3-YL))PHENYL]-2-PHENYLACETAMIDE

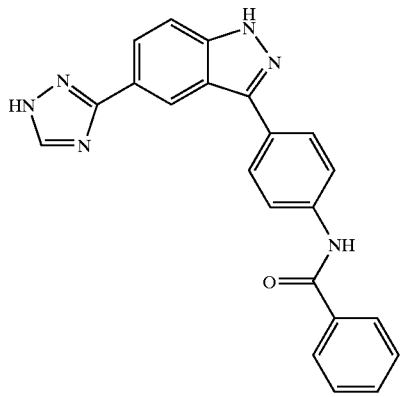

The title compound was prepared as described in Example 376, using 4-{1-perhydro-2H-pyran-2-yl-5-[1-(triphenylmethyl)(1,2,4-triazol-3-yl)]-1H-indazol-3-yl}phenylamine (0.303 g, 0.50 mmol) in tetrahydrofuran (4.5 mL) was added benzoyl chloride (0.10 mL, 0.76 mmol) and triethylamine (0.35 mL, 2.52 mmol). The final crude product was purified by preparative HPLC (30–80% acetonitrile to H$_2$O, 30 min.) (0.010 g, 5% yield): $^1$H NMR (DMSO-d$_6$) δ 10.37 (s, 1H), 8.68 (b)r s, 1H), 8.07 (d, 1H), 7.95 (br s, 2H), 7.80 (d, 2H), 7.69 (br s, 1H), 7.30 (m, 5H), 3.69 (s, 2H); ES-MS (m/z) 395 [M+1]$^+$.

Example 378

N-[4-(5-(1H-1,2,4-TRIAZOL-3-YL)(1H-INDAZOL-3-YL))PHENYL]-2-METHOXYACETAMIDE

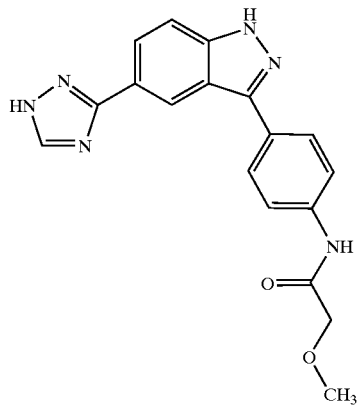

The title compound was prepared as described in Example 376, using 4-{1-perhydro-2H-pyran-2-yl-5-[1-(triphenylmethyl)(1,2,4-triazol-3-yl)]-1H-indazol-3-yl}phenylamine (0.302 g, 0.50 mmol) in tetrahydrofuran (4.5 mL) was added methoxyacetyl chloride (0.07 mL, 0.75 mmol) and triethylamine (0.35 mL, 2.52 mmol). The final crude product was purified by preparative HPLC (5–100% acetonitrile to H$_2$O, 30 min.) (0.015 g, 9% yield): $^1$H NMR (CD3OD) δ 8.75 (d, 1H), 8.40 (s, 1H), 8.10 (dd, 1H), 8.02 (d, 2H), 7.83 (d, 2H), 7.68 (dd, 1H), 4,09 (s, 2H), 3.52 (s, 3H); ES-MS (m/z) 349 [M+1]$^+$.

Example 379

N-[4-(5-(1H-1,2,4-TRIAZOL-3-YL)(1H-INDAZOL-3-YL))PHENYL]-2-(DIMETHYLAMINO)ACETAMIDE

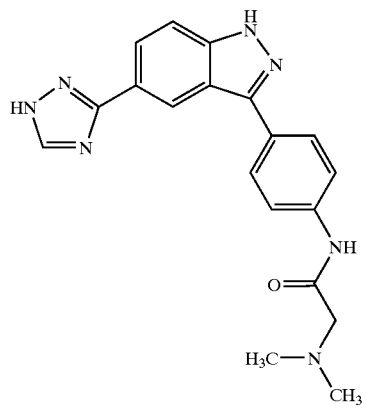

The title compound was prepared as described in Example 379, using 4-{1-Perhydro-2H-pyran-2-yl-5-[1-(triphenylmethyl)(1,2,4-triazol-3-yl)]-1H-indazol-3-yl}phenylamine (0.304 g, 0.50 mmol) in methylene chloride (3 mL) was added N,N-dimethylglycine hydrochloride (0.137 g, 0.98 mmol), 1-hydroxybenzotriazole (0.081 g, 0.60 mmol), and 1-ethyl-(3-dimethylaminopropyl) carbodiimide hydrochloride (0.115 g, 0.60 mmol). The final crude product was purified by preparative HPLC (10–70% acetonitrile in H$_2$O, 20 min.) (0.029 g, 16% yield): $^1$H NMR (DMSO-d$_6$) δ 14.3 (br s, 1H), 13.38 (br s, 1H), 9.91 (s, 1H), 8.69 (s, 1H), 8.08 (d, 1H), 7.95 (d, 2H), 7.87 (d, 2H), 7.68 (d, 1H), 3.12 (s, 2H), 2.30 (s, 6H); ES-MS (m/z) 362 [M+1]$^+$.

Example 380

[4-(5-(1H-1,2,4-TRIAZOL-3-YL)(1H-INDAZOL-3-YL))PHENYL](METHYLSULFONYL)AMINE

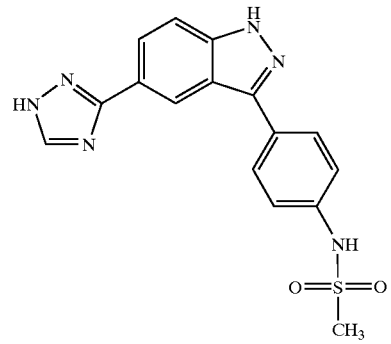

The title compound was prepared as described in Example 376, using 4-{1-perhydro-2H-pyran-2-yl-5-[1-(triphenylmethyl)(1,2,4-triazol-3-yl)]-1H-indazol-3-yl}phenylamine (0.258 g, 0.43 mmol) in tetrahydrofuran (4.5 mL) was added methanesulfonyl chloride (0.05 mL, 0.64 mmol) and triethylamine (0.30 mL, 2.14 mmol). The final crude product was purified by preparative HPLC (10–100% acetonitrile to H20, 20 min.) (0.042 g, 28% yield): ¹H NMR (CD3OD) δ 7.93 (dd, 1H), 8.54 (br s, 1H), 8.29 (dd, 1H), 8.20 (m, 2H), 7.87 (dd, 1H), 7.62 (m, 2H), 3.23 (s, 3H); ES-MS (m/z) 355 [M+1]⁺.

Example 381

[3-(5-(1H-1,2,4-TRIAZOL-3-YL)(1H-INDAZOL-3-YL))PHENYL]-N-(2-METHOXYETHYL) CARBOXAMIDE

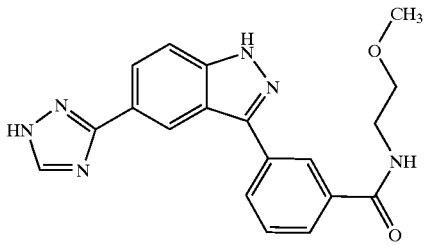

A. 3-Bromo-1-perhydro-2H-pyran-2-yl-1H-indazole-5-carboxamide

The title compound was prepared by adding the 3-bromo-1-perhydro-2H-pyran-2-yl-1H-indazole-5-carbonitrile (15.20 g, 49.65 mmol), ethanol (130 mL), 30% hydrogen peroxide (aqueous) (130 mL), and 6 N sodium hydroxide (aqueous) (9 mL) to a 2 liter round bottom flask. This mixture was heated at 50° C. for 1 Hour, and removed from the heat to allow to cool to room temperature. The pH was adjusted to ~3 by adding 6 N hydrochloride solution (aqueous) resulting in a precipitate. This precipitate was filtered and washed with water (15.13 g, 94%): ES-MS (m/z) 324 [M+1]⁺.

B. 2-(5-(1H-1,2,4-Triazol-3-yl)-3-bromo-1H-indazolyl)perhydro-2H-pyran

The title compound was prepared by reacting 3-bromo-1-perhydro-2H-pyran-2-yl-1H-indazole-5-carboxamide (15.13 g, 46.67 mmol) with N,N-dimethylformamide dimethyl acetal (134 mL) and heating to 80° C. for 3 hours. The reaction was allowed to cool to room temperature, and condensed to a brown oil that was exposed to atmospheric conditions minimally. To the crude oil was added glacial acetic acid (220 mL) and hydrazine (23 mL), and then the mixture was heated to 115° C. for 1.5 hours. The reaction was allowed to cool to room temperature, and subsequently added to water (500 mL) resulting in the formation of a white precipitate which was filtered and dried in a vacuum oven (15.05 g, 93% yield): ES-MS (m/z) 350 [M+1]⁺.

C. 2–13-Bromo-5-[1-(triphenylmethyl)(1,2,4-triazol-3-yl)]-1H-indazolyl}-perhydro-2H-pyran

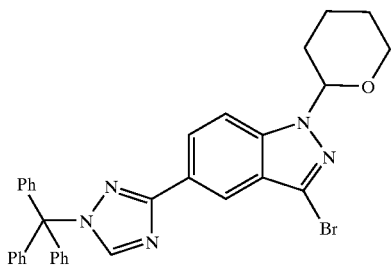

2-(5-(1H-1,2,4-triazol-3-yl)-3-bromo-1H-indazolyl) perhydro-2H-pyran (15.05 g, 43.22 mmol), triphenylmethyl chloride (19.54 g, 70.09 mmol), and triethylamine (9.9 mL, 71.02 mmol) was taken up in pyridine (115 mL) and heated at 50° C. overnight. The reaction was quenched with methanol (10 mL), cooled to room temperature, and condensed. The brown oil was dissolved in ethyl acetate and washed with sodium bicarbonate (saturated aqueous). Upon sonication in a ultrasonic bath a white to yellow precipitate formed that was filtered and washed with 10% ethyl acetate in hexanes. The precipitate was dried in a vacuum oven overnight (23.80 g, 93% yield): ES-MS (m/z) 590 [M+1]⁺.

D. Methyl 3-{1-perhydro-2H-pyran-2-yl-5-[1-(triphenylmethyl)(1,2,4-triazol-3-yl)]-1H-indazol-3-yl}benzoate The title compound was prepared as described for Example 375 A.

E. [3-(5-(1H-1,2,4-Triazol-3-yl)1H-indazol-3-yl)phenyl]-N-(2-methoxyethyl)carboxamide

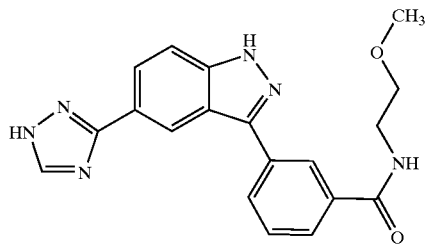

The title compound was prepared by dissolving methyl 3-{1-perhydro-2H-pyran-2-yl-5-[1-(triphenylmethyl)(1,2,4-triazol-3-yl)]-1H-indazol-3-yl}benzoate (0.403 g, 0.62 mmol) and lithium hydroxide (0.052 g, 2.17 mmol) in tetrahydrofuran (3 mL) and water (2 mL). This reaction mixture was heated to 50° C. reacted overnight. The reaction was monitored by thin layer chromatography (100% ethyl acetate). To this reaction, 1-hydroxybenzotriazole (0.256 g, 1.89 mmol), 1-ethyl-(3-dimethylaminopropyl) carbodiimide hydrochloride (0.369 g, 1.92 mmol), and 2-methoxyethylamine (0.16 mL, 1.87 mmol) were added and allowed to stir overnight at room temperature. The reaction was then diluted with ethyl acetate and washed with a 1:1 solution of sodium chloride (saturated aqueous): sodium bicarbonate (saturated aqueous) and partitioned. The aqueous layer was extracted with ethyl acetate (2x), and the organic layers were combined, dried with sodium sulfate, filtered, and condensed. The crude solid was subsequently taken up in 4 N hydrochloride solution in dioxane (8 mL), and stirred at 50° C. overnight. The reaction was quenched by adding the mixture dropwise to sodium bicarbonate (saturated aqueous) (100 mL). The mixture was then extracted with ethyl acetate (3x), and the organics combined, dried with sodium sulfate, filtered, and condensed. The compound was purified by preparative HPLC (10–80% acetonitrile in H₂O, 20 min.) (0.019 g, 9% yield): ¹H NMR (CD₃OD) δ 8.74 (s, 1H), 8.41 (t, 1H), 8.25 (br s, 1H), 8.15 (dt, 1H), 8.07 (d, 1H), 7.86 (dt, 1H), 7.63 (dd, 2H), 3.58 (s, 4H), 3.35 (s, 3H); ES-MS (m/z) 363 [M+1]⁺.

Example 382

[3-(5-(1H-1,2,4-TRIAZOL-3-YL)(1H-INDAZOL-3-YL))PHENYL]-N-BENZAMIDE

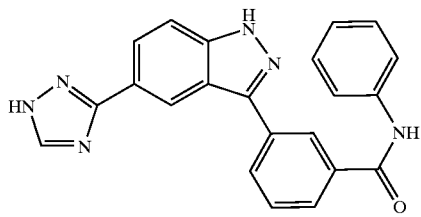

The title compound was prepared as described in Example 381, using methyl 3-{1-perhydro-2H-pyran-2-yl-5-[1-(triphenylmethyl)(1,2,4-triazol-3-yl)]-1H-indazol-3-yl}benzoate (0.407 g, 0.63 mmol) and lithium hydroxide (0.065 g, 2.17 mmol) in tetrahydrofuran (3 mL) and water (2 mL); 1-hydroxybenzotriazole (0.255 g, 1.89 mmol), aniline (0.172 mL, 1.89 mmol), 1-ethyl-(3-dimethylaminopropyl) carbodiimide hydrochloride (0.362 g, 1.89 mmol), and additional tetrahydrofuran (2 mL); 4 N hydrochloride solution in dioxane (10 mL). The final crude product was purified by preparative HPLC (10–80% acetonitrile in $H_2O$, 20 min.) (0.007 g, 3% yield over 3 steps): $^1$H NMR (CD3OD) δ 8.82 (s, 1H), 8.56 (t, 1H), 8.38 (br s, 1H), 8.25 (dt, 1H), 8.12 (d, 1H), 8.01 (dt, 1H), 7.73 (m, 4H), 7.38 (t, 2H), 7.17 (t, 1H); ES-MS (m/z) 381.0 $[M+1]^+$.

Example 383

[3-(5-(1H-1,2,4-TRIAZOL-3-YL)(1H-INDAZOL-3-YL))PHENYL]-N-(2-PHENETHYL)CARBOXAMIDE

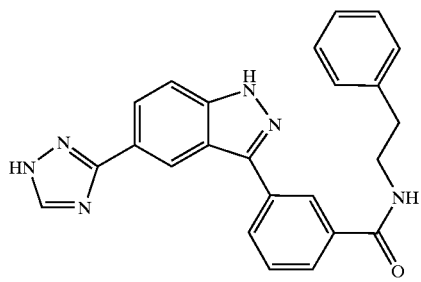

The title compound was prepared as described in Example 381, using methyl 3-{1-perhydro-2H-pyran-2-yl-5-[1-(triphenylmethyl)(1,2,4-triazol-3-yl)]-1H-indazol-3-yl}benzoate (0.405 g, 0.63 mmol) and lithium hydroxide (0.061 g, 2.04 mmol) in tetrahydrofuran (3 mL) and water (2 mL); 1-hydroxybenzotriazole (0.256 g, 1.89 mmol), phenethylamine (0.239 mL, 1.89 mmol), 1-ethyl-(3-dimethylaminopropyl) carbodiimide hydrochloride (0.363 g, 1.89 mmol), and additional tetrahydrofuran (2 mL); 4 N hydrochloride solution in dioxane (10 mL). The final crude product was purified by preparative HPLC (10–90% acetonitrile in $H_2O$, 20 min.) (0.020 g, 8% yield over 3 steps): $^1$H NMR (CD3OD) δ 8.77 (s, 1H), 8.40 (br s, 1H), 8.39 (s, 1H), 8.19 (d, 1H), 8.13 (d, 1H), 7.85 (d, 1H), 7.67 (m, 2H), 7.27 (m, 4H), 7.14 (m, 1H), 3.66 (t, 2H), 2.97 (t, 2H); ES-MS (m/z) 409 $[M+1]^+$.

Example 384

[3-(5-(1H-1,2,4-TRIAZOL-3-YL)(1H-INDAZOL-3-YL))PHENYL-N-(2-PIPERIDYLETHYL)CARBOXAMIDE

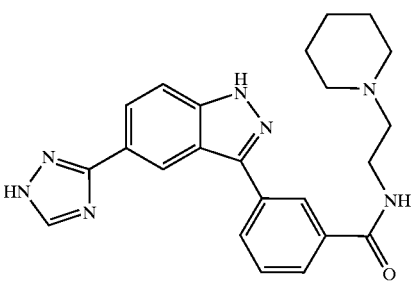

The title compound was prepared as described in Example 381, using methyl 3-{1-perhydro-2H-pyran-2-yl-5-[1-(triphenylmethyl)(1,2,4-triazol-3-yl)]-1H-indazol-3-yl}benzoate (0.402 g, 0.62 mmol) and lithium hydroxide (0.083 g, 1.98 mmol) in tetrahydrofuran (3 mL) and water (2 mL); 1-hydroxybenzotriazole (0.255 g, 1.89 mmol), 1-(2-aminoethyl)piperidine (0.267 mL, 1.87 mmol), 1-ethyl-(3-dimethylaminopropyl) carbodiimide hydrochloride (0.361 g, 1.88 mmol), and additional tetrahydrofuran (2 mL); 4 N hydrochloride solution in dioxane (10 mL). The final crude product was purified by preparative HPLC (10–90% acetonitrile in $H_2O$, 20 min.) (0.072 g, 28% yield over 3 steps): $^1$H NMR (CD$_3$OD) δ 8.80 (dd, 1H), 8.47 (t, 1H), 8.24 (s, 1H), 8.21 (dt, 2H), 8.13 (dd, 1H), 7.91 (dt, 1H), 7.67 (d, 2H), 3.62 (t, 2H), 2.65 (t, 2H), 2.55 (br s, 4H), 1.63 (m, 4H), 1.48 (d, 2H); ES-MS (m/z) 416 $[M+1]^+$.

Example 385

3-{3-[N-(2-PIPERIDYLETHYL)CARBAMOYL]PHENYL}-1H-INDAZOLE-5-CARBOXAMIDE

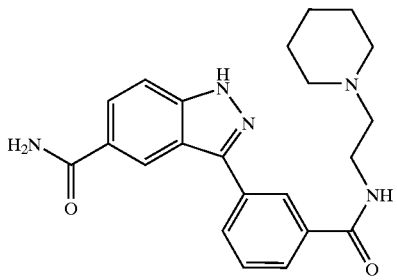

A. Methyl 3-(5-carbamoyl-1-perhydro-2H-pyran-2-yl-1H-indazol-3-yl)benzoate

The title compound was prepared as described in Example 381, using 3-bromo-1-perhydro-2H-pyran-2-yl-1H-indazole-5-carboxamide (5.007 g, 15.54 mmol), in ethylene glycol dimethyl ether (77 mL), 3-methoxycarbonylphenyl boronic acid (4.175 g, 23.20 mmol), [1,1'-bis(diphenylphosphino-ferrocene] complex with dichloromethane (1:1) (1.105 g, 1.35 mmol) and potassium phosphate (16.408 g, 77.29 mmol) (1.190 g, 20% yield): ES-MS (m/z) 380 $[M+1]^+$.

B. 3–13-[N-(2-Piperidylethyl)carbamoyl]phenyl}-1H-indazole-5-carboxamide

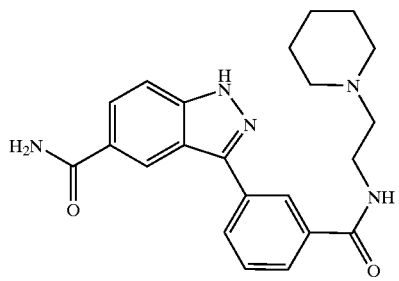

The title compound was prepared as described in Example 381 E, using methyl 3-(5-carbamoyl-1-perhydro-2H-pyran-2-yl-1H-indazol-3-yl)benzoate (0.297 g, 0.78 mmol) and lithium hydroxide (0.102 g, 2.43 mmol) in tetrahydrofuran (2.5 mL) and water (2 mL); 1-hydroxy-7-azabenzotriazole (0.325 g, 2.39 mmol), 1-(2-aminoethyl)piperidine (0.335 mL, 2.39 mmol), 1-ethyl-(3-dimethylaminopropyl) carbodiimide hydrochloride (0.452 g, 2.35 mmol), and additional tetrahydrofuran (2 mL); 4 N hydrochloride solution in dioxane (10 mL). The final crude product was purified by preparative HPLC (5–40% acetonitrile to H$_2$O, 30 min.) (0.025 g, 8% yield over 3 steps): $^1$H NMR (CD$_3$OD) δ 8.71 (s, 1H), 8.47 (t, 1H), 8.19 (dt, 1H), 8.01 (dd, 1H), 7.91 (dt, 1H), 7.66 (t, 2H), 3.62 (t, 2H), 2.65 (t, 2H), 2.57 (br s, 4H), 1.65 (m, 4H), 1.51 (d, 2H); ES-MS (m/z) 392.4 [M+1]$^+$.

Example 386

[3-(5-(1H-1,2,4-TRIAZOL-3-YL)(1H-INDAZOL-3-YL))PHENYL-N-(2-MORPHOLIN-4-YLETHYL)CARBOXAMIDE

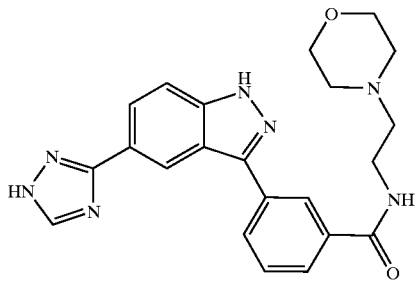

The title compound was prepared as described in Example 381, using methyl 3-{1-perhydro-2H-pyran-2-yl-5-[1-(triphenylmethyl)(1,2,4-triazol-3-yl)]-1H-indazol-3-yl}benzoate (0.595 g, 0.92 mmol) and lithium hydroxide (0.069 g, 2.87 mmol) in tetrahydrofuran (3 mL) and water (2 mL); 1-hydroxybenzotriazole (0.373 g, 2.76 mmol), 4-(2-aminoethyl)morpholine (0.362 mL, 2.76 mmol), 1-ethyl-(3-dimethylaminopropyl) carbodiimide hydrochloride (0.535 g, 2.79 mmol), and additional tetrahydrofuran (2 mL); 4 N hydrochloride solution in dioxane (10 mL). The final crude product was purified by preparative HPLC (10–90% acetonitrile in H$_2$O, 20 min.) (0.030 g, 8% yield over 3 steps): $^1$H NMR (CD$_3$OD) δ 8.82 (t, 1H), 8.47 (t, 1H), 8.29 (s, 1H), 8.22 (dt, 1H), 8.14 (dd, 1H), 7.92 (dt, 1H), 7.67 (t, 2H), 3.70 (t, 4H), 3.62 (t, 2H), 2.67 (t, 2H), 2.58 (t, 4H); ES-MS (m/z) 418 [M+1]$^+$.

Example 387

[3-(5-(1H-1,2,4-TRIAZOL-3-YL)(1H-INDAZOL-3-YL))PHENYL-N-CYCLOHEXYLCARBOXAMIDE

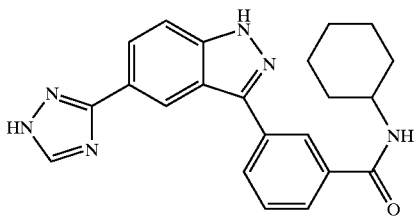

The title compound was prepared as described in Example 381, using methyl 3-{1-perhydro-2H-pyran-2-yl-5-[1-(triphenylmethyl)(1,2,4-triazol-3-yl)]-1H-indazol-3-yl}benzoate (0.401 g, 0.62 mmol) and lithium hydroxide (0.046 g, 1.92 mmol) in tetrahydrofuran (3 mL) and water (2 mL); 1-hydroxybenzotriazole (0.252 g, 1.86 mmol), cyclohexylamine (0.213 mL, 1.86 mmol), 1-ethyl-(3-dimethylaminopropyl) carbodiimide hydrochloride (0.357 g, 1.86 mmol), and additional tetrahydrofuran (2 mL); 4 N hydrochloride solution in dioxane (10 mL). The final crude product was purified by preparative HPLC (10–90% acetonitrile to H$_2$O, 20 min.) (0.015 g, 6% yield over 3 steps): $^1$H NMR (CD$_3$OD) δ 8.79 (s, 1H), 8.43 (t, 1H), 8.40 (br s, 1H), 8.19 (dt, 1H), 8.12 (d, 1H), 7.88 (dt, 1H), 7.70 (d, 1H), 7.65 (t, 1H), 3.92 (br s, 1H), 2.01 (m, 2H), 1.83 (m, 2H), 1.71 (d, 1H), 1.43 (m, 4H), 1.25 (m, 1H); ES-MS (m/z) 387 [M+1]$^+$.

Example 388

[3-(5-(1H-1,2,4-TRIAZOL-3-YL)(1H-INDAZOL-3-YL))PHENYL-N-CYCLOPENTYLCARBOXAMIDE

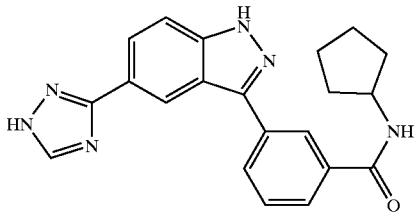

The title compound was prepared as described in Example 381, using methyl 3-{1-perhydro-2H-pyran-2-yl-5-[1-(triphenylmethyl)(1,2,4-triazol-3-yl)]-1H-indazol-3-yl}benzoate (0.402 g, 0.62 mmol) and lithium hydroxide (0.045 g, 1.88 mmol) in tetrahydrofuran (3 mL) and water (2 mL); 1-hydroxybenzotriazole (0.253 g, 1.87 mmol), cyclopentylamine (0.184 mL, 1.87 mmol), 1-ethyl-(3-dimethylaminopropyl) carbodiimide hydrochloride (0.360 g, 1.88 mmol), and additional tetrahydrofuran (2 mL); 4 N hydrochloride solution in dioxane (10 mL). The final crude product was purified by preparative HPLC (10–90% acetonitrile to H$_2$O, 20 min.) (0.012 g, 5% yield over 3 steps): $^1$H NMR (CD$_3$OD) δ 8.80 (s, 1H), 8.44 (s, 1H), 8.20 (d, 1H), 8.13 (d, 1H), 7.89 (dd, 1H), 7.70 (d, 1H), 7.66 (t, 1H), 3.60 (m, 1H), 2.07 (m, 2H), 1.82 (m, 2H), 1.68 (m, 4H); ES-MS (m/z) 373 [M+1]$^+$.

Example 389

[3-(5-(1H-1,2,4-TRIAZOL-3-YL)(1H-INDAZOL-3-YL))PHENYL-N-(4-FLUOROPHENYL)CARBOXAMIDE

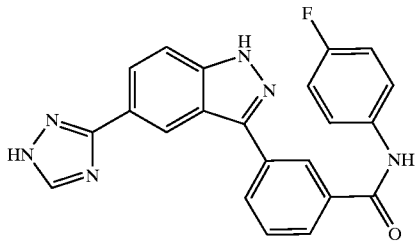

The title compound was prepared as described in Example 381, using methyl 3-{1-perhydro-2H-pyran-2-yl-5-[1-(triphenylmethyl)(1,2,4-triazol-3-yl)]-1H-indazol-3-yl}benzoate (0.400 g, 0.62 mmol) and lithium hydroxide (0.046 g, 1.92 mmol) in tetrahydrofuran (3 mL) and water (2 mL); 1-hydroxybenzotriazole (0.254 g, 1.88 mmol), 4flouroaniline (0.176 mL, 1.86 mmol), 1-ethyl-(3-dimethylaminopropyl) carbodiimide hydrochloride (0.361 g, 1.88 mmol), and additional tetrahydrofuran (2 mL); 4 N hydrochloride solution in dioxane (10 mL). The final crude product was purified by preparative HPLC (30–80% acetonitrile in $H_2O$, 20 min.) (0.017 g, 7% yield over 3 steps): $^1$H NMR ($CD_3OD$) δ 8.82 (dd, 1H), 8.57 (t, 1H), 8.37 (s, 1H), 8.26 (dt, 1H), 8.13 (dd, 1H), 8.01 (dt, 1H), 7.75 (m, 4H), 7.13 (t, 2H); ES-MS (m/z) 399 $[M+1]^+$.

Example 390

[3-(5-(1H-1,2,4-TRIAZOL-3-YL)(1H-INDAZOL-3-YL))PHENYL-N-{2-[1-BENZYL(4-PIPERIDYL)]}ETHYLCARBOXAMIDE

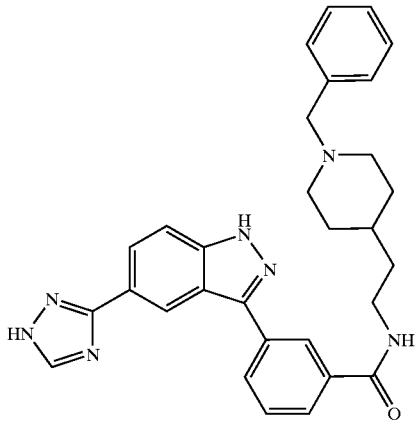

The title compound was prepared as described in Example 381, using methyl 3-{1-perhydro-2H-pyran-2-yl-5-[1-(triphenylmethyl)(1,2,4-triazol-3-yl)]-1H-indazol-3-yl}benzoate (0.800 g, 1.24 mmol) and lithium hydroxide (0.090 g, 3.76 mmol) in tetrahydrofuran (4 mL) and water (2 mL); 1-hydroxybenzotriazole (0.506 g, 3.74 mmol), 4-(2-aminoethyl)-1-benzylpiperidine (0.820 mL, 3.72 mmol), 1-ethyl-(3-dimethylaminopropyl) carbodiimide hydrochloride (0.716 g, 3.74 mmol), and additional tetrahydrofuran (4 mL); 4 N hydrochloride solution in dioxane (15 mL). The final crude product was purified by preparative HPLC (10–90% acetonitrile in $H_2O$, 20 min.) (0.007 g, 1% yield over 3 steps): $^1$H NMR ($CD_3OD$) δ 8.80 (s, 1H), 8.43 (t, 1H), 8.38 (s, 1H), 8.21 (dt, 1H), 8.13 (dd, 1H), 7.89 (dt, 1H), 7.68 (m, 2H), 7.33 (m, 5H), 3.62 (s, 2H), 3.49 (t, 2H), 2.99 (d, 2H), 2.17 (t, 2H), 1.85 (d, 2H), 1.62 (dd, 2H), 1.40 (m, 3H); ES-MS (m/z) 506 $[M+1]^+$.

Example 391

[3-(5-(1H-1,2,4-TRIAZOL-3-YL)(1H-INDAZOL-3-YL))PHENYL-N-((1R,2R)-2-PHENYLCYCLOPROPYL)CARBOXAMIDE

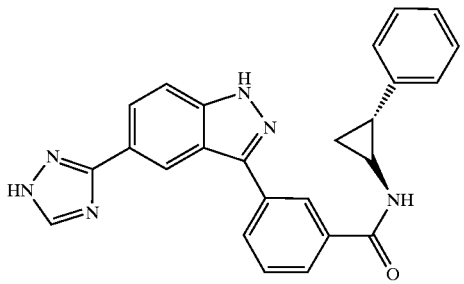

The title compound was prepared as described in Example 381, using methyl 3-{1-perhydro-2H-pyran-2-yl-5-[1-(triphenylmethyl)(1,2,4-triazol-3-yl)]-1H-indazol-3-yl}benzoate (0.600 g, 0.93 mmol) and lithium hydroxide (0.067 g, 2.79 mmol) in tetrahydrofuran (4 mL) and water (2 mL); 1-hydroxybenzotriazole (0.380 g, 2.81 mmol), trans-2-phenylcyclopropylamine hydrochloride (0.474 g, 2.79 mmol), 1-ethyl-(3-dimethylaminopropyl) carbodiimide hydrochloride (0.540 g, 2.81 mmol), and additional tetrahydrofuran (4 mL); 4 N hydrochloride solution in dioxane (12 mL). The final crude product was purified by precipitation from hexanes in ethyl acetate (0.046 g, 12% yield over 3 steps): $^1$H NMR ($CD_3OD$) δ 8.99 (d, 1H), 8.79 (s, 1H), 8.47 (t, 1H), 8.21 (dt, 1H), 8.12 (d, 1H), 7.92 (dt, 1H), 7.68 (dd, 2H), 7.23 (m, 5H), 3.11 (m, 1H), 2.24 (m, 1H), 1.37 (m, 2H); ES-MS (m/z) 421 $[M+1]^+$.

Example 392

[3-(5-(1H-1,2,4-TRIAZOL-3-YL)(1H-INDAZOL-3-YL))PHENYL-N-CYCLOPROPYLCARBOXAMIDE

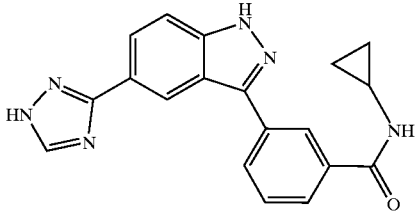

The title compound was prepared as described in Example 381, using methyl 3-{1-perhydro-2H-pyran-2-yl-5-[1-(triphenylmethyl)(1,2,4-triazol-3-yl)]-1H-indazol-3-yl}benzoate (0.405 g, 0.63 mmol) and lithium hydroxide (0.050 g, 2.09 mmol) in tetrahydrofuran (2.5 mL) and water (1.5 mL); 1-hydroxybenzotriazole (0.257 g, 1.90 mmol), cyclopropylamine (0.130 mL, 1.88 mmol), 1-ethyl-(3-dimethylaminopropyl) carbodiimide hydrochloride (0.364 g, 1.90 mmol), and additional tetrahydrofuran (2.5 mL); 4 N hydrochloride solution in dioxane (10 mL). The final crude product was purified by precipitation from hexanes in ethyl acetate (0.073 g, 34% yield over 3 steps): $^1$H NMR (CD$_3$OD) δ 8.79 (s, 1H), 8.43 (t, 1H), 8.40 (br s, 1H), 8.20 (dt, 1H), 8.12 (dd, 1H) 7.88 (dt, 1H), 7.70 (dd, 1H), 7.66 (t, 1H), 2.92 (m, 1H), 0.85 (m, 2H), 0.72 (m, 2H); ES-MS (m/z) 345 [M+1]$^+$.

Example 393

[3-(5-(1H-1,2,4-TRIAZOL-3-YL)(1H-INDAZOL-3-YL))PHENYL-N-(3-PYRIDYL)CARBOXAMIDE

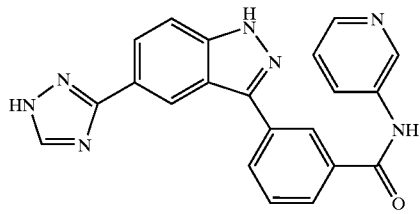

The title compound was prepared as described in Example 381, using methyl 3-{1-perhydro-2H-pyran-2-yl-5-[1-(triphenylmethyl)(1,2,4-triazol-3-yl)]-1H-indazol-3-yl}benzoate (0.400 g, 0.62 mmol) and lithium hydroxide (0.045 g, 1.88 mmol) in tetrahydrofuran (2.5 mL) and water (1.5 mL); 1-hydroxybenzotriazole (0.255 g, 1.89 mmol), 3-aminopyridine (0.257 g, 2.73 mmol), 1-ethyl-(3-dimethylaminopropyl) carbodiimide hydrochloride (0.357 g, 1.86 mmol), and additional tetrahydrofuran (2.5 mL); 4 N hydrochloride solution in dioxane (10 mL). The final crude product was purified by precipitation from hexanes in ethyl acetate (0.045 g, 19% yield over 3 steps): $^1$H NMR (CD$_3$OD) δ 9.02 (d, 1H), 8.87 (s, 1H), 8.62 (t, 1H), 8.30 (m, 3H), 8.18 (d, 1H), 8.03 (dt, 1H), 7.98 (s, 1H), 7.74 (t, 1H) 7.61 dd, 1H), 7.48 (m, 1H); ES-MS (m/z) 382 [M+1]$^+$.

Example 394

[3-(5-(1H-1,2,4-TRIAZOL-3-YL)(1H-INDAZOL-3-YL))PHENYL-N-(5,6,7,8-TETRAHYDRONAPHTHYL)CARBOXAMIDE

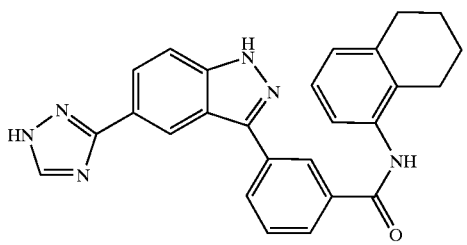

The title compound was prepared as described in Example 381, using methyl 3-{1-perhydro-2H-pyran-2-yl-5-[1-(triphenylmethyl)(1,2,4-triazol-3-yl)]-1H-indazol-3-yl}benzoate (0.401 g, 0.621 mmol) and lithium hydroxide (0.048 g, 2.00 mmol) in tetrahydrofuran (2.5 mL) and water (1.5 mL); 1-hydroxybenzotriazole (0.252 g, 1.86 mmol), 1,2,3,4-tetrahydro-1-naphthylamine (0.288 mL, 1.96 mmol), 1-ethyl-(3-dimethylaminopropyl) carbodiimide hydrochloride (0.360 g, 1.88 mmol), and additional tetrahydrofuran (2.5 mL); 4 N hydrochloride solution in dioxane (10 mL). The final crude product was purified by preparative HPLC (30–80% acetonitrile in H$_2$O, 20 min.) (0.035 g, 13% yield over 3 steps): $^1$H NMR (CD$_3$OD) δ 8.82 (s, 1H), 8.59 (s, 1H), 8.37 (br s, 1H), 8.26 (dt, 1H), 8.12 (d, 1H), 8.04 (d, 1H), 7.72 (t, 2H), 7.24 (d, 1H), 7.15 (t, 1H), 7.05 (d, 1H), 2.81 (m, 4H), 1.81 (m, 4H); ES-MS (m/z) 435 [M+1]$^+$.

Example 395

[3-(5-(1H-1,2,4-TRIAZOL-3-YL)(1H-INDAZOL-3-YL))PHENYL-N-[1-BENZYL(4-PIPERIDYL)] CARBOXAMIDE

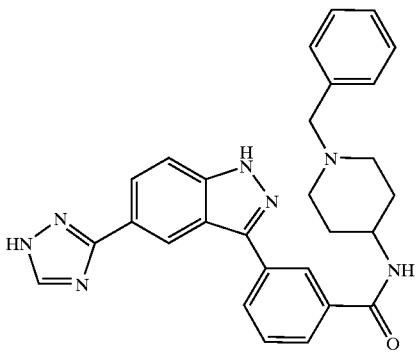

The title compound was prepared as described in Example 381, using methyl 3-{1-perhydro-2H-pyran-2-yl-5-[1-(triphenylmethyl)(1,2,4-triazol-3-yl)]-1H-indazol-3-yl}benzoate (0.401 g, 0.62 mmol) and lithium hydroxide (0.049 g, 2.05 mmol) in tetrahydrofuran (2.5 mL) and water (1.5 mL); 1-hydroxybenzotriazole (0.254 g, 1.88 mmol), 4-amino-1-benzylpiperidine (0.380 mL, 1.86 mmol), 1-ethyl-(3-dimethylaminopropyl) carbodiimide hydrochloride (0.360 g, 1.88 mmol), and additional tetrahydrofuran (2 mL); 4 N hydrochloride solution in dioxane (10 mL). The final crude product was purified by precipitation from hexanes in ethyl acetate (0.040 g, 13% yield over 3 steps): $^1$H NMR (CD$_3$OD) δ 8.80 (dd, 1H), 8.44 (t, 1H), 8.36 (br s, 1H), 8.20 (dt, 1H), 8.12 (dd, 1H), 7.89 (ddd, 1H), 7.70 (dd, 1H), 7.66 (t, 2H), 7.34 (m, 5H), 3.98 (m, 1H), 3.64 (s, 2H), 3.02 (d, 2H), 2.30 (t, 2H), 2.01 (d, 2H), 1.77 (m, 2H); ES-MS (m/z) 478 [M+1]$^+$.

Example 396

[3-(5-(1H-1,2,4-TRIAZOL-3-YL)(1H-INDAZOL-3-YL))PHENYL-N-[1-BENZYLPYRROLIDIN-3-YL] CARBOXAMIDE

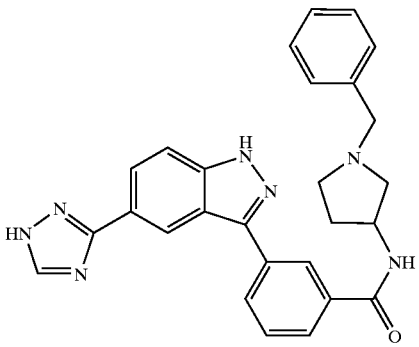

The title compound was prepared as described in Example 381, using methyl 3-{1-perhydro-2H-pyran-2-yl-5-[1-(triphenylmethyl)(1,2,4-triazol-3-yl)]-1H-indazol-3- yl}benzoate (0.402 g, 0.62 mmol) and lithium hydroxide (0.048 g, 2.00 mmol) in tetrahydrofuran (2.5 mL) and water (1.5 mL); 1-hydroxybenzotriazole (0.254 g, 1.88 mmol), 1-benzyl-3-aminopyrrolidine (0.336 g, 1.91 mmol), 1-ethyl-(3-dimethylaminopropyl) carbodiimide hydrochloride (0.359 g, 1.87 mmol), and additional tetrahydrofuran (2 mL); 4 N hydrochloride solution in dioxane (10 mL). The final crude product was purified by precipitation from hexanes in ethyl acetate (0.015 g, 5% yield over 3 steps): $^1$H NMR (CD$_3$OD) δ 8.79 (dd, 1H), 8.46 (t, 1H), 8.36 (s, 1H), 8.20 (dt, 1H), 8.13 (dd, 1H), 7.90 (dt, 1H), 7.71 (dd, 1H), 7.66 (t, 1H), 7.33 (m, 5H), 4.62 (m, 1H), 3.73 (d, 2H), 3.00 (dd, 1H), 2.88 (m, 1H), 2.67 (m, 2H), 2.40 (m, 1H), 1.92 (m, 1H); ES-MS (m/z) 464 [M+1]$^+$.

Example 397

[3-(5-(1H-1,2,4-TRIAZOL-3-YL)(1H-INDAZOL-3-YL))PHENYL-N-(METHYLETHYL)CARBOXAMIDE

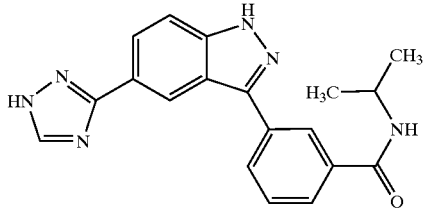

The title compound was prepared as described in Example 381, using methyl 3-{1-perhydro-2H-pyran-2-yl-5-[1-(triphenylmethyl)(1,2,4-triazol-3-yl)]-1H-indazol-3-yl}benzoate (0.402 g, 0.62 mmol) and lithium hydroxide (0.046 g, 1.92 mmol) in tetrahydrofuran (2.5 mL) and water (1.5 mL); 1-hydroxybenzotriazole (0.255 g, 1.89 mmol), isopropylamine (0.159 mL, 1.87 mmol), 1-ethyl-(3-dimethylaminopropyl) carbodiimide hydrochloride (0.360 g, 1.88 mmol), and additional tetrahydrofuran (2 mL); 4 N hydrochloride solution in dioxane (10 mL). The final crude product was purified by precipitation from hexanes in ethyl acetate (0.060 g, 28% yield over 3 steps): $^1$H NMR (CD$_3$OD) δ 8.79 (dd, 1H), 8.43 (t, 1H), 8.39 (br s, 1H), 8.19 (dt, 1H), 8.11 (dd, 1H), 7.88 (dt, 1H), 7.70 (dd, 1H), 7.65 (t, 1H), 4.27 (m, 1H), 1.30 (d, 6H); ES-MS (m/z) 347 [M+1]$^+$.

Example 398

[3-(5-(1H-1,2,4-TRIAZOL-3-YL)(1H-INDAZOL-3-YL))PHENYL-N-CYCLOBUTYLCARBOXAMIDE

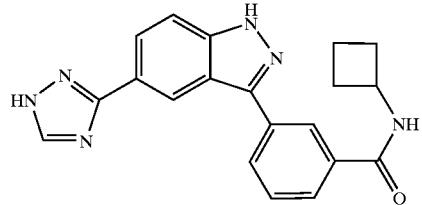

The title compound was prepared as described in Example 381, using methyl 3-{1-perhydro-2H-pyran-2-yl-5-[1-(triphenylmethyl)(1,2,4-triazol-3-yl)]-1H-indazol-3-yl}benzoate (0.647 g, 1.00 mmol) and lithium hydroxide (0.073 g, 3.05 mmol) in tetrahydrofuran (3.5 mL) and water (2 mL); 1-hydroxybenzotriazole (0.406 g, 3.00 mmol), cyclobutylamine (0.256 mL, 3.00 mmol), 1-ethyl-(3-dimethylaminopropyl) carbodiimide hydrochloride (0.575 g, 3.00 mmol), and additional tetrahydrofuran (2 mL); 4 N hydrochloride solution in dioxane (10 mL). The final crude product was purified by precipitation from hexanes in ethyl acetate (0.023 g, 6% yield over 3 steps): $^1$H NMR (CD$_3$OD) δ 9.29 (s, 1H), 8.85 (d, 1H), 8.48 (t, 1H), 8.20 (dt, 1H), 8.09 (dd, 1H), 7.92 (dt, 1H), 7.83 (dd, 1H), 7.68 (t, 1H), 4.57 (m, 1H), 2.37 (m, 2H), 2.17 (m, 2H), 1.82 (m, 2H); ES-MS (m/z) 359 [M+1]

Example 399

[3-(5-(1H-1,2,4-TRIAZOL-3-YL)(1H-INDAZOL-3-YL))PHENYL-N-(4-PYRIDYL)CARBOXAMIDE

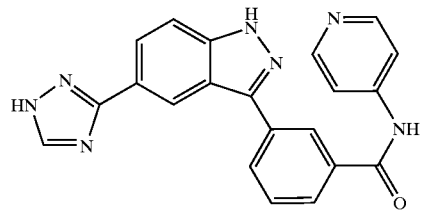

The title compound was prepared as described in Example 381, using methyl 3-{1-perhydro-2H-pyran-2-yl-5-[1-(triphenylmethyl)(1,2,4-triazol-3-yl)]-1H-indazol-3-yl}benzoate (0.499 g, 0.773 mmol) and lithium hydroxide (0.057 g, 2.38 mmol) in tetrahydrofuran (2 mL) and water (1.5 mL); Coupling was performed after volatiles were removed with O-benzotriazol-1yl-N,N,N',N'-tetramethyluronium hexaflourophosphate (0.326 g, 0.859 mmol), 4-aminopyridine (0.085 g, 0.903 mmol), and N,N-dimethylformamide (4 mL); 4 N hydrochloride solution in dioxane (10 mL). The final crude product was purified by precipitation from hexanes in ethyl acetate (0.023 g, 6% yield over 3 steps): $^1$H NMR (CD$_3$OD) δ 8.85 (s, 1H), 8.59 (t, 1H), 8.47 (dd, 2H), 8.30 (d, 1H), 8.24 (s, 1H), 8.15 (dd, 1H), 8.03 (dt, 1H), 7.92 (dd, 2H), 7.74 (t, 1H), 7.68 (d, 1H); ES-MS (m/z) 382 [M+1]$^+$.

Example 400

SYNTHESIS OF [3-(4-FLUOROPHENYL)(1H-INDAZOL-5-YL)]-N-(2-HYDROXYETHYL)CARBOXAMIDE

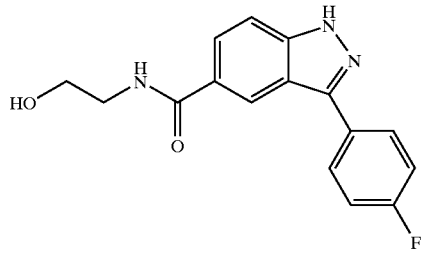

A. [3-(4-Fluorophenyl)(1H-indazol-5-yl)]-N-(2-hydroxyethyl)carboxamide

The title compound was prepared as described in Example 76. To a solution of 3-(4-fluorophenyl)-1H-indazole-5-carboxylic acid (0.200 g, 0.781 mmol) in tetrahydrofuran (5 mL) was added 1-hydroxybenzotriazole hydrate (0.316 g, 2.34 mmol) followed by 1-(3-dimethylaminopropyl)-3- ethylcarbodiimide hydrochloride (0.449 g, 2.34 mmol), ethanolamine (0.141 mL, 2.34 mmol) and N,N-dimethylformamide (2 mL). The solution was stirred for 16 h at room temperature. Water (40 mL) was added and the solid was filtered and dried in a vacuum oven which gave the title compound (0.161 g, 69% yield): $^1$H NMR (DMSO-$d_6$) δ 13.45 (s, 1H), 8.61 (t, 1H), 8.56 (s, 1H), 8.08 (AB quartet, 2H), 7.93 (dd, 1H), 7.62 (d, 1H), 7.40 (t, 2H), 4.76 (t, 1H), 3.54 (q, 2H), 3.80 (q, 2H); ES-MS (m/z) 300 [M+1]$^+$.

Example 401

SYNTHESIS OF [3-(4-FLUOROPHENYL)(1H-INDAZOL-5-YL)]-N-(3-HYDROXYPROPYL) CARBOXAMIDE

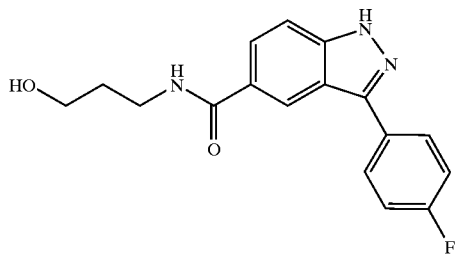

A. [33-(4-Fluorophenyl)(1H-indazol-5-yl)]-N-(3-hydroxypropyl)carboxamide

The title compound was prepared as described in Example 76. To a solution of 3-(4-fluorophenyl)-1H-indazole-5-carboxylic acid (0.200 g, 0.781 mmol) in tetrahydrofuran (5 mL) was added 1-hydroxybenzotriazole hydrate (0.316 g, 2.34 mmol) followed by 1-(3-dimethylaminopropyl)-3-ethylcarbodiimide hydrochloride (0.449 g, 2.34 mmol), 3-amino-1-propanol (0.178 mL, 2.34 mmol) and N,N-dimethylformamide (2 mL). The solution was stirred for 16 h at room temperature. Water (40 mL) was added and the solid was filtered and dried in a vacuum oven to give the title compound (0.192 g, 78% yield): $^1$H NMR (DMSO-$d_6$) δ 13.45 (s, 1H), 8.59 (t, 1H), 8.53 (s, 1H), 8.08 (AB quartet, 2H), 7.91 (dd, 1H), 7.62 (d, 1H), 7.40 (t, 2H), 4.50 (t, 1H), 3.48 (q, 2H), 3.36 (q, 2H), 1.71 (pentet, 2H); ES-MS (m/z) 314 [M+1]$^+$.

Example 402

SYNTHESIS OF [3-(4-FLUOROPHENYL)(1H-INDAZOL-5-YL)]-N-(2-METHOXYETHYL) CARBOXAMIDE

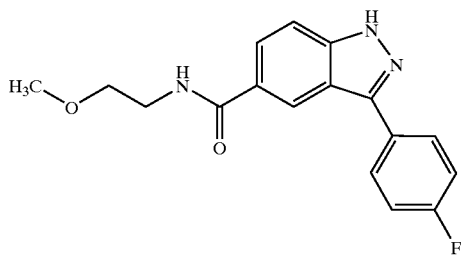

A. [3-(4-Fluorophenyl)(1H-indazol-5-yl)]-N-(2-methoxyethyl)carboxamide

The title compound was prepared as described in Example 76. To a solution of 3-(4-fluorophenyl)-1H-indazole-5-carboxylic acid (0.200 g, 0.781 mmol) in tetrahydrofuran (5 mL) was added 1-hydroxybenzotriazole hydrate (0.316 g, 2.34 mmol) followed by 1-(3-dimethylaminopropyl)-3-ethylcarbodiimide hydrochloride (0.449 g, 2.34 mmol), 2-methoxyethylamine (0.203 mL, 2.34 mmol) and N,N-dimethylformamide (2 mL). The solution was stirred for 16 h at room temperature. Water (40 mL) was added and the reaction mixture was extracted with ethyl acetate. The combined organic layers were dried over anhydrous sodium sulfate, filtered and evaporated. The residue was purified by preparative HPLC (10–90% acetonitrile/water). The pure fractions were made basic with ammonium hydroxide, and the solution evaporated under reduced pressure, diluted with water and filtered to give the title compound (0.162 g, 66% yield): $^1$H NMR (DMSO-$d_6$) δ 13.45 (s, 1H), 8.70 (t, 1H), 8.56 (s, 1H), 8.08 (AB quartet, 2H), 7.92 (dd, 1H), 7.63 (d, 1H), 7.40 (t, 2H), 3.49 (s, 3H), 3.34 (m, 2H), 3.28 (s, 2H); ES-MS (m/z) 314 [M+1]$^+$.

Example 403

SYNTHESIS OF [3-(4-FLUOROPHENYL)(1H-INDAZOL-5-YL)]-N-(OXOLAN-2-YLMETHYL) CARBOXAMIDE

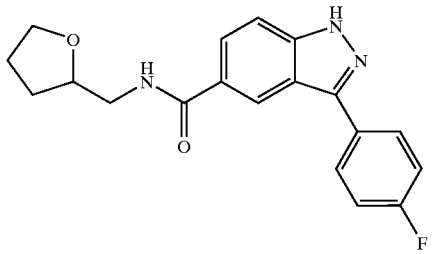

A. [3-(4-Fluorophenyl)(1H-indazol-5-yl)]-N-(Oxolan-2-ylmethyl)carboxamide

The title compound was prepared as described in Example 76. To a solution of 3-(4-fluorophenyl)-1H-indazole-5-carboxylic acid (0.200 g, 0.781 mmol) in tetrahydrofuran (5 mL) was added 1-hydroxybenzotriazole hydrate (0.316 g, 2.34 mmol) followed by 1-(3-dimethylaminopropyl)-3-ethylcarbodiimide hydrochloride (0.449 g, 2.34 mmol), tetrahydrofurfurylamine (0.242 mL, 2.34 mmol) and N,N-dimethylformamide (2 mL). The solution was stirred for 16 h at room temperature. Water (40 mL) was added and the reaction mixture was extracted with ethyl acetate. The combined organic layers were dried over anhydrous sodium sulfate, filtered and evaporated. The residue was purified by preparative HPLC (10–90% acetonitrile/water). The pure fractions were made basic with ammonium hydroxide, the solution evaporated under reduced pressure, diluted with water and filtered which gave the title compound (0.198 g, 74% yield): $^1$H NMR (DMSO-$d_6$) δ 13.43 (s, 1H), 8.71 (t, 1H), 8.56 (m, 1H), 8.08 (AB quartet, 2H), 7.92 (dd, 1H), 7.62 (dd, 1H), 7.40 (t, 2H), 4.01 quartet, 1H), 3.79 (q, 1H), 3.63 (q, 1H), 3.36 (m, 2H), 1.97 (m, 1H), 1.83 (m, 2H), 1.62 (m, 1H); ES-MS (m/z) 340 [M+1]$^+$.

Example 404

SYNTHESIS OF 3-(2H,3H-BENZO[E]1,4-DIOXIN-6-YL)-1H-INDAZOLE-5-CARBOXAMIDE

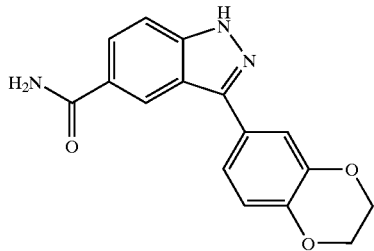

A. 3-(2H,3H-Benzo [e]1,4-dioxin-6-yl)-1H-indazole-5-carbonitrile

The title compound was prepared as described in Example 405 using 3-bromo-1-perhydro-2H-pyran-2-yl-1H-indazole-5-carbonitrile (0.354 g, 1.15 mmol), in ethylene glycol dimethyl ether (20 mL), 2H,3H-benzo[e]1,4-dioxin-6-boronic acid (0.250 g, 1.39 mmol), [1,1'-bis(diphenyl phosphino-ferrocene] complex with dichloromethane (1:1) (0.094 g, 0.11 mmol) and potassium phosphate (2.40 g, 11.5 mmol). Solvent was removed using a rotary evaporator and purification of the residue by column chromatography (silica gel, 20% ethyl acetate/hexanes) gave a solid. methanol (30 mL) and aqueous 6 N hydrochloric acid (30 mL) were added to the solid and the mixture was heated at 45° C. for 5 h. Water (30 mL) was added and the solid was filtered and dried in a vacuum oven to afford the title compound (0.230 g, 71% yield over 2 steps): ES-MS (m/z) 278 [M+1]$^+$.

B. 3-(2H,3H-Benzo[e]1,4-dioxin-6-yl)-1H-indazole-5-carboxamide

A mixture of 3-(2H,3H-benzo[e]1,4-dioxin-6-yl)-1H-indazole-5-carbonitrile (0.230 g, 0.83 mmol), 95% ethanol, aqueous 30% hydrogen peroxide (3 mL), and 6.0 N aqueous sodium hydroxide (1 mL) was heated at 45° C. for 3 h. The reaction mixture was diluted with water (80 mL) and acidified to pH 6 with 3 N hydrochloric acid. The solid was filtered and dried in a vacuum oven and gave the title compound (0.098 g, 50% yield): $^1$H NMR (DMSO-d$_6$) δ 13.31 (s, 1H), 8.55 (s, 1H), 8.17 (br s, 1H), 7.92 (d, 1H), 7.57 (d, 1H), 7.52 (m, 2H), 7.31 (br s, 1H), 7.02 (d, 1H), 4.32 (s, 4H); ES-MS (m/z) 296 [M+1]$^+$.

Example 405

SYNTHESIS OF 6-(5-(1H-1,2,4-TRIAZOL-3-YL)-1H-INDAZOL-3-YL)-2H,3H-BENZO[E]1,4-DIOXIN

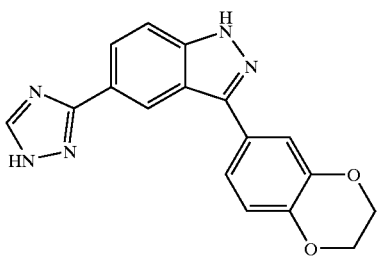

A. 6-(5-(1H-1,2,4-Triazol-3-yl)-1H-indazol-3-yl)-2H,3H-benzo[e]1,4-dioxin

The title compound was prepared by heating a mixture of 3-(2H,3H-benzo[e]1,4-dioxin-6-yl)-1H-indazole-5-carboxamide (0.098 g, 0.33 mmol), and N,N-dimethylformamide dimethyl acetal (30 mL) at 90° C. for 2 h. The reaction mixture was evaporated. To the concentrate was added glacial acetic acid (40 mL) and anhydrous hydrazine (0.50 mL). The mixture was stirred overnight at room temperature. Water (40 mL) was added to the mixture, and the acetic acid was removed on a rotary evaporator. The remaining mixture was extracted with ethyl acetate. The combined organic extracts were dried over anhydrous sodium sulfate, filtered and evaporated. Purification of the residue by column chromatography (silica gel, 75% ethyl acetate/hexanes) afforded the title compound (0.80 g, 75% yield): $^1$H NMR (DMSO-d$_6$) δ 14.33 (br d, 1H), 13.38 (br s, 1H), 8.64 (s, 1H), 8.08 (d, 1H), 7.68 (d, 1H), 7.47 (m, 1H), 7.06 (d, 1H), 4.33 (s, 4H); ES-MS (m/z) 320 [M+1]$^+$.

Example 406

SYNTHESIS OF 3-(3-QUINOLYL)-1H-INDAZOLE-5-CARBOXAMIDE

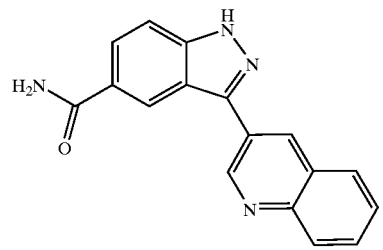

A. 3-(1.1-Dimethyl-1-stannaethyl-1-perhydro-2H-pyran-2-yl-1H-indazole-5-carbonitrile A mixture of 3-bromo-1-perhydro-2H-pyran-2-yl-1H-indazole-5-carbonitrile (0.311 g, 1.0 mmol), tetrakis(triphenylphosphine)palladium (0.115 g, 0.1 mmol) and hexamethylditin (1.0 g, 3.0 mmol) in dioxane (10 mL) was heated at 80° C. for 2 h. The reaction mixture was cooled and aqueous 10% potassium fluoride (10 mL) was added. The mixture was extracted with ethyl acetate. The combined organic extracts were dried over anhydrous sodium sulfate, filtered and evaporated. Purification of the residue by column chromatography (silica gel, 7–10% ethyl acetate/hexanes) afforded the title compound (0.250 g, 63% yield): ES-MS (m/z) 390 [M+1]$^+$.

B. 3-(3-Quinolyl)-1H-indazole-5-carboxamide

A mixture of the 3-(1,1-dimethyl-1-stannaethyl)-1-perhydro-2H-pyran-2-yl-1H-indazole-5-carbonitrile (0.250 g, 0.64 mmol), 3-bromoquinoline (0.088 mL, 0.64 mmol) and tetrakis(triphenylphosphine)palladium (0.074 g, 0.064 mmol) in N,N-dimethylformamide (5 ml) was heated at 80° C. for 14 h. The mixture was cooled to room temperature, diluted with water and the filtered solid was dried in the vacuum oven. Purification of the solid by column chromatography (silica gel, 30% ethyl acetate/hexanes) gave an intermediate solid which was dissolved in methanol (30 mL). Aqueous 6 N hydrochloric acid (30 mL) was added and the mixture heated at 45° C. for 4 h. The reaction mixture was poured into water, basified with potassium carbonate and the yellow solid collected by suction filtration. A mixture of this product, methanol (20 mL), aqueous 6 N sodium hydroxide (2 mL) and aqueous 30% hydrogen peroxide (3 mL) was heated at 45° C. for 3 h. Water (30 mL) was added and the solid collected. Purification of the residue by preparative HPLC (20–80% acetonitrile/water) gave the title compound (0.075 g, 41% yield): $^1$H NMR (DMSO-$d_6$) δ 13.73 (s, 1H), 9.61 (d, 1H), 9.01 (s, 1H), 8.81 (s, 1H), 8.22 (m, 2H), 8.11 (d, 1H), 8.02 (d, 1H), 7.83 (t, 1H), 7.71 (t, 2H), 7.43 (br s, 1H); ES-MS (m/z) 289 [M+1]$^+$.

Example 407

SYNTHESIS OF 3-(6-METHOXY-2-NAPHTHYL)-1H-INDAZOLE-5-CARBOXAMIDE

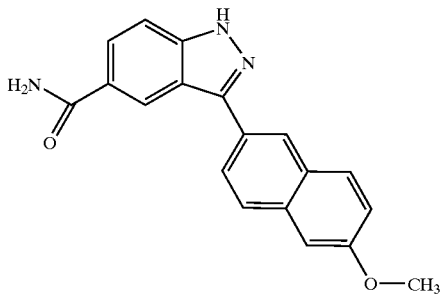

A. 3-(6-Methoxy-2-naphthyl-1H-indazole-5-carbonitrile

The title compound was prepared as described in Example 408 using 3-bromo-1-perhydro-2H-pyran-2-yl-1H-indazole-5-carbonitrile (0.500 g, 1.6 mmol), in ethylene glycol dimethyl ether (30 mL), 6-methoxynaphthalene-2-boronic acid (0.395 g, 2.0 mmol), [1,1'-bis(diphenyl phosphinoferrocene] complex with dichloromethane (1:1) (0.133 g, 0.16 mmol) and potassium phosphate (3.5 g, 16.3 mmol). Solvent was removed using a rotary evaporator and purification of the residue by column chromatography (silica gel, 20% ethyl acetate/hexanes) gave a solid. Methanol (50 mL) and aqueous 6 N hydrochloric acid (50 mL) were added to the solid and the mixture was heated at 45° C. for 5 h. One half of the methanol was evaporated, water was added and the solid filtered and dried in a vacuum oven to afford the title compound (0.230 g, 47% yield over 2 steps): ES-MS (m/z) 300 [M+1]$^+$.

B. 3-(6-Methoxy-2-naphthyl-1H-indazole-5-carboxamide

A mixture of 3-(6-methoxy-2-naphthyl)-1H-indazole-5-carbonitrile (0.230 g, 0.77 mmol), 95% ethanol (6 mL), aqueous 30% hydrogen peroxide (3 mL), and 6.0 N aqueous sodium hydroxide (1 mL, mmol) was heated at 45° C. for 3 h. The reaction mixture was diluted with water (30 mL) and acidified to pH 6 with 3 N hydrochloric acid. The solid was filtered and dried in a vacuum oven to give product (0.050 g, 20% yield): $^1$H NMR (DMSO-$d_6$) δ 13.45 (s, 1H), 8.72 (s, 1H), 8.50 (s, 1H), 8.18 (s, 1H), 8.15 (d, 1H), 8.02 (d, 1H), 7.95 (d, 1H), 7.61 (d, 1H), 7.37 (m, 2H), 7.22 (dd, 1H); ES-MS (m/z) 318 [M+1]$^+$.

Example 408

SYNTHESIS OF 6-(5-(1H-1,2,4-TRIAZOL-3-YL)(1H-INDAZOL-3-YL))-2-METHOXYNAPHTHALENE

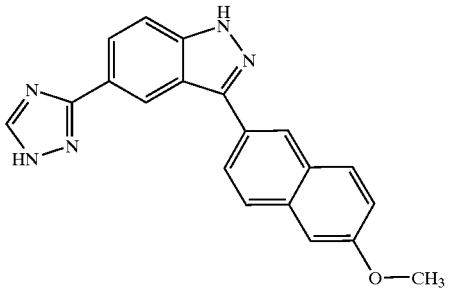

A. 6-(5-(1H-1,2,4-Triazol-3-yl)-1H-indazol-3-yl)-2H,3H-benzo[e]1,4-dioxin

A mixture of 3-(6-methoxy-2-naphthyl)-1H-indazole-5-carboxamide (0.10 g, 0.31 mmol), and N,N-dimethylformamide dimethyl acetal (50 mL) was heated at 90° C. for 2 h. The reaction mixture was evaporated and to the concentrate was added glacial acetic acid (40 mL) and anhydrous hydrazine (1 mL). The mixture was stirred overnight at room temperature. Water (30 mL) was added to the mixture, and the acetic acid was removed on a rotary evaporator. The remaining mixture was extracted with ethyl acetate. The combined organic extracts were dried over anhydrous sodium sulfate, filtered and evaporated. Purification of the residue by column chromatography (silica gel, 75% ethyl acetate/hexanes) afforded the title compound (0.065 g, 25% yield): $^1$H NMR (DMSO-$d_6$) δ 14.32 (d, 1H), 13.46 (d, 1H), 8.82 (d, 1H), 8.48 (d, 1H), 8.08 (m, 4H), 7.73 (dd, 1H), 7.42 (s, 1H), 7.25 (t, 1H); ES-MS (m/z) 342 [M+1]$^+$.

Example 409

SYNTHESIS OF 3-(3-(3-QUINOYL)-1H-INDAZOL-5-YL)-1H-1,2,4-TRIAZOLE

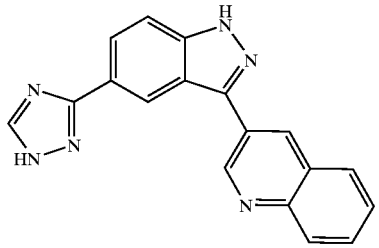

A. 3-(3-(3-quinoyl)-1H-indazol-5-yl)-1H-1,2,4-triazole

A mixture of 3-(3-quinolyl)-1H-indazole-5-carboxamide (0.045 g, 0.16 mmol), and N,N-dimethylformamide dimethyl acetal (30 mL) was heated at 90° C. for 2 h. The reaction mixture was evaporated and to the concentrate was added glacial acetic acid (30 mL) and anhydrous hydrazine (0.5 mL). The mixture was stirred overnight at room temperature. Water (30 mL) was added to the mixture and acetic acid was removed on a rotary evaporator. The remaining mixture was extracted with ethyl acetate. The combined organic extracts were dried over anhydrous sodium sulfate, filtered and evaporated. Purification of the residue by column chromatography (silica gel, 75% ethyl acetate/hexanes)

afforded the title compound (0.025 g, 50% yield): $^1$H NMR (DMSO-$d_6$) δ 9.56 (t, 1H), 8.86 (s, 1H), 8.74 (s, 1H), 8.15 (d, 1H), 8.08 (m, 2H), 7.90 (d, 1H), 7.75 (t, 1H), 7.65 (d, 2H); ES-MS (m/z) 313 [M+1]$^+$.

Example 410

SYNTHESIS OF 3-(2,3-DIHYDROBENZO[B]FURAN-5-YL)-1H-INDAZOLE-5-CARBOXAMIDE

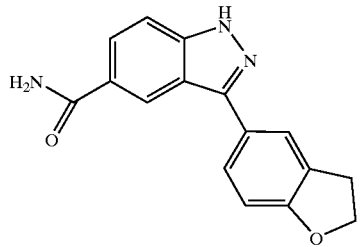

A. 3-(2,3-Dihydrobenzo[b]furan-5-yl)-1H-indazole-5-carbonitrile

The title compound was prepared as described in Example 411, using 3-bromo-1-perhydro-2H-pyran-2-yl-1H-indazole-5-carbonitrile (0.750 g, 2.45 mmol), in ethylene glycol dimethyl ether (50 mL), 2,3-dihydrobenzo[b]furan-5-boronic acid (0.480 g, 2.9 mmol), [1,1'-bis(diphenylphosphino-ferrocene] complex with dichloromethane (1:1) (0.200 g, 0.20 mmol) and potassium phosphate (5.2 g, 24 mmol). Solvent was removed using a rotary evaporator and purification of the residue by column chromatography (20% ethyl acetate/hexanes) gave a solid. Methanol (50 mL) and aqueous 6 N hydrochloric acid (50 mL) were added to the solid and the mixture was heated at 45° C. for 5 h. Water (40 mL) was added and the solid was filtered and dried in a vacuum oven to afford the title compound (0.350 g, 64% yield over 2 steps): ES-MS (m/z) 262 [M+1]$^+$.

B. 3-(2,3-Dihydrobenzo[b]furan-5-yl)-1H-indazole-5-carboxamide

A mixture of 3-(2,3-dihydrobenzo[b]furan-5-yl)-1H-indazole-5-carbonitrile (0.50 g, 1.9 mmol), 95% ethanol (6 mL), aqueous 30% hydrogen peroxide (3 mL), and 6.0 N aqueous sodium hydroxide (1 mL) was heated at 45° C. for 3 h. The reaction mixture was diluted with water (40 mL) and acidified to pH 6 with 3 N hydrochloric acid. The solid was filtered and dried in a vacuum oven to give product (0.080 g, 53% yield): $^1$H NMR (DMSO-$d_6$) δ 13.22 (s, 1H), 8.54 (s, 1H), 8.12 (s, 1H), 7.90 (d, 2H), 7.76 (d, 1H), 7.55 (d, 1H), 7.32 (s, 1H), 6.91 (d, 1H), 4.59 (t, 2H), 3.28 (t, 2H); ES-MS (m/z) 280 [M+1]$^+$.

Example 411

SYNTHESIS OF 5-(5-(1H-1,2,4-TRIAZOL-3-YL)-1H-INDAZOL-3-YL)-2,3-DIHYDROBENZO[B]FURAN

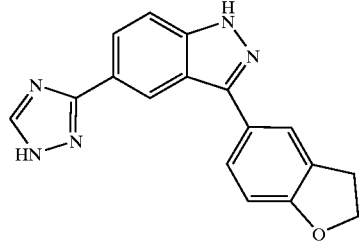

A. 5-(5-(1H-1,2,4-Triazol-3-yl)-1H-indazol-3-yl)-2,3-dihydrobenzo[b]furan

A mixture of 3-(2,3-dihydrobenzo[b]furan-5-yl)-1H-indazole-5-carbonitrile (0.080 g, 0.29 mmol), and N,N-dimethylformamide dimethyl acetal (80 mL) was heated at 90° C. for 2 h. The reaction mixture was evaporated and to the concentrate was added glacial acetic acid (40 mL) and anhydrous hydrazine (1 mL). The mixture was stirred overnight at room temperature. Water (40 mL) was added to the mixture and the acetic acid was removed on a rotary evaporator. The remaining mixture was extracted with ethyl acetate. The combined organic extracts were dried over anhydrous sodium sulfate, filtered and evaporated. Purification of the residue by column chromatography (silica gel, 75% ethyl acetate/hexanes) afforded the title compound (0.095 g, 100% yield): $^1$H NMR (DMSO-$d_6$) δ 14.20 (br s, 1H), 13.30 (s, 1H), 8.64 (s, 1H), 8.18 (br s, 1H), 8.07 (d, 1H), 7.86 (s, 1H), 7.74 (d, 1H), 7.67 (d, 1H), 6.96 (d, 1H), 4.62 (t, 2H), 3.31 (t, 2H); ES-MS (m/z) 304 [M+1]$^+$.

Example 412

SYNTHESIS OF N-[3-(5-(1H-1,2,4-TRIAZOL-3-YL)(1H-INDAZOL-3-YL))PHENYL]BENZAMIDE

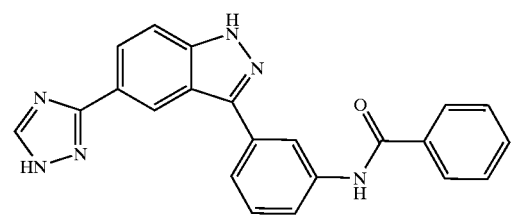

A. N-[3-(5-(1H-1,2,4-Triazol-3-yl)(1H-indazol-3-yl))phenyl]benzamide

To a solution of 3-{1-perhydro-2H-pyran-2-yl-5-[1-(triphenylmethyl)(1,2,4-triazol-3-yl)]-1H-indazol-3-yl}phenylamine (0.200 g, 0.33 mmol) in pyridine (2 mL) was added benzoyl chloride (0.046 mL, 0.40 mmol). The reaction was stirred at room temperature for 15 h. Water (10 mL) was added and the solid collected by suction filtration. The solid was dried in a vacuum oven for 3 h. The residue was dissolved in 4 N hydrochloric acid in 1,4-dioxane (10 mL) and the mixture was stirred at room temperature for 2 h. After neutralization with aqueous sodium bicarbonate, the reaction mixture was extracted with ethyl acetate. The combined organic fractions were dried over anhydrous sodium sulfate, filtered and evaporated. Addition of dichloromethane (10 mL) to the residue gave a solid which was

Example 413

SYNTHESIS OF N-[3-(5-(1H-1,2,4-TRIAZOL-3-YL)(1H-INDAZOL-3-YL))PHENYL](2,4-DICHLOROPHENYL)CARBOXAMIDE

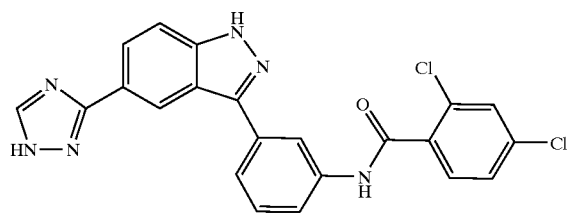

A. N-[3-(5-(1H-1,2,4-Triazol-3-yl)(1H-indazol-3-yl))phenyl](2,4-dichlorophenyl)carboxamide To a solution of 3-{1-perhydro-2H-pyran-2-yl-5-[1-(triphenylmethyl)(1,2,4-triazol-3-yl)]-1H-indazol-3-yl}phenylamine (0.200 g, 0.33 mmol) in pyridine (2 mL) was added 2,4-dichlorobenzyl chloride (0.056 mL, 0.40 mmol). The reaction was stirred at room temperature for 15 h. Water (10 mL) was added and the solid collected by suction filtration. The solid was dried in a vacuum oven for 3 h. The residue was dissolved in 4 N hydrochloric acid in 1,4-dioxane (10 mL) and the mixture was stirred at room temperature for 2 h. After neutralization with aqueous sodium bicarbonate, the reaction mixture was extracted with ethyl acetate. The combined organic fractions were dried over anhydrous sodium sulfate, filtered and evaporated. Addition of dichloromethane (10 mL) to the residue gave the title compound (0.070 g, 55% yield) which was isolated by filtration: $^1$H NMR (DMSO-$d_6$) δ 14.20 (br s, 1H), 13.44 (s, 1H), 10.75 (s, 1H), 8.69 (s, 1H), 8.36 (s, 1H), 8.06 (d, 1H), 7.78 (m, 3H), 7.68 (d, 2H), 7.55 (m, 2H); ES-MS (m/z) 449 [M+1]$^+$.

Example 414

SYNTHESIS OF N-[3-(5-(1H-1,2,4-TRIAZOL-3-YL)(1H-INDAZOL-3-YL))PHENYL](4-METHOXYPHENYL)CARBOXAMIDE

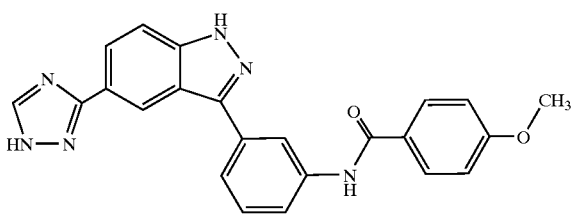

A. N-[3-(5-(1H-1,2,4-Triazol-3-yl)(1H-indazol-3-yl))phenyl](4methoxyphenyl)carboxamide To a solution of 3-{1-perhydro-2H-pyran-2-yl-5-[1-(triphenylmethyl)(1,2,4-triazol-3-yl)]-1H-indazol-3-yl}phenylamine (0.200 g, 0.33 mmol) in pyridine (2 mL) was added 4-methoxybenzoyl chloride (0.068 g, 0.40 mmol). The reaction was stirred at room temperature for 15 h. Water (10 mL) was added and the solid collected by suction filtration. The solid was dried in a vacuum oven for 3 h. The residue was dissolved in 4 N hydrochloric acid in 1,4-dioxane (10 mL) and the mixture was stirred at room temperature for 2 h. After neutralization with aqueous sodium bicarbonate, the reaction mixture was extracted with ethyl acetate. The combined organic fractions were dried over anhydrous sodium sulfate, filtered and evaporated. Addition of dichloromethane (10 mL) to the residue gave the title compound (0.090 g, 66% yield) which was isolated by filtration: $^1$H NMR (DMSO-$d_6$) δ 10.33 (s, 1H), 8.73 (s, 1H), 8.44 (s, 1H), 8.30 (s, 1H), 8.11 (d, 1H), 8.03 (d, 2H), 7.93 (d, 1H), 7.10 (m, 2H), 7.53 (t, 1H), 7.09 (d, 2H), 3.85 (s, 3H); ES-MS (m/z) 411 [M+1]$^+$.

Example 415

SYNTHESIS OF N-[3-(5-(1H-1,2,4-TRIAZOL-3-YL)(1H-INDAZOL-3-YL))PHENYL](4-METHYLPHENYL)CARBOXAMIDE

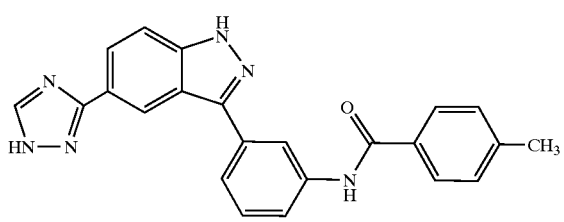

A. N-[3-(5-(1H-1,2,4-Triazol-3-yl)(1H-indazol-3-yl)phenyl](4-methylphenyl)carboxamide To a solution of 3-{1-perhydro-2H-pyran-2-yl-5-[1-(triphenylmethyl)(1,2,4-triazol-3-yl)]-1H-indazol-3-yl}phenylamine (0.140 g, 0.23 mmol) in pyridine (2 mL) was added 4-methylbenzoyl chloride (0.053 mL, 0.40 mmol). The reaction was stirred at room temperature for 15 h. Water (10 mL) was added and the solid collected by suction filtration. The solid was dried in a vacuum oven for 3 h. The residue was dissolved in 4 N hydrochloric acid in 1,4-dioxane (10 mL) and the mixture was stirred at room temperature for 2 h. After neutralization with aqueous sodium bicarbonate, the reaction mixture was extracted with ethyl acetate. The combined organic fractions were dried over anhydrous sodium sulfate, filtered and evaporated. Addition of dichloromethane (10 mL) to the residue gave the title compound (0.060 g, 65% yield) which was isolated by filtration: $^1$H NMR (DMSO-$d_6$) δ 10.41 (s, 1H), 8.74 (s, 1H), 8.46 (s, 1H), 8.33 (s, 1H), 8.10 (d, 1H), 7.94 (d, 3H), 7.72 (m, 2B), 7.54 (t, 1H), 7.36 (d, 2H), 2.40 (s, 3H); ES-MS (m/z) 395 [M+1]$^+$.

Example 416

SYNTHESIS OF N-[3-(5-(1H-1,2,4-TRIAZOL-3-YL)(1H-INDAZOL-3-YL))PHENYL](4-CHLOROPHENYL)CARBOXAMIDE

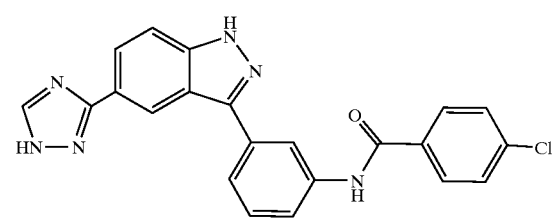

A. N-[3-(5-(1H-1,2,4-Triazol-3-yl)(1H-indazol-3-yl)phenyl](4-chlorophenyl)carboxamide To a solution of 3-{1-perhydro-2H-pyran-2-yl-5-[1-(triphenylmethyl)(1,2,4-triazol-3-yl)]-1H-indazol-3-yl}phenylamine (0.210 g, 0.35 mmol) in pyridine (2 mL) was added 4-chlorobenzoyl chloride (0.051 mL, 0.40 mmol). The reaction was stirred at room temperature for 15 h. Water (10 mL) was added and the solid collected by suction filtration. The solid was dried in a vacuum oven for 3 h. The residue was dissolved in 4 N hydrochloric acid in 1,4-dioxane (10 mL) and the mixture was stirred at room temperature for 2 h. After neutralization with aqueous sodium bicarbonate, the reaction mixture was extracted with ethyl acetate. The combined organic fractions were dried over anhydrous sodium sulfate, filtered and evaporated. Addition of dichloromethane (10 mL) to the residue gave the title compound (0.090 g, 62% yield) which was isolated by filtration: $^1$H NMR (DMSO-d$_6$) δ 14.20 (br s, 1H), 13.45 (br s, 1H), 10.54 (s, 1H), 8.73 (s, 1H), 8.44 (s, 1H), 8.10 (d, 1H), 8.04 (d, 2H), 7.93 (d, 1H), 7.76 (d, 1H), 7.71 (d, 1H), 7.64 (d, 2H), 7.56 (t, 1H); ES-MS (m/z) 415 [M+1]$^+$.

Example 417

SYNTHESIS OF N-[3-(5-(1H-1,2,4-TRIAZOL-3-YL)(1H-INDAZOL-3-YL))PHENYL]-2-METHYLPROPANAMIDE

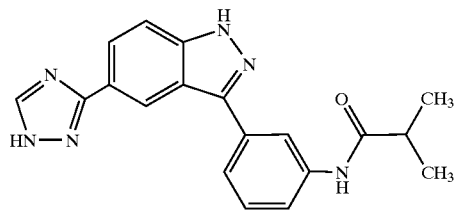

A. N-[3-(5-(1H-1,2,4-Triazol-3-yl)(1H-indazol-3-yl))phenyl]-2-methylpropanamide

To a solution of 3-{1-perhydro-2H-pyran-2-yl-5-[1-(triphenylmethyl)(1,2,4-triazol-3-yl)]-1H-indazol-3-yl}phenylamine (0.190 g, 0.33 mmol) in pyridine (2 mL) was added 2-methylpropanoyl chloride (0.042 mL, 0.40 mmol). The reaction was stirred at room temperature for 15 h. Water (10 mL) was added and the solid collected by suction filtration. The solid was dried in a vacuum oven for 3 h. The residue was dissolved in 4 N hydrochloric acid in 1,4-dioxane (10 mL) and the mixture was stirred at room temperature for 2 h. After neutralization with aqueous sodium bicarbonate, the reaction mixture was extracted with ethyl acetate. The combined organic fractions were dried over anhydrous sodium sulfate, filtered and evaporated. Addition of dichloromethane (10 mL) to the residue gave the title compound (0.005 g, 5% yield) which was isolated by filtration: $^1$H NMR (DMSO-d$_6$) δ 10.02 (s, 1H), 8.65 (s, 1H), 8.21 (s, 1H), 8.10 (br s, 1H), 7.78 (d, 1H), 7.65 (m, 2H), 7.45 (t, 1H), 2.63 (m, 1H), 1.19 (d, 6H); ES-MS (m/z) 347 [M+1]$^+$.

Example 418

SYNTHESIS OF N-[3-(5-(1H-1,2,4-TRIAZOL-3-YL)(1H-INDAZOL-3-YL))PHENYL]-3-METHYLBUTANAMIDE

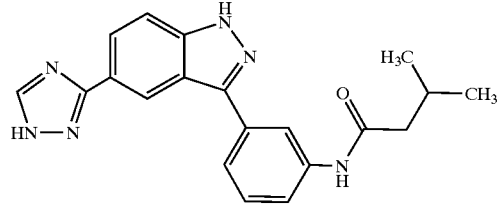

A. N-[3-(5-(1H-1,2,4-Triazol-3-yl)(1H-indazol-3-yl))phenyl]-3-methylbutanamide

To a solution of 3-{1-perhydro-2H-pyran-2-yl-5-[1-(triphenylmethyl)(1,2,4-triazol-3-yl)]-1H-indazol-3-yl}phenylamine (0.400 g, 0.66 mmol) in pyridine (4 mL) was added 3-methylbutanoyl chloride (0.100 mL, 0.80 mmol). The reaction was stirred at room temperature for 15 h. Water (10 mL) was added and the solid collected by suction filtration. The solid was dried in a vacuum oven for 3 h. The residue was dissolved in 4 N hydrochloric acid in 1,4-dioxane (10 mL) and the mixture was stirred at room temperature for 2 h. After neutralization with aqueous sodium bicarbonate, the reaction mixture was extracted with ethyl acetate. The combined organic fractions were dried over anhydrous sodium sulfate, filtered and evaporated. Addition of dichloromethane (10 mL) to the residue gave the title compound (0.005 g, 5% yield) which was isolated by filtration: $^1$H NMR (DMSO-d$_6$) δ 14.20 (br s, 1H), 13.43 (s, 1H), 10.08 (s, 1H), 8.69 (s, 1H), 8.25 (s, 1H), 8.10 (d, 1H), 7.75 (d, 1H), 7.69 (t, 3H), 7.49 (t, 1H), 2.24 (d, 2H), 2.18 (m, 1H), 0.96 (d, 6H); ES-MS (m/z) 361 [M+1]$^+$.

Example 419

SYNTHESIS OF N-[3-(5-(1H-1,2,4-TRIAZOL-3-YL)(1H-INDAZOL-3-YL))PHENYL]-2-MORPHOLIN-4-YLACETAMIDE

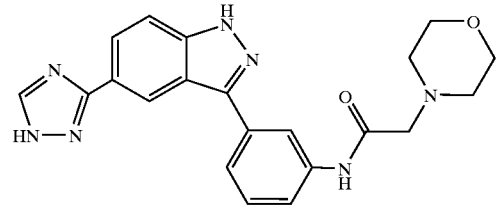

A. N-[3-(5-(1H-1,2,4-Triazol-3-yl)(1H-indazol-3-yl))phenyl]-2-morpholin-4-yl-acetamide To a solution of 3-{1-perhydro-2H-pyran-2-yl-5-[1-(triphenylmethyl)(1,2,4-triazol-3-yl)]-1H-indazol-3-yl}phenylamine (0.400 g, 0.66 mmol) in tetrahydrofuran (4 mL) was added 2-chloroacetyl chloride (0.030 mL, 0.36 mmol) followed by N,N-diisopropylethylamine (0.116 mL, 0.66 mmol). The reaction was stirred at room temperature for 4 h. Water (20 mL) was added and the reaction mixture was extracted with ethyl acetate. The combined organic organic extracts were dried over anhydrous sodium sulfate, filtered and evaporated. The residue was dissolved in N,N-dimethylformamide (5 mL) and morpholine (0.577 mL, 6.6 mmol) was added. The mixture was stirred at room temperature for 14 h. Water (30 mL) was added and the mixture extracted with ethyl acetate. The combined organic fractions were dried over anhydrous sodium sulfate, filtered and evaporated. The residue was dissolved in 4 N hydrochloric acid in 1,4-dioxane (10 mL) and the mixture was stirred at room temperature for 2 h. Dioxane was removed with a rotary evaporator and the residue was purified by preparative HPLC. The desired fractions were neutralized with ammonium hydroxide, extracted with butanol and evaporated to give the title compound (0.130 g, 49% yield): $^1$H NMR (DMSO-d$_6$) δ 14.22 (br d, 1H), 13.50 (d, 1H), 10.00 (s, 1H), 8.65 (m, 1H), 8.05 (m, 1H), 7.69 (m, 2H), 7.26 (s, 1H), 6.75 (s, 1H), 1.74 (s, 2H), 1.32 (t, 4H), 1.24 (t, 4H); ES-MS (m/z) 404 [M+1]$^+$.

Example 420

SYNTHESIS OF N-[3-(5-(1H-1,2,4-TRIAZOL-3-YL)(1H-INDAZOL-3-YL))PHENYL]-2-(4-METHYLPIPERAZINYL)ACETAMIDE

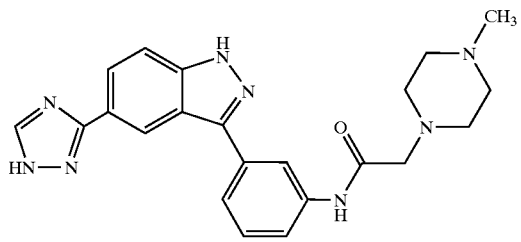

A. N-[3-(5-(1H-1,2,4-Triazol-3-yl)(1H-indazol-3-yl))phenyl]-2-(4-methylpiperazinyl)acetamide To a solution of 3-{1-perhydro-2H-pyran-2-yl-5-[1-(triphenylmethyl)(1,2,4-triazol-3-yl)]-1H-indazol-3-yl}phenylamine (0.400 g, 0.66 mmol) in tetrahydrofuran (4 mL) was added 2-chloroacetyl chloride (0.083 mL, 1.0 mmol) followed by N,N-diisopropylethylamine (0.116 mL, 0.66 mmol). The reaction was stirred at room temperature for 4 h. Water (20 mL) was added and the reaction mixture was extracted with ethyl acetate. The combined organic organic extracts were dried over anhydrous sodium sulfate, filtered and evaporated. The residue was dissolved in N,N-dimethylformamide (5 mL) and N-methylpiperazine (0.320 mL, 3.3 mmol) was added. The mixture was stirred at room temperature for 14 h. Water (30 mL) was added and the mixture extracted with ethyl acetate. The combined organic fractions were dried over anhydrous sodium sulfate, filtered and evaporated. The residue was dissolved in 4 N hydrochloric acid in 1,4-dioxane (10 mL) and the mixture was stirred at room temperature for 2 h. Dioxane was removed with a rotary evaporator and the residue was purified by preparative HPLC. The desired fractions were neutralized with ammonium hydroxide, extracted with butanol and evaporated to give the title compound (0.150 g, 54% yield): $^1$H NMR (DMSO-d$_6$) δ 13.45 (br s, 1H), 10.04 (s, 1H), 8.73 (s, 1H), 8.34 (d, 2H), 8.10 (d, 1H), 7.75 (d, 1H), 7.69 (d, 2H), 7.48 (t, 1H), 2.15 (s, 3H), 1.80 (m, 8H), 1.33 (s, 3H). ES-MS (m/z) 417 [M+1]$^+$.

Example 421

SYNTHESIS OF 3-[3-(4-FLUOROPHENYL)(1H-INDAZOL-3-YL)]-5-[(4PYRROLIDINYLPIPERIDYL)METHYL]-1H-1,2,4-TRIAZOLE

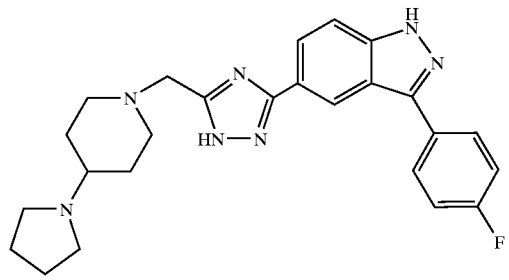

A. 3-[3-(4-Fluorophenyl)(1H-indazol-3-yl)]-5-[(4-pyrrolidinylpiperidyl)methyl]-1H-1,2,4-triazole To a solution of methyl 2-(4-pyrrolidinylpiperidyl)acetate (0.500 g, 2.2 mmol) in anhydrous ethanol (0.5 mL) was added hydrazine (0.070 mL, 2.2 mmol) and the mixture was heated at 80° C. for 14 h. The solvent was removed using a rotary evaporator and the product dried in a vacuum oven for 6 h. To the residue dissolved in methanol (4 mL) was added ethoxy[3-(4-fluorophenyl)(1H-indazol-5-yl)]methanimine hydrochloride (0.300 g, 0.94 mmol) followed by a commercial solution of 4.37 M sodium methoxide (0.480 mL). The mixture was heated at 90° C. for 14 h and then the reaction was quenched with water. The pH was adjusted to neutral and the crude product was extracted with ethyl acetate. Purification of the residue by preparative HPLC gave the title compound (0.018 g, 5% yield): $^1$H NMR (DMSO-d$_6$) δ 14.00 (br s, 1H), 13.45 (s, 1H), 8.60 (s, 1H), 8.05 (m, 3H), 7.70 (d, 1H), 7.43 (t, 2H), 3.59 (s, 2H), 2.83 (d, 3H), 2.10 (t, 4H), 1.80 (d, 3H), 1.64 (s, 5H), 1.40 (d, 3H), 1.22 (s, 1H); ES-MS (m/z) 446 [M+1]$^+$.

Example 422

SYNTHESIS OF 3-[3-(4-FLUOROPHENYL)(1H-INDAZOL-3-YL)]-5-(PYRROLIDINYLMETHYL)-1H-1,2,4-TRIAZOLE

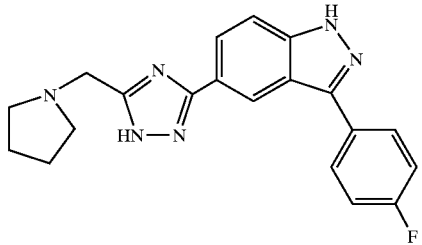

A. 3-[3-(4-Fluorophenyl)(1H-indazol-3-yl)-5-(pyrrolidinylmethyl)-1H-1,2,4-triazole To a solution of pyrrolidine (2.0 mL, 24 mmol) in acetonitrile (20 mL) was added an excess of potassium carbonate (2.0 g) and methyl bromoacetate (2.5 mL, 26 mmol). The mixture was stirred at room temperature for 14 h. The mixture was filtered and the acetonitrile removed by rotary evaporator. The resulting solid was dried in a vacuum oven for 4 h. The product was dissolved in ethanol (5 mL), hydrazine (0.750 mL) was added and the mixture was heated at 80° C. for 16 h. Solvent was removed using a rotary evaporator to provide solid hydrazide. To a suspension of ethoxy[3-(4-fluorophenyl)(1H-indazol-5-yl)]methanimine hydrochloride (0.500 g, 1.56 mmol) in methanol (5 mL) was added hydrazide (0.670 g, 4.7 mmol) and the mixture was heated in a sealed tube at 95° C. for 48 h. The solvent was removed using a rotary evaporator and gave a solid residue. Purification of the residue by preparative HPLC gave the title compound (0.200 g, 35% yield): $^1$H NMR (DMSO-$d_6$) δ 14.00 (br s, 1H), 13.40 (br s, 1H), 8.60 (s, 1H), 8.05 (m, 3H), 7.66 (d, 1H), 7.40 (t, 2H), 7.27 (br s, 1H), 6.68 (br s, 1H), 3.74 (s, 2H), 2.49 (t, 2H), 1.72 (m, 4H); ES-MS (m/z) 363 [M+1]$^+$.

Example 423

SYNTHESIS OF ({3-[3-(6-METHOXY(2-NAPHTHYL))(1H-INDAZOL-5-YL)](1H-1,2,4-TRIAZOL-5-YL)}METHYL)DIMETHYLAMINE

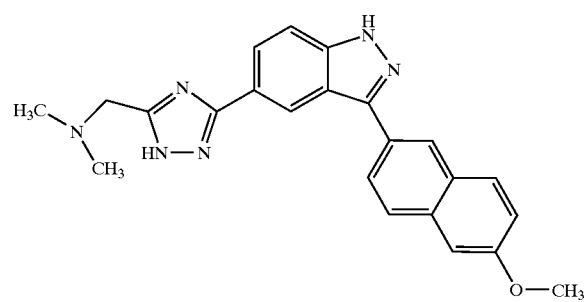

A. 3-(6-Methoxy-2-naphthyl)-1H-indazole-5-carbonitrile

The title compound was prepared as described in Example 161, using 3-bromo-1-perhydro-2H1-pyran-2-yl-1H-indazole-5-carbonitrile (0.500 g, 1.6 mmol), in ethylene glycol dimethyl ether (30 mL), 6-methoxynaphthalene-2-boronic acid (0.395 g, 2.0 mmol), [1,1'-bis(diphenyl phosphino-ferrocene] complex with dichloromethane (1:1) (0.133 g, 0.16 mmol) and potassium phosphate (3.5 g, 16.3 mmol). Solvent was removed using a rotary evaporator and purification of the residue by column chromatography (silica gel, 20% ethyl acetate/hexanes) gave a solid. Methanol (50 mL) and aqueous 6 N hydrochloric acid (50 mL) were added to the solid and the mixture was heated at 45° C. for 5 h. One half of the methanol was evaporated, water was added and the solid filtered and dried in a vacuum oven to afford the title compound (0.230 g, 47% yield over 2 steps): ES-MS (m/z) 300 [M+1]$^+$.

B. Ethoxy-[3-(6-methoxy(2-naphthyl))(1H-indazol-5-yl)]methanimine

A solution of 3-(6-methoxy-2-naphthyl)-1H-indazole-5-carbonitrile (0.430 g, 1.12 mmol) and absolute ethanol (50 mL) in a pressure tube was cooled to 0° C. using an ice-bath. Anhydrous hydrochloric acid was bubbled through the cooled solution for 5 min, the reaction mixture was sealed and the solution was stirred for 72 h at room temperature. The solvent was removed using a rotary evaporator. The yellow solids was stirred with ether, filtered and dried in a vacuum oven which gave ethoxy[3-(6-methoxy(2-naphthyl)) (1H-indazol-5-yl)]methanimine hydrochloride (0.388 g, 100% yield): ES-MS (rn/z) 346 [M+1]$^+$.

C. ({3-[3-(6-Methoxy(2-naphthyl))(1H-indazol-5-yl)](1H-1,2,4-triazol-5-yl)}methyl)dimethylamine To a suspension of ethoxy[3-(6-methoxy(2-naphthyl)) (1H-indazol-5-yl)]methanimine (0.430 g, 1.13 mmol) in methanol (5 mL) was added N-amino-2-(dimethylamino)acetamide (0.396 g, 3.38 mmol) and 4.3 M sodium methoxide (0.578 mL, 2.49 mmol). The mixture was heated in a sealed tube at 95° C. for 16 h. The solvent was removed using a rotary evaporator and gave a solid residue. Purification of the residue by preparative HPLC (10–80%, acetonitrile/water) gave the title compound (0.025 g, 5% yield): $^1$H NMR (DMSO-$d_6$) δ 13.95 (br s, 1H), 13.40 (br s, 1H), 8.73 (s, 1H), 8.44 (s, 1H), 8.09 (t, 2H), 8.00 (t, 2H), 7.68 (d, 1H), 7.39 (d, 1H), 7.21 (dd, 1H), 3.90 (s, 3H), 3.60 (s, 2H), 2.22 (s, 6H); ES-MS (m/z) 399 [M+1]$^+$.

Example 424

SYNTHESIS OF 2-METHOXY-6-{5-[5-(PYRROLIDINYLMETHYL)(1H-1,2,4-TRIAZOL-3-YL)](1H-INDAZOL-3-YL)}NAPHTHALENE

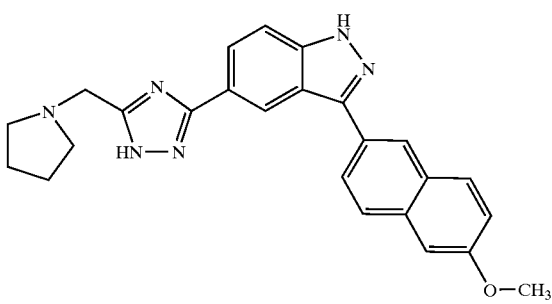

A. 2-Methoxy-6–15-[5-(pyrrolidinylmethyl)(1H-1,2,4-triazol-3-yl)](1H-indazol-3-yl)}naphthalene The title compound was prepared using the same procedure as for Example 423. To a suspension of ethoxy[3-(6-methoxy(2-naphthyl))(1H-indazol-5-yl)]methanimine (0.386 g, 1.01 mmol) in methanol (5 mL) was added N-amino-2-pyrrolidinylacetamide (0.433 g, 3.03 mmol) and 4.3 M sodium methoxide (0.518 mL, 2.23 mmol). The mixture was heated in a sealed tube at 95° C. for 16 h. The solvent was removed using a rotary evaporator which gave a solid residue. Purification of the residue by preparative HPLC (30–100%, acetonitrile/water) gave the title compound (0.045 g, 10% yield): $^1$H NMR (DMSO-$d_6$) δ 13.41 (br s, 1H), 8.73 (s, 1H), 8.44 (s, 1H), 8.09 (t, 2H), 8.00 (t, 2H), 7.68 (d, 1H), 7.39 (d, 1H), 7.23 (dd, 1H), 3.91 (s, 3H), 3.75 (s, 2H), 2.53 (m, 4H), 2.49 (m, 4H); ES-MS (m/z) 425 [M+1]$^+$.

Example 425

SYNTHESIS OF N-PHENYL(3-{5-[5-(PYRROLIDINYLMETHYL)(1H-1,2,4-TRIAZOL-3-YL)](1H-INDAZOL-3-YL)}phenyl) CARBOXAMIDE

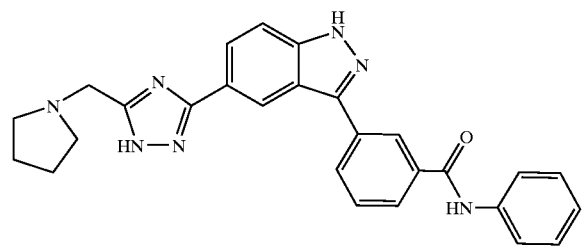

A. [3-(5-Cyano-1-perhydro-2H-pyran-2-yl(1H-indazol-3-yl))phenyl]-N-benzamide

The title compound was prepared in a similar method as described in Example 365. To a solution of 3-(5-cyano-1- perhydro-2H-pyran-2-yl-1H-indazol-3-yl)benzoic acid (0.600 g, 1.73 mmol) in anhydrous THF (15 mL) and anhydrous DMF (6.5 mL) was added 1-hydroxybenzotriazole (0.701 g, 5.19 mmol) followed by 1-(3-dimethylaminopropyl)-3-ethylcarbodiimide hydrochloride (0.995 g, 5.19 mmol) and aniline (0.473 mL, 5.19 mmol). The reaction mixture was stirred at room temperature for 16 h. The reaction mixture was partitioned between ethyl acetate and water, washed with brine, dried over $Na_2SO_4$ and evaporated during which the product began to precipitate as a colorless solid. Hexanes were added and the desired product was collected by vacuum filtration (0.630 g, 86%) ES-MS (m/z) 423 [M+H]+.

B. {3-[5-(Ethoxyiminomethyl)(1H-indazol-3-yl)]phenyl}-N-benzamide

A solution of [3-(5-cyano-1-perhydro-2H-pyran-2-yl(1H-indazol-3-yl))phenyl]-N-benzamide (0.430 g, 1.12 mmol) and absolute ethanol (50 mL) in a pressure tube was cooled to 0° C. using an ice-bath. Anhydrous hydrochloric acid was bubbled through the cooled solution for 5 min, the reaction mixture was sealed and the solution was stirred for 72 h at room temperature. The solvent was removed using a rotary evaporator. The yellow solids was stirred with ether, filtered and dried in a vacuum oven which gave the {3-[5-(ethoxyiminomethyl)(1H-indazol-3-yl)]phenyl}-N-benzamide hydrochloride (0.431 g, 100% yield): ES-MS (m/z) 385 [M+1]+.

C. N-phenyl(3-{5-[5-(pyrrolidinylmethyl)(1H-1,2,4-triazol-3-yl)](H-indazol-3-yl)}phenyl)carboxamide To a suspension of {3-[5-(ethoxyiminomethyl)(1H-indazol-3-yl)]phenyl}-N-benzamide (0.450 g, 0.984 mmol) in methanol (5 mL) was added N-amino-2-pyrrolidinylacetamide (0.422 g, 2.95 mmol) and 4.3 M sodium methoxide (0.503 mL, 2.16 mmol). The mixture was heated in a sealed tube at 95° C. for 14 h. The solvent was removed using a rotary evaporator and gave a solid residue. Purification of the residue by column chromatography (30% methanol/ethyl acetate) gave the title compound (0.153 g, 33% yield): $^1$H NMR (DMSO-$d_6$) δ 13.58 (br s, 1H), 10.44 (s, 1H), 8.67 (s, 1H), 8.54 (s, 1H), 8.20 (d, 1H), 8.09 (d, 1H), 8.00 (d, 1H), 7.80 (d, 2H), 7.73 (t, 1H), 7.70 (d, 1H), 7.36 (t, 2H), 7.11 (t, 1H), 3.78 (s, 2H), 2.53 (m, 4H), 2.48 (m, 4H); ES-MS (m/z) 464 [M+1]+.

Example 426

SYNTHESIS OF 6-{5-[5-(PYRROLIDINYLMETHYL)-1H-1,2,4-TRIAZOL-3-YL]-1H-INDAZOL-3-YL}-2H,3H-BENZO[E]1,4-DIOXIN

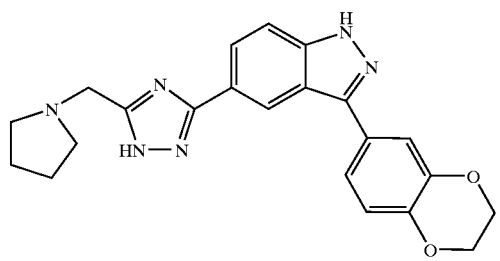

A. 3-(2H,3H-benzo[e]1,4-dioxin-6-yl)-1H-indazole-5-carbonitrile

The title compound was prepared using 3-bromo-1-perhydro-2H-pyran-2-yl-1H-indazole-5-carbonitrile (0.354 g, 1.15 mmol), in ethylene glycol dimethyl ether (20 mL), 2H,3H-benzo[e]1,4-dioxin-6-boronic acid (0.250 g, 1.39 mmol), [1,1'-bis(diphenyl phosphino-ferrocene] complex with dichloromethane (1:1) (0.094 g, 0.11 mmol) and potassium phosphate (2.40 g, 11.5 mmol). Solvent was removed using a rotary evaporator and purification of the residue by column chromatography (silica gel, 20% ethyl acetate/hexanes) gave a solid. Methanol (30 mL) and aqueous 6 N hydrochloric acid (30 mL) were added to the solid and the mixture was heated at 45° C. for 5 h. Water (30 mL) was added and the solid was filtered and dried in a vacuum oven to afford the title compound (0.230 g, 71% yield over 2 steps): ES-MS (m/z) 278 [M+1]+.

B. (3-(2H,3H-Benzo[e]1,4-dioxin-6-yl)(1H-indazol-5-yl))ethoxymethanimine

A solution of 3-(2H,3H-benzo[e]1,4-dioxin-6-yl)-1H-indazole-5-carbonitrile (0.430 g, 112 mmol) and absolute ethanol (50 mL) in a pressure tube was cooled to 0° C. using an ice-bath. Anhydrous hydrochloric acid was bubbled through the cooled solution for 5 min, the reaction mixture was sealed and the solution was stirred for 72 h at room temperature. The solvent was removed using a rotary evaporator. The yellow solids were stirred with ether, filtered and dried in a vacuum oven which gave the (3-(2H,3H-benzo[e]1,4-dioxin-6-yl)(1H-indazol-5-yl))ethoxymethanimine hydrochloride (0.363 g, 100% yield): ES-MS (m/z) 324 [M+1]+.

C. 6–5-[5-(Pyrrolidinylmethyl)-1H-1,2,4-triazol-3-yl]-1H-indazol-3-yl}-2H,3H-benzo[e]1.4-dioxin To a suspension of (3-(2H,3H-benzo[e]1,4-dioxin-6-yl)(1H-indazol-5-yl))ethoxymethanimine (0.336 g, 0.935 mmol) in methanol (5 mL) was added N-amino-2-pyrrolidinylacetamide (0.400 g, 2.80 mmol) and 4.3 M sodium methoxide (0.479 mL, 2.06 mmol). The mixture was heated in a sealed tube at 95° C. for 14 h. The solvent was removed using a rotary evaporator and gave a solid residue. Purification of the residue by preparative HPLC (30–100% acetonitrile/water) gave the title compound (0.061 g, 16% yield): $^1$H NMR (DMSO-$d_6$) δ 13.90 (br s, 1H), 13.30 (br s, 1H), 8.56 (s, 1H), 8.03 (d, 1H), 7.62 (d, 1H), 7.43 (m, 2H), 7.04 (d, 1H), 4.32 (s, 4H), 3.75 (s, 2H), 2.52 (m, 4H), 2.48 (m, 4H); ES-MS (m/z) 403 [M+1]+.

Example 427

SYNTHESIS OF [3-(4-FLUOROPHENYL)(1H-INDAZOL-5-YL)]-N-(3-OXO-3-PYRROLIDINYLPROPYL)CARBOXAMIDE

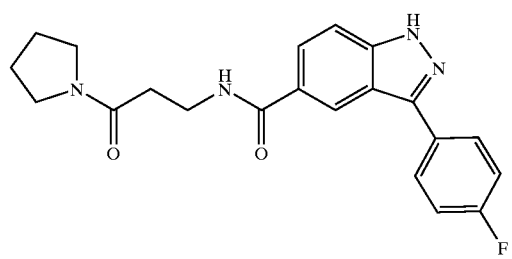

A. [3-(4-Fluorophenyl)(1H-indazol-5-yl)]-N-(3-oxo-3-pyrrolidinylpropyl)carboxamide To a solution containing Example 88 (0.155 g, 0.474 mmol) in tetrahydrofuran (4 mL) was added I-hydroxybenzotriazole hydrate (0.192 g, 1.42 mmol) followed by 1-(3-dimethylaminopropyl)-3-ethylcarbodiimide hydrochloride (0.272 g, 1.42 mmol) pyrrolidine (0.119 mL, 1.42 mmol) and N,N-dimethylformamide (2 mL). The solution was stirred for 16 h at room temperature. Water (40 mL) was added and the reaction mixture was extracted with ethyl acetate. The combined organic layers were dried over anhydrous sodium sulfate, filtered and evaporated. The residue was purified by preparative HPLC (10–90% acetonitrile/water). The pure fractions were basified with ammonium hydroxide, evaporated under reduced pressure, diluted with water and filtered which gave the title compound (0.120 g, 66% yield): $^1$H NMR (DMSO-$d_6$) δ 13.50 (s, 1H), 8.73 (t, 1H), 8.59 (s, 1H), 8.13 (AB quartet, 2H), 7.96 (d, 1H), 7.68 (d, 1H), 7.45 (t, 2H), 3.57 (q, 1H), 3.46 (t, 1H), 3.35 (t, 2H), 2.62 (t, 1H), 2.56 (s, 1H), 1.90 (quartet, 1H), 1.80 (quartet, 1H); ES-MS (m/z) 381 $[M+1]^+$.

Example 428

SYNTHESIS OF 3-{[3-(4-FLUOROPHENYL)(1H-INDAZOL-5-YL)]CARBONYLAMINO}-N-METHYL PROPANAMIDE

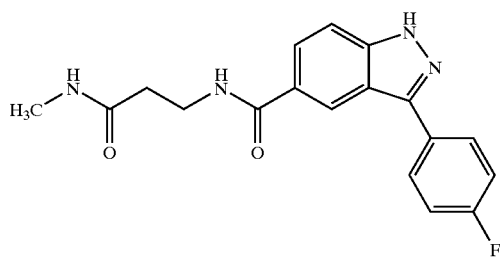

A. 3-{[3-(4-fluorophenyl)(1H-indazol-5-yl)]carbonylamino}-N-methyl propanamide

To a solution containing Example 88 (0.200 g, 0.611 mmol) in tetrahydrofuran (5 mL) was added 1-hydroxybenzotriazole hydrate (0.247 g, 1.83 mmol) followed by 1-(3-dimethylaminopropyl)-3-ethylcarbodiimide hydrochloride (0.351 g, 1.83 mmol), methyl amine (2 M in tetrahydrofuran; 0.915 mL, 1.83 mmol) and N,N-dimethylformamide (2 mL). The solution was stirred for 3 h at room temperature. Water (40 mL) was added and the reaction mixture was extracted with ethyl acetate. The combined organic layers were dried over anhydrous sodium sulfate, filtered and evaporated. The residue was purified by preparative HPLC (10–90% acetonitrile/water). The pure fractions were made basic with ammonium hydroxide, and the solution evaporated under reduced pressure, diluted with water and filtered to give the title compound (0.130 g, 63% yield): $^1$H NMR (DMSO-$d_6$) δ 13.45 (s, 1H), 8.68 (t, 1H), 8.53 (s, 1H), 8.07 (AB quartet, 2H), 7.90 (d, 1H), 7.84 (d, 1H), 7.62 (d, 1H), 7.39 (t, 2H), 3.49 (q, 1H), 3.33 (s, 3H), 2.57 (d, 1H), 2.50 (m, 1H), 2.38 (t, 1H); ES-MS (m/z) 341 $[M+1]^+$.

Example 429

SYNTHESIS OF 3-{[3-(4-FLUOROPHENYL)(1H-INDAZOL-5-YL)]CARBONYLAMINO}-N,N-DIMETHYL PROPANAMIDE

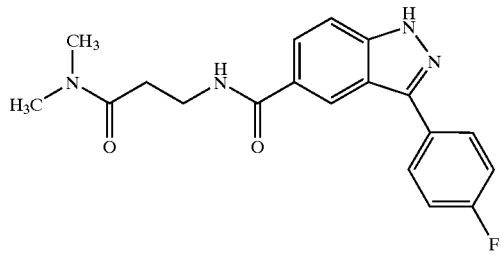

A. 3-{3-(4-Fluorophenyl)(1H-indazol-5-yl)]carbonylamino}-N,N-dimethyl propanamide To a solution containing Example 88 (0.200 g, 0.611 mmol) in tetrahydrofuran (5 mL) was added 1-hydroxybenzotriazole hydrate (0.247 g, 1.83 mmol) followed by 1-(3-dimethylaminopropyl)-3-ethylcarbodiimide hydrochloride (0.351 g, 1.83 mmol), dimethyl amine (2 M in tetrahydrofuran; 0.915 mL, 1.83 mmol) and N,N-dimethylfornamide (2 mL). The solution was stirred for 3 h at room temperature. Water (40 mL) was added and the reaction mixture was extracted with ethyl acetate. The combined organic layers were dried over anhydrous sodium sulfate, filtered and evaporated. The residue was purified by preparative HPLC (10–90% acetonitrile/water). The pure fractions were basified with ammonium hydroxide, evaporated at reduced pressure, diluted with water and filtered to give the title compound (0.140 g, 65% yield): $^1$H NMR (DMSO-$d_6$) δ 13.43 (s, 1H), 8.66 (t, 1H), 8.53 (s, 1H), 8.07 (AB quartet, 2H), 7.90 (d, 11–1), 7.62 (d, 1H), 7.40 (t, 2H), 3.50 (q, 2H), 2.97 (m, 3H), 2.83 (m, 3H), 2.61 (t, 2H); ES-MS (m/z) 355 $[M+1]^+$.

Example 430

SYNTHESIS OF 3-{[3-(4-FLUOROPHENYL)(1H-INDAZOL-5-YL)]CARBONYLAMINO}-N-(2-METHOXYETHYL)PROPANAMIDE

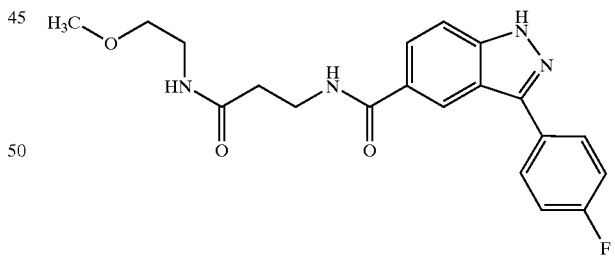

A. 3-{[3-(4-Fluorophenyl)(1H-indazol-5-yl)]carbonylamino}-N-(2-methoxyethyl)propanamide To a solution containing Example 88 (0.200 g, 0.611 mmol) in tetrahydrofuran (5 mL) was added 1-hydroxybenzotriazole hydrate (0.247 g, 1.83 mmol) followed by 1-(3-dimethylaminopropyl)-3-ethylcarbodiimide hydrochloride (0.351 g, 1.83 mmol), 2-methoxyethylamine (0.159 mL, 1.83 mmol) and N,N-dimethylformamide (2 mL). The solution was stirred for 3 h at room temperature. Water (40 mL) was added and the reaction mixture was extracted with ethyl acetate. The combined organic layers were dried over anhydrous sodium sulfate, filtered and evaporated. The residue was purified by preparative HPLC (10–90% acetonitrile/water). The pure fractions were basified with ammonium hydroxide, evaporated at reduced pressure, diluted with water and filtered which gave the title compound (0.143 g, 61% yield): $^1$H NMR (DMSO-$d_6$) δ 13.42 (s, 1H), 8.66 (t, 1H), 8.52 (s, 1H), 8.07 (AB quartet, 2H), 7.99 (t, 1H), 7.90 (d, 1H), 7.62 (d, 1H), 7.39 (t, 2H), 3.50 (q, 2H), 3.33 (s, 3H), 3.30 (m, 1H), 3.21 (m, 1H), 3.18 (d, 2H), 2.50 (m, 1H), 2.41 (t, 2H); ES-MS (m/z) 385 [M+1]$^+$.

Example 437

Assays for Measuring Activity of Compounds

The compounds of this invention may be assayed for their activity according to the following procedures.
JNK2 Assay To 10 μL of the test compound in 20% DMSO/80% dilution buffer consisting of 20 mM HEPES (pH 7.6), 0.1 mM EDTA, 2.5 mM magnesium chloride, 0.004% Triton x100, 2 μg/mL leupeptin, 20 mM β-glycerolphosphate, 0.1 mM sodium vanadate, and 2 mM DTT in water is added 30 μL of 50 ng His6-JNK2 in the same dilution buffer. The mixture is preincubated for 30 minutes at room temperature. Sixty microliter of 10 μg GST-c-Jun(1–79) in assay buffer consisting of 20 mM HEPES (pH 7.6), 50 mM sodium chloride, 0.1 mM EDTA, 24 mM magnesium chloride, 1 mM DTT, 25 mM PNPP, 0.05% Triton x100, 11 μM ATP, and 0.5 μCi γ-$^{32}$P ATP in water is added and the reaction is allowed to proceed for 1Hour at room temperature. The c-Jun phosphorylation is terminated by addition of 150 μL of 12.5% trichloroacetic acid. After 30 minutes, the precipitate is harvested onto a filter plate, diluted with 50 μL of the scintillation fluid and quantified by a counter. The $IC_{50}$ values are calculated as the concentration of the test compound at which the c-Jun phosphorylation is reduced to 50% of the control value. Preferred compounds of the present invention have an $IC_{50}$ value ranging 0.01–10 μM in this assay.
JNK3 Assay To 10 μL of the test compound in 20% DMSO/80% dilution buffer consisting of 20 mM HEPES (pH 7.6), 0.1 mM EDTA, 2.5 mM magnesium chloride, 0.004% Triton x100, 2 μg/mL leupeptin, 20 mM β-glycerolphosphate, 0.1 mM sodium vanadate, and 2 mM DTT in water is added 30 μL of 200 ng His6-JNK3 in the same dilution buffer. The mixture is preincubated for 30 minutes at room temperature. Sixty microliter of 10 pg GST-c-Jun(1–79) in assay buffer consisting of 20 mM HEPES (pH 7.6), 50 mM sodium chloride, 0.1 mM EDTA, 24 mM magnesium chloride, 1 mM DTT, 25 mM PNPP, 0.05% Triton x100, 11 μM ATP, and 0.5 μCi γ-$^{32}$P ATP in water is added and the reaction is allowed to proceed for 1Hour at room temperature. The c-Jun phosphorylation is terminated by addition of 150 μL of 12.5% trichloroacetic acid. After 30 minutes, the precipitate is harvested onto a filter plate, diluted with 50 μL of the scintillation fluid and quantified by a counter. The $IC_{50}$ values are calculated as the concentration of the test compound at which the c-Jun phosphorylation is reduced to 50% of the control value. Preferred compounds of the present invention have an $IC_{50}$ value ranging 0.01–10 μM in this assay.
Jurkat T-Cell Il-2 Production Assay Jurkat T cells (clone E6-1) are purchased from the American Tissue Culture Collection and maintained in growth media consisting of RPMI 1640 medium containing 2 mM L-glutamine (Mediatech), with 10% fetal bovine serum (Hyclone) and penicillin/streptomycin. All cells are cultured at 37° C. in 95% air and 5% $CO_2$. Cells are plated at a density of 0.2×10$^6$ cells per well in 200 μL of media. Compound stock (20 mM) is diluted in growth media and added to each well as a 10× concentrated solution in a volume of 25 μL, mixed, and allowed to pre-incubate with cells for 30 minutes. The compound vehicle (dimethylsulfoxide) is maintained at a final concentration of 0.5% in all samples. After 30 minutes the cells are activated with PHA (phorbol myristate acetate; final concentration 50 μg/mL) and PHA (phytohemagglutinin; final concentration 2 μg/mL). PMA and PHA are added as a 10× concentrated solution made up in growth media and added in a volume of 25 μL per well. Cell plates are cultured for 10 hours. Cells are pelleted by centrifugation and the media removed and stored at −20° C. Media aliquots are analyzed by sandwich ELISA for the presence of IL-2 as per the manufacturers instructions (Endogen). The $IC_{50}$ values are calculated as the concentration of the test compound at which the Il-2 production was reduced to 50% of the control value. Preferred compounds of the present invention have an $IC_{50}$ value ranging 0.1–30 μM in this assay.
Rat in Vivo LPS-Induced TNF-α Production Assay Male CD rats procured from Charles River Laboratories at 7 weeks of age were allowed to acclimate for one week prior to use. A lateral tail vein was cannulated percutaneously with a 22-gage over-the-needle catheter under brief isoflurane anesthesia. Rats were administered test compound either by intravenous injection via the tail vein catheter or oral gavage 15 to 180 min prior to injection of 0.05 mg/kg LPS (E. coli 055:BS). Catheters were flushed with 2.5 mL/kg of normal injectable saline. Blood was collected via cardiac puncture 90 minutes after LPS challenge. Plasma was prepared using lithium heparin separation tubes and frozen at −80° C. until analyzed. TNF-α levels were determined using a rat specific TNF-α ELISA kit (Biosource). The $ED_{50}$ values are calculated as the dose of the test compound at which the TNF-α production is reduced to 50% of the control value. Preferred compounds of the present invention have an $ED_{50}$ value ranging 1–30 mg/kg in this assay.

Example 438

Activity of Representative Compounds

Representative compounds of this invention were assayed for their ability to inhibit, for example, JNK2 by the assays set forth in Example 437. As noted above, preferred compounds of this invention have an $IC_{50}$ value ranging 0.01–10 μM in the above assays.

To this end, compounds having an $IC_{50}$ value in the JNK2 assay of 10 μM or less include the compounds of Examples 5–8, 10–14, 16–23, 25–28, 34–39, 42–44, 45–46, 49–55, 57, 59, 61–122, 124, 127–129, 131, 134–136, 139–142, 144–187, 189–220, 222–233, 235–249, 251–269, 271, 274, 278, 280–314, 316–355, 357–361, 363–399, 404–405, 407–420 and 422–426.

Preferred compounds of this invention have an $IC_{50}$ value in the JNK2 assay of 1 μM or less, and include the compounds of Examples 6, 11, 13–14, 16–20, 38, 44–45, 50–55, 57, 59, 61–63, 65, 68–74, 80–81, 84–85, 87–97, 99, 101, 105–107, 109–122, 124, 127–129, 131, 140, 147, 149–151, 153–155, 157–162, 164–187, 189–220, 222–233, 236–248, 251–258, 260–269, 271, 274–278, 280–314, 316–355, 357–361, 363–399, 404–405, 407–420 and 422–426.

More preferred compounds of this invention have an $IC_{50}$ value in the JNK2 assay of 0.5 μM or less, and include the compounds of Examples 69, 70, 118–119,162, 164, 166, 167–171, 173–176, 178, 199, 207–209, 211, 215–216, 219–220, 222, 224–226, 229–231, 236–237, 246, 253, 257–258, 260–263, 266–268, 271, 275, 285–286, 289, 292, 295–297, 299, 301, 306, 308–311, 314, 316–320, 327–335, 337, 340, 342, 353, 357–361, 363, 365, 367–372, 381–384, 386–399, 412, 414, 417–419, 422 and 424–425.

It will be appreciated that, although specific embodiments of the invention have been described herein for purposes of illustration, various modifications may be made without departing from the spirit and scope of the invention. Such modifications are intended to fall within the scope of the appended claims.

A number of references have been cited, the entire disclosures of which are incorporated herein by reference.

What is claimed is:

1. A compound having the structure:

or a pharmaceutically acceptable salt thereof, wherein:

A is —$(CH_2)_bC\equiv C(CH_2)_c$—;

$R_1$ is aryl, heteroaryl or heterocycle fused to phenyl, each being optionally substituted with one to four substituents independently selected from $R_3$;

$R_2$ is —$R_3$, —$R_4$, —$(CH_2)_bC(=O)R_5$, —$(CH_2)_bC(=O)OR_5$, —$(CH_2)_bC(=O)NR_5R_6$, —$(CH_2)_bC(=O)NR_5(CH_2)_cC(=O)R_6$, —$(CH_2)_bNR_5C(=O)R_6$, —$(CH_2)_bNR_5C(=O)NR_6R_7$, —$(CH_2)_bNR_5R_6$, —$(CH_2)_bOR_5$, —$(CH_2)_bSO_dR_5$ or —$(CH_2)_bSO2NR_5R_6$;

b and c are the same or different and at each occurrence independently selected from 0, 1, 2, 3 or 4;

d is at each occurrence 0, 1 or 2;

$R_3$ is at each occurrence independently halogen, hydroxy, carboxy, alkyl, alkoxy, haloalkyl, acyloxy, thioalkyl, sulfinylalkyl, sulfonylalkyl, hydroxyalkyl, aryl, substituted aryl, arylalkyl, substituted arylalkyl, heterocycle, substituted heterocycle, heterocyclealkyl, substituted heterocyclealkyl, —$C(=O)OR_8$, —$C(O)R_8$, —$C(O)NR_8R_9$, —$C(=O)NR_8OR_9$, —$SO_2NR_8R_9$, —$NR_8SO_2R_9$, —CN, —$NO_2$, —$NR_8R_9$, —$NR_8C(=O)R_9$, —$NR_8C(=O)(CH_2)_bOR_9$, —$NR_8C(=O)(CH_2)_bR_9$, —$O(CH_2)_bNR_8R_9$, or heterocycle fused to phenyl;

$R_4$ is alkyl, aryl, arylalkyl, heterocycle or heterocyclealkyl, each being optionally substituted with one to four substituents independently selected from $R_3$, or $R_4$ is halogen or hydroxy;

$R_5$, $R_6$ and $R_7$ are the same or different and at each occurrence independently hydrogen, alkyl, aryl, arylalkyl, heterocycle or heterocyclealkyl, wherein each of $R_5$, $R_6$ and $R_7$ are optionally substituted with one to four substituents independently selected from $R_3$; and $R_8$ and $R_9$ are the same or different and at each occurrence independently hydrogen, alkyl, aryl, arylalkyl, heterocycle, or heterocyclealkyl, or $R_8$ and $R_9$ taken together with the atom or atoms to which they are bonded form a heterocycle, wherein each of $R_8$, $R_9$, and $R_8$ and $R_9$ taken together to form a heterocycle are optionally substituted with one to four substituents independently selected from $R_3$.

2. A compound having the structure:

or a pharmaceutically acceptable salt thereof, wherein:

A is a direct bond, —$(CH_2)_a$—, —$(CH_2)_bCH=CH(CH_2)_c$—, or —$(CH_2)_bC\equiv C(CH_2)_c$—;

$R_1$ is aryl, heteroaryl or heterocycle fused to phenyl, each being optionally substituted with one to four substituents independently selected from $R_3$;

$R_2$ is —$(CH_2)_bC(=O)R_5$;

a is 1, 2, 3, 4, 5 or 6;

b and c are the same or different and at each occurrence independently selected from 0, 1, 2, 3 or 4;

$R_3$ is at each occurrence independently halogen, hydroxy, carboxy, alkyl, alkoxy, haloalkyl, acyloxy, thioalkyl, sulfinylalkyl, sulfonylalkyl, hydroxyalkyl, aryl, substituted aryl, arylalkyl, substituted arylalkyl, heterocycle, substituted heterocycle, heterocyclealkyl, substituted heterocyclealkyl, —$C(=O)OR_8$, —$C(=O)R_8$, —$C(O)NR_8R_9$, —$C(=O)NR_8OR_9$, —$SO_2NR_8R_9$, —$NR_8SO_2R_9$, —CN, —$NO_2$, —$NR_8R_9$, —$NR_8C(=O)R_9$, —$NR_8C(=O)(CH_2)_bOR_9$, —$NR_8C(=O)(CH_2)_bR_9$, —$O(CH_2)_bNR_8R_9$, or heterocycle fused to phenyl;

$R_5$, $R_6$ and $R_7$ are the same or different and at each occurrence independently alkyl, aryl, arylalkyl, heterocycle or heterocyclealkyl, wherein each of $R_5$, $R_6$ and $R_7$ are optionally substituted with one to four substituents independently selected from $R_3$; and $R_8$ and $R_9$ are the same or different and at each occurrence independently hydrogen, alkyl, aryl, arylalkyl, heterocycle, or heterocyclealkyl, or $R_8$ and $R_9$ taken together with the atom or atoms to which they are bonded form a heterocycle, wherein each of $R_8$, $R_9$, and $R_8$ and $R_9$ taken together to form a heterocycle are optionally substituted with one to four substituents independently selected from $R_3$.

3. A compound having the structure:

or a pharmaceutically acceptable salt thereof, wherein:

A is a direct bond, —$(CH_2)_a$—, —$(CH_2)_bCH=CH(CH_2)_c$—, or —$(CH_2)_bC\equiv C(CH_2)_c$—;

$R_1$ is aryl, heteroaryl or heterocycle fused to phenyl, each being optionally substituted with one to four substituents independently selected from $R_3$;

$R_2$ is —$(CH_2)_bC(=O)NR_5R_6$;

a is 1, 2, 3, 4, 5 or 6;

b and c are the same or different and at each occurrence independently selected from 0, 1, 2, 3 or 4;

$R_3$ is at each occurrence independently halogen, hydroxy, carboxy, alkyl, alkoxy, haloalkyl, acyloxy, thioalkyl, sulfinylalkyl, sulfonylalkyl, hydroxyalkyl, aryl, substituted aryl, arylalkyl, substituted arylalkyl, heterocycle, substituted heterocycle, heterocyclealkyl, substituted heterocyclealkyl, —C(=O)OR$_8$, —C(=O)R$_8$, —C(O)NR$_8$R$_9$, —C(=O)NR$_8$OR$_9$, —SO$_2$NR$_8$R$_9$, —NR$_8$SO$_2$R$_9$, —CN, —NO$_2$, —NR$_8$R$_9$, —NR$_8$C(=O)R$_9$, —NR$_8$C(=O)(CH$_2$)$_b$OR$_9$, —NR$_8$C(=O)(CH$_2$)$_b$R$_9$, —O(CH$_2$)$_b$NR$_8$R$_9$, or heterocycle fused to phenyl;

$R_5$, $R_6$ and $R_7$ are the same or different and at each occurrence independently hydrogen, alkyl, aryl, arylalkyl, heterocycle or heterocyclealkyl, wherein each of $R_5$, $R_6$ and $R_7$ are optionally substituted with one to four substituents independently selected from $R_3$; and $R_8$ and $R_9$ are the same or different and at each occurrence independently hydrogen, alkyl, aryl, arylalkyl, heterocycle, or heterocyclealkyl, or $R_8$ and $R_9$ taken together with the atom or atoms to which they are bonded form a heterocycle, wherein each of $R_8$, $R_9$, and $R_8$ and $R_9$ taken together to form a heterocycle are optionally substituted with one to four substituents independently selected from $R_3$.

4. A compound having the structure:

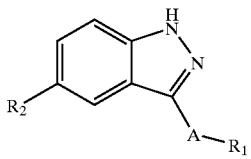

or a pharmaceutically acceptable salt thereof, wherein:
A is a direct bond, —(CH$_2$)$_a$—, —(CH$_2$)$_b$CH=CH(CH$_2$)$_c$—, or —(CH$_2$)$_b$C≡C(CH$_2$)$_c$—;

$R_1$ is aryl, heteroaryl or heterocycle fused to phenyl, each being optionally substituted with one to four substituents independently selected from $R_3$;

$R_2$ is —(CH$_2$)$_b$NR$_5$C(=O)R$_6$;

a is 1, 2, 3, 4, 5 or 6;

b and c are the same or different and at each occurrence independently selected from 0, 1, 2, 3 or 4;

$R_3$ is at each occurrence independently halogen, hydroxy, carboxy, alkyl, alkoxy, haloalkyl, acyloxy, thioalkyl, sulfinylalkyl, sulfonylalkyl, hydroxyalkyl, aryl, substituted aryl, arylalkyl, substituted arylalkyl, heterocycle, substituted heterocycle, heterocyclealkyl, substituted heterocyclealkyl, —C(O)OR$_8$, —C(=O)R$_8$, —C(O)NR$_8$R$_9$, —C(=O)NR$_8$OR$_9$, —SO$_2$NR$_8$R$_9$, —NR$_8$SO$_2$R$_9$, —CN, —NO$_2$, —NR$_8$R$_9$, —NR$_8$C(=O)R$_9$, —NR$_8$C(=O)(CH$_2$)$_b$OR$_9$, —NR$_8$C(=O)(CH$_2$)$_b$R$_9$, —O(CH$_2$)$_b$NR$_8$R$_9$, or heterocycle fused to phenyl;

$R_5$, $R_6$ and $R_7$ are the same or different and at each occurrence independently hydrogen, alkyl, aryl, arylalkyl, heterocycle or heterocyclealkyl, wherein each of $R_5$, $R_6$ and $R_7$ are optionally substituted with one to four substituents independently selected from $R_3$; and $R_8$ and $R_9$ are the same or different and at each occurrence independently hydrogen, alkyl, aryl, arylalkyl, heterocycle, or heterocyclealkyl, or $R_8$ and $R_9$ taken together with the atom or atoms to which they are bonded form a heterocycle, wherein each of $R_8$, $R_9$, and $R_8$ and $R_9$ taken together to form a heterocycle are optionally substituted with one to four substituents independently selected from $R_3$.

5. A compound having the structure:

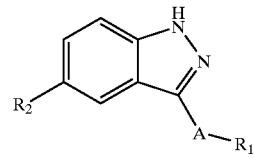

or a pharmaceutically acceptable salt thereof, wherein:

A is a direct bond, —(CH$_2$)$_a$—, —(CH$_2$)$_b$CH=CH(CH$_2$)$_c$—, or —(CH$_2$)$_b$C≡C(CH$_2$)$_c$—;

$R_1$ is aryl, heteroaryl or heterocycle fused to phenyl, each being optionally substituted with one to four substituents independently selected from $R_3$;

$R_2$ is $R_4$;

a is 1, 2, 3, 4, 5 or 6;

b and c are the same or different and at each occurrence independently selected from 0, 1, 2, 3 or 4;

$R_3$ is at each occurrence independently halogen, hydroxy, carboxy, alkyl, alkoxy, haloalkyl, acyloxy, thioalkyl, sulfinylalkyl, sulfonylalkyl, hydroxyalkyl, aryl, substituted aryl, arylalkyl, substituted arylalkyl, heterocycle, substituted heterocycle, heterocyclealkyl, substituted heterocyclealkyl, —C(=O)OR$_8$, —C(=O)R$_8$, —C(O)NR$_8$R$_9$, —C(=O)NR$_8$OR$_9$, —SO$_2$NR$_8$R$_9$, —NR$_8$SO$_2$R$_9$, —CN, —NO$_2$, —NR$_8$R$_9$, —NR$_8$C(=O)R$_9$, —NR$_8$C(=O)(CH$_2$)$_b$OR$_9$, —NR$_8$C(=O)(CH$_2$)$_b$R$_9$, —O(CH$_2$)$_b$NR$_8$R$_9$, or heterocycle fused to phenyl;

$R_4$ is 3-triazolyl, optionally substituted at its 5-position with:

(a) a $C_1$–$C_4$ straight or branched chain alkyl group optionally substituted with a hydroxyl, methylamino, dimethylamino or 1-pyrrolidinyl group; or (b) a 2-pyrrolidinyl group;

$R_5$, $R_6$ and $R_7$ are the same or different and at each occurrence independently hydrogen, alkyl, aryl, arylalkyl, heterocycle or heterocyclealkyl, wherein each of $R_5$, $R_6$ and $R_7$ are optionally substituted with one to four substituents independently selected from $R_3$; and $R_8$ and $R_9$ are the same or different and at each occurrence independently hydrogen, alkyl, aryl, arylalkyl, heterocycle, or heterocyclealkyl, or $R_8$ and $R_9$taken together with the atom or atoms to which they are bonded form a heterocycle, wherein each of $R_8$, $R_9$, and $R_8$ and $R_9$ taken together to form a heterocycle are optionally substituted with one to four substituents independently selected from $R_3$.

6. A compound having the structure:

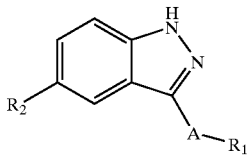

or a pharmaceutically acceptable salt thereof, wherein:

A is a direct bond, —(CH$_2$)$_a$—, —(CH$_2$)$_b$CH=CH(CH$_2$)$_c$—, or —(CH$_2$)$_b$C≡C(CH$_2$)$_c$—;

R$_1$ is aryl, heteroaryl or heterocycle fused to phenyl, each being optionally substituted with one to four substituents independently selected from R$_3$;

R$_2$ is R$_4$;

a is 1, 2, 3, 4, 5 or 6;

b and c are the same or different and at each occurrence independently selected from 0, 1, 2, 3 or 4;

R$_3$ is at each occurrence independently halogen, hydroxy, carboxy, alkyl, alkoxy, haloalkyl, acyloxy, thioalkyl, sulfinylalkyl, sulfonylalkyl, hydroxyalkyl, aryl, substituted aryl, arylalkyl, substituted arylalkyl, heterocycle, substituted heterocycle, heterocyclealkyl, substituted heterocyclealkyl, —C(=O)OR$_8$, —C(=O)R$_8$, —C(O)NR$_8$R$_9$, —C(=O)NR$_8$OR$_9$, —SO$_2$NR$_8$R$_9$, —NR$_8$SO$_2$R$_9$, —CN, —NO$_2$, —NR$_8$R$_9$, —NR$_8$C(=O)R$_9$, —NR$_8$C(=O)(CH$_2$)$_b$OR$_9$, —NR$_8$C(=O)(CH$_2$)$_b$R$_9$, —O(CH$_2$)$_b$NR$_8$R$_9$, or heterocycle fused to phenyl;

R$_4$ is tetrazole;

R$_5$, R$_6$ and R$_7$ are the same or different and at each occurrence independently hydrogen, alkyl, aryl, arylalkyl, heterocycle or heterocyclealkyl, wherein each of R$_5$, R$_6$ and R$_7$ are optionally substituted with one to four substituents independently selected from R$_3$; and R$_8$ and R$_9$ are the same or different and at each occurrence independently hydrogen, alkyl, aryl, arylalkyl, heterocycle, or heterocyclealkyl, or R$_8$ and R$_9$ taken together with the atom or atoms to which they are bonded form a heterocycle, wherein each of R$_8$, R$_9$, and R$_8$ and R$_9$ taken together to form a heterocycle are optionally substituted with one to four substituents independently selected from R$_3$.

7. A compound having the structure:

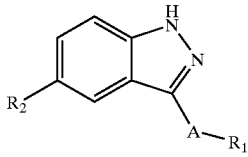

or a pharmaceutically acceptable salt thereof, wherein:

A is a direct bond, —(OH$_2$)$_a$—, —(CH$_2$)$_b$CH=CH(CH$_2$)$_c$—, or —(CH$_2$)$_b$C≡C(CH$_2$)$_c$—;

R$_1$ is aryl, heteroaryl or heterocycle fused to phenyl, each being optionally substituted with one to four substituents independently selected from R$_3$;

R$_2$ is R$_4$, a is 1, 2, 3, 4, 5 or 6;

b and c are the same or different and at each occurrence independently selected from 0, 1, 2, 3 or 4;

R$_3$ is at each occurrence independently halogen, hydroxy, carboxy, alkyl, alkoxy, haloalkyl, acyloxy, thioalkyl, sulfinylalkyl, sulfonylalkyl, hydroxyalkyl, aryl, substituted aryl, arylalkyl, substituted arylalkyl, heterocycle, substituted heterocycle, heterocyclealkyl, substituted heterocyclealkyl, —C(=O)OR$_8$, —O(=O)R$_8$, —C(O)NR$_8$R$_9$, —C(=O)NR$_8$OR$_9$, —SO$_2$NR$_8$R$_9$, —NR$_8$SO$_2$R$_9$, —CN, —NO$_2$, —NR$_8$R$_9$, —NR$_8$C(=O)R$_9$, —NR$_8$C(=O)(CH$_2$)$_b$OR$_9$, —NR$_8$C(=O)(CH$_2$)$_b$R$_9$, —O(CH$_2$)$_b$NR$_8$R$_9$, or heterocycle fused to phenyl;

R$_4$ is imidazole;

R$_5$, R$_6$ and R$_7$ are the same or different and at each occurrence independently hydrogen, alkyl, aryl, arylalkyl, heterocycle or heterocyclealkyl, wherein each of R$_8$, R$_6$ and R$_7$ are optionally substituted with one to four substituents independently selected from R$_3$; and R$_8$ and R$_9$ are the same or different and at each occurrence independently hydrogen, alkyl, aryl, arylalkyl, heterocycle, or heterocyclealkyl, or R$_8$ and R$_9$ taken together with the atom or atoms to which they are bonded form a heterocycle, wherein each of R$_8$, R$_9$, and R$_8$ and R$_9$ taken together to form a heterocycle are optionally substituted with one to four substituents independently selected from R$_3$.

8. A compound having the structure:

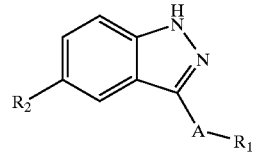

or a pharmaceutically acceptable salt thereof, wherein:

—A—R$_1$ is phenyl, optionally substituted with one to four substituents independently selected from halogen, alkoxy, —NR$_8$C(=O)R$_9$, —C(=O)NR$_8$R$_9$, and —O(CH$_2$)$_b$NR$_8$R$_9$;

R$_2$ is 3-triazolyl or 5-tetrazolyl;

a is 1, 2, 3, 4, 5 or 6;

b is 2 or 3;

c is at each occurrence 0, 1, 2, 3 or 4;

R$_3$ is at each occurrence independently halogen, hydroxy, carboxy, alkyl, alkoxy, haloalkyl, acyloxy, thioalkyl, sulfinylalkyl, sulfonylalkyl, hydroxyalkyl, aryl, substituted aryl, arylalkyl, substituted arylalkyl, heterocycle, substituted heterocycle, heterocyclealkyl, substituted heterocyclealkyl, —C(=O)OR$_8$, —C(=O)R$_8$, —C(O)NR$_8$R$_9$, —C(=O)NR$_8$OR$_9$, —SO$_2$NR$_8$R$_9$, —NR$_8$SO$_2$R$_9$, —CN, —NO$_2$, —NR$_8$R$_9$, —NR$_8$C(=O)R$_9$, —NR$_8$C(=O)(CH$_2$)$_b$OR$_9$, —NR$_8$C(=O)(CH$_2$)$_b$R$_9$, —O(CH$_2$)$_b$NR$_8$R$_9$, or heterocycle fused to phenyl;

R$_5$, R$_6$ and R$_7$ are the same or different and at each occurrence independently hydrogen, alkyl, aryl, arylalkyl, heterocycle or heterocyclealkyl, wherein each of R$_5$, R$_6$ and R$_7$ are optionally substituted with one to four substituents independently selected from R$_3$; and R$_8$ and R$_9$ are the same or different and at each occurrence independently hydrogen, alkyl, aryl, arylalkyl, heterocycle, or heterocyclealkyl, or $R_8$ and $R_9$ taken together with the atom or atoms to which they are bonded form a heterocycle, wherein each of $R_8$, $R_9$, and $R_8$ and $R_9$ taken together to form a heterocycle are optionally substituted with one to four substituents independently selected from $R_3$.

9. A compound having the structure:

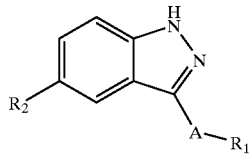

or a pharmaceutically acceptable salt thereof, wherein:
A is a direct bond, $-(CH_2)_a-$, $-(CH_2)_b CH=CH(CH_2)_c-$, or $-(CH_2)_b C\equiv C(CH_2)_c-$;

$R_1$ is aryl, heteroaryl or heterocycle fused to phenyl, each being optionally substituted with one to four substituents independently selected from $R_3$;

$R_2$ is $R_4$;

a is 1, 2, 3, 4, 5 or 6;

b and c are the same or different and at each occurrence independently selected from 0, 1, 2, 3 or 4;

$R_3$ is at each occurrence independently halogen, hydroxy, carboxy, alkyl, alkoxy, haloalkyl, acyloxy, thioalkyl, sulfinylalkyl, sulfonylalkyl, hydroxyalkyl, aryl, substituted aryl, arylalkyl, substituted arylalkyl, heterocycle, substituted heterocycle, heterocyclealkyl, substituted heterocyclealkyl, $-C(=O)OR_8$, $-C(=O)R_8$, $-C(O)NR_8R_9$, $-C(=O)NR_8OR_9$, $-SO_2NR_8R_9$, $-NR_8SO_2R_9$, $-CN$, $-NO_2$, $-NR_8R_9$, $-NR_8C(=O)R_9$, $-NR_8C(=O)(CH_2)_bOR_9$, $-NR_8C(=O)(CH_2)_bR_9$, $-O(CH_2)_bNR_8R_9$, or heterocycle fused to phenyl;

$R_4$ is 3-triazolyl, optionally substituted at its 5-position with:
(a) methyl, n-propyl, isopropyl, 1-hydroxyethyl, 3-hydroxypropyl, methylaminomethyl, dimethylaminomethyl, 1-(dimethylamino)ethyl, 1-pyrrolidinylmethyl or 2-pyrrolidinyl;

$R_5$, $R_6$ and $R_7$ are the same or different and at each occurrence independently hydrogen, alkyl, aryl, arylalkyl, heterocycle or heterocyclealkyl, wherein each of $R_5$, $R_6$ and $R_7$ are optionally substituted with one to four substituents independently selected from $R_3$; and $R_8$ and $R_9$ are the same or different and at each occurrence independently hydrogen, alkyl, aryl, arylalkyl, heterocycle, or heterocyclealkyl, or $R_8$ and $R_9$ taken together with the atom or atoms to which they are bonded form a heterocycle, wherein each of $R_8$, $R_9$, and $R_8$ and $R_9$ taken together to form a heterocycle are optionally substituted with one to four substituents independently selected from $R_3$.

10. A composition comprising the compound of claim 1 and a pharmaceutically acceptable carrier.

11. A composition comprising the compound of claim 2 and a pharmaceutically acceptable carrier.

12. A composition comprising the compound of claim 3 and a pharmaceutically acceptable carrier.

13. A composition comprising the compound of claim 4 and a pharmaceutically acceptable carrier.

14. A composition comprising the compound of claim 5 and a pharmaceutically acceptable carrier.

15. A composition comprising the compound of claim 6 and a pharmaceutically acceptable carrier.

16. A composition comprising the compound of claim 7 and a pharmaceutically acceptable carrier.

17. A composition comprising the compound of claim 8 and a pharmaceutically acceptable carrier.

18. A composition comprising the compound of claim 9 and a pharmaceutically acceptable carrier.

19. A compound of claim 1, wherein the compound is:
3-(2-phenylethynyl)-1H-indazole-5-carboxamide, or a pharmaceutically acceptable salt thereof.

20. A compound of claim 2, wherein the compound is:
1-{(3-(4-fluorophenyl)-1H-indazol-5-yl)carbonyl}piperidine-4-carboxylic acid;
3-(4-fluorophenyl)(1H-indazol-5-yl)pyrrolidinyl ketone;
3-(4-fluorophenyl)(1H-indazol-5-yl)piperazinyl ketone;
1-(3-(4-fluorophenyl)-1H-indazol-5-yl)-2-phenylethan-1-one;
1-(3-(4-fluorophenyl)-1H-indazol-5-yl)ethan-1-one; or a pharmaceutically acceptable salt thereof.

21. A compound of claim 3, wherein the compound is:
3-(4-fluorophenyl)-1H-indazole-5-carboxamide;
(3-(4-fluorophenyl)(1H-indazol-5-yl))-N-benzamide;
N-(2-(dimethylamino)ethyl)3-(4-fluorophenyl)(1H-indazol-5-yl))carboxamide;
methyl 4-{(3-(4-fluorophenyl)-1H-indazol-5-yl)carbonylamino}benzoate;
4-{3-(4-fluorophenyl)-1H-indazol-5-yl)carbonylamino}benzoic acid;
4-{(3-(4-fluorophenyl)-1H-indazole-5-yl)carbonylamino}benzamide;
(3-(4-fluorophenyl)(1H-indazol-5-yl))-N-(2-pyridyl)carboxamide;
(3-(4-fluorophenyl)(1H-indazol-5-yl))-N-(3-pyridyl)carboxamide;
(3-(4-fluorophenyl)(1H-indazol-5-yl))-N-(4-pyridyl)carboxamide;
tert-butyl 3-{(3-(4-fluorophenyl)-1H-indazol-5-yl)carbonylamino)propanoate;
(3-(4-fluorophenyl)(1H-indazol-5-yl))-N-(3-hydroxyphenyl)carboxamide;
3-{(3-(4-fluorophenyl)-1H-indazol-5-yl)carbonylamino)propanoic acid;
(3-(4-fluorophenyl)(1H-indazol-5-yl))-N-(3-nitrophenyl)carboxamide;
tert-butyl-2-{(3-(4-fluorophenyl)-1H-indazol-5-yl)carbonylamino}acetate;
4-{(3-(4-fluorophenyl)-1H-indazol-5-yl)carbonylamino}butanoic acid;
N-(3-aminophenyl)(3-(4-fluorophenyl)(1H-indazol-5-yl))carboxamide;
2-{(3-(4-fluorophenyl)-1H-indazol-5-yl)carbonylamino}acetic acid;
5-{(3-(4-fluorophenyl)-1H-indazol-5-yl)carbonylamino}pentanoic acid;
4-({(3-(4-fluorophenyl)-1H-indazol-5-yl)carbonylamino}methyl)benzoic acid;
(3-(4-fluorophenyl)(1H-indazol-5-yl))-N-(4-pyridylmethyl)carboxamide;
2-(4-{(3-(4-fluorophenyl)-1H-indazol-5-yl)carbonylamino}phenyl)acetic acid;
(3-(4-fluorophenyl)(1H-indazol-5-yl))-N,N-dimethylcarboxamide;

(3-(4-fluorophenyl)(1H-indazol-5-yl))-N-methylcarboxamide;
N-(3-aminoethyl)(3-(4-fluorophenyl)(1H-indazol-5-yl))carboxamide;
N-(3-aminopropyl)(3-(4-fluorophenyl)(1H-indazol-5-yl))carboxamide;
(3-(4-fluorophenyl)(1H-indazol-5-yl))-N-(2-hydroxypropyl)carboxamide;
N-(2H-1,2,3,4-tetrazol-5-yl)(3-(4-fluorophenyl)(1H-indazol-5-yl))carboxamide;
{3-(4-fluorophenyl)(1H-indazol-5-yl)}-N-(3-morpholin-4-ylpropyl)carboxamide;
(3-(4-fluorophenyl)(1H-indazol-5-yl)}-N-(3-pyridylmethyl)carboxamide;
N-(((2R)-2-hydroxycyclohexyl)methyl)(3-(4-fluorophenyl)(1H-indazole-5-yl)carboxamide
(3-(4-fluorophenyl)(1H-indazol-5-yl))-N-(2-(1-methylimidazol-5-yl)ethyl)carboxamide);
(3-(4-fluorophenyl)(1H-indazol-5-yl))-N-(2-pyridylmethyl)carboxamide
N-(2-carbamoylethyl)(3-(4-fluorophenyl)(1H-indazol-5-yl))carboxamide;
N-(3-carbamoylpropyl)(3-(4-fluorophenyl)(1H-indazol-5-yl))carboxamide;
3-(4-methoxyphenyl)-1H-indazole-5-carboxamide;
3-(4-hydroxyphenyl)-1H-indazole-5-carboxamide;
3-(2-naphthyl)-1H-indazole-5-carboxamide;
3-benzo(b)thiophen-2-yl-1H-indazole-5-carboxamide;
3-benzo(d)furan-2-yl-1H-indazole-5-caxboxamide;
3-(3-(methylethyl)phenyl)-1H-indazole-5-carboxamide;
3-(4-(dimethylamino)phenyl)-1H-indazole-5-carboxamide;
3-(3-furyl)-1H-indazole-5-carboxamide;
3-{4-(2-(dimethylamino)ethoxy)phenyl}-1H-indazole-5-carboxamide;
3-(3,4-dimethoxyphenyl)-1H-indazole-5-carboxamide;
3-(3-aminophenyl)-1H-indazole-5-carboxamide;
3-(2H-benzo(d)1,3-dioxolen-5-yl)-1H-indazole-5-carboxamide;
(3-benzo(d)furan-2-yl(1H-indazol-5-yl))-N-(methylethyl)carboxamide;
(3-benzo(d)furan-2-yl(1H-indazol-5-yl))-N-(2-methoxyethyl)carboxamide;
(3-benzo(d)furan-2-yl(1H-indazol-5-yl))-N-(2-(dimethylamino)ethyl)carboxamide;
(3-benzo(d)furan-2-yl(1H-indazol-5-yl))-N-(4-(dimethylamino)butyl)carboxamide;
(3-benzo(d)furan-2-yl(1H-indazol-5-yl))-N-(3-(dimethylamino)propyl)carboxamide;
(3-benzo(d)furan-2-yl(1H-indazol-5-yl))-N-(2-methylpropyl)carboxamide;
(3-benzo(d)furan-2-yl(1H-indazol-5-yl))-N-methylcarboxamide;
3-(3-(3-pyridylcarbonylamino)phenyl)-1H-indazole-5-carboxamide;
3-(3-(2-methoxyacetylamino)phenyl)-1H-indazole-5-carboxamide;
3-(3-(4-pipendylcarboxyamino)phenyl)-1H-indazole-5-carboxamide;
(1S)-1-{N-(3-(5-carbamoyl(1H-indazol-3-yl))phenyl)carbamoyl}ethyl acetate;
3-{3-(2-methoxyethyl)amino)phenyl}-1H-indazole-5-carboxamide;
3-(3-(3-piperidylpropanoylamino)phenyl)-1H-indazole-5-carboxamide;
3-(3-(2-furylcarbonylamino)phenyl)-1H-indazole-5-carboxamide;
3-{3-(2-(dimethylamino)acetylamino)phenyl}-1H-indazole-5-carboxamide;
3-(3-(2-phenylacetylamino)phenyl)-1H-indazole-5-carboxamide;
3-{3-(2-(4-methoxyphenyl)acetylamino)phenyl}-1H-indazole-5-carboxamide;
3-{3-(2-(2-methyl-1,3-thiazol-5-yl)acetylamino)phenyl}-1H-indazole-5-carboxamide;
3-(3-(oxolan-3yl-carbonylamino)phenyl)-1H-indazole-5-carboxamide;
3-(3-(2-(3-thienyl)acetylamino)phenyl)-1H-indazole-5-carboxamide;
3-(3-(2-thienylcarbonylamino)phenyl)-1H-indazole-5-carboxamide;
3-(3-(2-(4-pyridyl)acetylamino)phenyl)-1H-indazole-5-carboxamide;
3-(3-(2-(2-pyridyl)acetylamino)phenyl)-1H-indazole-5-carboxamide;
3-{3-(2-(4-fluorophenyl)acetylamino)phenyl}-1H-indazole-5-carboxamide;
3-(3-(cyclopropylcarbonylamino)phenyl-1H-indazole-5-carboxamide;
3-{3-((3-hydroxyphenyl)carbonylamino)phenyl}-1H-indazole-5-carboxamide;
3-{3-(2-(2,4-dichlorophenyl)acetylamino)phenyl}-1H-indazole-5-carboxamide;
3-(3-{2-(4-(trifluoromethyl)phenyl)acetylamino}phenyl)-1H-indazole-5-carboxamide;
3-(3-{2-(4-(dimethylamino)phenyl)acetylamino}phenyl)-1H-indazole-5-carboxamide;
3-{3-(2-(2-chloro-4-fluorophenyl)acetylamino)phenyl}-1H-indazole-5-carboxamide;
3-{3-(2-(4-chlorophenyl)acetylamino)phenyl}-1H-indazole-5-carboxamide;
3-(3-(3-phenylpropanoylamino)phenyl)-1H-indazole-5-carboxamide;
3-{3-(3-(4-fluorophenyl)propanoylamino)phenyl}-1H-indazole-5-carboxamide;
3-{3-(2-(3,4-difluorophenyl)acetylamino)phenyl}-1H-indazole-5-carboxamide;
3-{3-(2-(2-fluorophenyl)acetylamino)phenyl}-1H-indazole-5-carboxamide;
3-(3-(2-phenylpropanoylamino)phenyl}-1H-indazole-5-carboxamide;
3-(3-(2-piperidylethoxy)phenyl}-1H-indazole-5-carboxamide;
N-ethyl-3-{(3-(4-fluorophenyl)(1H-indazol-5-yl))carbonylamino}propanamide;
(3-(4-fluorophenyl)(1H-indazol-5-yl))-N-(3-methoxypropyl)carboxamide;
3-{3-(N-(2-piperidylethyl)carbamoyl)phenyl}-1H-indazole-5-carboxamide;
(3-(4-fluorophenyl)(1H-indazol-5-yl))-N-(2-hydroxyethyl)carboxamide;
(3-(4-fluorophenyl)(1H-indazol-5-yl))-N-(3-hydroxypropyl)carboxamide;

(3-(4-fluorophenyl)(1H-indazol-5-yl))-N-(2-metoxyethyl)carboxamide;
(3-(4-fluorophenyl)(1H-indazol-5-yl))-N-(oxolan-2-ylmethyl)carboxamide;
3-(2H, 3H-benzo(e)1,4-dioxin-6-yl)-1H-indazole-5-carboxamide;
3-(3-quinolyl)-1H-indazole-5-carboxamide;
3-(6-methoxy-2-naphthyl)-1H-indazole-5-carboxamide;
3-(2,3-dihyddrobenzo(b)furan-5-yl)-1H-indazole-5-carboxamide;
(3-(4-fluorophenyl)(1H-indazol-5-yl))-N-(3-oxo-3-pyrrolidinylpropyl)carboxamide;
3-{(3-(4-fluorophenyl)(1H-indazol-5-yl))carbonylamino}-N-methyl propanamide;
3-{(3-(4-fluorophenyl)(1H-indazol-5-yl))carbonylamino}-N,N-dimethyl propanamide;
3-{(3-(4-fluorophenyl)(1H-indazol-5-yl))carbonylamino}-N-(2-methoxyethyl)propanamide; or a pharmaceutically acceptable salt thereof.

22. A compound of claim 4, wherein the compound is:
phenyl-N-(3-phenyl(1H-indazol-5-yl))carboxamide;
N-(3-phenyl(1H-indazol-5-yl))-2-pyridylcarboxamide;
methyl 4-(N-(3-phenyl-1H-indazol-5-yl)carbamoyl)benzoate,
4-(N-(3-phenyl-1H-indazol-5-yl)carbamoyl)benzoic acid;
(2-hydroxyphenyl)-N-(3-phenyl(1H-indazol-5-yl)carboxamide,
N-(3-phenyl-1H-indazole-5-yl))acetamide;
(4-aminophenyl)-N-(3-phenyl(1H-indazol-5-yl))carboxamide;
(3-aminophenyl)-N-(3-phenyl(1H-indazol-5-yl))carboxamide;
N-(3-(4-fluorophenyl)(1H-indazol-5-yl))(2-methylphenyl)carboxamide;
N-(3-(4-fluorophenyl)(1H-indazol-5-yl))(2-methoxyphenyl)carboxamide;
N-(3-(4-fluorophenyl)(1H-indazol-5-yl))(4-phenylphenyl)carboxamide;
benzo(b)thiophen-2-yl-N-(3-(4-fluorophenyl)(1H-indazol-5-yl))carboxamide;
methyl 4-{N-(3-(4-fluorophenyl)-1H-indazol-5-yl)carbamoyl}benzoate;
N-(3-(4-fluorophenyl)(1H-indazol-5-yl))-2-pyridylcarboxamide;
4-{N-(3-(4-fluorophenyl)-1H-indazol-5-yl)carbamoyl}benzoic acid;
cyclopropyl-N-(3-(4-fluorophenyl)(1H-indazol-5-yl))carboxamide;
methyl 4-{N-(3-(4-fluorophenyl)(1H-indazol-5-yl))-N-methylcarbamoyl}benzoate;
4-{N-(3-fluorophenyl)(1H-indazol-5-yl))-N-methylcarbamoyl}benzoic acid;
methyl 3-{N-((4-fluorophenyl)-1H-indazol-5-yl)carbamoyl}benzoate;
3-{N-(3-(4-fluorophenyl)-1H-indazol-5-yl)carbamoyl}benzoic acid;
N-(3-(4-fluorophenyl)-(1H-indazol-5-yl))(4-(N-methylcarbamoyl)phenyl)carboxamide;
4-{N-(3-(4-fluorophenyl)-1H-indazol-5-yl)carbamoyl}benzamide;
1-4-{N-(3-(4-methoxyphenyl)-1H-indazol-5-yl)carbamoyl}benzoic acid;
4-(N-3-(4-pyridyl)-1H-indazol-5-yl)carbamoyl)benzoic acid;
N-(3-(4-fluorophenyl)(1H-indazol-5-yl)benzamide;
(3,4-bis(trifluoromethyl)phenyl)-N-(3-(4-fluorophenyl)(1H-indazol-5-yl))carboxamide;
N-(3-(4-fluorophenyl)(1H-indazol-5-yl))-2-furylcarboxamide;
N-(3-(4-fluorophenyl)(1H-indazol-5-yl))(3,4-dichlorophenyl)carboxamide;
N-(3-(4-fluorophenyl)(1H-indazol-5-yl))(2-hydroxyphenyl)carboxamide;
N-(3-(4-fluorophenyl)(1H-indazol-5-yl))-4-pyridylcarboxamide;
N-(3-(4-fluorophenyl)(1H-indazol-5-yl))-3-pyridylcarboxamide;
N-(3-(4-fluorophenyl)(1H-indazol-5-yl))-2-thienylcarboxamide;
N-(3-(4-fluorophenyl)(1H-indazol-5-yl))morpholin-4-yl-carboxamide;
[N-(((2R)-2-hydroxycyclohexyl)methyl)(3-(4-fluorophenyl)(1H-indazol-5-yl))carboxamide;] or a pharmaceutically acceptable salt thereof.

23. A compound of claim 5, wherein the compound is:
3-(3-(4-fluorophenyl)-1H-indazol-5-yl)-1H-1,2,4-triazole;
5-(3-(4-fluorophenyl)(1H-indazole-5-yl))-3-methyl-4H-1,2,4-triazole;
5-{3-(4-fluorophenyl)(1H-indazole-5-yl)]-3-(methylethyl)-4H-1,2,4-triazole;
1-{5-(3-(4-fluorophenyl)-1H-indazole-5-yl)4H-1,2,4-triazol-3-yl}propan-2-ol;
5-(3-(4-fluorophenyl)(1H-indazol-5-yl))-3-propyl-4H-1,2,4-triazole;
5-{3-(3-(methylethyl)phenyl)-1H-indazol-5-yl}-1H-1,2,4-triazole;
4-(5-(1H-1,2,4-triazol-5-yl)-1H-indazol-3-yl)phenol;
(4-(5-(1H-1,2,4-triazol-5-yl)(1H-indazol-3-yl))phenyl)dimethylamine;
{2-(4-(5-(1H-1,2,4-triazol-5-yl)(1H-indazol-3-yl))phenoxy)ethyl}dimethylamine;
3-(5-(1H-1,2,4-triazol-5-yl)-1H-indazol-3-yl)furan;
1-(5-(1H-1,2,4-triazol-5-yl)(1H-indazol-3-yl))-4-methoxybenzene;
5-(3-naphthyl-1H-indazol-5-yl)-1H-1,2,4-triazole;
3-(5-(1H-1,2,4-triazol-3-yl)-1H-indazol-3-yl)thiophene;
5-(3-(2-naphthyl)-1H-indazol-5-yl)-1H-1,2,4-triazole;
3-(5-(1H-1,2,4-triazol-3-yl)-1H-indazol-3-yl)phenylamine;
3-(3-(3,4-dichlorophenyl)-1H-indazol-5-yl)-1H-1,2,4-triazole;
3-(5-(1H-1,2,4-triazol-5-yl)-1H-indazol-3-yl)benzo(b)thiophene;
3-(3-(4-methylphenyl)-1H-indazol-5-yl)-1H-1,2,4-triazole;
N-(3-(5-(1H-1,2,4-triazol-3-yl)-1H-indazol-3-yl)phenyl)acetamide;
5-(3-(3-chlorophenyl)-1H-indazol-5-yl)-1H-1,2,4-triazole;
2-(5-(1H-1,2,4-triazol-5-yl)-1H-indazol-3-yl)benzo(b)furan;

1-(5-(1H-1,2,4-triazol-5-yl)(1H-indazol-3-yl))-4-(methylsulfonyl)benzene;
1-(5-(1H-1,2,4-triazol-5-yl)(1H-indazol-3-yl))-4-(methylsulfinyl)benzene;
5-(5-(1H-1,2,4-triazol-5-yl)-1H-indazol-3-yl)-2H-benzo(d)1,3-dioxolene;
4-(5-(1H-1,2,4-triazol-5-yl)-1H-indazol-3-yl)phenylamine;
5-{3-(4-(trifluoromethyl)phenyl)-1H-indazol-5-yl}-1H-1,2,4-triazole;
(3-(5-(1H-1,2,4-triazol-3-yl)(1H-indazol-3-yl))phenyl)(methylsulfonyl)amine;
N-(3-(5-(1H-1,2,4-triazol-3-yl)(1H-indazol-3-yl))phenyl)-2-methoxyacetamide;
N-(3-(5-(1H-1,2,4-triazol-3-yl)(1H-indazol-3-yl))phenyl)-2-phenylacetamide;
N-(3-(5-(1H-1,2,4-triazol-3-yl)(1H-indazol-3-yl))phenyl)-2-furylcarboxamide;
5-(3-(2-phenylethynyl)-1H-indazol-5-yl)-1H-1,2,4-triazole;
N-(3-(5-(1H-1,2,4-triazol-3-yl)(1H-indazol-3-yl))phenyl)-3-pyridylcarboxamide;
1-{5-{3-(4-fluorophenyl)1H-indazol-5-yl}-4H-1,2,4-Triazol-3-yl}ethan-1-ol;
1-{5-(3-(4-fluorophenyl)-1H-indazol-5-yl}-4H-1,2,4-triazol-3-yl}propan-2-ol;
{3-(3-(5-(1H-1,2,4-triazol-5-yl)(1H-indazol-3-yl))phenoxy)propyl}dimethylamine;
{2-(3-(5-(1H-1,2,4-triazol-5-yl)(1H-indazol-3-yl))phenoxy)ethyl}dimethylamine;
1-(5-(1H-1,2,4-triazol-5-yl)(1H-indazol-3-yl))-3-(2-morpholin-4-yl-ethoxy)benzene;
1-(5-(1H-1,2,4-triazol-5-yl)(1H-indazol-3-yl))-3-(2-pyrrolidinylethoxy)benzene;
1-(5-(1H-1,2,4-triazol-5-yl)(1H-indazol-3-yl))-3-(2-piperidylethoxy)benzene;
1-{2-(3-(5-(1H-1,2,4-triazol-5-yl)-1H-indazol-3-yl)phenoxy)ethyl}pyrrolidin-2-one;
1-(5-(1H-1,2,4-triazol-5-yl)(1H-indazol-3-yl))-3-(2-piperazinylethoxy)benzene;
1-(5-(1H-1,2,4-triazol-5-yl)(1H-indazol-3-yl))-3-(3-piperdylpropoxy)benzene;
4-{2-(3-(5-(1H-1,2,4-triazol-5-yl)(1H-indazol-3-yl))phenoxy)ethyl}-1-acetylpiperazine;
2-(3-(5-(1H-1,2,4-triazol-5-yl)-1H-indazol-3-yl)phenoxy)ethylamine;
1-(5-(1H-1,2,4-triazol-5-yl)(1H-indazol-3-yl))-3-(2-cyclohexylethoxy)benzene;
1-(5-(1H-1,2,4-triazol-5-yl)(1H-indazol-3-yl))-3-(2-azaperhyroepinylethoxy)benzene;
N-(4-(5-(1H-1,2,4-triazol-5-yl)(1H-indazol-3-yl))phenyl)-2-furyl caroxamide;
(3-(5-(1H-1,2,4-triazol-5-yl)(1H-indazol-3-yl))phenyl)-N-benzyl caroxamide;
5-(3-(2-chlorophenyl)-1H-indazol-3-yl)-1H-1,2,4-triazole;
(3-(5-(1H-1,2,4-triazol-5-yl)(1H-indazol-3-yl))phenyl)-N-(2,2-dimehtylpropyl)carboxamide;
(3-(5-(1H-1,2,4-triazol-5-yl)(1H-indazol-3-yl))phenyl)-N-(cyclopropylmethyl)carboxamide;
(3-(5-(1H-1,2,4-trizol-5-yl)(1H-indazol-3-yl))phenyl)-N-(3-pyridylmethyl)carboxamide;
(3-(5-(1H-1,2,4-triazol-5-yl)(1H-indazol-3-yl))phenyl)-4-methyl piperazinyl ketone;
(3-(5-(1H-1,2,4-triazol-5-yl)(1H-indazol-3-yl))phenyl)-N-((4-fluorophenyl)methyl)carboxamide;
(3-(5-(1H-1,2,4-triazol-5-yl)(1H-indazol-3-yl))phenyl)-N-indan-2-ylcarboxamide;
(3-(5-(1H-1,2,4-triazol-5-yl)(1H-indazol-3-yl))phenyl)-N-((1R)indanyl)carboxamide;
(3-(5-(1H-1,2,4-triazol-5-yl)(1H-indazol-3-yl))phenyl)-N-((1S)indanyl)carboxamide;
(3-(5-(1H-1,2,4-triazol-5-yl)(1H-indazol-3-yl))phenyl)-N-((1S,2R)-2-hydroxyindanyl)carboxamide;
(3-(5-(1H-1,2,4-triazol-5-yl)(1H-indazol-3-yl))phenyl)-N-((2S,1R)-2-hydroxyindanyl)carboxamide;
(3-(5-(1H-1,2,4-triazol-5-yl)(1H-indazol-3-yl))phenyl)-N-(1-methyl-1-phenylethyl)carboxamide;
(3-(5-(1H-1,2,4-triazol-5-yl)(1H-indazol-3-yl))phenyl)-N-(tert-butyl)carboxamide;
(3-(5-(1H-1,2,4-triazol-5-yl)(1H-indazol-3-yl))phenyl)-N-((1R)-1-phenylethyl)carboxamide;
1-(5-(1H-1,2,4-triazol-5-yl)(1H-indazol-3-yl))-3-(2-piperidylethoxy)benzene;
(3-(5-(1H-1,2,4-triazol-5-yl)(1H-indazol-3-yl))phenyl-isoindolin-2-yl ketone;
(3-(5-(1H-1,2,4-triazol-5-yl)(1H-indazol-3-yl))phenyl)-N-(2-(dimethylamino)ethyl)carboxamide;
1-(5-(1H-1,2,4-triazol-5-yl)(1H-indazol-3-yl))-3-(2-piperidylethoxy)benzene;
(3-(5-(1H-1,2,4-triazol-5-yl)(1H-indazol-3-yl))phenyl)-N-(1R)indanyl benzene;
{5-(3-(4-fluorophenyl)-1H-indazol-5-yl)-4H-(1,2,4)-triazol-3-ylmethyl}-dimethyl-amine;
N-(3-(5-(1H-1,2,4-triazol-3-yl)(1H-indazol-3-yl))phenyl)-3-piperidylpropanamide;
N-(3-(5-(1H-1,2,4-triazol-3-yl)(1H-indazol-3-yl))phenyl)-2-hydroxypropanamide;
N-(3-(5-(1H-1,2,4-triazol-3yl-)(1H-indazol-3-yl))phenyl)-2-(dimethylamino)acetamide;
N-(3-(5-(1H-1,2,4-triazol-3-yl)-1H-indazol-3-yl)phenyl)butanamide;
N-(3-(5-(1H-1,2,4-triazol-3-yl)(1H-indazol-3-yl))phenyl)-2-phenoxypropanamide;
N-(3-(5-(1H-1,2,4-triazol-3-yl)(1H-indazol-3-yl))phenyl)-3,3-dimethylbutanamide;
N-(3-(5-(1H-1,2,4-triazol-3-yl)(1H-indazol-3-yl))phenyl cyclopropylcarboxamide;
N-(3-(5-(1H-1,2,4-triazol-3-yl)(1H-indazol-3-yl))phenyl (6-chloro-3-pyridyl))carboxamide;
N-(3-(5-(1H-1,2,4-triazol-3-yl)(1H-indazol-3-yl))phenyl cyclopentylcarboxamide;
N-(3-(5-(1H-1,2,4-triazol-3-yl)(1H-indazol-3-yl))phenyl benzo(b)thiophen-2-carboxamide;
N-(3-(5-(1H-1,2,4-triazol-3-yl)(1H-indazol-3-yl))phenyl)-2-pyridylcarboxamide;
N-(3-(5-(1H-1,2,4-triazol-3-yl)(1H-indazol-3-yl))phenyl)-3-furylcarboxamide;
N-(3-(5-(1H-1,2,4-triazol-3-yl)(1H-indazol-3-yl))phenyl)-2-hydroxy-2-phenylacetamide;
N-(3-(5-(1H-1,2,4-triazol-3-yl)(1H-indazol-3-yl))phenyl isoxazol-5-ylcarboxamide;
N-(3-(5-(1H-1,2,4-triazol-3-yl)(1H-indazol-3-yl))phenyl) pentanamide;

N-(3-(5-(1H-1,2,4-triazol-3-yl)(1H-indazol-3-yl))phenyl)-4-pyridylcarboxamide;
N-(3-(5-(1H-1,2,4-triazol-3-yl)(1H-indazol-3-yl))phenyl)-2-cyclohexylacetamide;
N-(3-(5-(1H-1,2,4-triazol-3-yl)(1H-indazol-3-yl))phenyl)-3-propanamide;
N-(3-(5-(1H-1,2,4-triazol-3-yl)(1H-indazol-3-yl))phenyl)-2-(4-fluorophenyl)acetic acid;
N-(3-(5-(1H-1,2,4-triazol-3-yl)(1H-indazol-3-yl))phenyl) (2R)-2-hydroxy-2-phenylacetamide;
N-(3-(5-(1H-1,2,4-triazol-3-yl)(1H-indazol-3-yl))phenyl) (2S)-2-hydroxy-2-phenylacetamide;
(2-{3-(3-(4-fluorophenyl)(1H-indazol-5-yl))(1H-1,2,4-triazol-5-yl)}ethyl)dimethylamine;
diethyl({3-(3-(4-fluorophenyl)(1H-indazol-5-yl))(1H-1,2,4-triazol-5-yl)}methyl)amine;
({3-(3-(4-fluorophenyl)(1H-indazol-5-yl))(1H-1,2,4-triazol-5-yl)}methyl)methylamine;
({3-(3-(4-fluorophenyl)(1H-indazol-5-yl))(1H-1,2,4-triazol-5-yl)}ethyl)dimethylamine;
(2R)-N-(3-(5-{5-((dimethylamino)methyl)(1H-1,2,4-triazol-3-yl)}(1H-indazol-3-yl))phenyl)-2-hydroxy-2-phenylacetamide;
N-(3-(5-{5-((dimethylamino)methyl)(1H-1,2,4-triazol-3-yl)}(1H-indazol-3-yl))phenyl)-3,3-dimethylbutanamide;
N-(3-(5-{5-((dimethylamino)methyl)(1H-1,2,4-triazol-3-yl)}(1H-indazol-3-yl))phenyl)-3-methylbutanamide;
N-(3-(5-{5-((dimethylamino)methyl)(1H-1,2,4-triazol-3-yl)}(1H-indazol-3-yl))phenyl)-3-pyridylcarboxamide;
(3-(5-{5-((dimethylamino)methyl)(1H-1,2,4-triazol-3-yl)}(1H-indazol-3-yl))phenyl)-N-((4-fluorophenyl)methyl)carboxamide;
(3-(5-{5-((dimethylamino)methyl)(1H-1,2,4-triazol-3yl)}(1H-indazol-3-yl))phenyl)-N-(tert-butyl)methyl)carboxamide;
((1R)indanyl)(3-(5-{5-((dimethylamino)methyl)(1H-1,2,4-triazol-3-yl)}(1H-indazol-3-yl))phenyl)carboxamide;
({3-(3-(4-methoxyphenyl)(1H-indazol-5-yl))(1H-1,2,4-triazol-5-yl)}methyl)dimethylamine;
{(3-(3-(2H-benzo(d)1,3-dioxolen-5-yl))(1H-indazol-5-yl))(1H-1,2,4-triazol-5-yl)}methyl}dimethylamine;
(3-(5-(3-((dimethylamino)methyl)(1H-1,2,4-triazol-5-yl)(1H-indazol-3-yl))phenyl)-N-(2-piperidylethyl)carboxamide;
((5-(3-benzo(D)furan-2-yl(1H-indazol-5-yl))(1H-1,2,4-triazol-3-yl))methyl)dimethylamine;
(3-(5-(3-((dimethylamino)methyl)(1H-1,2,4-triazol-5-yl)(1H-indazol-3-yl))phenyl)-N-benzamide;
(3-(5-(3-((dimethylamino)methyl)(1H-1,2,4-triazol-5-yl))(1H-indazol-3-yl))phenyl)-N-(4-fluorophenyl)carboxamide-2HCl;
(3-(5-(3-((dimethylamino)methyl)(1H-1,2,4-triazol-5-yl)(1H-indazol-3-yl))phenyl)-N-indan-2-yl-carboxamide;
(3-(5-(3-((dimethylamino)methyl)(1H-1,2,4-triazol-5-yl)(1H-indazol-3-yl))phenyl)-N-cyclopropylcarboxamide;
(3-(5-(3-((dimethylamino)methyl)(1H-1,2,4-triazol-5-yl))(1H-indazol-3-yl))phenyl)-N-cyclobutylcarboxamide-2HCl;
1-(5-(1H-1,2,4-triazol-3-yl)(1H-indazol-3-yl)-3-(2-methoxyethoxy)benzene;
1-(5-(1H-1,2,4-triazol-3-yl)(1H-indazol-3-yl)-3-(3-pyridylmethoxy)benzene;
3-(5-(1H-1,2,4-triazol-3-y)-1H-indazol-3-yl)benzoic acid;
3-(5-(1H-1,2,4-triazol-3-yl)-1H-indazol-3-yl)benzoic acid N-(4-(5-(1H-1,2,4-triazol-3-yl)(1H-indazol-3-yl))phenyl)-2-(3-pyridyl)acetamide;
N-(4-(5-(1H-1,2,4-triazol-3-yl)(1H-indazol-3-yl))phenyl)-2-phenylacetamide;
N-(4-(5-(1H-1,2,4-triazol-3-yl)(1H-indazol-3-yl))phenyl)-2-methoxyacetamide;
N-(4-(5-(1H-1,2,4-triazol-3-yl)(1H-indazol-3-yl))phenyl)-2-(dimethylamino)acetamide;
(4-(5-(1H-1,2,4-triazol-3-yl)(1H-indazol-3-yl))phenyl)(methylsulfonyl)amine;
(3-(5-(1H-1,2,4-triazol-3-yl)(1H-indazol-3-yl))phenyl)-N-(2-methoxyethyl)carboxamide;
(3-(5-(1H-1,2,4-triazol-3-yl)(1H-indazol-3-yl))phenyl)-N-benzamide;
(3-(5-(1H-1,2,4-triazol-3-yl)(1H-indazol-3-yl))phenyl)-N-(2-phenethyl)carboxamide;
(3-(5-(1H-1,2,4-triazol-3-yl)(1H-indazol-3-yl))phenyl-N-(2-piperidylethyl)carboxamide;
(3-(5-(1H-1,2,4-triazol-3-yl)(1H-indazol-3-yl))phenyl-N-(2-morpholin-4-ylethyl)carboxamide;
(3-(5-(1H-1,2,4-triazol-3-yl)(1H-indazol-3-yl))phenyl-N-cyclohexylcarboxamide;
(3-(5-(1H-1,2,4-triazol-3-yl)(1H-indazol-3-yl))phenyl-N-cyclopentylcarboxamide;
(3-(5-(1H-1,2,4-triazol-3-yl)(1H-indazol-3-yl))phenyl-N-(4-fluorophenyl)carboxamide;
(3-(5-(1H-1,2,4-triazol-3-yl)(1H-indazol-3-yl))phenyl-N-((1R,2R)-2-phenylcyclopropyl)carboxamide;
(3-(5-(1H-1,2,4-triazol-3-yl)(1H-indazol-3-yl))phenyl-N-cyclopropylcarboxamide;
(3-(5-(1H-1,2,4-triazol-3-yl)(1H-indazol-3-yl))phenyl-N-(3-pyridyl)carboxamide;
(3-(5-(1H-1,2,4-triazol-3-yl)(1H-indazol-3-yl))phenyl-N-(5,6,7,8-tetrahydronaphthyl)carboxamide;
(3-(5-(1H-1,2,4-triazol-3-yl)(1H-indazol-3-yl))phenyl-N-(1-benzyl(4-piperidyl))carboxamide;
(3-(5-(1H-1,2,4-triazol-3-yl)(1H-indazol-3-yl))phenyl-N-(1-benzylpyrrolidin-3-yl)carboxamide;
(3-(5-(1H-1,2,4-triazol-3-yl)(1H-indazol-3-yl))phenyl-N-(methylethyl)carboxamide;
(3-(5-(1H-1,2,4-triazol-3-yl)(1H-indazol-3-yl))phenyl-N-cyclobutylcarboxamide;
(3-(5-(1H-1,2,4-triazol-3-yl)(1H-indazol-3-yl))phenyl-N-(4-pyridyl)carboxamide;
6-(5-(1H-1,2,4-triazol-3-yl)-1H-indazol-3-yl)-2H,3h-benzo(e)1,4-dioxin;
6-(5-(1H-1,2,4-triazol-3-yl)(1H-indazol-3-yl))-2-methoxynaphthalene;
3-(3-(3-quinoyl)-1H-indazol-5-yl)-1H-1,2,4-triazole;
5-(5-(1H-1,2,4-triazol-3-yl)-1H-indazol-3-yl)-2,3-dihydrobenzo(b)furan;
N-(3-(5-(1H-1,2,4-triazol-3-yl)(1H-indazol-3-yl))phenyl) benzamide;
N-(3-(5-(1H-1,2,4-triazol-3-yl)(1H-indazol-3-yl))phenyl) (2,4-dichlorophenyl)carboxamide;
N-(3-(5-(1H-1,2,4-triazol-3-yl)(1H-indazol-3-yl))phenyl) (4-methoxyphenyl)carboxamide;

N-(3-(5-(1H-1,2,4-triazol-3-yl)(1H-indazol-3-yl))phenyl)(4-methylphenyl)carboxamide;

N-(3-(5-(1H-1,2,4-triazol-3-yl)(1H-indazol-3-yl))phenyl)(4-chlorophenyl)carboxamide;

N-(3-(5-(1H-1,2,4-triazol-3-yl)(1H-indazol-3-yl))phenyl)-2-methylpropanamide;

N-(3-(5-(1H-1,2,4-triazol-3-yl)(1H-indazol-3-yl))phenyl)-3-methylbutanamide;

N-(3-(5-(1H-1,2,4-triazol-3-yl)(1H-indazol-3-yl))phenyl)-2-morpholin-4-yl-acetamide;

N-(3-(5-(1H-1,2,4-triazol-3-yl)(1H-indazol-3-yl))phenyl)-2-(4-methylpiperazinyl)acetamide;

2-methoxy-6-{5-(5-(pyrrolidinylmethyl)(1H-1,2,4-triazol-3-yl)(1H-indazol-3-yl)}naphthalene;

N-phenyl(3-{5-(5-(pyrrolidinylmethyl)(1H-1,2,4-triazol-3-yl))(1H-indazol-3-yl)}phenyl)carboxamide;

6-{5-(5-(pyrrolidinylmethyl)-1H-1,2,4-triazol-3-yl)-1H-indazol-3-yl}-2H,3H-benzo(e)1,4-dioxin; or a pharmaceutically acceptable salt thereof.

24. A compound of claim 6, wherein the compound is:

5-(3-(4-fluorophenyl)-1H-indazol-5-yl)-2H-1,2,3,4-tetrazole;

1-(5-(2H-1,2,3,4-tetrazol-5-yl)(1H-indazol-3-yl))-2-methoxybenzene;

5-(3-(3-pyridyl)-1H-indazol-5-yl)-2H-1,2,3,4-tetrazole;

2-(5-(2H-1,2,3,4-tetrazol-5-yl)-1H-indazol-3-yl)thiophene;

5-{3-(4-(methylethyl)phenyl)-1H-indazol-5-yl}-2H-1,2,3,4-tetrazole;

2-(5-(2H-1,2,3,4-tetrazol-5-yl)-1H-indazol-3-yl)furan;

3-(5-(2H-1,2,3,4-tetrazol-5-yl)-1H-indazol-3-yl)phenylamine;

5-(5-(1H-1,2,3,4-tetraazol-5-yl)-1H-indazol-3-yl)-2H-benzo(d)1,3-dioxolene;

3-(5-(2H-1,2,3,4-tetrazol-5-yl)-1H-indazol-3-yl)thiophene;

5-(3-(2-naphthyl)-1H-indazol-5-yl)-1H-1,2,3,4-tetrazole;

1-(5-(1H-1,2,3,4-tetraazol-5-yl)(1H-indazol-3-yl))-4-methoxybenzene;

1-(5-(1H-1,2,3,4-tetraazol-5-yl)(1H-indazol-3-yl))-4-(2-methylpropoxy)benzene;

5-(3-(4-chlorophenyl)-1H-indazol-5-yl)-2H-1,2,3,4-tetrazole;

1-(5-(2H-1,2,3,4-tetrazol-5-yl)(1H-indazol-3-yl))-3-methoxybenzene;

5-(3-(4-pyridyl)-1H-indazol-5-yl)-2H-1,2,3,4-tetrazole;

2-(5-(2H-1,2,3,4-tetraazol-5-yl)-1H-indazol-3-yl)benzo(b)furan;

2-(5-(2H-1,2,3,4-tetrazol-5-yl)-1H-indazol-3-yl)phenol;

3-(5-(2H-1,2,3,4-tetrazol-5-yl)-1H-indazol-3-yl)phenol;

5-(3-(2-phenylethynyl)-1H-indazol-5-yl)-1H-1,2,3,4-tetrazole;

5-(3-(2-phenylethyl)-1H-indazol-5-yl)-2H-1,2,3,4-tetrazole;

N-(3-(5-(2H-1,2,3,4-tetrazol-5-yl)(1H-indazol-3-yl))phenyl)-2-methoxyacetamide;

2-(5-(1H-1,2,3,4-tetraazol-5-yl)-1H-indazol-3-yl)benzo(b)thiophene;

1-(5-(1H-1,2,3,4-tetraazol-5-yl)(1H-indazol-3-yl))-4-(2-morpholin-4-ylethoxy)benzene;

N-(3-(5-2H-1,2,3,4-tetrazol-5-yl)(1H-indazol-3-yl))phenyl)2-phenoxypropanamide;

N-(3-(5-(2H-1,2,3,4-tetrazol-5-yl)(1H-indazol-3-yl))phenyl)-3-piperidylpropanamide;

N-(3-(5-(2H-1,2,3,4-tetrazol-5-yl)(1H-indazol-3-yl))phenyl)-2-furylcarboxamide;

1-(5-(1H-1,2,3,4-tetraazol-5-yl)(1H-indazol-3-yl))-3-(2-morpholin-4-ylethoxy)benzene;

4-(5-(2H-1,2,3,4-tetraazol-5-yl)(1H-indazol-3-yl))-1,2-dimethoxybenzene;

N-(3-(5-(2H-1,2,3,4-tetrazol-5-yl)(1H-indazol-3-yl))phenyl)-3-methoxypropanamide;

N-(3-(5-(2H-1,2,3,4-tetrazol-5-yl)(1H-indazol-3-yl))phenyl)-3-pyridylcarboxamide;

{3-(4-(5-(1H-1,2,3,4-tetrazo-5-yl)(1H-indazol-3-yl))phenoxy)propyl}dimethylamine;

{3-(3-(5-(1H-1,2,3,4-tetrazol-5-yl)(1H-indazol-3-yl))phenoxy)propyl}dimethylamine;

{2-(3-(5-(1H-1,2,3,4-tetrazol-5-yl)(1H-indazol-3-yl))phenoxy)ethyl}dimethylamine;

N-(3-(5-(2H-1,2,3,4-tetrazol-5-yl)(1H-indazol-3-yl))phenyl)(2S)-2-hydroxypropanamide;

N-(4-(5-(2H-1,2,3,4-tetrazol-5-yl)(1H-indazol-3-yl))phenyl)-3-pyridylcarboxamide;

or a pharmaceutically acceptable salt thereof.

25. A compound of claim 7, wherein the compound is:

3-(4-fluorophenyl)-5-imidazol-2-yl-1H-indazole, or a pharmaceutically acceptable salt thereof.

26. A compound, wherein the compound is:

3-phenyl-5-(phenylmethoxy)-1H-indazole;

(3-(4-fluorophenyl)(1H-indazol-5-yl)(phenylsulfonyl)amine;

3-(4-fluorophenyl)-1H-indazole-5-carboxylate;

(3-(4-fluorophenyl)(1H-indazol-5-yl))-N-(phenylmethoxy)carboxamide;

3-(4-fluorophenyl)-1H-indazole-5-carbohydroxamic acid;

N-((tert-butoxy)carbonylamino)(3-(4-fluorophenyl)(1H-indazol-5-yl))carboxamide;

N-amino(3-(4-fluorophenyl)(1H-indazol-5-yl))carboxamide;

methyl-3-benzo(B)thiophen-2-yl-1H-indazole-5-carboxylate;

3-benzo(B)thiophen-2-yl-1H-indazole-5-carboxylic acid;

or a pharmaceutically acceptable salt thereof.

* * * * *

UNITED STATES PATENT AND TRADEMARK OFFICE
CERTIFICATE OF CORRECTION

PATENT NO.   : 6,897,231 B2
DATED        : May 24, 2005
INVENTOR(S)  : Bhagwat et al.

It is certified that error appears in the above-identified patent and that said Letters Patent is hereby corrected as shown below:

Column 310,
Lines 4-48, please delete claim 2.

Column 310, line 49 through Column 311, line 27,
Please delete claim 3.

Column 313,
Line 61, please replace "-$(OH_2)_a$-" with -- -$(CH_2)_a$- --.

Column 314,
Line 10, please replace "-$O(=O)R_8$-" with -- -$C(=O)R_8$- --.

Column 315,
Lines 62-63, please delete claim 11.
Lines 64-65, please delete claim 12.

Column 316,
Lines 13-22, please delete claim 20.

Column 316, line 23 through Column 319, line 21,
Please delete claim 21.

Signed and Sealed this

Twenty-fifth Day of October, 2005

JON W. DUDAS
*Director of the United States Patent and Trademark Office*